US011835520B2

(12) United States Patent
Mueller et al.

(10) Patent No.: US 11,835,520 B2
(45) Date of Patent: Dec. 5, 2023

(54) **SYSTEM, METHOD, APPARATUS AND DIAGNOSTIC TEST FOR *PLASMODIUM VIVAX***

(71) Applicant: The Walter and Eliza Hall Institute of Medical Research, Parkville (AU)

(72) Inventors: Ivo Mueller, Mount Macedon (AU); Takafumi Tsuboi, Ehime Prefecture (JP); Michael White, Melbourne (AU); Rhea Longley, Brunswick West (AU)

(73) Assignee: The Walter and Eliza Hall Institute of Medical Research, Parkville (AU)

( * ) Notice: Subject to any disclaimer, the term of this patent is extended or adjusted under 35 U.S.C. 154(b) by 1008 days.

(21) Appl. No.: 16/472,269

(22) PCT Filed: Dec. 21, 2017

(86) PCT No.: PCT/IB2017/001776
§ 371 (c)(1),
(2) Date: Jun. 21, 2019

(87) PCT Pub. No.: WO2018/130871
PCT Pub. Date: Jul. 19, 2018

(65) Prior Publication Data
US 2021/0132063 A1    May 6, 2021

Related U.S. Application Data

(60) Provisional application No. 62/438,963, filed on Dec. 23, 2016.

(51) Int. Cl.
*G01N 33/573* (2006.01)
*G01N 33/569* (2006.01)
*C07K 14/415* (2006.01)
*C07K 16/20* (2006.01)
*G01N 33/68* (2006.01)

(52) U.S. Cl.
CPC ..... *G01N 33/56905* (2013.01); *C07K 14/415* (2013.01); *C07K 16/205* (2013.01); *G01N 33/6857* (2013.01); *G01N 2333/445* (2013.01)

(58) Field of Classification Search
None
See application file for complete search history.

(56) References Cited

PUBLICATIONS

Chuquiyauri et al., "Genome-Scale Protein Microarray Comparison of Human Antibody Responses in Plasmodium vivax Relapse and Reinfection," Am. J. Trop. Med. Hyg., 93(4), 2015, pp. 801-809.
Kerkhof et al., "Serological markers to measure recent changes in malaria at population level in Cambodia," Malaria Journal, 15 (1), 2016, pp. 529.
Longley et al., "High Efficacy of Primaquine Treatment for Plasmodium vivax in Western Thailand," Am. J. Trop. Med. Hyg., Nov. 2, 2016;95(5): 1086-1089.
Longley et al., "Acquisition and Longevity of Antibodies to Plasmodium vivax Peerythrocytic Antigens in Western Thailand," Clin Vaccine Immunol. Dec. 9, 2015;23(2): 117-24.
Wampfler et al., "Strategies for Detection of *Plasmodium* species Gametocytes," 2013 PLOS One 8:e76316.
Rosanas-Urgell et al., "Comparison of diagnostic methods for the detection and quantification of the four sympatric *Plasmodium* species in field samples from Papua New Guinea," 2010, Malaria Journal, 9:361.
Lu et al., "Profiling the humoral immune responses to Plasmodium vivax infection and identification of candidate immunogenic rhoptry-associated membrane antigen (RAMA)," 2014 J. Proteomics 102:66-82.
Sawasaki et al., "A cell-free protein synthesis system for high-throughput proteomics," 2002, Proc Natl Acad Sci USA 99: 14652-14657.
Sawasaki et al., "A bilayer cell-free protein synthesis system for high-throughput screening of gene products," 2002, FEBS Lett 514:102-105.
Sawasaki et al., "The Wheat Germ Cell-Free Expression System," 2007, Methods of Mol Biol 375:95-106.
Sawasaki et al., "Methods of High-Throughput Materialization of Genetic Information Based on Wheat Germ Cell-Free Expression System," 2005, Methos of Mol Biol 310:131-144.
Matsuoka et al., "Simple Screening Method for Autoantigen Proteins Using the N-Terminal Biotinylated Protein Library Produced by Wheat Cell-Free Synthesis," 2010, J. Proteome Res, 9:4264-4273.
Franca et al., "Plasmodium vivax Reticulocyte Binding Proteins Are Key Targets of Naturally Acquired Immunity in Young Papua New Guinean Children," 2016, PLOS Negl Trop Dis 10:e0004639.
Finney et al., "Predicting Antidisease Immunity Using Proteome Arrays and Sera from Children Naturally Exposed to Malaria," 2014, Mol Cell Proteomics 13 (10) 2646-2660.
Longley et al., "Comparative assessment of vaccine encoding ten malaria antigens identifies two protective liver-stage candidates," 2015 Sci Rep 5:11820.
White, et al., "Determinants of relapse perioicity in Plasmodium vivax malaria," 2011, Malaria Journal 10, 10:297.
Mueller et al., "Key gaps in the knowledge of Plasmodium vivax, a neglected human malaria parasite," 2009, Lancet Infectious Diseases 9, 555-566.
White et al., "Dynamics of the Antibody Response to Plasmodium falciparum Infection in African Children," 2014, Journal of Infectious Diseases 210, 1115-1122.

(Continued)

*Primary Examiner* — Jennifer E Graser
(74) *Attorney, Agent, or Firm* — Hoffmann & Baron, LLP

(57) ABSTRACT

A system, method, apparatus and diagnostic test for *Plasmodium vivax*, to determine a likelihood of a specific timing of infection by *P. vivax* in a subject, and hence identify individuals with a high probability of being infected with otherwise undetectable liver-stage hypnozoites. The system, method, apparatus and diagnostic test relate to the identification of hypnozoites ("dormant" liver-stages), or at least of the likelihood of the subject being so infected. Optionally and preferably, the specific timing relates to recent infections, for example within the last 9 months.

25 Claims, 30 Drawing Sheets
Specification includes a Sequence Listing.

(56) References Cited

PUBLICATIONS

Yman et al., "Antibody acquisition models: A new tool for serological surveillance of malaria transmission intensity," 2016, Scientific Reports 6, doi:10. 1038/srep 19472.
Kirkpatrick et al., "Optimization by Simulated Annealing," 1983, Science 220, 671-680.

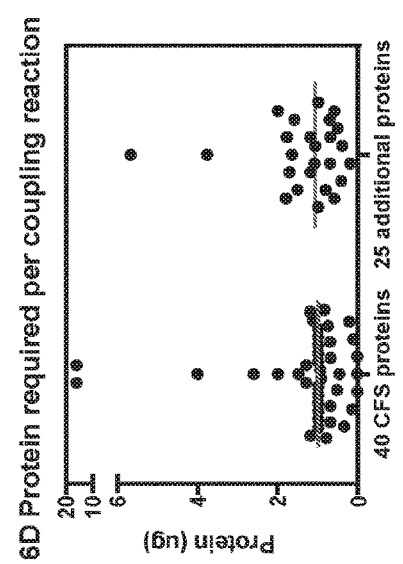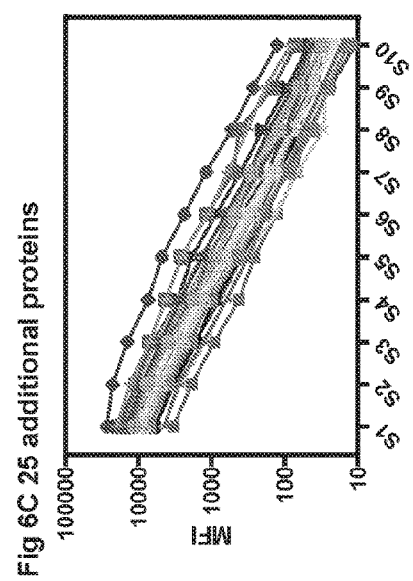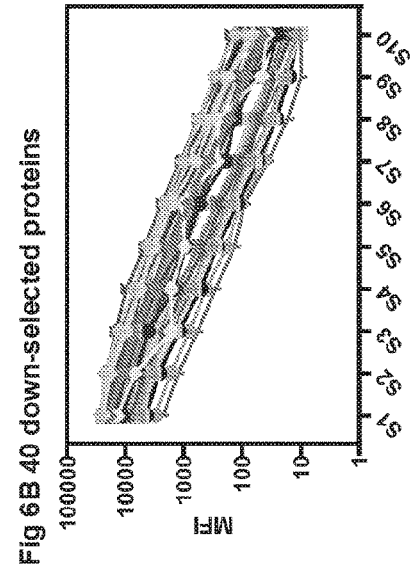

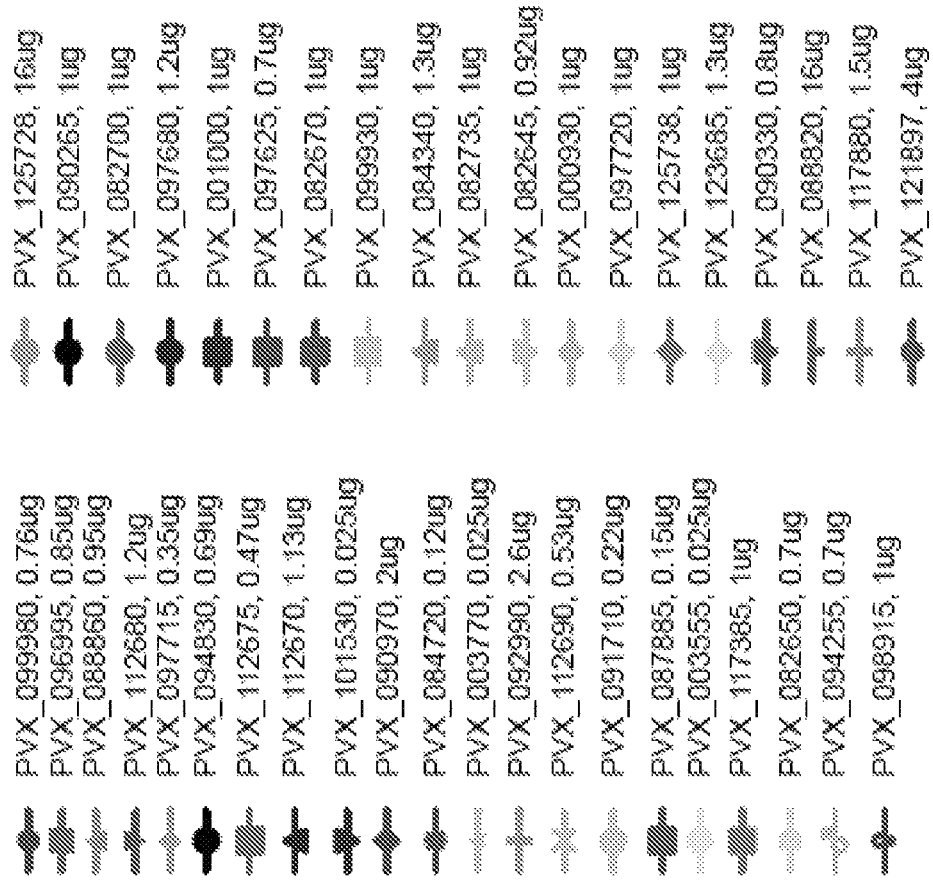
Figure 6E (key to Figure 6B)

Figure 6F (key to Figure 6C)

SYSTEM, METHOD, APPARATUS AND DIAGNOSTIC TEST FOR *PLASMODIUM VIVAX*

CROSS REFERENCE TO RELATED APPLICATIONS

The present invention is a national stage application which claims priority from PCT Application No. PCT/IB2017/001776 filed Dec. 21, 2017, and U.S. Application No. 62/438,963 filed Dec. 23, 2016. Applicants claim the benefits of 35 U.S.C. § 120 as to the said PCT application, and priority under 35 U.S.C. § 119 as to the said U.S. provisional application, and the entire disclosures of all applications are incorporated herein by reference in their entireties.

SEQUENCE LISTING

This application contains a Sequence Listing, submitted in ASCII format via EFS-Web, and hereby incorporated by reference in its entirety. The ASCII copy, created on May 29, 2019, is named "2762-9 PCTUS_ST25.txt" and is 392.5 KB in size.

FIELD OF THE INVENTION

The present invention is of a system, method, apparatus and diagnostic test for relapsing *Plasmodium* species (i.e *Plasmodium vivax* and *Plasmodium ovale*), and in particular, to such a system, method, apparatus and diagnostic test for *Plasmodium vivax* for characterizing at least one aspect of infection in a subject or a population of subjects.

BACKGROUND OF THE INVENTION

*Plasmodium vivax* (*P. vivax*) is one of five species of parasites that cause malaria in humans. This disease is marked by severe fever and pain, and can be fatal. The symptoms are caused by the parasite's infection, and destruction, of red blood cells in the subject. Infection of new subjects occurs when infectious mosquitoes take a blood meal from humans and inoculate parasites with their saliva.

Like one other species that infects humans, *P. ovale*, *P. vivax* has the ability to "hide" in the liver of a subject and remain dormant—and asymptomatic—before (re-)emerging to cause renewed bloodstage infections and malarial symptoms. Transmission from humans to mosquitoes can only occur when the sexual stages of the parasite (gametocytes) are circulating in the blood. Liver-stage infection with hypnozoites is completely undetectable and asymptomatic, and transmission to mosquitoes is not possible. *P. falciparum* and *P. knowlesi* do not have this ability. *P. malariae* can cause recurrent infections but it remains unclear if these infections persist in the bloodstream, the liver or another organ. This ability to hide from the immune system in the liver for prolonged periods makes *P. vivax* and *P. ovale* particularly difficult to detect and treat.

FIG. 1 shows the overall life cycle of the *P. vivax* parasite (see Mueller, I. et al. Key gaps in the knowledge of *Plasmodium vivax*, a neglected human malaria parasite. Lancet Infectious Diseases 9, 555-566 (2009)). During a blood meal, a malaria-infected female *Anopheles* mosquito inoculates sporozoites into the human host (1). Sporozoites infect liver cells (2) and either enter a dormant hypnozoite state or mature into schizonts (3), which rupture and release merozoites (4). After this initial replication in the liver (exo-erythrocytic schizogony A), the parasites undergo asexual multiplication in the erythrocytes (erythrocytic schizogony B). Merozoites infect red blood cells (5). The ring stage trophozoites mature into schizonts, which rupture releasing further merozoites into the blood stream (6). Some parasites differentiate into sexual erythrocytic stages (gametocytes) (7). Blood stage parasites are responsible for the clinical manifestations of the disease.

The gametocytes, male (microgametocytes) and female (macrogametocytes), are ingested by an *Anopheles* mosquito during a blood meal (8). The parasites' multiplication in the mosquito is known as the sporogonic cycle (C). While in the mosquito's stomach, the microgametes penetrate the macrogametes generating zygotes (9). The zygotes in turn become motile and elongated (ookinetes) (10) which invade the midgut wall of the mosquito where they develop into oocysts (11). The oocysts grow, rupture, and release sporozoites (12), which make their way to the mosquito's salivary glands. Inoculation of the sporozoites (1) into a new human host perpetuates the malaria life cycle.

Diagnosis of subjects with *P. vivax* infections is of paramount importance to reducing or even eliminating transmission in a population. Such diagnosis would also significantly help individual subjects to receive proper treatment, including those that have only silent liverstage infections. Given the high degree of population mobility today, particularly in response to natural disasters or human conflicts, accurate and rapid diagnosis of all *P. vivax* infections has become even more important to controlling the disease. In addition, as transmission in countries decreases (as each population approaches elimination of the disease), population-level surveillance becomes increasingly important. This surveillance will aid in determining residual areas of transmission within a country, and can also be used to provide evidence for the absence of transmission indicating that elimination has been achieved.

Some proteins have been very well studied and characterized for diagnostic purposes. For example, merozoite surface protein 1 (MSP1), in particular certain C-terminal MSP1-19 fragments and the N-terminal Pv200L fragments have been described as suitable diagnostic antigens. Some examples of prior publications related to this protein include U.S. Pat. No. 6,958,235, which focuses on a fragment of this protein for diagnostic purposes; WO9208795A1, which focuses on this protein for diagnosis; and US20100119539. Merozoite surface protein 3 (MSP3) is described with regard to a diagnostic tool in U.S. Pat. No. 7,488,489. MSP3.10 [merozoite surface protein 3 alpha (MSP3a)] is described as part of the family of merozoite surface protein 3 like proteins for diagnostic and other purposes in US20070098738. Rhoptry associated membrane antigen is described with regard to a diagnostic tool in EP0372019 B 1. Many other proteins were described in relation to their immunogenicity and hence their therapeutic utility as part of a vaccine. Some non-limiting examples are given below.

| UniProt | Annotation[1] | Patent information |
|---|---|---|
| A5K3N8 | rhoptry neck protein 2, putative (RON2) | Vaccine including this protein (US20160158332); specifically described and claimed for diagnosis in EP2520585, no family members, abandoned in 2013 |
| A5KBS6 | hypothetical protein, conserved (PvLSA3[d]) | WO2015091734 (vaccine) |
| A5K4Z2 | apical merozoite antigen 1 (PvAMA1) | U.S. Pat. No. 9,364,525 (one of a list of antigens for a vaccine, downloaded as US20100150998); WO2006037807 - structure of this antigen; U.S. Pat. No. 7,150,875 - vaccine specifically directed at this antigen |
| A5K0N7 | translocon component PTEX150, putative (PTEX150) | US20140348870 - Especially preferred antigens are post-challenge immunity associated antigens that are identified via pre-infection suppressive treatment, controlled sub-symptomatic infection to develop immunity, and comparative proteomic differential analysis. WO2010127398 - more focused on treatment |
| A5KBL6 | merozoite surface protein 5 | WO2014186798 - immune stimulation (1 of a long list of diseases and antigens); U.S. Pat. No. 8,350,019 (focuses on this protein for diagnostic use); WO2015031904 - use of this protein to determine if an individual is protected against malaria; WO2016030292 - focused on treatment; US20110020387 - malaria vaccine |
| A5K800 | MSP7 [merozoite surface protein 7 (MSP7)] | EP2990059 - therapeutic but mentions MSP7 specifically |
| A5K736 | reticulocyte binding protein 2b (RBP2b) | U.S. Pat. No. 8,703,147 - treatment and prevention of malaria |
| A5KAV2 | merozoite surface protein 3 (MSP3.3) | EP2223937 - prevention and treatment of malaria; describes the gene family that includes this protein for diagnosis and treatment - EP1689866 |
| A5KAU1 | merozoite surface protein 8, putative | US20140348870 - identified this protein as immunogenic |
| A5K806 | thrombospondin-related anonymous protein (PvTRAP/SSP2) | Immunogenic, part of a vaccine: US20100272745, U.S. Pat. No. 7,790,186, U.S. Pat. No. 7,150,875, WO2013142278, WO2015091734 |
| A5KDR7 | Duffy receptor precursor (DBP) | mentioned as immunogenic protein, part of a vaccine: U.S. Pat. No. 7,790,186 |
| A5KAW0 | MSP3.10 [merozoite surface protein 3 alpha (MSP3a)] | US20070098738 - describes entire protein family; US707129 - describes various members of this family as being immunogenic |

Still other proteins have barely been described or characterized in the literature. In some cases, these proteins have not yet been described with regard to their stage in the *P. vivax* life cycle. In other cases, an initial determination of the stage has been made but their diagnostic or therapeutic utility is not known. A non-limiting list of some of these proteins is provided below. A further list is provided with regard to Appendix I, although optionally any annotated proteins from *P. vivax* in Uniprot (http://www.uniprot.org/uniprot/) or another suitable protein database could be included.

| Uniprot | Protein name |
|---|---|
| A5K7E7 | hypothetical protein, conserved |
| A5K482 | hypothetical protein, conserved |
| A5K0Q6 | hypothetical protein, conserved |
| A5K4N0 | hypothetical protein, conserved |
| A5KAP7 | hypothetical protein, conserved |
| A5K4I6 | hypothetical protein, conserved |
| A5K659 | hypothetical protein, conserved |
| A5KB45 | hypothetical protein, conserved |

Very few attempts have been made to characterize the life cycle of the parasite within the body for diagnostic purposes, in terms of the dynamics of the proteins or antibody responses to specific proteins present in the blood. For example, an assay for determining a state of protective immunity is described in US20160216276. However, the disclosure relates to diagnostic assays for identifying individuals that are protected against *Plasmodium falciparum* caused malaria. As noted above, *P. falciparum* does not have a dormant liver stage with long-latency giving rise to relapses. This patent application does not mention *P. vivax*.

Other prior art disclosures for diagnostics focus only on the blood stage of *P. vivax*, which again prevents a complete picture of the dynamics of the infection in the subject from being determined. U.S. Pat. No. 6,231,861 and US20090117602 both suffer from this deficiency.

In other cases, where a plurality of antigens were examined for malarial diagnostics of *P. vivax*, the results still did not provide a complete picture of the dynamics of the infection in the subject. For example, "Genome-Scale Protein Microarray Comparison of Human Antibody Responses in *Plasmodium vivax* Relapse and Reinfection" (Chuquiyauri et al; Am. J. Trop. Med. Hyg., 93(4), 2015, pp. 801-809) suffered from the following drawbacks:
  i) It only features antibody signatures that differentiate between blood-stage infections that are thought to stem either from direct infections or relapsing infections;
  ii) The phenotypes are of poor quality because they are focused on genotyping with only one gene, so may overestimate the number of new infections vs relapses;
  iii) They are only looking at the presence and titer of antigens at one timepoint (i.e. at the time of infection).

In another example, "Serological markers to measure recent changes in malaria at population level in Cambodia" (Kerkhof et al; Malaria Journal, 15 (1), 2016, pp. 529, the authors calculated estimated antibody half-lives to 19 *Plasmodium* proteins, including 5 *P. vivax* proteins. These 5 proteins are well-known vaccine candidates (CSP, AMA1, EBP, DBP and MSP1), and the work included no formal antigen down-selection. A major limitation of this study is that individuals were only assessed for malaria prevalence every 6 months, and hence the estimated half-lives are not a true biological reflection of what occurs in the absence of re-infection. The authors only identified one *P. vivax* antigen, EBP, that had an estimated antibody half-life of less than 2 years.

BRIEF SUMMARY OF THE INVENTION

The present invention, in at least some embodiments, is of a system, method, apparatus and diagnostic test for *Plasmodium vivax*, to determine a likelihood of a specific timing of infection by *P. vivax* in a subject, and hence identify individuals with a high probability of being infected with otherwise undetectable liver-stage hypnozoites. According to at least some embodiments, the system, method, apparatus and diagnostic test relate to the identification of hypnozoites ("dormant" liver-stages), or at least of the likelihood of the subject being so infected. Optionally and preferably, the specific timing relates to recent infections, for example within the last 9 months. Without wishing to be limited by a closed list, the present invention is able to identify such recent infections, and not just current infections.

Non-limiting examples of elapsed time periods since an infection include time since infection ranging from 0 to 12 months, and each time period in between, by month, by week, and/or by day. Optionally and preferably a particular time period is determined as a binary decision of a more recent or an older infection, with each time point as a cut-off. As a non-limiting example, one such cut off could determine whether an infection in a subject was within the past 9 months or later than the past 9 months.

Optionally the timing of such an infection may also be determined, such that one or more of the following parameters may be determined. One such parameter is optionally whether the infection is a first infection in the patient, of *P. vivax* generally or of a particular strain of *P. vivax*. As there is no sterilizing immunity in malaria, immunity to one strain does not necessarily confer immunity to another, different strain. However, as described in greater detail below with regard to the examples, the present invention was tested by using samples from three different regions (including Brazil, Thailand and the Solomon Islands). These three populations are genetically highly diverse and represent the major part of the global genetic variation in *P. vivax*. Consequently, the present inventors believe, without wishing to be limited by a single hypothesis, that it will work anywhere in the world. Other parameters relate to time elapsed from the previous infection.

According to at least some embodiments, the antibody measurements may optionally be used to provide an estimation of elapsed time since last infection. An estimate of the time since last *P. vivax* blood-stage infection—depending on the available calibration data—can be defined either as the time since last PCR-detectable blood-stage parasitemia, or as the time since last infective mosquito bite. Time since last infection can be estimated continuously or categorically. Concurrent estimation of uncertainty will be important.

According to at least some embodiments, the antibody measurements may optionally be used to provide a determination of medium-term serological exposure, for example a frequency of infections during a particular time period and/or time since last infection.

According to at least some embodiments, there is provided a system, method, apparatus and diagnostic test for detection of a "silent" (asymptomatic or presymptomatic) infection by *P. vivax*.

According to at least some embodiments, there is provided a system, method, apparatus and diagnostic test for detection of a dormant infection, in which *P. vivax* is present in the liver but is not present at detectable levels in the blood. As described herein, detection of a dormant infection optionally comprises prediction from an indirect measurement of an antibody level.

During the life cycle of *P. vivax*, blood-stage forms of the parasite can initially be present at the same time as arrested liver forms, as described in the Background of the Invention. Even after the blood-stage infection has cleared, hypnozoites can still be present in the liver, and the parasite may still be indirectly detected via persisting antibody responses against the primary blood-stage infection. According to at least some embodiments, there is provided a system, method, apparatus and diagnostic test for detection of antibodies to malarial proteins that are present in the blood that indicate a high degree of probability of liver-stage infection.

According to at least some embodiments, there is provided a system, method, apparatus and diagnostic test for determination of the progression of infection by *P. vivax* in a population of a plurality of subjects. Optionally, it is possible to determine the rate of propagation of a particular *Plasmodium* species in a population not previously exposed to that species.

With regard to the diagnostic test, in at least some embodiments, there is provided a plurality of antibodies that bind to a plurality of antigens in a blood sample taken from the subject. Optionally any suitable tissue biological sample from a subject may be used for detecting a presence and/or level of a plurality of antibodies.

According to at least some embodiments, the dynamics of the measured antibodies preferably include a combination of short-lived and long-lived antibodies. Without wishing to be limited by a single hypothesis or a closed list, such a combination is useful to reduce measurement error.

Optionally the level of antibodies is measured at one time point or a plurality of time points.

Optionally, the presence of the actual antibodies in the blood of the subject is measured at a plurality of time points to determine decay in the level of the antibody in the blood. Such a decay in the level is then optionally and preferably fitted to a suitable model as described herein, in order to determine at least one of the infection parameters as described above. More preferably, decay of the level of a plurality of different antibodies is measured. Optionally and more preferably, the different antibodies are selected to have a range of different half-lives. Optionally, a maximum number of different antibodies is measured, which is optionally up to 20 or as few as two, or any integral number in between. According to at least some embodiments, the number of antibodies is preferably 4 or 8.

According to at least some embodiments, the level is measured of at least one antibody to a protein selected from the group consisting of: PVX_099980, PVX_112670, PVX_087885, PVX_082650, PVX_088860, PVX_112680, PVX_112675, PVX_092990, PVX_091710, PVX_117385, PVX_098915, PVX_088820, PVX_117880, PVX_121897, PVX_125728, PVX_001000, PVX_084340, PVX_090330, PVX_125738, PVX_096995, PVX_097715, PVX_094830, PVX_101530, PVX_090970, PVX_084720, PVX_003770, PVX_112690, PVX_003555, PVX_094255, PVX_090265, PVX_099930, PVX_123685, PVX_002550, PVX_082700, PVX_097680, PVX_097625, PVX_082670, PVX_082735, PVX_082645, PVX_097720, PVX_000930, PVX_094350, PVX_099930, PVX_114330, PVX_088820, PVX_080665, PVX_092995, PVX_087885, PVX_003795, PVX_087110, PVX_087670, PVX_081330, PVX_122805, RBP1b (P7), RBP2a (P9), RBP2b (P25), RBP2cNB (M5), RBP2-P2 (P55), PvDBP R3-5, PvGAMA, PvRipr, PvCYRPA, Pv DBPII (AH), PvEBP, RBP1a (P5) and Pv DBP (SacI).

Preferably, the level is measured of at least one antibody to a protein selected from the group consisting of PVX_099980, PVX_112670, PVX_087885, PVX_082650, PVX_088860, PVX_112680, PVX_112675, PVX_092990, PVX_091710, PVX_117385, PVX_098915, PVX_088820, PVX_117880, PVX_121897, PVX_125728, PVX_001000, PVX_084340, PVX_090330, PVX_125738, PVX_096995, PVX_097715, PVX_094830, PVX_101530, PVX_090970, PVX_084720, PVX_003770, PVX_112690, PVX_003555, PVX_094255, PVX_090265, PVX_099930 and PVX_123685.

More preferably, the level is measured of at least one antibody to a protein selected from the group consisting of PVX_099980, PVX_112670, PVX_087885, PVX_082650, PVX_096995, PVX_097715, PVX_094830, PVX_101530, PVX_090970, PVX_084720, PVX_003770, PVX_112690, PVX_003555, PVX_094255, PVX_090265, PVX_099930 and PVX_123685.

Most preferably, the level is measured of at least one antibody to a protein selected from the group consisting of PVX_099980, PVX_112670, PVX_087885 and PVX_082650.

According to at least some embodiments, preferably the level is measured of at least one antibody to a protein selected from the group consisting of RBP2b, L01, L31, X087885, PvEBP, L55, PvRipr, L54, L07, L30, PvDBPII, L34, X092995, L12, RBP1b, L23, L02, L32, L28, L19, L36, L41, X088820 and PvDBP.SacI.

More preferably the level is measured of at least one antibody to a protein selected from the group consisting of RBP2b, L01, L31, X087885, PvEBP, L55, PvRipr, L54, L07, L30, PvDBPII, L34, X092995, L12 and RBP1b.

Also more preferably the level is measured of at least one antibody to a protein selected from the group consisting of RBP2b, L01, L31, X087885, PvEBP, L55, PvRipr and L54.

Most preferably the level is measured of at least one antibody to a protein selected from the group consisting of RBP2b and L01.

A table containing additional proteins against which antibodies may optionally be measured is provided herein in Appendix I, as described in greater detail below, such that the level of one or more of these antibodies may optionally be measured.

Appendix II gives a list of preferred proteins against which antibodies may be measured, while Appendix III shows a complete set of data for antibodies against the proteins in Appendix II. Appendix III is given in two parts, due to the size of the table: Appendix IIIA and Appendix IIIB. The references to gene identifiers in Appendix II are the common ones used for *Plasmodium*—from PlasmoDB website: http://plasmodb.org/plasmo/.

For any protein described herein, optionally a fragment and/or variant may be used for detecting the presence and/or level of one or more antibodies in a biological sample taken from a subject.

According to at least some embodiments, a biologically-motivated model of the decay of antibody titers over time is used to determine a statistical inference of the time since last infection. The model preferably uses previously determined decay rates of a plurality of different antibodies to determine a likelihood that infection in the subject occurred within a particular time period. Optionally such previously determined decay rates may be achieved through estimation of antibody decay rates from longitudinal data, or estimation of decay rates from cross-sectional antibody measurements.

With regard to estimation of antibody decay rates from longitudinal data, preferably such an estimation is performed as described in equation (1), which is a mixed-effects linear regression model:

$$\log(A_{ijk}) \sim (\alpha_k^0 + \alpha_{ik}) + (r_k^0 + r_{ik})t_j + \varepsilon_k$$

$$\alpha_{ik} \sim N(0, \sigma_{a,k})$$

$$r_{ik} \sim N(0, \sigma_{r,k})$$

$$\varepsilon_k \sim N(0, \sigma_{m,k}) \quad \text{(Equation 1)}$$

For the above equation to be true, the following assumptions were made. We assume that for individual i we have measurements of antibody titer $A_{ijk}$ at time j to antigen k. We assume that at time 0, antibody titers are Normally distributed5 with mean $\alpha_k^0$ and standard deviation $\sigma_{a,k}$ on a log-scale. We assume that an individual's rate of antibody decay is drawn from a Normal distribution with mean $r_k^0$ and standard deviation $\sigma_{r,k}$.

According to at least some embodiments, the plurality of different antibodies selected maximizes probability of determining at least one of the infection parameters as described above. A method for such a selection process is described below in Example 3. Optionally the plurality of antibodies is selected for determining an answer to a binary determinant, such as for example, whether an individual was infected before x months ago or after as previously described.

According to at least some embodiments, the model for determining at least one parameter about the infection in the subject may optionally comprise one or more of the following algorithms: linear discriminant analysis (LDA), quadratic discriminant analysis (QDA), combined antibody dynamics (CAD), decision trees, random forests, boosted trees and modified decision trees.

According to at least some embodiments, the levels of antibody in a blood-sample can be measured and summarized in a variety of ways, for input to the above described model.

a) Continuous measurement

A continuous measurement that has a monotonic relationship with antibody titer. It can be compared with a titration curve to produce an estimate of antibody titer.

b) Binary classification

Assesses whether antibody levels are greater or less than some threshold c) Categorical classification Assigns antibody levels to one of a set of pre-defined categories, e.g. low, medium, high. A categorical classification can be generated via a series of binary classifications.

According to at least some embodiments, antibody levels may optionally be measured in a subject in a number of different ways, including but not limited to, bead-based assays (e.g. AlphaScreen® or Luminex® technology), the enzyme linked immuosorbent assay (ELIS A), protein microarrays and the luminescence immunoprecipitation system (LIPS). All the aforementioned methods generate a continuous measurement of antibody.

BRIEF DESCRIPTION OF THE DRAWINGS

FIGS. 6B-6F show additional development and optimization of the Luminex bead-array assay for all 65 proteins assessed in the validation study as follows. FIG. 6B shows 40 down-selected proteins. FIG. 6C shows the remaining 25 proteins. Log-linear standard curves were achieved for all proteins. The amount of protein for one bulk reaction of 500 ul beads is shown in FIG. 6D, with the line indicating the median (1 and 1.08 ug, respectively). FIG. 6E provides a key to FIG. 6B. FIG. 6F provides a key to FIG. 6C.

DESCRIPTION OF AT LEAST SOME EMBODIMENTS

Figure 1:
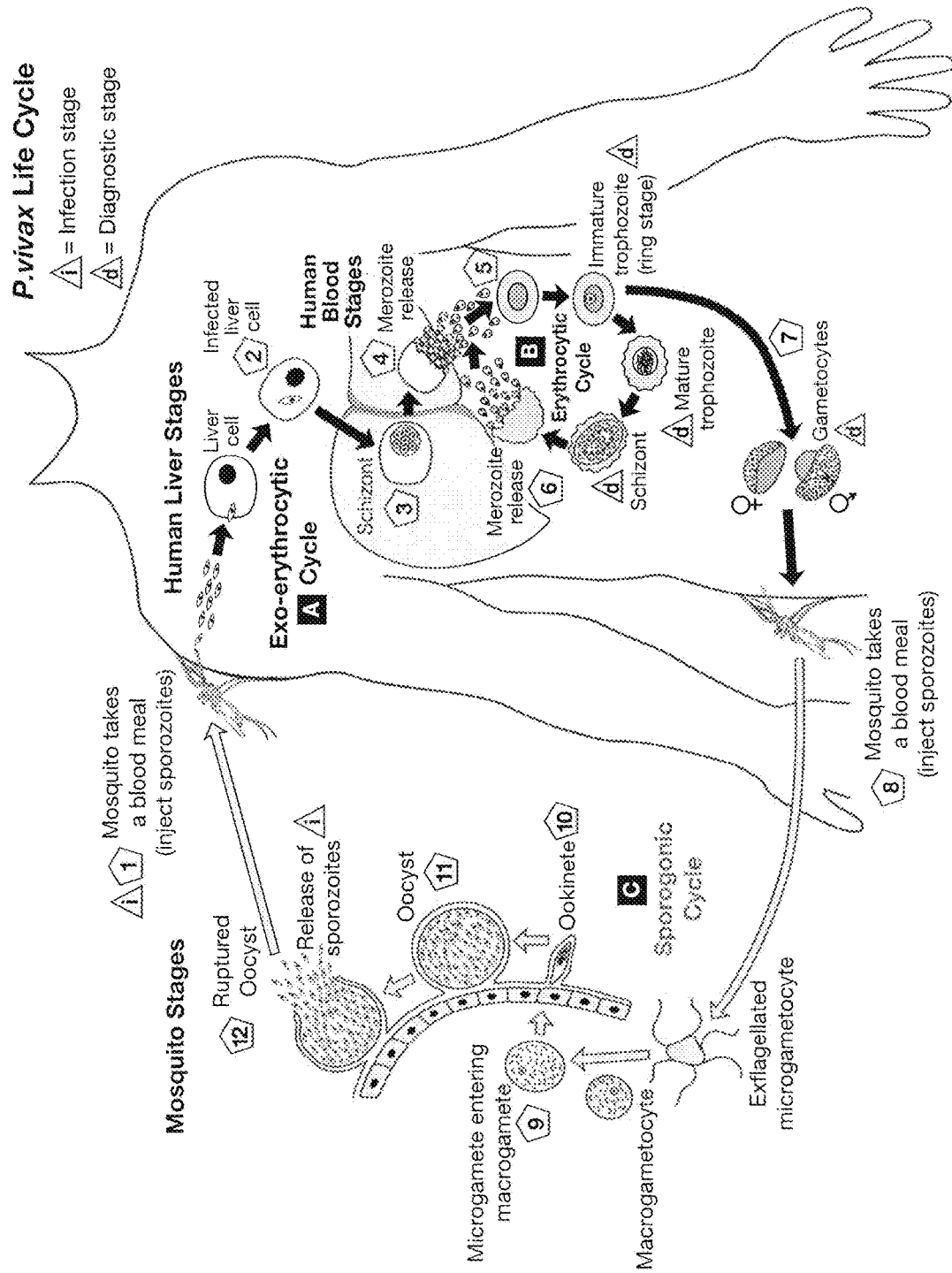
FIG. 1 shows a background art description of the lifecycle of *P. vivax* (see Mueller, I. et al. Key gaps in the knowledge of *Plasmodium vivax*, a neglected human malaria parasite. Lancet Infectious Diseases 9, 555-566 (2009)).

The present invention, in at least some embodiments, is of a system, method, apparatus and diagnostic test for at least *Plasmodium vivax*, and optionally other species such as *P. ovale*, to determine a likelihood of a concurrent or the specific timing of a recent past infection by *P. vivax* in a subject, and hence identify individuals with a high probability of being infected with otherwise undetectable liver-stage hypnozoites. According to at least some embodiments, the system, method, apparatus and diagnostic test relate to the identification of hypnozoites ("dormant" liver-stages), or at least of the likelihood of the subject being so infected. Optionally and preferably, the specific timing relates to recent infections, for example within the last 9 months. Without wishing to be limited by a closed list, the present invention is able to identify such recent infections, and not just current infections.

According to at least some embodiments, the antibody measurements may optionally be used to provide an estimation of elapsed time since last infection. An estimate of the time since last *P. vivax* blood-stage infection—depending on the available calibration data, the time since last infection can be defined either as the time since last PCR-detectable blood-stage parasitemia, or as the time since last infected mosquito bite. Time since last infection can be estimated continuously or categorically. Concurrent estimation of uncertainty will be important.

According to at least some embodiments, the antibody measurements may optionally be used to provide a determination of medium-term serological exposure, for example a frequency of infections during a particular time period and/or time since last infection.

According to at least some embodiments, there is provided a system, method, apparatus and diagnostic test for detection of a "silent" (asymptomatic or presymptomatic) infection by *P. vivax*.

Protein Nomenclature

Throughout the below experiments, simplified names have been used for the proteins assessed. In the antigen discovery experiments using the AlphaScreen® assay, 342 proteins were assessed. These proteins were given codes consisting of single letters followed by 2 numbers in most instances, and on occasion 3 numbers.

In the validation experiments using the multiplexed assay (Luminex® technology), 40 proteins (out of the 53 potential candidates down-selected) were assessed. These proteins have been given codes beginning with 'L' followed by 2 numbers. These proteins were supplemented by an additional 25 proteins expressed in a variety of systems. These proteins have been given codes beginning with 'V' or 'X' followed by 2 numbers. The codes used for the tested candidates are outlined below, as well as in Appendix II, in reference to their PlasmoDB gene ID (plasmodb.org).

| PlasmoDB ID | AlphaScreen | Luminex |
|---|---|---|
| PVX_099980 | D10 | L01 |
| PVX_096995 | J12 | L02 |
| PVX_088860 | L19 | L03 |
| PVX_097715 | N17 | L07 |
| PVX_112680 | K21 | L06 |
| PVX_094830 | N13 | L10 |
| PVX_112675 | B19 | L11 |
| PVX_112670 | G21 | L12 |
| PVX_101530 | D21 | L05 |
| PVX_090970 | E10 | L14 |
| PVX_084720 | B8 | L18 |
| PVX_003770 | P17 | L19 |
| PVX_092990 | H14 | L20 |
| PVX_112690 | K10 | L21 |
| PVX_091710 | F13 | L22 |
| PVX_087885 | N9 | L23 |
| PVX_003555 | O21 | L24 |

A complete list of all sequences considered, plus the sequences themselves, may be found in Appendices I and II combined. These sequences include the reference to the amino acid and nucleic acid sequence records of the relevant antigens, plus actual sequences generated for testing. The actual amino acid sequences generated for testing include a methionine at the start (N-terminus) and a His-tag at the end (C-terminus) as non-limiting examples only. The nucleic acid sequences so generated correspond to these amino acid sequences. It should be noted that the sequences listed are intended as non-limiting examples only, as different sequences and/or different antigens may optionally be used with the present invention, additionally or alternatively. The amino acid sequences for the specific proteins referred to herein may optionally be obtained from Uniprot or another suitable protein database.

Example 1—Testing of Antigens

This non-limiting Example relates to testing of antibody responses to various *P. vivax* proteins, present in the blood, as potential antigens for a diagnostic test.

Materials and Methods

Ethics Statement.

The relevant local ethics committees approved all field studies and all patients gave informed consent or assent. The Ethics Committee of the Faculty of Tropical Medicine, Mahidol University, Thailand approved the Thai antigen discovery and validation studies (MUTM 2014-025-01 and 02, and MUTM 2013-027-01, respectively). The Ethics Review Board of the Fundação de Medicina Tropical Dr. Heitor Vieira Dourado (FMT-HVD) (957.875/2014) approved the Brazilian antigen discovery study. The samples used from Brazil for the validation study were approved by the FMT-HVD (51536/2012), by the Brazilian National Committee of Ethics (CONEP) (349.211/2013) and by the Ethics Committee of the Hospital Clinic, Barcelona, Spain (2012/7306). The National Health Research and Ethics Committee of the Solomon Islands Ministry of Health and Medical Services (HRC12/022) approved collection of the samples used from the Solomon Islands for the validation study. The Human Research Ethics Committee at WEHI approved samples for use in Melbourne (#14/02).

Field Sites and Sample Collection: Antigen Discovery Study.

Samples from two longitudinal cohorts, located in Thailand and Brazil, were used for the antigen discovery studies. The longitudinal study in Thailand was conducted from April 2014 to September 2015, as previously described (Longley et al., Am J Trop Med Hyg. 2016 Nov. 2; 95(5): 1086-1089). Briefly, 57 symptomatic *P. vivax* patients were enrolled from either the Tha Song Yang malaria clinic or hospital. Patients with glucose-6-phosphate dehydrogenase (G6PD) deficiency and those aged younger than 7 years or more than 80 years were excluded. Patients were treated with chloroquine (25 mg base/kg body weight, administered over 3 days) and primaquine (15 mg daily, for 14 days) according to the standard Thai treatment regimen. Antimalarial drugs were given under directly-observed treatment in order to reduce the likelihood of treatment failure and the presence of recurrent infections during follow-up. Volunteers were followed for 9-months following enrolment, with finger-prick blood samples collected at enrolment and week 1, then every 2 weeks for 6 months, then every month until the end of the study. Blood was separated into packed red cells and plasma at the field site. All blood samples were analysed by both light microscopy and quantitative PCR (qPCR) for the presence of blood-stage parasites. A sub-set of volunteers, n=32, were selected for use in the antigen discovery project. These volunteers had no detectable recurrent infections during 9-months follow-up, and were the first to complete follow-up.

The longitudinal study in Brazil followed the same format as in Thailand. The study was conducted from May 2014 to May 2015. 91 malaria patients at Fundação de Medicina Tropical Doutor Heitor Vieira Dourado in Manaus aged between 7 and 70 years were enrolled. Individuals with G6PD deficiency or chronic diseases were not enrolled. Patients were treated according to the guidelines of the Brazilian Ministry of Health (3 days chloroquine, 7 days primaquine). Follow-up intervals with finger-prick blood sample collection were as in the Thai study. A sub-set of volunteers, n=33, whom had no detectable recurrent infections during 9-months follow-up, were selected for use in the antigen discovery project.

Field Sites and Sample Collection: Validation Study.

For the validation studies, samples collected from four observational longitudinal cohort studies, conducted in Thailand, Brazil and the Solomon Islands, were used (data from the Solomon Islands not shown). Samples were collected from a cohort of volunteers every month for 1 year. Plasma samples from the final cohort time-point were used in the validation study, n=829 Thailand, n=925 Brazil, and n=751 Solomon Islands.

The Thailand observational cohort was conducted from May 2013 to June 2014 in the Kanchanaburi and Ratchaburi provinces of western Thailand. The design of this study has been published (Longley et al, Clin Vaccine Immunol. 2015 Dec. 9; 23(2):117-24). Briefly, a total of 999 volunteers were enrolled (aged 1-82 years, median 23 years). Volunteers were sampled every month over the yearlong cohort, with 14 active case detection visits performed in total. A total of 609 volunteers attended all visits, with 829 attending the final visit. At each visit, volunteers completed a brief survey outlining their health over the past month (to determine the possibility of missed malarial infections), in addition to travel history and bed net usage. A finger-prick blood sample was also taken and axillary temperature recorded. Blood samples were separated into packed red blood cells, for detection of malaria parasites, and plasma, for antibody measurements, at the field sites. In addition to the monthly active case detection visits, passive case detection was also performed routinely by local malaria clinics.

The Brazilian observational cohort was conducted from April 2013 to April 2014 in three neighbouring communities located on the outskirts of Manaus, Amazonas State. Briefly, a total of 1274 residents of all age groups were enrolled (range 0-102 years, median 25 years). Volunteers were sampled every month over the yearlong period, with 13 active case detection visits performed in total. At each visit a finger-prick blood sample was collected, with the exception of children aged less than one in which blood was collected from the heel or big toe. As per the Thai cohort study, at each visit body temperature was also recorded and a questionnaire undertaken outlining the participants' health, bed net usage and travel history. Passive case detection was performed routinely by local health services. Blood samples were processed as per the Thai cohort. Plasma samples from 925 volunteers were available from the final visit.

The Solomon Islands observational cohort was conducted from May 2013 to May 2014 in 20 villages on the island of Ngella, Solomon Islands. 1111 children were initially enrolled, and after exclusion of children who withdrew, had inconsistent attendance or failed to meet other inclusion criteria, 860 remained (Quah & Waltmann, in preparation). The age of the children ranged from 6 months to 12 years, with a median age of 5.6 years. Over the yearlong cohort, children were visited approximately monthly, with 11 active case detection visits in total. Of the 860 children, 751 attended the final visit. At each visit, a brief survey was conducted as per the Thai cohort, temperature recorded and a finger-prick blood sample taken. Blood was separated into packed red cells for qPCR and plasma for antibody measurements. In addition to the monthly active case detection visits, local health clinics and centres also performed passive case detection routinely.

Negative Control Samples: Melbourne and Thai Red Cross, Melbourne Blood Donors

Three panels of control samples were collected from individuals with no known previous exposure to malaria. The first panel was collected from the Volunteer Blood Donor Registry (VBDR) at the Walter and Eliza Hall of Medical Research in Melbourne, Australia. These individuals are not screened for diseases but a record of their past travel, medical history and current drug use is recorded. 102 volunteers from the VBDR were utilized (median age 39 years, range 19-68). The second panel was collected from the Australian Red Cross (Melbourne, Australia). 100 samples were utilized (median age 52 years, range 18-77), and these individuals were screened as per the standard conditions of the Australian Red Cross. Finally, another control panel was collected from the Thai Red Cross (Bangkok, Thailand). Samples from 72 individuals were utilized, but no demographic data was available (hence the age range is unknown). Standard Thai Red Cross screening procedures exclude individuals from donating blood if they had a past malaria infection with symptoms within the last three years, and individuals who have travelled to malaria-endemic regions within the past year.

All studies (antigen discovery and validation) detected malaria parasites by quantitative PCR as previously described (2, 3).

Protein Expression.

Proteins were preferably expressed as full-length proteins, to ensure that any possible antibody recognition site was covered. For very large proteins, fragments were expressed that together cover the entire protein. These were treated as individual constructs in the down-selection process. The proteins were first produced at a small-scale with a biotin tag for the antigen discovery study, at Ehime University. A panel of 342 *P. vivax* proteins were assessed, including well-known *P. vivax* proteins such as potential vaccine candidates (i.e. MSP1, AMA1, CSP), orthologs of immunogenic *P. falciparum* proteins and proteins with a predicted signal peptide (SP) and/or 1-3 transmembrane domains (TM) (4). The genes were amplified by PCR and cloned into the pEU_E01 vector with N-terminal His-b1s tag (CellFree Sciences, Matsuyama, Japan). *P. vivax* genes were obtained either from parent clones (4), using SAL-1 cDNA, or commercially synthesized from Genscript (Japan). The recombinant proteins were expressed without codon optimization using the wheat germ cell-free (WGCF) system as previously described (5). WGCF synthesis of the *P. vivax* protein library was based on the previously described bilayer diffusion system (6). For biotinylation of proteins, 500 nM D-biotin (Nacalai Tesque, Kyoto, Japan) was added to both the translation and substrate layers. Crude WGCF expressed BirA (1 µl) was added to the translation layer. In vitro transcription and cell-free protein synthesis for the *P. vivax* protein library were carried out using the GenDecoder 1000 robotic synthesizer (CellFree Sciences) as previously described (7, 8). Expression of the proteins was confirmed by western blot using HRP-conjugated streptavidin.

Large-scale protein expression for the down-selected candidates was then performed (CellFree Sciences Tokyo, Japan). Genes were synthesized by GenScript (Japan) and the products cloned into the pEU-E01-MCS expression vector. The sequence of all gene synthesis products and their correct insertion into the expression vector was confirmed by full-length sequencing of the vector inserts. Transcription was performed utilizing SP6 RNA polymerase (80 U/µl) and the SP6 promoter in the pEU-E01-MCS expression vector. For large-scale expression, a dialysis-based refeeding assay was used, with protein expression and solubility first tested on a 50 µl scale. The test results then enabled production on a 3 ml scale (maintained for up to 72 hours, 15° C.) to produce at least 300 µg of each target protein, using the wheat germ extract WEPRO7240H. The proteins were manually purified one-time on an affinity matrix (Ni Sepharose 6 Fast Flow from GE Healthcare, Chalfont, United Kingdom) using a batch method (all proteins were expressed with a His-tag at the C terminus). The purified proteins were stored and shipped in the following buffer: 20 mM Na-phosphate pH 7.5, 0.3 M NaCl, 500 mM imidazole and 10% (v/v) glycerol. Protein yields and purity were determined using 15% SDS page followed by Coomassie Brilliant Blue staining using standard laboratory methods. In addition, proteins were also analyzed by Western Blot using an anti-His-tag antibody.

An additional 25 proteins were also used in the validation study. 12 proteins were produced using the wheat-germ cell free system described above at Ehime University, and were selected based on associations with past exposure in preliminary work conducted in a PNG cohort. The remaining 13 proteins were produced using standard *E. coli* methods, and were selected based on their predicted high immunogenicity (due to their status as potential vaccine candidates). References can be found in Appendix II.

AlphaScreen® Assay for the Antigen Discovery Study.

The AlphaScreen® assay was used to measure antibody responses in the antigen discovery study. Plasma samples from the sub-set of volunteers (n=32 Thailand, n=33 Brazil)

were used from four time-points, enrolment (week 0) and weeks 12, 24 and 36. Responses were measured against 342 *P. vivax* proteins. The assay was conducted as previously reported (9), with slight modifications. The protocol was automated by use of the JANUS Automated Workstation (PerkinElmer Life and Analytical Science, Boston, Mass.). Reactions were carried out in 25 µl of reaction volume per well in 384-well OptiPlate microtiter plates (PerkinElmer). First, 0.1 µl of the translation mixture containing a recombinant *P. vivax* biotinylated protein was diluted 50-fold (5 ill), mixed with 10 µl of 4000-fold diluted plasma in reaction buffer (100 mM Tris-HCL [pH 8.0], 0.01% [v/v] Tween-20 and 0.1% [w/v] bovine serum albumin), and incubated for 30 min at 26° C. to form an antigen-antibody complex. Subsequently, a 10 µl suspension of streptavidin-coated donor-beads and acceptor-beads (PerkinElmer) conjugated with protein G (Thermo Scientific, Waltham, Mass.) in the reaction buffer was added to a final concentration of 12 m/ml of both beads. The mixture was incubated at 26° C. for one hour in the dark to allow the donor and acceptor-beads to optimally bind to biotin and human IgG, respectively. Upon illumination of this complex, a luminescence signal at 620 nm was detected by the EnVision plate reader (PerkinElmer) and the result was expressed as AlphaScreen counts. A translation mixture of WGCF without template mRNA was used as a negative control. Each assay plate contained a standard curve of total biotinylated rabbit IgG. This enabled standardisation between plates using a 5-paramater logistic standard curve. All samples were run in triplicate. Reading the plates was conducted in a randomized manner to avoid biases.

Multiplexed Bead-Based Assay for the Validation Study.

For validation of the down-selected candidate serological markers, IgG levels were measured in plasma collected from the last time-point of the longitudinal observation studies. IgG measurements were performed using a multiplexed bead-based assay as previously described (10). In brief, $2.5 \times 10^6$ COOH microspheres (Bio-Rad, USA) were prepared for protein coupling by incubation for 20 minutes at room temperature in 100 mM monobasic sodium phosphate (pH 6.2), 50 mg/ml N-Hydroxysulfosuccinimide sodium salt and 50 mg/ml N-(3-Dimethylaminopropyl)-N'-ethylcarbodiimide hydrochloride. Proteins were then added and incubated overnight at 4° C. Optimal amounts of protein were determined experimentally, in order to achieve a log-linear standard curve when using a positive control plasma pool generated from hyper-immune PNG donors. Each assay plate subsequently included this 2-fold serial dilution standard curve (1/50 to 1/25600), to enable standardisation between plates.

The assay was run by incubating 50 µl of the protein-coupled microspheres (500 microspheres/well) with 50 µl test plasma (at 1/100 dilution) in 96-well multiscreen filter plates (Millipore, USA) for 30 minutes at room temperature, on a plate shaker. Plates were washed 3 times and then incubated for a further 15 minutes with the detector antibody, PE-conjugated anti-human IgG (1/100 dilution, Jackson ImmunoResearch, USA). The plates were once again washed and then assayed on a Luminex 200™ instrument. All median fluorescent intensity (MFI) values were converted to relative antibody unites using the plate-specific standard curve (five-parameter logistic function, as previously described in detail (10)).

Statistical Modelling.

The models are described in greater detail below (see Example 3).

Statistical Analysis.

All data manipulation and statistical analyses were performed in either R version 3.2.3 (11), Prism version 6 (GraphPad, USA) or Stata version 12.1 (StataCorp, USA).

Results

Down-Selection of Candidate Serological Markers.

Figure 2:
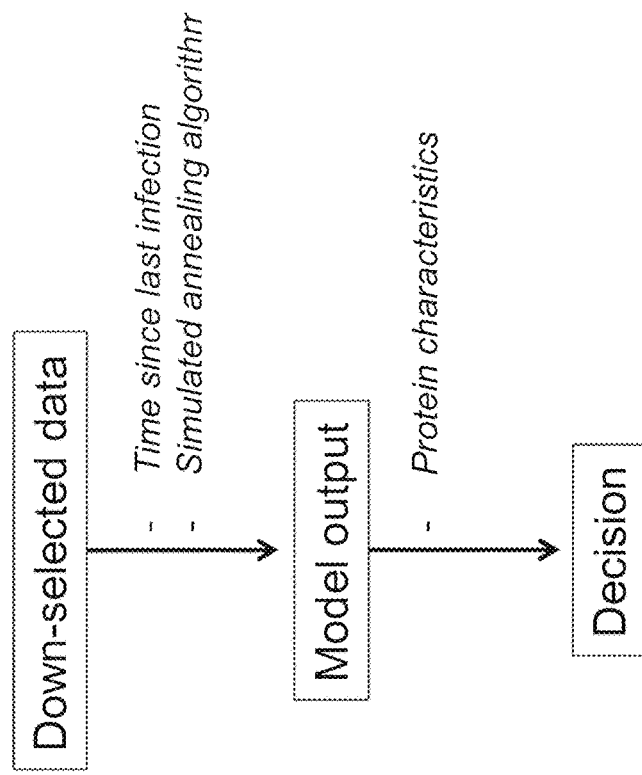
FIG. 2 shows a method for data processing and down-selection of candidate serological markers.
Figure 2:
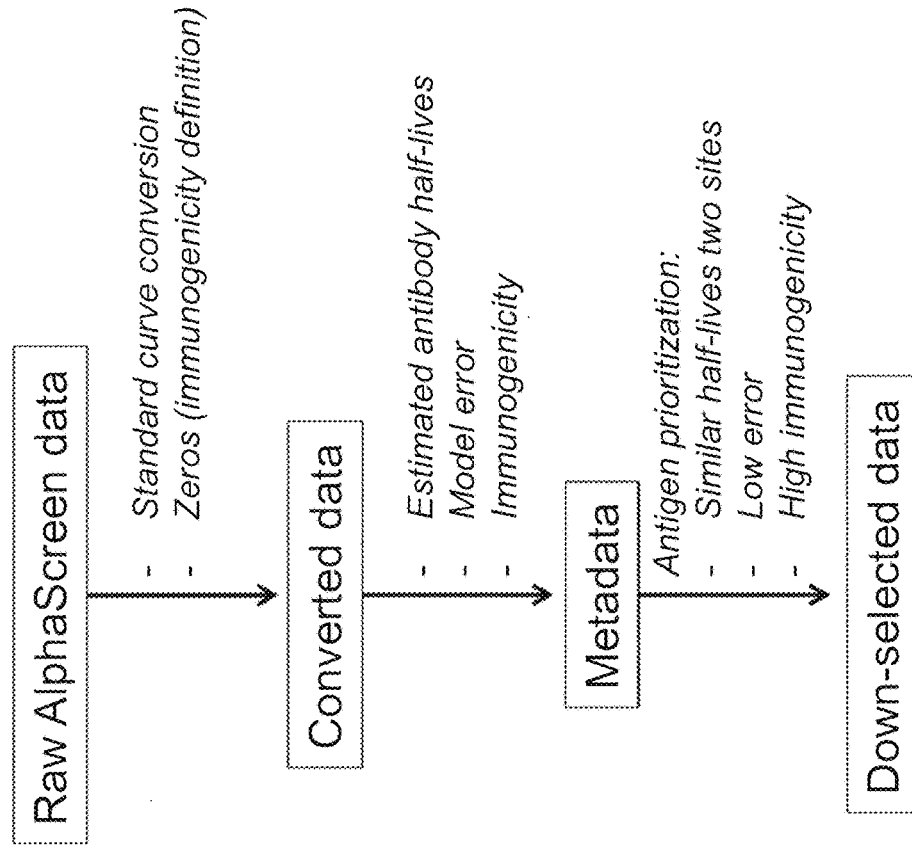

The data were processed and candidate serological markers down-selected following the pipeline shown in FIG. 2. The raw AlphaScreen data was converted based on the plate-specific standard curve, resulting in relative antibody units ranging from 0-400. Using the converted data, seropositivity was defined as a relative antibody unit greater than 0. For proteins that were defined as immunoreactive (more than 10% individuals seropositive at baseline, time of *P. vivax* infection), an estimated antibody half-life was determined using a mixed-effects linear regression model, described in detail below (see Statistical modelling). Using the metadata on immunoreactivity and half-life, an initial round of antigen down-selection was performed, with prioritisation of antigens that had similar estimated half-lives in both the Thai and Brazilian datasets (neither site more than double the other), high levels of seropositivity at baseline (more than 50% individuals seropositive, i.e. relative antibody units above 0), and low levels of error estimated in the model. Three rounds of initial down-selection were performed, resulting in approximately 100 antigens for the next round of model-based down-selection.

The model-based down-selection was performed in two stages: first, by calculating the estimated time since last infection based on antibody levels at 0, 3, 6 and 9 months (and comparing this with the known time since infection), and second, by determining the best combination of antigens for accurately detecting the time since last infection.

In more detail, FIG. 2 shows a pipeline for down-selection of candidate serological markers. As shown in the process of FIG. 2A, antigens were first down-selected based on prioritization of metadata characteristics such as similar levels of estimated antibody longevity in Thailand and Brazil, high levels of immunogenicity at the time of infection and low levels of error estimated in the model. As shown in the process of FIG. 2B, using the initial down-selected antigens, further modelling was performed to identify the optimal combination of antigens able to accurately estimate the time since last infection. A final decision on candidate serological markers was made using output from this modelling and other protein characteristics, as detailed above.

Figure 3:
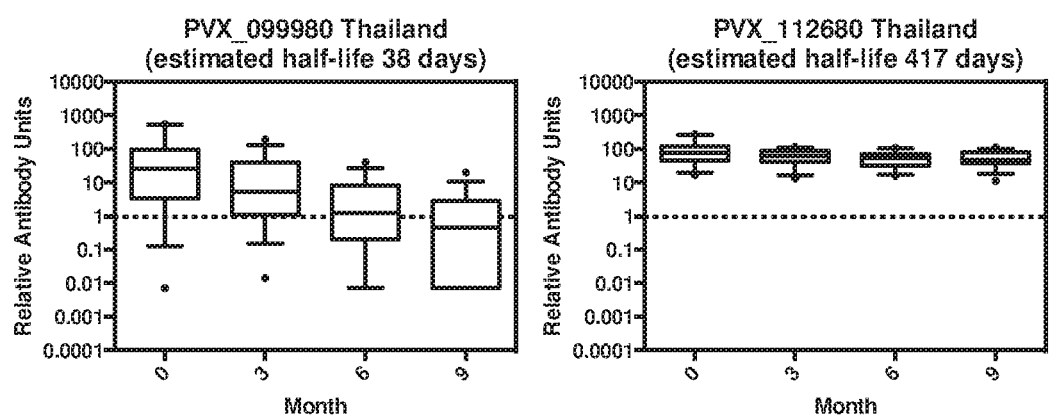
FIG. 3 shows an example of two differing antibody kinetic profiles. Antibody responses at the four time-points measured in the AlphaScreen® assay are shown for two proteins, PVX_099980 and PVX_122680. An arbitrary positivity cut-off is marked at 0.94 (the average of the wheat germ extract control well +6× standard deviation). Data is generated from 32 individuals in Thailand.
Figure 4:
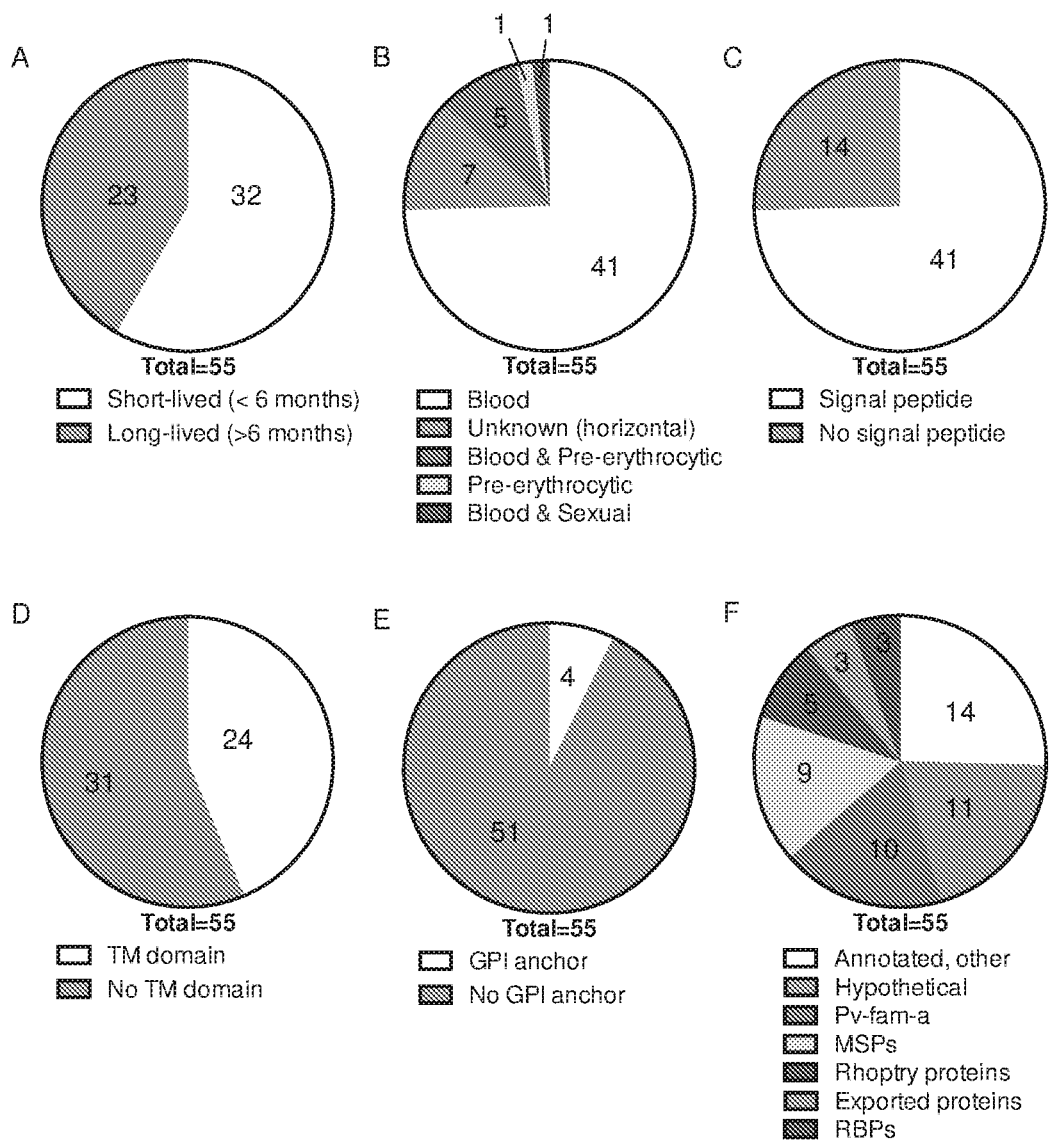
FIG. 4 shows characteristics of the top 55 protein constructs. (A) Length of the estimated antibody half-lives, note for 4 proteins the classification was different between Thailand and Brazil. (B)-(F) Details of protein characteristics as determined by PlasmoDB release 25 or published literature: (B) predicted expression stage, (C) presence of a signal peptide sequence, (D) presence of transmembrane domain/s, (E) presence of a GPI anchor, (F) annotation. TM=transmembrane domains, MSPs=merozoite surface proteins, RBPs=reticulocyte binding proteins.

As expected, different antibody kinetic profiles over 9-months were observed for different proteins (see FIG. 3 for an example). Antigen down-selection was performed as described in detail in the Materials and Methods, essentially by prioritizing antigens with high levels of immunogenicity, similar estimated half-lives between Thailand and Brazil and low levels of error estimated in the model. The initial down-selection was followed by further model-based down selection. The model-based down-selection was used to determine the ability of various proteins to predict the time since last infection, utilizing the same datasets from Thailand and Brazil, and to determine the best combination of proteins to do so successfully (see for example FIG. 20 and its accompanying description). Antigens were excluded from selection if they had less than a 40% probability of inclusion in a 40-antigen panel that was able to accurately determine the time since last infection. Remaining antigens were then ranked according to a high probability of inclusion in a successful 20-antigen panel. When required, ranking in 30 and 40-antigen panels was also considered. Antigens were excluded if they had unfavorable protein production characteristics, such as low-yield in the small-scale WGCF expression or presence of aggregates. Three rounds of selection were performed: the first resulted in 12 proteins, the second in a further 12, and the third in an additional 31 candidates. A final list of 55 protein constructs (53 unique proteins) representing candidate serological markers of recent exposure to *P. vivax* infection was generated (two fragments were included from two different antigens). Characteristics of these proteins are highlighted in FIG. 4.

Validation of Candidate Serological Markers.

Geographical validation (that is validation across different regions) was performed as follows.

Figure 5:
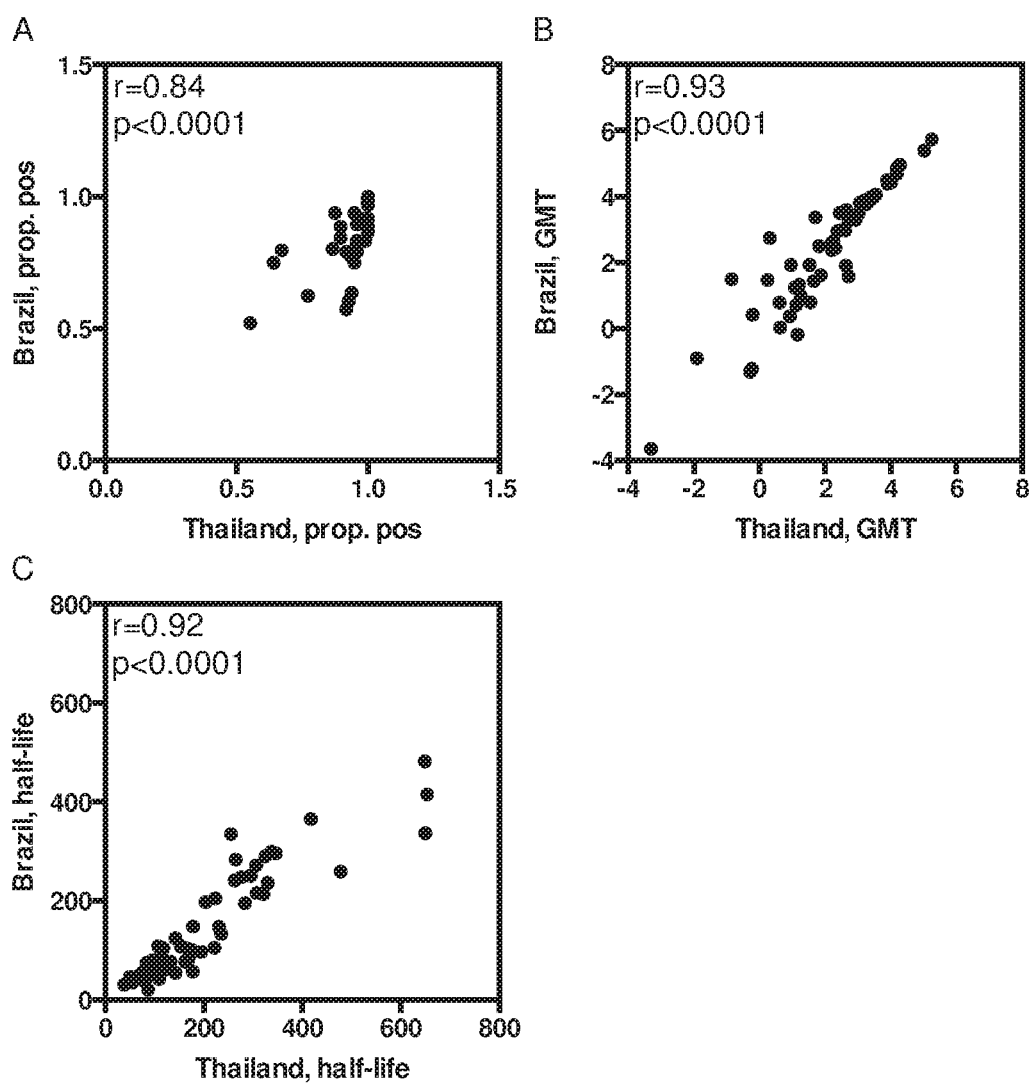
FIG. 5 shows correlation between antibody measurements in Thailand and Brazil. Correlation of data from the antigen discovery study generated using the AlphaScreen® assay. Correlations are shown for the 55 down-selected candidate serological markers. (A) Comparison of the proportion of individuals defined as positive at time of *P. vivax* infection (antibody value above the lower point of the standard curve, i.e. 0). (B) Comparison of the geometric mean antibody titers (GMT). (C) Comparison of the estimated antibody half-lives. Spearman correlation coefficients, r, are shown. Data was generated from 32 individuals in Thailand and 33 in Brazil.

The down-selected markers were chosen based on antibody data from individuals in Thailand, Brazil and the Solomon Islands, three discrete geographical areas. Despite this, there was a strong correlation between the antibody responses measured, in terms of both immunogenicity (seropositivity rates) and antibody level at time of *P. vivax* infection, as well as the estimated antibody half-lives calculated from consecutive time-points. This is shown in FIG. 5.

Validation in association with recent and past infection was performed as well.

Figure 6A:
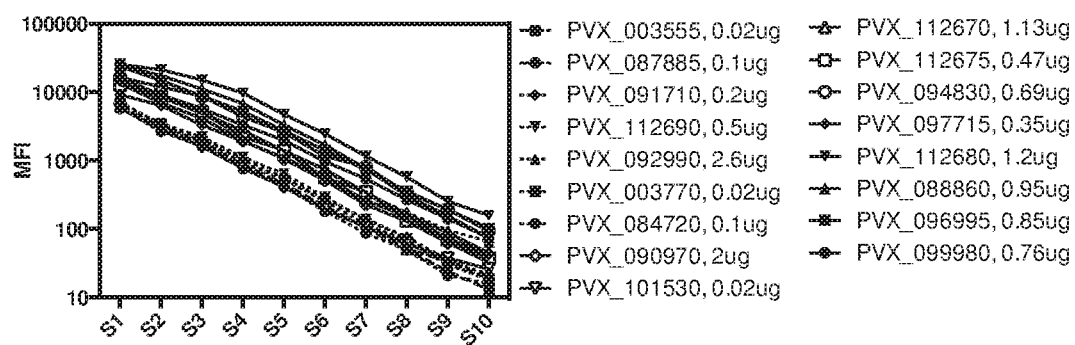
FIG. 6A shows optimization of Luminex® bead-array assay for the first 17 proteins. Log-linear standard curves were achieved for all proteins, using the amounts of protein shown for one bulk reaction of 500 μl beads.
Figure 6F:
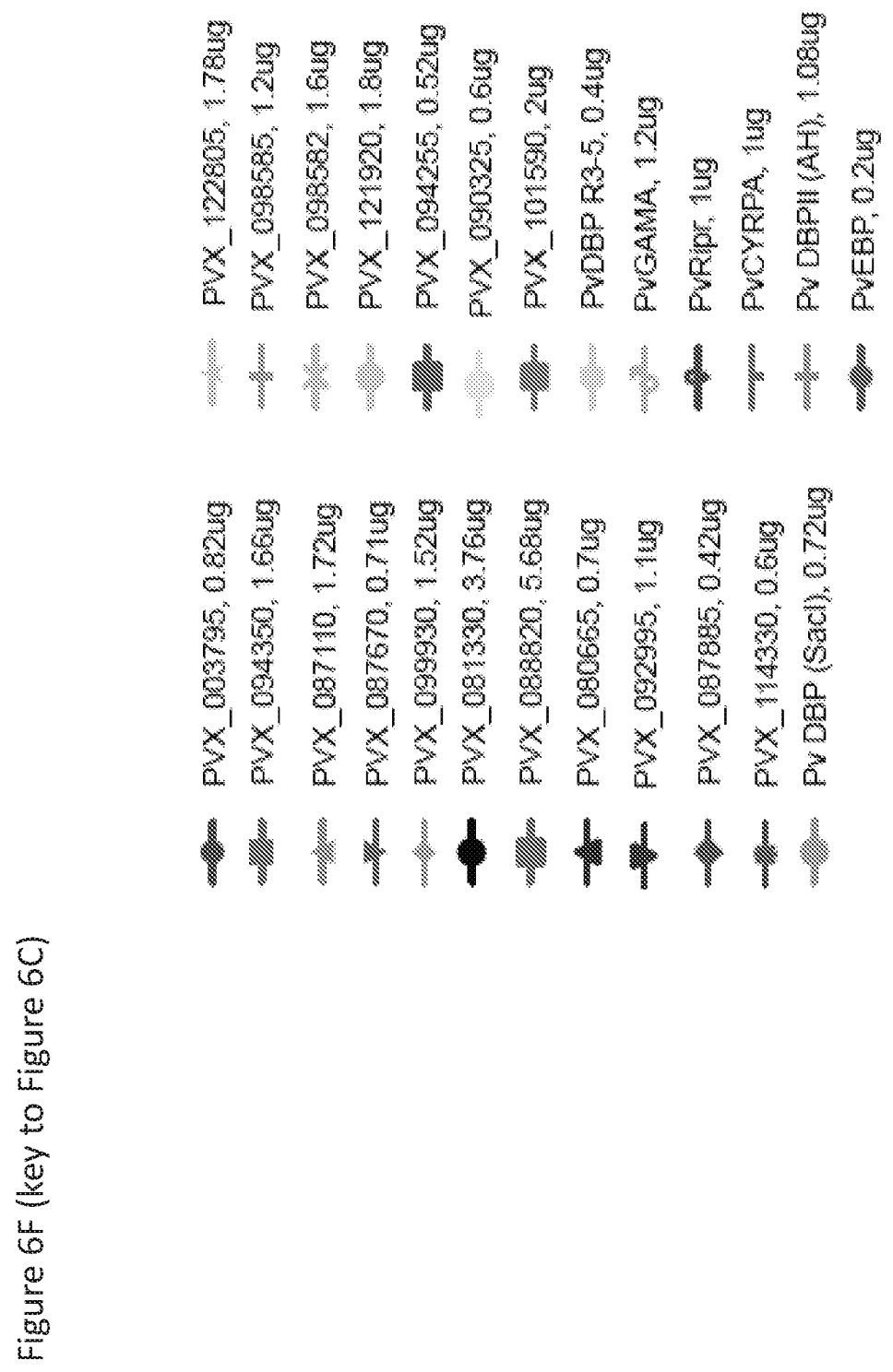
Figure 22:
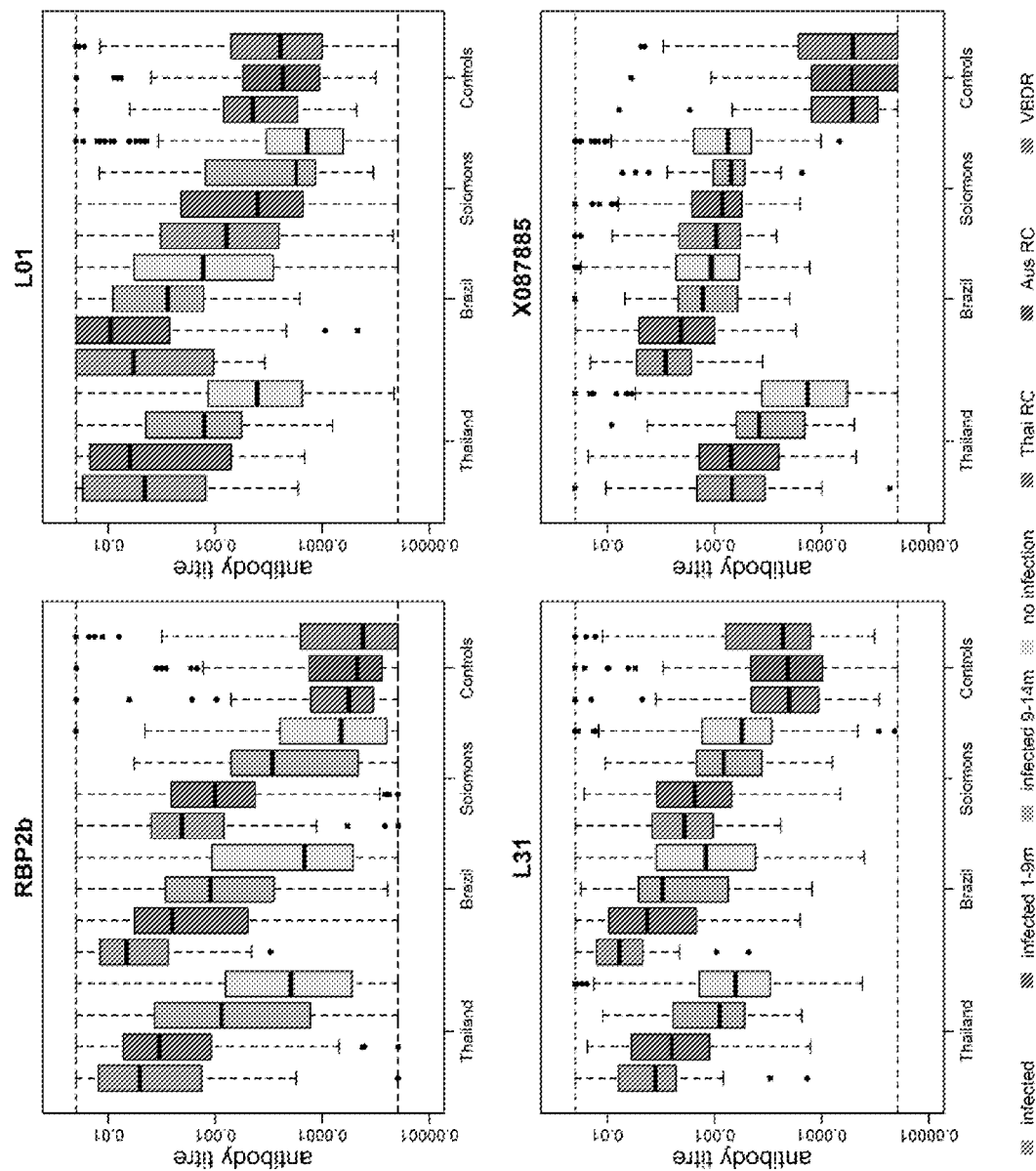
FIG. 22 shows measured antibody titers to four P. vivax antigens from Thailand, Brazil and the Solomon Islands, and from three panels of negative controls. The box plots show the median, interquartile range and 95% range of measured antibody titers. The horizontal dashed lines represent the lower and upper limits of detection.

The Luminex® bead-array assay has been successfully established for 40 of the 55 proteins identified in the antigen discovery study (FIG. 6) as well as for the additional 25 proteins (65 total). Plasma samples from three observational cohorts (final time-point) have been screened against these 65 proteins, Thai (n=829), Brazilian (n=925) and Solomon Islands (n=751), in addition to 3 sets of non-exposed (malaria) controls (two panels from Australia and one panel from Thailand). An example of the responses in these cohorts, with relation to time since last infection, to 4 of 65 proteins is shown in FIG. 22, described with regard to Example 4 below.

Figure 7:
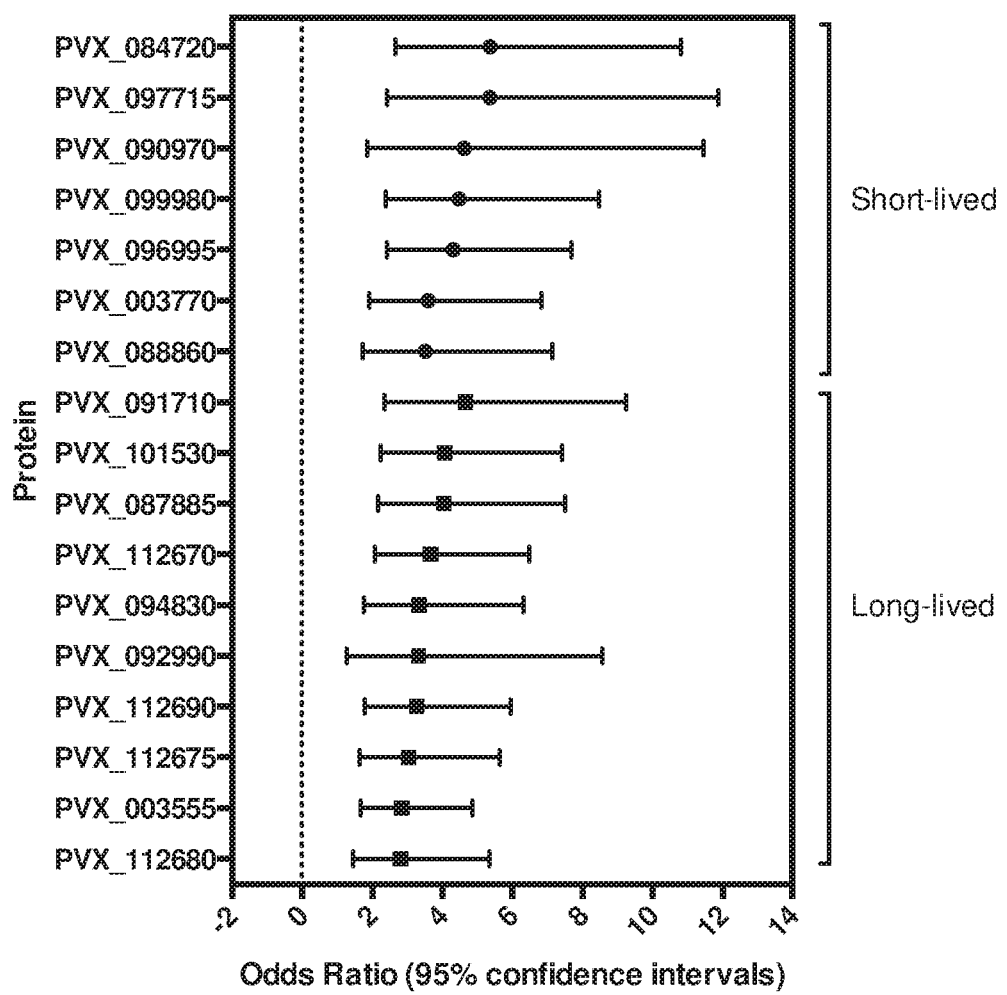
FIG. 7 shows the association of antibody levels with current *P. vivax* infections in the Thai validation cohort. Antibody responses were measured at the last time-point of the Thai cohort against the first 17 proteins assessed, using the Luminex® bead-array assay. The association between antibody responses and current infection was assessed using a logistic regression model, adjusting for age, sex and occupation. Odds ratios are shown, with 95% confidence intervals. Associations for all antibodies were significant ($p<0.05$). The estimate of antibody half-life shown is based on the antigen discovery dataset (AlphaScreen®).
Figure 8:
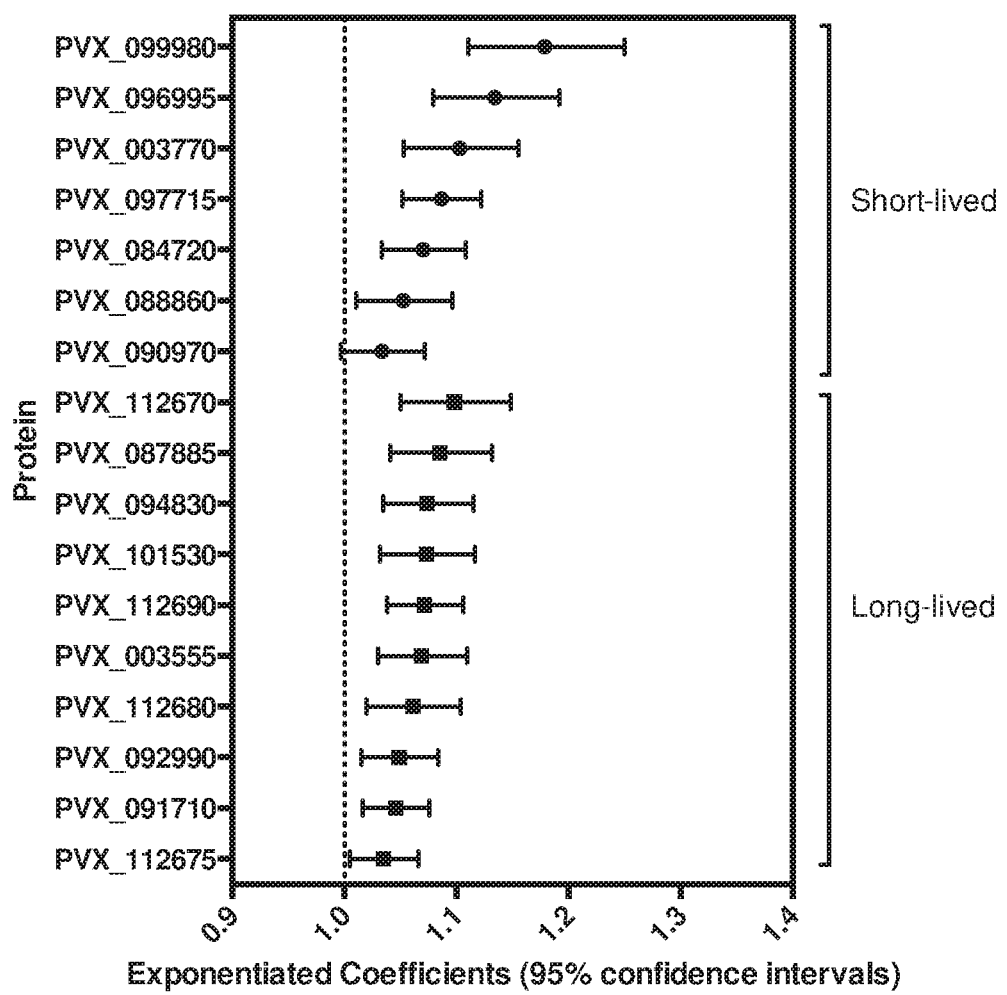
FIG. 8 shows association of antibody levels with past *P. vivax* exposure in the Thai validation cohort. Antibody responses were measured at the last time-point of the Thai cohort against the first 17 proteins assessed, using the Luminex® bead-array assay. The association between antibody responses and total exposure over the past year was assessed using a generalised linear model, adjusting for age, sex, occupation and current infection status. Exponentiated coefficients are shown, with 95% confidence intervals. Associations for all antibodies, except PVX_09070, were significant ($p<0.05$). The estimate of antibody half-life shown is based on the antigen discovery dataset (AlphaScreen®).

In the Thai cohort, antibody levels measured to all 17 proteins, selected for performing the first set of tests, were strongly associated with the presence of current *P. vivax* infections (logistic regression model, odds ratios of 2.8-5.4, p<0.05) (FIG. 7). In addition, antibody levels to 16 of 17 proteins at the last visit of the cohort study were positively and significantly associated with past exposure to *P. vivax* infections based on PCR results during the yearlong assessment period (measured as the molecular force of blood-stage infection, (molFOI) (generalised linear model, exponentiated coefficients of 1.03-1.18, p<0.05) (FIG. 8). The exception was for PVX_090970, exponentiated coefficient 1.03, p=0.073.

Figure 9:
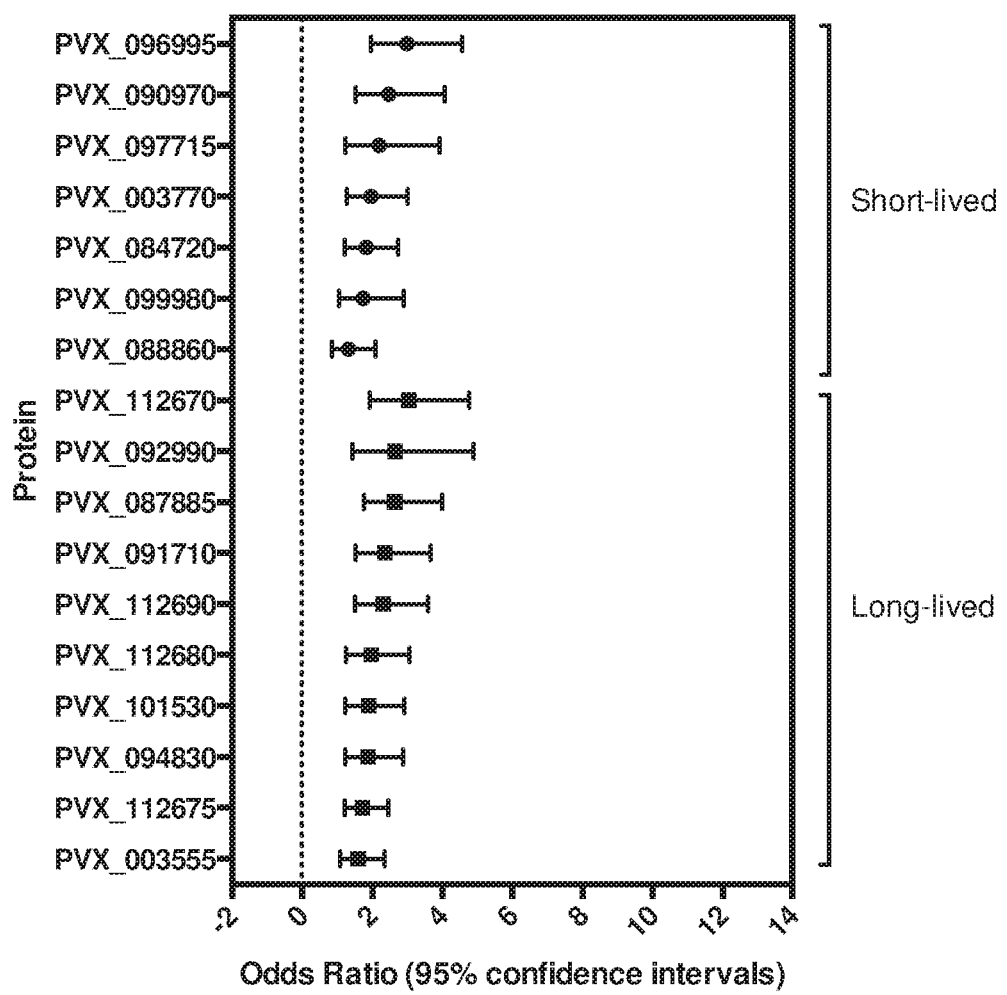
FIG. 9 shows the association of antibody levels with current *P. vivax* infections in the Brazilian validation cohort. Antibody responses were measured at the last time-point of the Brazilian cohort against the first 17 proteins assessed, using the Luminex® bead-array assay. The association between antibody responses and current infection was assessed using a logistic regression model, adjusting for age, sex and occupation. Odds ratios are shown, with 95% confidence intervals. Associations for all antibodies, except PVX_088860, were significant ($p<0.05$). The estimate of antibody half-life shown is based on the antigen discovery dataset (AlphaScreen®).
Figure 10:
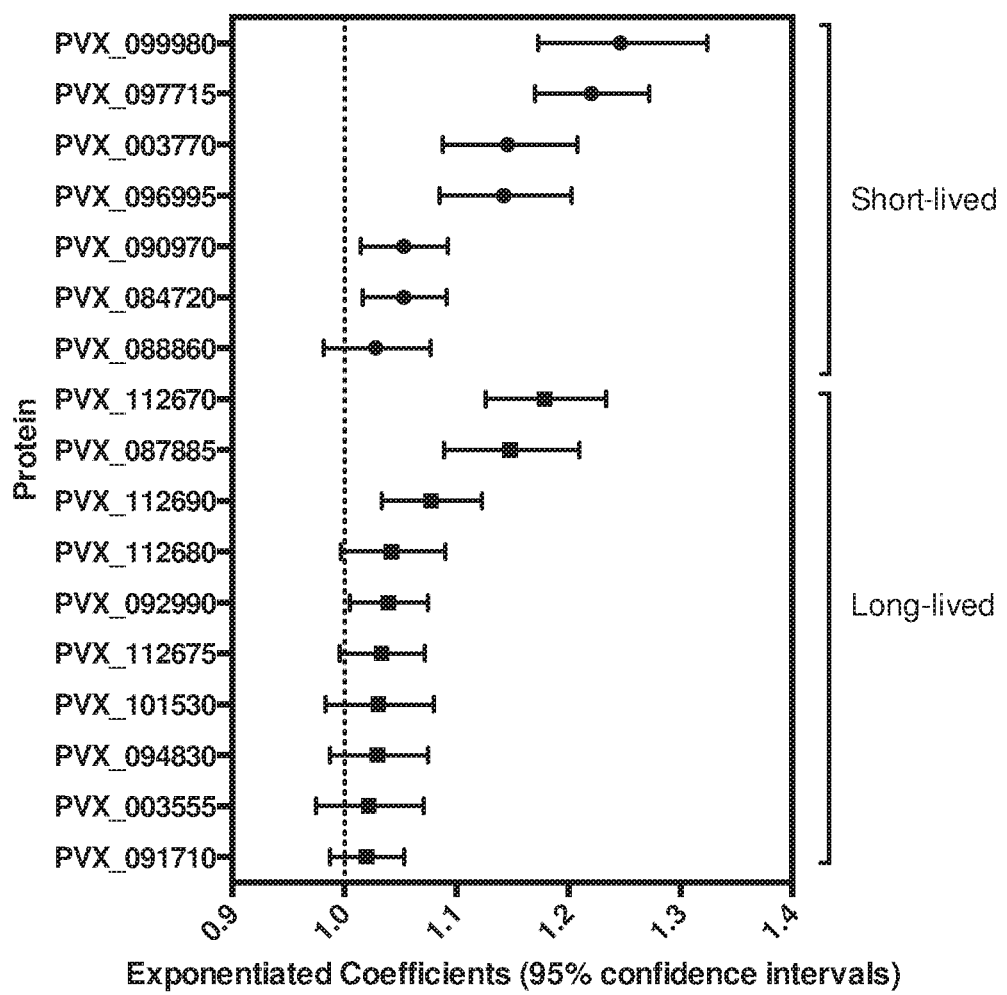
FIG. 10 shows the association of antibody levels with past *P. vivax* exposure in the Brazilian validation cohort. Antibody responses were measured at the last time-point of the Brazilian cohort against the first 17 proteins assessed, using the Luminex® bead-array assay. The association between antibody responses and total exposure over the past year was assessed using a generalised linear model, adjusting for age, sex, occupation and current infection status. Exponentiated coefficients are shown, with 95% confidence intervals. Associations for 10 of the 17 antibodies were significant ($p<0.05$). The estimate of antibody half-life shown is based on the antigen discovery dataset (AlphaScreen®).

In the Brazilian cohort, the effect size, overall, was not as great as for Thailand. Nevertheless, antibody levels to 16 of 17 proteins were strongly associated with the presence of current *P. vivax* infections (logistic regression model, odds ratios of 1.59-3.04, p<0.05) (FIG. 9). The exception was for PVX_088860, with an odds ratio of 1.33 (p=0.21). Antibody levels to 10 of 17 proteins at the last visit of the cohort were positively and significantly associated with past exposure to *P. vivax* (molFOI) (generalised linear model, exponentiated coefficients of 1.04-1.18, p<0.05) (FIG. 10). Of the antibodies with estimated 'short' half-lives (less than 6 months), there was one exception, PVX_088860, with an exponentiated coefficient of 1.03 (p=0.24). Of the antibodies with estimated 'long' half-lives (more than 6 months), 6 of 10 were not associated with past exposure (exponentiated coefficients of 1.02-1.04, p>0.05).

Various statistical methods can be used to test the association between antibody level to certain proteins and past (recent) or current exposure to *P. vivax* infections. For most proteins, there was a clear significant association with both past and current *P. vivax* infections, which is promising for the use of these antigens as serological markers. For others, there was a trend towards an association, which did not reach significance. In a final test, it will be an antibody signature that is used for classification of recent infection, made up of antibody responses to a multitude of proteins. Therefore the lack of significance for some individual proteins does not imply that they will not be useful in the final classification algorithm.

These analyses show that 16 of 17 proteins generate antibodies that are strongly associated with both current infections and 10 of 17 with past *P. vivax* exposure in both Thailand and Brazil, demonstrating that a majority of these antigens have the potential to detect both concurrent and recent past P: *vivax* infections.

REFERENCES

1. Longley R J, Reyes-Sandoval A, Montoya-Diaz E, Dunachie S, Kumpitak C, Nguitragool W, Mueller I, Sattabongkot J. 2015. Acquisition and longevity of antibodies to *Plasmodium vivax* pre-erythrocytic antigens in western Thailand. Clin Vaccine Immunol doi:10.1128/cvi.00501-15.
2. Wampfler R, Mwingira F, Javati S, Robinson L, Betuela I, Siba P, Beck H P, Mueller I, Felger I. 2013. Strategies for detection of *Plasmodium* species gametocytes. PLoS One 8:e76316.
3. Rosanas-Urgell A, Mueller D, Betuela I, Barnadas C, Iga J, Zimmerman P A, del Portillo H A, Siba P, Mueller I, Felger I. 2010. Comparison of diagnostic methods for the detection and quantification of the four sympatric *Plasmodium* species in field samples from Papua New Guinea. Malar J 9:361.
4. Lu F, Li J, Wang B, Cheng Y, Kong D H, Cui L, Ha K S, Sattabongkot J, Tsuboi T, Han E T. 2014. Profiling the humoral immune responses to *Plasmodium vivax* infection and identification of candidate immunogenic rhoptry-associated membrane antigen (RAMA). J Proteomics 102:66-82.
5. Sawasaki T, Ogasawara T, Morishita R, Endo Y. 2002. A cell-free protein synthesis system for high-throughput proteomics. Proc Natl Acad Sci USA 99:14652-14657.
6. Sawasaki T, Hasegawa Y, Tsuchimochi M, Kamura N, Ogasawara T, Kuroita T, Endo Y. 2002. A bilayer cell-free protein synthesis system for high-throughput screening of gene products. FEBS Lett 514:102-105.
7. Sawasaki T, Morishita R, Gouda M D, Endo Y. 2007. Methods for high-throughput materialization of genetic information based on wheat germ cell-free expression system.
8. Sawasaki T, Gouda M D, Kawasaki T, Tsuboi T, Tozawa Y, Takai K, Endo Y. 2005. The wheat germ cell-free expression system: methods for high-throughput materialization of genetic information. Methods Mol Biol 310:131-144.

9. Matsuoka K, Komori H, Nose M, Endo Y, Sawasaki T. 2010. Simple screening method for autoantigen proteins using the N-terminal biotinylated protein library produced by wheat cell-free synthesis. J Proteome Res 9:4264-4273.
10. Franca C T, Hostetler J B, Sharma S, White M T, Lin E, Kiniboro B, Waltmann A, Darcy A W, Li Wai Suen C S, Siba P, King C L, Rayner J C, Fairhurst R M, Mueller I. 2016. An Antibody Screen of a *Plasmodium vivax* Antigen Library Identifies Novel Merozoite Proteins Associated with Clinical Protection. PLoS Negl Trop Dis 10:e0004639.
11. Team RC. 2015. R: A language and environment for statistical computing, R Foundation for Statistical Computing, Vienna, Austria. https://www.R-projects.org/.

Example 2—Illustrative Diagnostic Test

A diagnostic test according to at least some embodiments of the present invention could optionally include any of bead-based assays previously described (AlphaScreen® assay and multiplexed assay using Luminex® technology).

In addition to the ability to measure antibody responses using the bead-based assays previously described, other methods could also be used, including, but not limited to, the enzyme linked immunosorbent assay (ELISA) (1), protein microarray (2) and the luminescence immunoprecipitation system (LIPs) (3).

Antibody measurements via ELISA rely on coating of specialised plates with the required antigen, followed by incubation with the plasma sample of interest. IgG levels are detected by incubation with a conjugated secondary antibody followed by substrate, for example a horseradish peroxidase-conjugated anti-IgG and ABTS [2,2=-azinobis (3-ethylbenzothiazo-line-6-sulfonic acid)-diammonium salt].

Protein microarray platforms offer a high-throughput system for measuring antibody responses. Proteins of interest are spotted onto microarray chips then probed with plasma samples. The arrays are then further incubated with a labeled anti-immunoglobulin and analysed using a microarray scanner.

The LIPs assay utilizes cell lysate containing the expressed antigen fused to a *Renilla* luciferase reporter protein. Plasma samples are incubated with a defined amount of this lysate, with protein A/G beads used to capture the antibody. The amount of antibody-bound antigen-luciferase is measured by the addition of a coelenterazine substrate, and the light emitted measured using a luminometer.

Any of these assays may optionally be combined with a reader and if necessary, an analyzer device, to form an apparatus according to at least some embodiments of the present invention. The reader would read the test results and the analyzer would then analyze them according to any of the previously described algorithms and software.

REFERENCES

1. Longley R J, Reyes-Sandoval A, Montoya-Diaz E, Dunachie S, Kumpitak C, Nguitragool W, Mueller I, Sattabongkot J. 2015. Acquisition and longevity of antibodies to *Plasmodium vivax* pre-erythrocytic antigens in western Thailand. Clin Vaccine Immunol doi:10.1128/cvi.00501-15.
2. Finney O C, Danziger S A, Molina D M, Vignali M, Takagi A, Ji M, Stanisic D I, Siba P M, Liang X, Aitchison J D, Mueller I, Gardner M J, Wang R. 2014. Predicting anti-disease immunity using proteome arrays and sera from children naturally exposed to malaria. Mol Cell Proteomics doi:10.1074/mcp.M113.036632.
3. Longley R J, Salman A M, Cottingham M G, Ewer K, Janse C J, Khan S M, Spencer A J, Hill AV. 2015. Comparative assessment of vaccine vectors encoding ten malaria antigens identifies two protective liver-stage candidates. Sci Rep 5:11820.

Example 3—Illustrative Software Process for Diagnosis

This Examples relates to processes for estimation of time since last *P. vivax* infection using measurements of antibody titers, which may optionally be provided through software.

a. Section 1 relates to calibration and validation of the input data, as well as non-limiting examples of models and algorithms which may optionally be used to analyze the data. Section 2 provides additional information on the algorithms utilized.

Section 1—Overview of Calibration Data and Algorithms

Calibration and Validation Data

Both the down-selection of antigens for incorporation into a diagnostic test, and the calibration and validation of algorithms for providing classifications of recent *P. vivax* infection given blood samples, will depend on the available epidemiological data. Data will be required on the demography of the populations under investigation, serological measurements, and monitoring for parasitemia and clinical episodes. Table 1 provides an overview of the data sets that are used.

Algorithm Inputs and Outputs

A diagnostic test will take a blood sample as input and provide data to inform a decision making process as output. The type of data generated will depend on the technological specifications of the diagnostic platform. The outputted data can then be used as input for some algorithm to inform a decision making process. The following factors need to be taken into consideration when defining the inputs and outputs of a decision making algorithm:

1) Number of antigens

The number of antigens to which antibodies can be measured will be restricted by the technological specifications of the diagnostic platform under consideration. Measurement of antigens to a greater number of antibodies will in theory provide more data as input for an algorithm, potentially increasing predictive power.

TABLE 1

Overview of data sets used for antigen down-selection and algorithm calibration and validation.

| | demographic data | | | serological data | | | parasitological data | | |
|---|---|---|---|---|---|---|---|---|---|
| region | number | age | number of antigens | samples per person | platform | samples per person | PCR positive | clinical |
| Antigen down-selection | | | | | | | | | |
| Thailand | 32 | 29 (7, 71) | 342 | 4 | AlphaScreen | 17 | enrolment | enrolment |
| Brazil | 33 | | 342 | 4 | AlphaScreen | 17 | enrolment | enrolment |
| Algorithm calibration and validation | | | | | | | | | |
| Thailand | 829 | 25 (2, 79) | 65 | 1 | Luminex | 14 | 97/829 | 25/829 |
| Brazil | 928 | 25 (0, 102) | 65 | 1 | Luminex | 13 | 236/928 | 80/928 |
| Solomon Islands | 860 | 5.5 (0.5, 12.7) | 65 | 1 | Luminex | 11 | 294/860 | 35/860 |
| Negative controls | | | | | | | | | |
| Australian Red Cross | 100 | 52 (18, 77) | 65 | 1 | Luminex | 1 | no | no |
| Thai Red Cross | 72 | | 65 | 1 | Luminex | 1 | no | no |
| Australian donors | 102 | 39 (19, 68) | 65 | 1 | Luminex | 1 | no | no |

2) Measurement of antibody levels

The levels of antibody in a blood-sample can be measured and summarised in a variety of ways.

a) Continuous measurement

A continuous measurement that has a monotonic relationship with antibody titer. It can be compared with a titration curve to produce an estimate of antibody titer.

b) Binary classification

Assesses whether antibody levels are greater or less than some threshold.

c) Categorical classification

Assigns antibody levels to one of a set of pre-defined categories, e.g. low, medium, high. A categorical classification can be generated via a series of binary classifications.

3) Decision making requirements

The result of a diagnostic test and accompanying algorithm can be used to inform a decision on whether or not to treat, as well as to inform surveillance systems.

a) Classification of recent infection

A binary output corresponding to whether or not there was an infection with *P. vivax* blood-stage parasites in the past 9 months. This can be presented as a binary classification, or as a probabilistic classification. This can be adjusted for a range of different temporal thresholds: 3 months, 6 months, 12 months, 18 months.

b) Estimation of time since last infection

An estimate of the time since last *P. vivax* blood-stage infection—depending on the available calibration data the time since last infection can be defined either as the time since last PCR-detectable blood-stage parasitemia, or as the time since last mosquito bite. Time since last infection can be estimated continuously or categorically. Concurrent estimation of uncertainty will be important.

c) Medium-term serological exposure

Given sufficient calibration data, the algorithms described here can be modified to provide extended measurements of an individual's recent to medium term *P. vivax* exposure, e.g. how many infections in the last 2 years?

4) Computational and analytic capabilities

An algorithm's complexity will be restricted by the analytic resources accompanying the diagnostic platform. In a low resource setting, we may require a decision to be made given a sequence of binary outputs from a rapid diagnostic test (sero-negative or sero-positive) without any access to computational devices. At the other extreme, in a high resource setting we may have continuous measurements of antibodies to multiple antigens accompanied with algorithms encoded in computational software.

a) No access to computational devices. Algorithms implemented via 'easy to follow' instructions on paper charts.

b) Algorithm implemented in software that can be installed on a portable computation device such as a smartphone or tablet. May require the manual entry of output from the diagnostic platform.

c) Computational software with encoded algorithms integrated within the diagnostic platform.

Algorithms

There is a wide range of algorithms for classification and regression in the statistical inference and machine learning literature (Hastie, Tibshirani & Friedman[3]). A classification algorithm can take a diverse range of input data and provide some binary or categorical classification as output. A regression algorithm can take similar input, but provides a continuous prediction as output. Table 2 provides an overview of some algorithms that can be used for classification problems. Four of these have been regularly described in the statistical learning literature: linear discriminant analysis (LDA); quadratic discriminant analysis (QDA); decision trees; and random forests. One of these has been specifically developed for the application at hand: combined antibody dynamics (CAD). The candidate algorithms are classified according to a number of factors. The degree of transparency describes the straightforwardness and reproducibility of an algorithm. A decision tree is considered very transparent as it can be followed by a moderately well-informed individual, as it requires answering a sequence of questions in response to measured data. This simple, logical structure makes decision trees particularly popular with doctors. Because of the transparency and ease of use, decision trees are sometimes referred to as glass box algorithms. At the other extreme, algorithms such as random forests are considered to be black box algorithms where there may be no obvious association between the inputs and outputs.

where $\mu_k$, and $\Sigma_k$ are the mean and p*p covariance matrix of the training data of each class.

In the case of LDA, all classes are assumed to have the same covariance matrix ($\Sigma_{new}=\Sigma_{old}=\Sigma$), and the classification between new and old infections can be evaluated via the log ratio:

TABLE 2

Overview of algorithms suitable for classification of recent *P. vivax* infection or estimation of time since last *P. vivax* infection.

| algorithm | data needs | transparent | stochastic | time predicted | comments |
|---|---|---|---|---|---|
| linear discriminant analysis (LDA) | continuous | + | no | no | The assumption of common covariance for each category may be too restrictive. |
| quadratic discriminant analysis (QDA) | continuous | + | no | no; categorical estimation possible, incorporation of uncertainty challenging | There is an approximate equivalence between the QDA classification space and that predicted by the CAD algorithm. |
| decision trees | binary | +++ | no | no; possible via regression trees or categorical estimation | Very transparent and simple to implement in low technology settings. |
| random forests | continuous | -- | yes | no; possible via regression trees or categorical estimation | Potentially very powerful but requires considerable computational resources. |
| combined antibody dynamics (CAD) | continuous | ++ | no | yes; with uncertainty | A biologically motivated representation of antibodies following infection; prior information on decay rates can be incorporated. |

Section 2—Expanded Details of Algorithms

Here we provide an overview of classification algorithms such as LDA, QDA, decision trees and random forests which have already been described extensively elsewhere (Hastie, Tibshirani & Friedman[3]). We also provide an extended description of the combined antibody dynamics (CAD) algorithm.

Linear and Quadratic Discriminant Analysis

The theory of linear discriminant analysis (LDA) and quadratic discriminant analysis (QDA) is described in detail in "The Elements of Statistical Learning: Data Mining, Inference and Prediction" by Hastie, Tibshirani & Friedman[6]. We provide a brief overview of how these methods may be applied. A key assumption for LDA and QDA classification algorithms is that individuals who have similar antibody titers are likely to have the same classification. It is convenient to compare individuals with different antibody profiles via Euclidean distance of log antibody titers. An LDA or QDA classifier can be implemented by fitting multivariate Gaussian distributions to the clusters of data points representing 'old' and 'new' infections. Assume we have measurements of p antibodies. Denote $k \in \{new, old\}$ to represent the classes of training individuals with new and old infections. These can be modelled as multivariate Gaussians:

$$f_k(x) = \frac{1}{(2\pi)^{p/2}|\Sigma_k|^{1/2}} e^{-\frac{1}{2}(x-\mu_k)^T \Sigma_k^{-1}(x-\mu_k)}$$

$$\log\left(\frac{P(new|X=x)}{P(old|X=x)}\right) = -\frac{1}{2}(\mu_{new}+\mu_{old})^T \Sigma^{-1}(\mu_{new}-\mu_{old}) + x^T \Sigma^{-1}(\mu_{new}-\mu_{old})$$

which is linear in x. The two categories are therefore separated by a hyperplane in p-dimensional space.

In QDA, the restriction that $\Sigma_{new}=\Sigma_{old}=\Sigma$ is relaxed and it can be shown that the classification boundary is described by a conic section in p-dimensional space.

LDA and QDA have consistently been shown to provide robust classification for a wide range of problems. The predictive power of these algorithms can be assessed through cross-validation whereby the data is split into training and testing data sets. The algorithm is calibrated using the training data set and subsequently validated using the test data set. An important method for assessing an algorithm's predictive power is to evaluate the sensitivity and specificity. In this context, we define sensitivity to be the proportion of recent infections correctly classified as recent infections, and we define specificity to be the proportion of old infections correctly classified as old infections.

Figure 25:
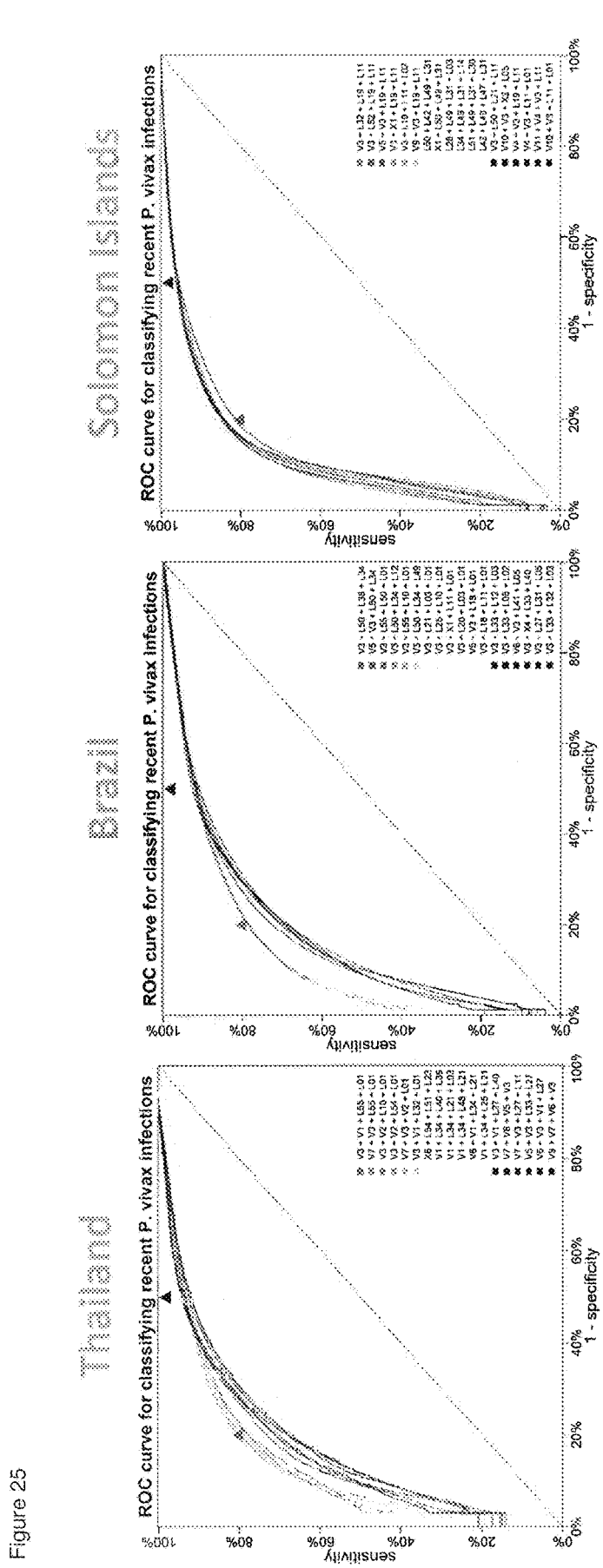
FIG. 25 shows cross-validated Receiver Operating Characteristic (ROC) curves from linear discriminant analysis (LDA) classifiers trained and tested using combinations of four antigens from Thailand, Brazil and The Solomon Islands.

A receiver operating characteristic (ROC) curve allows for detailed investigation of the association between sensitivity and specificity. At one extreme, we could obtain 100% sensitivity and 0% specificity by simply classifying all blood samples as new infections. At the other extreme, we could obtain 100% specificity and 0% sensitivity by classifying all blood samples as old infections. FIG. 25 shows ROC curves describing the classification performance of LDA algorithms for combinations of 4 antigens in Thailand, Brazil and the Solomon Islands.

Decision Trees and Random Forests

Tree-based algorithms partition the space spanned by the data into a set of rectangles with a unique classification applied to each rectangle. Similarly to the LDA and QDA classification algorithms, a great deal of theoretical information is supplied in the book "The Elements of Statistical Learning: Data Mining, Inference and Prediction".

There are several powerful methods for extending decision tree classifiers including bagging (bootstrapp aggregating), boosting and random forests3. These methods can lead to substantially improved classifiers but typically require more computation and more data. In addition to providing powerful classifiers, these algorithms can provide important diagnostics for investigating the association between the signal in the input and the output.

Figure 23A:
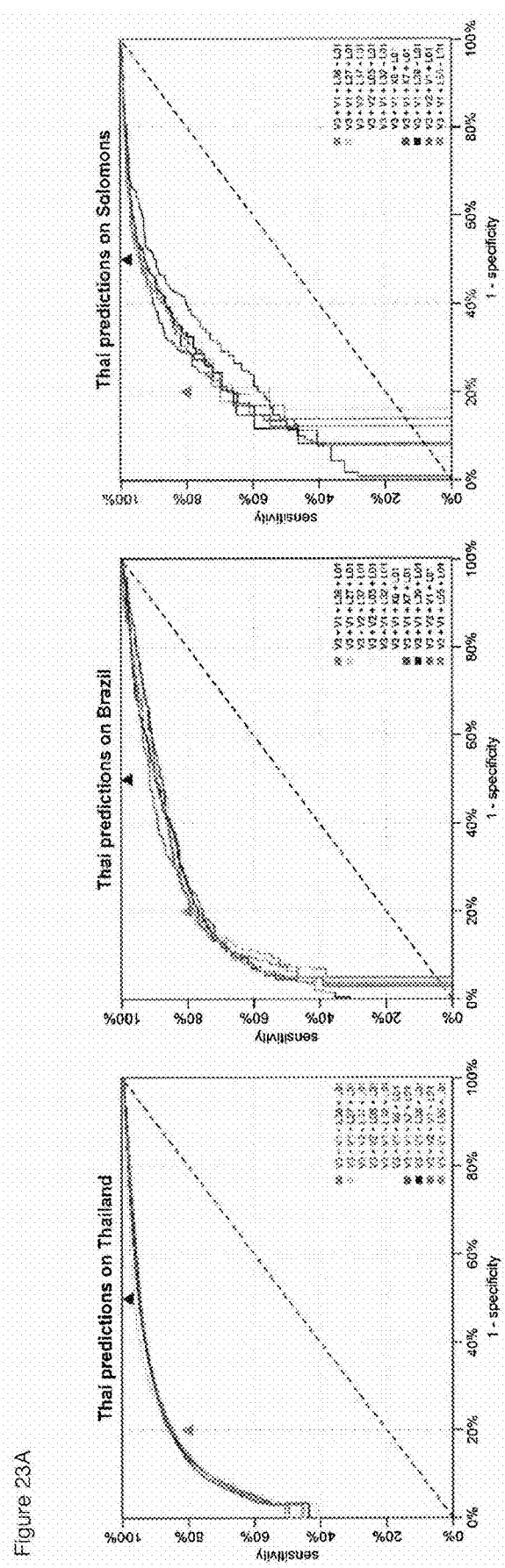
FIGS. 23A-23C show an overview of cross-validated random forests classification algorithms. The classifiers were trained on data from either Thailand, Brazil or The Solomon Islands.
Figure 23B:
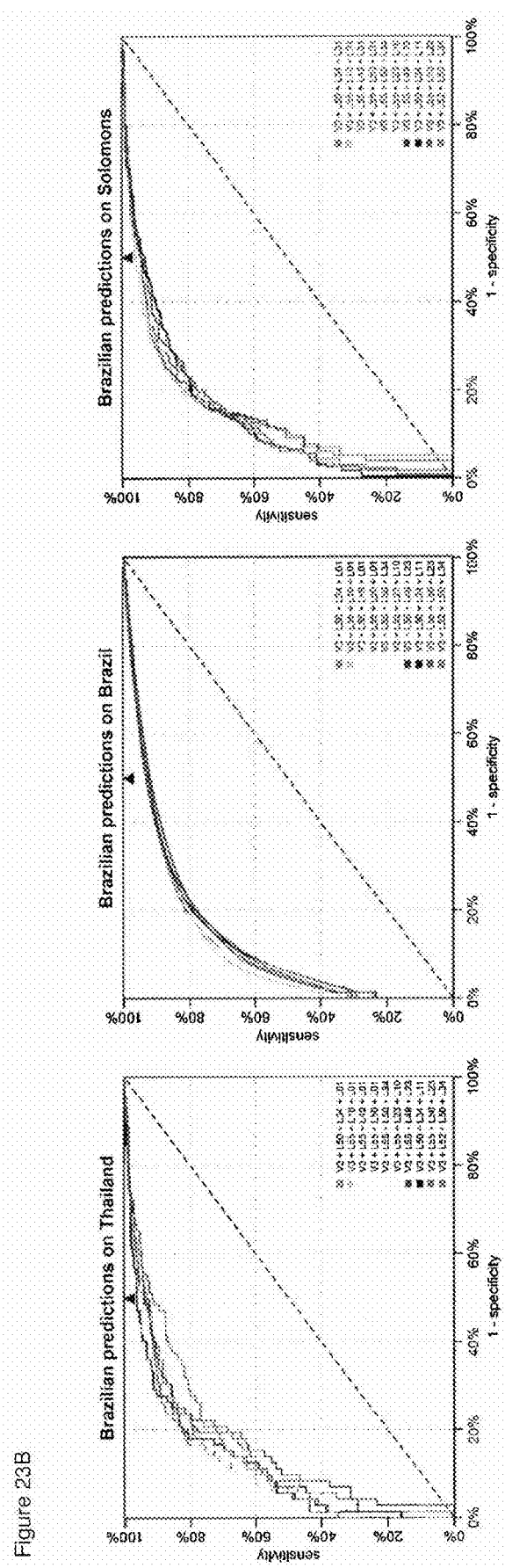
Figure 23C:
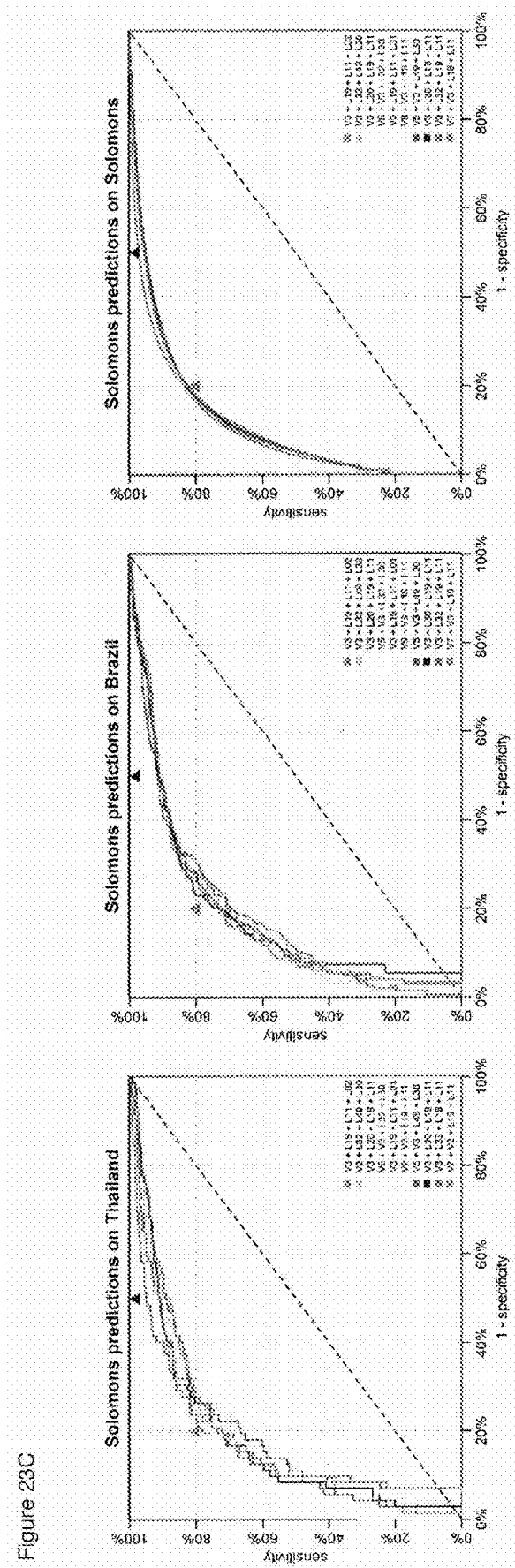

FIG. 23A-C shows the ROC curves for cross-validated random forests classifiers applied to data sets from Thailand, Brazil and Solomon Islands. Notably, when the training and testing data sets are from the same region, there are many combinations of four antigens that allow sensitivity >80% and specificity >80%. When training and testing data sets are from different regions, it was still possible to obtain combinations of four antigens with sensitivity >80% and specificity >80%.

Modelling of Antibody Dynamics

Figure 13:
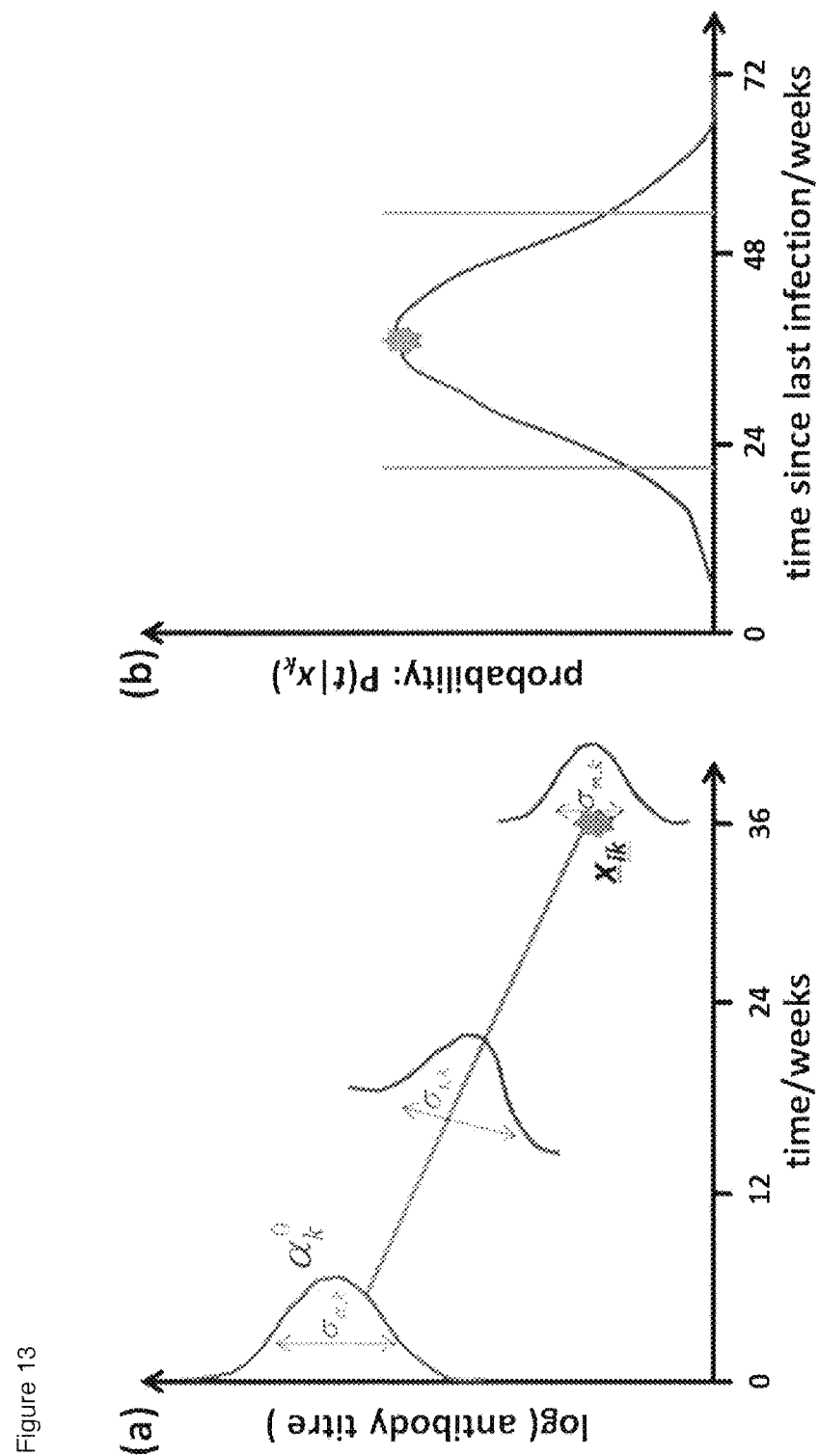
FIG. 13 presents the association between measured antibody titer $x_{ik}$ and time since infection t. (a) There are three sources of variation in the antibody titer $x_{ik}$ measured at time t since last infection: (i) variation in initial antibody titer; (ii) between individual variation in antibody decay rate; and (iii) measurement error. (b) Given estimates of the sources of variation, we can estimate the distribution of the time since last infection. The maximum likelihood estimate and the 95% confidence intervals of our estimate are indicated in blue.

A key premise of the proposed diagnostic test is that following infection with *P. vivax* blood-stage parasites, an antibody response will be generated that will change predictably over time (FIG. 13). Here we present a subset of the data that demonstrates how antibodies to *P. vivax* antigens change over time.

Longitudinal Antibody Titers Following Clinical *P. vivax*

Figure 11:
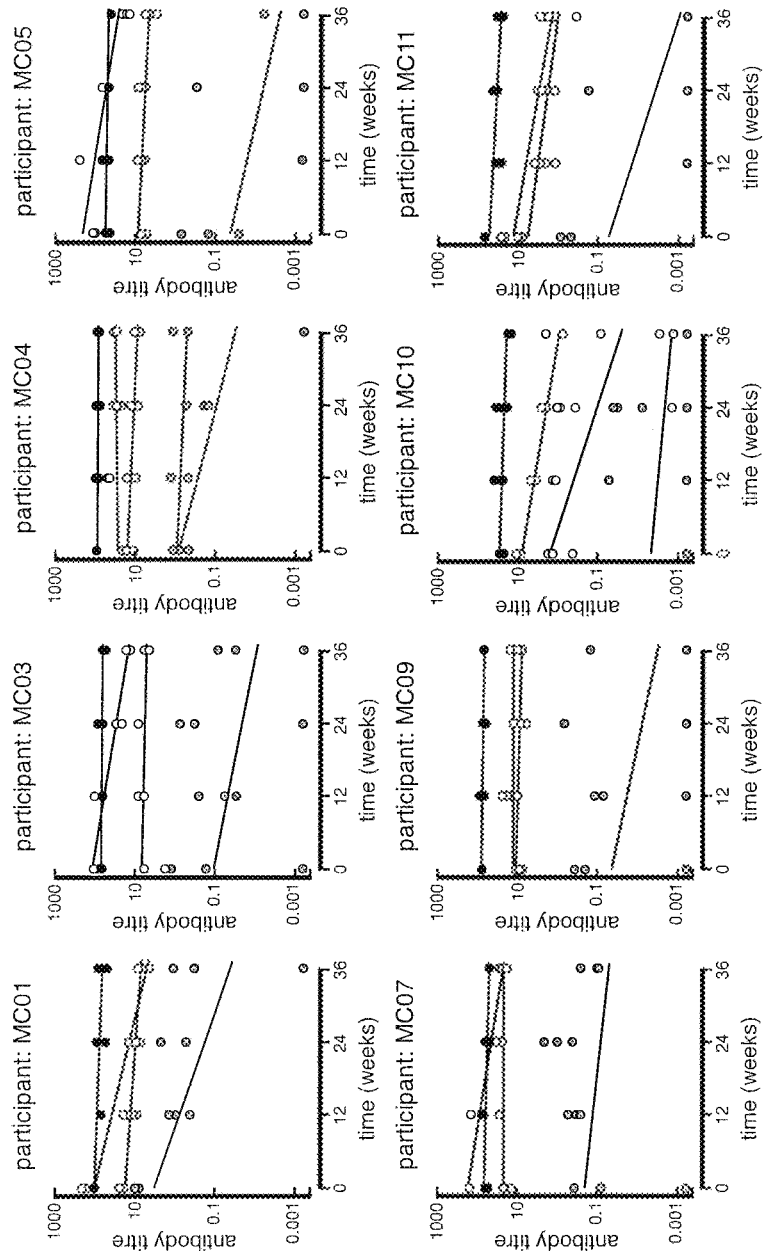
FIG. 11 shows longitudinal antibody dynamics of 4 antigens from 8 Thai participants in the antigen discovery cohort. For each blood sample antibody titers were measured in triplicate, using the AlphaScreen® assay. Each colour corresponds to antibodies to a different antigen. The lines represent the fit of the mixed-effects regression model described below.

We have data from longitudinal cohorts in Thailand and Brazil where participants were followed for up to 36 weeks after a symptomatic clinical episode of *P. vivax* (see also Table 1/Materials and Methods in Example 1, antigen discovery cohorts). Participants were treated with primaquine, and blood samples were frequently tested to ensure they remained free from re-infection. Antibody levels to a wide range of antigens were measured at 12 week intervals to investigate the changing antibody dynamics. The sample data in FIG. 11 illustrates that antibodies exhibit a range of different half-lives—a pattern consistent with the rest of the data (see also FIG. 3). Another important general feature of the data is exhibited here: rapidly decaying antibodies (short half-life) exhibit much more measurement error than slowly decaying antibodies (long-lived half-life).

The decay of anti-malaria antibodies following infection can be described by an exponential or a bi-phasic exponential distribution[4]. Because of the sampling frequency (every 12 weeks) we assume that antibodies decay exponentially. Exponential decay equates to linear decay on a log scale. Therefore we utilise linear regression models. In particular, we utilise a mixed-effects linear regression framework so that we can estimate both the mean rate of antibody decay as well as the standard deviation.

We assume that for individual i we have measurements of antibody titer Auk at time j to antigen k. We assume that at time 0, antibody titers are Normally distributed5 with mean $\alpha_k^0$ and standard deviation $\sigma_{a,k}$ on a log-scale. We assume that an individual's rate of antibody decay is drawn from a Normal distribution with mean $r_k^0$ and standard deviation $\sigma_{r,k}$. The antibody dynamics in the population can therefore be described by the following mixed-effects linear regression model:

$$\log(A_{ijk}) \sim (\alpha_k^0 + \alpha_{ik}) + (r_k^0 + r_{ik})t_j + \varepsilon_k$$

$$\alpha_{ik} \sim N(0, \sigma_{a,k})$$

$$r_{ik} \sim N(0, \sigma_{r,k})$$

$$\varepsilon_k \sim N(0, \sigma_{m,k}) \quad \text{(Equation 1)}$$

This model can be fitted to data using the lmer package in R. FIG. 11 shows a sample of the fitted profiles of antibody dynamics.

Estimation Using Antibodies to a Single Antigen

Figure 12:
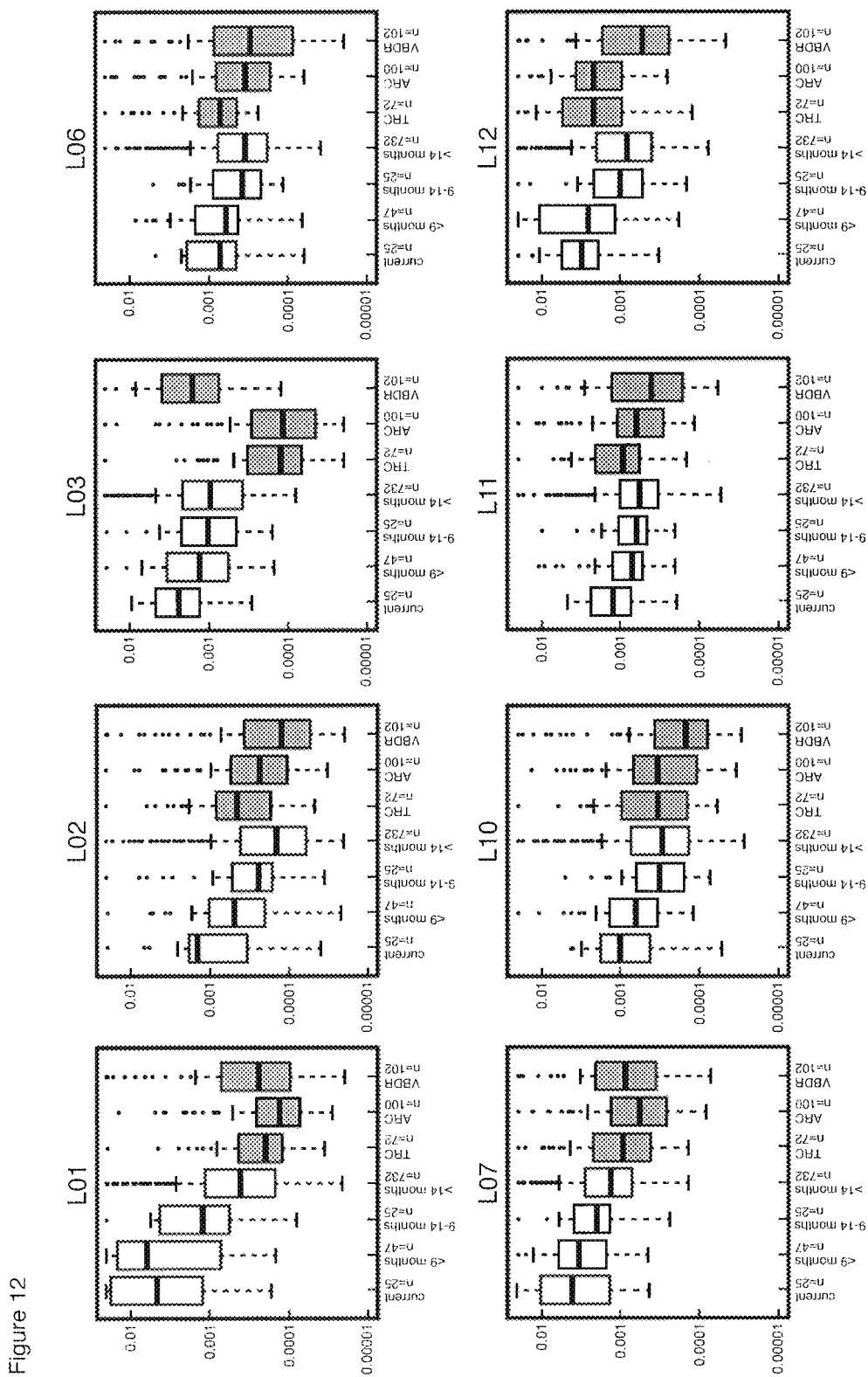
FIG. 12 shows the relationship between antibody titers to 8 *P. vivax* antigens and time since last PCR-detectable in individuals from a malaria-endemic region of Thailand (validation study, antibodies measured via Luminex® bead-array assay). The grey bars denote individuals with current infection (n=25); infection within the last 9 months (n=47); infection 9-14 months ago (n=25); and no infection detected within the last 14 months (n=732). The orange bars show the antibody titers from three different panels of negative controls.

Here we describe an algorithm that uses a biologically-motivated model of the decay of antibody titers over time to facilitate statistical inference of the time since last infection. A key requirement of this algorithm is that it requires some prior knowledge of the decay rates of antibodies. This can be achieved either through estimation of antibody decay rates from longitudinal data as described in equation (1), or estimation of decay rates from cross-sectional antibody measurements as presented in FIG. 12.

The linear regression model for the decay of antibody titers described in equation (1) has three sources of variation: (i) variation in initial antibody titer following infection; (ii) between individual variation in antibody decay rate; and (iii) measurement error. Notably, all these sources of variations are described by Normal distributions (FIG. 13a) so their combined variation will also be described by a Normal distribution. Therefore, the expected log antibody titer to antigen k in individual i at time t can be described by the following distribution.

$$x_{ik} \sim N(\alpha_k^0 + r_k t, \sigma_{a,k}^2 + t^2 \sigma_{r,k}^2 + \sigma_{m,k}^2) \quad (2)$$

The probability distribution of the expected antibody titer to antigen k in individual i at time t is given by the following distribution:

$$P(x_{ik}|t) = \frac{1}{\sqrt{2\pi(\sigma_{a,k}^2 + t^2\sigma_{r,k}^2 + \sigma_{m,k}^2)}} e^{-\frac{(x_{ik} - \alpha_k^0 - r_k^0 t)^2}{2(\sigma_{a,k}^2 + t^2\sigma_{r,k}^2 + \sigma_{m,k}^2)}} \quad (3)$$

Note that we have $x_{ik} \in (-\infty, +\infty)$, as $x_{ik}$ denotes the log antibody titer and measurements of antibody titer are assumed to be positive. The probability distribution for the time since infection t given measured antibody titer $x_{ik}$ can be calculated by inverting equation (3) using Bayes rule[3].

$$P(t|x_{ik}) = \frac{P(x_{ik}|t)P(t)}{P(x_{ik})} \quad (4)$$

The time since last infection will have a lower bound of zero. We can choose to impose an upper bound of either the individual's age 'α' or positive infinity. Choosing positive infinity allows us to better handle the case where an individual was never infected—the low measured antibody titers will be consistent with a very large time since last infection, possibly greater than the age of the individual. Therefore we should only restrict t to the interval (0, a) if we know for certain that the individual has been infected. In practice, we choose some large time $t_{max}$ for our upper bound. We assume P(t) denotes a uniform distribution on the interval (0, $t_{max}$).

$P(x_{ik})$ is a normalising constant which is calculated via numerical integration to ensure that $P(t|x_{ik})$ denotes a probability distribution.

Equation (4) provides a probability distribution for the time since last infection. For the purposes of a diagnostic test we may be more interested in obtaining a binary classification, e.g. was the individual infected within the last 9 months. It is usually not possible to definitively make such a categorisation, but we can instead calculate their probabilities as follows:

$$P_{0-9m}(x^{ik}) = \int_0^9 P(t|x_{ik})dt$$

$$P_{9m+}(x_{ik}) = \int_9^{t^{max}} P(t|x_{ik})dt \quad (5)$$

Combined Antibody Dynamics: Estimation Using Antibodies to Multiple Antigens Previously, we described how the antibody titer to a single antigen can be used to estimate the time since last infection. However, in practice there is too much noise to make an accurate estimate of time since last infection with a single antigen. Increasing the number of measured antibodies can increase the information content in our data allowing us to obtain more accurate estimates of time since last infection. In particular, selecting antibodies with a range of half-lives may increase our power to resolve infection times more accurately.

Figure 14:
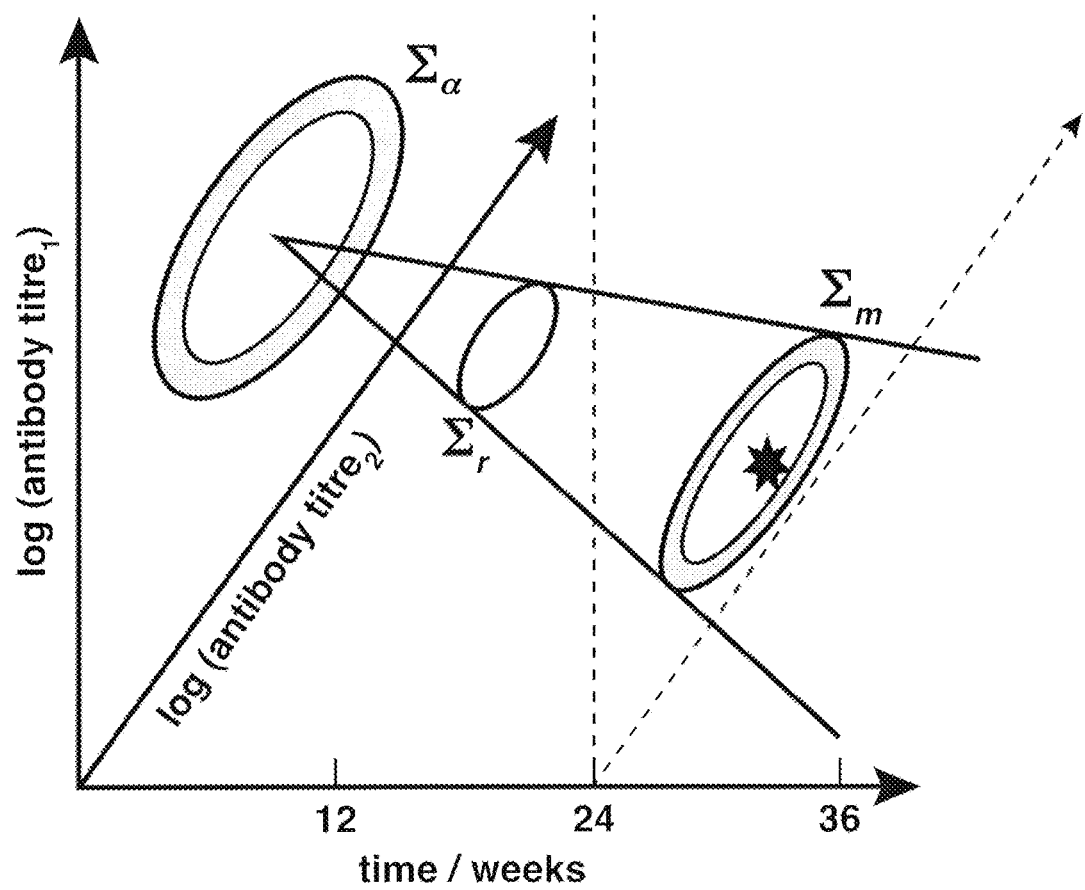
FIG. 14 shows the dynamics of multiple antibodies. The variance in initial antibody titer, antibody decay rates and measurement error are now described by covariance matrices, which account for the correlations between antibodies.
Figure 15:
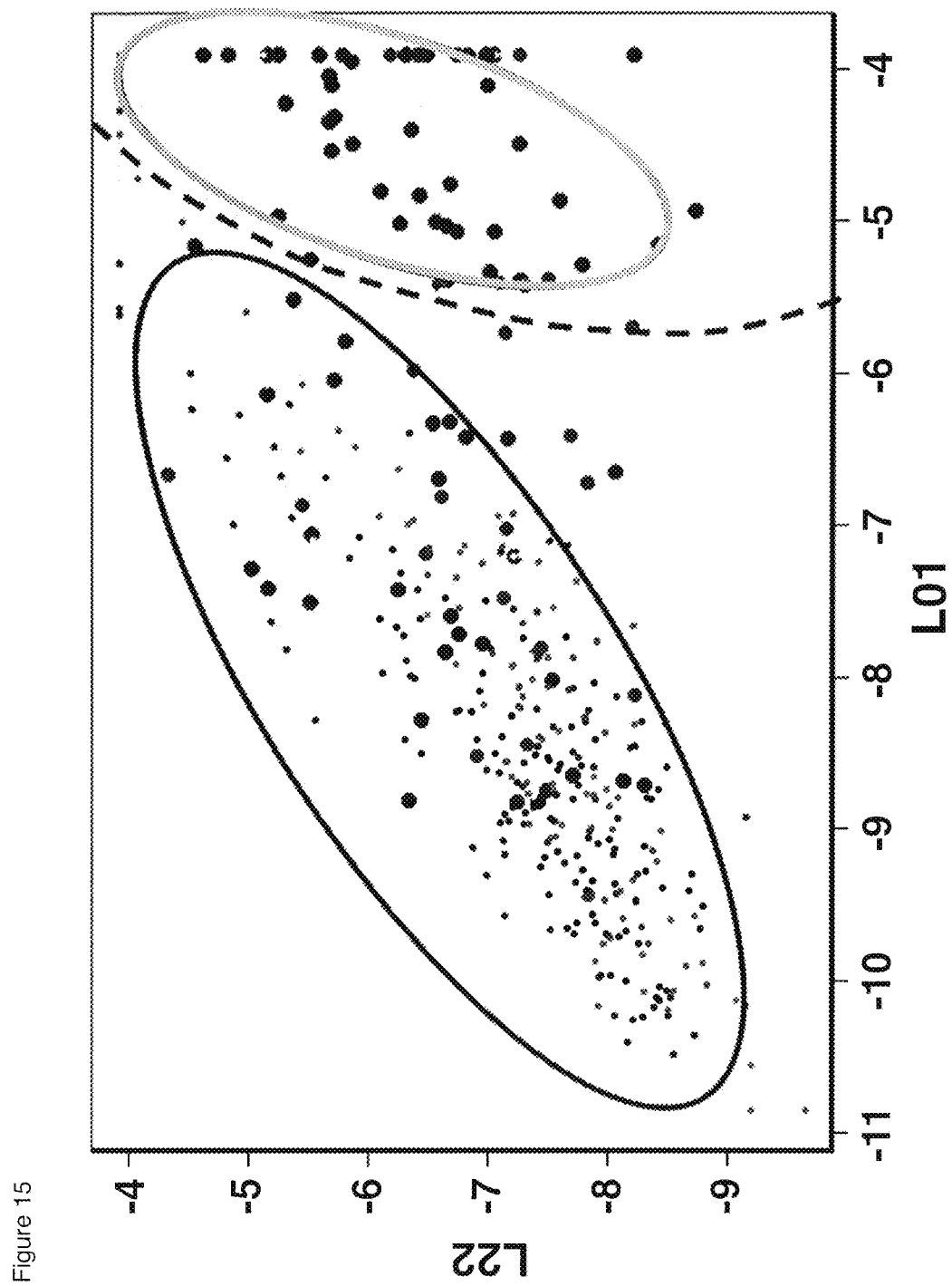
FIG. 15 shows an example of QDA classification for participants from the Thai validation cohort. Antibody measurements were made using the Luminex® bead-array assay. Each point corresponds to a measurement from a single individual with log(anti-L01 antibody titer) on the x-axis and log(anti-L22 antibody titer) on the y-axis. The blue ellipse represents the multivariate Gaussian fitted to data from individuals with 'old' infections and the red ellipse represents the multivariate Gaussion fitted to data from individuals with 'new' infections. The dashed lack line represents the boundary for classifying individuals according to whether or not they have had a recent infection.
Figure 16:
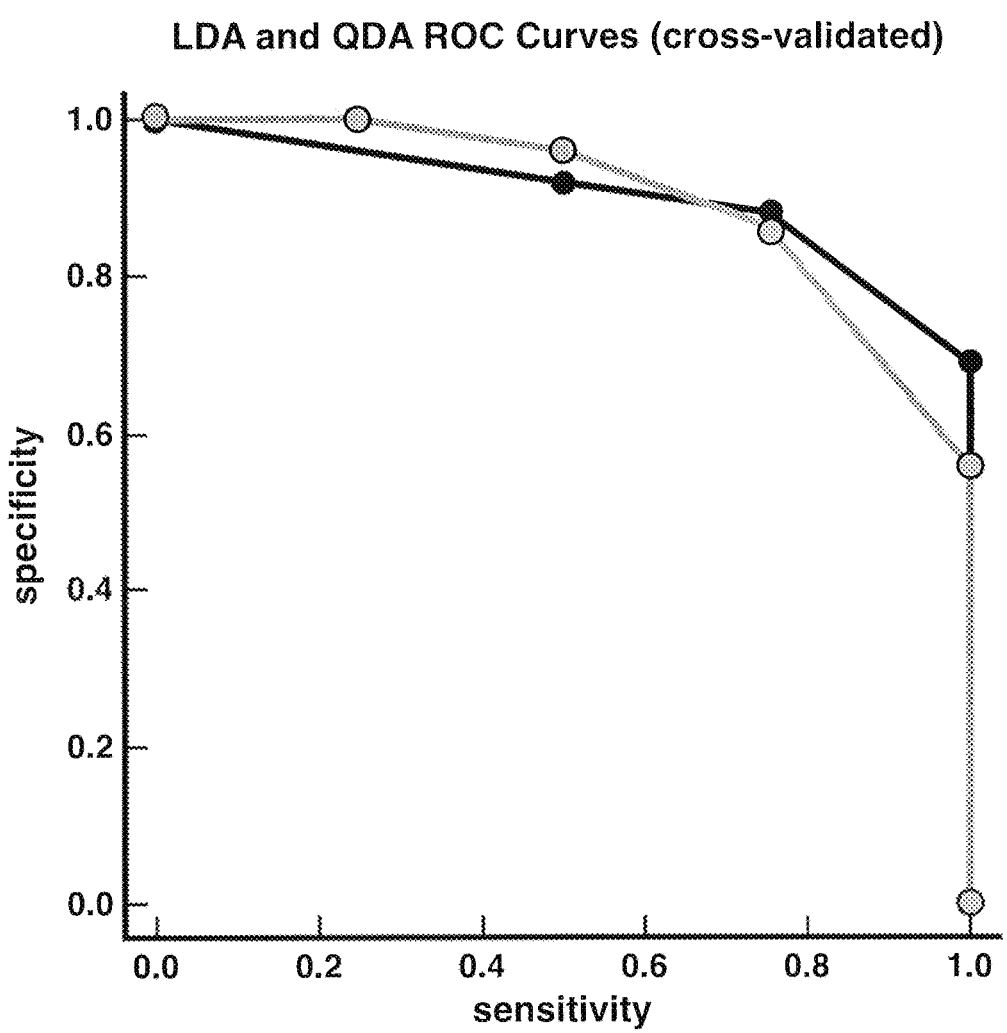
FIG. 16 shows receiver operator characteristic (ROC) curves estimated via cross-validation for LDA (blue) and QDA (black) classification algorithms, using the Thai validation data measured via the Luminex® bead-array assay.
Figure 17:
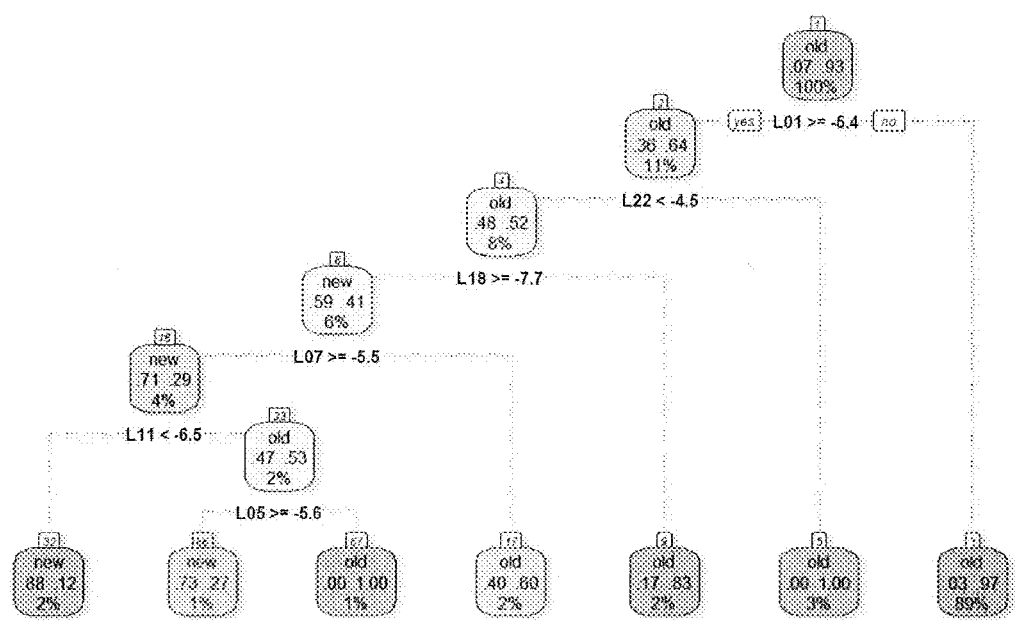
FIG. 17 shows an example of a decision tree for classifying old versus new infections using measurements of antibodies to 6 P. vivax antigens, using the Thai validation data measured via the Luminex® bead-array assay.
Figure 18:
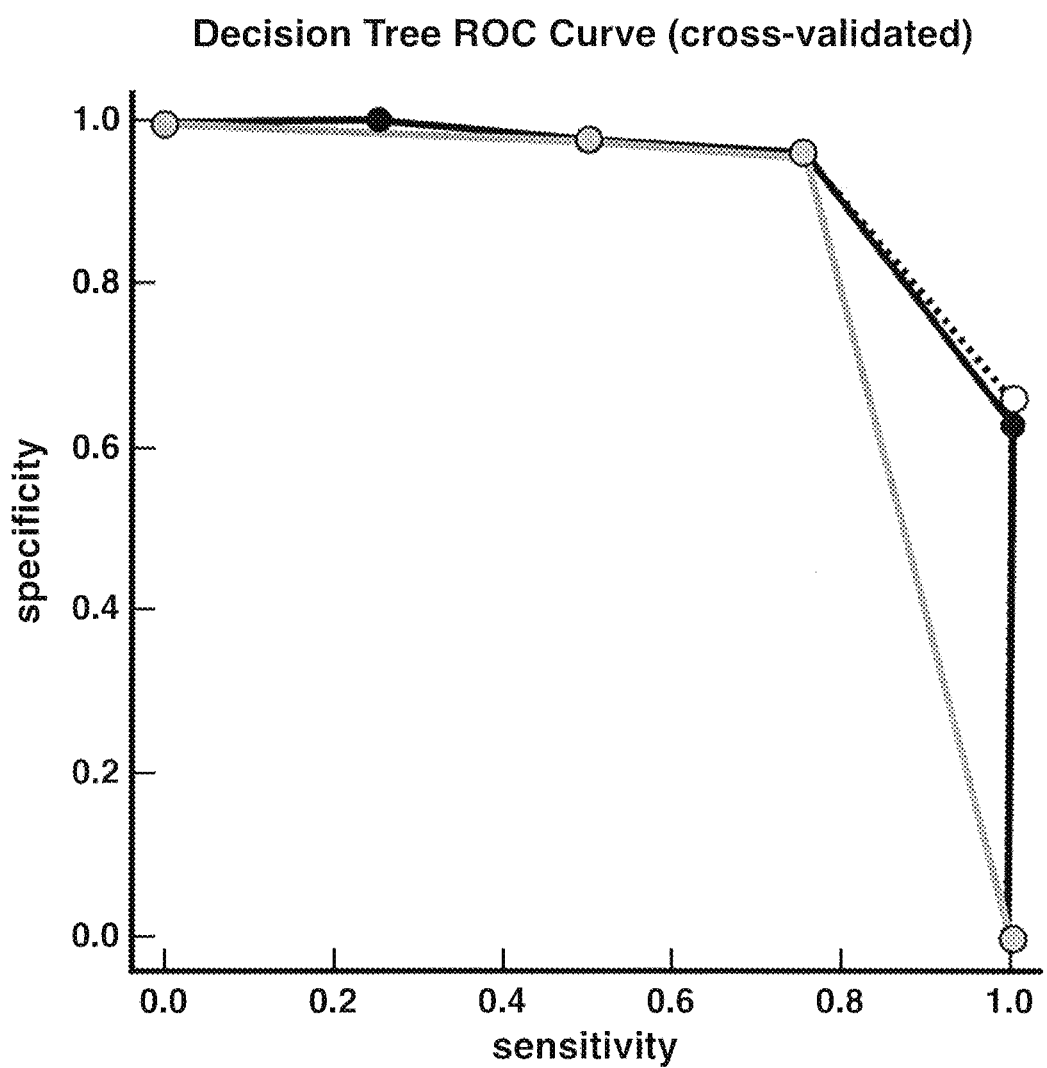
FIG. 18 shows ROC curve demonstrating the association between sensitivity and specificity for a decision tree algorithm, using the Thai validation data measured via the Luminex® bead-array assay. These curves have been generated through cross-validation by splitting the data into training and testing sets. The algorithm is formulated using the training data set and the sensitivity and specificity evaluated on the testing data set. The colours correspond to different subsets of antigens. Notably, we can obtain nearly 80% sensitivity with specificity >95%.
Figure 19:
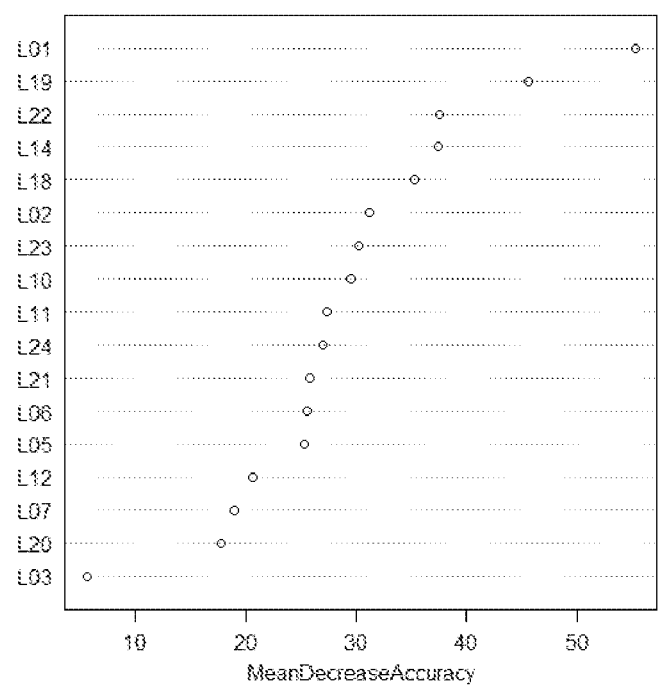
FIG. 19 shows a random forest variable importance plot of the contribution of antibodies to 17 antigens towards correct classification of infections into 'new' versus 'old', using the Thai validation data measured via the Luminex® bead-array assay. Antigens with greater values of 'MeanDecreaseAccuracy' are considered the most informative. Therefore L01 provides the most information for classification purposes.

FIG. 14 shows a schematic of the dynamics of antibodies to two antigens. We have rapidly decaying antibody 1 and slowly decaying antibody 2. At baseline, antibody titers are likely to be correlated, so we assume that initial titer following infection is described by a multivariate Normal distribution with covariance matrix $E_a$. The between individual rates of antibody decay may also be correlated (i.e. all antibody titers may decay particularly quickly in some individuals) so we also assume that decay rates are described by a multivariate Normal distribution with covariance matrix $\Sigma_r$. Finally, there will be measurement error associated with each antibody. In particular, we assume the measurement errors between different antibodies are independent so that the total measurement error can be described by a multivariate Normal distribution with diagonal covariance matrix $E_m$.

$$P(x_i|t) = \quad (6)$$
$$(2\pi)^{-\frac{k}{2}}|\Sigma_\alpha + t^2\Sigma_r + \Sigma_m|^{-\frac{1}{2}} e^{-\frac{1}{2}(x_i - \alpha^0 - r^0 t)^T (\Sigma_\alpha + t^2\Sigma_r + \Sigma_m)^{-1}(x_i - \alpha^0 - r^0 t)}$$

The method for estimating the time since last infection given the multivariate probability distribution for the measured vector of antibody titers $x_i$ is the same as described in equation (4).

Selecting Optimal Combinations of Antigens

Machine learning algorithms take data from a large number of streams and identify which data streams have the most signal for classifying output. Such methods typically involve a greedy algorithm which will provide a good but not necessarily optimal solution. Greedy algorithms take the next best step, i.e. including the next antigen that gives the biggest increase in predictive power. As such they may provide a locally optimal solution but not necessarily a globally optimal solution. Simulated annealing algorithms provide an alternative to greedy algorithms that provide a higher likelihood of obtaining a globally optimal solution.

Here we describe how a simulated annealing algorithm can be applied to the combined antibody dynamics (CAD) classifier to select a combination of antigens that provides optimal predictive power. Assume that P measurements of antibodies are available. We want to select some subset of these that maximises predictive power. Denote y to be a vector of 0's and 1's indicating whether the $p^{th}$ antibody is included in our panel. Thus for example we may have $$y=(0,0,1,1,0,1,0,0,1) \quad (7)$$

The vector of binary states depicted in equation (7) will correspond to a vector of antibody measurements as follows:

$$x_i = (x_{i,1}, x_{i,2}, x_{i,3}, x_{i,4}) \quad (8)$$

Given data from I individuals on measured antibody responses, we can calculate the probability that the individual was infected within the last 9 months $P_{0-9m}(X_i)$ or greater than 9 months ago $P_{9m+}(x_i)$. Let $z_i$ be an indicator denoting whether individual I was infected in the last 9 months ($z_i=1$) or not ($z_i=0$). We can then write down the likelihood of the data as follows:

$$L(y) = \prod_{i=1}^{I} P_{0-9m}(x_i)^{z_i} P_{9m+}(x_i)^{1-z_i} \quad (9)$$

The challenge is to select a binary vector y corresponding to a combination of antigens that maximises the likelihood in equation (9) and thus has the highest likelihood of correctly classifying infections according to whether they occurred in the last 9 months.

Figure 20:
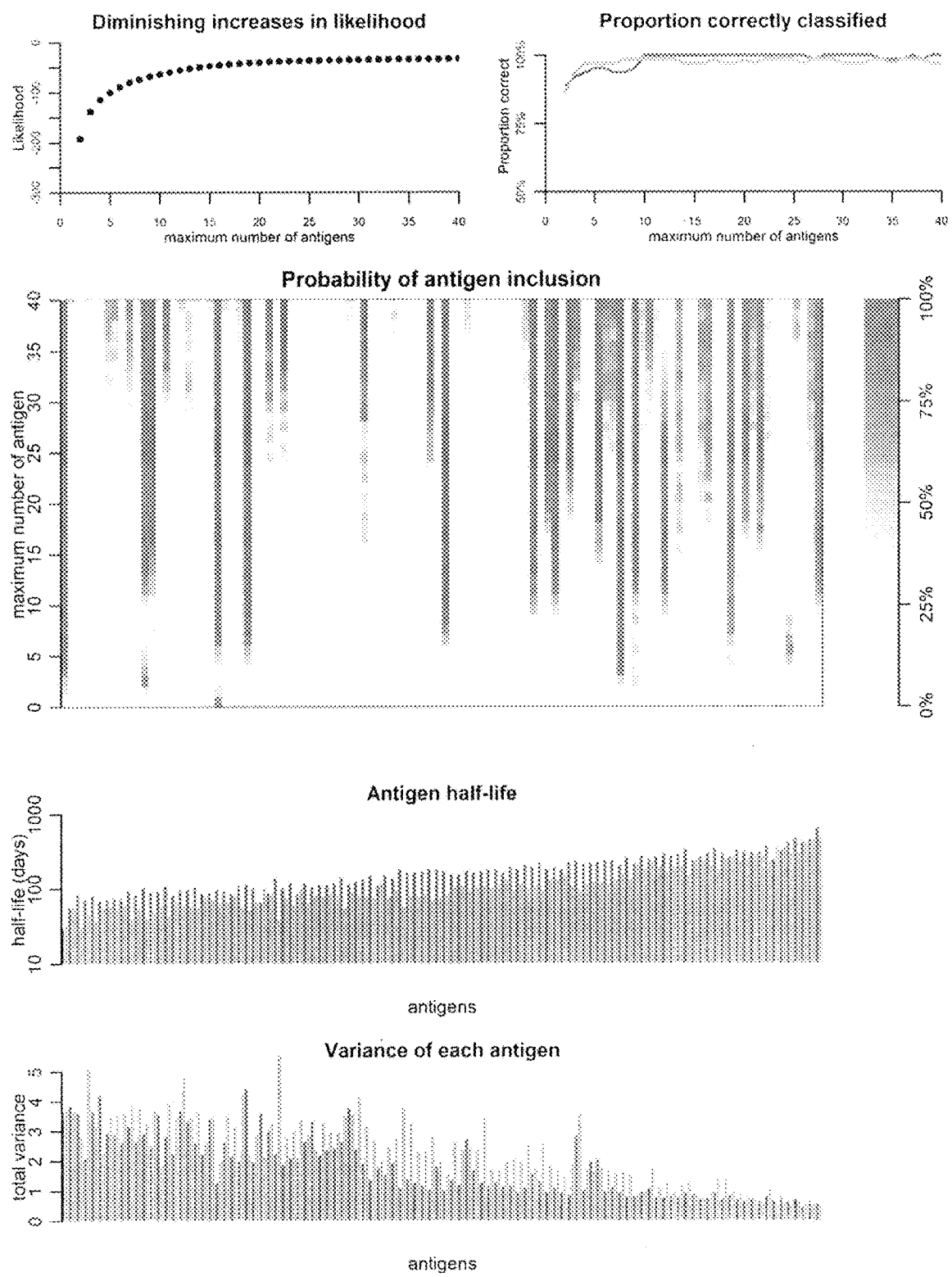
FIG. 20 shows an example of antigen down-selection using the simulated annealing algorithm. Data comes from the antigen discovery study using the AlphaScreen® assay. (A) Including additional antigens increases the likelihood that infection times will be correctly classified, but with diminishing returns. (B) Each column of the heatmap denotes one of K=98 antigens. The y-axis denotes the maximum number of antigens that can be included in a panel. Red antigens are more likely to be included in a panel of a given size. (C) Example of predicting time since last infection in 4 individuals using a panel of 15 antigens. The vertical dashed line at 6 months represents an infection occurring 6 months ago. The solid black curve denotes the estimated distribution of the time since last infection. The green point denotes the maximum likelihood estimate of the model, and the vertical green bars denote the 95% confidence intervals. The red, shaded area denotes infection within the last 9 months. If more than 50% of the probability mass of the distribution is in this region, then the infection will be classified as having occurred within the last 9 months.

If we have P antigens, there are $2^P$ combinations of antigens. For P >15 it is not computationally feasible to test all possible combinations. We therefore utilise a simulated annealing algorithm for exploring the state space of combinations and identifying the optimal combinations subject to various constraints (e.g. enforcing a maximum of 10 antigens to a panel). FIG. 20 shows the results, and this contributed to the initial down-selected of antigens as described in Example 1.

REFERENCES

1 White, N. J. Determinants of relapse periodicity in *Plasmodium vivax* malaria. *Malaria Journal* 10, doi: 29710.1186/1475-2875-10-297 (2011).
2 Mueller, I. et al. Key gaps in the knowledge of *Plasmodium vivax*, a neglected human malaria parasite. *Lancet Infectious Diseases* 9, 555-566 (2009).
3 Hastie, T., Tibshirani, R. & Friedman, J. *The elements of statistical learning: Data mining, inference, and prediction*. Second edn, (Springer, 2009).
4 White, M. T. et al. Dynamics of the Antibody Response to *Plasmodium falciparum* Infection in African Children. *Journal of Infectious Diseases* 210, 1115-1122, doi: 10.1093/infdis/jiu219 (2014).
5 Yman, V. et al. Antibody acquisition models: A new tool for serological surveillance of malaria transmission intensity. *Scientific Reports* 6, doi:10.1038/srep19472 (2016).
6 The Elements of Statistical Learning: Data Mining, Inference and Prediction" by Hastie, Tibshirani & Friedman; 2001, Springer.
7 Kirkpatrick, S., Gelatt Jr, C. D. & Vecchi, M. P. Optimization by simulated annealing. *Science* 220, 671-680 (1983).

Example 4—Additional Testing of Antigens

This non-limiting Example relates to additional testing of antibody responses to various *P. vivax* proteins, present in the blood, as potential antigens for a diagnostic test. It further relates to selection of *Plasmodium vivax* antigens for classification of samples with past blood-stage infections.

The blood collection and laboratory work was generally performed according to the materials and methods described in Example 1.

Overview of Epidemiological Cohorts

Figure 21:
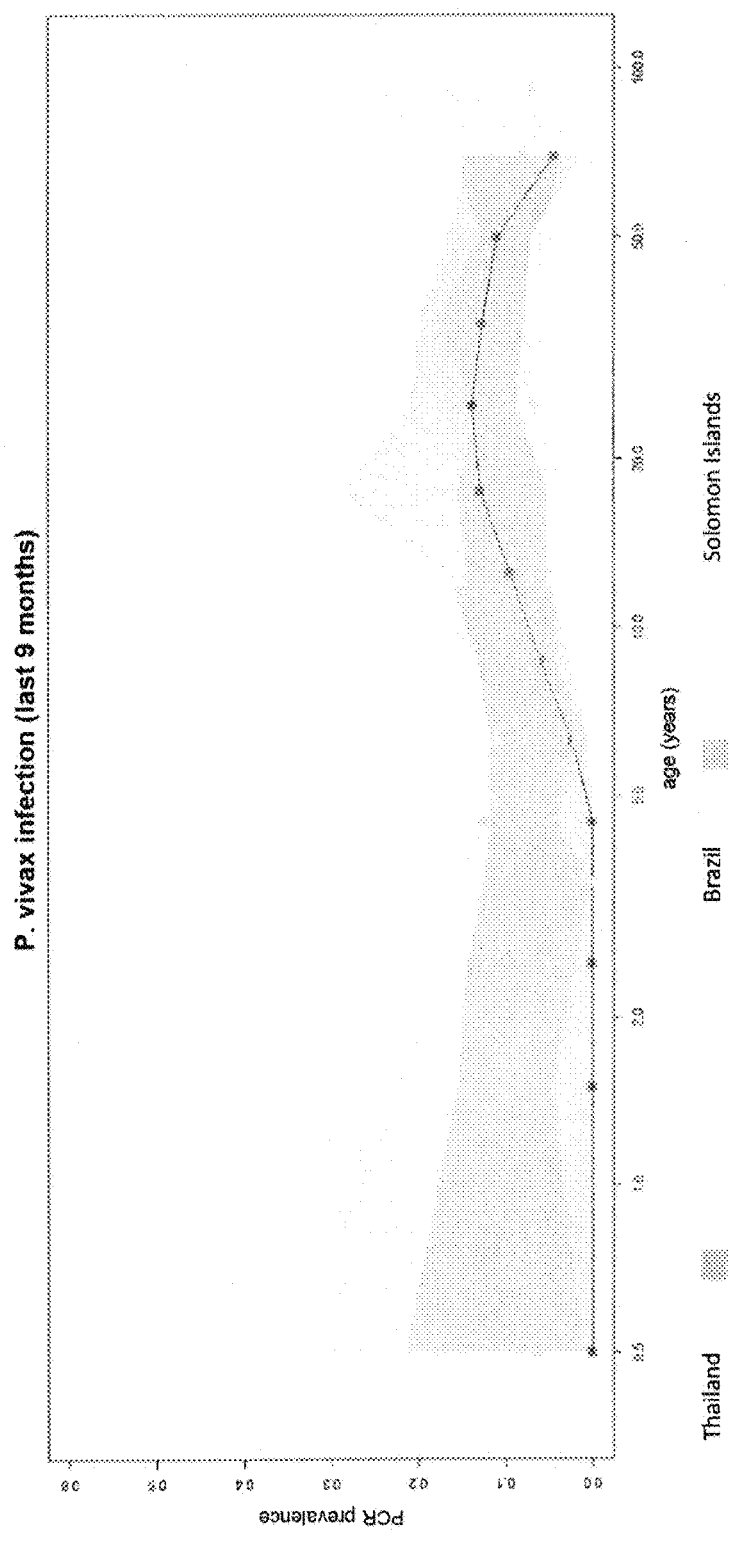
FIG. 21 shows comparison of age-stratified prevalence of PCR detectable blood-stage infection within the last 9 months.

Data was obtained from longitudinal cohorts in three different regions of the *P. vivax* endemic world. In each cohort, approximately 1,000 individuals were followed over time for approximately 1 year, with active case detection samples taken every month. These samples were supplemented by passive case detection samples from individuals experiencing clinical episodes of *P. vivax* or *P. falciparum*. An overview of the data collected is shown in Table 3, and age-stratified prevalence of PCR detectable blood-stage infection within the last 9 months is shown in FIG. 21.

In addition data was obtained from three cohorts of negative controls who were highly to have ever been exposed to malaria. These cohorts consisted of 102 individuals from the Victorian Blood Donor Registry (VBDR), 100 individuals from the Australian Red Cross, and 72 individuals from the Thai Red Cross (residents of Bangkok with no reported history of malaria).

TABLE 3

Epidemiological overview of cohorts analysed for the association between *P. vivax* antibody titers and time since last PCR detectable infection. Number of samples per individual and age are shown as median with range.

| | Thailand | Brazil | Solomon Islands |
|---|---|---|---|
| number of individuals | 829 | 928 | 860 |
| samples per individual | 14 (4, 18) | 13 (4, 16) | 10 (6, 11) |
| Female | 454 (54.8%) | 471 (50.7%) | 416 (48.4%) |
| age (years) | 24 (1, 78) | 25 (0, 103) | 5.5 (0.5, 12.7) |
| PCR infection during study | 97 (11.7%) | 236 (25.4%) | 294 (34.2%) |
| PCR infection in last 9 months | 72 (8.7%) | 205 (22.1%) | 265 (30.8%) |
| PCR infection in last 3 months | 44 (5.3%) | 119 (12.8%) | 156 (18.1%) |
| PCR infection at last final time point | 25 (3.0%) | 40 (4.3%) | 93 (10.8%) |

Measured Antibody Responses

In each of the three longitudinal cohorts, antibody responses were measured at the final time point to allow investigation of the association between antibody response and time since last infection. The antibody responses to 65 antigens were measured. 40 of these antigens were selected following a previously published down-selection procedure from a starting panel of 342 wheat-germ expressed proteins. These 40 proteins were supplemented by another 25 purified *P. vivax* proteins obtained from collaborators. These *P. vivax* antigens were coupled to COOH micro-beads, and a multiplexed Luminex assay was used to measure Mean Fluorescence Intensity (MFI) for each antigen in each sample. MFI measurements were converted to antibody titers by calibrated to measurements from a hyper-immune pool of Papua New Guinean adults. FIG. 22 shows the measured response from 4 of the 65 antigens, and the variation with time since last infection.

Selection of Optimal Combinations of Antigens for Classification

Initial Investigation of Combinations of Parameters

Of the 65 *P. vivax* proteins considered, 5 were excluded because of poor immunogenicity which resulted in missing data from a large proportion of samples. This resulted in a panel of 60 antigens for detailed investigation and further down-selection. The aim is to identify combinations of up to 5 antigens that can provide accurate classification within a single cohort, and identify combinations of 8-15 antigens that can accurately across multiple cohorts with a wide range of transmission intensities and age ranges.

Without wishing to be limited by a single hypothesis, selection optimized for three classification targets:

1. Surveillance target. Select combinations of antigens such that both sensitivity and specificity are given equal weight in optimisation. This is done by maximising the area under the curve (AUC) of a receiver operating characteristic (ROC) curve.
2. Serological Screen and Treat (SSAT) target. Select combinations of antigens that maximise sensitivity (e.g. >95%) while enforcing a lower bound on specificity (e.g. >50%).
3. Surveillance target. Select combinations of antigens that maximise specificity (e.g. >95%) while enforcing a lower bound on sensitivity (e.g. >50%).

The first step is to identify combinations of antigens for which there is a strong signal enabling classification. This was done by using a linear discriminant analysis (LDA) classifier to test all combinations of antigen of size up to 5. Above size 5, it was not computationally feasible to evaluate all possible combinations. Therefore for n>5, combinations of size n+1 were evaluated by identifying the optimal 500 combinations of size n antigens and including all positive individually.

Optimisation of Algorithms Given Most Likely Parameter Combinations

Given a subset of n antigens, a range of classification algorithms were considered: LDA, quadratic discriminant analysis (QDA), decision trees, and random forests. For a given algorithm and subset of antigens classification performance was assessed through cross-validation. The key to cross-validation is to use disjoint training and testing data sets to assess classification of performance. For each cohort, this is done by randomly selecting ⅔ of the data as the training set and testing the algorithm on the remaining ⅓. This is repeated 200 times and the average of the cross-validated ROC curves is calculated.

FIGS. 23A-23C show cross-validated ROC curves for assessing the classification performance of random forests algorithms (determined according to the randomForests library in R). In cases where algorithms were trained and tested on data from the same region, many different combinations of 4 antigens resulted in sensitivity and specificity greater than 80%. Even when an algorithm was trained on data from one region and then tested on data from another region of the world, it was still possible to obtain combinations of antigens with both sensitivity and specificity greater than 80%, with the exception of algorithms trained on data from Thailand and tested on data from the Solomon Islands.

Ranking of Antigens

Figure 24:
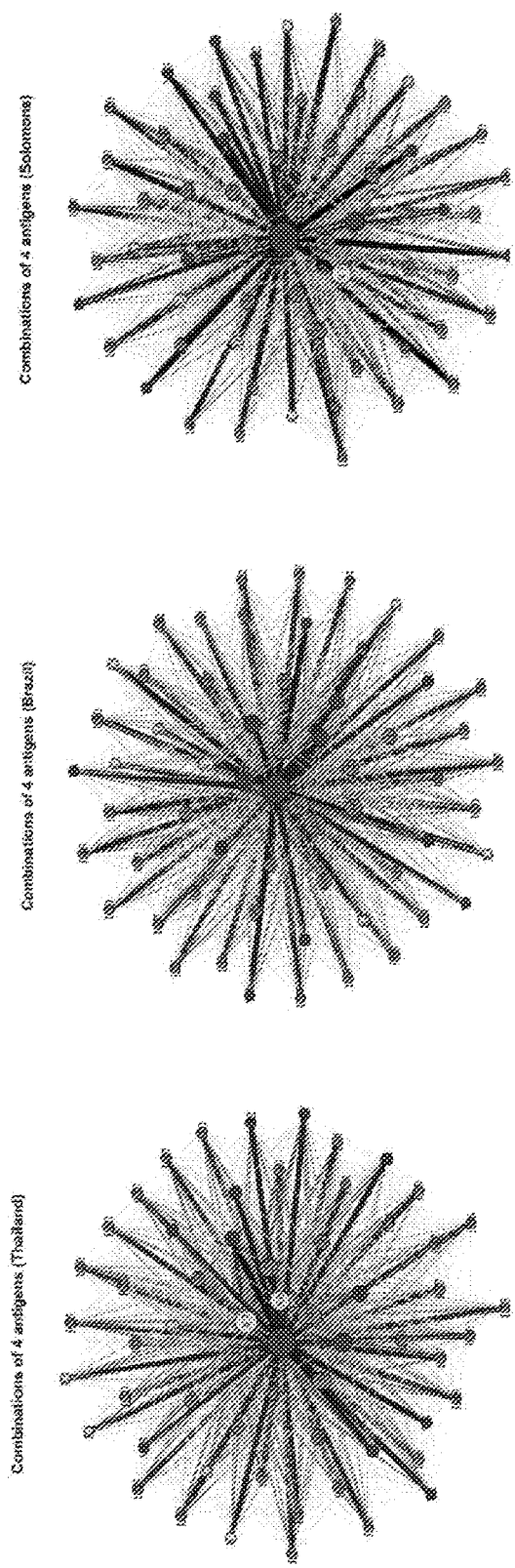
FIG. 24 shows an exemplary network visualization of combinations of 4 antigens. The size of the node represents the probability that an antigen appears in the best performing combinations. The width and darkness of the edges represents the probability that two antigens are selected together in the best performing combinations. Red denotes proteins purified at high yield by CellFree Sciences (the 40 down selected proteins, the results for which are shown in FIG. 6B). Blue denotes vaccine candidate antigens. Green denotes proteins expressed in wheat-germ by Ehime University. Blue and green proteins are the 25 additional proteins, the results for which are shown in FIG. 6C.

Multiple factors determine whether or not an antigen will contribute to classification of recent infection. These include but are not limited to: antibody dynamics; immunogenicity of recent infections compared to old infections and measurements from control samples; area under the ROC curve when considering one antigen at a time; frequency of selection in top combinations of antigens. FIG. 24 shows a network visualisation of how combinations of 4 antigens are selected. The size of each node represents the likelihood that an antigen is selected, and the width and colour of an edge represents the probability that a pair of antigens are selected in combination. Therefore, the most commonly selected antigens are biggest and cluster in the centre of the network. There was a high degree of consistency in the antigens that were selected in each of the three cohorts, with the most strongly identified antigens being RBP2b (V3), L01, L31, X087885 (X7), PvEBP (V11), L55, PvRipr (V8) and L54.

Table 4 shows a ranking of antigens according to a range of criteria. The top two antigens, RBP2b and L01, are preferred candidates. The next six antigens are likely candidates. The next seven antigens are possible candidates. Also included are an additional nine antigens worth further consideration.

TABLE 4

List of antigens ranked according to their contribution to classification of individuals with PCR detectable blood-stage *P. vivax* in the last 9 months. The area under the curve (AUC) is based on using antibody titers to a single antigen for classification. Combinations of antigens were investigated by assessing classification performance of linear discriminant analysis (LDA) for all combination of 4 antigens from the initial panel of 60 antigens. Recent infection sero-positivity shows the proportion of individuals with PCR detectable *P. vivax* in the last 9 months, with the threshold of sero-positivity defined as the geometric mean titer (GMT) plus two standard deviations of the negative controls.

| antigen | Area Under Curve (1 antigen) | | | Top 1% of combination (4 antigens) | | | Recent infection sero-positivity | | |
|---|---|---|---|---|---|---|---|---|---|
| | Thailand | Brazil | Solomons | Thailand | Brazil | Solomons | Thailand | Brazil | Solomons |
| RBP2b (V3) | 0.849 | 0.818 | 0.868 | 89.7% | 98.5% | 100.0% | 70.8% | 64.4% | 45.7% |
| L01 | 0.812 | 0.787 | 0.697 | 43.5% | 23.9% | 4.3% | 51.4% | 56.6% | 14.3% |
| L31 | 0.805 | 0.762 | 0.766 | 5.0% | 2.7% | 3.7% | 25.0% | 38.0% | 7.4% |
| X087885 (X7) | 0.807 | 0.748 | 0.697 | 20.3% | 9.2% | 14.6% | 41.7% | 81.0% | 50.9% |
| PvEBP (V11) | 0.794 | 0.739 | 0.707 | 5.0% | 2.4% | 3.1% | 55.6% | 41.0% | 7.8% |
| L55 | 0.79 | 0.781 | 0.643 | 17.2% | 20.9% | 2.6% | 38.9% | 29.8% | 3.5% |
| PvRipr (V8) | 0.754 | 0.772 | 0.646 | 3.0% | 9.1% | 3.1% | 31.9% | 29.3% | 4.8% |
| L54 | 0.79 | 0.727 | 0.654 | 5.6% | 4.4% | 3.1% | 26.4% | 19.0% | 2.2% |
| L07 | 0.747 | 0.765 | 0.599 | 3.1% | 5.3% | 2.8% | 27.8% | 41.5% | 3.9% |
| L30 | 0.732 | 0.61 | 0.609 | 2.3% | 3.8% | 5.4% | 47.2% | 11.7% | 9.6% |
| PvDBPII (V10) | 0.74 | 0.773 | 0.639 | 1.7% | 2.6% | 4.0% | 20.8% | 47.3% | 3.5% |
| L34 | 0.767 | 0.746 | 0.67 | 4.5% | 16.6% | 2.2% | 12.5% | 19.0% | 3.9% |
| X092995 (X6) | 0.792 | 0.703 | 0.642 | 11.5% | 1.9% | 5.6% | 15.3% | 34.1% | 10.0% |
| L12 | 0.755 | 0.731 | 0.637 | 3.5% | 6.1% | 2.9% | 16.7% | 15.1% | 3.0% |
| RBP1b (V1) | 0.533 | 0.578 | 0.525 | 24.1% | 4.7% | 2.5% | 0.0% | 0.0% | 0.0% |
| L23 | 0.759 | 0.753 | 0.658 | 4.0% | 14.8% | 2.9% | 12.5% | 19.5% | 5.7% |
| L02 | 0.746 | 0.724 | 0.677 | 2.7% | 3.7% | 3.9% | 15.3% | 13.7% | 2.6% |
| L32 | 0.705 | 0.651 | 0.493 | 3.7% | 1.9% | 30.2% | 4.2% | 3.9% | 0.4% |
| L28 | 0.759 | 0.744 | 0.667 | 3.8% | 2.5% | 2.4% | 45.8% | 33.2% | 9.1% |
| L19 | 0.753 | 0.67 | 0.664 | 2.6% | 2.3% | 6.5% | 33.3% | 19.5% | 10.9% |
| L36 | 0.727 | 0.698 | 0.662 | 3.2% | 1.8% | 2.8% | 36.1% | 22.0% | 10.4% |
| L41 | 0.702 | 0.66 | 0.636 | 2.55 | 1.7% | 3.3% | 29.2% | 17.6% | 8.3% |
| X088820 (X4) | 0.723 | 0.666 | 0.638 | 4.0% | 1.8% | 6.7% | 15.3% | 35.6% | 14.8% |
| PvDBP..SacI (V13) | 0.716 | 0.761 | 0.616 | 1.7% | 2.6% | 7.2% | 16.7% | 36.6% | 1.3% |

FIG. 25 shows Receiver Operating Characteristic (ROC) curves for assessing the trade-off between sensitivity and specificity for a cross-validated linear discriminant analysis (LDA) classifier applied to data from Thailand, Brazil and the Solomon Islands.

Appendix I

| No. | Protein Name | Protein Reference | Insert aa sequence (add M as start/His-tag at C-term) | Insert DNA sequence (Start from ATG to His-tag stop codon) |
|---|---|---|---|---|
| 1 | merozoite surface protein 1 (MSP1), MSP1-19 | PVX_099980 | MNESKEILSQLLNVQTQLLTMSSEH TCIDTNVPDNAACYRLDGTEEWRC LLTFKEEGGKCVPASNVTCKDNNG GCAPEAECKMTDSNKIVCKCTKEGS EPLFEGVFCSHHHHHH (SEQ ID NO: 1) | ATGAACGAGTCCAAGGAGATCCTCAGCCAACTCCTGAACGTGCAAACC CAGCTCCTGACCATGTCCAGCGAGCACACCTGCATCGACACCAACGTCC CAGACAACGCCGCCTGCTACAGGTACCTGGACGGCACCGAGGAGTGG CGCTGCCTCCTGACCTTCAAGGAAGAGGGCGGCAAGTGCGTGCCAGCC TCCAACGTCACCTGCAAGGACAACAACGGCGGCTGCGCTCCAGAGGCT GAGTGCAAGATGACCGACAGCAACAAGATCGTGTGCAAGTGCACCAA GGAAGGCTCCGAGCCACTCTTCGAGGGCGTCTTCTGCAGCCACCACCA CCACCACCACTGA (SEQ ID NO: 2) |
| 2 | tryptophan-rich antigen (Pv-fam-a) | PVX_096995 | MKTETVTSRSNPHQAIEYANQGPS RDKVEEWKRNAWTDWMVQLDDD WKDFNAQIEEEKKAWIEEKEGDWV ILLKHLQNKWLHFNPNLDAEYQTD MLAKSETWDERQWKMWISTEGKQ LLEMDLKKWFTNNEMIYCKWTMDE WNEWKNEKIKEWVTSEWKESEDQ YWSKYDDATIQTLTVAERNQWFKW KERIYREGIEWKNWIAIKESKFVNA NWNSWSEWKNEKRLEFNDWIEAF VEKWIRQKQWLIWTDERKNFANRQ KAAPGGVAAAPGVFAPRPAFGAPS GFAPRPGFAAPSQPPRYSFAAASG YVAPSATSEAAPATSEAPASAEATT ALSSETTTPVNPEETAASPEAATPV NPEETAASSETTTVNPEATPVNPEA PVAEPEKKEEEPAAEPLLAIEPAQT EPAALEAAPSTSAHHHHHH (SEQ ID NO: 3) | ATGAAGACCGAGACGGTGACCTCCAGGAGCAACCCACACCAAGCCATC GAGTACGCCAACCAGGGCCCATCCAGGGACAAGGTGGAGGAGTGGAA GCGCAACGCCTGGACCGACTGGATGGTCCAACTCGACGACGACTGGA AGGACTTCAACGCCCAGATCGAGGAAGAGAAGAAGGCCTGGATTGAG GAGAAGGAAGGCGACTGGGTCATCCTCCTGAAGCACCTCCAAACACAA GTGGCTGCACTTCAACCCAAACCTCGACGCCGAGTACCAGACCGACAT GCTGGCCAAGTCCGAGACGTGGGACGAGAGGCAGTGGAAGATGTGG ATCAGCACCGAGGGCAAGCAGCTCCTGGAGATGGACCTCAAGAAGTG GTTCACCAACAACGAGATGATCTACTGCAAGTGGACCATGGACGAGTG GAACGAGTGGAAGAACGAGAAGATCAAGGAGTGGGTGACCTCCGAGT GGAAGGAGAGCGAGGACCAATACTGGTCCAAGTACGACGACGCCACC ATCCAAACCCTGACCGTCGCCGAGCGCAACCAGTGGTTCAAGTGGAAG GAGAGGATCTACCGCGAGGGCATCGAGTGGAAGAACTGGATCGCCAT CAAGGAGAGCAAGTTCGTGAACGCCAACTGGAACTCCTGGTCTGAGTG GAAGAACGAGAAAGGCTGGAGTTCAACGACTGGATCGAGGCCTTCG TCGAGAAGTGGATCCGCCAAAAGCAGTGGCTGATCTGGACCGACGAG AGGAAGAACTTCGCCAACCGCCAAAAGGCTGCTCCAGGCGGCGTGGC TGCCGCCCCAGGCGTCTTCGCCCCACGCCCAGCCTTCGGCGCCCATCC GGCTTCGCCCCAAGGCCAGGCTTCGCTGCTCCAAGCCAGCCACCACGC TACTCCTTCGCTGCCGCCAGCGGCTACGTGGCTCCATCCGCTACCAGCG AGGCTGCTCCAGCCACCTCCGAGGCCCCAGCCAGCGCCGAGGCTACCA CCGCTCTCTCCAGCGAGACGACCACCCCAGTCAACCCAGAGGAGACGG CTGCTAGCCCGGAGGCTGCTACCCCAGTGAACCCGGAGGAGACGGCT GCCTCCAGCGAGACGACGACGGTCAACCCAGAGGCCACCCCGGTGAA CCCAGAGGCTCCAGTGGCTGAGCCAGAGAAGAAGGAAGAGGAGCCA GCTGCTGAGCCACTGCTCGCTATCGAGCCAGCTCAAACCGAGCCAGCT GCTCTGGAGGCTGCTCCATCCACCAGCGCCCACCACCACCACCACCACT GA (SEQ ID NO: 4) |
| 3 | sporozoite invasion-associated protein 2, putative (SIAP2) | PVX_088860 | MQLELEPAPDYESTSPTVPVRLLLH DDYAPNAEDMFGPEASQVMTNLYE TIDEDGTTTDGYQNGSDDDQSNQS DSNDDAVMLNYLSNETDSFDELIDEI DNHKKKKKIYSPLRKPVLKRSDSSD SLSDYELDEVLRQTENEPEEDEDLD LSLEDSFEVINYPWKDILESSPYSTD HTNEEDFSSLEELELEDPVQEMNFG KLKFFEIGDPDLLIRKTPITPNTKTKS GLEKNGNNTEASNINQHEKEKMDK RKRRTHKQFKNPIENFSVTTTYDDF LKQNGLRDHPSKHQKDSSEPFVLD QYNYRNAKFKNVRFYILRMLYDNIK DIGLKEFQYLKSHKYEVEEFIKNILRN NLICLTFSQEDHLFNDAHLLIEKASIK SEHHHHHH (SEQ ID NO: 5) | ATGCAGCTGGAGCTGGAGCCAGCCCCAGACTACGAGTCCACCAGCCCA ACCGTGCCAGTCAGGCTCCTGCTCCACGACGACTACGCCCCAAACGCC GAGGACATGTTCGGCCCAGAGGCCTCCCAAGTGATGACCAACCTCTAC GAGACGATCGACGAGGACGGCACCACCACCGACGGCTACCAAAACGG CTCCGACGACGACCAAAGCAACCAGTCCGACAGCAACGACGGCGCCGT CATGCTCAACTACCTGTCCAACGAGACGGACAGCTTCGACGAGCTCATC GACGAGATCGACAACCACAAGAAGAAGAAGAAGATCTACTCCCCACTC AGGAAGCCAGTGCTGAAGCGCAGCGACTCCAGCGACTCCCTGAGCGA CTACGAGCTCGACGAGGTCCTGCGCCAGACCGAGAACGAGCCAGAGG AAGACGAGGACCTGGACCTCTCCCTGGAGGACAGCTTCGAGGTCATCA ACTACCCATGGAAGGACATCCTGGAGTCCAGCCCATACAGCACCGACC ACACCAACGAGGAAGACTTCTCCAGCCTGGAGGAGCTGGAGCTGGAG GACCCAGTCCAAGAGATGAACTTCGGCAAGCTGAAGTTCTTCGAGATC GGCGACCCAGACCTGCTCATCAGGAAGACCCCAATCACCCCAAACACC AAGACCAAGTCCGGCCTGGAGAAGAACGGCAACAACACCGAGGCCAG CAACATCAACCAGCACGAGAAGGAGAAGATGGACAAGCGCAAGAGGC GCACCCACAAGCAATTCAAGAACCCAATCGAGAACTTCTCCGTGACCAC CACCTACGACGACTTCCTCAAGCAAAACGGCCTGAGGGACCACCCCAAG CAAGCACCAGAAGGACTCCAGCGAGCCATTCGTGCTCGACCAATACAA CTACCGCAACGCCAAGTTCAAGAACGTCAGGTTCTACATCCTCCGCATG CTGTACGACAACATCAAGGACATCGGCCTCAAGGAGTTCCAGTACCTG AAGTCCCACAAGTACGAGGTCGAGGAGTTCATCAAGAACATCCTCAGG AACAACCTCATCTGCCTGACCTTCAGCCAAGAGGACCACCTGTTCAACG ACGCCCACCTGCTCATCGAGAAGGCCTCCATCAAGAGCGAGCACCACC ACCACCACCACTGA (SEQ ID NO: 6) |

Appendix I-continued

| No. | Protein Name | Protein Reference | Insert aa sequence (add M as start/His-tag at C-term) | Insert DNA sequence (Start from ATG to His-tag stop codon) |
|---|---|---|---|---|
| 4 | rhoptry neck protein 2, putative (RON2) | PVX_117880 | MNAGDGQGVYGGNGINNPLVYHVQ HGVNIPNSNSDKKASDHTPDEDEDT YGRTRNKRYMHRNPGEKYKGSNSP HDSNDDSGDTEYELNEGDVKRLTP KNKKGATTEEVDTYPYGKKTNGSEF PRMNGSETGHYGYNNTGSGGHND ENGYTPIIVKYDNTHAKNRANEIEEN LNKGEYSRIKMAKGKKGQKSGGYE SDGEDSDVDSSNVFYVDNGQDMLI KEKMSRSEGPDEMSEEGLNVKYKA QRGPVNYHFSNYMNLDKRNTLSSN EIELQKMIGPKFSEEVNKYCRLNEPS SKKGEFLNVSFEYSRALEELRSEMI NELQKRKAVGSNYYNNILNAIYTSM NRKNANFGRDAYEDKSFISEANSFR NEEMQPLSAKYNKILROYLCHVFVG NPGVNQLERLYPHNLALGELIEPIRR KYNKLASSSVGLNYEIYIASSSNIYLM GHLLMLSLAYLSYNSYFVQGLKPFY SLETMLMANSDYSFFMYNEVCNVY YHPKGTFNKDITFIPIESRPGRHSTY VGERKVTCDLLELILNAYTLINVHEIQ KVFNTSEAYGYENSISFGHNAVRIFS QVCPRDDAKNTFGCDFEKSTLYNS KVLKMDEGDKENQRSLKRAFDMLR TFAEIESTSHLGDPSPNYISLIFEQNL YTDFYKYLFWYDNRELINVQIRNAG RRKKGKKVKFVYDEFVKRGKQLKD KLIKIDAKYNARSKALLVFYALVDKYA NIFRKSENVRKFFLNDVSSIRHHLYL NSVLTKSPKSNLDSMKKTLEELQSL TNAPLKFIVRGNNLKFLNNVAKFENL FYVNLFIMSSLSRKHHHHHH (SEQ ID NO: 7) | ATGAACGCTGGCGACGGCCAAGGCGTGTACGGCGGAAACGGCATCAA CAACCCACTCGTGTACCACGTCCAGCACGGCGTCAACATCCCAAACTCC AACAGCGACAAGAAGGCCAGCGACCACACCCCAGACGAGGACGAGGA CACCTACGGCAGGACCCGCAACAAGAGGTACATGCACCGCAACCCAG GCGAGAAGTACAAGGGCTCCAACAGCCCACACGACTCCAACGACGACA GCGGCGACACCGAGTACGAGCTGAACGAGGGCGACGTGAAGAGGCTC ACCCCAAAGAACAAGAAGGGCGCCACCACCGAGGAAGTGGACACCTA CCCATACGGCAAGAAGACCAACGGCAGCGAGTTCCCACGCATGAACG GCTCCGAGACGGGCCACTACGGCTACAACAACACCGGCAGCGGCGGC CACAACGACGAGAACGGCTACACCCCAATCATCGTGAAGTACGACAAC ACCCACGCCAAGAACAGGGCCAACGAGATCGAGGAGAACCTCAACAA GGGCGAGTACTCCCGCATCAAGATGGCCAAGGGCAAGAAGGGCCAAA AGTCCGGCGGCTACGAGAGCGACGGCGAGGACTCCGACGTCGACTCC AGCAACGTGTTCTACGTCGACAACGGCCAGGACATGCTGATCAAGGAG AAGATGTCCAGGAGCGAGGGCCCAGACGAGATGAGCGAGGAAGGCC TCAACGTGAAGTACAAGGCCCAAAGGGGCCCAGTCAACTACCACTTCT CCAACTACATGAACCTGGACAAGCGCAACACCCTCTCCAGCAACGAGA TCGAGCTCCAGAAGATGATCGGCCCAAAGTTCAGCGAGGAAGTGAAC AAGTACTGCAGGCTGAACGAGCCATCCAGCAACAAGAAGGGCGAGTT CCTCAACGTCTCCTTCGAGTACAGCAGGGCCCTGGAGGAGCTGAGGTCCGA GATGATCAACGAGCTGCAAAAGCGCAAGGCCGTGGGCAGCAACTACT ACAACAACATCCTCAACGCCATCTACACCTCCATGAACAGGAAGAACGC CAACTTCGGCCGCGACGCCTACGAGGACAAGTCCTTCATCAGCGAGGC CAACAGCTTCAGGAACGAGGATGCAACCACTCTCCGCCAAGTACAA CAAGATCCTGCGCCAGTACCTCTGCCACGTGTTCGTCGGCAACCCAGGC GTGAACCAACTGGAGCGCCTGTACTTCCACAACCTCGCCCTGGGCGAG CTGATCGAGCCAATCAGGCGCAAGTACAACAAGCTGGCCTCCAGCTCC GTCGGCCTCAACTACGAGATCTACATCGCCAGCTCCAGCAACATCTACC TCATGGGCCACCTCCTGATGCTCAGCCTGGCCTACCTGTCCTACAACAG CTACTTCGTGCAGGGCCTCAAGCCATTCTACTCCCTGAAACCATGCTC ATGGCCAACTCCGACTACAGCTTCTTCATGTACAACGAGGTGTGCAACG TCTACTACCACCCAAAGGGCACCTTCAACAAGGACATCACCTTCATCCC AATCGAGAGCAGGCCAGGCAGGCACTCCACCTACGTGGGCGAGAGGA AGGTCACCTGCGACCTCCTGGAGCTCATCCTGAACGCCTACACCCTGAT CAACGTGCACGAGATCCAAAAGGTCTTCAACACCAGCGAGGCCTACGG CTACGAGAACTCCATCAGCTTCGGCCACAACGCCGTGAGGATCTTCTC CAGGTCTGCCCACGCGACGACGCCAAGAACACCTTCGGCTGCGACTTC GAGAAGAGCACCCTGTACAACTCCAAGGTGCTCAAGATGGACGAGGG CGACAAGGAGAACCAGAGGTCCCTGAAGCGCGCCTTCGACATGCTCCG CACCTTCGCCGAGATCGAGTCCACCAGCCACCTCGGCGACCCAAGCCC AAACTACATCTCCCTGATCTTCGAGCAAAACCTCTACACCGACTTCTACA AGTACCTGTTCTGGTACGACAACAGGGAGCTCATCAACGTGCAGATCC GCAACGCCGGCAGGCGCAAGAAGGGCAAGAAGGTGAAGTTCGTCTAC GACGAGTTCGTCAAGAGGGGCAAGCAACTGAAGGACAAGCTCATCAA GATCGACGCCAAGTACAACGCCCGCAGCAAGGCCCTCCTGGTGTTCTA CGCCCTGGTCGACAAGTACGCCAACATCTTCAGGAAGTCCGAGAACGT GCGCAAGTTCTTCCTCAACGACGTCTCCAGCATCAGGCACCACCTCTAC CTGAACAGCGTGCTGACCAAGTCCCCAAAGAGCAACCTCGACAGCATG AAGAAGACCCTGGAGGAGCTGCAGTCCCTCACCAACGCCCCACTGAAG TTCATCGTCAGGGGCAACAACCTGAAGTTCCTCAACAACGTGGCCAAG TTCGAGAACCTGTTCTACGTGAACCTCTTCATCATGTCCAGCCTCTCCCG CAAGCACCACCACCACCACCACTGA (SEQ ID NO: 8) |
| 5 | Plasmodium exported protein, unknown function | PVX_101530 | MNVNKKSSGEENNTKQALGLRVSR TLAKDGANENAEEGLSEEEEEAVEE GEEEAVEEGEEEVVEEGEEVVEG EEEEVVEGEEEVVEDEEVVEGEEYA EGEEPVEGEEYAEGEEPVEGEEPV VEEYAEGEEPVEGEEYAEGEEPV EGEEVVEGEEVVEGEEVAEGEEVA EGEEVAEGEEVAEGEEVVEGEEVA EGEEVAEGEEAAEEGAAEEGATEE GATEEGATKEEATEKAAEGEETAES EKPAEEQPTTFVETVEKKVEPVSKP PFKPLFPVDEKYLETLEDIAQSFLKE FQEAEGKRKQKKVKKRAKKITKKLA KEYAKKFKSKKKHHHHHH (SEQ ID NO: 9) | ATGAACGTCAACAAGAAGTCCAGCGGCGAGGAGAACAACACCAAGCA AGCTCTGGGCCTGAGGGTGTCCCGCACCCTCGCTAAGGACGGCGCCAA CGAGAACGCCGAGGAGGGCCTCAGCGAGGAAGAGGAAGAGGCCGTC GAGGAAGGCGAGGAAGAGGCCGTGGAGGAAGGCGAGGAAGAGGTG GTCGAGGAAGGGGCGAGGAAGTGGTCGAGGGCGAGGAAGAGGAA GTGGTGGAGGGGAGGAAGAGGTGGTGGAGGATGAGGAAGTGGTG GAGGGCGAGGAGTACGCTGAGGGCGAGGAGCCGGTGGAGGGGGAG GAGTACGCCGAGGGGGAGGAGCCAGTGGAGGGCGAGGAGCAGTGG AGGTGGAGGAGTACGCGGAGGGGGAGGAGCCGGTGGAAGGTGAGG AGTACGCCGAGGGCGAGGAGCCTGTCGAGGGGGAGGAAGTGGTGGA AGGCGAGGAAGTGGTGGAAGGTGAGGAAGTGGCTGAGGGCGAGGA AGTGGCCGAGGGGGAGGAAGTGGCCGAGGGCGAGGAAGCCGTGGA GGGCGAGGAAGTGGCCGAGGGGGAGGAAGTGGCGAGGGCGAGGA AGTGGCCGAAGGCGAGGAGGCCGCTGAGGAAGGCGCTGCCGAGGAA GGCGCCACGGAGGAAGGCGCTACCGAGGAAGGCGCCACCAAGGAAG AGGCCACCGAGAAGGCTGCTGAGGGCGAGGAGACGGCTGAGTCCGA GAAGCCAGCTGAGGAGCAACCAACCACCTTCGTGGAGACGGTCGAGA AGAAGGTGGAGCCAGTCAGCAAGCCACCATTCAAGCCACTCTTCCCAG TCGACGAGAAGTACCTCGAAACCCTGGAGGACATCGCCCAATCCTTCCT |

Appendix I-continued

| No. | Protein Name | Protein Reference | Insert aa sequence (add M as start/His-tag at C-term) | Insert DNA sequence (Start from ATG to His-tag stop codon) |
|---|---|---|---|---|
| | | | | GAAGGAGTTCCAAGAGGCCGAGGGCAAGAGGAAGCAGAAGAAGGTG<br>AAGAAGCGCGCCAAGAAGATCACCAAGAAGCTCGCCAAGGAGTACGC<br>CAAGAAGTTCAAGTCCAAGAAGAAGCACCACCACCACCACCACTGA<br>(SEQ ID NO: 10) |
| 6 | tryptophan/threonine-rich antigen | PVX_112680 | MPKPDQKNLKGGVKNAPLQQRKGS<br>VPINPPKPVNDKLKDGSNKTETKNA<br>KNTLSKPPMQVTDKSKDEAKKTPLQ<br>STPKLTPKTKEVPKESNMEMWLKDT<br>KDEYENLKCQYRTCLYDWFRKINDE<br>YNELLNKLEEKWAKFPNDPKNKDVF<br>DNLKTSSLKNDEKKAQWMRKNLKD<br>LMREQVDEWLEGKKKIYEGMSPTY<br>WDAWEKKIAKGLMGAAWYKMNSS<br>GRTKEWDKLRNELETRYNKKIKSLW<br>GGFHRDVYFRFKEWIEEVFNKWIEN<br>KQIDTWMNSGKKHHHHHH<br>(SEQ ID NO: 11) | ATGCCAAAGCCAGACCAAAAGAACCTCAAGGGCGGCGTGAAGAACGC<br>CCCCACTGCAACAGAGGAAGGGCTCCGTGCCAATCAACCCACCAAAGCC<br>AGTCAACGACAAGCTCAAGGACGGCAGCAACAAGACCGAGACGAAGA<br>ACGCCAAGAACACCCTGTCCAAGCCACCAATGCAAGTGACCGACAAGA<br>GCAAGGACGAGGCCAAGAAGACCCCACTCCAGTCCACCCCAAAGCTGA<br>CCCCAAAGACCAAGGAAGTGCCAAAGGAGAGCAACATGGAGATGTGG<br>CTCAAGGACACCAAGGACGAGTACGAGAACCTCAAGTGCCAGTACAG<br>GACCTGCCTGTACGACTGGTTCCGCAAGATCAACGACGAGTACAACGA<br>GCTCCTGAACAAGCTGGAGGAGAAGTGGGCCAAGTTCCCAAACGACC<br>CAAAGAACAAGGACGTGTTCGACAACCTCAAGACCTCCAGCCTGAAGA<br>ACGACGAGAAGAAGGCCCAGTGGATGAGGAAGAACCTCAAGGACCTG<br>ATGAGGGAGCAGGTGGACGAGTGGCTGGAGGGCAAGAAGAAGATCT<br>ACGAGGGCATGTCCCCAACCTACTGGGACGCCTGGGAGAAGAAGATC<br>GCTAAGGGCCTGATGGGCGCTGCTTGGTACAAGATGAACTCCTCCGGC<br>AGGACCAAGGAGTGGGACAAGCTCAGGAACGAGCTCGAAACCCGCTA<br>CAACAAGAAGATCAAGTCCCTCTGGGGCGGCTTCCACAGGGACGTGTA<br>CTTCCGCTTCAAGGAGTGGATCGAGGAAGTGTTCAACAAGTGGATCGA<br>GAACAAGCAAATCGACACCTGGATGAACAGCGGCAAGAAGCACCACC<br>ACCACCACCACTGA (SEQ ID NO: 12) |
| 7 | hypothetical protein | PVX_097715 | MQYSIVKNEITKRRKPKIRNESPPDG<br>NSPGGGKNNAAGNNGGGDNNAKN<br>KAANKAANNAANKAANNAANNAAN<br>NAANNAANNAANNAANNAANNAAN<br>NAANNAANNANEQNGNKKKKGKPK<br>KEEADLPVQAQNENDRNKIEDIADE<br>AELFAEEAKMLADLASKRSKEVEQIL<br>SSIPENKFGSEPKEDAIFAAKDAVRA<br>SEDAMKAAQKARAAETVTQANEEK<br>DKAKTAKELAERSAQIVKKNAVEALK<br>EFGKIAEAAEMEAIKIPIPENLKPKKK<br>VKQPRAAAQKVEPTQATAHKVVPP<br>PAEPPRAPSPPPPPAKPEAAPPAKE<br>VAPAVTTPEAPKEEAPKADAAPAAP<br>QPAAESKVAKEPTDQSAENQSDSL<br>YKETNIKEGTEEAGTGQEQKQEPEL<br>QNLLEQQMNIFYILVQFFKSKIKALIK<br>FLLILVSHHHHHH<br>(SEQ ID NO: 13) | ATGCAATACTCCATCGTGAAGAACGAGATCACCAAGAGGCGCAAGCCA<br>AAGATCAGGAACGAGTCCCCACCAGACGGCAACAGCCCAGGCGGCGG<br>CAAGAACAACGCTGCTGGCAACAACGGCGGCGGCAACAACGCCA<br>AGAACAAGGCTGCTAACAAGGCTGCTAACAACGCCGCCAACAAGGCC<br>GCCAACAACGCTGCTAACAACGCCGCGAACAACGCCGCCAACAACGCC<br>GCCAACAACGCAGCTAACAACGCCGCTAACAACGCGGCCAACAACGCC<br>GCCAACAACGCGGCGAACAACGCTGCCAACAACGCCAACGAGCAAAA<br>CGGCAACAAGAAGAAGAAGGGCAAGCCAAAGAAGGAAGCCGAC<br>CTCCCAGTGCAAGCCCAGAACGAGAACGACAGGAACAAGATCGAGGA<br>CATCGCTGACGAGGCTGAGCTGTTCGCTGAGGAAGCCAAGATGCTCGC<br>CGACCTGGCCTCCAAGCGCAGCAAGGAAGTGGAGCAGATCCTCTCCAG<br>CATCCCAGAGAACAAGTTCGGCTCCGAGCCAAAGGAAGACGCCATCTT<br>CGCTGCTAAGGACGCCGTGAGGGCTAGCGAGGACGCCATGAAGGCTG<br>CTCAAAAGGCCAGGGCCGCTGAGACGGTCACCCAGGCCAACGAGGAG<br>AAGGACAAGGCTAAGACCGCTAAGGAGCTGGCTGAGAGGTCCGCTCA<br>AATCGTGAAGAAGAACGCTGTCGAGGCCCTGAAGGAGTTCGGCAAGA<br>TCGCCGAGGCCGCCGAGATGGAGGCCATCAAGATCCCCAATCCCAGAG<br>AACCTGAAGCCAAAGAAGAAGGTGAAGCAACCAAGGGCCGCCGCCCA<br>AAAGGTGGAGCCAACCCAAGCTACCGCTCACAAGGTGGTGCCACCACC<br>AGCTGAGCCACCACGCGCCCATCCCCACCACCACCACCACCAGCTAAGCCA<br>GAGGCTGCCCCACCAGCTAAGGAAGTGGCTCCAGCTGTCACCACCCCA<br>GAGGCTCCAAAGGAAGAGGCCCCAAAGGCTGACGCTGCTCCAGCTGC<br>CCCACAGCCAGCCGCCGAGTCCAAGGTCGCCAAGGAGCCAACCGACCA<br>GAGCGCCGAGAACCAATCCGACAGCCTCTACAAGGAGACGAACATCAA<br>GGAAGGCACCGAGGAAGCCGGCACCGGCCAAGAGCAGAAGCAAGAG<br>CCAGAGCTCCAAAACCTCCTGGAGCAACAGATGAACATCTTCTACATCC<br>TGGTGCAGTTCTTCAAGTCCAAGATCAAGGCCCTCATCAAGTTCCTCCT<br>GATCCTGGTCAGCCATCACCACCACCACCACTGA<br>(SEQ ID NO: 14) |
| 8 | 41K blood stage antigen precursor 41-3, putative | PVX_084420 | MDENTGWPIDYEFNSKTLPSIEVKLS<br>PPENPLPQVAAEIKLLESARLKLEEG<br>MMQKLEDEYNKSLSSAKIKIQDTVE<br>KSLSIFNDPNMLGSVISNSVKMLRSE<br>NVKKRTENVQAKHNLKKMQTVNQA<br>KSGPLPPPELRKHTSFLEQNYVNRV<br>LPSVKISLSELTEPSVEIKEKIEEMEQ<br>YRTDEEVAMFEMAISEFSILTDITILE<br>LEKQIQLQLNPPLVDKKVVHRALTKE<br>LKELEQREEKQKIKENFQRQSSFIEA<br>GEDEDTGNILNVKISQTDYGYPTVD<br>ELVMQMQKRRDISEKLERQKILDLQ<br>MKLLKAQSEMIKDALHFALSKVIAQY<br>SPLVETMKLESMRMLHHHHHH<br>(SEQ ID NO: 15) | ATGGACGAGAACACCGGCTGGCCAATCGACTACGAGTTCAACTCCAAG<br>ACCCTGCCAAGCATCGAGGTGAAGCTCTCCCCACCAGAGAACCCACTG<br>CCACAGTCGCCGCCGAGATCAAGCTCCTGGAGAGCGCCCGGCTGAA<br>GCTCGAAGAGGGCATGATGCAGAAGCTGGAGGACGAGTACAACAAGTC<br>CCTGTCCAGCGCCAAGATCAAGATCCAAGACACCGTGGAAGTCCCT<br>CAGCATCTTCAACGACCCAAACATGCTGGGCTCCGTGATCTCCAACAGC<br>GTCAAGATGCTCAGGAGCGAGAACGTGAAGAAGCGCACCGAGAACGT<br>CCAGGCCAAGCACAACCTCAAGAAGATGCAGACCGTCAACCAAGCCA<br>AGAGCGGCCCACTCCCACCACCAGAGCTGCGCAAGCACACCTCCTTCCTG<br>GAGCAAAACTACGTGAACAGGGTCCTGCCATCCGTGAAGATCTCCCTC<br>AGCGAGCTGACCGAGCCAAGCGTCGAGATCAAGGAGAAGATCGAGGA<br>GATGGAGCAGTACAGGACCGACGAGGAAGTGGCCATGTTCGAGATGG<br>CCATCTCCGAGTTCAGCATCCTCACCGACATCACCATCCTGGAGCTGGA<br>GAAGCAAATCCAGCTCCAACTGAACCCATTCCTCGTCGACAAGAAGGT<br>GGTCCACAGGGCCCTGACCAAGGAGCTCAAGGAGCTGGAGCAGCGCG<br>AGGAGAAGCAAAAGATCAAGGAGAACTTCCAGAGGCAATCCAGCTTC<br>ATCGAGGCTGGCGAGGACGAGGACACCGGCAACATCCTCAACGTGAA<br>GATCTCCCAGACCGACTACGGCTACCCAACCGTGGACGAGCTCGTCAT<br>GCAGATGCAAAAGAGGCGCGACATCTCCGAGAAGCTGGAGCGCCAGA<br>AGATCCTCGACCTGCAGATGAAGCTCCTGAAGGCCCAGAGCGAGATGA |

Appendix I-continued

| No. | Protein Name | Protein Reference | Insert aa sequence (add M as start/His-tag at C-term) | Insert DNA sequence (Start from ATG to His-tag stop codon) |
|---|---|---|---|---|
| | | | | TCAAGGACGCCCTCCACTTCGCCCTGTCCAAGGTCATCGCCCAATACAG CCCACTCGTCGAGACGATGAAGCTGGAGAGCATGAGGATGCTCCACCA CCACCACCACCACTGA (SEQ ID NO: 16) |
| 9 | rhoptry-associated protein 1, putative (RAP1) | PVX_085930 | MSSDGKSSASAKSGSKSGSKYGGS SYSDYSAYDSGSASSVGSREFENE MYEFALQHPMEKLTKEMDILKNDYT KVKEEEGKILDEEHKEIEEKRKEERL KMLAEGDVEKNKGDEEINFIKHDYT DTRIRGGFTEFLSNLNPFKKEIKPMK KEISLITYIPDKIVNKEKIMRDLGISHK YEPYQQSILYTCPNSVFFFDSMENL RKELDKNHEKEAITNKILDHNKECLK NFGLFDFELPDNKTKLGNVIGSIGEY HVRLYEIENDLLKYQPSLDYMTLAD DYKLVKNDVNTLENVNFCLLNPKTL EDFLKKKEIMELMGEDPIAYEEKFTK YMEESINCHLESLIYEDLDSSQDTKI VLKNVKSKLYLLONGLTYKSKKLINK LFNEIQKNPEPIFEKLTWIYENMYHL KRDYTFLAFKTVCDKYVSHNSIYTSL QGMTSYIIEYTRLYGACFKNITIYNAV ISGIHEQMKNLMKLMPRSGLLSDVH FEALLHKENKKITRTDYVLNDYDPSV KAYALTQVERLPMVSVINSFFEAKKK ALSKMLAQMKLDLFTLTNEDLKIPND KGANSKLTAKLISIYKAEIKKYFKEMR DDYVFLIKARYKGHYKKNYLLYKRLE HHHHHH (SEQ ID NO: 17) | ATGAGCAGCGACGGCAAGTCCAGCGCTTCCGCTAAGTCCGGCAGCAA GTCCGGCAGCAAGTACGGCGGCTCCAGCTACTCCGACTACAGCGCCTA CGATTCCGGCAGCGCCTCCAGCGTGGGCAGCCGCGAGTTCGAGAACG AGATGTACGAGTTCGCCCTGCAACACCCGATGGAGAAGCTCACCAAGG AGATGGACATCCTGAAGAACGACTACACCAAGGTGAAGGAAGAGGAA GGCAAGATCCTCGACGAGGAGCACAAGGAGATCGAGGAGAAGAGGA AGGAAGAGCGCCTCAAGATGCTGGCCGAGGGCGACGTGGAGAAGAA CAAGGGCGACGAGGAGATCAACTTCATCAAGCACGACTACACCGACAC CAGGATCCGCGGCGGCTTCACCGAGTTCCTCTCCAACCTGAACCCATTC AAGAAGGAGATCAAGCCGATGAAGAAGGAGATCTCCCTCATCACCTAC ATCCCAGACAAGATCGTCAACAAGGAGAAGATCATGCGCGACCTGGG CATCTCCCACAAGTACGAGCCATACCAACAGAGCATCCTCTACACCTGC CCAAACTCCGTGTTCTTCTTCGACAGCATGGAGAACCTCAGGAAGGAG CTGGACAAGAACCACGAGAAGGAAGCCATCACCAACAAGATCCTCGAC CACAACAAGGAGTGCCTCAAGAACTTCGGCCTGTTCGACTTCGAGCTCC CAGACAACAAGACCAAGCTGGGCAACGTCATCGGCTCCATCGGCGAGT ACCACGTGAGGCTCTACGAGATCGAGAACGACCTCCTGAAGTACCAAC CAAGCCTGGACTACATGACCCTCGCCGACGACTACAAGCTGGTGAAGA ACGACGTCAACACCCTGGAGAACGTGAACTTCTGCCTCCTGAACCCAA AGACCCTGGAGGACTTCCTCAAGAAGAAGGAGATCATGGAGCTGATG GGCGAGGACCCCAATCGCCTACGAGGAAGTTCACCAAGTACATGGA GGAGTCCATCAACTGCCACCTGGAGAGCCTGATCTACGAGGACCTCGA CTCCAGCCAAGACACCAAGATCGTGCTCAAGAACGTCAAGTCCAAGCT GTACCTCCTGCAGAACGGCCTCACCTACAAGAGCAAGAAGCTCATCAA CAAGCTGTTCAACGAGATCCAGAAGAACCCAGAGCCAATCTTCGAGAA GCTCACCTGGATCTACGAGAACATGTACCACCTGAAGCGCGACTACAC CTTCCTCGCCTTCAAGACCGTGTGCGACAAGTATGTGTCCCACAACAGC ATCTACACCTCCCTGCAAGGCATGACCAGCTACATCATCGAGTACACCA GGCTCTACGGCGCCTGCTTCAAGAACATCACCATCTACAACGCCGTCAT CTCCGGCATCCACGAGCAGATGAAGAACCTCATGAAGCTGATGCCAAG GTCCGGCCTCCTGAGCGACGTGCACTTCGAGGCCCTCCTGCACAAGGA GAACAAGAAGATCACCCGCACCGACTACGTGCTCAACGACTACGACCC ATCCGTCAAGGCCTACGCCCTGACCCAAGTGGAGAGGCTCCCAATGGT GTCCGTCATCAACAGCTTCTTCGAGGCCAAGAAGAAGGCCCTCAGCAA GATGCTGGCCCAGATGAAGCTCGACCTGTTCACCCTGACCAACGAGGA CCTCAAGATCCCAAACGACAAGGGCGCCAACTCCAAGCTCACCGCCAA GCTGATCAGCATCTACAAGGCCGAGATCAAGAAGTACTTCAAGGAGAT GAGGGACGACTACGTCTTCCTGATCAAGGCCCGCTACAAGGGGCACTA CAAGAAGAACTACCTCCTGTACAAGCGCCTGGAGCACCACCACCACCA CCACTGA (SEQ ID NO: 18) |
| 10 | hypothetical protein, conserved | PVX_094830 | MNTRASKFANSKRKRNGNAMRENK LNNDDVDHYSFLSLRTANEEKAATE NDSNNAKKEGEENTNGNEKKNEEN GSGNEKRNEENNANEKKNEQTNDQ SNGQSNSQTNIPKKNEAVPPEKKIN KENLLEYGTHDKDGHFIPSYKTLTDE ILSTNNSLERASSFLKIACSHIMKIVE FIPESKLSSQYIKVESKNVYIKDITSE CQNIFFSLEKLTMTMIVLNSKMNKLV YVQDKHHHHHH (SEQ ID NO: 19) | ATGAACACCAGGGCCTCCAAGTTCGCCAACAGCAAGAGGAAGCGCAA CGGCAACGCCATGCGCGAGAACAAGCTCAACAACGACGACGTGGACC ACTACTCCTTCCTCAGCCTGAGGACCGCTAACGAGGAGAAGGCTGCTA CCGAGACGACTCCAACAACGCCAAGAAGGAAGGCGAGGAGAACACC AACGGCAACGAGAAGAAGAACGAGGAGAACGCAGCGAACAACGAGA AGCGCAACGAGGAGAACAACGCTAACGAGAAGAAGAACGAGCAAACC AACGACCAGTCCAACGGCCAATCCAACAGCCAGACCAACATCCCAAAG AAGAACGAGGCCGTCCCACCAGAGAAGAAGATCAACAAGGAGAACCT CCTGGAGTACGGCACCCACGACAAGGACGGCCACTTCATCCCAAGCTA CAAGACCCTCACCGACGAGATCCTGTCCACCAACAACAGCCTGGAGAG GGCCTCCAGCTTCCTGAAGATCGCCTGCTCCCACATCATGAAGATCGTG GAGTTCATCCCAGAGTCCAAGCTGTCCAGCCAATACATCAAGGTGGAG AGCAAGAACGTCTACATCAAGGACATCACCTCCGAGTGCCAGAACATC TTCTTCAGCCTGGAGAAGCTGACCATGACCATGATCGTCCTCAACAGCA AGATGAACAAGCTGGTCTACGTGCAAGACAAGCACCACCACCACCACC ACTGA (SEQ ID NO: 20) |
| 11 | tryptophan-rich antigen (Pv-fam-a) | PVX_511267 | MPKPAQNLKGGVKKPSLQQTKSPL PSKPPKPVNDKLKDDSNKTETKDAK NGLNKPPKNINDKVKDGENKTPSQD LNEPSFKLPMRQKASSWDAWLKGT KKDYENLKCFAKGNLYDWLCSVRD SFELYLQSLESKWTSCSDNTTTVFL CECLAESSGWGDPQWESWVKKEL KEQLKTEAQAWISTKKKDFDGLTSK YFSLWKDHRRKELEEEAWKTKASS GGLSEWEELTDKMNTRYTNNLDNM WSNYSGDLLFRFDEWSPEVLEKWI ESKQWNQWVKKVRKHHHHHH (SEQ ID NO: 21) | ATGCCAAAGCCAGCCCAAAACCTCAAGGGCGGCGTGAAGAAGCCATC CCTCCAACAGACCAAGTCCCCACTGCCAAGCAAGCCACCAAAGCCAGT CAACGACAAGCTCAAGGACGACAGCAACAAGACCGAGACGAAGGACG CCAAGAACGGCCTGAACAAGCCACCCAAAGAACATCAACGACAAGGTG AAGGACGGCGAGAACAAGACCCCATCCCAAGACCTCAACGAGCCAAG CTTCAAGCTGCCAATGAGGCAAAAGGCCTCCAGCTGGGACGCTTGGCT CAAGGGCACCAAGAAGGACTACGAGAACCTGAAGTGCTTCGCCAAGG GCAACCTCTACGACTGGCTGTGCTCCGTCCGCGACAGCTTCGAGCTCTA CCTGCAATCCCTGGAGAGCAAGTGGACCTCCTGCAGCGACAACACCAC CACCGTGTTCCTCTGCGAGTGCCTCGCTGAGTCCAGCGGCTGGGGCGA CCCACAGTGGGAGTCCTGGGTCAAGAAGGAGCTCAAGGAGCAACTGA AGACCGAGGCCCAGGCCTGGATCAGCACCAAGAAGAAGGACTTCGAC GGCCTCACCTCCAAGTACTTCAGCCTGTGGAAGGACCACAGGCGCAAG |

Appendix I-continued

| No. | Protein Name | Protein Reference | Insert aa sequence (add M as start/His-tag at C-term) | Insert DNA sequence (Start from ATG to His-tag stop codon) |
|---|---|---|---|---|
| | | | | GAGCTGGAGGAAGAGGCCTGGAAGACCAAGGCCTCCAGCGGCGGCCT CTCCGAGTGGGAGGAGCTGACCGACAAGATGAACACCAGGTACACCA ACAACCTCGACAACATGTGGTCCAACTACAGCGGCGACCTCCTGTTCCG CTTCGACGAGTGGTCCCCAGAGGTGCTGGAGAAGTGGATCGAGAGCA AGCAGTGGAACCAGTGGGTGAAGAAGGTCAGGAAGCACCACCACCAC CACCACTGA (SEQ ID NO: 22) |
| 12 | trypto-phan-rich antigen (Pv-fam-a) | PVX_112670 | MVTEGGDNLDDDLGGDLEGLLGDD AEGGAAGGEGAAAAASAEGLSGEV ENELLYVKEDDDDAPAATPDEKPST SGEETPAAFVDLVNETVPPPAKAPL PLQTKAPQGPKIKDWNQWMKQAKK DFSGYKGTMHTQRHEWTKEKEDEL QKFCKYLEKRWMNYTGNIDRECRS DFLKSTQNWNESQWNKWVKSEGK HHMNKQPQKWLDYNKYKLQDWTN TEWNKWKTTVKEQLDDEEWKKKEA AGKTKEWIKCTDKMEKKCLKKTKKH CKNWEKKANSSFKKWEGDFTKKWT SNKQWNSWCKELEKHHHHHH (SEQ ID NO: 23) | ATGGTGACCGAGGGCGGCGACAACCTCGACGACGACCTCGGCGGCGA CCTGGAGGGCCTCCTGGGCGACGACGCTGAGGGCGGCGCCGCCGGCG GCGAGGGCGCTGCCGCCGCCGCCTCCGCCGAGGGCCTGAGCGGCGAG GTGGAGAACGAGCTCCTCTACGTGAAGGAAGACGACGACGACGCTCC AGCTGCTACCCCAGACGAGAACGCCATCCACCAGCGGCGAGGAGACGC CAGCTGCTTTCGTGGACCTCGTCAACGAGACGGTGCCACCACCAGCTA AGGCCCCACTCCCACTGCAAACCAAGGCCCCACAGGGCCCAAAGATCA AGGACTGGAACCAGTGGATGAAGCAGGCCAAGAAGGACTTCTCCGGC TACAAGGGCACCATGCACACCCAAAGGCACGAGTGGACCAAGGAGAA GGAAGACGAGCTGCAGAAGTTCTGCAAGTACCTGGAGAAGCGCTGGA TGAACTACACCGGCAACATCGACAGGGAGTGCCGCTCCGACTTCCTGA AGAGCACCCAAAACTGGAACGAGTCCCAGTGGAACAAGTGGGTGAAG AGCGAGGGCAAGCACCACCATGAACAAGCAATTCCAGAAGTGGCTGGA CTACAACAAGTACAAGCTCCAAGACTGGACCAACACCGAGTGGAACAA GTGGAAGACCACCGTCAAGGAGCAGCTGGACGACGAGGAGTGGAAG AAGAAGGAAGCCGCCGGCAAGACCAAGGAGTGGATCAAGTGCACCGA CAAGATGGAGAAGAAGTGCCTCAAGAAGACCAAGAAGCACTGCAAGA ACTGGGAGAAGAAGGCCAACTCCAGCTTCAAGAAGTGGGAGGGCGAC TTCACCAAGAAGTGGACCTCCAACAAGCAGTGGAACAGCTGGTGCAAG GAGCTGGAGAAGCACCACCACCACCACCACTGA (SEQ ID NO: 24) |
| 13 | Hyp, huge list of orthologs, paralogs, synteny with PyLSA3 (PyLSA3syn-2) | PVX_002550 | mAVEVVQEAADEVLEEEKIEEPLEIV EEEPVQVAAEEPVEEVLEEVVQEAA DEVMEEEKIEEPLEIVAEEPLEIVAEE PVQVAAEEVLVEKEEVNENILNIVEEI KESIVDKLEANEEASEEGNEDLLESA EEAAEEVAEEAVDTTTEADVVETVE EEAANATTEVSAEESLEVSTEAPEE TTESESHETFEEDILKNLEENKEANE NALEDIKEMKEEFLDYVEQRVEDNE NVLVDLLQHLERNAHVNESVLEDLE EIKEDLLANIQMAEEETRKEVTDASAE SAEEVEEPVEVSAEVAAEEPVEVAA EEPVEVTAEEPVEVTAEEPVEIPTEE NIFDVIEEIKEKVLENLEETTAESVAE SVGEGADENALDVLKEMQESLLENF GQKIEANENILASVLENIQEKVELNK SVLVDVLAELKEEAVSQRETAQEVA AELVEEAAEVPAVEVPEEEVVEPAV EVVEEPVEEEVVEPVVDVIEEPAVE VVEPVPEETVEEPVEVTAAEEPVEVT AEEPVEETVEEPVVEVVEEPVEEPV VEAIEEPVVEPVVEPAVEVIEDATEE PVEEAAEEPDVEVAEGSAIESVEEA FEQIIEDAAQVIAEESVEETAEQILEQ ATQQAVTEEAADAADVADAEEAVGTA QVVTEESVAEAIEDTVEEISAEPIQAT IEGIVGEVVESVEENIEAVEEAIKDIV EGAVEGAPELSLEEMIEDVMVGTVA EEDSAKEAAEETVEEVVQEDAAEEE AAKEAAEETVEEAEREATQEAVEET VEDVVEEVSAEAVEEIVLETPEGTSD ESVETVVEHAVEDSLGETIATIVDDV AEETTEKSEESVVDNLGVKVEEVLD VDVEEVAQEAADDVIMRVSENESEG ESGAESGEEVEELESALFEVEKDIKK KVLDMFSGNVEFDKESEKLALDLQ KNLLShhhhhh (SEQ ID NO: 25) | ATGGCTGTGGAGGTGGTCCAAGAGGCCGCTGACGAGGTGCTCGAAGA GGAGAAGATCGAGGAGCCACTGGAGATCGTGGAGGAAGAGCCAGTG CAAGTCGCCGCCGAGGAGCCAGTCGAGGAAGTGCTCGAAGAGGTGGT GCAAGAGGCCGCCGACGAGGTCATGGAGGAAGAAGATCGAGGAG CCTCTGGAGATCGTCGCTGAAGAACCTCTGGAGATCGTGGCTGAGGAG CCTGTGCAGGTGGCTGCCGAGGAAGTGCTGGTCGAGAAGGAAGAGGT GAACGAGAACATCCTCAACATCGTGGAGGAGATCAAGGAGAGCATCG TCGACAAGCTGGAGGCCAACGAGGAAGCCAGCGAGGAAGGCAACGA GGACCTCCTGGAGTCCGCTGAGGAAGCCGCTGAGGAAGTGGCTGAGG AAGCCGTGGACACCACCACCGAGGCTGACGTGGTGGAGACGGTGGAG GAAGAGGCCGCTAACGCTACCACCGAGGTGTCCGCTGAGGAGAGCCT GGAGGTGTCCACCGAGGCTCCAGAGGAAACGACCGAGTCCGAGAGCC ACGAGTTCGAGGAAGACATCCTGAAGAACCTGGAGGAGAACAAG GAAGCCAACGAGAACGCCCTGGAGGACATCAAGGAGATGAAGGAAG AGTTCCTCGACTACGTGGAGCAAAGGGTCGAGGACAACGAGAACGTG CTGGTCGACCTCCTGCAGCATCTGGAGCGCAACGCCCACGTGAACGAA AGCGTCCTGGAGGACCTGGAGGAGATCAAGGAAGACCTCCTGGCCAA CATCCAAATGGCCGAGGAGACGAGGAAGGAAGTGACCGACGCTTCCG CTGAGAGCGCTGAGGAAGTGGAGGAGCCCGTCGAGGTGTCCGCTGAG GTGGCTGCTGAGGAAGTGGAGGAACCGCTGTCGAGGTGGCCGCCGAGGAGCCAGTGGA GGTCACCGCTGAGGAGCCTGTTGAGGTGACGCTGAGGAGCCAGTGG AGATCCCAACCGAGGAGAACATCTTCGACGTGATCGAGGAGATCAAG GAGAAGGTCCTGGAGAACCTGGAGGAGACGACCGCTGAGAGCGTGG CTGAGTCCGTGGGCGAGGGCGCTGACGAGAACGCCCTGGACGTGCTC AAGGAGATGCAAGAGACCTCCTGGAGAACTTCGGCCAGAAGATCGA GGCCAACGAGAACATCCTGGCCAGCGTGCTGGAGAACATCCAGGAGA AGGTCGAGCTGAACAAGTCCGTGCTCGTCGACGTGCTGGCCGAGCTCA AGGAAGAGGCCGTGTCCCAAAGGGAGACGGCTCAAGAGGTGGCTGCT GAGCTGGTGGAGGAAGCCGCTGAGGTCCCAGCTGTGGAGCCAGTCGA AGGAAGGTGGTGGAGCAGCTGTGGAGGTGGTGGAGGAGCCTGTG GAGGAAGAGGTGGTCGAGCCAGTGGTCGACGTGATCGAGGAGCCTGC CGTGGAGGTCGTGGAGGTCCCAGTGGAGGAGACGGTCGAGGAGCCT GTGGAGGTTACCGCCGGAGGAGCCTGTGGAGGTCACGGCCGGAGGCC TGTCGAGGACGGTGGAGGAGCCAGTGGTCGAGGTGGTCGAGGAG CCAGTTGAGGAGCCTGTGGTCGAGGCCATCGAGGAGCCCGTCGTCGA GCCAGTGGTCGAGCCAGCCGTCGAGGTCATCGAGGACGCTACGGAGG AGCCGTGGAGGAAGCCGCCGAGGAGCCCGAGGACGTGGAGGTGGCTGA GGGCAGCGCCATCGAGTCCGTGGAGGAAGCCTTCGAGCAAATCATCG AGGACGCCGCCCAAGTGATCGCTGAGGAGAGCGTGGAGGAGACGGCT GAGCAAATCCTGGAGCAAGCCACCCAGGCCGTGACCGAGGAAGCCGC TGACGCTGCTGACGTGGCTGACGCTGAGGAAGCCGTGGGCACCGCTC AAGTCGTCACCGAGGAGAGCGTGGCTGAGGCTATCGAGGACACCGTC GAGGAGATCTCCGCCGAGCCAATCCAGGCCACCATCGAGGGCATCGTG GGCGAGGTCGTCGAGTCCGTCGAGGAGAACATCGAGGCCGTGGAGGA AGCCATCAAGGACATCGTGGAGGGCGCTGTGGAGGGCGCTCCAGAGC TCAGCCTGGAGGAGATGATCGAGGACGTCATGGTGGGCACCGTGGCT |

Appendix I-continued

| No. | Protein Name | Protein Reference | Insert aa sequence (add M as start/His-tag at C-term) | Insert DNA sequence (Start from ATG to His-tag stop codon) |
|---|---|---|---|---|
| | | | | GAGGAAGACTCCGCTAAGGAAGCCGCTGAGGAGACGGTGGAGGAAG<br>TGGTGCAAGAGGACGCTGCTGAGGAAGAGGCCGCCAAGGAAGCCGCC<br>GAAGAGACGGTGGAGGAAGCCGAGAGGGAGGCTACCCAAGAGGCCG<br>TCGAGGAGACGGTTGAGGACGTGGTCGAGGAAGTGTCCGCTGAGGCT<br>GTGGAGGAGATCGTCCTCGAAACCCCGGAGGGCACCTCCGACGAGAG<br>CGTGGAGACGGTGGTGGAGCACGCTGTGGAGGACTCCCTGGGCGAGA<br>CGATCGCCACCATCGTGGACGACGTCGCCGAGGAGACGACCGAGAAG<br>TCCGAGGAGAGCGTGGTCGACAACCTGGGCGTCAAGGTGGAGGAAGT<br>GCTCGACGTCGACGTGGAGGAAGTGGCCCAAGAGGCCGCCGACGACG<br>TGATCATGCGCGTCAGCGAGAACGAGTCCGAGGGCGAGAGCGGCGCT<br>GAGTCCGGCGAGGAAGTGGAGGAGCTGGAGAGCGCCCTCTTCGAGGT<br>GGAGAAGGACATCAAGAAGAAGGTTCCTCGACATGTTCAGCGGCAACG<br>TGGAGTTCGACGAGAAGGAGTCCGAGAAGCTCGCCCTGGACCTCCAG<br>AAGAACCTCCTGTCCCACCACCACCACCACCACTGA<br>(SEQ ID NO: 26) |
| 14 | conserved Plasmodium protein, unknown function | PVX_090970 | mTYMLMKDDDSHDDKDDENEEKKK<br>KEGKTNKDTNKIIKGESMTREDLLQL<br>LNEMLKLQTDMKNIVKDLIVVAKKNS<br>YDFMSVYNVAKTYNTVDPLGKYQIE<br>MPEFDKVVENYHFDPEVKETVSKLM<br>SSQENYYANMSETATLNVDKIIEIHH<br>FMLNELYKIDPEFKKIPNKHELDPKLI<br>ALVIQSIVSAKVEEEFNLTSEDVEASI<br>ANQQYALTSNMEFARVNIQMQTIMN<br>KFMGDhhhhhh (SEQ ID NO: 27) | ATGACCTACATGCTCATGAAGGACGACGACTCCCACGACGACAAGGAC<br>GACGAGAACGAGGAGAAGAAGAAGAAGGAAGGCAAGACCAACAAGG<br>ACACCAACAAGATCATCAAGGGCGAGAGCATGACCAGGGAGGACCTC<br>CTGCAACTCCTGAACGAGATGCTCAAGCTGCAGACCGACATGAAGAAC<br>ATCGTCAAGGACCTCATCGTGGTCGCCAAGAAGAACTCCTACGACTTCA<br>TGAGCGTGTACAACGTCGCCAAGACCTACAACACCGTGGACCCACTGG<br>GCAAGTACCAAATCGAGATGCCAGAGTTCGACAAGGTGGTCGAGAAC<br>TACCACTTCGACCCAGAGGTGAAGGAGACCGTGTCCAAGCTCATGTC<br>AGCCAGGAGAACTACTACGCCAACATGAGCGAGACGGCCACCCTGAA<br>CGTCGACAAGATCATCGAGATCCACCACTTCATGCTCAACGAGCTGTAC<br>AAGATCGACCCAGAGTTCAAGAAGATCCCAAACAAGCACGAGCTGGAC<br>CCAAAGCTCATCGCCCTCGTGATCCAATCCATCGTGAGCGCCAAGGTCG<br>AGGAAGAGTTCAACCTCACCTCCGAGGACGTCGAGGCCAGCATCGCCA<br>ACCAACAGTACGCCCTGACCTCCAACATGGAGTTCGCCCGCGTGAACA<br>TCCAAATGCAGACCATCATGAACAAGTTCATGGGCGACCACCACCACC<br>ACCACCACTGA (SEQ ID NO: 28) |
| 15 | conserved Plasmodium protein, unknown function | PVX_084815 | mAGGVSEEAIKKLKEIKKLELDILKDF<br>MKQDAGHADLYKKYHCIASDYISGN<br>PKGSSAEGPNLAKKGEKSKKGEKH<br>QNGEKPQNGEKPKKSFIEKIASFVSI<br>FSYNNVSKIYSEHVORIFPKARDHA<br>GDGSAGDAIYPDDKIETGKKQNQSS<br>YVQLSALNLMKRNMFLGGKDKSSE<br>HFEVGNLGSFYMIFGARNTDYPWA<br>CSCDPLQLIDYKEKKRNYVLCSNQV<br>DMSIQNADLFCNPKhhhhhh<br>(SEQ ID NO: 29) | ATGGCCGGCGGCGTCAGCGAGGAAGCCATCAAGAAGCTCAAGGAGAT<br>CAAGAAGCTGGAGCTGGACATCCTGAAGGACTTCATGAAGCAAGACG<br>CCGGCCACGCCGACCTCTACAAGAAGTACCACTGCATCGCCAGCGACT<br>ACATCTCCGGCAACCCAAAGGGCTCCAGCGCTGAGGGCCCAAACCTGG<br>CCAAGAAGGGCGAGAAGAGCAAGAAGGGCGAGAAGCACCAAAACGG<br>CGAGAAGCCACAGAACGGCGAGAAGCCAAAGAAGTCCTTCATCGAGA<br>AGATCGCCTCCTTCGTGAGCATCTTCTCCTACAACAACGTCAGCAAGAT<br>CTACTCCGAGCACGTGCAAAGGATCTTCCCAAAGGCCCGCGACCACGC<br>TGGCGACGGCAGCGCCGGCGACGCCATCTACCCAGACGACAAGATCG<br>AGACGGGCAAGAAGCAAAACCAGTCCAGCTACGTCCAGCTCTCCGCCC<br>TCAACCTGATGAAGCGCAACATGTTCCTGGGCGGCAAGGACAAGTCCA<br>GCGAGCACTTCGAAGTGGGCAACCTCGGCAGCTTCTACATGATCTTCG<br>GCGCCAGGAACACCGACTACCCATGGGCCTGCTCCTGCGACCCACTCC<br>AGCTGATCGACTACAAGGAGAAGAAGCGCAACTACGTGCTCTGCAGCA<br>ACCAAGTCGACATGTCCATCCAGAACGCCGACCTGTTCTGCAACCCAAA<br>GCACCACCACCACCACCACTGA (SEQ ID NO: 30) |
| 16 | tryptophan-rich antigen (Pv-fam-a) | PVX_090270 | mVSCTSLCLYIIYSLFLLNNVSLSIQV<br>KTNEIKNGONGSVQLKEKGGGVNL<br>APKVGTNITQKRDTKMAKKTVTKVA<br>KKKVTKVAEKTGTKVADKTGTKVAD<br>KTGTKVADKTGTKVAEKTGTKVADK<br>TGTKVAEKTGTNISQKEDEKGPPKE<br>DTQGTQKADAKAIQQADAQVSEKW<br>KKKEWKEWIKKAESDLDIFNALMDN<br>EKEKKWYSEKEKEWNKWIKGVEKK<br>WMHYNKNIYVEYRSLVFWVGLKWV<br>ESQWEKWILSDGLEFLVMDWKKWI<br>KENKSNFDEWLKSEWDTWTNSQM<br>EEWKSSNWKLNEDKRWEMWENDK<br>KWIKWLYLKDWINCSKWKKRIQKES<br>KEWLRWTKLKEEMYhhhhhh<br>(SEQ ID NO: 31) | ATGGTGTCCTGCACCAGCCTCTGCCTGTACATCATCTACAGCCTCTTCCT<br>CCTGAACAACGTGTCCCTGAGCATCCAAGTCAAGACCAACGAGATCAA<br>GAACGGCCAAAACGGCTCCGTCCAGCTCAAGGAGAAGGGCGGCGGC<br>TGAACCTGGCTCCAAAGGTCGGCACCAACATCACCCAGAAGAGGGACA<br>CCAAGATGGCCAAGAAGACCGTGACCAAGGTCGCCAAGAAGAAGGTC<br>ACGAAGGTCGCCGAGAAGACCGGCACCAAGGTGGCCGACAAGACCGG<br>CACCAAGGTCGCTGATAAGACCGGGGACGAAGGTCGCTGATAAGACCG<br>GCACCAAGGTGGCTGAGAAGACGGGCGAAGGTTGCTGATAAGAC<br>GGGGACCAAGGTGGCTGAGAAGACCGGCACCAACATCAGCCAAAAGG<br>AAGACGAGAAGGGCCCACCAAAGGAAGACACCCAAGGCACCCAGAAG<br>GCCGACGCCAAGGCCATCCAACAGGCCGACGCCCAGGTGAGCGAGAA<br>GTGGAAGAAGAAGGAGTGGAAGGAGTGGATCAAGAAGGCCGAGTCC<br>GACCTCGACATCTTCAACGCCCTGATGGACAACGAGAAGGAGAAGAA<br>GTGGTACAGCGAGAAGGAGAAGGAGTGGAACAAGTGGATCAAGGGC<br>GTGGAGAAGAAGTGGATGCACTACAACAAGAACATCTACGTCGAGTA<br>CAGGTCCCTCGTGTTCTGGGTCGGCCTGAAGTGGGTTGGAGTCCCAATG<br>GGAGAAGTGGATCCTCAGCGACGGCCTGGAGTTCCTGGTCATGGACTG<br>GAAGAAGTGGATCAAGGAGAACAAGTCCAACTTCGACGAGTGGCTCA<br>AGAGCGAGTGGGACACCTGGACCAACTCCCAGATGGAGGAGTGGAAG<br>TCCAGCAACTGGAAGCTGAACGAAGACAAGCGCTGGGAGATGTGGGA<br>GAACGACAAGAAGTGGATCAAGTGGCTCTACCTGAAGGACTGGATCA<br>ACTGCAGCAAGTGGAAGAAGAGGATCCAAAAGGAGTCCAAGGAGTG<br>GCTCCGCTGGACCAAGCTGAAGGAAGAGATGTACCACCACCACCACCA<br>CCACTGA (SEQ ID NO: 32) |

Appendix I-continued

| No. | Protein Name | Protein Reference | Insert aa sequence (add M as start/His-tag at C-term) | Insert DNA sequence (Start from ATG to His-tag stop codon) |
|---|---|---|---|---|
| 17 | apical membrane antigen 1, AMA1 (Orthologs with Pf vaccine candidates) | PVX_092275 | mGEDAEVENAKYRIPAGRCPVFGK GIVIENSDVSFLRPVATGDQKLKDG GFAFPNANDHISPMTLANLKERYKD NVEMMKLNDIALCRTHAASFVMAGD QNSSYRHPAVYDEKEKTCHMLYLS AQENMGPRYCSPDAQNRDAVFCFK PDKNESFENLVYLSKNVRNDWDKK CPRKNLGNAKFGLWVDGNCEEIPY VKEVEAEDLRECNRIVFGASASDQP TQYEEEMTDYQKIQQGFRQNNREM IKSAFLPVGAFNSDNFKSKGRGFNW ANFDSVKKKCYIFNTKPTCLINDKNFI ATTALSHPQEVDLEFPCSIYKDEIER EIKKQSRNMNLYSVDGERIVLPRIFIS NDKESIKCPCEPERISNSTCNFYVC NCVEKRAEIKENNQVVIKEEFRDYY ENGEEKSNKQhhhhhh (SEQ ID NO: 33) | ATGGGCGAGGACGCCGAGGTGGAGAACGCCAAGTACAGGATCCCAGC TGGCAGGTGCCCAGTGTTCGGCAAGGGCATCGTCATCGAGAACTCCGA CGTGAGCTTCCTCCGCCCAGTGGCTACCGGCGACCAAAAGCTGAAGGA CGGCGGATTCGCCTTCCCAAACGCCAACGACCACATCTCCCCAATGACC CTCGCCAACCTGAAGGAGAGGTACAAGGACAACGTGGAGATGATGAA GCTCAACGACATCGCTCTGTGCAGGACCCACGCTGCTAGCTTCGTGATG GCTGGCGACCAGAACTCCAGCTACAGGCACCCAGCCGTCTACGACGAG AAGGAGAAGACCTGCCACATGCTCTACCTGTCCGCCCAAGAGAACATG GGCCCAAGGTACTGCTCCCCAGACGCTCAGAACAGGGACGCTGTCTTC TGCTTCAAGCCAGACAAGAACGAGTCCTTCGAGAACCTCGTGTACCTG AGCAAGAACGTCAGGAACGACTGGGACAAGAAGTGCCCACGCAAGAA CCTCGGCAACGCCAAGTTCGGCCTGTGGGTGGACGGCAACTGCGAGG AGATCCCATACGTGAAGGAAGTGGAGGCCGAGGACCTCAGGGAGTGC AACAGGATCGTCTTCGGCGCTTCCGCTAGCGACCAACCAACCCAGTAC GAGGAAGAGATGACCGACTACCAAAAGATCCAACAGGGCTTCAGGCA GAACAACCGCGAGATGATCAAGTCCGCCTTCCTCCCAGTGGGCGCCTT CAACTCCGACAACTTCAAGAGCAAGGGCCGCGGCTTCAACTGGGCCAA CTTCGACAGCGTGAAGAAGAAGTGCTACATCTTCAACACCAAGCCAAC CTGCCTGATCAACGACAAGAACTTCATCGCCACCACCGCCCTCTCCCAC CCACAAGAGGTCGACCTGGAGTTCCCATGCAGCATCTACAAGGACGAG ATCGAGAGGGAGATCAAGAAGCAGTCCCGCAACATGAACCTCTACAGC GTGGACGGCGAGAGGATCGTCCTGCCACGCATCTTCATCTCCAACGAC AAGGAGAGCATCAAGTGCCCATGCGAGCCAGAGAGGATCTCCAACAG CACCTGCAACTTCTACGTGTGCAACTGCGTCGAGAAGAGGGCCGAGAT CAAGGAGAACAACCAAGTGGTCATCAAGGAAGAGTTCAGGGACTACT ACGAGAACGGCGAGGAGAAGTCCAACAAGCAGCACCACCACCACCAC CACTGA (SEQ ID NO: 34) |
| 18 | hypothetical protein | PVX_084720 | mNGNRNLNIKPTCHKSGKNDKANG SDNIANKGGAQHAANGATGTPSGS SNGKKGATTTSASAGQAGASGGMA APGMNPNFEQMMKPLNDMFKGNG EGLNIENIMNSDMFQNFFNSLMGGN PHDGAGGGQEILFKDMLNAMNAQG GGAPGAAATSGGANKDPNISVSPE QLNKINQLKDKLENVLKNVGVDVEQ LKENMQNENIMQNKDALRDLLANLP MNPGMMQNMMAGKDGNMFNMDP NQMMNMFNQLSQGKMNMKDFGM GDFMPPPVHANDQDAEDDSRGKAF VTNSSNNDINFAHKLNAFEYSNGPS EGMFQLYGMNNDDGVIDDGMSDSV GKNSALDVSGGSINRNLSDGDSAKE DSDESNANATSNSNATVPNKGGHE GGSANEVYSNEEELITSSGSKGDAN KLAGTGGYKNNNAFLDLNNLKKDAS AAKYGKDNSGDKSNGGNSNGGNN KVMNKRIGGKKKKTFKKKKNPGQIP FKMETLQKLVKEYTNTSNQKIMEKII KKYVSMSNQSARGNSEEEDDEEEA EDEKSAKDKNSEKEAELNMNEFSVK DIKKLISEGILTYEDLTEEELKKLAKP DDMFYELSPYANEEKDLSLNETSGV SNEQLNAFLRKNGSYHMSYDSKAID YLKQKKAEKKEEEQEDDNFYDAYK QIKNSYEGIPSNYYHDAPQLIGENYV FTSVYDKKKELIDFLKRSNGATDSSN SSAGKDKGNSAESGTYKSKYYDKY MKKLSEYRRREAFKILKKRRAQEKK MQKKQEMQNNSSNEVDYSEYFKKN GFINSSNGTVKTFSKDQLDNMVKQF NSDGDDIPSSSGAGADLGDNYSGV SGGGQFSPSGGSGNNPSGYVTFD GQNIVGPNENEEEEPTEDVLNEDDD NADDDDhhhhhh (SEQ ID NO: 35) | ATGAACGGCAACAGGAACCTGAACATCAAGCCAACCTGCCACAAGAGC GGCAAGAACGACAAGGCCAACGGCTCCGACAACATCGCTAACAAGGG CGGCGCCCAACACGCTGCTAACGGCGCCACCGGCACCCCAAGCGGCTC CAGCAACGGCAAGAAGGGCGCTACGACCACCAGCGCTTCCGCTGGCC AAGCTGGCGCTTCCGGCGGCATGGCCGCCCCAGGCATGAACCCAAACT TCGAGCAGATGATGAAGCCACTGAACGACATGTTCAAGGGCAACGGC GAGGGCCTCAACATCGAGAACATCATGAACAGCGACATGTTCCAGAAC TTCTTCAACTCCCTGATGGGCGGCAACCCACACGACGGCGCTGGCGGC GGCCAGGAGATCCTGTTCAAGGACATGCTCAACGCCATGAACGCCCAA GGCGGCGGCGCCCCAGGCGCTGCCGCCACCTCCGGCGGCGCCAACAA GGACCCAAACATCAGCGTCTCCCCAGAGCAGCTGAACAAGATCAACCA ACTCAAGGACAAGCTGGAGAACGTGCTCAAGAACGTGGGCGTCGACG TGGAGCAGCTCAAGGAGAACATGCAAAACGAGAACATCATGCAGAAC AAGGACGCTCTGAGGGACCTCCTGGCTAACCTCCCGATGAACCCAGGC ATGATGCAAAACATGATGGCCGGCAAGGACGGCAACATGTTCAACATG GACCCAAACCAGATGATGAACATGTTCAACCAACTCAGCCAGGGCAAG ATGAACATGAAGGACTTCGGCATGGGCGACTTCATGCCACCACCAGTC CACGCCAACGACCAAGACGCTGAGGACGACTCCCGCGGCAAGGCTTTC GTGACCAACTCCAGCAACAACGACATCAACTTCGCCCACAAGCTGAAC GCCTTCGAGTACAGCAACGGCCCATCCGAGGGCATGTTCCAGCTCTAC GGCATGAACAACGACGACGGCGTCATCGACGACGGCATGAGCGACTC CGTCGGCAAGAACAGCGCTCTGGACGTGAGCGGCGGCTCCATCAACA GGAACCTGAGCGACGGCGACTCCGCCAAGGAAGACAGCGACGAGTCC AACGCCAACGCCACCAGCAACTCCAACGCCACCGTCCCAAACAAGGGC GGCCACGAGGGCGGCAGCGCTAACGAGGTGTACTCCAACGAGGAAGA GCTGATCACCTCCAGCGGCTCCAAGGGCGACGTAACAAGCTGGCTGG CACCGGCGGCTACAAGAACAACAACGCCTTCCTCGACCTGAACAACCT GAAGAAGGACGCCAGCGCCGCCAAGTACGGCAAGGACAACAGCGGC GACAAGTCCAACGGCGGCAACTCCAACGGCGGCAACAACAAGGTCAT GAACAAGCGCATCGGCGGCAAGAAGAAGAAGACCTTCAAGAAGAAGA AGAACCCAGGCCAAATCCCATTCAAGATGGAGACGCTCCAGAAGCTGG TCAAGGAGTACACCAACACCAGCAACCAAAAGATCATGGAGAAGATCA TCAAGAAGTATGTGTCCATGTCCAACCAGAGCGCCAGGGGCAACTCCG AGGAAGAGGACGACGAGGAAGAGGCCGAGGAGAAGAGCGCCAA GGACAAGAACTCCGAGAAGGAAGCCGAGCTGAACATGAACGAGTTCA GCGTCAAGGACATCAAGAAGCTCATCTCCGAGGGCATCCTGACCTACG AGGACCTCACCGAGGAAGAGCTCAAGAAGCTGGCCAAGCCAGACGAC ATGTTCTACGAGCTCAGCCCATACGCCAACGAGGAGAAGGACCTCTCC CTGAACGAGACGAGCGGCGTGTCCAACGAGCAACTGAACGCCTTCCTC CGCAAGAACGGCTCCTACCACATGAGCTACGACTCCAAGGCCATCGAC TACCTGAAGCAAAAGAAGGCCGAGAAGAAGGAAGAGGAGCAAGAGG ACGACAACTTCTACGACGCCTACAAGCAAATCAAGAACAGCTACGAGG GCATCCCATCCAACTACTACCACGACGCCCCACAGCTCATCGGCGAGAA CTACGTCTTCACCAGCGTGTACGACAAGAAGAAGGAGCTGATCGACTT CCTCAAGAGGTCCAACGGCGCTACCGACTCCAGCAACTCCAGCGCTGG CAAGGACAAGGGCAACAGCGCTGAGTCCGGCACCTACAAGAGCAAGT ACTACGACAAGTACATGAAGAAGCTGTCCGAGTACAGGCGCAGGGAG |

Appendix I-continued

| No. | Protein Name | Protein Reference | Insert aa sequence (add M as start/His-tag at C-term) | Insert DNA sequence (Start from ATG to His-tag stop codon) |
|---|---|---|---|---|
| | | | | GCCTTCAAGATCCTCAAGAAGCGCAGGGCCCAGGAGAAGAAGATGCA AAAGAAGCAGGAGATGCAAAACAACTCCAGCAACGAGGTGGACTACT CCGAGTACTTCAAGGAGAACGGCTTCATCAACTCCAGCAACGGCACCG TCAAGACCTTCAGCAAGGACCAACTGGACAACATGGTGAAGCAGTTCA ACTCCGACGGCGACGACATCCCATCCAGCTCCGGCGCTGGCGCTGACC TCGGCGACAACTACAGCGGCGTGTCCGGCGGCGGCCAATTCAGCCCAT CCGGCGGCAGCGGCAACAACCCATCCGGCTACGTCACCTTCGACGGCC AGAACATCGTGGGCCCAAACGAGAACGAGGAGAGGAGCCAACCGA GGACGTGCTCAACGAGGACGACGACAACGCCGACGACGACGACCACC ACCACCACCACCACTGA (SEQ ID NO: 36) |
| 19 | merozoite surface protein 5 | PVX_003770 | mPLEVSLWGQGNAHLGTQTSRLLR ESGRNGQANRVNQADQADQVASP PISGKERRRGIGMTSNLQLLSGEDE KDSTSEEAPNLEGKDNADAGKDGE KEPSEKQSGDVDPTVTDAERAKDE NASVSEEEQMKTLDSGEDHTDDGN ADGGQGGGDGNDENQKGDGKEKE GGEEKKEDGKDDHEKGEKGSEGES GEKDEAAPKGDAAEKDKKLESKTAD AKVSEHKADDANPGGNKDSPEGES PKEGNPDDPSQKNPEAAGDDDSRL HLDNLDDKVPHYSALRNNRVEKGVT DTMVLNDIIGENAKSCSVDNGGCAD DQICIRIDNIGIKCICKEGHLFGDKCIL TKhhhhhh (SEQ ID NO: 37) | ATGCCGCTGGAGGTGTCCCTGTGGGGCCAGGGCAACGCTCACCTCGGC ACCCAAACCTCCCGCCTGCTCAGGGAGTCCGGCAGGAACGGCCAGGCC AACAGGGTGAACCAGGCTGACCAGGCTGACCAAGTGGCTTCCCCACCA ATCTCCGGCAAGGAGAGGCGCAGGGGCATCGGCATGACCTCCAACCTC CAACTCCTGAGCGGCGAGGACGGAGAAGGACTCCACCAGCGAGGAAGC CCCAAACCTGGAGGGCAAGGACAACGCTGACGCTGGCAAGGATGGCG AGAAGGAGCCATCCGAGAAGCAGAGCGGCGACGTGGACCCAACCGTC ACCGACGCTGAGAGGGCTAAGGACGAGAACGCTTCCGTCAGCGAGGA AGAGCAGATGAAGACCCTGGACAGCGGCGAGGAACCACACCGACGACG GCAACGCTGACGGCGGACAAGGCGGCGGCGACGGCAACGACGAGAA CCAAAAGGGCGACGGCAAGGAGAAGGAAGGCGGCGAGGAGAAGAA GGAAGACGGCAAGGACGACCACGAGAAGGGCGAGAAGGGCTCCGAG GGCGAGAGCGGCGAGAAGGACGAGGCTGCCGCCAAGGGCGACGCTG CCGAGAAGGACAAGAAGCTGGAGTCCAAGACCGCCGACGCCAAGGTG AGCGAGCACAAGGCTGACGACGCTAACCCAGGCGGCAACAAGGACTC CCCAGAGGGCGAGAGCCCAAAGGAAGGCAACCCAGACGACCCATCCC AGAAGAACCCGGAGGCTGCTGGCGACGACGACAGCCGCCTCCACCTG GACAACCTCGACGACAAGGTCCCACACTACTCCGCCCTGCGCAACAAC AGGGTGGAGAAGGGCGTCACCGACACCATGGTGCTGAACGACATCAT CGGCGAGAACGCCAAGTCCTGCAGCGTGGACAACGGCGGCTGCGCTG ACGACCAAATCTGCATCAGGATCGACAACATCGGCATCAAGTGCATCT GCAAGGAAGGCCACCTCTTCGGCGACAAGTGCATCCTGACCAAGCACC ACCACCACCACCACTGA (SEQ ID NO: 38) |
| 20 | TRAg (Pv-fam-a) | PVX_092990 | mDVLQLVIPSEEDIQLDKPKKDELGS GILSILDVHYQDVPKEFMEEEETAV YPLKPEDFAKEDSQSTEWLTFIQGL EGDWERLEVSLNKARERWMEQRN KEWAGWLRLIENKWSEYSQISTKGK DPAGLRKREWSDEKWKKWFKAEV KSQIDSHLKKWMNDTHSNLFKILVK DMSQFENKKTKEWLMNHWKKNER GYGSESFEVMTTSKLLNVAKSREW YRANPNIRRERRELMKWFLLKENEY LGQEWKKWTHWKKVKFFVFNSMC TTFSGKRLTKEEWNQFVNEIKVhhhh hh (SEQ ID NO: 39) | ATGGACGTGCTCCAACTGGTCATCCCAAGCGAGGAAGACATCCAGCTC GACAAGCCAAAGAAGGACGAGCTGGGCAGCGGCATCCTCTCCATCCTG GACGTGCACTACCAAGACGTCCCAAAGGAGTTCATGGAGGAAGAGGA AGAGACGGCCGTGTACCCACTCAAGCCAGAGGACTTCGCCAAGGAAG ACTCCCAAAGCACCGAGTGGCTCACCTTCATCCAAGGCCTGGAGGGCG ACTGGGAGAGGCTGGAGGTGTCCCTGAACAAGGCCAGGGAGCGCTGG ATGGAGCAAAGGAACAAGGAGTGGGCTGGCTGGCTCAGGCTGATCGA GAACAAGTGGTCCGAGTACAGCCAGATCTCCACCAAGGGCAAGGACC CGGCTGGCCTCAGGAAGCGCGAGTGGTCCGACGAAAAGTGGAAGAAG TGGTTCAAGGCCGAGGTGTCCCCTGAACAAGGCCAAGTCCAGGGAGTGGTACC GCGCCAACCCAAACATCAACCGCGAGAGGCGCGAGCTCATGAAGTGG TTCCTCCTGAAGGAGAACGAGTACCTGGGCCAAGAGTGGAAGAAGTG GACCCACTGGAAGAAGGTGAAGTTCTTCGTCTTCAACAGCATGTGCAC CACCTTCTCCGGCAAGCGCCTGACCAAGGAAGAGTGGAACCAGTTCGT GAACGAGATCAAGGTCCACCACCACCACCACCACTGA (SEQ ID NO: 40) |
| 21 | unspecified product | PVX_112690 | mEAMPKFPQNNLKGGLKDSPLKQP KSPLINGPPKPVNDKLKDDSNKTET KDAKNGLNKPPKNINDKVKDGENKT PSQDLNEPSFKLPMRQKESSWYTW LKGTKKDYETLKCFAKGNLYDWLCN VRESFDLYLQSLEKKWTTCSDSATT LFLCECFAESSGWNDSQWGNWMN NQLKEQLKTEAEAWISTKKKDPDGL TSKYFSLWKDHRRKELDADEWKNK VSSGGLSEWEELTNKMNTRYRNNL DNMWSHFSRDLFFNFDEWAPQVLE KWIENKQWNRWVKKVRKhhhhhh (SEQ ID NO: 41) | ATGGAGGCCATGCCAAAGTTCCCACAAAACAACCTCAAGGGCGGCCTG AAGGACTCCCCACTCAAGCAGCCAAAGAGCCCACTGATCAACGGCCCA CCAAAGCCAGTGAACGACAAGCTCAAGGACGACTCCAACAAGACCGA GACGAAGGACGCCAAGAACGGCCTGAACAAGCCACCAAAGAACATCA ACGACAAGGTCAAGGACGGCGAGAACAAGACCCCATCCCAAGACCTC AACGAGCCAAGCTTCAAGCTGCCAATGAGGCAGAAGGAGTCCAGCTG GTACACCTGGCTCAAGGGCACCAAGAAGGACTACGAGACGCTGAAGT GCTTCGCCAAGGGCAACCTCTACGACTGGCTGTGCAACGTGCGCGAGT CCTTCGACCTCTACCTGCAAAGCCTGGAGAAGAAGTGGACCACCTGCT CCGACAGCGCTACCACCCTCTTCCTGTGCGAGTGCTTCGCCGAGTCCAG CGGCTGGAACGACTCCCAGTGGGGCAACTGGATGAACAACCAACTCAA GGAGCAGCTGAAGACCGAGGCCGAGGCCTGGATCAGCACCAAGAAGA AGGACTTCGACGGCCTCACCTCCAAGTACTTCAGCCTGTGGAAGGACC ACAGGCGCAAGGAGCTGGACGCTGACGAGTGGAAGAACAAGGTGTCC AGCGGCGGCCTCAGCGAGTGGGAGGAGCTGACCAACAAGATGAACAC CAGGTACCGCAACAACCTCGACAACATGTGGTCCCACTTCAGCAGGGA CCTGTTCTTCAACTTCGACGAGTGGGCCCCACAAGTCCTGGAGAAGTG GATCGAGAACAAGCAGTGGAACCGCTGGGTGAAGAAGGTCCGCAAGC ACCACCACCACCACCACTGA (SEQ ID NO: 42) |

Appendix I-continued

| No. | Protein Name | Protein Reference | Insert aa sequence (add M as start/His-tag at C-term) | Insert DNA sequence (Start from ATG to His-tag stop codon) |
|---|---|---|---|---|
| 22 | petidase, M16 family | PVX_091710 | mQKAPNNGKNNYGLNDDELGAILF GLNYDSIAKNKDNLEKRKNVENESIF LRNFANEDTSKNTQSEKAQKEIKIET ETESVNSNEKEVATSQKSDTSNKNS SVENEKIELKNDELLGKNFEKDKVN KKGDNTNTTNNHDLTNSSEKQGVDI RGSKNMNNYLQKTGDTNIEKSESLQ KDVNIKNHNEEANDAKRLDSAQTNN EKSKISKDTIDKDVQSNELTNLASNR SNKKSQGLAKKENELKSANLEENHN AKKDLLKKDQKREDGKKITHPENSN SDQYGVQVSLNDEEKNTNTKSVSH SEDHSASYSGEKFGTHVSNSQKDM LKNIRPVQFDESAYGKLNGGSPEND ENEILNKINKNNENNFSEKVALRKGT KDRNEYEYFKLKSNDFKVLGIINKYS SRGGFSISVDCGGYDDFDEVPGVS NLLQHAIFYKSEKRNTTLLSELGKYS SEYNSCTSESSTSYYATAHSEDIYHL LNLFAENLFYPVFSEEHIQNEVKEIN NKYISIENNLESCLKIASQYITNFKYS KFFVNGNYTTLCENVLKNRLSIKNIL TEFHKKCYQPRNMSLTILLGNKVNT ADHYNMKDVENMVVHIFGKIKNESY PIDGDVIGKRINRMESERVNLYGKK DSYNDANFIHIEGRNEKEAAFLQSM NELHYALDLNOKSRYVEIIKKEEWG DQLYLYWSSKTNAELCKKIEEFGSM TFLREIFSDFRRNGLYYKISVENKYV YDLEVTSICNKYYLNFGILVKLTQRG RTNLAHLIHICNVFVNEIGKLFDRDSL DKGISKYILDYYREKALVTDLKFNSD NVNVSLDDLVIYSKRLLVHADDPSSL LTIHSLIEDKHKNDFRNHIKIThhhhhh (SEQ ID NO: 43) | ATGCAAAAGGCCCCAAACAACGGCAAGAACAACTACGGCCTCAACGAC GACGAGCTGGGCGCCATCCTCTTCGGCCTGAACTACGACAGCATCGCC AAGAACAAGGACAACCTGGAGAAGAGGAAGAACGTCGAGAACGAGT CCATCTTCCTGCGCAACTTCGCCAACGAGGACACCAGCAAGAACACCC AATCCGAGAAGGCCCAGAAGGAGATCAAGATCGAGACGGAGACGGA GTCCGTCAACAGCAACGAGAAGGAAGTGGCCACCTCCCAGAAGAGCG ACACCTCCAACAAGAACTCCAGCGTCGAGAACGAGAAGATCGAGCTGA AGAACGACGAGCTCCTGGGCAAGAACTTCGAGAAGGACAAGGTGAAC AAGAAGGGCGACAACACCAACACCACCAACAACCACGACCTCACCAAC TCCAGCGAGAAGCAAGGCGTCGACATCAGGGGCAGCAAGAACATGAA CAACTACCTCCAAAAGACCGGCGACACCAACATCGAGAAGTCCGAGG CCTGCAGAAGGACGTGAACATCAAGAACCACAACGAGGAAGCCAACG ACGCCAAGAGGCTGGACAGCGCCCAGACCAACAACGAGAAGAGCAAG ATCTCCAAGGACACCATCGACAAGGACGTGCAATCCAACGAGCTCACC AACCTGGCCAGCAACCGCTCCAACAAGAAGAGCCAGGGCCTCGCCAA GAAGGAGAACGAGCTCAAGTCCGCCAACCTGGAGGAGAACCACAACA CCAAGAAGGACCTCCTGAAGAAGGACCAAAAGAGGGAGGACGGCAA GAAGATCACCCACCCAGAGAACTCCAACAGCGACCAATACGGCGTGCA AGTGTCCCTGAACGACGAGGAGAAGAACACCAACACCAAGTCCGTCA GCCACTCCGAGGACCACAGCGCTTCCTACAGCGGCGAGAAGTTCGGCA CCCACGTCTCCAACAGCCAAAAGGACATGCTCAAGAACATCCGCCCAG TGCAGTTCGACGAGAGCGCTTACGGCAAGCTCAACGGCGGCTCCCCAG AGAACGACGAGAACGAGATCCTGAACAAGATCAACAAGAACAACGAG AACAACTTCAGCGAGAAGGTGGCCCTCAGGAAGGGCACCAAGGACCG CAACGAGTACGAGTACTTCAAGCTCAAGTCCAACGACTTCAAGGTCCT GGGCATCATCAACAAGTACTCCAGCAGGGGCGGCTTCTCCATCAGCGT GGACTGCGGCGGATACGACGACTTCGACGAGGTGCCAGGCGTCTCCA ACCTCCTGCAACACGCCATCTTCTACAAGAGCGAGAAGCGCAACACCA CCCTCCTGTCCGAGCTCGGCAAGTACTCCAGCGAGTACAACAGCTGCA CCTCCGAGTCCAGCACCAGCTACTACGCCACCGCCCACTCCGAGGACAT CTACCACCTCCTGAACCTCTTCGCCGAGAACCTGTTCTACCCAGTCTTCA GCGAGGAGCACATCCAAAACGAGGTGAAGGAGATCAACAACAAGTAC ATCTCCATCGAGAACAACCTGGAGAGCTGCCTGAAGATCGCCTCCCAG TACATCACCAACTTCAAGTACAGCAAGTTCTTCGTCAACGGCAACTACA CCACCCTCTGCGAGAACGTGCTCAAGAACAGGCTGAGCATCAAGAACA TCGAGTTCCACAAGAAGTGCTACCAGCCACGCAACATGTCCCTC ACCATCCTCCTGGGCAACAAGGTCAACACCGCCGACCACTACAACAT GAAGGACGTGGAGAACATGGTGGTCCACATCTTCGGCAAGATCAAGA ACGAGTCCTACCCAATCGACGGCGACGTCATCGGCAAGAGGATCAACC GCATGGAGAGCGAGAGGGTCAACCTCTACGGCAAGAAGGACTCCTAC AACGACGCCAACTTCATCCACATCGAGGGCCGCAACGAGAAGGAAGC CGCCTTCCTCCAAAGCATGAACGAGCTGCACTACGCCCTCGACCTGAAC CAGAAGTCCCGCTACGTGGAGATCATCAAGAAGGAAGAGTGGGGCGA CCAACTCTACCTGTACTGGTCCAGCAAGACCAACGCCGAGCTCTGCAA GAAGATCGAGGAGTTCGGCAGCATGACCTTCCTCCGCGAGATCTTCTC CGACTTCAGGCGCAACGGCCTGTACTACAAGATCAGCGTGGAGAACAA GTATGTGTACGACCTGGAGGTGACCTCCATCTGCAACAAGTACTACCTG AACTTCGGCATCCTCGTCAAGCTGACCCAAAGGGGCCGCACCAACCTC GCTCACCTGATCCACATCTGCAACGTGTTCGTCAACGAGATCGGCAAGC TCTTCGACAGGGACAGCCTGGACAAGGGCATCTCCAAGTACATCCTCG ACTACTACCGCGAGAAGGCCCTCGTGACCGACCTGAAGTTCAACAGCG ACAACGTGAACGTCTCCCTCGATGACCTGGTCATCTACAGCAAGAGGC TCCTGGTGCACGCCGACGACCCATCCAGCCTCCTGACCATCCACTCCCT CATCGAGGACAAGCATAAGAACGACTTCCGCAACCACATCAAGATCAC CCACCACCACCACCACTGA (SEQ ID NO: 44) |
| 23 | rhoptry-associated membrane antigen, RAMA | PVX_087885 | mKEAVKKGSKKAMKQPMHKPNLLE EEDFEEKESFSDDEMNGFMEESMD ASKLDAKKAKTTLRSSEKKKTPTSG MSGMSGSGATSAATEAATNMNATA MNAAAKGNSEASKKQTDLSNEDLF NDELTEEVIADSYEEGGNVGSEEAE SLTNAFDDKLLDQGVNENTLLNDNM IYNVNMVPHKKRELYISPHKHTSAAS SKNGKHHAADADALDKKLRAHELLE LENGEGSNSVIVETEEVDVDLNGGK SSGSVSFLSSVVFLLIGLLCFTNhhhh hh (SEQ ID NO: 45) | ATGAAGGAAGCCGTGAAGAAGGGCTCCAAGAAGGCCATGAAGCAACC AATGCACAAGCCAAACCTCCTGGAGGAAGAGGACTTCGAGGAGAAGG AGTCCTTCAGCGACGACGAGATGAACGGCTTCATGGAGGAGTCCATGG ACGCCAGCAAGCTGGACGCCAAGAAGGCCAAGACCACCCTCAGGTCC AGCGAGAAGAAGAAGACCCCAACCTCCGGCATGAGCGGCATGTCCGG CAGCGGCGCTACCAGCGCTGCTACCGAGGCCGCCACCAACATGAACGC TACCGCCATGAACGCTGCCGCCAAGGGCAACTCCGAGGCTAGCAAGAA GCAAACCGACCTCTCCAACGAGGACCTGTTCAACGACGAGCTCACCGA GGAAGTGATCGCCGACAGCTACGAGGAAGGCGGCAACGTGGGCTCCG AGGAAGCCGAGAGCCTGACCAACGCCTTCGACGACAAGCTCCTGGACC AGGGCGTGAACGAGAACACCCTCCTGAACGACAACATGATCTACAACG TGAACATGGTCCCACACAAGAAGAGGGAGCTCTACATCTCCCCACACA AGCACACCAGCGCCTCCAGCAAGAACGGCAAGCACCACGCTGCTG ACGCTGACGCTCTGGACAAGAAGCTCAGGGCTCACGAGCTCCTGGAGC TGGAGAACGGCGAGGGCTCCAACAGCGTGATCGTCGAGACGGAGGAA GTGGACGTGGACCTGAACGGCGGCAAGTCCTCCGGCTCCGTCAGCTTC CTCTCCAGCGTGGTCTTCCTCCTGATCGGCCTCCTGTGCTTCACCAACCA CCACCACCACCACCACTGA (SEQ ID NO: 46) |

Appendix I-continued

| No. | Protein Name | Protein Reference | Insert aa sequence (add M as start/His-tag at C-term) | Insert DNA sequence (Start from ATG to His-tag stop codon) |
|---|---|---|---|---|
| 24 | HP, conserved | PVX_003555 | mDDNGRRLPRKAAPPVDKAKQDVMKDIVNYLSKNMLAFVRQKRNVSGKEGEAPTGPSGAQGGDSSQYASKFTFTDHSVDFSKYNKLDKEKFAAKDDLKSRLKNEVVASMLDTEGDILTEEFGYLLRNYFDKVKLEEKKSQEAESAKPAEQEEEAEEAPEQKEEATAEKATEETTEAATEETTEAATEETTEAATEETTEAATEETTEAATEETTEAATEETTEAATEETTEAATEETTEAATEETTEAATEETTEAATEETTEAATEETTEAATEETTEAATEEATEGATEEGAEETTEEATEEGAEEEATEEGAEEEATEEGAEETTEEATEEGAEETTEETTEEGAEEEATEEGAEETTEEGAEEEAAEEGAEEGAEAATEEATEEATEEATEEATEEATEEATAEVAEAATPEKVTEEATEEEATEEGDNEPAEQAAEKEEDVKGGLMDNETYYNTLQELYEEIENDDKKEKEKIQKAKEQEELEKKLFKESKKGKKKEKKRRKKLCKMAKIVEKYAEEIPKDSERSLRYDKEEHIDDPDEMDDLLFGEFKTLEKYGTHKTSTFYYEMTCFDERLRDFEINTKLKEMEEVPEKWELLSLYWQSYRNERHKYLAVKKYLLEKFLELKTNQSTEALPKYNKKWKQCEEIVDNNFTKQHEHVNDVPYTFVAKENLSRDEFKEILNDVRASWhhhhhh (SEQ ID NO: 47) | ATGGACGACAACGGCAGGCGCCTCCCAAGGAAGGCTGCCCCACCAGTGGACAAGGCCAAGCAGGACGTGATGAAGGACATCGTCAACTACCTCTCCAAGAACATGCTGGCCTTCGTGAGGCAAAAGCGCAACGTCTCCGGCAAGGAAGGCGAGGCTCCAACCGGCCCAAGCGGCGCTCAAGGCGGCGACTCCAGCCAGTACGCCAGCAAGTTCACCTTCACCGACCACTCCGTGGACTTCAGCAAGTACAACAAGCTCGACAAGGAGAAGTTCGCCGCCAAGGACGACCTCAAGTCCAGGCTGAAGAACGAGGTGGTCGCCAGCATGCTCGACACCGAGGGCGACATCCTGACCGAGGAGTTCGGCTACCTCCTGCGCAACTACTTCGACAAGGTCAAGCTGGAGGAGAAGAAGTCCCAAGAGGCCGAGAGCGCTAAGCCAGCTGAGCAAGAGGAAGAGGCCGAGGAAGCCCCAGAGCAAAAGGAAGAGGCCACCGCTGAGGAGGCGTACCGAGGAGACGACCGAGGCTGCCACGGAGGAGACGACGGAGGCCGCCACGGAGGAGACGACCGAGGCCGCCACCGAGGAGACGACGGAGGCTGCCACTGAAGAGACGACCGAGGCTGCGACGGAAGAGACGACCGAGGCCGCGACGGAAGAGACGACTGAGGCTGCCACTGAGGAGACGACCGAGGCCGCGACGGAAGAGACGACCGAGGCCGCGACGGAAGAGACGACTGAGGCCGCGACGGAAGCCGCGACGGAAGAGACGACTGAAGCTGCGACGGAAGAAACGACTGAGGCCGCGACGGAAGAGACGACCGAGGCCGCGACGGAAGAGACGACTGAGGCCGCGACGGAAGCGGCCGAGGCCGCGACGGAAGCGGCTGAGGTTGCGGAAGCTGCGACGCCAGAGAAGGTCACAGAGGAAGCCACAGAGGAAGCCACCGAGGAAGGCGACAACGAGCCAGCTGAGCAGGCTGCTGAGAAGGAAGAGGACGTGAAGGGCGGCCTCATGGACAACGAGACGTACTACAACACCCTCCAAGAGCTGTACGAGGAGATCGAGACGACGACAAGGAGAAGGAGAAGATCCAAAAGGCCAAGGAGCAAGAGGAGCTGGAGAAGAAGCTGTTCAAGGAGTCCAAGAAGGGCAAGAAGAAGGAGAAGAAGAGGCGCAAGAAGCTCTGCAAGATGGCCAAGATCGTCGAGAAGTACGCCGAGGAGATCCCAAAGGACTCCGAGAGGAGCCTGCGCTACGACAAGGAAGAGCACATCGACGACCCCAGACGAGATGGACGACCTCCTGTTCGGCGAGTTCAAGACCCTGGAGAAGTACGGCACCCACAAGACCTCCACCTTCTACTACGAGATGACCTGCTTCGACGAGAGGCTCCGCGACTTCGAGATCAACACCAAGCTGAAGGAGATGGAGGAAGTGCCAGAGAAGTGGGAGCTCCTGTCCCTCTACTGGCAGAGCTACAGGAACGAGCGCCACAAGTACCTGGCCGTCAAGAAGTACCTCCTGGAGAAGTTCCTGGAGCTGAAGACCAACCAAAGCACCGAGGCCCTGCCAAAGTACAACAAGAAGTGGAAGCAGTGCGAGGAGATCGTCGACAACAACTTCACCAAGCAACACGAGCACGTGAACGACGTCTTCTACACCTTCGTGGCCAAGGAGAACCTCTCCAGGGACGAGTTCAAGGAGATCCTGAACGACGTTCCGCGCCAGCTGGCACCACCACCACCACCACTGA (SEQ ID NO: 48) |
| 25 | phosphatidylinositol-4-phosphate-5-kinase, putative | PVX_117385 | MRCCTKDAVNVESPKKVVVGETEEDTREEENPYEDLPTVTVTLSDGSVYTGTTKDNRVHGRGVLKYVNGDQYEGEFVDGKKEGKGKWTDKENNTYEGDWVKDKRHGHGVYKTAEGFIFEGEFANNKREGKGTIITPEKTKYVCSFQDDEEVGEVEFFFANGDHALGYIKDGYLCQNGRYEFKNGDIYVGNFEKGLFHGEGYYKWNNDANYTIYEGNYSEGKKHGKGQLINKDGRILCGMFRDNNMDGEFLEISPQGNQTKVLYDKGFFVKVLDKIEENLDVQEFLKDSIIHTTIFSDPTTYKKLYEITEKKKPQFRLNLKRTQPTShhhhhh (SEQ ID NO: 49) | ATGAGGTGCTGCACCAAGGACGCCGTCAACGTGGAGTCCCCAAAGAAGGTGGTCGTGGGCGAGACGGAGGAAGACACCAGGGAGGAAGAGAACCCATACGAGGACCTCCCAACCGTCACCGTGACCCTGTCCGACGGCAGCGTCTACACCGGCACCACCAAGGACAACAGGGTGCACGGCCGCGGCGTCCTCAAGTATGTGAACGGCGACCAATACGAGGGCGAGTTCGTCGACGGCAAGAAGGAAGGCAAGGGCAAGTGGACCGACAAGGAGAACAACACCTACGAGGGCGACTGGGTCAAGGACAAGAGGCACGGCCACGGCGTGTACAAGACCGCTGAGGGCTTCATCTTCGAGGGCGAGTTCGCCAACAACAAGCGCGAGGGCAAGGGCACCATCATCACCCCAGAGAAGACCAAGTATGTGTGCAGCTTCCAAGACGACGAGGAGGTGGGCGAGGTGGAGTTCTTCTTCGCCAACGGCGACCACGCCCTCGGCTACATCAAGGACGGCTACCTGTGCCAGAACGGCCGCTACGAGTTCAAGAACGGCGACATCTACGTGGGCAACTTCGAGAAGGGCCTGTTCCACGGCGAGGGCTACTACAAGTGGAACAACGACGCCAACTACACCATCTACGAGGGCAACTACTCCGAGGGCAAGAAGCACGGCAAGGGCCAACTCATCAACAAGGACGGCAGGATCCTGTGCGGCATGTTCCGCGACAACAACATGGACGGCGAGTTCCTGGAGATCAGCCCACAAGGCAACCAGACCAAGGTCCTCTACGACAAGGGCTTCTTCGTCAAGGTGCTGGACAAGATCGAGGAGAACCTCGACGTGCAGGAGTTCCTGAAGGACTCCATCATCCACACCACCATCTTCAGCGACCCAACCACCTACAAGAAGCTGTACGAGATCACCGAGAAGAAGAAGCCACAATTCAGGCTCAACCTGAAGCGCACCCAGCCAACCTCCCACCACCACCACCACCACTGA (SEQ ID NO: 50) |
| 26 | Plasmodium exported protein, unknown function | PVX_113225 | mNKLGTSLVEDATANGEFGLRVQRLLGGSRSSRDSIFADSFYDDDDDDDNNDKLFDYDSDHKSRREVKDRHHRHRHSHSRHKRRHSHKHRTSSRSRREKEESSTTNDDDDEVLSLSRFDVDDDKDDRSHSRYSVDYDDENDDEPSSSRPASTDYDDIIDLTNARRSGSKYRISSMDIELYPEHEDEYLFEGKRRSG | ATGAACAAGCTGGGCACCAGCCTCGTGGAGGACGCTACCGCTAACGGCGAGTTCGGCCTCCGCGTCCAAAGGCTGCTGGGCGGCTCCAGGTCCAGCCGCGACGCATCTTCGCCGACTCCTTCTACGATGATGACGACGACGACAACAACGACAAGCTGTTCGACTACGACAGCGACCACAAGTCCAGGCGCGAGGTGAAGGACAGGCACCACAGGCACAGGCACAGCCACTCCCACCGCCACAAGAGGCGCCACAGCCACAAGCACAGGACCTCCAGCCGCTCCAGGGAGAAGGAAGAGTCCAGCACCACCAACGACGACGACGAGGTGCTCAGCCTGTCCAGGTTCGACGTCGACGACGACAAGGAC |

Appendix I-continued

| No. | Protein Name | Protein Reference | Insert aa sequence (add M as start/His-tag at C-term) | Insert DNA sequence (Start from ATG to His-tag stop codon) |
|---|---|---|---|---|
| | | | GVLKKADNYCENKIFDALSALDKYK EYYGEERRVMKQAAYRKATKVFAIP GAAALSPLIITLFLTTSNVVALPLAAS AVILGGILYKKSKDKSDYGRPHLKSI TYhhhhhh (SEQ ID NO: 51) | GACAGGAGCCACTCCCGCTACAGCGTGGACTACGACGACGAGAACGA CGACGAGCCATCCAGCTCCAGGCCAGCCTCCACCGACTACGACGACAT CATCGACCTCACCAACGCTAGGCGCAGCGGCTCCAAGTACCGCATCAG CTCCATGGACATCGAGCTCTACCCAGAGCACGAGGACGAGTACCTGTT CGAGGGCAAGAGGCGCAGCGGCGGCGTCCTGAAGAAGGCTGACAACT ACTGCGAGAACAAGATCTTCGACGCCCTCTCCGCCCTGGACAAGTACA AGGAGTACTACGGCGAGGAGAGGCGCGTGATGAAGCAGGCCGCCTAC AGGAAGGCCACCAAGGTCTTCGCTATCCCAGGCGCTGCCGCCCTCAGC CCACTGATCATCACCCTCTTCCTGACCACCAGCAACGTGGTGGCTCTCC CACTGGCTGCTTCCGCCGTCATCCTCGGCGGCATCCTGTACAAGAAGA GCAAGGACAAGTCCGACTACGGCCGCCCACACCTCAAGTCCATCACCT ACCACCACCACCACCACCACTGA (SEQ ID NO: 52) |
| 27 | tryptophan-rich antigen (Pv-fam-a) | PVX_090265 | MEAARGVSGLVPSSNSLQEITLRYK DKLLNMDKEQMILTLGVTMIAITSAV AFGVLATHGDINDFLGVESDEESEK KKEIVEKSEEWKREWSNWLKKLE QDWKVFNEKLQNEKKTFLEEKEED WNTWIKSVEKKWTHFNPNMDKEFH TNMMRRSINWTESQWREWIQTEGR LYLDIEWKKWFFENQSRLDELIVKK WIQWKKDKIINWLMSDWKRAEQEH WEEFEEKSWSSKFFQIFEKRNYEDF KDRVSDEWEDWFEWVKRKDNIFIT NVLDQWIKWKEEKNLLYNNWADAF VTNWINKKQWVVWVNERRNLAAKA KAALNKKKhhhhhh (SEQ ID NO: 53) | ATGGAGGCTGCCAGGGGCGTGTCCGGCCTCGTCCCATCCAGCAACAGC CTCCAAGAGATCACCCTGCGCTACAAGGACAAGCTCCTGAACATGGAC AAGGAGCAGATGATCCTCACCCTGGGCGTCACCATGATCGCTATCACCT CCGCTGTGGCTTTCGGCGTCCTGGCTACCCACGGCGACATCAACGACTT CCTGGGCGTCGAGTCCGACGAGGAGAGCGAGAAGAAGAAGGAGATC GTGGAGAAGTCCGAGGAGTGGAAGAGGAAGGAGTGGAGCAACTGGC TCAAGAAGCTGGAGCAAGACTGGAAGGTCTTCAACGAGAAGCTCCAG AACGAGAAGAAGACCTTCCTGGAGGAGAAGGAAGAGGACTGGAACAC CTGGATCAAGTCCGTGGAGAAGAAGTGGACCCACTTCAACCCAAACAT GGACAAGGAGTTCCACACCAACATGATGAGGCGCTCCATCAACTGGAC CGAGAGCCAATGGCGCGAGTGGATCCAGACCGAGGGCAGGCTCTACC TGGACATCGAGTGGAAGAAGTGGTTCTTCGAGAACCAAAGCAGGCTC GACGAGCTGATCGTGAAGAAGTGGATCCAGTGGAAGAAGGACAAGAT CATCAACTGGCTCATGTCCGACTGGAAGCGCGCCGAGCAAGAGCACTG GGAGGAGTTCGAGGAGAAGAGCTGGTCCAGCAAGTTCTTCCAGATCTT CGAGAAGCGCAACTACGAGGACTTCAAGGACCGCGTGAGCGACGAGT GGGAGGACTGGTTCGAGTGGGTCAAGCGCAAGGACAACATCTTCATC ACCAACGTGCTGGACCAGTGGATCAAGTGGAAGGAAGAGAAGAACCT CCTGTACAACAACTGGGCCGACGCCTTCGTCACCAACTGGATCAACAA GAAGCAGTGGGTGGTCTGGGTGAACGAGAGGCGCAACCTCGCTGCTA AGGCTAAGGCTGCCCTGAACAAGAAGAAGCACCACCACCACCACCACT GA (SEQ ID NO: 54) |
| 28 | MSP7 family | PVX_082700 | mTKGPSGPPPNKKLNANALHFLRG KLELLNKISEEQVSPDFKKNVELLK KKIEELQGKAEKDKSKTDGEDTTPK EQQEDQNVSQNGLEEQAPSDSNEG EAQEENTQVKNVIFTEKEEAVDEEA EKEDTAVISEKANFPNEESQGNDET QTQESIEGEASPGVVVDETDDSPEG EPLSGLETEGNSSAESAPNEPDVNT THTAVDTHMPADANIGVDTNMPFDT PPHPSGENPGAPQETHLPSIDENAN RRASRMKHMSSFLNGLLTNQSNNK KEIFFHPYYGPYFNHGGYYNYDPYY NYAPAYNPFVSQARDYEVIKKLLDA CFNKGEGADPNVPCIIDIFKKVLDDE RFRNELKTFMYDLYEFLKKNDVLSD DEKKNELMRFFFDNAFQLVNPMFYY hhhhhh (SEQ ID NO: 55) | ATGACCAAGGGCCCATCCGGCCCACCACCAAACAAGAAGCTCAACGCC AACGCCCTCCACTTCCTGAGGGGCAAGCTGGAGCTCCTGAACAAGATC TCCGAGGAGCAAGTGGTCAGCCCAGACTTCAAGAAGAACGTCGAGCTC CTCAAGAAGAAGATCGAGGAGCTCCAGGGCAAGGCCGAGAAGGACAA GTCCAAGACCGACGGCGAGGACACCACCCCAAAGGAGCAACAAGAGG ACCAAAACGTGAGCCAGAACGGCCTGGAGGAGCAAGCTCCGTCCGAC AGCAACGAGGGCGAGGCTCAAGAGGAGAACACCCAGGTCAAGAACGT GATCTTCACCGAGAAGGAAGAGGCCGTCGACGAGGAAGCCGAGAAG GAAGACACCGCCGTGATCTCCGAGAAGGCCAACTTCCCAAACGAGGA GAGCCAGGGCAACGACGAGACGCAAACCCAAGAGTCCATCGAGGGCG AGGCTAGCCCGGGCGTGGTGGTGGACGAGACGGACGACTCCCCGGAG GGCGAGCCACTCAGCGGCCTCGAAACCGAGGGCAACTCCAGCGCTGA GTCCGCTCCCAACGAGCCCGACGTCAACACCACCCACCGCTGTGGA CACCCACATGCCAGCTGACGCCAACATCGGCGTCGACACCAACATGCC ATTCGACACCCCACCACACCCAAGCGGCGAGAACCCGGGCGCCCCACA AGAGACGCACCTCCCATCCATCGACGAGAACGCCAACAGGCGCGCCAG CAGGATGAAGCACATGTCCAGCTTCCTGAACGGCCTCCTGACCAACCA GTCCAACAACAAGAAGGAGATCTTCTTCCACCCATACTACGGCCCATAC TTCAACCACGGCGGATACTACAACTACGACCCATACTACAACTACGCCC CAGCCTACAACCCATTCGTCAGCCAAGCCCGCGACTACGAGGTCATCA AGAAGCTCCTGGACGCCTGCTTCAACAAGGGCGAGGGCGCTGACCCA AACGTCCCATGCATCATCGACATCTTCAAGAAGGTGCTCGACGACGAG AGGTTCCGCAACGAGCTGAAGACCTTCATGTACGACCTCTACGAGTTCC TGAAGAAGAACGACGTCCTCAGCGACGACGAGAAGAAGAACGAGCTG ATGAGGTTCTTCTTCGACAACGCCTTCCAGCTCGTGAACCCAATGTTCT ACTACCACCACCACCACCACTGA (SEQ ID NO: 56) |
| 29 | Hyp, huge list of orthologs, paralogs, synteny with Py LSA3 (PyLSA3syn-3) | PVX_002550 | mFSGGVGDDEEEEEEEGEEGESE RDDSERDYAGRDDAGRDDAERND AERDDAERNDAERDDAERDHAERD HADKAESDRESSLEANENRLVKLSE GGESEPALLEVEEDIKQTVLGMFSL KGEFDEAESEKLALDLQKNLLSMLS GNMEDNDDEYEDINDEEYEEVEEDY EEEKLGKPVEVVVEDATEEAVDEVV GVVQEPEEEGAEESDKDTGEVSEE EVAKEAADEVMEEEKKEEAGEPSV VVEEPSVVVKEPSVVVKEPSVVVEE PSVVVEEPSVVVEEPSVVVEEPAFT | ATGTTCAGCGGCGGCGTGGGCGACGACGAGGAAGAGGAAGAGGAAG AGGAAGGCGAGGAAGGCGAGAGCGAGAGGGACGACTCCGAGAGGG ACTACGCTGGCAGGGACGATGCCGGCAGGGACGACGCCGGAGGAA CGACGCCGAGCGCGATGATGCTGAGCGCAACGACGCCGAGCGCGACG ACGCCGAGAGGGACCACGCCGAGCGCGACCACGCCGACAAGGCCGAG TCCGACAGGGAGTCCAGCCTGGAGGCCAACGAGAACAGGCTGGTGAA GCTCAGCGAGGGCGGCGAGTCCGAGCCAGCCCTGCTCGAGGTGGAGG AAGACATCAAGCAAACCGTCCTGGGCATGTTCAGCCTCAAGGGCGAGT TCGACGAGGCCGAGTCCGAGAAGCTCGCCCTGGACCTCCAGAAGAACC TCCTGTCCATGCTCAGCGGCAACATGGAGGACAACGACGACGAGTACG AGGACATCGACGAGGAGTACGAGGAAGTGGAGGAAGACTACGAGGA AGAGAAGCTCGGCAAGCCAGTGGAGGTGGTCGTGGAGGACGCCACCG |

Appendix I-continued

| No. | Protein Name | Protein Reference | Insert aa sequence (add M as start/His-tag at C-term) | Insert DNA sequence (Start from ATG to His-tag stop codon) |
|---|---|---|---|---|
| | | | VEEPAFTVEEPAITVEEPAITVEEPVF TVEEPVFTVEEPAFTVEEPAFTVEEP AFTVEEPATTVEELVEEVLKVAEEEV ATEAVEKDGEEAEEQVTEESVEEDE EESGEEEGEESEEEETEESAEEEVA KESVEEEVAKEAEEESEESGEESAEE EKEKAEEPVAPVDEVLKEGMQKIEE SVKEALGVVQEAVDKVAEEEQTEQ AQGPAEAGPVGVVKEPEEEEESEE EGEEGEEGEEGEEEEEEESEEEES EEGESEAGESEAGKSDAAESEVAE SEAGEPAEDQAGMDAKMKDELLGM LSEKMKAEGKDLDKLPPEVKKNLLD MLAGNMEMDDEEEEGEEEGEDLG NEELDLQKNLLEMLSGKGGFNPNM LGNLKELEALQKSVPGLMGKAQGIS PAEIESLKSMFSGAFDSRGFKGMPQ MKLPAELQSIMMPKKEEKGKPQGA QAKAKVPAKAGVQKPKAQDIMPS RRIRDLFVLPKEIFGSLKNFKESALKF ANHIGLNLETIKKHLTTVKNFLLRVDA VVDKEIGNIIEAGKSPQNVVQANEGF LDKMKRLVNKYKIFSIPFFAGMGSFG Fhhhhhh (SEQ ID NO: 57) | AGGAAGCCGTGGACGAGGTGGTGGGCGTCGTGCAAGAGCCAGAGGA AGAGGGCGCTGAGGAGAGCGACAAGGACACCGGCGAGGTGTCCGAG GAAGAGGTGGCCAAGGAAGCCGCCGACGAGGTCATGGAGGAAGAGA AGAAGGAAGAGGCCGGCGAGCCATCCGTGGTGGTGGAGGAGCCAAG CGTGGTCGTGAAGGAGCCATCCGTCGTGGTCAAGGAGCCTTCCGTGGT CGTGGAGGAGCCTAGCGTCGTCGTCGAGGAGCCTTCCGTCGTGGTGG AGGAGCCCAGCGTGGTCGTCGAGGAGCCAGCCTTCACCGTGGAGGAG CCTGCCTTCACCGTCGAGGAGCCAGCCATCACCGTGGAGGAGCCCGCT ATCACGGTGGAGGAGCCAGTGTTCACCGTGGAAGAACCCGTGTTCACC GTGGAAGAGCCCGCCTTCACCGTTGAGGAGCCCGCCTTCACCGTAGAA GAGCCTGCCTTCACCGTTGAAGAACCAGCTACCACCGTGGAGGAGCTG GTGGAGGAAGTGCTCAAGGTGGCTGAGGAAGAGGTGGCTACCGAGG CTGTGGAGAAGGACGGCGAGGAAGCCGAGGAGCAAGTCACCGAGGA GAGCGTCGAGGAAGACGAGGAAGAGTCCGGCGAGGAAGAGGGCGA GGAGAGCGAGGAAGAGGAGACCGAGGAGTCCGCTGAGGAAGAGGTG GCGAAGGAGAGCGTGGAGGAAGAGGTGGCTAAGGAAGCCGAGGAGT CCGAGGAGAGCGGGGAGGAGAGCGCTGAGGAAGAGAAGGAGAAGG CCGAGGAGCCAGTGGCTCCAGTGGACGAGGTCCTGAAGGAAGGCATG CAGAAGATCGAGGAGAGCGTGAAGGAAGCCCTGGGCGTGGTCCAAG AGGCCGTGGACAAGGTCGCCGAGGAAGAGCAGACCGAGCAGGCTCA GGGCCCAGCTGAGGCTGGCCCCAGTCGGCGTGGTCAAGGAGCCTGAGG AAGAGGAAGAGTCTGAGGAAGAGGGCGAGGAAGGCGAGGAAGGCG AGGAAGGCGAGGAAGAGGAAGAGGAAGAGAGTGAGGAAGAGGAGT CTGAGGAAGGCGAGTCCGAGGCTGGGGAGAGCGAGGCTGGCAAGA CGACGCCGCCGAGTCCGAGGTGGCCGAGAGCGAGGCCGGCGAGCCG GCTGAGGACCAAGCTGGCATGGACGCCAAGATGAAGGACGAGCTCCT GGGCATGCTGAGCGAGAAGATGAAGGCCGAGGGCAAGGACCTGGAC AAGCTCCCACCAGAGGTCAAGAAGAACCTCCTGGACATGCTCGCCGGC AACATGGAGATGGACGATGAGGAAGAGGAAGGCGAGGAAGAGGGC GAAGACCTGGGCAACGAGGAGCTCGACCTCCAGAAGAACCTCCTGGA GATGCTCTCCGGCAAGGGCGGCTTCAACCCAAACATGCTGGGCAACCT CAAGGAGCTGGAGGCCCTCCAAAAGAGCGTGCCAGGCCTGATGGGCA AGGCTCAGGGCATCTCCCCAGCTGAGATCGAGTCCCTCAAGAGCATGT TCTCCGGCGCCTTCGACAGCAGGGGCTTCAAGGGCATGCCACAGATGA AGCTGCCAGCCGAGCTCCAGTCCATCATGATGCCAAAGAAGGAAGAG AAGGGCAAGCCACAAGGCGCTCAAGCTAAGGCTAAGGTGCCAGCTAA GGCTGGCCAAGTCCAGAAGCCAAAGGCCCAGGACATCATGCCAAGCA GGCGCATCCGCGACCTGTTCGTGCTCCCAAAGGAGATCTTCGGCAGCC TGAAGAACTTCAAGGAGTCCGCCCTCAAGTTCGCCAACCACATCGGCCT GAACCTGGAGACCATCAAGAAGCACCTCACCACCGTGAAGAACTTCCT CCTGAGGGTCGACGCCGTGGTCGACAAGGAGATCGGCAACATCATCG AGGCCGGCAAGTCCCCACAAAACGTGGTCCAGGCCAACGAGGGCTTCC TGGACAAGATGAAGCGCCTCGTGAACAAGTACAAGATCTTCAGCATCC CATTCTTCGCCGGCATGGGCTCCTTCGGCTTCCACCATCACCACCATCAC TGA (SEQ ID NO: 58) |
| 30 | MSP7-like protein | PVX_082650 | mQLGIQKKKKNLEQDAMHALMKKLE SLYKLSATDNGEIFNKEIDALKKQID QLHQHGGGNEGESLGHLLESEAAD DSGKKTIFGVDEDDLDNYDADFIGQ SKGKIKGQADTTAVAKPPTGSGAGA HGSHSPPKPSVLVVPGKSGKEDSV ATLENGYESIHGEDEPREDSTSHDS PPALPVGRSEGDSSASGGGTEGQQ PDPASARGSQASGGRGGDQTNT TQPAGGQQSSSAARSLQAPHAGDS QLPNAGGDPQSPAAAGHQQPPTSP PANNEGTTVTQESALAATPPKGTAD SNDAKIKYLDKLYDEVLTTSDNTSGI HVPDYHSKYNTIRQKYEYSMNPVEY EIVKNLFNVGFKNDGAASSDATPLV DVFKKALADEKQAEFDNFVHGLYG FAKRHSYLSEARMKDNKLYSDLLKN AISLMSTLQVShhhhhh (SEQ ID NO: 59) | ATGCAGCTCGGCATCCAAAAGAAGAAGAAGAACCTGGAGCAGGACGC CATGCACGCCCTCATGAAGAAGCTGGAGAGCCTGTACAAGCTCTCCGC CACCGACAACGGCGAGATCTTCAACAAGGAGATCGACGCCCTGAAGA AGCAAATCGACCAGCTCCACCAACACGGCGGCGGAAACGAGGGCGAG AGCCTGGGCCACCTCCTGGAGAGCGAGGCTGCTGACGACTCCGGCAA GAAGACCATCTTCGGCGTGGACGAGGACGACCTGGACAACTACGACG CCGACTTCATCGGCCAGAGCAAGGGCAAGATCAAGGGCCAGGCTGACA CCACCGCTGTGGCTAAGCCACCAACCGGCAGCGGCGCTGGCGCTCACG GCAGCCACTCCCCACCAAAGCCATCCGTGCTCGTGGTCCCAGGCAAGA GCGGCAAGGAAGACTCCGTCGCCACCCTGGAGAACGGCTACGAGAGC ATCCACGGCGAGGACGAGCCCAAGGGAGGACAGCACCTCCCACGACTC CCCACCAGCTCTCCCAGTGGGCCGCAGCGAGGGCGACTCCAGCGCTTC CGGCGGCGGCACCGAGGGCCAACAGCCAGACCCAGCTAGCGCCAGGG GCAGCCAGGCTTCCGGCGGCAGGGCGGCGGCGACCAAACCAACACC ACCCAACCAGCTGGCGGCCAACAGTCCAGCTCCGCTGCTAGGAGCCTG CAGGCCCCACACGCTGGCGACAGCCAGCTCCCCAACGCCGGCGGCGA CCCACAATCCCCAGCTGCCGCCGGCCACCAACAGCCACCAACCTCCCCA CCAGCTAACAACGAGGGCACCACCGTGACCCAAGAGTCCGCTCTGGCT GCTACCCCACCAAAGGGCACCGCCGACTCCAACGACGCCAAGATCAAG TACCTGGACAAGCTCTACGACGAGGTGCTGACCACCAGCGACAACACC TCCGGCATCCACGTCCCAGACTACCACAGCAAGTACAACACCATCCGCC AAAAGTACGAGTACTCCATGAACCCAGTGGAGTACGAGATCGTCAAGA ACCTCTTCAACGTGGGCTTCAAGAACGACGGCGCTGCCAGCTCCGACG CTACCCCACTGGTGGACGTCTTCAAGAAGGCCCTCGCCGACGAGAAGT TCCAGGCCGAGTTCGACAACTTCGTCCACGGCCTGTACGGCTTCGCCAA GAGGCACAGCTACCTCTCCGAGGCCCGCATGAAGGACAACAAGCTGTA CAGCGACCTCCTGAAGAACGCCATCAGCCTGATGTCCACCCTCCAAGTG TCCCACCACCACCACCACCACTGA (SEQ ID NO: 60) |

Appendix I-continued

| No. | Protein Name | Protein Reference | Insert aa sequence (add M as start/His-tag at C-term) | Insert DNA sequence (Start from ATG to His-tag stop codon) |
|---|---|---|---|---|
| 31 | reticulocyte binding protein 2b (RBP2b) | PVX_094255 | mAAYNTVLQIYKYSDDIVRKQEKCE QLVKDGKDICLKFKSINEIKVMIQNSK GKESTLSAKVSHSFNKLSELNKIKCN DESYDAILETPSREELNKLRSTFKQE KDTIANQAKLSGYKTDFETHIGKLND LAKIVDNLKASETLPKNIEEKKTSINLI STKLETIEKEIESINSSFDQLLEKGKK CEMTKYKLVRDSLSTKINDHSAIIKD NQKKATEYLTYIQNNHISIFKDIDMLN ENLGEKSVSRYAIAKIEEANDLSAQL TAAVSEYEAIANSIRKEFTNISDHTE MDTLENEAKMLKEHYDNLINKKNIIT ELHNKINLIKLLEIRATSDKYVDIAELL GEVVKDQKKKLQEAKNKLDTLKDHI AVKEKELINHDSSFTLVSIKAFDEIYD DIKYNVGQLHTLEVTNFDELKKGKT YEEENVTHLLNRRETLONDLHNYEEK DKLKNTNIEMSNEENNQIRQTSEVIK KLESEFQNLLKIIQQSNTLCSNDNIK QFISDILKKVETIRERFVKNFPEREKY HQIEINYNEIKGIVKEVDTNPEISIFTE KINTYIRQKIRSAHHLEDAQKIKDIIED VTSNYRKIKSKLSQVNNALDRIKIKK SEMDTLFESLSKENANNYNSAKYFL VDSDKIIKHLEDQVSKMSSLISYAER EIKELEEKVYShhhhhh (SEQ ID NO: 61) | ATGGCCGCCTACAACACCGTGCTCCAAATCTACAAGTACTCCGACGACA TCGTGAGGAAGCAAGAGAAGTGCGAGCAGCTGGTCAAGGACGGCAA GGACATCTGCCTCAAGTTCAAGTCCATCAACGAGATCAAGGTCATGATC CAGAACAGCAAGGGCAAGGAGTCCACCCTCAGCGCCAAGGTGTCCCA CAGCTTCAACAAGCTCAGCGAGCTGAACAAGATCAAGTGCAACGACGA GAGCTACGACGCCATCCTCGAAACCCCATCCAGGGAGGAGCTCAACAA GCTGCGCAGCACCTTCAAGCAAGAGAAGGACACCATCGCCAACCAGGC CAAGCTCTCCGGCTACAAGACCGACTTCGAGACGCACATCGGCAAGCT CAACGACCTGGCCAAGATCGTGGACAACCTCAAGGCCAGCGAGACGCT GCCAAAGAACATCGAGGAGAAGAAGACCTCCATCAACCTCATCAGCAC CAAGCTCGAAACCATCGAGAAGGAGATCGAGTCCATCAACTCCAGCTT CGACCAACTCCTGGAGAAGGGCAAGAAGTGCGAGATGACCAAGTACA AGCTCGTCAGGGACTCCCTGAGCACCAAGATCAACGACCACTCCGCCA TCATCAAGGACAACCAAAAGAAGGCCACCGAGTACCTCACCTACATCC AGAACAACCACATCAGCATCTTCAAGGACATCGACATGCTCAACGAGA ACCTGGGCGAGAAGTCCGTGAGCAGGTACGCCATCGCCAAGATCGAG GAAGCCAACGACCTCTCCGCTCAACTCACCGCTGCCGTCAGCGAGTAC GAGGCTATCGCCAACTCCATCCGCAAGGAGTTCACCAACATCTCCGACC ACACCGAGATGGACACCCTGGAGAACGAGGCCAAGATGCTGAAGGAG CACTACGACAACCTCATCAACAAGAAGAACATCATCACCGAGCTCCACA ACAAGATCAACCTGATCAAGCTCCTGGAGATCCGCACCAGCGACA AGTATGTGGACATCGCCGAGCTCCTGGGCGAGGTGGTCAAGGACCAA AAGAAGAAGCTGCAAGAGGCCAAGAACAAGCTCGACACCCTGAAGGA CCACATCGCCGTGAAGGAGAAGGAGCTGATCAACCACGACTCCAGCTT CACCCTCGTCAGCATCAAGGCCTTCGACGAGATCTACGACGACATCAA GTACAACGTGGGCCAACTCCACACCCTGGAGGTCACCAACTTCGACGA GCTCAAGAAGGGCAAGACCTACGAGGAGAACGTGACCCACCTCCTGA ACAGGCGCGAGACGCTCCAGAACGACCTGCACAACTACGAGGAGAAG GACAAGCTCAAGAACACCAACATCGAGATGTCCAACGAGGAGAACAA CCAAATCAGGCAGACCAGCGAGGTCATCAAGAAGCTGGAGTCCGAGT TCCAAAACCTCCTGAAGATCATCCAACAGTCCAACACCCTCTGCAGCAA CGATAACATCAAGCAGTTCATCAGCGACATCCTGAAGAAGGTGGAGAC GATCAGGGAGCGCTTCGTCAAGAACTTCCCAGAGCGCGAGAAGTACCA CCAAATCGAGATCAACTACAACGAGATCAAGGGCATCGTGAAGGAAG TGGACACCAACCCAGAGATCTCCATCTTCACCGAGAAGATCAACACCTA CATCAGGCAAAAGATCAGGAGCGCTCACCACCTGGAGGACGCTCAGA AGATCAAGGACATCATCGAGGACGTGACCTCCAACTACAGGAAGATCA AGTCCAAGCTGAGCCAAGTCAACAACGCCCTCGACCGCATCAAGATCA AGAAGAGCGAGATGGACACCCTCTTCGAGTCCCTGAGCAAGGAGAAC GCCAACAACTACAACAGCGCCAAGTACTTCCTGGTGGACTCCGACAAG ATCATCAAGCACCTGGAGGACCAAGTGTCCAAGATGTCCAGCCTGATC AGCTACGCCGAGCGCGAGATCAAGGAGCTGGAGGAGAAGGTCTACTC CCACCACCACCACCACCACTGA (SEQ ID NO: 62) |
| 32 | MSP3.3 [merozoite surface protein 3 beta (MSP3b)] | PVX_097680 | mNVATRGEIVNLKNPNLRNGWSMK NLSAQNEENIVHSDGSDDVTDKEED GEVLEGQKGSPKKSAEQKVHAQEE VNKESLKSKAQNAKAEAEKAAKAE SAKENTLDALEKVNVPTELNNEKNF AESAATEAKKQEKISTEAAEEEVKEIE VDGQLEKLKNEEEKTAKKARKQEIK TEIAEQAAKAQAAKTEAETAQKDAT TAKDEAIKETGKPKSQNTTKAVTMA TEEEKKTKDEAQTASEKAGKTAEEA QKEVGKETADDDKEVSQLEEEIKEL ERILKIVKDLASEASSASDNAKKAKL KTQIAAEVVKAEKARIEAEEAEKEAG EAKTKTEATEKEVLKISDESKAAKVK KAVEKAKEAEKQAKSEAEKAKGMA DDAGGKGTTNLEDVLTKLSEVLTSV KSLASNAEVASKNAKKEMTKAQIAA EVAKAEKAKIEAENAKLLADTASKAA ENIAKSSKAAKIANNVSTIAAEKSKVA TEAADEEAAKALDETENPESKIAEVTE KATKAVNAAEEAKKEKAKAEVAVEV AHAEVAKEKAQEAKEAAKQVADKS KLEKAIQAADKASEKANEASKLAEEA LSNLESLEKETGEIVEKVNAIEQKVQ TAKNAAIEAHKEKTKAEIAVEVAKAE EAKKEADNAKVAAEKAKETAEKIAKT SKSTEKITEEVRKATEFAKTAGDETT LAATKAESEIPSEEKNQKELLDSIKQ KAESAFQASQEAIKAKTEAENFLEIA KEVPKAEAAKEEAQKAATAAEEEAKT EVLKIAEEVNKSDASESEKKKIETAA | ATGAACGTCGCCACCAGGGGCGAGATCGTGAACCTGAAGAACCCCAAA CCTCCGCAACGGCTGGAGCATGAAGAACCTGTCCGCCCAAAACGAGGA GAACATCGTCCACTCCGACGGCAGCGACGACGTGACCGACAAGGAAG AGGACGGCGAGGTGCTGGAGGGCCAGAAGGGCAGCCCAAAGAAGTC CGCCGAGCAAAAGGTCCACGCCCAAGAGGAAGTGAACAAGGAGTCCC TCAAGTCAAAGGCCCAAAACGCCAAGGCTGAGGCTGAGAAGGCTGCT AAGGCTGCCGAGTCCGCCAAGGAGAACACCCTCGACGCCCTGGAGAA GGTGAACGTCCCAACCGAGCTCAACAACGAGAAGAACTTCGCTGAGA GCGCTGCTACCGAGGCCAAGAAGCAGGAGAAGATCTCCACCGAGGCC GCCGAGGAAGTGAAGGAGATCGAGGTGGACGGCCAACTGGAGAAGC TGAAGAACGAGGAAGAGAAGACCGCCAAGAAGGCCAGGAAGCAGGA GATCAAGACCGAGATCGCTGAGCAAGCTGCTAAGGCTCAGGCTGCTAA GACCGAGGCCGAGACGGCCCAAAAGGACGCCACCACCGCCAAGGACG AGGCCATCAAGGAGACGGGCAAGCCAAAGAGCCAGAACACCACCAAG GCCGTCACCATGGCCACCGAGGAAGAAGAAGACCAAGGACGAGGC TCAAACCGCTTCCGAGAAGGCTGGCAAGACCGCTGAGGAAGCCAGA AGGAAGTGGGCAAGGAGACGGCCGACGACGACAAGGAAGTGTCCCA ACTCGAAGAGGAGATCAAGGAGCTGGAGAGGATCCTCAAGATCGTGA AGGACCTGGCTAGCGAGGCCTCCAGCGCTTCCGACAACGCCAAGAAG GCCAAGCTCAAGACCCAAATCGCTGCTGAGGTGGTCAAGGCTGAGAA GGCTAGGATCGAGGCTGAGGAAGCCGAGAAGGAAGCCGGCGAGGCT AAGACCAAGACCGAGGCTACCGAGAAGGAAGTGCTGAAGATCTCCGA CGAGAGCAAGGCCGCCAAGGTCAAGAAGGCCGTGGAGAAGGCCAAG GAAGCCGAGAAGCAAGCCAAGTCCGAGGCTGAGAAGGCTAAGGGCAT GGCTGACGACGCCGGCGGCAAGGGCACCACCAACCTGGAGGACGTGC TCACCAAGCTCTCCGAGGTCCTGACCTCCGTGAAGTCCCTGGCTTCCAA CGCTGAGGTGGCTTCCAAGAACGCCAAGAAGGAGATGACCAAGGCTC AGATCGCTGCTGAGGTGGCTAAGGCTGAGAAGGCCAAGATCGAGGCC GAGAACGCCAAGCTGCTGGCTGACACCGCTAGCAAGGCTGCCGAGAA CATCGCCAAGTCCAGCAAGGCCGCCAAGATCGCCAACAACGTCAGCAC CATCGCCGCCGAGAAGTCCAAGGTGGCTACCGAGGCTGCTGACGAGG |

| No. | Protein Name | Protein Reference | Insert aa sequence (add M as start/His-tag at C-term) | Insert DNA sequence (Start from ATG to His-tag stop codon) |
|---|---|---|---|---|
| | | | NETAGEAEKAATFAKEAADAAKDTN KAVTLAVAKEKVEKALKAAKEAKKA NEKASYALIRTKKQYALEPLEITSEA GYNITEKEEQVKEEIEEQDDKASEE EEEDTQQIDQTQIDEVDISVDNEEEE EGAAEEQIEGEKDTPTKEAKEEQTS GEKILDDKEAHKTLAEKFKDSNTAKT GGVEFLETLISDVGEDTLKNLQQDL HQYFKGKhhhhhh (SEQ ID NO: 63) | CTGCCAAGGCCCTCGACGAGACGGAGAACCCAGAGTCCAAGATCGCC GAGGTGACCGAGAAGGCTACCAAGGCTGTGAACGCTGCTGAGGAAGC CAAGAAGGAGAAGGCCAAGGCTGAGGTGGCTGTGGAGGTGGCTCAC GCTGAGGTGGCTAAGGAGAAGGCCAAGAGGCCAAGGAAGCCGCCA AGCAGGTGGCCGACAAGAGCAAGCTGGAGAAGGCCATCCAAGCCGCC GACAAGGCCAGCGAGAAGGCCAACGAGGCCTCCAAGCTCGCCGAGGA AGCCCTCAGCAACCTGGAGTCCCTGGAGAAGGAGACGGGCGAGATCG TCGAGAAGGTGAACGCCATCGAGCAAAAGGTGCAGACCGCCAAGAAC GCCGCCATCGAGGCCCACAAGGAGAAGACCAAGGCTGAGATCGCTGT GGAGGTCGCCAAGGCCGAGGAAGCCAAGAAGGAAGCCGACAACGCC AAGGTGGCTGCTGAGAAGGCTAAGGAGACGGCCGAGAAGATCGCCAA GACCTCCAAGAGCACCGAGAAGATCACCGAGGAAGTGAGGAAGGCTA CCGAGTTCGCTAAGACCGCTGGCGACGAGACGACCCTGGCTGCTACCA AGGCTGAGAGCGAGATCCCATCCGAGGAGAAGAACCAAAAGGAGCTC CTGGACAGCATCAAGCAGAAGGCCGAGAGCGCCTTCCAAGCCTCCCAA GAGGCCATCAAGGCCAAGACCGAGGCCGAGAACTTCCTGGAGATCGC CAAGGAAGTGCCAAAGGCCGAGGCCGCCAAGGAAGAGGCCCAAAAG GCTGCTACGGCCGCTGAGGAAGCCAAGACCGAGGTCCTCAAGATCGCC GAGGAAGTGAACAAGTCCGACGCCTCCGAGAGCGAGAAGAAGAAGAT CGAGACGGCTGCTAACGAGGCGGCTGGCGAGGCCGAGAAGGCCGCTA CCTTCGCTAAGGAAGCCGCTGACGCTGCTAAGGACACCAACAAGGCCG TCACCCTGGCCGTGGCCAAGGAGAAGGTCGAGAAGGCCCTCAAGGCC GCCAAGGAAGCCAAGAAGGCCAACGAGAAGGCCAGCTACGCCCTGAT CCGCACCAAGAAGCAGTACGCCCTGGAGCCACTGGAGATCACCTCCGA GGCCGGCTACAACATCACCGAGAAGGAAGAGCAAGTGAAGGAAGAG ATCGAGGAGCAGGACGACAAGGCCAGCGAGGAAGAGGAAGAGGACA CCCAACAGATCGACCAAACCCAGATCGACGAGGTCGACATCTCCGTGG ACAACGAGGAAGAGGAAGAGGGCGCTGCTGAGGAGCAAATCGAGGG CGAGAAGGACACCCCAACCAAGGAAGCCAAGGAAGAGCAGACCTCCG GCGAGAAGATCCTGGACGACAAGGAAGCCCACAAGACCCTCGCCGAG AAGTTCAAGGACAGCAACACCGCTAAGACCGGCGGCGTCGAGTTCCTC GAAACCCTCATCTCCGACGTGGGCGAGGACACCCTGAAGAACCTCCAA CAGGACCTCCACCAGTACTTCAAGGGCAAGCACCACCACCACCACCACT GA (SEQ ID NO: 64) |
| 33 | hypothetical protein, conserved | PVX_001000 | mNNYGKLKHGKWDDGSYSERTRW RMLSGDDHDDLLPSCDSPGGRNDE HQVNKEVSRTAPSEKVKVVDKETG ESMLVDVGESGGKSSPGVAEESGP SLRGRDVRDVRVDQETRETLQGGA TNRRDLTQHGEEETGDDSKRAKQD DEAGVRSMLNDTVTAIKDNGSNLLR SVIGQINFVQGSAELLKVANEEERQ PSGGSVLSKEGEEATPGDFLGGNN PNGGEKGELPNGTKNDVMIKGYAN VLLNEGKHVLVGNVRNFLSRVFNLIV REKIMTRMCHRGGEASIERSGEPVG ERSGEPTGERSGDPTGERSGDPTG ERSGEPTGERSGEPTGERSGEPTA ERSGEPTAERSDEPTAERSDEPTAD PKGDPTNCRLPKRSATKFYQSEDLY NYYSSLEEMLGKGIRWKTDRVSR YFTFSPSKKIKDNFEEVMNNKVFIES VRSILFDSHKKNKKAVFSSFAVVVET LFSLIKEEKVIADMYSYVKLFFQDLDI LNLKVLHFLSSSSTENTQFVGPPDL SLTNFEYILAKIYSRSVLANILSPKMN HSDSKKLSKLLTRRENNLKFSFLEG VKMVHSAIPSEGVSAVVLGNAGGQ VNVPIPGADDTLCKFIPIRKKLLYERL SVTRKVAEEVILDYLFRLLLRKVHEY VLEhhhhhh (SEQ ID NO: 65) | ATGAACAACTACGGCAAGCTCAAGCACGGCAAGTGGGACGACGGCTC CTACAGCGAGAGGACCAGGTGGAGGATGCTGTCCGGCGACGACCAC GACGTCCTCCCCATCCTGCGACAGCCCAGGCGGCAGGAACGACGAGC ACCAAGTCAACAAGGAAGTGTCCAGGACCGCCCCAAGCGAGAAGGTG AAGGTGGTCGACAAGGAGACCGGCGAGTCCATGCTGGTGGACGTGGG CGAGAGCGGCGGCAAGTCCTCCCCAGGCGTGGCTGAGGAGTCCGGCC CAAGCCTGCGCGGCAGGGACGTGCGCGACGTCAGGGTGGACCAAGAG ACCCGCGAGACCCTGCAGGGCGGCGCCACCAACAGGCGCGACCTCAC CCAACACGGCGAGGAAGAGACCGGCGACGACAGCAAGCGCGCTAAGC AGGACGACGAGGCTGGCGTCAGGTCCATGCTCAACGACACCGTGACC GCCATCAAGGACAACGGCTCCAACCTCCTGCGCAGCGTCATCGGCCAA ATCAACTTCGTGCAAGGCAGCGCTGAGCTCCTGAAGGTCGCCAACGAG GAAGAGCGCCAGCCATCCGGCGGCAGCGTGCTGTCCAAGGAAGGCGA GGAAGCCACCCCAGGCGACTTCCTCGGCGGCAACAACCCGAACGGCG GCGAGAAGGGCGAGCTGCCAAACGGCACCAAGAACGACGTCATGATC AAGGGCTACGCCAACGTGCTCCTGAACGAGGGCAAGCACGTCCTCGTG GGCAACGTCCGCAACTTCCTGTCCAGGGTGTTCAACCTCATCGTCAGGG AGAAGATCATGACCAGGATGTGCCACAGGGGCGGCGAGGCTAGCATC GAGAGGTCCGGCGAGCCAGTGGGGGAGCGCTCCGGCGAGCCAACCG GCGAGAGGAGCGGCGACCCAACCGGCGAGAGGTCTGGCGACCCTACG GGGGAGAGGAGCGGGGAGCCTACCGGCGAGCGCAGCGGGGAGCCTA CGGGCGAGAGGTCCGGGGAGCCTACCGCTGAGAGAAGCGGCGAGCC AACCGCTGAGAGGAGCGATGAGCCTACCGCTGAGAGGTCCGACGAGC CAACCGCTGACCCAAAGGGCGACCCAACCAACTGCCGCCTCCCAAAGA GGTCCGCCACCAAGTTCTACCAAAGCGAGGACCTGTACAACTACTACTC CAGCCTGGAGGAGATGCTCAAGGGCAGGGGCATCAGGTGGAAGACC GACCGCGTCAGCAGGTACTTCACCTTCTCCCCAAGCAAGAAGATCAAG GACAACTTCGAGGAAGTGATGAACAACAAGGTCTTCATCGAGAGCGTG CGCTCCATCCTCTTCGACTCCCACAAGAAGAACAAGAAGGCCGTGTTCT CCAGCTTCGCCGTGGTCGTGGAGACCCTGTTCAGCCTCATCAAGGAAG AGAAGGTCATCGCCGACATGTACTCCTACGTGAAGCTGTTCTTCCAAGA CCTCGACATCCTGAACCTCAAGGTCCTGCACTTCCTCTCCAGCTCCAGCA CCGAGAACACCCAGTTCGTGGGCCCACCAGACCTGAGCCTCACCAACT TCGAGTACATCCTCGCCAAGATCTACTCCCGCAGCGTCCTGGCCAACAT CCTCAGCCCAAAGATGAACCACTCCGACAGCAAGAAGCTGTCCAAGCT CCTGACCAGGCGCGAGAACAACCTGAAGTTCTCCTTCCTGGAGGGCGT CAAGATGGTGCACAGCGCTATCCCATCCGAGGGCGTGAGCGCTGTGGT GCTGGGCAACGCTGGCGGCCAGGTCAACGTGCCAATCCCAGGCGCCG |

Appendix I-continued

| No. | Protein Name | Protein Reference | Insert aa sequence (add M as start/His-tag at C-term) | Insert DNA sequence (Start from ATG to His-tag stop codon) |
|---|---|---|---|---|
| | | | | ACGACACCCTCTGCAAGTTCATCCCAATCAGGAAGAGCTCCTGTACGA GCGCCTGTCCGTCACCAGGAAGGTGGCCGAGGAAGTGATCCTGGACT ACCTCTTCCGCCTCCTGCTCAGGAAGGTGCACGAGTATGTGCTGGAGC ACCATCACCACCATCACTGA (SEQ ID NO: 66) |
| 34 | merozoite surface protein 8 (GPI-anchored, C24) | PVX_097625 | mGNVSPPNFNDNRVGNNGNKGN GNDNDVPSFIGGNNNNVNGNNDDN IFNKNGKDVTRNDGDAKDGENRNN KKNENGSGSNENNSIANADNGSGK SDANANQIDEDGNKMDEASLKKILKI VDEMENIQGLLDGDYSILDKYSVKLV DEDDGETNKRKIIGEYDLKMLKNILL FREKISRVCENKYNKNLPVLLKKCS NVDDPKLSKSREKIKKGLAKNNMSIE DFVVGLLEDLFEKINEHFIKDDSFDL SDYLADFELINYIIMHETSELIDELLNII ESMNFRLESGSLEKMVKSAESGMN LNCKMKEDIIHLLKKSSAKFFKIEIDR KTKMIYPVQATHKGANMKQLALSFL QKNNVCEHKKCPLNSNCYVINGEEV CRCLPGFSDVKIDNVMNCVRDDTLD CSNNNGGCDVNATCTLIDKKIVCEC KDNFEGDGIYChhhhhh (SEQ ID NO: 67) | ATGGGCAACGTGTCCCCACCAAACTTCAACGACAACAGGGTCAACGGC AACAACGGCAACAAGGGCAACGGCAACGACAACGACGTGCCAAGCTT CATCGGCGGCAACAACAACAACGTCAACGGCAACAACGACGACAACAT CTTCAACAAGAACGGCAAGGACGTGACCCGCAACGACGGCGACGCTA AGGACGGCGAGAACCGCAACAACAAGAAGAACGAGAACGGCTCCGGC AGCAACGAGAACAACTCCATCGCCAACGCTGACAACGGCTCCGGCAAG AGCGACGCCAACGCCAACCAAATCGACGAGGACGGCAACAAGATGGA CGAGGCCAGCCTCAAGAAGATCCTGAAGATCGTGGACGAGATGGAGA ACATCCAGGGCCTCCTGGACGGCGACTACTCCATCCTCGACAAGTACA GCGTGAAGCTGGTCGACGAGGACGACGGCGAGACGAACAAGAGGAA GATCATCGGCGAGTACGACCTCAAGATGCTGAAGAACATCCTCCTGTTC AGGGAGAAGATCTCCCGCGTCTGCGAGAACAAGTACAACAAGAACCTC CCAGTGCTCCTGAAGAAGTGCAGCAACGTCGACGACCCAAAGCTCTCC AAGAGCCGCGAGAAGATCAAGAAGGGCCTGGCTAAGAACAACATGTC CATCGAGGACTTCGTGGTCGGCCTCCTGGAGGACCTGTTCGAGAAGAT CAACGAGCACTTCATCAAGGACGACTCCTTCGACCTCAGCGACTACCTG GCCGACTTCGAGCTCATCAACTACATCATCATGCACGAGACGTCCGAGC TGATCGACGAGCTCCTGAACATCATCGAGAGCATGAACTTCAGGCTGG AGTCCGGCAGCCTGGAGAAGATGGTGAAGTCCGCCGAGAGCGGCATG AACCTCAACTGCAAGATGAAGGAAGACATCATCCACCTTCTGAAGAAG TCCAGCGCCAAGTTCTTCAAGATCGAGATCGACCGCAAGACCAAGATG ATCTACCCAGTGCAAGCCACCCACAAGGGCGCCAACATGAAGCAACTC GCCCTGTCCTTCCTCCAGAAGAACAACGTCTGCGAGCACAAGAAGTGC CCACTGAACAGCAACTGCTACGTGATCAACGGCGAGGAAGTGTGCAG GTGCCTCCCAGGCTTCTCCGACGTCAAGATCGACAACGTGATGAACTG CGTCCGCGACGACACCCTCGACTGCAGCAACAACAACGGCGGCTGCGA CGTGAACGCTACCTGCACCCTGATCGACAAGAAGATCGTCTGCGAGTG CAAGGACAACTTCGAGGGCGACGGCATCTACTGCCACCACCACCACCA CCACTGA (SEQ ID NO: 68) |
| 35 | adenylate kinase-like protein 2, putative (AKLP2) | PVX_087110 | METLLDSETLKNYEKETNEYIRKKKV EKLFDVILKNVLVNKPENVYLYIKNI YSFLLNKIFVIGPPLLKITPTLCSAIAS CFSYYHLSASHMIESYTTGEVDDAA ESSTSKKLVSDDLICSIVKSNINQLNA KQKRGYVVEGFPGTNLQADSCLRH LPSYVFVLYADEEYIIYDKYEQENNV KIRSDMNSQTFDENTQLFEVAEFNT NPLKDEVKVYLRNhhhhhh (SEQ ID NO: 69) | ATGGAGACGCTCCTGGACTCCGAGACGCTCAAGAACTACGAGAAGGA GACGAACGAGTACATCAGGAAGAAGAAGGTGGAGAAGCTCTTCGACG TCATCCTCAAGAACGTGCTGGTCAACAAGCCAGAGAACGTGTACCTGT ACATCTACAAGAACATCTACAGCTTCCTCCTGAACAAGATCTTCGTCATC GGCCCACCACTCCTGAAGATCACCCCAACCCTCTGCTCCGCCATCGCCT CCTGCTTCAGCTACTACCACCTGTCCGCCAGCCACATGATCGAGAGCTA CACCACCGGCGAGGTGGACGACGCTGCTGAGTCCAGCACCTCCAAGAA GCTCGTGAGCGACGACCTGATCTGCTCCATCGTCAAGAGCAACATCAA CCAACTCAACGCCAAGCAGAAGAGGGGCTACGTGGTCGAGGGCTTCC CAGGCACCAACCTCCAGGCTGACTCCTGCCTCAGGCACCTGCCAAGCTA CGTGTTCGTCCTGTACGCCGACGAGGAGTACATCTACGACAAGTACGA GCAGGAGAACAACGTGAAGATCAGGTCCGACATGAACAGCCAAACCT TCGACGAGAACACCCAGCTGTTCGAGGTCGCCGAGTTCAACACCAACC CACTCAAGGACGAGGTGAAGGTCTACCTGCGCAACCACCACCACCACC ACCACTGA (SEQ ID NO: 70) |
| 36 | MSP7-like protein | PVX_082670 | mKPGVEKKKKLEEDVIGILRRKLESL QKRSLTNSDGKLKKEIELVKKQIQEL QKYEKGEAGKKVDATLGEEPGVES AEEQPLSVEEAGDTQDEDRLDELE GVEDFEEENLEQSEQVEEAEVVEEA EEEAGDAEEEQPAEAEEEDGSLLEEA PNSVERKAEGAIAEFEEADVEEGAE ADEGVETDEGADADEASLGSFDLE GELIEEDLQESFDLEGEQEEEDLQE GFKSEEEANQGGQLPREIPPHGEEA VEPPLRGNKPSMEYVGNLHSDVGP TEGSANQISPPSVDEKGKEDGDKYK SASQDGGNSVGINNFGGCFQGGNS NGICPLDIFKKVLEDENFLQEFDSFIH NLYGSSKNNTPWGGDKMGNENLY MDLFTNALSFLNTIEVIhhhhhh (SEQ ID NO: 71) | ATGAAGCCAGGCGTGGAGAAGAAGAAGAAGCTCGAAGAGGACGTCA TCGGCATCCTGCGCAGGAAGCTGGAGTCCCTGCAAAAGAGGTCCCTCA CCAACAGCGACGGCAAGCTCAAGAAGGAGATCGAGCTGGTCAAGAAG CAAATCCAGGAGCTGCAGAAGTACGAGAAGGGCGAGGCTGGCAAGA AGGTGGACGCTACCCTGGGCGAGGAGCCCGGGCGTGGAGTCCGCTGAG GAGCAACCACTGAGCGTGGAGGAAGCCGGCGACACCCAGGACGAGG ACAGGCTCGACGAGCTGGAGGGCGTCGAGGACTTCGAGGAAGAGAA CTGGAGCAAAGCGAGCAGGTGGAGGAAGCCGAGGTGGTGGAGGAAG CCGAGGAAGAGGCCGGCGACGCTGAGGAAGAGCAACCGGCTGAGGC TGAGGAAGACGGCTCCCTCCTCGAAGAGGCCCCAAACAGCGTGGAGA GGAAGGCTGAGGGCGCTATCGCTGAGTTCGAGGAAGCCGACGTCGAG GAAGGCGCCGAGGCCGACGAGGCGTGGAGACGACGAGGCGCTG ACGCTGACGAGGCTTCCCTGGGCAGCTTCGACCTGGAGGGCGAGCTG ATCGAGGAAGACCTCCAGGAGTCTTTCGACCTGGAGGGGAGCAAGA GGAAGAGGACCTCCAAGAGGGCTTCAAGAGCGAGGAAGAGGCCAAC CAAGGCGGCCAGCTGCCAAGGGAGATCCCACCACACGGCGAGGAAGC CGTGGAGCCACCACTCCGCGGCAACAAGCCCATCCATGGAGTATGTGGG CAACCTGCACAGCGACGTGGGCCCAACCGAGGGCAGCGCCAACCCAAA TCTCCCCACCAAGCGTCGACGAGAAGGGCAAGGAAGACGGCGACAAG TACAAGTCCGCCAGCCAAGACGGCGGAAACTCCGTGGGCATCAACAAC TTCGGCGGATGCTTCCAGGGCGGCAACAGCAACGGCATCTGCCCACTC GACATCTTCAAGAAGGTCCTGGAGGACGAGAACTTCCTGCAGGAGTTC |

Appendix I-continued

| No. | Protein Name | Protein Reference | Insert aa sequence (add M as start/His-tag at C-term) | Insert DNA sequence (Start from ATG to His-tag stop codon) |
|---|---|---|---|---|
| | | | | GACTCCTTCATCCACAACCTGTACGGCTCCAGCAAGAACAACACCCCCAT GGGGCGGCGACAAGATGGGCAACGAGAACCTCTACATGGACCTGTTC ACCAACGCCCTCAGCTTCCTGAACACCATCGAGGTCATCCACCACCAC ACCACCACTGA (SEQ ID NO: 72) |
| 37 | high molecular weight rhoptry protein-2, putative | PVX_099930 | mELSHSLSVKNAPDASALNIEVEKD KKKICKNAFQYINVAELLSPREEETY VQKCEEVLDTIKNDSPDESAEAEINE FILSLLHARSKYTIINDSDEEVLSKLL RSINGSISEEAALKRAKQLITFNRFIK DKAKVKNVQEMLVISSKADDFMNEP KQKMLQKIIDSFELYNDYLVILGSNIN IAKRYSSETFLSIKNEKFCSDIHLCQ KFYEQSIIYYRLKVIFDNLVTYVDQNS KHFKKEKLLELLNMDYRVNRESKVH ENYVLEDETVIPTMRITDIYDQDRLIV EVVQDGNSKLMHGRDIEKREISERYI VTVKNLRKDLNDEGLYADLMKTVKN YVLSITQIDNDISNLVRELDHEDVEKh hhhhh (SEQ ID NO: 73) | ATGGAGCTCTCCCACAGCCTGTCCGTGAAGAACGCTCCAGACGCTAGC GCTCTCAACATCGAGGTCGAGAAGGACAAGAAGAAGATCTGCAAGAA CGCCTTCCAATACATCAACGTCGCCGAGCTCCTGTCCCCAAGGGAGGA AGAGACTTACGTGCAGAAGTGCGAGGAAGTGCTGGACACCATCAAGA ACGACAGCCCAGACGAGTCCGCTGAGGCTGAGATCAACGAGTTCATCC TCAGCCTCCTGCACGCCCGCTCCAAGTACACCATCATCAACGACAGCGA CGAGGAAGTGCTGAGCAAGCTCCTGAGGTCCATCAACGGCAGCATCTC CGAGGAAGCCGCTCTCAAGAGGGCTAAGCAACTGATCACCTTCAACAG GTTCATCAAGGACAAGGCCAAGGTGAAGAACGTCCAGGAGATGCTCG TCATCTCCAGCAAGGCCGACGACTTCATGAACGAGCCAAAGCAAAAGA TGCTCCAGAAGATCATCGACAGCTTCGAGCTGTACAACGACTACCTCGT GATCCTGGGCTCCAACATCAACATCGCCAAGCGCTACTCCAGCGAGAC GTTCCTCAGCATCAAGAACGAGAAGTTCTGCTCCGACCACATCCACCTG TGCCAAAAGTTCTACGAGCAGAGCATCATCTACTACAGGCTCAAGGTC ATCTTCGACAACCTGGTGACCTACGTCGACCAAAACTCCAAGCACTTCA AGAAGGAGAAGCTCCTGGAGCTCCTGAACATGGACTACAGGGTGAAC CGCGAGTCCAAGGTGCACGAGAACTACGTCCTGGAGGACGAGACTGT GATCCCAACCATGCGCATCACCGACATCTACGACCAAGACAGGCTCATC GTGGAGGTGGTCCAGGACGGCAACAGCAAGCTGATGCACGGCAGGG ACATCGAGAAGCGCGAGATCTCCGAGAGGTACATCGTGACCGTCAAG AACCTCCGCAAGGACCTGAACGACGAGGGCCTCTACGCCGACCTGATG AAGACCGTGAAGAACTACGTCCTCAGCATCACCCAGATCGACAACGAC ATCTCCAACCTCGTGAGGGAGCTGGACCACGAGGACGTCGAGAAGCA CCACCACCACCACCACTGA (SEQ ID NO: 74) |
| 38 | IMP-specific 5'-nucleoti-dase | PVX_084340 | MEKLDIPPHEMYEDMQQAFREQDK YDFLAISDGSVINSYMKKNVVDWNN RYSYNQLKNKDSLIMFLVDIFRSLFL SNCIDKNIDNVLSSIEEMFTDHYYNP MHSRLKYLIDDVGIFFTKLPITKAFHT YNKKYRITKRLYAPPTFNEVRHILNL AQILSLEDGLDLLTFDADETLYPDGY DFHDEVLASYISSLLKKMNIAIVTAAS YSNDAEKYQKRLENLLRYFSKHNIE DGSYENFYVMGGESNYLFKCNEDA NLYSVPEEEWYHYKKYVNKETVEQI LDISQKCLQQVITDFKLCAQIQRKEK SIGLVPNKIPSANNQKEQKNYMIKYE VLEEAVIRVKKEIVKNKITAPYCAFNG GQDLWVDIGNKAEGLIILQKLLKIEKK KCCHIGDQFLHSGNDFPTRFCSLTL WISNPQETKACLKSIMNLNMKSFIPE VLYENEhhhhhh (SEQ ID NO: 75) | ATGGAGAAGCTCGACATCCCACCACACGAGATGTACGAGGACATGCAA CAGGCCTTCAGGGAGCAAGACAAGTACGACTTCCTGGCCATCTCCGAC GGCAGCGTGATCAACTCCTACATGAAGAAGAACGTGGTCGACTGGAAC AGGTACTCCTACAACCAGCTCAAGAACAAGGACAGCCTCATCATG TTCCTGGTGGACATCTTCCGCTCCCTCTTCCTGAGCAACTGCATCGACA AGAACATCGACAACGTCCTGTCCAGCATCGAGGAGATGTTCACCGACC ACTACTACAACCCAATGCACAGCAGGCTCAAGTACCTGATCGACGACG TGGGCATCTTCTTCACCAAGCTCCCAATCACCAAGGCCTTCCACACCTAC AACAAGAAGTACAGGATCACCAAGCGCCTGTACGCCCCACCAACCTTC AACGAGGTCCGCCACATCCTCAACCTGGCCCAAATCCTCTCCCTGGAGG ACGGCCTCGACCTCCTGACCTTCGACGCCGACGAGACCTTGTACCCAG ACGGCTACGACTTCCACGACGAGGTCCTCGCCAGCTACATCTCCAGCCT CCTGAAGAAGATGAACATCGCCATCGTCACCGCCGCCTCCTACAGCAA CGACGCCGAGAAGTACCAGAAGAGGCTGGAGAACCTCCTGCGCTACTT CTCCAAGCACAACATCGAGGACGGCAGCTACGAGAACTTCTACGTGAT GGGCGGCGAGTCCAACTACCTCTTCAAGTGCAACGAGGACGCCAACCT GTACAGCGTCCCAGAGGAAGAGTGGTACCACTACAAGAAGTATGTGA ACAAGGAGACGGTCGAGCAAATCCTCGACATCTCCCAGAAGTGCCTGC AACAAGTGATCACCGACTTCAAGCTCTGCGCCCAAATCCAGAGGAAGG AGAAGTCCATCGGCCTGGTCCCAAACAAGATCCCAAGCGCCAACAACC AAAAGGAGCAGAAGAACTACATGATCAAGTACGAGGTGCTCGAAGAG GCCGTGATCCGCGTCAAGAAGGAGATCGTCAAGAACAAGATCACCGCT CCATACTGCGCCTTCAACGGCGGCAAGACCTGTGGGTGGACATCGGC AACAAGGCCGAGGGCCTCATCATCCTGCAAAAGCTCCTGAAGATCGAG AAGAAGAAGTGCTGCCACATCGGCGACCAGTTCCTCCACAGCGGCAAC GACTTCCCAACCCGCTTCTGCTCCCTCACCCTGTGGATCAGCAACCCAC AGGAGACGAAGGCCTGCCTCAAGTCCATCATGAACCTGAACATGAAGA GCTTCATCCCAGAGGTCCTCTACGAGAACGAGCACCACCACCACCACCA CTGA (SEQ ID NO: 76) |
| 39 | subpelli-cular microtu-bule protein 1, putative (SPM1) | PVX_098915 | MEIIAEKPKVKFNFASEEYKNCDSSD YSECAEDYGRPNGKDYFYANRILSL DRNSEQRRKESPSKRPGLCVDEICT CGFHRCPKIVKSLPFDGESNYRSEF GPKPLPELPPRQEAKLTRSLPFEGE SNYRSEFGPKPLPELPPRVEQKPPK SLPFDGESNYRSEFGPKPLPELPPR VEQKPPKSLPFDGESNYRSEFGPKP LPELPPRVEQKPPKSLPFEGESNYR SEFGPKPLPELPPRVEQKPPKSLPF EGESNYRSEFGPKALPELPPRVEQK PPKSLPFEGESNYRSEFGPKPLPAL PPRVETKLVKSLPFEGESNYRSEFG PKPLPELPPRVEQKPPKSLPFEGES NYRSEFGPKPLPALPPRVVTKLVKS | ATGGAGATCATCGCCGAGAAGCCAAAGGTCAAGTTCAACTTCGCCTCC GAGGAGTACAAGAACTGCGACTCCAGCGACTACTCCGAGTACGGCTGA GGACTACGGCAGGCCAAACGGCAAGGACTACTTCTACGCCAACAGGAT CCTCTCCCTGGACCGCAACAGCGAGCAGAGGCGCAAGGAGTCCCCAA GCAAGAGGCCAGGCCTCTGCGTGGACGAGATCTGCACCTGCGGCTTCC ACCGCTGCCCAAAGATCGTCAAGTCCCTGCCATTCGACGGCGAGTCCA ACTACCGCAGCGAGTTCGGCCCAAAGCCACTCCCAGAGCTGCCACCA GGCAAGAGGCCAAGCTCACCCGCAGCCTGCCATTCGAGGGCGAGTCC AACTACAGGTCCGAGTTCGGGCCTAAGCCTCTGCCTGAGCTGCCACCA CGCGTGGAGCAGAAGCCAAGCTCACCAAAGTCCTCCTTTGATGGGGAGGG AACTACAGGAGTGAATTCGGGCCTAAGCCGCTGCCCGAGCTGCCACCA CGCGTCGAGCAGAAGCCACCAAAGAGCTCCCTTTCGATGGCGAGAGC AACTACAGGAGCGAATTTGGGCCTAAGCCGCTGCCGGAACTGCCACCA CGCGTGGAACAAAAGCCACCAAAGAGCTGCCTTTCGAGGGGGAGTC CAACTACAGGAGTGAGTTTGGGCCTAAGCCGTTGCCTGAACTGCCACC |

Appendix I-continued

| No. | Protein Name | Protein Reference | Insert aa sequence (add M as start/His-tag at C-term) | Insert DNA sequence (Start from ATG to His-tag stop codon) |
|---|---|---|---|---|
| | | | LPFEGESNYRSEFGPKPLPEIPPRV EQKPPKSLPFEGESNYRSEFGPKPL PELPPRVEQKPPKSLPFEGESNYRS EFGPKQLPELPPRQEAKLTRSLPFE GESSYRSEYVRKAIPICPVNLLKYP APTYPSEHVFWDSACKRWYhhhhhh (SEQ ID NO: 77) | ACGCGTCGAACAGAAACCACCAAAAAGCCTCCCTTTCGAGGGCGAGAG CAACTACCGCTCCGAGTTCGGCCCAAAGGCTCTGCCGGAGCTGCCACC ACGCGTGGAACAGAAACCACCAAAGAGCCTCCCCTTCGAGGGGGAGA GCAATTATCGCTCTGAGTTCGGGCCAAAGCCGCTGCCGGCTCTGCCACC ACGCGTGGAGACGAAGCTCGTCAAGAGCCTCCCGTTCGAGGGGGAGA GCAATTATCGCTCCGAATTTGGGCCTAAAACCACTGCCTGAACTGCCACC ACGCGTGGAACAGAAGCCACCAAAAAGCCTCCCCTTTGAAGGGGAGA GCAATTACCGCTCCGAGTTCGGGCCCAAGCCGCTGCCGGCCCTGCCAC CACGCGTGGTCACCAAGCTCGTGAAGTCCCTCCCCTTGAAGGCGAGA GCAACTACAGATCTGAGTTCGGGCCTAAGCCACTCCCAGAGATCCCAC CACGCGTCGAGCAAAAACCACCAAAATCTCTCCCCTTTGAGGGTGAGA GCAATTATCGCTCAGAGTTCGGGCCCAAGCCTCTGCCGGAGCTGCCAC CACGCGTCGAACAGAAGCCACCAAAGAGCTTACCTTTTGAAGGGGAGA GCAACTACCGCAGTGAATTCGGCCCAAAGCAGCTGCCAGAACTGCCAC CAAGGCAAGAGGCCAAACTCACCCGCTCCCTGCCTTTCGAGGGCGAGT CCAGCTACAGGAGCGAGTATGTGAGGAAGGCCATCCCAATCTGCCCAG TCAACCTCCTGCCAAAGTACCCAGCCCCAACCTACCCATCCGAGCACGT GTTCTGGGACAGCGCCTGCAAGCGCTGGTACCACCACCACCACCACCA CTGA (SEQ ID NO: 78) |
| 40 | trypto-phan-rich antigen (Pv-fam-a) | PVX_088820 | mAAANRPNANGFVSPTLIGFGELSI QESEEFKRMAWNNWMLRLESDWK HFNDSVEEAKTKWLHERDSAWSD WLRSLQSKWSHYSEKMLKEHKSNV MEKSANWNDTQWGNWIKTEGRKIL EAQWEKWIKKGDDQLQKLILDKWV QWKNDKIRSWLSSEWKTEEDYYWA NVERATTAKWLQEAEKMHWLKWKE RINRESEQWVNWVQMKESVYINVE WKKWPKWKNDKKILFNKWSTNLVY KWTLKKQWNVWIKEANTAPQVhhhh hh (SEQ ID NO: 79) | ATGGCTGCCGCCAACAGGCCAAACGCCAACGGCTTCGTCTCCCCAACC CTCATCGGCTTCGGCGAGCTGTCCATCCAAGAGAGCGAGGAGTTCAAG AGGATGGCCTGGAACAACTGGATGCTCCGCCTGGAGTCCGACTGGAA GCACTTCAACGACAGCGTGGAGGAAGCCAAGACCAAGTGGCTGCACG AGAGGGACTCCGCTTGGAGCGACTGGCTCCGCTCCCTGCAGAGCAAGT GGTCCCACTACAGCGAGAAGATGCTGAAGGAGCACAAGTCCAACGTC ATGGAGAAGAGCGCCAACTGGAACGACACCCAATGGGGCAACTGGAT CAAGACCGAGGGCCGCAAGATCCTGGAGGCCCAGTGGGAGAAGTGG ATCAAGAAGGGCGACGACCAACTGCAGAAGCTCATCCTGGACAAGTG GGTCCAGTGGAAGAACGACAAGATCAGGTCCTGGCTCTCCAGCGAGT GGAAGACCGAGGAAGACTACTACTGGGCTAACGTGGAGAGGGCTACC ACCGCTAAGTGGCTCCAAGAGGCCGAGAAGATGCACTGGCTGAAGTG GAAGGAGAGGATCAACCGCGAGTCCGAGCAATGGGTGAACTGGGTCC AGATGAAGGAGAGCGTGTACATCAACGTCGAGTGGAAGAAGTGGCCA AAGTGGAAGAACGATAAGAAGATCCTGTTCAACAAGTGGAGCACCAA CCTCGTGTACAAGTGGACCCTGAAGAAGCAGTGGAACGTCTGGATCAA GGAAGCCAACACCGCCCCACAGGTGCACCACCACCACCACCACTGA (SEQ ID NO: 80) |
| 41 | PvTRAP/SSP2 | PVX_082735 | mEKVVDEVKYSEEVCNESVDLYLLV DGSGSIGYPNWITKVIPMLNGLINSL SLSRDTINLYMNLFGNYTTELIRLGS GQSIDKRQALSKVTELRKTYTPYGT TNMTAALDEVQKHLNDRVNREKAIQ LVILMTDGVPNSKYRALEVANKLKQ RNVSLAVIGVGQGINHQFNRLIAGC RPREPNCKFYSYADWNEAVALIKPFI AKVCTEVERVANCGPWDPWTACSV TCGRGTHSRSRPSLHEKCTTHMVS ECEEGECPVEPEPLPVPAPLPTVPE DVNPRDTDDENENPNFNKGLDVPD EDDDEVPPANEGADGNPVEENVFP PADDSVPDESNVLPLPPAVPGGSSE EPPADVQNNPDSPEELPMEQEVPQ DNNVNEPERSDSNGYGVNEKVIPN PLDNERDMANKNKTVHPGRKDSAR DRYARPHGSTHVNNNRANENSDIP NNPVPSDYEQPEDKAKKSSNNGYK hhhhhh (SEQ ID NO: 81) | ATGGAGAAGGTGGTCGACGAGGTGAAGTACAGCGAGGAAGTGTGCA ACGAGTCCGTCGACCTCTACCTCCTGGTGGACGGCTCCGGCAGCATCG GCTACCCAAACTGGATCACCAAGGTCATCCCAATGCTCAACGGCCTGAT CAACTCCCTCAGCCTGTCCCGCGACACCATCAACCTCTACATGAACCTG TTCGGCAACTACACCACCGAGCTCATCAGGCTGGGCAGCGGCCAATCC ATCGACAAGCGCCAGGCCCTCAGCAAGGTGACCGAGCTGAGGAAGAC CTACACCCCATACGGCACCACCAACATGACCGCCGCCCTCGACGAGGT GCAAAAGCACCTGAACGACAGGGTCAACCGCGAGAAGGCCATCCAGC TCGTGATCCTGATGACCGACGGCGTCCCAAACAGCAAGTACCGCGCCC TGGAGGTGGCCAACAAGCTGAAGCAAAGGAACGTCTCCCTGGCCGTG ATCGGCGTGGGCCAAGGCATCAACCACCAGTTCAACAGGCTGATCGCT GGCTGCAGGCCACGCGAGCCAAACTGCAAGTTCTACAGCTACGCTGAC TGGAACGAGGCTGTGGCTCTCATCAAGCCATTCATCGCCAAGGTCTGC ACCGAGGTGGAGAGGGTGGCTAACTGCGGCCCATGGGACCCGTGGAC CGCTTGCTCCGTGACCTGCGGCAGGGGCACCCACAGCAGGTCCCGCCC AAGCCTGCACGAGAAGTGCACCACCCACATGGTGTCCGAGTGCGAGG AAGGCGAGTGCCCAGTGGAGCCAGAGCCACTGCCGGTCCCAGCCCCA CTGCCAACCGTGCCAGAGGACGTCAACCCAAGGGACACCGACGACGA GAACGAGAACCCAAACTTCAACAAGGGCCTCGACGTGCCAGACGAGG ACGACGACGAGGTCCCACCAGCTAACGAGGGCGTGACGGCAACCA GTGGAGGAGAACGTCTTCCCACCAGCCGACGACAGCGTGCCAGACGA GTCCAACGTGCTGCCACTGCCACCAGCTGTGCCAGGCGGCTCCAGCGA GGAGTTCCCAGCTGACGTCCAAAACAACCCAGACTCCCCAGAGGAGCT CCCGATGGAGCAAGAGGTGCCACAGGACAACAACGTCAACGAGCCAG AGCGCAGCGACTCCAACGGCTACGGCGTGAACGAGAAGGTCATCCCA AACCCACTGGACAACGAGAGGGACATGGCCAACAAGAACAAGACCGT GCACCCGGGCAGGAAGGACAGCGCCAGGGACCGCTACGCCAGGCCAC ACGGCTCCACCCACGTGAACAACAACAGGGCCAACGAGAACAGCGAC ATCCCAAACAACCCAGTCCCATCCGACTACGAGCAGCCAGGGACAAG GCCAAGAAGTCCAGCAACAACGGCTACAAGCACCACCACCACCACCAC TGA (SEQ ID NO: 82) |

Appendix I-continued

| No. | Protein Name | Protein Reference | Insert aa sequence (add M as start/His-tag at C-term) | Insert DNA sequence (Start from ATG to His-tag stop codon) |
|---|---|---|---|---|
| 42 | MSP7-like protein | PVX_082645 | mDDKKDKENEHKEDADKKNNDELK TLKGKLQKIRVQIKDDKLPQKISEEQI SVLKKKLEDFKNLKSEHEAKLASEK GDTSAGGEGELGLSDKEFVGQNVK ANGDAAGVSGEQGASGGSGQGEA GPSSPADEQDDDNEAVQWGPATEE VVAEAMSDEGPQEQGAEGGPSNPT DDQAEEATPGPSKPASGASGSQGA SDSSNDSAEPTSAAAAAPAGPTAA AASPQVKHVDTLCDELLAGENKKNV LDEGEDHSQYNIFRKQYDKMVLNKT EYNISLKLLDTMLTNGQVEREKKNTL IKTFKKALYDKQYSEKLRNLISGVYA FAKRNNFIDGDKVKEGDYSKLFEYIG CMMNTLELhhhhhh (SEQ ID NO: 83) | ATGGACGACAAGAAGGACAAGGAGAACGAGCACAAGGAAGACGCCG ATAAGAAGAACAACGACGAGCTCAAGACCCTGAAGGGCAAGCTCCAA AAGATCAGGGTGCAGATCAAGGACGACAAGCTGCCACAAAAGATCTC CGAGGAGCAGATCAGCGTCCTCAAGAAGAAGCTGGAGGACTTCAAGA ACCTCAAGTCCGAGCACGAGGCCAAGCTGGCCTCCGAGAAGGGCGAC ACCTCCGCCGGCGGCGAGGGCGAGCTGGGCCTGTCCGACAAGGAGTT CGTGGGCCAAAACGTCAAGGCCAACGGCGACGCCGCCGGCGTGAGCG GCGAGCAAGGCGCCTCCGGCGGCAGCGGCCAGGGCGAGGCTGGCCC ATCCAGCCCAGCCGACGAGCAAGACGACGACAACGAGGCTGTCCAGT GGGGCCCAGCTACCGAGGAAGTGGTGGCTGAGGCTATGTCCGACGAG GGCCCACAAGAGCAGGGCGCTGAGGGCGGCCCAAGCAACCCAACCGA CGACCAAGCTGAGGAAGCCACCCCAGGCCCATCCAAGCCAGCTTCCGG CGCTTCCGGCAGCCAGGGCGCTTCCGACTCCAGCAACGACTCCGCCGA GCCAACCAGCGCTGCCGCCGCCGCCGCCCCAGCTGGCCCAACCGCTGC CGCCGCCAGCCCACAGGTGAAGCACGTGGACACCCTCTGCGACGAGCT CCTGGCTGGCGAGAACAAGAAGAACGTGCTGGACGAGGGCGAGGAC CACTCCCAATACAACATCTTCAGGAAGCAGTACGACAAGATGGTCCTCA ACAAGACCGAGTACAACATCAGCCTCAAGCTCCTGGACACCATGCTGA CCAACGGCCAAGTGGAGCGCGAGAAGAAGAACACCCTCATCAAGACC TTCAAGAAGGCCCTGTACGACAAGCAGTACTCCGAGAAGCTCAGGAAC CTGATCAGCGGCGTGTACGCCTTCGCCAAGCGCAACAACTTCATCGAC GGCGACAAGGTGAAGGAAGGCGACTACAGCAAGCTCTTCGAGTACAT CGGCTGCATGATGAACACCCTGGAGCTGCACCACCACCACCACCACTG A (SEQ ID NO: 84) |
| 43 | early transcribed membrane protein (etramp 10.2) | PVX_111065 | mKRHATRGALHSLKSIEHEVQRKKN KKKKIILYSIGSILALAAVIATGVGIGM YIKKKKKNSLEKLQQIEPQKLESKTD ESDPLLGKSEAAKVEVKGDSEEVPQ EVSSPSEALDVEPPVSEALNMEPAV GESANFEDSAKGEVDIEPVSEVESIE PVSEVESIEPVSEVESIEPSVDEVMD AAEPISTEPVNVEPAGNETENIVPTS FEQVNIEPAVSEAFSQERSGEETAD FEDSVKEDVIPESPPVESVTIEAENI QPMNVEQMNVDPTVSDAESIEPTPV EAVDIEPVNVEPVNVEPAVSETMSQ EPSLDEVENVESAVNEMMSQEPSA EETANFAHSIKEDVSPESTSVESLDV ESSVSEPMSTDPSPVESVSMESVD SETVNVESIDSETVNVEPSDETSKV EADVQQFTDEELSTIGNVADKASDG PAPEASDFPDSIFEENLDNANPPLKL EDALVDPPASDEAQPEPSHPNEAV GAAKSAESAEADQISHSGSGDASPS APSSSDDTSGSKNSGTSGKDRLFKT YDSDVEPPIVPEKYPTVGVKEAPKM GFAEMAFKNIFDTFSKVADASKVLTP EKQSAPEKQSAPEKQSAPEKQSAP EKHSTPPKQSTSPKESTSPKQPAPP KPSTSPKQSAPAKQSAPPKQSAPAK QSAPAKNAAPPQSASSSRFFSSSSN GNKGFGLRLFSDASSSNNKKGRAG NPIIRFKRRANhhhhhh (SEQ ID NO: 85) | ATGAAGAGGCACGCTACCCGCGGCGCCCTCCACTCCCTGAAGAGCATC GAGCACGAGGTGCAAAGGAAGAAGAACAAGAAGAAGAAGATCATCCT CTACTCCATCGGCAGCATCCTGGCTCTGGCTGCCGTGATCGCTACCGGC GTCGGCATCGGCATGTACATCAAGAAGAAGAAGAACAGCCTGGA GAAGCTGCAACAGATCGAGCCACAAAAGCTGGAGTCCAAGACCGACG AGAGCGACCCACTCCTGGGCAAGAGCGAGGCTGCTAAGGTGGAGGTC AAGGGCGACTCCGAGGAAGTGCCACAAGAGGTGTCCTCCCCGAGCGA GGCTCTGGACGTGGAGCCACCAGTCTCCGAGGCCCTGAACATGGAGCC AGCCGTGGGCGAGTCCGCCAACTTCGAGGACAGCGCCAAGGGCGAGG TCGACATCGAGCCAGTGTCCGAGGTCGAGTCTATTGAACAGTGTCCG AGGTGGAGTCTATTGAGCCAGTGTCCGAAGTCGAGAGCATCGAGCCAT CCGTGGACGAGGTCATGGACGCTGCTGAGCCAATCAGCACCGAGCCA GTGAACGTCGAGCCAGCCGGCAACGAGACGGAGAACATCGTGCCAAC CTCCTTCGAGCAAGTGAACATCGAGCCAGCCGTCAGCGAGGCCTTCTC CCAAGAGAGGAGCGGCGAGGAGACGGCTGACTTCGAGGACTCCGTGA AGGAAGACGTCATCCCAGAGTCCCCACCAGTGGAGAGCGTCACCATCG AGGCCGAGAACATCCAACCGATGAACGTGGAGCAGATGAACGTGGAC CCAACCGTCTCCGACGCCGAGAGCATCGAGCCAACCCCAGTGGAGGCC GTGGATATCGAGCCTGTCAACGTGGAGCCTGTCAACGTTGAGCCAGCC GTGTCCGAGCGATGAGCCAAGAGCCATCCCTCGACGAGGTGGAGAA CGTCGAGAGCGCCGTCAACGAGATGATGTCCCAGGAGCCATCCGCTGA GGAGACGGCCAACTTCGCCCACTCCATCAAGGAAGACGTGAGCCCAGA GAGCACCTCCGTCGAGTCCCTGGACGTGGAGTCCAGCGTCAGCGAGCC AATGTCCACCGACCCAAGCCCAGTGGAGAGCGTCTCCATGGAGTCCGT GGACAGCGAGACGGTGAACGTCGAGTCCATCGATTCCGAGACGGTCA ACGTGGAGCCCATCGACGAGCGAGCAAGGTGGAGGCCGACTCCAA CAGTTCACCGACGAGGAGCTCAGCACCATCGGCAACGTGGCTGACAAG GCTTCCGACGGCCCAGCTCCAGAGGCCTCCGACTTCCCAGACAGCATCT TCGAGGAGAACCTCGACAACGCCAACCCACCACCTCAAGCTGGAGGACG CTCTGGTGGACCCCACCGCTAGCGACGAGGCTCAACCAGAGCCATCCC ACCCAAACGAGGCTGTGGGCGCTGCTAAGTCCGCTGAGAGCGCTGAG GCTGACCAAATCAGCCACTCCGGCAGCGGCGACGCTTCCCCAAGCGCT CCATCCAGCTCCGACGACACCTCCGGCAGCAAGAACTCCGGCACCAGC GGCAAGGACAGGCTCTTCAAGACCTACGACTCCGACGTGGAGCCACCA ATCGTCCCAGAGAAGTACCCAACCGTGGGCGTGAAGGAAGCCCCAAA GATGGGCTTCGCCGAGATGGCCTTCAAGAACATCTTCGACACCTTCTCC AAGGTGGCTGACGCTAGCAAGGTCCTGACCCCAGAGAAGCAATCCGCC CCAGAGAAGCAGAGCGCTCCTGAGAAGCAGAGCGCTCCCGAGAAGCA GAGCGCCCCAGAGAAGCACTCCACCCCACCAAAGCAATCCACCAGCCC AAAGGAGTCCACCAGCCCAAAGCAGCCAGCCCCACCAAAGCCATCCAC CAGCCCTAAGCAGTCCGCTCCAGCTAAGCAGTCCGCCCCACCAAAGCA GAGCGCTCCAGCTAAGCAATCCGCTCCAGCTAAGAACGCTGCCCCACC ACAGAGCGCCAGCTCCAGCAGGTTCTTCTCCAGCTCCAGCAACGGCAA CAAGGGCTTCGGCCTCAGGCTGTTCTCCGACGCCTCCAGCTCCAACAAC AAGAAGGGCAGGGCCGGCAACCCAATCATCCGCTTCAAGAGGCGCGC CAACCACCACCACCACCACCACTGA (SEQ ID NO: 86) |

Appendix I-continued

| No. | Protein Name | Protein Reference | Insert aa sequence (add M as start/His-tag at C-term) | Insert DNA sequence (Start from ATG to His-tag stop codon) |
|---|---|---|---|---|
| 44 | hypothetical protein, conserved | PVX_091500 | MNNPAEVVAAHLRRTGNSNEIRQAS HVESVGGSANSSLDDDDGGGYDSA APPGELHTTGDAPPGEFRTTGVVPP GRQKGGKKRMFKIKKKKSLTPLHID DGGFTQGGEAKGPDVALESFAITRK RRRPPLLGRGVVESSNIELTSKLGG KLGSKLGGKLNPTLSLVASRAVDGL LGGVHKHMQGPFSLDLDGTNNSPL ATPIVTPNLYSNISTPFNMHNGIPPS APAPMALPPQGVQVPLPNAQPQPP PSVATTATAAPAATSPMASPTTPTP AASTGVPPPPGIQLATNAMTYPQMN MQNVMTANQMAQNPAFNIHPTATN LRDDPGNVNYNEVVTITIGIVICLFLF CFVFGCIVKMCKPAKRRRhhhhhh (SEQ ID NO: 87) | ATGAACAACCCAGCTGAGGTGGTGGCTGCTCACCTGAGGCGCACCGGC AACTCCAACGAGATCAGGCAGGCTAGCCACGTGGAGAGCGTCGGCGG CTCCGCTAACTCCAGCCTCGACGACGACGACGGCGGCGGATACGACAG CGCTGCCCCACCAGGCGAGCTCCACACCACCGGCGACGCCCCACCAGG CGAGTTCCGCACCACCGGCGTGGTCCCACCAGGCAGGCAAAAGGGCG GCAAGAAGCGCATGTTCAAGATCAAGAAGAAGAAGTCCCTCACCCCAC TGCACATCGACGACGGCGGCTTCACCCAGGGCGGCGAGGCTAAGGGC CCAGACGTGGCTCTGGAGTCCTTCGCCATCACCAGGAAGAGGCGCAGG CCACCACTCCTGGGCCGCGGCGTGGTCGAGTCCAGCAACATCGAGCTC ACCAGCAAGCTGGGCGGCAAGCTCGGCTCCAAGCTGGGCGGCAAGCT CAACCCGACCCTCAGCCTGGTGGCCTCCAGGGCCGTGGACGGCCTCCT GGGCGGCGTGCACAAGCACATGCAAGGCCCATTCAGCCTCGACCTGGA CGGCACCAACAACTCCCCACTGGCCACCCCAATCGTCACCCCAAACCTC TACTCCAACATCAGCACCCCATTCAACATGCACAACGGCATCCCACCAA GCGCTCCAGCTCCAATGGCTCTGCCACCACAAGGCGTGCAGGTCCCAC TCCCAAACGCCCAACCACAACCACCATCCGTGGCTACCACCGCTAC CGCTGCTCCAGCTGCTACCAGCCCAATGGCTTCCCCAACCACCCAACC CCAGCTGCTAGCACCGGCGTGCCACCACCACCAGGCATCCAGCTGGCC ACCAACGCCATGACCTACCCACAGATGAACATGCAGAACGTCATGACC GCCAACCAAATGGCCCAGAACCCAGCCTTCAACATCCACCCGACCGCTA CCAACCTCAGGGACGACCCAGGCAACGTGAACTACAACGAGGTGGTC ACCATCACCATCGGCATCGTCATCTGCCTCTTCCTGTTCTGCTTCGTGTT CGGCTGCATCGTCAAGATGTGCAAGCCGGCTAAGCGCAGGCGCCATCA CCACCACCACCACTGA (SEQ ID NO: 88) |
| 45 | hypothetical protein, conserved | PVX_090145 | mSKTGNNNRNAKNAKGGGGGGKR GNNEANKNDGMSGKGSQKGKKKD PGGGGTPKGQGKGPEQGKQKNKK GEDSHFDEYIKDMKNSQDEDNFMD ELNRFEKNFHDEDFESDENLFNYGK GGTHSGEFNKIGELNSGNYNEMKP DANDYQYFDNEDILEGDEDLTNIWN KNMQNFEPSTLLTFEIQGNSEEYLF EEVTSLNTYFRGVFYSNNESDDNKI LFFITDPDGEVIYKKEASEGIFYFYTQ KIGVYTITLKNSKWMGKKLTTVALGL GESPSLKSEHIKDFTNYIDKIVAETKR LKNELKYLSSKHMTHIEKMKKITNKA FLYCFIKLFVLVFLSLFTIYYIKNLVSN KRVLhhhhhh (SEQ ID NO: 89) | ATGTCCAAGACCGGCAACAACAACAGGAACGCCAAGAACGCTAAGGG CGGCGGCGGCGGCGGCAGGAGGGCAACAACGAGGCCAACAAGAAC GACGGCATGTCCGGCAAGGGCAGCCAAAAGGGCAAGAAGAAGGACC CAGGCGGCGGCGGCACCCCGAAGGGCCAGGGCAAGGGCCCAGAGCA AGGCAAGCAGAAGAACAAGAAGGGCGAGGACTCCCACTTCGACGAGT ACATCAAGGACATGAAGAACAGCCAAGACGAGGACAACTTCATGGAC GAGCTCAACAGGTTCGAGAAGAACTTCCACGACGAGGACTTCGAGTCC GACGAGAACCTGTTCAACTACGGCAAGGGCGGCACCCACTCCGGCGA GTTCAACAAGATCGGCGAGCTCAACAGCGGCAACTACAACGAGATGA AGCCAGACGCCAACGACTACCAGTACTTCGACAACGAGGACATCCTGG AGGGCGACGAGGACCTGACCAACATCTGGAACAAGAACATGCAAAAC TTCGAGCCAAGCACCCTCCTGACCTTCGAGATCCAGGGCAACTCCGAG GAGTACCTCTTCGAGGAAGTGACCAGCCTGAACACCTACTTCCGCGGC GTCTTCTACTCCAACAACGAGAGCGACGACAACAAGATCCTGTTCTTCA TCACCGACCCAGACGGCGAGGTCATCTACAAGAAGGAAGCCTCCGAG GGCATCTTCTACTTCTACACCCAAAAGATCGGCGTGTACACCATCACCC TCAAGAACAGCAAGTGGATGGGCAAGAAGCTGACCACCGTGGCTCTG GGCCTGGGCGAGTCCCCAAGCCTCAAGAGCGAGCACATCAAGGACTTC ACCAACTACATCGACAAGATCGTCGCCGAGCAGAAGAGGCTGAAGAA CGAGCTCAAGTACCTGTCCAGCAAGCACATGACCCACATCGAGAAGAT GAAGAAGATCACCAACAAGGCCTTCCTCTACTGCTTCATCAAGCTCTTC GTGCTGGTCTTCCTCTCCCTGTTCACCATCTACTACATCAAGAACCTCGT GAGCAACAAGCGCGTCCTGCACCACCACCACCACCACTGA (SEQ ID NO: 90) |
| 46 | hypothetical protein, conserved | PVX_119265 | MNNHQAVKQQMNPKGSKEQNRMV APNSNMPGGMRDLAYHRNNGNNE MGKMNMNANGQQHNAGSSNTYNS NSINNNYSLGLYIDNPQNAFVFDE NDLKTLFSHYKGAKNIRILNDKAAAQ ITFNDKNMIQQVRKDINGLTITDGTI RCIILNEGKIVEQFLPFSANDPASAQ QKGGSNQSGDSTVDMLKKLANLLQ PERAMDSSMAPKMGDNGGLSATG SVNMGASIATNVGMGGNMPTNAM GGVITTNANVSANVSANVSANPMPG KNQVKNKMGNHAIYNNGGSHFNQA HMNKGEPGENNPYATKRLSRIELIDI FGFPVEFDVMKKILGKNNSNISYIKE QTNNSVSIEIKGKPFNEAPIVERMHV SVSSDDLIGYKKATELIVKLLNSIFEE FYDFCYEKNYPVPENLSFKRHEYMY NPDGSTKYVGFKDKWHVMKDSYRT DYSFRKNKGLQKNDKDKRMHGGAF GGHPNLSIGYANQNAPQGDFKEMN hhhhhh (SEQ ID NO: 91) | ATGAACAACCACCAAGCCGTCAAGCAACAGATGAACCCAAAGGGCTCC AAGGAGCAGAACAGGATGGTTGGCCCCAAACAGCAACATGCCAGGCGG CATGAGGGACCTCGCTTACCACAGGAACAACGGCAACAACGAGATGG GCAAGATGAACATGAACGCCAACGGCAACAGCACAACGCCGGCTCCA GCAACACCTACAACTCCAACTCCATCAACAACAACAACTACTCCCTCGG CCTGTACATCGACAACCCACAAAACGCCTTCGTCTTCGACGAGAACGAC CTCAAGACCCTGTTCAGCCACTACAAGGGCGCCAAGAACATCAGGATC CTCAACGACAAGGCTGCCGCCCAGATCACCTTCAACGACAAGAACATG ATCCAACAGGTCAGGAAGGACATCAACGGCCTGACCATCACCGACATC GGCACCATCCGCTGCATCATCCTCAACGAGGGCAAGATCGTGGAGCAA TTCCTGCCATTCTCCGCCAACGACCCTGCTAGCGCTCAACAGAAGGGC GGCTCCAACCAAAGCGGCGACTCCACCGTGGACATGCTGAAGAAGCTC GCTAACCTCCTGCAGCCAGAGAGGGCCATGGACTCCAGCATGGCCCCA AAGATGGGCGACAACGGCGGCCTCTCCGCTACCGGCTCCGTCAACATG GGCGCCTCCATCGCCACCAACGTGGGCATGGGCGGCAACATGCCAACC AACGCCAACATGGGCGGCGTCATCACCACCAACGCCAACGTGAGCGCC AACGTCTCCGCTAACGTGAGCGCTAACCCAATGCCAGGCAAGAACCAA GTGAAGAACAAGATGGGCAACCACGCCATCTACAACAACGGCGGCTCC CACTTCAACCAGGCCCACATGAACAAGGGCGAGCCAGGCGAGAACAA CCCATACGCCACCAAGAGGCTCAGCCGCATCGAGCTGATCGACATCTTC GGCTTCCCAGTCGAGTTCGACGTGATGAAGAAGATCCTCGGCAAGAAC AACAGCAACATCTCCTACATCAAGGAGCAAACCAACAACTCCGTCAGC ATCGAGATCAAGGGCAAGCCATTCAACGAGGCCCCAATCGTGGAGCG CATGCACGTGTCCGTCTCCAGCGACGACCTCATCGGCTACAAGAAGGC |

| No. | Protein Name | Protein Reference | Insert aa sequence (add M as start/His-tag at C-term) | Insert DNA sequence (Start from ATG to His-tag stop codon) |
|---|---|---|---|---|
| | | | | CACCGAGCTGATCGTCAAGCTCCTGAACAGCATCTTCGAGGAGTTCTAC GACTTCTGCTACGAGAAGAACTACCCAGTGCCAGAGAACCTGTCCTTCA AGAGGCACGAGTACATGTACAACCCAGACGGCAGCACCAAGTATGTG GGCTTCAAGGACAAGTGGCACGTGATGAAGGACTCCTACAGGACCGA CTACAGCTTCCGCAAGAACAAGGGCCTCCAGAAGAACGACAAGGACA AGAGGATGACTCGGCGGCGCTTTCGGCGGCACACCCAAACCTGAGCAT GGCTACGCCAACCAAAACGCCCCACAGGGCGACTTCAAGGAGATGAA CCACCACCACCACCACCACTGA (SEQ ID NO: 92) |
| 47 | rhoptry neck protein 2, putative (RON2) | PVX_ 117880 | mREAKGSVRDGKQYVKTKSPTYTP QKKTKVIFYMPGQEQEEEEDDNDP NGSKKNGKSDTGANKGTHMGSKTD AGNSPSGLNKGSGVGSGSRPASNN YKGNAGGGINIDMSPHGDNSNKGQ QGNAGLNKNQEDTLRDEYEKIRKQE EEEEERINNQRRADMKRAQRGKNK FGDDKGVQDShhhhhh (SEQ ID NO: 93) | ATGCGCGAGGCTAAGGGCTCCGTGCGCGACGGCAAGCAATACGTCAA GACCAAGAGCCCAACCTACACCCCACAGAAGAAGACCAAGGTCATCTT CTACATGCCAGGCCAAGAGCAAGAGGAAGAGGAAGACGACAACGACC CAAACGGCTCCAAGAAGAACGGCAAGAGCGACACCGGCGCCAACAAG GGCACCCACATGGGCTCCAAGACCGACGCTGGCAACTCCCCGAGCGGC CTCAACAAGGGCTCCGGCGTGGGCTCCGGCAGCAGGCCAGCCAGCAA CAACTACAAGGGCAACGCCGGCGGCGGCATCAACATCGACATGTCCCC ACACGGCGACAACAGCAACAAGGGCCAACAGGGCAACGCCGGCCTCA ACAAGAACCAAGAGGACACCCTGAGGGACGAGTACGAGAAGATCCGC AAACAAGAGGAGGAAGAGGAGCGCATCAACAACCAAAGGCGCG CTGACATGAAGAGGGCTCAGAGGGGCAAGAACAAGTTCGGCGACGAC AAGGGCGTGCAAGACAGCCACCACCACCACCACCACTGA (SEQ ID NO: 94) |
| 48 | tryptophan-rich antigen (Pv-fam-a) | PVX_ 121897 | mSSQSAVDYIEQEPLDILNLEEGDLE VTEQWKDNEWHNWKLKLEEDWDS FSTSLIRDKKDFMKIKTDELNGWLNL EENKWNNFSGYLSDGYKNYLLKKS EKWNDADWENWANTEMVAHLDKD YHLWSLNTERSVNALVRGEWNQW QHDKMSSWLSSDWKKVGAMYWDL QESRNWASYSHTDDMKEHWIKWN DRNARENIEWSKWVQNKEYFIMYA RHSDIEQWKYDNYALYSTWRNDFIN RWVSEKKWNSILNhhhhhh (SEQ ID NO: 95) | ATGTCCAGCCAAAGCGCCGTGGACTACATCGAGCAGGAGCCACTCGAC ATCCTCAACCTCGAAGAGGGCGACCTGGAGTTCACCGAGCAGTGGAA GGACAACGAGTGGCACAACTGGAAGCTCAAGCTCGAAGAGGACTGGG ACTCCTTCAGCACCTCCCTCATCAGGGACAAGAAGGACTTCATGAAGAT CAAGACCGACGAGCTGAACGGCTGGCTCAACCTGGAGGAGAACAAGT GGAACAACTTCAGCGGCTACCTCTCCGACGGCTACAAGAACTACCTCCT GAAGAAGTCCGAGAAGTGGAACGACGCCGACTGGGAGAACTGGGCC AACACCGAGATGGTGGCCCACCTCGACAAGGACTACCACCTCTGGAGC CTGAACACCGAGAGGTCCGTGAACGCTCTGGTCCGCGGCGAGTGGAA CCAATGGCAGCACGACAAGATGTCCAGCTGGCTCTCCAGCGACTGGAA GAAGGTCGGCGCCATGTACTGGGACCTGCAGGAGCAGGAACTGGG CCAGCTACTCCCACACCGACGACATGAAGGAGCACTGGATCAAGTGGA ACGACAGGAACGCCCGCGAGAACATCGAGTGGTCCAAGTGGGTGCAA AACAAGGAGTACTTCATCATGTACGCCCGCCACAGCGACATCGAGCAG TGGAAGTACGACAACTACGCCCTCTACTCCACCTGGAGGAACGACTTC ATCAACCGCTGGGTCAGCGAGAAGAAGTGGAACTCCATCCTGAACCAC CACCACCACCACCACTGA (SEQ ID NO: 96) |
| 49 | tryptophan-rich antigen (Pv-fam-a) | PVX_ 125728 | mKSSNEIERLTHVKLKDTSEWTENV EEWVKDEWHEWMDEVQMDWKEF NSSLESEKNKWFGKKEKEMMELIKS IEDKWLDFNENMHEVLNYAILKISLM WSFSEWQKWINKDGKRIIENQWER WTISNKNLYYKIIMKEWFKWKNKKIK QWLKRNWLHHEGRILENWERLPYT KILAMSEKKPWFNSNAQVINERDYF LIWIKKKEDFLVNEERDKWENWEYY KNDFFQTWMDSFLSHWLNIKKRDIL HSQShhhhhh (SEQ ID NO: 97) | ATGAAGTCCAGCAACGAGATCGAGAGGCTCACCCACGTGAAGCTGAA GGACACCTCCGAGTGGACCGAGAACGTGGAGGAGTGGGTCAAGGAC GAGTGGCACGAGTGGATGGACGAGGTCCAGATGGACTGGAAGGAGTT CAACTCCAGCCTGGAGTCCGAGAAGAACAAGTGGTTCGGCAAGAAGG AGAAGGAGATGATGGAGCTGATCAAGAGCATCGAGGACAAGTGGCTC GACTTCAACGAGAACATGCACGAGGTGCTCAACTACGCCATCCTCAAG ATCTCCCTGATGTGGTCCTTCAGCGAGTGGCAAAAGTGGATCAACAAG GACGGCAAGAGGATCATCGAGAACCAGTGGGAGCGCTGGACCATCAG CAACAAGAACCTGTACTACAAGATCATCATGAAGGAGTGGTTCAAGTG GAAGAACAAGAAGATCAAGCAATGGCTCAAGAGGAACTGGCTGCACC ACGAGGGCAGGATCCTGGAGAACTGGGAGCGCCTGCCATACACCAAG ATCCTGGCCATGTCCGAGAAGAAGCCATGGTTCAACAGCAACGCCCAA GTGATCAACGAGAGGGACTACTTCCTGATCTGGATCAAGAAGAAGGA AGACTTCCTCGTCAACGAGGAGCGCGACAAGTGGGAGAACTGGGAGT ACTACAAGAACGACTTCTTCCAAACCTGGATGGACTCCTTCCTCAGCCA CTGGCTGAACATCAAGAAGCGCGACATCCTCCACTCCCAGAGCCACCA CCACCACCACCACTGA (SEQ ID NO: 98) |
| 50 | reticulocyte binding protein 2 precursor (PvRBP-2), putative | PVX_ 090330 | mRLKHDHNLLPNYANLMRDDQNGQ NSENRGDNINNHNKNHNDQNNHNG NNDNSINSEYLKTSHLQNSSAMVHL NDHKITTKPARYSYIQRSKIYAFNPN NKKIENINNELHShhhhhh (SEQ ID NO: 99) | ATGAGGCTCAAGCACGACCACAACCTCCTGCCAAACTACGCCAACCTG ATGAGGGACGACCAAAACGGCCAGAACTCCGAGAACCGCGGCGACAA CATCAACAACCACAACAAGAACCACAACGACCAAAACAACCACAACGG CAACAACGACAACTCCATCAACAGCGAGTACCTCAAGACCAGCCACCT GCAGAACTCCAGCGCCATGGTGCACCTCAACGACCACAAGATCACCAC CAAGCCAGCCAGGTACTCCTACATCCAACGCAGCAAGATCTACGCCTTC AACCCAAACAACAAGAAGATCGAGAACATCAACAACGAGCTGCACTCC CACCACCACCACCACCACTGA (SEQ ID NO: 100) |

Appendix I-continued

| No. | Protein Name | Protein Reference | Insert aa sequence (add M as start/His-tag at C-term) | Insert DNA sequence (Start from ATG to His-tag stop codon) |
| --- | --- | --- | --- | --- |
| 51 | histone-lysine N-methyltransferase, H3 lysine-4 specific, putative (SET10) | PVX_123685 | mSMEQGTPIVFPHKEGTILTKGTNN LAVAHKEEVHRSEEETTLKGLKEEL PHEHTLAIQKYDPSFGRGGSPGSGS TEHTNGSFSNSYETILYNKSNDVVK NLKEIKKGAPFGGVISDAVSCPASSS SNTGGNKNLCFSNMMKLSKKILGFP LLTDFERGMSTNQPCLPLSDHLKRL SVCTVCYSKHNDLAKAIICRVTKMHF EANYNDGLGDEDMFKTSSECIQSVI RELANTIKEYRKRELSGAYVQELAR SGSSSYRSCSSSSYSSRGGSCAGS RGDGLAGSHGEIHAVIAGPPLTDDH NDIGAEAHSPSSSLKLPPQKPFYGM MSDPPCSDRRPGDTNNPFENNTPP LLWDNKVNYTDDYTCKRGEVNSTL GKRPHEEDNKGSSQKKSKLRTKPS NDTIGGENGDSLKGGTDEGKTHEG GGNVGSCTAQGGADQLPRSDLCRD PRGDPCVDPLPEQHAHRSKDENQK GDKNDIHFAGEKLDEIEAPGDQKGN YVTLENISKASNFIPLLGVELGSTKIQ REFTNGTYVGTVTEQIKDEHGNPFF VVTYEDGDAEWMTPCFLFQELLKQ STNSVDYPLATTFKEVFNPEFKKDL KLSNCSLELKIERRKRKSNCESASN NNSVSKRQKHAQEENSSRKKKQRF hhhhhh (SEQ ID NO: 101) | ATGTCCATGGAGCAAGGCACCCCAATCGTGTTCCCACACAAGGAAGGC ACCATCCTCACCAAGGGCACCAACAACCTGGCCGTGGCCCACAAGGAA GAGGTGCACAGGAGCGAGGAAGAGACGACCCTCAAGGGCCTGAAGG AAGAGCTCCCACACGAGCACACCCTGGCCATCCAGAAGTACGACCCAA GCTTCGGCCGCGGCGGCTCCCCAGGCAGCGGCAGCACCGAGCACACC AACGGCTCCTTCAGCAACTCCTACGAGACGATCCTCTACAACAAGTCCA ACGACGTGGTCAAGAACCTGAAGGAGATCAAGAAGGGCGCTCCATTC GGCGGCGTGATCTCCGACGCCGTCTCCTGCCCGGCCTCCAGCTCCAGC AACACCGGCGGCAACAAGAACCTCTGCTTCAGCAACATGATGAAGCTC TCCAAGAAGATCCTGGGCTTCCCACTCCTGACCGACTTCGAGAGGGGC ATGAGCACCAACCAACCATGCCTCCCACTGAGCGACCACCTCAAGCGC CTGTCCGTGTGCACCGTCTGCTACAGCAAGCACAACGACCTGGCCAAG GCCATCATCTGCAGGGTGACCAAGATGCACTTCGAGGCCAACTACAAC GACGGCCTCGGCGACGAGGACATGTTCAAGACCTCCAGCGAGTGCATC CAATCCGTGATCCGCGAGCTGGCCAACACCATCAAGGAGTACAGGAAG CGCGAGCTGTCCGGCGCCTACGTCCAAGAGCTCGCTAGGTCCGGCTCC AGCTCCTACAGGAGCTGCAGCTCCAGCTCCTACAGCTCCAGGGGCGGC AGCTGCGCTGGCTCCCGCGGCGACGGCCTCGCCGGCTCCCACGGCGAG ATCCACGCCGTCATCGCTGGCCCACCACTGACCGACGACCACAACGAC ATGGGCGCTGAGGCTCACGGCCCAAGCTCCAGCCTCAAGCTGCCACCA CAAAAGCCATTCTACGGCATGATGTCCGACCCACCATGCTCCGACAGG CGCCCAGGCGACACCAACAACCCATTCGAGAACAACACCCCACCACTCC TGTGGGACAACAAGGTGAACTACACCGACGACTACACCTGCAAGAGG GGCGAGGTCAACTCCACCCTCGGCAAGCGCCCACACGAGGAAGACAA CAAGGGCTCCAGCCAGAAGAAGTCCAAGCTCAGGACCAAGCCAAGCA ACGACACCATCGGCGGCGAGAACGGCGACAGCCTGAAGGGCGGCACC GACGAGGGCAAGACCCACGAGGGCGGCGGCAACGTGGGCTCCTGCAC CGCCCAAGGCGGCGCCGACCAGCTCCCAAGGTCCGACCTGTGCAGGG ACCCACGCGGCGACCCATGCGTCGACCCACTCCCAGAGCAACACGCCC ACCGCTCCAAGGACGAGAACCAGAAGGGCGACAAGAACGACATCCAC TTCGCCGGCGAGAAGCTCGACGAGATCGAGGCCCCAGGCGACCAAAA GGGCAACTACGTGACCCTGGAGAACATCAGCAAGGCCTCCAACTTCAT CCCGCTCCTGGGCGTGGAGCTGGCAGCACCAAGATCCAACGCGAGTT CACCAACGGCACCTACGTGGGCACCGTCACCGAGCAGATCAAGGACG AGCACGGCAACCCATTCTTCGTGGTCACCTACGAGGACGGCGACGCTG AGTGGATGACCCCATGCTTCCTCTTCCAAGAGCTCCTGAAGCAGAGCAC CAACTCCGTGGACTACCCACTGGCCACCACCTTCAAGGAAGTGTTCAAC CCAGAGTTCAAGAAGGACCTCAAGCTGAGCAACTGCTCCCTGGAGCTG AAGATCGAGAGGCGCAAGAGGAAGTCCAACTGCGAGAGCGCCTCCAA CAACAACAGCGTGTCCAAGCGCCAAAAGCACGCCCAAGAGGAGAACT CCTCCAGGAAGAAGAAGCAGCGCTTCCACCACCACCACCACTGA (SEQ ID NO: 102) |
| 52 | reticulocyte binding protein 1 precursor, putative | PVX_125738 | mTFNDGSDEISTAQKYKTDVEGIIDK LNVIDETINGINSTLDELLELGNNCQL HRTFLISSSSLNNKIAKFLVEIREQKEN TKKCFQYVKRNHQHLANFVSELHKT QGGIFENVLVDNTPDADKYYHEFM EIEQEATKIVKDIKKEIYHLNDDVDEP VLEKRIKDVINTYNKLKTKKVQMDQS YKNMYITKLREVEGSHDLFNQVAQLI RGETDKKGKALSERENNLHSIYNFV KLHETELHNLYAKYTPEYMEKINKIF DDINARMIAVDLNDDHSSEYSDVKR HEHEHEAMLLMDATNNLSKEVEMMQN ESGGKNDGINGGKSQLVEDYTNTM SEFTEQAKTVAKKIHDSKGDYANMF DHIRENEAMLERIDLKKKDIKEILAHL NRMKEYLLKKLSEEEKLHHMREKLE EVNTSTDEIVKKFRTYDQMVDISQNI DIKNVQSKRYDSVDEIDKEMSYIKTH NKDLIDSKFIVERALENDKRKKSEMA QIFSTISRDNSSMYEYAKSFFDSVLK EIEKLTQMIRNMDKLINENEAVMEKL KDQRRELQNVENASTDLGKLEEVD KMAQTKSETELSERNDSRNAKDGA TYSTLMDDKETDSVNGEETKQENV | ATGACCTTCAACGACGGCAGCGACGAGATCTCCACCGCCCAAAAGTAC AAGACCGACGTGGAGGGCATCATCGACAAGCTGAACGTCATCGACGA GACGATCAACGGCATCAACAGCACCCTGGACGAGCTCCTGGAGCTCGG CAACAACTGCCAACTCCACAGGACCTTCCTGATCTCCAGCTCCTCCCTCAAC AACAAGATCGCCAAGTTCCTCGTGGAGATCAGGGAGCAGAAGGAGAA CACCAAGAAGTGCTTCCAATACGTGAAGCGCAACCACCAGCACCTGGC CAACTTCGTCTCCGAGCTCCACAAGACCCAAGGCGGCATCTTCGAGAA CGTCAACCTGGTGGACAACACCCCAGACGCCGACAAGTACTACCACGA GTTCATGGAGATCGAGCAAGAGGCCACCAAGATCGTCAAGGACATCA AGAAGGAGATCTACCACCTGAACGACGACGTGGACGAGCCAGTCCTG GAGAAGAGGATCAAGGACGTGATCAACACCTACAACAAGCTGAAGAC CAAGAAGGTCCAGATGGACCAGTCCTACAAGAACATGTACATCACCAA GCTGAGGGAGGTGGAGGGCAGCCACGACCTGTTCAACCAAGTCGCCC AGCTCATCAGGGGCGAGACGGACAAGAAGGGCAAGGCCCTGTCCGAG CGCGAGAACAACCTCCACAGCATCTACAACTTCGTGAAGCTGCACGAG ACGGAGCTCCACAACCTGTACGCCAAGTACACCCCAGAGTACATGGAG AAGATCAACAAGATCTTCGACGACATCAACGCCAGGATGATCGCCGTG GACCTCAACGACGACCACAGCTCCGAGTACAGCGACGTCAAGCGCCAC GAGCACGAGGCCATGCTCCTGATGGACGCCACCAACAACCTGTCCAAG GAAGTGGAGATGATGCAGAACGAGAGCGGCGGCAAGAACGACGGCA TCAACGGCGGCAAGTCCCAACTCGTGGAGGACTACACCAACACCATGA GCGAGTTCACCGAGCAGGCCAAGACCGTCGCCAAGAAGATCCACGACT CCAAGGGCGACTACGCCAACATGTTCGACCACATCAGGGAGAACGAG GCCATGCTGGAGCGCATCGACCTCAAGAAGAAGGACATCAAGGAGAT |

Appendix I-continued

| No. | Protein Name | Protein Reference | Insert aa sequence (add M as start/His-tag at C-term) | Insert DNA sequence (Start from ATG to His-tag stop codon) |
|---|---|---|---|---|
| | | | VVKKGLPPQTDIYTSVVLKNDRNDQ KSEKIGEKKSNKPVGTEENIQHSSYL NNDNSNNDIDVGTLYTLGGYNAPND NYNTNESGDDINEEAKKKRNAVLFV YVGGLFSALFICIGAVFYLLHRKIGIE GVGKSDHEKKPTIEDTKIEVFEETNG SKRNVKDEVIDVPFVDMEDNLhhhhh h (SEQ ID NO: 103) | CCTCGCCCACCTGAACAGGATGAAGGAGTACCTCCTGAAGAAGCTGTC CGAGGAAGAGAAGCTCCACCACATGCGCGAGAAGCTCGAAGAGGTGA ACACGACCACCGACGAGATCGTCAAGAAGTTCCGCACCTACGACCAAA TGGTGGACATCTCCCAGAACATCGACATCAAGAACGTGCAAAGCAAGC GCTACGACTCCGTCGACGAGATCGACAAGGAGATGTCCTACATCAAGA CCCACAACAAGGACCTGATCGACAGCAAGTTCATCGTCGAGAGGGCCC TGGAGAACGACAAGCGCAAGAAGAGCGAGATGGCCCAAATCTTCAGC ACCATCTCCAGGGACAACAGCTCCATGTACGAGTACGCCAAGAGCTTC TTCGACTCCGTGCTGAAGGAGATCGAGAAGCTCACCCAGATGATCCGC AACATGGACAAGCTCATCAACGAGAACGAGGCCGTCATGGAGAAGCT GAAGGACCAAAGGCGCGAGCTCCAGAACGTGGAGAACGCCTCCACCG ACCTCGGCAAGCTCGAAGAGGTGGACAAGATGGCCCAGACCAAGAGC GAGACGGAGCTGTCCGAGAGGAACGACAGCCGCAACGCTAAGGACG GCGCTACCTACTCCACCCTCATGGACGACAAGGAGACGGACAGCGTGA ACGGCGAGGAGACGAAGCAAGAGAACGTGGTCGTGAAGAAGGGCCT GCCACCACAGCCCGACATCTACACCAGCGTCGTGCTCAAGAACGACAG GAACGACCAAAAGTCCGAGAAGATCGGCGAGAAGAAGAGCAACAAGC CAGTGGGCACCGAGGAGAACATCCAGCACAGCTCCTACCTCAACAACG ACAACTCCAACAACGACATCGACGTGGGCACCCTCTACACCCTGGGCG GCTACAACGCCCCCAACGACAACTACAACACCAACGAGAGCGGCGACG ACATCAACGAGGAAGCCAAGAAGAAGAGGAACGCCGTGCTCTTCGTCT ACGTGGGCGGCCTCTTCTCCGCCCTTGTTCATCTGCATCGGCGCCGTGTT CTACCTCCTGCACCGCAAGATCGGCATCGAGGGCGTCGGCAAGAGCGA CCACGAGAAGAAGCCAACCATCGAGGACACCAAGATCGAGGTGTTCG AGGAGACGAACGGCTCCAAGCGCAACGTCAAGGACGAGGTCATCGAC GTGCCATTCGTCGACATGGAGGACAACCTCCACCACCACCACCACCACT GA (SEQ ID NO: 104) |
| 53 | PvDBP (region II); Duffy receptor precursor (DBP) | PVX_ 110810 | mGEHKTDSKTDNGKGANNLVMLDY ETSSNGQPAGTLDNVLEFVTGHEG NSRKNSSNGGNPYDIDHKKTISSAII NHAFLQNTVMKNCNYKRKRRERDW DCNTKKDVCIPDRRYQLCMKELTNL VNNTDTNFHRDITFRKLYLKRKLIYD AAVEGDLLLKLNNYRYNKDFCKDIR WSLGDFGDIIMGTDMEGIGYSKVVE NNLRSIFGTDEKAQQRRKQWWNES KAQIWTAMMYSVKKRLKGNFIWICK LNVAVNIEPQIYRWIREWGRDYVSE LPTEVQKLKEKCDGKINYTDKKVCK VPPCQNACKSYDQWITRKKNQWDV LSNKFISVKNAEKVQTAGIVTPYDILK QELDEFNEVAFENEINKRDGAYIELC VCSVEEAKKNTQEVVhhhhhh (SEQ ID NO: 105) | ATGGGCGAGCACAAGACCGACTCCAAGACCGACAACGGCAAGGGCGC CAACAACCTGGTCATGCTCGACTACGAGACGTCCTCCAACGGCCAGCC AGCTGGCACCCTGGACAACGTGCTGGAGTTCGTCACCGGCCACGAGG GCAACAGCAGGAAGAACTCCAGCAACGGCGGCAACCCATACGACATC GACCACAAGAAGACCATCTCCAGCGCCATCATCAACCACGCTTTCCTGC AGAACACCGTGATGAAGAACTGCAACTACAAGAGGAAGAGGCGCGAG CGCGACTGGGACTGCAACACCAAGAAGGACGTCTGCATCCCAGACAG GCGCTACCAACTCTGCATGAAGGAGCTGACCAACCTCGTGAACAACAC CGACACCAACTTCCACAGGGACATCACTTTCCGCAAGCTGTACCTCAAG AGGAAGCTGATCTACGACGCTGCTGTGGAGGGCGACCTCCTGCTCAAG CTCAACAACTACAGGTACAACAAGGACTTCTGCAAGGACATCCGCTGG TCCCTGGGCGACTTCGGCGACATCATCATGGGCACCGACATGGAGGGC ATCGGCTACTCCAAGGTGGTCGAGAACAACCTCCGCAGCATCTTCGGC ACCGACGAGAGGGCCCAACAGAGGCGCAAGCAATGGTGGAACGAGTC CAAGGCCCAGATCTGGACCGCCATGATGTACAGCGTGAAGAAGAGGC TGAAGGGCAACTTCATCTGGATCTGCAAGCTCAACGTGGCCGTCAACA TCGAGCCACAGATCTACAGGTGGATCCGAGGAGTGGGGCAGGGACTAC GTCTCCGAGCTGCCAACCGAGGTGCAAAAGCTCAAGGAGAAGTGCGA CGGCAAGATCAACTACACCGACAAGAAGGTGTGCAAGGTCCCACCATG CCAAAACGCCTGCAAGAGCTACGACCAGTGGATCACCAGGAAGAAGA ACCAATGGGACGTCCTGTCCAACAAGTTCATCAGCGTGAAGAACGCCG AGAAGGTCCAGACCGCCGGCATCGTGACCCCATACGACATCCTGAAGC AAGAGCTCGACGAGTTCAACGAGGTGGCCTTCGAGAACGAGATCAAC AAGCGCGACGGCGCCTACATCGAGCTCTGCGTGTGCAGCGTCGAGGA AGCCAAGAAGAACACCCAAGAGGTGGTCCACCACCACCACCACCACTG A (SEQ ID NO: 106) |
| 54 | MSP3.10 [merozo- ite surface protein 3 alpha (MSP3a)] | PVX_ 097720 | mVIGGSPNNEAPNSSRHHLRNGFP GKNDSLPHEEPNNLEGKNESSDQC DTINLGQVTEKEKKTIEQASVQAQD ATKPEANNAEQIQAELQKVKTAKDE SATAAKDAETAKKNAVDAGKGLDAA KGAIKKAEEAAAEAKKQAGIAEKAEK DAEAAGKKDKLEDVNSQVQIAVEAS TKAKDKKTEAEIAVEIVKAVVAKEEA QKASDEAQKACEKAQKAHAKAQKA SDTTKTVETFKTNAEAAAKNAKEKA GNANKAATEAESANELSVAKQKAKD AEEEAAKEAKKEQVKAEIAAEVAKAK VAKEEADAAQKKAEAAAKKIVDKIAQD TKVPEAQREAKLATQTASKATEAAT EAGKKAQEAEESSKEAEEKAETSDA VKGKADAEEAAKAAGEAKKASIETEIAI EVAKAEVLNAEVKKTAQEAEKDATE AKEQAEKAKAAAEEAKTHGEKAEKV GESTKAHSDEAQQENKNAKDASEE AENRAVDALEEAYAVEAHLARTKNA | ATGGTCATCGGCGGCTCCCCCAAACAACGAGGCCCCAAACTCCAGCAGG CACCACCTCCGCAACGGCTTCCCAGGCAAGAACGACTCCCTCCCACACG AGGAGCCAAACAACCTGGAGGGCAAGAACGAGTCCAGCGACCAATGC GACACCATCAACCTGGGCCAGGTGACCGAGAAGGAGAAGAAGACCAT CGAGCAAGCTAGCGTCCAAGCTCAGGACGCTACCAAGCCAGAGGCCA ACAACGCCGAGCAAATCCAGGCCGAGCTCCAAAAGGTGAAGACCGCT AAGGACGAGTCCGCTACCGCTGCTAAGGACGCTGAGACGGCCAAGAA GAACGCTGTGGACGCTGGCAAGGGCCTGGACGCCGCCAAGGGCGCCA TCAAGAAGGCTGAGGAAGCCGCCGCCGAGGCCAAGAAGCAGGCTGGC ATCGCCGAGAAGGCTGAGAAGGACGCTGAGGCTGCTGGCAAGAAGG ACAAGCTGGAGGACGTGAACAGCCAAGTCCAGATCGCCGTGGAAGCG TCCACCAAGGCCAAGGACAAGAAGACCGAGGCCGAGATCGCCGTGGA GATCGTCAAGGCCGTGGTCGCCAAGGAAGAGGCCCAAAAGGCTAGCG ACGAGGCTCAGAAGGCTTGCGAGAAGGCCCAAAAGGCTCACGCTAAG GCTCAGAAGGCTTCCGACACCACCAAGACCGTGGAGACGTTCAAGACC AACGCCGAGGCTGCCGCCAAGAACGCCAAGGAGAAGGCTGGCAACGC TAACAAGGCTGCTACCGAGGCTGAGAGCGCTAACGAGCTCTCCGTGGC CAAGCAGAAGGCCAAGGACGCCGAGGAAGCCGCCAAGGAAGCCAAG AAGGAGCAAGTCAAGGCTGAGATCGCTGCTGAGGTGGCTAAGGCTAA GGTGGCTAAGGAAGAGGCCGACGCTGCTCAGAAGAAGGCTGAGGCC |

Appendix I-continued

| No. | Protein Name | Protein Reference | Insert aa sequence (add M as start/His-tag at C-term) | Insert DNA sequence (Start from ATG to His-tag stop codon) |
|---|---|---|---|---|
| | | | AESAKSATDMSELEKAKEEAIDAANI<br>AHQKWLKATQAATIAKEKKEAAKVA<br>AEKAQTAANVVKDKAAKAEAKKAET<br>EAVKAAVEARAAAEEAKQEAAKVGA<br>SKEPQETKNKANVEAEATGNEAKKA<br>EDAAEEAKEAAKKANEATDANVARS<br>EADKAIAAAKKAKKAREKAAYGLLKT<br>KNQYVLEPLDISPESADNITSKEEQV<br>KEEMEDQGDEDSNEAEVEEALPNG<br>SGAQEEDVNLEMDDEEEVEEVEEN<br>VATNQQTGGKREKRNTNDTVDDTN<br>ADKQFGDEFDTYNDIKKVTEALVKS<br>MTSLVSDDPSVGDTINEFLSDMNHL<br>FLSWhhhhhh<br>(SEQ ID NO: 107) | GCCAAGAAGATCGTGGACAAGATCGCCCAAGACACCAAGGTGCCGGA<br>GGCTCAGAGGGAGGCTAAGCTGGCTACCCAGACCGCTAGCAAGGCTA<br>CCGAGGCCGCCACCGAGGCTGGCAAGAAGGCTCAAGAGGCCGAGGA<br>GTCCAGCAAGGAAGCCGAGGAGAAGGCTGAGACGAGCGACGCTGTG<br>AAGGGCAAGGCTGACGCTGCTGAGAAGGCTGCTGGCGAGGCCAAGAA<br>GGCTTCCATCGAGACGGAGATCGCCATCGAGGTCGCCAAGGCCGAGG<br>TGCTCAACGCCGAGGTCAAGAAGACCGCTCAAGAGGCCGAGAAGGAC<br>GCTACCGAGGCCAAGGAGCAAGCCGAGAAGGCCAAGGCTGCCGCCGA<br>GGAAGCCAAGACCCACGGCGAGAAGGCTGAGAAGGTGGGCGAGAGC<br>ACCAAGGCCCACTCCGACGAGGCCCAACAGGAGAACAAGAACGCCAA<br>GGACGCCAGCGAGGAAGCCGAGAACAGGGCTGTGGACGCTCTCGAAG<br>AGGCCTACGCTGTGGAGGCTCACCTGGCTAGGACCAAGAACGCTGCTG<br>AGTCCGCTAAGAGCGCTACCGACATGTCCGAGCTGGAGAAGGCCAAG<br>GAAGAGGCCATCGACGCCGCCAACATCGCCCACCAAAAGTGGCTCAAG<br>GCTACCCAGGCTGCTACCATCGCTAAGGAGAAGAAGGAAGCCGCCAA<br>GGTGGCTGCTGAGAAGGCTCAGACCGCTGCCAACGTGGTCAAGGACA<br>AGGCTGCTAAGGCTGAGGCCAAGAAGGCTGAGACGGAGGCCGTCAAG<br>GCTGCTGTGGAGGCCAGGGCCGCCGCCGAGGAAGCCAAACAAGAGGC<br>CGCTAAGGTCGGCGCTAGCAAGGAGCCACAAGAGACGAAGAACAAGG<br>CTAACGTGGAGGCTGAGGCTACCGGCAACGAGGCCAAGAAGGCCGAG<br>GACGCTGCTGAGGAAGCCAAGGAAGCCGCCAAGAAGGCTAACGAGGC<br>TACCGACGCTAACGTGGCTAGGTCCGAGGCTGACAAGGCTATCGCCGC<br>CGCCAAGAAGGCCAAGAAGGCCCGCGAGAAGGCTGCTTACGGCCTCC<br>TGAAGACCAAGAACCAATACGTGCTGGAGCCACTGGACATCTCCCCAG<br>AGAGCGCCGACAACATCACCTCCAAGGAAGAGCAGGTGAAGGAAGAG<br>ATGGAGGACCAAGGCGACGAGGACAGCAACGAGGCCGAGGTGGAGG<br>AAGCCCTGCCAAACGGCTCCGCGCTCAAGAGGAAGACGTCAACCTG<br>GAGATGGACGACGAGGAAGAGGTGGAGGAAGTGGAGGAGAACGTG<br>GCCACCAACCAACAGACCGGCGGCAAGAGGGAGAAGCGCAACACCAA<br>CGACACCGTCGACGACACCAACGCCGACAAGCAATTCGGCGACGAGTT<br>CGACACCTACAACGACATCAAGAAGGTGACCGAGGCCCTCGTCAAGTC<br>CATGACCAGCCTGGTGTCCGACGACCCATCCGTGGGCGACACCATCAA<br>CGAGTTCCTCAGCGACATGAACCACCTCTTCCTGTCCTGGCACCACCA<br>CCACCACCACTGA (SEQ ID NO: 108) |
| 55 | sexual stage antigen s16, putative | PVX_000930 | mENNKIKGGKVPPPSVPTGNNSDN<br>NVPKKDGGENNPPPDAENALQELK<br>NFTKNLEKKTTTNRNIIISTTVINMVLL<br>VLLSGLIGYNTKKGFKKGQMGSVKE<br>VTPEAQKGKLhhhhhh<br>(SEQ ID NO: 109) | ATGGAGAACAACAAGATCAAGGGCGGCAAGGTGCCACCACCATCCGT<br>CCCAACCGGCAACAACTCCGACAACAACGTGCCAAAGAAGGACGGCG<br>GCGAGAACAACCCACCACCAGACGCCGAGAACGCCCTCCAAGAGCTGA<br>AGAACTTCACCAAGAACCTGGAGAAGAAGACCACCACCAACAGGAAC<br>ATCATCATCTCCACCACCGTCATCAACATGGTGCTCCTGGTCCTCCTGA<br>GCGGCCTGATCGGCTACAACACCAAGAAGGGCTTCAAGAAGGGCCAAA<br>TGGGCTCCGTGAAGGAAGTGACCCCAGAGGCCCAGAAGGGCAAGCTC<br>CACCACCACCACCACCACTGA (SEQ ID NO: 110) |
| 56 | Positive Control? | | | |
| 57 | Negative Control? | | | |

APPENDIX II

TABLE 5 list of protein references for additional 25 proteins

| Protein Code | Protein Name | Protein Reference | Source |
|---|---|---|---|
| X1 | PVX_094350 | PVX_094350 | Ehime University |
| X2 | PVX_099930 | PVX_099930 | Ehime University |
| X3 | PVX_114330 | PVX_114330 | Ehime University |
| X4 | PVX_088820 | PVX_088820 | Ehime University |
| X5 | PVX_080665 | PVX_080665 | Ehime University |
| X6 | PVX_092995 | PVX_092995 | Ehime University |
| X7 | PVX_087885 | PVX_087885 | Ehime University |
| X8 | PVX_003795 | PVX_003795 | Ehime University |
| X9 | PVX_087110 | PVX_087110 | Ehime University |
| X10 | PVX_087670 | PVX_087670 | Ehime University |
| X11 | PVX_081330 | PVX_081330 | Ehime University |
| X12 | PVX_122805 | PVX_122805 | Ehime University |
| V1 | RBP1b (P7) | PVX_098582 | WEHI |
| V2 | RBP2a (P9) | PVX_121920 | WEHI |
| V3 | RBP2b (P25) | PVX_094255 | WEHI |
| V4 | RBP2cNB (M5) | PVX_090325 | WEHI |

TABLE 5-continued list of protein references for additional 25 proteins

| Protein Code | Protein Name | Protein Reference | Source |
|---|---|---|---|
| V12 | RBP1a (P5) | PVX_098585 | WEHI |
| V5 | RBP2-P2 (P55) | PVX_101590 | WEHI |
| V11 | PvEBP | KMZ83376.1 | IPP |
| V10 | Pv DBPII (AH) | AAY34130.1 | IPP |
| V13 | Pv DBPII (SalI) | PVX_110810 | IPP |
| V6 | PvDBP R3-5 | PVX_110810 | WEHI |
| V7 | PvGAMA | PVX_088910 | WEHI |
| V8 | PvRipr | PVX_095055 | WEHI |
| V9 | PvCYRPA | PVX_090240 | WEHI |

List of protein sequences (insert aa sequence)

X1:
(SEQ ID NO: 111)
ENPVRHSVDIKSEDFVVLISLQNLQTFIMIGYTAVNKDHLNFDFSYLWALCIGTGLFIYSL

ISFVLIRSLALSKIDIGKYVLELLFSLSIIATCSLSIIIDSFKIANMQLLFFSFALTGYAYYNL

MSLFFFCTLVGMTIQYNLSFTGFRAHSTSFFFLDMLSYLVQMIGGNILYFRMYELCTLIVI

SKRNPCKYVVASKEVKQVEKQIFSSLENSYMCIKSKTYSDLTCTNDLLNKDSQSVVGRD

TNPKWNSPIGTSYQDKVNHTKKLLLRRGKRDKRYPKGGGGARLTCAKHSAYHNSRSL

ANCASKNTPICTTNFRISNTLSLKNHFNPNLTLEASPPVCKKCVSEKNSHKDNEYKNGEE

RKKAKRGIKSGTANKSNQLGNHGGDATQVANPTYRTTSHGGDATQVAYPTYRTTSHG

GDATQVDSPTHPTTSHGGNNSSSGHPQDDEVLIPIRGTNATNDAAATYNSNASWIKTAA

VIDVSVEGKQKKGGHQTFAGNPVNSSANFPSDKKPSYNSHRNGGTPPPNEQLRYYACPC

YQTHSSGSSLSEVPSGQTTKRKNSAHNSVEGGNPKMDNQQSRRVSNKRVDGATGEEHD

HPSDPPADNPNGNSNTYHC

X2
(SEQ ID NO: 112)
ELSHSLSVKNAPDASALNIEVEKDKKKICKNAFQYINVAELLSPREEETYVQKCEEVLDT

IKNDSPDESAEAEINEFILSLLHARSKYTIINDSDEEVLSKLLRSINGSISEEAALKRAKQLI

TFNRFIKDKAKVKNVQEMLVISSKADDFMNEPKQKMLQKIIDSFELYNDYLVILGSNINI

AKRYSSETFLSIKNEKFCSDHIHLCQKFYEQSIIYYRLKVIFDNLVTYVDQNSKHFKKEKL

LELLNMDYRVNRESKVHENYVLEDETVIPTMTITDIYDQDRLIVEVVQDGNSKLMHGR

DIEKREISERYIVTVKNLRKDLNDEGLYADLMKTVKNYVLSITQIDNDISNLVRELDHED

VEK

X3
(SEQ ID NO: 113)
LPWTKKRKAVNQMGIIKDMSQELRTKAEQLPTPEDISAKIHRVDKEVIDKLNKDIIEEEN

LDKHKPHVCQEPAYERDYSYLCPEDWVKNSNDQCWGIDYDGHCEALKYFQDYSVEEK

KEFEMNCCVLWPKLKNEGMKGAHKKDLLRGSISSNNGLIIKPKYL

X4
(SEQ ID NO: 114)
ELKKNNAALTSQRSSSRTTSTRSYKNAPKNSTSFLSRLSILIFALSCAIFVNTASGAAANR

PNANGFVSPTLIGFGELSIQESEEFKRMAWNNWMLRLESDWKHFNDSVEEAKTKWLHE

RDSAWSDWLRLQSKWSHYSEKMLKEHKSNVMEKSANWNDTQWGNWIKTEGRKILE

AQWEKWIKKGDDQLQKLILDKWVQWKNDKIRSWLSSEWKTEEDYYWANVERATTAK

WLQEAEKMHWLKWKERINRESEQWVNWVQMKESVYINVEWKKWPKWKNDKKILFN

KWSTNLVYKWTLKKQWNVWIKEANTAPQV

X5

(SEQ ID NO: 115)
KGVTLSCVFSHASEEREGGTGTFALSNEPIYYAPSGGLAPCALISRGLSGDEEGSGEDGG

EDGDGDGGEDSAEDNAEDGDDDGGEDGGLPGGRFPYEEGKKSSLVSDAPSDLLDGDA

DEHAAEDGGAKRKMSKKEEEAEDNKIDKLVNAEMKKLEAGEEANKDPDAEPEKEDQG

SGQGQRAKLRCSNKLNYIQVTANGQREGDLFGENDGESAPAFVEIPHEVEEESGGVPTK

HDEAGEAAAAEEPHNRVDRAEKENNAKDLKFVEGERERQRSSPPSNGYSQNSFVELKG

VPDKLPPNFTNSLGSSPTHSNLEKPVYKHLPWSILASDSGSNTGSWADVNSSTYNVSPFS

FTSIRSGNSLHLLPMNFQIQNSIVKVTDEEYDKLKLKNSVKVYDKNALVDYKYEIFEVKE

GEEYNDGNDPYEERNGEEGDAGGEGGSDGEGDADSKSYQNNKSDGRGFFDGTLVTYTI

IILAGVIILLLSFVIYYYDIINKVKRRMSAKRKNNKSMAIANDTSAGMYMGDTYMENPH

V

X6

(SEQ ID NO: 116)
SQGCSGYRLPPPKRWFTFTSRPYCKTAAYYELKHMPYYVDAVSASENVKHEKWNNWL

KEMKISLTEKLEKESQEYMEKLEQQWDEFMKNSEDKWRHYNPQMEEEYQCSVYPLGL

KWDDEKWTAWFYEKGLWCLKKSFKTWLTDSKKGYNTYMKNLLQEFGKQFYEDWCR

RPEKRREDKICKRWGQKGLRNDNYYSLKWMQWRNWKNRNHDQKHVWVTLMKDAL

KEYTGPEFKLWTEFRKEKIDFYKQWMQAFAEQWTQDKQWNTWTEERNEYMKKKKEE

EAKKKAASKKKAASKKGGAAKKAPKKAPTKKAAPGTKAPAKKAAPKKVAAPNAA

X7

(SEQ ID NO: 117)
KEAVKKGSKKAMKQPMHKPNLLEEEDFEEKESFSDDEMNGFMEESMDASKLDAKKAK

TTLRSSEKKKTPTSGMSGMSGSGATSAATEAATNMNATAMNAAAKGNSEASKKQTDL

SNEDLFNDELTEEVIADSYEEGGNVGSEEAESLTNAFDDKLLDQGVNENTLLNDNMIYN

VNMVPHKKRELYISPHKHTSAASSKNGKHHAADADALDKKLRAHELLELENGEGSNSV

IVETEEVDVDLNGGKSSGSVSFLSSVVFLLIGLLCFTN

X8

(SEQ ID NO: 118)
NLSNDCKKGANNSFKLIVHTSDDILTLKWKVTGEGAAPGNKADVKKYKLPTLERPFTSV

QVHSANAKSKIIESKFYDIGSGMPAQCSAIATNCFLSGSLEIEHCYHCTLLEKKLAQDSEC

FKYVSSEAKELIEKDTPIKAQEEDANSADHKLIESIDVILKAVYKSDKDEEKKELITPEEV

DENLKKELANYCTLLKEVDTSGTLNNHQMANEEETFRNLTRLLRMHSEENVVTLQDKL

RNAAICIKHIDKWILNKRGLTLPEEGYPSEGYPPEEYPPEELLKEIEKEKSALNDEAFAKD

TNGVIHLDKPPNEMKFKSPYFKKSKYCNNEYCDRWKDKTSCMSNIEVEEQGDCGLCWI

FASKLHLETIRCMRGYGHFRSSALFVANCSKRKPEDRCNVGSNPTEFLQIVKDTGFLPLE

SDLPYSYSDAGNSCPNKRNKWTNLWGDTKLLYHKRPNQFAQLGYVSYESSRFEHSID

LFIDILKREIQNKGSVIIYIKTNNVIDYDFNGRVVHSLCGHKDADHAANLIGYGNYISAGG

EKRSYWIVRNSWGYYWGDEGNFKVDMYGPEGCKRNFIHTAVVFKIDLGIVEVPKKDEG

SIYSYFVQYVPNFLHSLFYVSYGKGADKGAAVVTGQAGGAVVTGQTETPTPEAAKNGD

QPGAQGSEAEVAEGGQAGNEAPGGLQESAVSSQTSEVTPQSSITAPQIGAVAPQIGAAAP

QIDVAAPQIDVVAPQTRSVDAPQTSSVAAHPPNVTPQNVTLGEGQHAGGVGSLIPADN

-continued

X9

(SEQ ID NO: 119)
ETLLDSETLKNYEKETNEYIRKKKVEKLFDVILKNVLVNKPENVYLYIYKNIYSFLLNKIF

VIGPPLLKITPTLCSAIASCFSYYHLSASHMIESYTTGEVDDAAESSTSKKLVSDDLICSIV

KSNINQLNAKQKRGYVVEGFPGTNLQADSCLRHLPSYVFVLYADEEYIYDKYEQENNV

KIRSDMNSQTFDENTQLFEVAEFNTNPLKDEVKVYLRN

X10

(SEQ ID NO: 120)
YPKKNFDKPDPTSPYQGQYGESEEQRQGYGIPPNPTMINLTGNQDQRPNVLQQFGINNK

NVMQFLINMFVYVAAILVSLKIWDYMSYSKCDYYKDLLLRIVRYQSHMNDGKMA

X11

(SEQ ID NO: 121)
SRIDKQPIQSSYLFQDNAVPPVRFSAVDADLFSIGVVHTEEQIFMDDANWVISSVPSKYL

NLHLLKTGSRPHFSHFSVSMNTGCNLFIASPVGETFPLSPSKDGATWKAFETDDSVEVIH

RETKEKRIYKLKFIPLKSGALLKVDVLKGIPFWVISQGRKILPTICSGDEEVLSNPQNEVF

KECTSSSSLSPEFDCLAGLSTYHRDKKNHTWKTSSGSIGQFIKIFFNKPVQITKFRFKPRD

DLLSWPSEVALQFDTDEEVIIPILHTHNMGQNTTRLEHPIITTSVKVEVRDMYERASENT

GGSFEVIGSTCQMMEDDYMTHHAVIDITECDRRLESLPDVMPLTKGSKFLAICPRPCLSS

SNGGVIYGSDVYSTDSAVCGAAVHAGVCSREGEGSCHFLVVVRGGRANFVGALQNNV

LSLSRGGGGSGSGSSTSSDGDGDSDSSTSRANFSFSLSSASGFGGGPRGAHAEAAPSSYSI

VFKPRDHLAPTNGFLVDSGREFTSYGSVAYGWKREVSPSSSFSSPSPSYTSPPLEEPTLLR

GDSSSFNGIYSGGIEFPPASASQNCISQLDCQTNFWKFQMQENGTYFVQVLVGNKTSPEK

QKAFVELNGVPIIKGVDLGPDEVFNATDRVQVTNRALVLTSTCLGGESACSRARVSIMA

VQIVKT

X12

(SEQ ID NO: 122)
NGMNKDKDAEITPPPFIVLPGGKKIHMLQSEYEYDVLRDMYRTDEANGGSGEKESHPSG

DGAIRRNEFFKLFHHREGHYKFVIKNVPTKLSDLLQKGGNEQETDLFPLLYRSLQFACSA

DGTWPYARREVAFFKNGSVHCEAEFQNELSVRRTPRSGKKSFGRFPRGTLIKSSDLRSKI

VEGNSYDKRAAPLKSEKKKKALFLHPESVLYKMEEIFFYENPSVKSEIVGFVLFHDVCT

VTSLGHGAHPVNSPFLGSDLLEMIFGYCILHGFKKIRVKSESLNYETGIRTSFIEILLNGKT

ALEHLGLRLTNVAKFSKELYYVITGYTWKSDLVLSPIVRFEHDLYVHHDIEERFFLYVNK

MYRNMLHDLSFSCDENYYPYKNCYDIYPSVRRSQNNLCLFELNPIYEELKELFPDSCNIG

QRVRKCYEEIKKNVVCTHNGEGGEDGCKYYQFIVNTFIKPRRKTSFFIYHNMYVQEYLS

KKSYPYYLLLSEVIKNEENNFLEKGNYDLVADAQTHLFLNYVLQNSTFFIFWNFSTEFW

KRFRYIQAGPTGATSTPQKGQAVFCPMAYAYEFVEHLDTFYVRG

V6

(SEQ ID NO: 123)
SVEEAKKNTQEVVTNVDNAAKSQATNSNPISQPVDSSKAEKVPGDSTHGNVNSG

QDSSTTGKAVTGDGQNGNQTPAESDVQRSDIAESVSAKNVDPQKSVSKRSDDTASVTGI

AEAGKENLGASNSRPSESTVEANSPGDDTVNSASIPVVSGENPLVTPYNGLRHSKDNSDS

DGPAESMANPDSNSKGETGKGQDNDMAKATKDSSNSSDGTSSATGDTTDAVDREINKG

VPEDRDKTVGSKDGGGEDNSANKDAATVVGEDRIRENSAGGSTNDRSKNDTEKNGAS

TPDSKQSEDATALSKTESLESTESGDRTTNDTTNSLENKNGGKEKDLQKHDFKSNDTPN

EEPNSDQTTDAEGHDRDSIKNDKAERRKHMNKDTFTKNTNSHHLN

V7

(SEQ ID NO: 124)
IRNGNNPQALVPEKGADPSGGQNNRSGENQDTCEIQKMAEEMMEKMMKEKDV

FSSIMEPLQSKLTDDHLCSKMKYTNICLHEKDKTPLTFPCTSPQYEQLIHRFTYKKLCNS

KVAFSNVLLKSFIDKKNEENTFNTIIQNYKVLSTCIDDDLKDIYNASIELFSDIRTSVTEITE

KLWSKNMIEVLKTREQTIAGILCELRNGNNSPLVSNSFSYENFGILKVNYEGLLNQAYAA

FSDYYSYFPAFAISMLEKGGLVDRLVAIHESLTNYRTRNILKKINEKSKNEVLNNEEIMH

SLSSYKHHAGGTRGAFLQSRDVREVTQGDVSVDEKGDRATTAGGNQSASVAAAAPKD

AGPTVAAPNTAATLKTAASPNAAATNTAAPPNMGATSPLSNPLGTSSLQPKDVAVLV

RDLLKNTNIIKFENNEPTSQMDDEEIKKLIESSFFDLSDNTMLMRLLIKPQAAILLIIESFIM

MTPSPTRDAKTYCKKALVNGQLIETSDLNAATEEDDLINEFSSRYNLFYERLKLEEL

V8

(SEQ ID NO: 125)
KEYCDQLSFCDVGLTHHFDTYCKNDQYLFVHYTCEDLCKTCGPNSSCYGNKYK

HKCLCNSPFESKKNHSICEARGSCDAQVCGKNQICKMVDAKATCTCADKYQNVNGVC

LPEDKCDLLCPSNKSCLLENGKKICKCINGLTLQNGECVCSDSSQIEEGHLCVPKNKCKR

KEYQQLCTNEKEHCVYDEQTDIVRCDCVDHFKRNERGICIPVDYCKNVTCKENEICKVV

NNTPTCECKENLKRNSNNECVFNNMCLVNKGNCPIDSECIYHEKKRHQCLCHKKGLVA

INGKCVMQDMCRSDQNKCSENSICVNQVNKEPLCICLFNYVKSRSGDSPEGGQTCVVD

NPCLAHNGGCSPNEVCTFKNGKVSCACGENYRPRGKDSPTGQAVKRGEATKRGDAGQ

PGQAHSANENACLPKTSEADQTFTFQYNDDAAIILGSCGIIQFVQKSDQVIWKINSNNHF

YIFNYDYPSEGQLSAQVVNKQESSILYLKKTHAGKVFYADFELGHQGCSYGNMFLYAH

REEA

V9

(SEQ ID NO: 126)
SKNIIILNDEITTIKSPIHCITDIYFLFRNELYKTCIQHVIKGRTEIHVLVQKKINSAW

ETQTTLFKDHNWFELPSVFNFIHNDEIIIVICRYKQRSKREGTICKRWNSVTGTIYQKEDV

QIDKEAFANKNLESYQSVPLTVKNKKFLLICGILSYEYKTANKDNFISCVASEDKGRTWG

TKILINYEELQKGVPYFYLRPIIFGDEFGFYFYSRISTNNTARGGNYMTCTLDVTNEGKKE

YKFKCKHVSLIKPDKSLQNVAKLNGYYITSYVKKDNFNECYLYYTEQNAIVVKPKVQN

DDLNGCYGGSFVKLDESKALFIYSTGYGVQNIHTLYYTRYD

List of polynucleotide sequences (insert bp sequence)

X1

(SEQ ID NO: 127)
GAGAACCCCCGTGAGGCACTCGGTGGACATAAAGTCGGAAGACTTCGTCG

TCCTGATTTCGCTCCAAAACCTGCAGACCTTCATCATGATAGGGTACACA

GCCGTGAACAAAGACCACCTGAATTTCGACTTCTCCTACTTATGGGCCCT

CTGCATCGGGACGGGCCTCTTCATATACTCCCTCATCAGCTTTGTACTCA

TAAGATCCCTAGCACTGTCAAAAATAGACATAGGCAAATACGTCCTGGAG

CTGCTATTCAGTTTGAGTATAATCGCCACATGTTCACTCTCCATAATAAT

TGACTCTTTCAAAATAGCCAACATGCAGTTGCTTTTTTTTCGTTCGCTT

TAACGGGCTATGCCTACTACAATTTGATGAGCCTCTTCTTTTTCTGCACA

CTGGTAGGAATGACCATTCAGTACAATTTAAGTTTCACTGGGTTCAGAGC

GCATTCGACTTCTTTCTTCTTTTTAGATATGCTATCTTACCTAGTGCAAA

TGATAGGAGGGAACATCCTCTACTTTCGCATGTACGAGCTGTGTACCCTA

ATCGTCATTTCGAAGAGGAACCCCTGCAAGTATGTTGTCGCATCGAAGGA

AGTGAAACAAGTGGAGAAGCAAATTTTCTCTTCTTTATTTAATTCTTACA

TGTGCATCAAGTCCAAAACTTATTCAGATTTAACCTGCACTAATGATCTG

TTAAATAAAGACAGTCAATCTGTTGTCGGTAGGGATACGAACCCTAAGTG

GAACTCCCCCATTGGTACTTcCTACCAGGATAAGGTCAATATACGAAGA

AGTTACTCCTTCGGAGGGGAAAACGGGACAAACGCTACCCCAAAGGGGGA

GGGGGAGCTCGACTAACATGTGCAAAACATAGTGCCTACCATAATAGCCG

AAGTCTTGCCAACTGTGCCAGTAAGAATACCCCCATTTGCACAACTAACT

TTAGGATATCTAACACCCTTTCACTTAAAAATCATTTCAACCCTAACCTA

```
ACCTTAGAAGCGTCTCCCCCCGTTTGTAAAAAATGCGTTTCGGAAAAGAA

TAGCCATAAGGATAATGAGTACAAAAACGGGGAAGAGAGAAAAAAAGCAA

AACGTGGTATCAAGTCGGGCACTGCAAACAAGTCTAACCAGTTGGGCAAC

CACGGGGGGGACGCTACGCAGGTGGCTAATCCTACCTACAGAACTACTTC

CCACGGGGGGGACGCAACCCAGGTGGCTTATCCTACCTACAGAACTACTT

CCCACGGGGGGGACGCAACGCAGGTGGATAGTCCTACCCACCCAACTACC

TCCCATGGGGGGAACAACTCGTCGAGCGGGCACCCCCAAGACGACGAAGT

GCTCATCCCCATTAGGGGAACCAACGCCACTAACGATGCAGCCGCCACCT

ACAACTCGAACGCTAGTTGGATCAAAACCGCTGCGGTTATTGACGTGTCT

GTGGAGGGGAAGCAGAAAAAGGGGGGACATCAAACGTTCGCGGGCAATCC

CGTAAATTCATCCGCTAATTTCCCATCGGACAAGAAACCTTCCTACAACT

CGCACCGCAACGGAGGTACTCCCCCCCCAAATGAACAACTCAGGTACTAC

GCCTGCCCCTGCTACCAGACCCACTCCAGCGGATCGTCCCTCAGTGAGGT

GCCCTCGGGACAAACGACGAAGCGGAAAAATAGTGCGCACAACTCGGTTG

AAGGGGGAAACCCCAAAATGGATAATCAGCAAAGTCGCCGCGTGAGTAAC

AAGCGGGTAGATGGCGCAACGGGTGAGGAACATGACCACCCAAGTGACCC

CCCCGCAGATAACCCAAATGGAAACTCCAACACCTACCACTGC

X2
                                            (SEQ ID NO: 128)
GAGCTGAGCCACAGCTTGTCCGTGAAGAACGCGCCGGACGCGAGCGCGCT

GAACATCGAGGTGGAGAAGGACAAAAAGAAGATCTGCAAAAACGCATTCC

AATACATAAACGTAGCTGAGCTGTTTGTCCCCAAGGGAGGAAGAAACCTA

CGTGCAGAAATGTGAAGAGGTCCTAGACACAATAAAGAATGACAGTCCAG

ATGAATCGGCAGAAGCAGATAAACGAATTTATACTGAGCTTACTGCACGC

TCGTTCTAAGTATACCATAATAAATGACTCAGATGAGGAGGTACTGAGCA

AGCTCCTGAGGAGTATCAACGGATCGATAAGTGAAGAGGCAGCGTTGAAG

AGAGCCAAACAGCTAATCACATTCAATCGGTTTATAAAAGACAAAGCGAA

GGTAAAAAATGTGCAAGAGATGCTAGTAATAAGTAGCAAAGCAGATCACT

TCATGAATGAGCCGAAGCAAAAAATGCTCCAAAAAATTATAGATTCGTTT

GAACTGTATAATGATTACCTAGTCATTTTAGGGTCAAATATTAACATCGC

CAAGAGGTACTCCTCAGAAACGTTTCTTTCTATTAAAAATGAAAAGTTCT

GCTCAGACCACATCCACTTATGCCAGAAGTTCTACGAGCAGTCTATCATT

TACTACAGATTGAAGGTTATTTTTGATAACCTGGTGACTTATGTAGATCA

AAATTCCAAGCATTTTAAAAAGGAAAAGTTGCTGGAGCTTCTAAATATGG

ATTATAGGGTCAATCGAGAGTCGAAGGTGCATGAAAATTACGTGCTGGAG

GATGAGACGGTCATCCCCACGATGCGCATTACAGACATTTACGATCAAGA

TAGGCTAATTGTTGAGGTCGTTCAGGATGGAAATAGCAAGCTGATGCACG

GCAGGGATATTGAGAAGAGGGAAATCAGCGAGAGGTACATCGTCACCGTG

AAGAACCTGCGCAAGGACCTCAACGACGAGGGGCTCTACGCCGACTTGAT

GAAGACCGTCAAGAACTACGTGCTCTCCATCACGCAGATCGACAACGACA

TTTCCAACCTCGTGCGCGAGCTCGACCACGAGGATGTGGAGAAG

X3
                                            (SEQ ID NO: 129)
CTACCATGGACGAAGAAAAGAAAGGCGGTGAACCAAATGGGCATCATAAA

AGATATGTCGCAGGAGCTTAGGACTAAGGCCGAACAGCTTCCAACCCCCG

AGGATATATCAGCCAAAATTCACAGAGTAGATAAAGAGGTCATCGATAAG

TTAAACAAAGACATCATAGAGGAAGAAAATTTAGACAAGCACAAACCGCA

CGTCTGCCAGGAGCCAGCATACGAGAGGGACTATTCGTACCTATGTCCCG

AAGACTGGGTGAAGAACTCCAACGATCAGTGCTGGGGCATAGACTACGAT

GGTCACTGTGAAGCGCTAAAATATTTTCCAAGATTATTCTGTAGAGGAGA

AAAAAGAATTTGAAATGAACTGCTGCGTCTTGTGGCCTAAGCTAAAAAAT

GAAGGCATGAAAGGAGCGCACAAGAAGGACCTCCTAAGGGGATCGATAAG

TTCAAACAATGGGTTAATAATAAAGCCGAAATATTTG

X4
                                            (SEQ ID NO: 130)
GAATTGAAGAAGAACAATGCCGCGTTGACCTCACAAAGGTCATCTTCTAG

AACCACATCCACAAGGAGCTACAAAAATGCCCCAAAAAATTCCACTTCAT

TCCTTTCTCGTTTATCTATTCTGATATTTGCCTTATCATGTGCTATTTTT

GTAAATACTGCATCAGGGGCGGCAGCTAATAGACCAAACGCGAATGGCTT

CTGTGTCACCTACTTTAATAGGATTTGGCGAATTAAGCATCCAAGAATCA

GAAGAATTCAAAAGAATGGCTTGGAATAATTGGATGTTGCGATTGGAGTC

CGACTGGAAACATTTTAACGATTCTGTTGAAGAAGCCAAAACCAAATGGC

TTCATGAAAGAGACTCAGCTTGGTCTGATTGGCTTCGTTCCTTGCAAAGT

AAATGGTCTCACTATAGTGAAAAAATGCTTAAAGAACACAAAAGTAATGT

TATGGAAAAATCAGCCAACTGGAATGACACGCAATGGGGAAATTGGATAA

AAACTGAAGGAAGAAAAATTCTAGAAGCGCAATGGGAAAAATGGATTAAA

AAAGGTGATGACCAATTACAAAAGTTAATTTTAGATAAATGGGTTCAATG

GAAAAATGATAAGATCCGATCCTGGTTATCCAGTGAATGGAAAACCGAAG

AAGATTACTACTGGGCAAATGTAGAGCGCGCTACAACAGCAAAATGGTTG

CAAGAAGCAGAGAAATGCATTGGCTTAAATGGAAAGAAAGAATTAACAG

AGAGTCTGAACAATGGGTGAACTGGGTCCAAATGAAAGAAAGCGTTTACA

TCAATGTAGAATGGAAAAAATGGCCCAAATGGAAAAATGATAAAAAAATT

CTATTTAACAAATGGTCAACTAACCTTGTCTACAAATGGACACTGAAAAA

GCAGTGGAACGTTTGGATTAAGGAAGCAAATACTGCACCCCAAGTT

X5
                                            (SEQ ID NO: 131)
AAGGGTGTCACCTTGAGTTGCGTTTTTTCCCATGCGAGTGAGGAACGTGA

GGGTGGCACAGGGACATTTGCTTTGAGCAATGAGCCGATTTATTACGCCC

CTAGTGGGGGCTGGCGCCGTGCGCGCTCATCAGCAGAGGGTTAAGCGGG

GATGAGGAGGGTAGCGGCGAGGACGGCGGTGAAGATGGCGACGGAGATGG

TGGTGAAGACAGCGCTGAGGACAACGCTGAGGATGGAGACGATGATGGTG

GCGAAGATGGCGGCTTGCCCGGGGGACGCTTCCCATACGAAGAAGGAAAA

AAGAGTAGCCTTGTGAGCGACGCACCCAGCGACCTCCTGGATGGAGATGC

GGATGAACATGCCGCCGAAGATGGGGGAGCGAAGCGAAAGATGAGTAAGA
```

AGGAGGAAGAGGCGGAGGATAACAAAATTGACAAGTTGGTAAATGCGGAA

ATGAAAAAGCTCGAGGCAGGGGAAGAGGCGAACAAGGATCCCGACGCAGA

ACCAGAAAAGAGGACCAGGGAAGTGGCCAAGGACAAAGGGCGAAGCTGA

GGTGCTCAAACAAGCTAAATTACATACAGGTGACGGCGAATGGCCAAAGG

GAGGGCGACCTCTTTGGCGAGAACGACGGGGAGAGCGCCCCAGCTTTCGT

GGAGATACCCCACGAGGTTGAGGAGGAAAGCGGCGGTGTGCCCACAAAGC

ATGACGAAGCGGGGAAGCAGCTGCGGCGGAGGAACCACATAACCGCGTC

GACCGAGCGGAAAAAGAAAACAACGCGAAGGACTTAAAATTTGTGGAGGG

GGAGCGAGAAAGACAAAGGAGCAGCCCCCCCTCGAATGGATATTCCCAAA

ACAGCTTTGTCGAACTGAAAGGTGTGCCCGATAAATTGCCCCCTAATTTA

CCAACTCGCTTGGTAGCTCCCCAACGCACAGTAATTTGGAGAAACCAGTT

TATAAGCACTTACCCTGGTCTATCCTGGCATCCGACTCTGGTTCGAACAC

CGGGTCCTGGGCAGACGTCAACAGTAGTACCTACAATGTGAGTCCATTCA

GTTTCACCTCAATACGTAGTGGTAACTCTCTGCATCTACTGCCGATGAAT

TTCCAAATCCAAAACTCCATCGTGAAAGTAACTGATGAGGAGTATGACAA

ATTGAAGCTTAAAAACAGCGTCAAAGTGTATGACAAAAATGCCCTGGTAG

ATTATAAGTATGAAATTTTGAGGTGAAGGAAGGGGAGGAATATAATGAT

GGGAATGACCCTTATGAGGAAAGGAATGGGGAAGAAGGGGATGCAGGTGG

AGAGGGGGGTTCCGATGGGGAGGGAGATGCAGATTCTAAATCATATCAAA

ATAACAAATCGGATGGACGTGGGTTCTTCGATGGGACCTTAGTAACCTAC

ACCATTATCATTTTAGCTGGTGTTATAATTCTGCTGCTAAGTTTTGTCAT

TTATTACTACGATATAATAAATAAGGTGAAGAGGCGAATGAGTGCCAAGC

GGAAGAACAACAAATCTATGGCCATCGCGAATGATACATCCGCGGGGATG

TACATGGGCGACACCTACATGGAGAATCCCCACGTT

X6
(SEQ ID NO: 132)
TCACAAGGATGTTCAGGATACCGTTTACCACCACCAAAAAGATGGTTTAC

CTTCACTTCTCGACCATACTGTAAAACAGCTGCATATTATGAACTTAAAC

ATATGCCATATTATGTAGATGCAGTTAGTGCATCAGAAAACGTAAAACAT

GAGAAATGGAATAACTGGTTAAAAGAAATGAAAATATCATTAACTGAAAA

ATTAGAAAAAGAATCACAAGAATATATGGAAAAATTGGAACAGCAATGGG

ATGAATTMTGAAAAATTCAGAAGATAAATGGAGGCTATTATAATCCCCAA

ATGGAAGAAGAATATCAATGTAGTGTTTATCCACTTGGATTAAAATGGGA

TGATGAAAGTGGACTGCATGTTTTATGAAAAAGGATTATGGTGTTTGA

AGAAAACTCTTTAAAACATGGCTCACTGATTCTAAAAAAGGTTACAACAC

CTACATGAAAAATCTTTTACAGGAATTGGTAAACAATTTTATGAAGATT

GGTGTCGTAGACCTGAAAAACGTCGTGAAGATAAAATTTGCAAGAGATGG

GGACAAAAAGGATTACGTAATGACAATTACTATTCGTTAAAGTGGATGCA

GTGGAGAAATTGGAAAAACAGAAACCACGATCAAAAACATGTGTGGGTAA

CTCTTATGAAGGATGCGCTAAAGGAATATACGGGGCCCGAATTCAAATTA

TGGACTGAGTTTAGAAAAGAAAAGATAGACTTTTACAAGCAATGGATGCA

AGCTTTCGCCGAACAGTGGACACAAGACAAACAATGGAATACGTGGACTG

AAGAAAGAAATGAATATATGAAAAAGAAAAAAGAAGAAGAAGCAAAAAAA

AAAGCAGCATCAAAAAAAAAAGCAGCATCAAAAAAAGGAGGAGCAGCAAA

AAAGGCACCAGCAAAAAAGGCACCAACAAAAAAAGCCGCACCAGGAACAA

AGGCACCAGCAAAAAAAGCAGCACCTAAAAAAGTTGCAGCACCAAATGCA

GCA

X7
(SEQ ID NO: 133)
AAGGAGGCAGTGAAGAAGGGGTCCAAGAAGGCAATGAAGCAGCCCATGCA

CAAGCCGAACCTTCTTGAAGAGGAAGACTTTGAGGAGAAAGAATCCTTTT

CGGATGACGAGATGAATGGGTTCATGGAGGAGAGCATGGATGCTTCTAAG

TTGGATGCGAAGAAGGCCAAGACGACCCTCAGGAGCTCGGAGAAGAAGAA

GACTCCAACGAGCGGAATGAGTGGAATGAGTGGAAGCGGCGCCACCAGCG

CAGCCACCGAGGCAGCCACGAACATGAACGCCACCGCCATGAACGCCGCT

GCTAAGGGCAACAGCGAGGCGAGCAAAAAGCAAACCGACTTGTCCAACGA

AGACCTGTTCAACGACGAGCTCACAGAAGAGGTCATTGCAGATTCGTACG

AAGAGGGAGGAAACGTGGGAAGCGAGGAAGCCGAAAGCCTCACAAATGCA

TTTGACGACAAGCTACTAGACCAAGGAGTGAATGAAAATACTCTGCTGAA

CGACAACATGATTTACAACGTCAATATGGTTCCACATAAGAAGCGAGAAT

TATACATCTCCCCACACAAGCATACCTCTGCAGCAAGCAGTAAAAATGGC

AAACATCATGCGGCGGACGCGGACGCTTTGGACAAAAAACTGAGGGCTCA

CGAGCTGCTCGAGCTGGAAAACGGAGAAGGCAGCAACTCAGTCATTGTCG

AAACGGAAGAAGTGGATGTTGACCTAAACGGAGGAAAGTCAAGCGGCTCC

GTGTCCTTCCTCAGCTCCGTAGTCTTCTTGCTCATCGGATTGTTATGTTT

CACCAAT

X8
(SEQ ID NO: 134)
AACCTGAGCAACGATTGCAAAAAAGGAGCCAACAACAGCTTTAAGTTAAT

CGTGCACACCAGCGATGATATTTTTGACACTCAAGTGGAAGGTCACTGGGG

AAGGGGCAGCTCCAGGCAACAAAGCAGATGTAAAGAAGTACAAACTCCCT

ACCCTAGAGAGGCCTTTCACTTCCGTGCAAGTGCATTCAGCCAACGCCAA

GTCGAAGATAATCGAAAGCAAATTTTACGACATTGGCAGCGGCATGCCAG

CCCAGTGCAGCGCGATCGCCACGAACTGCTTCCTCAGCGGCAGCCTCGAA

ATCGAGCACTGCTACCACTGCACCCTGTTGGAGAAGAAGCTGGCCCAAGA

CAGCGAGTGCTTCAAGTACGTCTCGAGTGAAGCGAAGGAGTTGATCGAGA

AAGACACGCCGATTAAAGCTCAAGAAGAAGACGCCAACTCTGCAGACCAC

AAACTGATCGAGTCCATAGACGTGATACTAAAGGCAGTGTACAAATCAGA

TAAAGATGAGGAAAAGAAGGAGCTCATCACCCCGGAGGAAGTGGACGAAA

ATTTGAAGAAGAGCTAGCCAATTATTGTACCCTACTGAAGGAGGTAGAC

ACAAGTGGCACTCTTAACAACCACCAGATGGCAAACGAAGAGGAAACGTT

CAGAAATTTGACTCGACTGTTGCGAATGCATAGCGAAGAAAACGTGGTGA

CCCTTCAGGACAAACTGAGAAACGCAGCCATATGCATCAAGCACATCGAC

AAGTGGATTCTTAACAAGAGGGGGTTGACCCTACCGGAAGAAGGGTACCC

-continued

ATCGGAAGGGTACCCCCCAGAAGAGTACCCCCCGGAGGAACTCCTCAAAG

AAATCGAGAAGGAAAAAAGCGCTCTGAATGATGAAGCGTTCGCTAAAGAT

ACCAACGGAGTCATCCACCTGGATAAGCCTCCCAACGAAATGAAATTTAA

ATCCCCCTATTTTAAAAAGAGCAAATACTGTAACAATGAGTACTGTGATA

GGTGGAAAGATAAAACGAGTTGCATGTCAAATATAGAAGTGGAAGAGCAA

GGGGATTGCGGGCTCTGTTGGATTTTCGCCTCTAAGTTACACTTAGAAAC

GATCAGGTGCATGAGAGGGTATGGCCACTTCCGCAGCTCCGCTCTGTTTG

TGGCCAACTGCTCGAAGAGGAAGCCAGAAGATAGATGCAACGTGGGTTCT

AACCCTACAGAGTTTCTTCAAATTGTTAAGGACACGGGATTTTTACCTCT

AGAGTCCGATCTCCCCTACAGCTATAGCGACGCGGGGAACTCCTGCCCCA

ATAAAAGAAACAAGTGGACCAACCTGTGGGGGATACCAAACTGCTGTAT

CATAAGAGACCCAATCAGTTTGCACAAACACTCGGGTACGTTTCCTACGA

AAGCAGTCGCTTTGAGCACAGCATCGACCTCTTCATAGACATCCTCAAAA

GGGAAATTCAAACAAAGGCTCCGTTATCATTTACATAAAAACCAACAAT

GTCATCGATTATGACTTTAATGGAAGAGTCGTCCACAGCCTATGTGGCCA

TAAGGATGCAGATCATGCCGCTAACCTGATCGGTTATGGTAACTACATCA

GTGCTGGTGGGAGAAGAGGTCCTATTGGATTGTGCGAAACAGCTGGGGG

TACTACTGGGGAGATGAAGGCAACTTTAAGGTTGACATGTACGGCCCGGA

GGGATGCAAACGGAACTTCATCCACACGGCTGTTGTGTTTAAGATAGACC

TGGGCATCGTCGAAGTCCCGAAGAAGGACGAGGGGTCCATTTATAGCTAC

TTCGTTCAGTACGTCCCCAACTTTTTGCACAGCCTTTTCTACGTGAGTTA

CGGTAAGGGTGCTGATAAGGGAGCGGCGGTGGTGACAGGGCAGGCGGGAG

GAGCGGTAGTCACAGGACAGACTGAAACGCCCACTCCGGAGGCCGCTAAA

AATGGGGATCAGCCAGGAGCACAGGGTAGCGAGGCAGAAGTCGCGGAGGG

TGGCCAGGCAGGAAATGAAGCCCCGGGAGGGTTGCAAGAGAGTGCTGTTT

CGTCGCAAACGAGTGAGGTTACGCCGCAATCTAGTATAACTGCTCCGCAA

ATCGGTGCAGTTGCCCCACAAATCGGTGCAGCTGCCCCACAAATCGATGT

AGCCGCCCCACAAATCGATGTAGTCGCCCCACAAACGAGGTCCGTTGACG

CCCCCCAAACGAGCTCGGTTGCCGCCCACCCCCCAAACGTGACGCCGCAG

AACGTGACGCTTGGGGAGGGCCAGCACGCGGGGGGTGTAGGCTCCCTCAT

CCCCGCGGACAAC

X9

(SEQ ID NO: 135)

GAAACCCTGCTAGACAGCGAAACGTTAAAGAACTACGAAAAGGAAACGAA

CGAATACATTCGCAAAAAAAAGTGGAGAAACTGTTCGATGTTATTTTAA

AAAATGTTCTGGTAAACAAACCGGAAAATGTATACCTGTACATATACAAG

AACATTTATTCCTTCCTTTTGAACAAAATTTTTGTGATCGGCCCTCCTTT

GCTGAAAATTACTCCCACCTTATGTTCTGCGATTGCCAGCTGCTTTAGCT

ACTACCACCTCAGCGCCTCGCACATGATCGAGTCTTACACTACTGGTGAA

GTAGATGACGCTGCAGAGAGTTCCACAAGCAAAAAGTTAGTCAGTGACGA

CTTAATCTGCTCCATCGTTAAAAGCAACATAAACCAGCTGAACGCGAAGC

AAAAGCGGGGTATGTAGTCGAAGGGTTCCCCGGCACCAATCTTCAGGCA

-continued

GACAGTTGCCTACGGCATTTGCCATCTTACGTTTTTGTCCTGTACGCCGA

CGAAGAGTACATTTATGACAAGTACGAACAAGAGAACAACGTAAAAATTC

GTTCAGACATGAACAGCCAAACTTTTGATGAAAACACACAGTTGTTCGAA

GTGGCCGAGTTCAACACGAATCCGCTGAAGGATGAGGTAAAGGTCTACTT

AAGGAAC

X10

(SEQ ID NO: 136)

TATCCAAAAAAGAACTCGACAAACCCGACCCAACTTCCCCATACCAAGGA

CAATATGGAGAGTCTGAGGAACAAAGACAAGGTTATGGAATCCCCCCCAA

CCCAACCATGATTAACCTTACTGGTAACCAAGACCAACGACCAAATGTAT

TGCAACAATTTGGAATAAACAACAAAAATGTAATGCAGTTTTTAATAAAC

ATGTTTGTGTACGTTGCTGCTATATTAGTTAGTTTAAAAATATGGGACTA

CATGTCTTACAGCAAATGTGATTATTACAAAGATTTATTATTAAGAATTG

TAAGATACCAATCACACATGAATGATGGTAAGATGGCC

X11

(SEQ ID NO: 137)

AGCCGCATCGACAAGCAGCCCATCCAGAGCAGCTACCTCTTCCAGGATAA

CGCAGTCCCGCCTGTTCGATTCTCCGCAGTAGATGCAGACCTGTTTTCCA

TTGGAGTAGTTCACACAGAGGAGCAAATATTTATGGACGACGCCAACTGG

GTGATTAGCAGCGTGCCCAGTAAGTACCTGAACTTGCATCTACTCAAAAC

GGGTTCTAGACCCCATTTTTCGCACTTCTCCGTATCTATGAACACGGGTT

GCAACCTATTCCATCGCTTCCACCGGTGGGGAAACCTTCCCCTTGAGTC

CCTCCAAAGATGGAGCGACGTGGAAAGCATTTGAAACGGACGACAGTGTA

GAGGTGATTCACAGAGAGACGAAGGAAAAGAGAATCTATAAGCTCAAGTT

CATTCCTCTGAAGAGTGGGGCTCTCCTAAAGGTTGACGTTTTGAAGGGAA

TTCCCTTTTGGGTTATCTCACAAGGGAGGAAAATCCTACCAACGATTTGT

TCTGGAGATGAGGAGGTGCTATCAAACCCACAGAATGAGGTCTTCAAAGA

GTGCACATCGTCGAGTAGTCTCTCTCCCGAATTTGATTGTCTAGCCGGGC

TGAGCACCTACCATAGGGATAAGAAGAACCACACGTGGAAAACCTTCTAG

CGGATCTATAGGTCAGTTTATAAAGATCTTCTTCAATAAGCCCGTACAAA

TTACCAAGTTTAGGTTTAAGCCCAGAGACGACCTGCTGTCTTGGCCCTCC

GAAGTAGCTCTCCAATTCGATACCGATGAGGAGGTGATCATACCAATTCT

GCATACGCACAATATGGGGCAGAACACGACTAGGCTAGAACACCCAATCA

TCACCACCTCTGTTAAGGTAGAAGTGAGAGACATGTACGAACGGGCAAGT

GAAAATACAGGAGGTTCTTTCGAGGTAATTGGAAGCACATGCCAGATGAT

GGAAGACGACTACATGACGCACCATGCTGTTATAGACATCACCGAGTGTG

ATCGTAGGTTGGAGTCCCTCCCAGATGTTATGCCCTTAACGAAGGGGAGC

AAATTTCTGGCCATTTGTCCCCGCCCCTGCTTGAGCAGCTCCAATGGGGG

AGTCATTTACGGGTCAGATGTTTATTCCACAGATTCTGCCGTATGTGGGG

CGGCCGTACACGCGGGGGTGTGCAGCCGTGAGGGGGAGGCAGCTGCCAC

TTCCTCGTTGTGGTGCGCGGCGGGCGGGCCAACTTCGTGGGGGCTCTCCA

GAACAACGTCCTGTCTCTCAGTCGGGGTGGTGGCGGTAGCGGTAGCGGTA

GCTCCACCAGTAGCGATGGCGATGGCGATAGCGATAGCTCCACCAGTAGG
GCCAACTTCTCATTTTCCCTCTCCAGTGCGTCAGGGTTCGGGGGGGTCC
GCGCGGGGCCCACGCAGAAGCCGCGCCAAGCAGCTACTCCATTGTGTTCA
AGCCGAGGGACCATTTGGCTCCAACGAACGGCTTTCTAGTAGACTCAGGG
AGAGAGTTCACCAGCTACGGAAGCGTTGCCTACGGATGGAAGAGGGAGGT
TTCTCCTTCGTCCTTCTTTTTCCTCTCCTTCTCCTAGCTACACTTCCCCC
CCGTTGGAAGAACCGACGCTGCTTAGGGGGACTCCTCCTCATTCAATGG
GATTTACTCCGGGGGATAGAATTCCCCCCCGCCTCGGCTAGCCAAAATT
GCATTTCCCAACTGGATTGCCAGACCAACyrCTGGAAGTTTCAGATGCAA
GAAAATGGCACCTACTTTGTGCAGGTGCTAGTGGGGAATAAAACTTCCCC
TGAGAAGCAGAAGGCCTTCGTCGAGCTGAATGGCGTTCCCATCATAAAGG
GGGTGGACCTTGGCCCAGACGAGGTCTTCGTCGCCACTGACCGCGTGCAG
GTGACGAACCGGGCCCTCGTCCTCACGTCCACTTGCCTGGGCGGCGAGAG
TGCCTGCTCGCGGGCGCGCGTCAGCATCATGGCGGTCCAGATTGTGAAGA
CG

X12

(SEQ ID NO: 138)
AACGGTATGAATAAAGACAAAGACGCAGAGATTACTCCCCCTCCGTTCAT
CGTCTTGCCGGGTGGAAAAAAAATCCACATGCTGCAAAGCGAATACGAGT
ATGACGTTCTGCGGGATATGTACCGAACGGATGAGGCGAATGGGGGAAGT
GGTGAGAAGGAGAGTCACCCCTCTGGGGATGGTGCAATCAGAAGAAACGA
ATTTTTTAAACTTTTTTCACCACAGGGAGGGTCATTATAAGTTTGTTATC
AAAAATGTTCCCACCAAATTGAGCGACCTTTTGCAGAAAGGTGGCAACGA
ACAGGAGACAGACCTAVTTCCTCTTTTATACAGGAGTCTGCAATTCGCAT
GCAGCGCAGACGGGACGTGGCCATATGCCAGAAGAGAGGTGGCCTTTTTT
AAAAACGGGAGCGTCCACTGCGAAGCGGAATTTCAAAACGAGTTATCAGT
GAGGAGAACCCCCCGAAGTGGGAAGAAATCATTTGGACGTTTTCCAAGGG
GGACACTAATAAAAAGTAGCGACCTGAGGAGCAAAATTGTGGAGGGGAAT
TCTTATGATAAAAGGGCCGCACCCCTGAAGAGTGAAAAAAAAAGAAGGC
TCTCTTTTTACACCCAGAAAGTGTGCTATACAAAATGGAAGAAATATTTT
TTTATGAAAATCCAAGTGTCAAAAGTGAAATTGTCGCATTTTGTTCTTTT
TCATGATGTTGTCTCACAGTAACGTCCTTAGGACATGGAGCACATCCCGT
TAACTCCCCCTTTTTGGGAAGCGACCTGCTGGAGATGATATTTGGCTACT
GCATTTTACACGGGTTTAAAAAAATCAGAGTGAAAAGCGAATCCTTAAAT
TACGAAACTGGGATAAGGACCTCATTCATTGAGATTTTACTCAACGGAAA
AACAGCACTTGAACATTTAGGGTTAAGACTTACAAACGTAGCGAAGTTTT
CTAAAGAACTGTATTATGTAATCACTGGGTATACGTGGAAAAGTGATTTG
GTGCTATCACCCATAGTAAGGTTTGAACATGATTTATACGTGCATCACGA
CATAGAGGAGCGATTTTTCCTTTACGTGAATAAAATGTATAGGAATATGC
TCCACGATTTC1TCCTTCTCTTGTGATGAAAATTATTATCCTTATAAAAA
TTGTTATGACATCTACCCCTCCGTGAGAAGGAGTCAAAATAATCTTTGTC
TCTTCGAACTGAATCCCATATATGAAGAATTGAAGGAGCTCTTTCCAGAC

TCTTGTAATATTGGCCAACGCGTTAGAAAATGCTATGAGGAGATAAAAAA
AAACGTTGTCTGCACACATAACGGTGAAGGAGGAGAAGACGGATGTAAGT
ACTACCAATTTATTGTAAATACATTCATAAAGCCGAGGAGGAAAACGTCG
TTTTTTTVTTTTVTCACAATATGTATGTACAGGAATATCTTTCAAAGAAA
TCCTACCCCTATTACTTGCTACTCAGTGAGGTTATAAAAAATGAAGAAAA
TAACTTTCTCGAAAAAGGCAACTACGACTTAGTGGCCGATGCACAGACGC
ACCTCTTCTTAAATTACGTTTTGCAAAATTCTACCTTTTTTATCTTTTGG
AATTTCTCTACCGAATELTGGAAAAGGTTTCGGTACATCCAGGCTGGCCC
AACCGGGGCCACTTCCACACCGCAGAAGGGGCAAGCTGTGTTTTGCCCCA
TGGCCTATGCGTACGAATTTGTGGAGCACCTCGACACGTTTTATGTGAGG
GGG

V6

(SEQ ID NO: 139)
TCCGTTGAAGAGGCTAAAAAAAATACTCAGGAAGTTGTGACAAATGTGGA
CAATGCTGCTCTAAATCTTCAGGCCACCAATTCAAATCCGATAAGTCACT
CCTGTAGATAGTAGTAAAGCGGAGAAGGTTCCAGGAGATTCTACGCATGG
AAATGTTAACAGTGGCCAAGATAGTTCTACCACAGGTAAAGCTGTTACGG
GGGATGGTCAAAATGGAAATCAGACACCTGCAGAAAGCGATGTACAGCGA
AGTGATATTGCCGAAAGTGTAAGTGCTAAAAATGTTGATCCGCAGAAATC
TGTAAGTAAAAGAAGTGACGACACTGCAAGCGTTACAGGTATTGCCGAAG
CTGGAAAGGAAAACTTAGGCGCATCAAATAGTCGACCTTCTGAGTCCACC
GTTGAAGCAAATAGCCCAGGTGATGATACTGTGAACAGTGCATCTATACC
TGTAGTGAGTGGTGAAAACCCATTGGTAACCCCCTATAATGGTTTGAGGC
ATTCGAAAGACAATAGTGATAGCGATGGACCTGCGGAATCAATGGCGAAT
CCTGATTCAAATAGTAAAGGTGAGACGGGAAAGGGGCAAGATAATGATAT
GGCGAAGGCTACTAAAGATAGTAMAATAGTTCAGATGGTACCAGCTCTGC
TACGGGTGATACTACTGATGCAGTTGATAGGGAAATTAATAAAGGTGTTC
CTGAGGATAGGGATAAAACTGTAGGAAGTAAAGATGGAGGGGGGAAGAT
AACTCTGCAAATAAGGATGCAGCGACTGTAGTTGGTGAGGATAGAATTCG
TGAGAACAGCGCTGGTGGTAGCACTAATGATAGATCAAAAAATGACACGG
AAAAGAACGGGGCCTCTACCCCTGACAGTAAACAAAGTGAGGATGCAACT
GCGCTAAGTAAAACCGAAAGTTTAGAATCAACAGAAAGTGGAGATAGAAC
TACTAATGATACAACTAACAGTTTAGAAAATAAAAATGGAGGAAAAGAAA
AGGATTTACAAAAGCATGATTTTAAAAGTAATGATACGCCGAATGAAGAA
CCAAATTCTGATCAAACTACAGATGCAGAAGGACATGACAGGGATAGCAT
CAAAAATGATAAAGCAGAAAGGAGAAAGCATATGAATAAAGATACTTTTA
CGAAAAATACAAATAGTCACCATTTAAAT

V7

(SEQ ID NO: 140)
ATACGGAATGGAAACAACCCGCAGGCATTAGTTCCTGAAAAGGGCGCTGA
CCCGAGTGGGGCCAGAACAACCGCTCCGGAGAAAACCAAGACACGTGCG
AAATTCAAAAGATGGCCGAAGAAATGATGGAAAAAATGATGAAGGAAAAA

GACGTGTTTAGCTCCATCATGGAACCTCTCCAGAGCAAATTAACTGACGA
TCATCTGTGTTCAAAAATGAAATATACGAACATTTGTCTTCACGAAAAGG
ACAAAACTCCCTTGACCTTCCCCTGCACAAGTCCGCAGTACGAACAGCTA
ATTCATCGCTTCACTTATAAAAAGTTGTGCAACTCCAAGGTGGCCTTTAG
CAACGTCTTGCTCAAATCCTTCATCGATAAAAAAATGAAGAAAACACAT
TTAACACGATCATACAGAATTACAAAGTTCTGTCCACTTGCATTGACGAT
GATTTGAAGGACATTTATAATGCATCCATAGAGTTATTCTCCGACATAAG
AACCTCCCTTCACAGAAATTACCGAAAAGTTGTGGTCCAAAAATATGATC
GAAGTTTTAAAGACAAGAGAGCAAACATTGCAGGCATTTTATGTGAGTTA
AGAAATGGAAATAATTCTCCCCTAGTATCGAACAGTTTTTCCTATGAAAA
TTTTGGAATTCTCAAGGTTAATTATGAGGGATTACTAAACCAGGCGTATG
CGGCCTTTTCAGACTACTATTCATACTTTCCCGCTTTTGCCATTAGCATG
TTAGAAAAGGGAGGGTTGGTCGACCGCTTGGTCGCCATCCATGAGAGCTT
GACCAACTACAGGACGAGAAATATTCTCAAGAAGATCAATGAGAAGTCCA
AAAATGAGGTCCTCAATAATGAAGAAATTATGCACAGCTTGAGCAGTTAC
AAGCACCATGCCGGGGCACGCGTGGCGCCTTCCTGCAGTCCAGAGATGT
GCGCGAAGTTACGCAAGGAGATGTGAGCGTTGATGAGAAGGGCGACCGGG
CCACCACCGCGGGGGGCAACCAAAGCGCAAGCGTGGCTGCGGCGGCCCCG
AAGGATGCGGGCCCAACCGTGGCTGCTCCTAACACTGCTGCTACGCTCAA
AACGGCTGCTTCCCCAACGCGGCTGCTACTAACACTGCTGCTCCCCCCA
ACATGGGTGCCACCTCCCCGCTGAGCAACCCCCTGTACGGCACCAGCTCC
CTGCAGCCAAAGGACGTCGCGGTGCTGGTCAGAGATCTGCTCAAGAACAC
GAACATCATCAAGTTCGAGAATAACGAACCGACTAGCCAAATGGACGATG
AAGAAATTAAGAAGCTCATTGAGAGCTCCTTTTTCGACTTGAGCGACAAC
ACCATGTTAATGCGGTTGCTCATAAAGCCGCAGGCGGCCATCTTACTAAT
CATTGAGTCCTTCATTATGATGACGCCCTCCCCCACGAGGGACGCCAAGA
CCTATTGCAAGAAAGCCCTAGTTAATGGCCAGCTAATCGAAACCTCAGAT
TTAAACGCGGCGACGGAGGAAGACGACCTCATAAACGAGTTTTCCAGCAG
GTACAATTTATTCTACGAGAGGCTCAAGCTGGAGGAGTTG

V8
(SEQ ID NO: 141)
AAGGAGTACTGCGACCAGCTTAGCTTTTGCGATGTGGaTTGACACACCAC
TVTGATACGTAVTGTAAGAATGACCAGTACCTGTTCGTTCACTACACTTG
TGAGGACCTCTGCAAAACGTGTGGCCCTAATTCGTCCTGCTACGGAAACA
AGTACAAACATAAGTGCCTGTGCAATAGCCCCTTCGAGAGTAAAAAGAAC
CATTCCATTTGCGAAGCACGAGGTAGCTGCGATGCACAGGTATGCGGCAA
GAATCAAATTTGCAAAATGGTAGACGCTAAAGCAACATGCACATGTGCAG
ATAAATACCAAAATGTGAATGGGGTGTGTCTACCGGAAGATAAGTGCGAC
CTTCTGTGCCCCTCAAACAAATCGTGCCTGCTGGAAAATGGGAAAAAAAT
ATGCAAGTGCATTAATGGGTTGACTCTACAGAACGGCGAGTGCGTCTGCT
CGGATAGCAGCCAAATTGAAGAAGGACACCTCTGTGTCGCCCAAGAATAA
ATGTAAACGGAAGGAGTACCAACAGCTCTGCACCAATGAGAAGGAACACT
GTGTGTATGATGAGCAGACGGACATTGTGCGGTGCGACTGCGTGGACCAC
TTCAAGCGGAACGAACGGGGAATTTGCATCCCAGTCGACTACTGCAAAAA
TGTCACCTGCAAGGAAAATGAGATTTGCAAAGTTGTTAATAATACACCCA
CATGTGAGTGTAAAGAAAATTTAAAAAGAAATACTTAACAATGAATGTGT
ATTCAATAACATCTGTGTCTTGTTAATAAAGGGAACTGCCCCATTGATTC
GGAGTGCATTTATCACGAGAAAAAAGGCATCAGTGTTTGTGCCATAAGA
AGGGCCTCGTCGCCATTAATGGCAAGTGCGTCATGCAGGACATGTGCAGG
AGCGATCAGAACAAATGCTCCGAAAATTCCATTTGTGTAAATCAAGTGAA
TAAAGAACCGCTGTGCATATGTTTGTTTAATTATGTGAAGAGTCGGTCGG
GCGACTCGCCCGAGGGTGGACAGACGTGCGTGGTGGACAATCCCTGCCTC
GCGCACAACGGGGCTGCTCGCCAAACGAGGTTTGCACGTTCAAAAATGG
AAAGGTAAGTTGCGCCTGCGGGGAGAACTACCGCCCCAGGGGGAAGGACA
GCCCAACGGGACAAGCGGTCAAACGGGGGAAGCGACCAAACGGGGTGAC
GCGGGTCAGCCCGGGCAGGCGCACTCAGCAAATGAGAACGCGTGCCTGCC
CAAGACGTCCGAGGCGGACCAAACCTTCACCTTCCAGTACAACGACGACG
CGGCCATCATTCTCGGGTCCTGCGGAATTATACAGTTTGTGCAAAAGAGC
GATCAGGTCATTTGGAAAATTAACAGCAACAATCACTTTTACATTTTTAA
TTATGACTATCCATCTGAGGGTCAGCTGTCGGCACAAGTCGTGAACAAGC
AGGAGAGCAGCATTTTGTACTTAAAGAAAACCCACGCGGGGAAAGTCTTT
TACGCCGACTTTGAGTTGGGTCATCAGGGATGCTCCTACGGAAACATGTT
TCTCTACGCCCACCGGGAGGAGGCT

V9
(SEQ ID NO: 142)
AGCAAAAACATTATTATTCTGAACGATGAAATTACCACCATTAAAAGCCC
GATTCATTGCATTACCGATATTTATTTTCTGTTTCGCAACGAACTGTATA
AAACCTGCATTCAGCATGTGATTAAAGGCCGCACCGAAATTCATGTGCTG
GTGCAGAAAAAAATTAACAGCGCGTGGGAAACCCAGACCACCCTGTTTAA
AGATCATATGTGGTTTGAACTGCCGAGCGTGTTTAACTTTATTCATAACG
ATGAAATTATTATTGTGATTTGCCGCTATAAACAGCGCAGCAAACGCGAA
GGCACCATTTGCAAACGCTGGAACAGCGTGACCGGCACCATTTATCAGAA
AGAAGATGTGCAGATTGATAAAGAAGCCTTTTGCGAACAAAAACCTGGAA
AGCTATCAGAGCGTGCCGCTGACCGTGAAAAACAAAAAATTTCTGCTGAT
TTGCGGCATTCTGAGCTATGAATATAAAACCGCGAACAAAGATAACTTTA
TTAGCTGCGTGGCGAGCGAAGATAAAGGCCGCACCTGGGGCACCAAAATT
CTGATTAACTATGAAGAACTGCAGAAAGGCGTGCCGTATTTTTATCTGCG
CCCGATTATTTTTGGCGATGAATTTGGCTTTTATTTTTATAGCCGCATTA
GCACCAACAACACCGCGCGCGGCGGCAACTATATGACCTGCACCCTGGAT
GTGACCAACGAAGGCAAAAAGAATATAAATTTAAATGCAAACATTTGAG
CCTGATTAAACCGGATAAAGCCTGCAGAACGTGGCGAAACTGAACGGCT
ATTATATTACCAGCTATGTGAAAAAAGATAACTTTAACGAATGCTATCTG
TATTATACCGAACAGAACGCGArrGTGGTGAAACCGAAAGTGCAGAACGA

-continued

TGATCTGAACGGCTGCTATGGCGGCAGCTTTGTGAAACTGGATGAAAGCA

AAGCGCTGTTTATTTATAGCACCGGCTATGGCGTGCAGAACATTCATACC

CTGTATTATACCCGCTATGAT

TABLE 6 references associated with proteins

| Protein Code | 5' position to 3' (bp) | amino acid position | reference |
|---|---|---|---|
| X1 | (4-1845) | | Lu J Proteomics 2014 |
| X2 | (67-1161) | | Lu J Proteomics 2014 |
| X3 | (70-555) | | Lu J Proteomics 2014 |
| X4 | (4-948) | | Lu J Proteomics 2014 |
| X5 | (73-1659) | | Lu J Proteomics 2014 |
| X6 | (73-1074) | | Lu J Proteomics 2014 |
| X7 | (1384-2190) | | Lu J Proteomics 2014 |
| X8 | (559-2871) | | Lu J Proteomics 2014 |
| X9 | (4-660) | | Lu J Proteomics 2014 |
| X10 | (4-342) | | Lu J Proteomics 2014 |
| X11 | (1264-3261) | | Lu J Proteomics 2014 |
| X12 | (1957-3702) | | Lu J Proteomics 2014 |
| V1 | | 140 to 1275 | Hietanen 2015 Infection and Immunity PMID: 26712206 |
| V2 | | 160 to 1135 | Hietanen 2015 Infection and Immunity PMID: 26712206 |
| V3 | | 161 to 1454 | Hietanen 2015 Infection and Immunity PMID: 26712206 |
| V4 | | 501 to 1300 | Hietanen 2015 Infection and Immunity PMID: 26712206 |
| V12 | | 160 to 1170 | Hietanen 2015 Infection and Immunity PMID: 26712206 |
| V5 | | 161-641 | Franca 2017 Elife PMID: 28949293 |
| V11 | | Region II | Franca 2017 Elife PMID: 28949293 |
| V10 | | Region II | |
| V13 | | Region II | |
| V6 | (1522-2697) | | |
| V7 | (29-551) | | |
| V8 | (552-1075) | | |
| V9 | (30-366) | | |

APPENDIX IIIA

| | Area Under Curve (1 antigen) | | Top 1% of 2 antigen combis | | | Top 1% of 3 antigen combis | | | Top 1% of 4 antigen combis | | | (<9m GMT)/(12m GMT) | | | (<9m GMT)/(-ve control GMT) | | |
|---|---|---|---|---|---|---|---|---|---|---|---|---|---|---|---|---|---|
| | Thailand | Brazil | Solomons | Thailand | Brazil | Solomons | Thailand | Brazil | Solomons | Thailand | Brazil | Solomons | Thailand | Brazil | Solomons | Thailand | Brazil | Solomons |
| RBP2a | 0.849 | 0.818 | 0.868 | 100 | 100 | 100 | 95.3 | 96.2 | 100 | 89.7 | 98.5 | 100 | 10.85 | 8.53 | 11.84 | 31.33 | 26.31 | 13.91 |
| L01 | 0.812 | 0.787 | 0.697 | 5.9 | 5.9 | 0 | 21.1 | 13.5 | 2.3 | 43.5 | 23.9 | 4.3 | 7.41 | 4.49 | 4.09 | 10.73 | 17.26 | 2.1 |
| L31 | 0.805 | 0.762 | 0.766 | 0 | 0 | 0 | 2.6 | 2.6 | 2.3 | 5 | 2.7 | 3.7 | 3.9 | 3.05 | 2.56 | 8.62 | 12.32 | 5.1 |
| X087885 | 0.807 | 0.748 | 0.697 | 5.9 | 0 | 0 | 16.7 | 4.7 | 7 | 20.3 | 9.2 | 14.6 | 4.28 | 1.79 | 1.2 | 9.82 | 34.44 | 15.93 |
| PvEBP | 0.747 | 0.739 | 0.707 | 0 | 0 | 0 | 1.8 | 1.8 | 1.8 | 5 | 2.4 | 3.1 | 6.53 | 5.18 | 2.01 | 21.12 | 8.91 | 2.61 |
| L55 | 0.79 | 0.781 | 0.643 | 5.9 | 5.9 | 0 | 14.6 | 12.3 | 1.5 | 17.2 | 20.9 | 2.6 | 4.94 | 4.42 | 1.95 | 7.9 | 7.91 | 1.19 |
| PvRipr | 0.754 | 0.772 | 0.646 | 0 | 0 | 5.9 | 1.8 | 5.6 | 2 | 3 | 9.1 | 3.1 | 5.01 | 2.98 | 2.57 | 7.02 | 7.89 | 1.07 |
| L54 | 0.79 | 0.727 | 0.654 | 5.9 | 0 | 0 | 3.5 | 2.6 | 1.8 | 5.6 | 4.4 | 2.5 | 4.4 | 3.11 | 1.88 | 5.39 | 3.82 | 1.3 |
| L07 | 0.747 | 0.765 | 0.599 | 0 | 0 | 0 | 2.3 | 4.7 | 1.8 | 3.1 | 5.3 | 5.4 | 2.56 | 1.53 | 1.45 | 4.3 | 6.29 | 1.35 |
| L30 | 0.732 | 0.61 | 0.609 | 0 | 0 | 0 | 1.2 | 2.3 | 2.9 | 2.3 | 3.8 | 4 | 4.14 | 1.55 | 1.55 | 13.36 | 2.24 | 1.79 |
| PVDBPII | 0.74 | 0.773 | 0.639 | 0 | 0 | 5.9 | 0.6 | 3.2 | 3.2 | 1.7 | 2.6 | 2.2 | 2.76 | 4.89 | 1.79 | 5.14 | 15.42 | 1.34 |
| L34 | 0.767 | 0.746 | 0.67 | 5.9 | 5.9 | 0 | 3.8 | 7.3 | 0.6 | 4.5 | 16.6 | 5.6 | 3.22 | 2.99 | 1.84 | 3.87 | 4.78 | 1.46 |
| X092995 | 0.792 | 0.703 | 0.642 | 5.9 | 5.9 | 0 | 13.7 | 1.5 | 2 | 11.5 | 1.9 | 2.9 | 2.88 | 1.41 | 1.03 | 4.64 | 8.55 | 4.19 |
| L12 | 0.755 | 0.731 | 0.637 | 5.9 | 0 | 5.9 | 3.2 | 3.8 | 1.8 | 3.5 | 6.1 | 2.5 | 3.19 | 2.73 | 1.46 | 3.81 | 3.47 | 1.8 |
| rBP1b | 0.533 | 0.578 | 0.525 | 5.9 | 5.9 | 0 | 17.5 | 4.1 | 1.2 | 24.1 | 4.7 | 2.9 | 1.23 | 1.44 | 1.11 | 0.67 | 0.79 | 0.84 |
| L23 | 0.759 | 0.753 | 0.658 | 0 | 0 | 0 | 1.5 | 7 | 1.2 | 4 | 14.8 | 2.9 | 2.95 | 2.67 | 1.86 | 4.3 | 5.09 | 1.59 |
| L02 | 0.746 | 0.724 | 0.677 | 0 | 0 | 0 | 1.5 | 2.3 | 2.3 | 2.7 | 3.7 | 3.9 | 3.7 | 3 | 1.76 | 3.89 | 4.07 | 1.82 |
| L32 | 0.705 | 0.651 | 0.493 | 0 | 0 | 5.9 | 1.8 | 1.2 | 17 | 3.7 | 1.9 | 30.2 | 2.79 | 2.44 | 1.61 | 2.24 | 0.81 | 0.31 |
| L28 | 0.759 | 0.755 | 0.667 | 0 | 0 | 0 | 2.6 | 1.2 | 1.2 | 3.8 | 2.5 | 6.5 | 2.92 | 2.44 | 1.43 | 5.74 | 5.24 | 2.14 |
| L19 | 0.758 | 0.67 | 0.654 | 5.9 | 5.9 | 0 | 1.5 | 0.9 | 3.2 | 2.6 | 2.3 | 2.8 | 3.66 | 2.18 | 1.09 | 6.58 | 3.11 | 4.89 |
| L36 | 0.727 | 0.698 | 0.682 | 0 | 0 | 0 | 1.5 | 0.9 | 2 | 3.2 | 1.8 | 3.8 | 2.95 | 2.44 | 1.99 | 3.28 | 3.2 | 1.8 |
| L41 | 0.702 | 0.66 | 0.686 | 0 | 0 | 0 | 1.5 | 0.6 | 2 | 2.3 | 1.7 | 6.7 | 2.12 | 1.91 | 1.72 | 4.99 | 3.03 | 1.9 |
| X088820 | 0.723 | 0.666 | 0.633 | 5.9 | 0 | 0 | 4.4 | 0.6 | 3.8 | 4 | 1.8 | 7.2 | 1.9 | 1.28 | 0.99 | 4.04 | 8.58 | 5.87 |
| PvDBP.Sa | 0.716 | 0.751 | 0.616 | 0 | 5.9 | 0 | 0.3 | 2.6 | 8.8 | 3.7 | 2.6 | 1.6 | 3.01 | 4.78 | 1.85 | 3.96 | 12.35 | 0.83 |
| RBP2a | 0.692 | 0.731 | 0.662 | 0 | 0 | 0 | 3.5 | 1.2 | 0.9 | 5.4 | 1.8 | 3.8 | 2.42 | 2.49 | 1.47 | 2.46 | 4.6 | 1.5 |
| L18 | 0.736 | 0.663 | 0.622 | 0 | 0 | 5.9 | 2.3 | 2 | 2.3 | 3.1 | 4.5 | 6.6 | 2.22 | 1.41 | 0.93 | 2.53 | 2.33 | 4.31 |
| RBP2cNB | 0.744 | 0.7 | 0.551 | 5.9 | 0 | 0 | 1.5 | 1.2 | 11.1 | 3.6 | 1.9 | 10.3 | 3.02 | 2.3 | 1.57 | 3.87 | 3.23 | 0.64 |
| L27 | 0.735 | 0.663 | 0.585 | 0 | 5.9 | 0 | 2.9 | 1.5 | 2 | 4.5 | 2.4 | 2.3 | 2.34 | 2.24 | 1.66 | 1.67 | 1.2 | 0.63 |
| L42 | 0.697 | 0.632 | 0.593 | 0 | 0 | 5.9 | 1.5 | 0.9 | 1.5 | 2.9 | 1.8 | 2.8 | 2.81 | 1.91 | 1.85 | 4.44 | 2.89 | 1.19 |
| L14 | 0.701 | 0.637 | 0.581 | 0 | 0 | 0 | 3.5 | 1.2 | 1.5 | 4.1 | 2 | 3.1 | 1.94 | 1.51 | 1.33 | 2.85 | 2.23 | 1.07 |
| X099930 | 0.71 | 0.63 | 0.573 | 0 | 0 | 0 | 3.8 | 0.9 | 1.5 | 4.1 | 1.7 | 2.5 | 1.75 | 1.27 | 0.94 | 2.85 | 3.15 | 2.07 |
| PvDBP.R3 | 0.685 | 0.67 | 0.554 | 5.9 | 5.9 | 5.9 | 2 | 4.1 | 2.6 | 3 | 3 | 2.7 | 2.51 | 2.19 | 1.73 | 2.57 | 3.11 | 0.51 |
| L22 | 0.725 | 0.622 | 0.562 | 0 | 0 | 0 | 2.3 | 4.1 | 1.5 | 5.6 | 5.6 | 2.4 | 1.98 | 1.25 | 0.99 | 2.28 | 2.13 | 1.3 |
| RBP1a | 0.668 | 0.669 | 0.565 | 5.9 | 0 | 0 | 0 | 1.5 | 0.9 | 1.2 | 2.7 | 1.9 | 2.4 | 2.32 | 2.49 | 1.45 | 2.06 | 2.59 |
| PvCYRPA | 0.779 | 0.563 | 0.532 | 0 | 0 | 5.9 | 0.6 | 0.9 | 14 | 2 | 1.9 | 10.3 | 2.37 | 1.25 | 1.46 | 4.55 | 1.59 | 0.31 |
| L10 | 0.719 | 0.588 | 0.553 | 0 | 5.9 | 0 | 1.2 | 6.1 | 1.2 | 2.4 | 9.3 | 2.3 | 2.14 | 1.31 | 1.04 | 3.61 | 1.39 | 1.43 |
| L24 | 0.656 | 0.595 | 0.605 | 0 | 0 | 0 | 5.3 | 2.9 | 1.2 | 5.5 | 5.6 | 2.8 | 2.01 | 1.33 | 0.88 | 1.75 | 1.71 | 5.03 |
| L21 | 0.653 | 0.597 | 0.602 | 0 | 5.9 | 0 | 1.5 | 1.8 | 1.8 | 3 | 2.6 | 4.1 | 2 | 1.55 | 0.93 | 1.47 | 1.35 | 3.08 |
| L51 | 0.679 | 0.625 | 0.547 | 5.9 | 0 | 5.9 | 4.1 | 2.5 | 3.5 | 6.2 | 3.7 | 5.4 | 1.85 | 1.48 | 1.31 | 2.04 | 1.74 | 0.89 |
| L25 | 0.67 | 0.593 | 0.58 | 0 | 0 | 0 | 0.9 | 1.2 | 0.9 | 2.1 | 6 | 2.8 | 1.61 | 1.14 | 0.96 | 1.63 | 1.76 | 2.05 |
| L33 | 0.65 | 0.608 | 0.584 | 0 | 0 | 0 | 1.8 | 1.2 | 0.9 | 3.7 | 3.1 | 1.6 | 1.83 | 1.43 | 1.37 | 2.2 | 1.82 | 1.05 |
| L20 | 0.674 | 0.619 | 0.544 | 0 | 0 | 0 | 1.2 | 1.2 | 1.5 | 2.7 | 2.1 | 2.9 | 1.71 | 1.31 | 1.23 | 2.35 | 2.08 | 0.82 |
| X114330 | 0.666 | 0.594 | 0.577 | 0 | 0 | 0 | 1.5 | 6.4 | 11.1 | 2.2 | 2.6 | 3 | 1.44 | 1.15 | 1.03 | 2.53 | 2.2 | 1.78 |
| L50 | 0.713 | 0.604 | 0.494 | 0 | 5.9 | 5.9 | 1.2 | 1.8 | 1.2 | 2.9 | 8.6 | 7.3 | 2.15 | 1.55 | 1.4 | 2.23 | 1.34 | 0.45 |
| L06 | 0.686 | 0.583 | 0.54 | 0 | 0 | 0 | 1.5 | 2.3 | 2 | 2.5 | 3.1 | 2.3 | 1.91 | 1.33 | 0.92 | 1.91 | 1.41 | 1.57 |
| L05 | 0.686 | 0.607 | 0.499 | 0 | 5.9 | 0 | 2 | 1.2 | 1.2 | 3.9 | 4.7 | 3.4 | 2.23 | 1.44 | 1.03 | 2.1 | 1.9 | 0.72 |
| X080665 | 0.678 | 0.595 | 0.522 | 0 | 0 | 0 | 1.5 | 3.8 | 1.2 | 2.1 | 6.2 | 3.6 | 1.8 | 1.25 | 0.9 | 2.64 | 1.8 | 1.21 |

APPENDIX IIIA-continued

| | Area Under Curve (1 antigen) | | | Top 1% of 2 antigen combis | | | Top 1% of 3 antigen combis | | | Top 1% of 4 antigen combis | | | (<9m GMT)/(12m GMT) | | | (<9m GMT)/(-ve control GMT) | | |
|---|---|---|---|---|---|---|---|---|---|---|---|---|---|---|---|---|---|---|
| | Thailand | Brazil | Solomons | Thailand | Brazil | Solomons | Thailand | Brazil | Solomons | Thailand | Brazil | Solomons | Thailand | Brazil | Solomons | Thailand | Brazil | Solomons |
| L39 | 0.673 | 0.56 | 0.537 | 5.9 | 0 | 0 | 4.1 | 1.2 | 1.5 | 4 | 2.4 | 2.8 | 1.64 | 1.12 | 0.96 | 2.96 | 1.57 | 1.5 |
| X094350 | 0.641 | 0.602 | 0.516 | 0 | 0 | 0 | 1.5 | 2 | 1.8 | 2.7 | 3.2 | 4.2 | 1.47 | 1.3 | 0.96 | 1.79 | 1.7 | 1.15 |
| L11 | 0.652 | 0.594 | 0.49 | 0 | 5.9 | 5.9 | 3.8 | 4.4 | 5 | 5.3 | 7.7 | 10.7 | 1.58 | 1.2 | 0.96 | 1.67 | 1.29 | 0.92 |
| L38 | 0.64 | 0.543 | 0.552 | 0 | 5.9 | 0 | 1.2 | 5.3 | 1.5 | 3 | 6.3 | 2.6 | 1.59 | 1.6 | 1.19 | 1.18 | 1 | 0.89 |
| L37 | 0.628 | 0.608 | 0.487 | 0 | 5.9 | 5.9 | 2.6 | 2 | 3.2 | 5.1 | 3.7 | 4.9 | 1.54 | 1.49 | 1.15 | 1.17 | 0.92 | 0.73 |
| PvGAMA | 0.646 | 0.57 | 0.495 | 0 | 0 | 5.9 | 2.3 | 1.2 | 6.7 | 5.3 | 2.5 | 6.5 | 1.64 | 1.08 | 1.32 | 1.45 | 0.74 | 0.53 |
| L49 | 0.577 | 0.532 | 0.6 | 0 | 5.9 | 5.9 | 1.8 | 19.6 | 8.2 | 2.5 | 11.9 | 13.6 | 1.26 | 1.29 | 0.89 | 1.24 | 0.4 | 0.34 |
| L47 | 0.641 | 0.513 | 0.539 | 0 | 5.9 | 5.9 | 0.9 | 5.8 | 4.7 | 1.9 | 6.8 | 4.8 | 1.52 | 1.23 | 1.21 | 1.73 | 0.51 | 0.38 |
| L48 | 0.552 | 0.586 | 0.523 | 5.9 | 0 | 0 | 2.9 | 1.2 | 1.2 | 4.8 | 2.4 | 2.7 | 1.16 | 1.34 | 0.98 | 1.3 | 1.56 | 1.23 |
| RBP2.P2 | 0.596 | 0.544 | 0.515 | 5.9 | 5.9 | 5.9 | 5 | 14.6 | 17 | 6.5 | 8.9 | 24.9 | 1.48 | 1.14 | 1.16 | 0.94 | 0.66 | 0.46 |
| L03 | 0.579 | 0.503 | 0.566 | 5.9 | 5.9 | 0 | 2.6 | 2.3 | 2 | 3.8 | 4.1 | 4.4 | 1.59 | 1.4 | 0.93 | 0.82 | 0.8 | 0.51 |
| L52 | 0.526 | 0.562 | 0.524 | 5.9 | 5.9 | 5.9 | 4.4 | 4.7 | 4.1 | 4.9 | 4.8 | 6.3 | 1.29 | 1.01 | 1.07 | 0.56 | 0.6 | 0.58 |
| L40 | 0.564 | 0.55 | 0.495 | 0 | 0 | 0 | 1.8 | 1.5 | 1.2 | 3.3 | 2.7 | 3.2 | 1.23 | 1.01 | 0.91 | 1.08 | 1.79 | 1.09 |

APPENDIX IIIB

| | (<9m) > (>12m GMT + 2*ds(>12m)) | | | (<9m) > (-ve cont GMT + 2*sd(-ve cont)) | | | age trend | | | age trend (P value) | | |
|---|---|---|---|---|---|---|---|---|---|---|---|---|
| | Thailand | Brazil | Solomons | Thailand | Brazil | Solomons | Thailand | Brazil | Solomons | Thailand | Brazil | Solomons |
| RBP2a | 34.7 | 19 | 47 | 70.8 | 64.4 | 45.7 | 1.02 | 0.63 | 1.06 | 0 | 0 | 0 |
| L01 | 36.1 | 0 | 24.3 | 51.4 | 56.6 | 14.3 | 0.39 | 0.52 | 0.24 | 0 | 0 | 0.0043 |
| L31 | 22.2 | 0 | 7.8 | 25 | 38 | 7.4 | 0.41 | 0.34 | 0.23 | 0 | 0 | 3.00E-04 |
| X087885 | 15.3 | 7.8 | 5.7 | 41.7 | 81 | 50.9 | 0.53 | 0.13 | -0.1 | 0 | 2.00E-04 | 0.0466 |
| PvEBP | 26.4 | 22.9 | 20 | 55.3 | 41 | 7.8 | 1.08 | 0.59 | 0.21 | 0 | 0 | 0 |
| L55 | 27.8 | 17.1 | 13.9 | 38.9 | 29.8 | 3.5 | 0.48 | 0.46 | 0.44 | 0 | 0 | 0 |
| PvRipr | 25 | 15.1 | 23.5 | 31.9 | 29.3 | 4.8 | 0.55 | 0.42 | 0.2 | 0 | 0 | 0.0013 |
| L54 | 23.6 | 16.1 | 14.3 | 26.4 | 19 | 2.2 | 0.48 | 0.33 | 0.24 | 0 | 0 | 0 |
| L07 | 22.2 | 0 | 8.3 | 27.8 | 41.5 | 3.9 | 0.22 | 0.34 | 0.19 | 0 | 0 | 4.00E-04 |
| L30 | 23.6 | 9.8 | 10.9 | 47.2 | 11.7 | 9.6 | 0.85 | 0.16 | 0.05 | 0 | 2.00E-04 | 0.4217 |
| PVDBPII | 15.3 | 19 | 10.4 | 20.8 | 47.3 | 3.5 | 0.4 | 0.63 | 0.1 | 0 | 0 | 0.076 |
| L34 | 15.3 | 12.2 | 10.9 | 12.5 | 19 | 3.9 | 0.35 | 0.35 | 0.18 | 0 | 0 | 2.00E-04 |
| X092995 | 12.5 | 3.4 | 1.7 | 15.3 | 34.1 | 10 | 0.33 | 0.09 | -0.03 | 0 | 0.0034 | 0.4924 |
| L12 | 23.6 | 12.7 | 5.2 | 16.7 | 15.1 | 3 | 0.36 | 0.22 | -0.07 | 0 | 0 | 0.1928 |
| rBP1b | 2.8 | 4.4 | 4.3 | 0 | 0 | 0 | -0.12 | 0.12 | -0.06 | 0.001 | 1.00E-04 | 0.1077 |
| L23 | 9.7 | 13.7 | 11.7 | 12.5 | 19.5 | 5.7 | 0.29 | 0.22 | 0.1 | 0 | 0 | 0.0824 |
| L02 | 15.3 | 10.7 | 7.4 | 15.3 | 13.7 | 2.6 | 0.31 | 0.4 | 0.02 | 0 | 0 | 0.6554 |
| L32 | 13.9 | 20.5 | 10 | 4.2 | 3.9 | 0.4 | 0.15 | 0.31 | 0.25 | 0.0016 | 0 | 1.00E-04 |
| L28 | 18.1 | 12.7 | 8.3 | 45.8 | 33.2 | 9.1 | 0.46 | 0.32 | 0.26 | 0 | 0 | 0 |
| L19 | 20.8 | 9.8 | 3.9 | 33.3 | 19.5 | 10.9 | 0.62 | 0.31 | -0.14 | 0 | 0 | 0.0036 |
| L36 | 18.1 | 14.6 | 11.3 | 36.1 | 22 | 10.4 | 0.63 | 0.36 | 0.3 | 0 | 0 | 0 |
| L41 | 9.7 | 9.3 | 7.8 | 29.2 | 17.6 | 8.3 | 0.39 | 0.41 | 0.32 | 0 | 0 | 0 |
| X088820 | 12.5 | 0 | 0 | 15.3 | 35.6 | 14.8 | 0.17 | 0.07 | -0.02 | 0 | 0.0032 | 0.5905 |
| PvDBP.Sa | 18.1 | 16.6 | 11.3 | 16.7 | 36.6 | 1.3 | 0.39 | 0.61 | 0.18 | 0 | 0 | 0.0016 |
| RBP2a | 18.1 | 13.2 | 9.1 | 18.1 | 22.4 | 3.5 | 0.3 | 0.34 | 0.1 | 0 | 0 | 0.0144 |
| L18 | 15.3 | 3.4 | 4.3 | 11.1 | 6.3 | 10.4 | 0.11 | 0.08 | -0.17 | 0.0022 | 0.0106 | 1.00E-04 |
| RBP2cNB | 23.6 | 16.6 | 10 | 18.1 | 17.6 | 1.7 | 0.43 | 0.35 | 0.44 | 0 | 0 | 0 |
| L27 | 15.3 | 13.2 | 10 | 0 | 0 | 0 | 0.1 | 0.3 | 0.15 | 0.0021 | 0 | 3.00E-04 |
| L42 | 16.7 | 12.7 | 16.1 | 29.2 | 20 | 7 | 0.5 | 0.3 | 0.27 | 0 | 0 | 0 |
| L14 | 12.5 | 3.9 | 5.2 | 9.7 | 5.9 | 1.3 | 0.05 | 0.18 | 0.02 | 0.1401 | 0 | 0.6094 |
| X099930 | 5.6 | 6.8 | 1.7 | 8.3 | 17.6 | 6.1 | 0.06 | 0.02 | -0.06 | 0.0734 | 0.4923 | 0.1513 |
| PvDBP.R3 | 13.9 | 9.8 | 8.7 | 13.9 | 11.2 | 0.9 | 0.36 | 0.33 | 0.16 | 0 | 0 | 0.0047 |
| L22 | 9.7 | 3.4 | 3 | 4.2 | 5.9 | 2.6 | 0.11 | 0.16 | -0.08 | 0.0012 | 0 | 0.0611 |
| RBP1a | 18.1 | 16.1 | 10.4 | 8.3 | 18 | 1.3 | 0.36 | 0.44 | 0.12 | 0 | 0 | 0.0239 |
| PvCYRPA | 16.7 | 0 | 4.8 | 29.2 | 11.7 | 0 | 0.43 | -0.02 | 0.15 | 0 | 0.6208 | 0.0046 |
| L10 | 8.3 | 4.4 | 3 | 12.5 | 4.4 | 1.3 | 0.47 | 0.16 | -0.17 | 0 | 0 | 3.00E-04 |
| L24 | 9.7 | 6.8 | 3.9 | 4.2 | 7.3 | 7 | 0.12 | 0.14 | -0.21 | 0.0069 | 3.00E-04 | 0 |
| L21 | 8.3 | 6.3 | 3.5 | 2.8 | 6.3 | 6.1 | 0.04 | 0.13 | -0.19 | 0.3593 | 4.00E-04 | 0 |
| L51 | 4.2 | 3.9 | 4.8 | 2.8 | 3.9 | 2.6 | 0.25 | 0.22 | 0.31 | 0 | 0 | 0 |
| L25 | 11.1 | 2.4 | 0.9 | 6.9 | 4.9 | 3.9 | 0.04 | 0.04 | -0.15 | 0.3008 | 0.232 | 0.0025 |
| L33 | 11.1 | 4.9 | 5.2 | 6.9 | 5.9 | 0.9 | 0.21 | 0.22 | 0.24 | 0 | 0 | 0 |
| L20 | 9.7 | 0 | 4.3 | 0 | 0 | 0 | 0.01 | 0.11 | 0.02 | 0.7715 | 1.00E-04 | 0.7011 |
| X114330 | 5.6 | 5.9 | 3 | 8.3 | 10.7 | 4.3 | 0.11 | 0.05 | -0.09 | 4.00E-04 | 0.103 | 0.054 |
| L50 | 11.1 | 5.4 | 6.5 | 5.6 | 4.4 | 0.9 | 0.13 | 0.27 | 0.2 | 6.00E-04 | 0 | 0 |
| L06 | 6.9 | 4.4 | 1.7 | 2.8 | 3.4 | 0.4 | -0.03 | 0.01 | -0.35 | 0.4684 | 0.6901 | 0 |
| L05 | 12.5 | 8.8 | 3.5 | 5.6 | 9.8 | 0.4 | 0.13 | 0.15 | -0.11 | 0.0018 | 1.00E-04 | 0.0232 |
| X080665 | 4.2 | 4.4 | 1.3 | 2.8 | 4.4 | 0.4 | 0.14 | 0.08 | -0.09 | 7.00E-04 | 0.0263 | 0.0757 |
| L39 | 6.9 | 3.9 | 3.5 | 6.9 | 4.4 | 3.5 | 0.04 | 0.07 | -0.15 | 0.2562 | 0.053 | 0.0064 |
| X094350 | 2.8 | 0 | 1.3 | 0 | 0 | 0 | 0.01 | 0.12 | 0.11 | 0.7336 | 0 | 0.0116 |
| L11 | 6.9 | 3.4 | 2.6 | 1.4 | 2.4 | 0 | 0.16 | 0.1 | -0.1 | 0 | 0.0027 | 0.0126 |
| L38 | 6.9 | 3.4 | 3.9 | 0 | 0 | 0 | -0.03 | 0.1 | 0.06 | 0.465 | 0.0011 | 0.0898 |
| L37 | 2.8 | 4.9 | 3.9 | 0 | 2.4 | 1.3 | -0.03 | 0.16 | 0.05 | 0.3436 | 0 | 0.2103 |
| PvGAMA | 9.7 | 6.8 | 9.1 | 6.9 | 2.9 | 0.9 | 0.19 | 0.14 | 0.05 | 0 | 0 | 0.1987 |
| L49 | 9.7 | 3.9 | 3 | 0 | 0 | 0 | -0.09 | 0 | -0.21 | 0.0088 | 0.9079 | 2.00E-04 |
| L47 | 12.5 | 4.4 | 5.2 | 5.6 | 1 | 0 | 0.02 | 0.15 | -0.06 | 0.5816 | 0 | 0.3004 |
| L48 | 0 | 0 | 3.5 | 0 | 0 | 0 | -0.08 | 0 | -0.14 | 0.0173 | 0.9939 | 0.0011 |
| RBP2.P2 | 5.6 | 4.9 | 4.3 | 0 | 0 | 0 | -0.01 | 0.13 | -0.02 | 0.7196 | 0 | 0.5467 |
| L03 | 2.8 | 0 | 3 | 1.4 | 4.4 | 0.4 | -0.03 | 0.03 | -0.16 | 0.4053 | 0.3609 | 2.00E-04 |
| L52 | 1.4 | 5.9 | 3 | 0 | 0.5 | 0 | -0.15 | 0.15 | 0.01 | 2.00E-04 | 0 | 0.8287 |
| L40 | 9.7 | 0 | 0 | 0 | 0 | 0 | -0.09 | 0.04 | -0.15 | 0.0058 | 0.1846 | 0.0018 |

Any and all references to publications or other documents, including but not limited to, patents, patent applications, articles, webpages, books, etc., presented in the present application, are herein incorporated by reference in their entirety.

Example embodiments of the devices, systems and methods have been described herein. As noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, systems and apparatuses which may further include any and all elements from any other disclosed methods, systems, and apparatuses, including any and all elements corresponding to target particle separation, focusing/concentration. In other words, elements from one or another disclosed embodiments may be interchangeable with elements from other disclosed embodiments. In addition, one or more features/elements of disclosed embodiments may be removed and still result in patentable subject matter (and thus, resulting in yet more embodiments of the subject disclosure). Correspondingly, some embodiments of the present disclosure may be patentably distinct from one and/or another reference by specifically lacking one or more elements/features. In other words, claims to certain embodiments may contain negative limitation to specifically exclude one or more elements/features resulting in embodiments which are patentably distinct from the prior art which include such features/elements.

What is claimed is:

1. A diagnostic test for *Plasmodium vivax* or *Plasmodium ovale*, to determine a likelihood of a specific timing of infection by *P. vivax* or *P. ovale* in a subject by determining a level of antibodies to a plurality of antigens in a blood sample from the subject, wherein the level is measured of antibody to protein selected from at least one of RBP2b (P25) (PVX_094255) (SEQ ID NO:61) or PVX_099980 (L01) (SEQ ID NO:1) and of at least one antibody to a protein selected from the group consisting of PVX_112670 (SEQ ID NO:23), PVX_087885 (SEQ ID NO:45), PVX_096995 (SEQ ID NO:3), PVX_097625 (SEQ ID NO:67) and PVX_000930 (SEQ ID NO:109), wherein the level of antibody is correlated with the time since infection.

2. The test of claim 1, the level is measured of antibody to protein RBP2b (P25) (PVX_094255) (SEQ ID NO:61) and PVX_099980 (L01) (SEQ ID NO:1) and of antibody to at least one protein selected from the group consisting of
PVX_112670 (SEQ ID NO:23), PVX_087885 (SEQ ID NO:45), PVX_096995 (SEQ ID NO:3), PVX_097625 (SEQ ID NO:67), PVX_000930 (SEQ ID NO:109), PVX_084720 (SEQ ID NO:35) and PVX_003770 (SEQ ID NO:37).

3. The test of claim 2, wherein the level is measured of antibody to protein RBP2b (P25) (PVX_094255) (SEQ ID NO:61) and PVX_099980 (L01) (SEQ ID NO:1) and of antibody to at least two proteins selected from the group consisting of PVX_112670 (SEQ ID NO:23), PVX_087885 (SEQ ID NO:45), PVX_096995 (SEQ ID NO:3), PVX_097625 (SEQ ID NO:67), PVX_000930 (SEQ ID NO:109), PVX_084720 (SEQ ID NO:35) and PVX_003770 (SEQ ID NO:37).

4. The test of claim 1, wherein a model of the decay of antibody titers over time is used to determine the time since last infection.

5. The test of claim 4, comprising determining a level of 2 to 8 antibodies.

6. The test of claim 1, wherein the level of antibodies is measured at a plurality of time points.

7. The test of claim 1, wherein antibody levels are measured in the subject and time since infection is estimated continuously, wherein antibody level is compared with a titration curve to provide an estimate of antibody titer.

8. The test of claim 7, wherein antibody levels are measured according to a method selected from the group consisting of bead-based assays, the enzyme linked immuosorbent assay (ELISA), protein microarrays and the luminescence immunoprecipitation system (LIPS).

9. A method for diagnosis of *P. vivax*, comprising performing the diagnostic test of claim 1, wherein the level of antibody and the timing of infection identifies individuals with a high probability of being infected with liver-stage hypnozoites.

10. The test of claim 1, wherein said specific timing identifies whether and when to an infection occurred within an elapsed time period of 0 to 12 months.

11. The test of claim 10, wherein said time period is differentiated by month, by week, or by day.

12. The test of claim 10, wherein a particular time period is determined as a binary decision of a more recent or an older infection, with each time point as a cut-off.

13. The test of claim 12, wherein said cut off determines whether an infection in a subject was within the past 9 months or later than the past 9 months.

14. The test of claim 1, comprising further determining an estimate of the time since last *P. vivax* blood-stage infection according to the time since last PCR-detectable blood-stage parasitemia, or as the time since last infective mosquito bite.

15. The test of claim 14 comprising determining a frequency of infections during a particular time period and/or time since last infection.

16. The test of claim 1 for detecting an asymptomatic infection by *P. vivax*.

17. The test of claim 1 for detecting a dormant infection, wherein the level of antibody indicates *P. vivax* is present in the liver but is not present at significant levels in the blood.

18. The test of claim 1 for detecting antibodies to malarial proteins that are present in the blood wherein the level of antibody and the timing of infection indicate a high degree of probability of liver-stage infection.

19. The test of claim 1 wherein the level of antibody and the timing of infection provides for determining progression of infection by *P. vivax* in a population of a plurality of subjects.

20. The test of claim 1 wherein the level of antibody and the timing of infection provides for determining whether the infection is starting or whether the infection has reached a peak in terms of exposure of individuals who are naïve to the particular strain of *P. vivax* causing the infection.

21. The test of claim 1 for measuring antibodies in the blood of the subject at a plurality of time points to determine decay in the level of each antibody in the blood; and fitting such decay to a suitable model to determine at least one infection parameter selected from probability of liver-stage infection, determination of the progression of infection, and rate of propagation of the *Plasmodium* species in a population.

22. The test of claim 21, wherein decay in the level of a plurality of different antibodies is determined and the different antibodies are selected to have a range of different half-lives.

23. The test of claim 21, wherein from two up to twenty different antibodies are measured.

24. The test of claim 1, wherein a model for determining at least one parameter about the infection in the subject is selected from the group consisting of linear discriminant analysis (LDA), quadratic discriminant analysis (QDA), combined antibody dynamics (CAD), decision trees, random forests, boosted trees and modified decision trees.

25. The test of claim 1, wherein the level is measured of a plurality of antibodies that bind to proteins from the group consisting of PVX_099980 (L01) (SEQ ID NO:1), PVX_112670 (SEQ ID NO:23), PVX_087885 (SEQ ID NO:45), PVX_096995 (SEQ ID NO:3), RMP2b (PVX_094255) (SEQ ID NO:61), PVX_097625 (SEQ ID NO:67), PVX_000930 (SEQ ID NO:109), PVX_084720 (SEQ ID NO:35) and PVX_003770 (SEQ ID NO:37).

* * * * *

SEQUENCE LISTING

<160> NUMBER OF SEQ ID NOS: 142

<210> SEQ ID NO 1
<211> LENGTH: 115
<212> TYPE: PRT
<213> ORGANISM: Plasmodium vivax

<400> SEQUENCE: 1

Met Asn Glu Ser Lys Glu Ile Leu Ser Gln Leu Leu Asn Val Gln Thr
1               5                   10                  15

Gln Leu Leu Thr Met Ser Ser Glu His Thr Cys Ile Asp Thr Asn Val
            20                  25                  30

Pro Asp Asn Ala Ala Cys Tyr Arg Tyr Leu Asp Gly Thr Glu Glu Trp
        35                  40                  45

Arg Cys Leu Leu Thr Phe Lys Glu Glu Gly Gly Lys Cys Val Pro Ala
    50                  55                  60

Ser Asn Val Thr Cys Lys Asp Asn Asn Gly Gly Cys Ala Pro Glu Ala
65                  70                  75                  80

Glu Cys Lys Met Thr Asp Ser Asn Lys Ile Val Cys Lys Cys Thr Lys
                85                  90                  95

Glu Gly Ser Glu Pro Leu Phe Glu Gly Val Phe Cys Ser His His His
            100                 105                 110

His His His
        115

<210> SEQ ID NO 2
<211> LENGTH: 348
<212> TYPE: DNA
<213> ORGANISM: Plasmodium vivax

<400> SEQUENCE: 2
atgaacgagt ccaaggagat cctcagccaa ctcctgaacg tgcaaaccca gctcctgacc      60
atgtccagcg agcacacctg catcgacacc aacgtcccag acaacgccgc ctgctacagg     120
tacctggacg gcaccgagga gtggcgctgc ctcctgacct tcaaggaaga gggcggcaag     180
tgcgtgccag cctccaacgt cacctgcaag gacaacaacg gcggctgcgc tccagaggct     240
gagtgcaaga tgaccgacag caacaagatc gtgtgcaagt gcaccaagga aggctccgag     300
ccactcttcg agggcgtctt ctgcagccac caccaccacc accactga                  348

<210> SEQ ID NO 3
<211> LENGTH: 427
<212> TYPE: PRT
<213> ORGANISM: Plasmodium vivax

<400> SEQUENCE: 3

Met Lys Thr Glu Thr Val Thr Ser Arg Ser Asn Pro His Gln Ala Ile
1               5                   10                  15

Glu Tyr Ala Asn Gln Gly Pro Ser Arg Asp Lys Val Glu Glu Trp Lys
            20                  25                  30

Arg Asn Ala Trp Thr Asp Trp Met Val Gln Leu Asp Asp Asp Trp Lys
        35                  40                  45

Asp Phe Asn Ala Gln Ile Glu Glu Lys Lys Ala Trp Ile Glu Glu
 50                  55                  60

Lys Glu Gly Asp Trp Val Ile Leu Leu Lys His Leu Gln Asn Lys Trp
 65                  70                  75                  80

Leu His Phe Asn Pro Asn Leu Asp Ala Glu Tyr Gln Thr Asp Met Leu
                 85                  90                  95

Ala Lys Ser Glu Thr Trp Asp Glu Arg Gln Trp Lys Met Trp Ile Ser
            100                 105                 110

Thr Glu Gly Lys Gln Leu Leu Glu Met Asp Leu Lys Lys Trp Phe Thr
        115                 120                 125

Asn Asn Glu Met Ile Tyr Cys Lys Trp Thr Met Asp Glu Trp Asn Glu
130                 135                 140

Trp Lys Asn Glu Lys Ile Lys Glu Trp Val Thr Ser Glu Trp Lys Glu
145                 150                 155                 160

Ser Glu Asp Gln Tyr Trp Ser Lys Tyr Asp Asp Ala Thr Ile Gln Thr
                165                 170                 175

Leu Thr Val Ala Glu Arg Asn Gln Trp Phe Lys Trp Lys Glu Arg Ile
            180                 185                 190

Tyr Arg Glu Gly Ile Glu Trp Lys Asn Trp Ile Ala Ile Lys Glu Ser
        195                 200                 205

Lys Phe Val Asn Ala Asn Trp Asn Ser Trp Ser Glu Trp Lys Asn Glu
210                 215                 220

Lys Arg Leu Glu Phe Asn Asp Trp Ile Glu Ala Phe Val Glu Lys Trp
225                 230                 235                 240

Ile Arg Gln Lys Gln Trp Leu Ile Trp Thr Asp Glu Arg Lys Asn Phe
                245                 250                 255

Ala Asn Arg Gln Lys Ala Ala Pro Gly Gly Val Ala Ala Ala Pro Gly
            260                 265                 270

Val Phe Ala Pro Arg Pro Ala Phe Gly Ala Pro Ser Gly Phe Ala Pro
        275                 280                 285

Arg Pro Gly Phe Ala Ala Pro Ser Gln Pro Pro Arg Tyr Ser Phe Ala
290                 295                 300

Ala Ala Ser Gly Tyr Val Ala Pro Ser Ala Thr Ser Glu Ala Ala Pro
305                 310                 315                 320

Ala Thr Ser Glu Ala Pro Ala Ser Ala Glu Ala Thr Thr Ala Leu Ser
                325                 330                 335

Ser Glu Thr Thr Thr Pro Val Asn Pro Glu Thr Ala Ala Ser Pro
            340                 345                 350

Glu Ala Ala Thr Pro Val Asn Pro Glu Glu Thr Ala Ala Ser Ser Glu
        355                 360                 365

Thr Thr Thr Val Asn Pro Glu Ala Thr Pro Val Asn Pro Glu Ala Pro
370                 375                 380

Val Ala Glu Pro Glu Lys Lys Glu Glu Glu Pro Ala Ala Glu Pro Leu
385                 390                 395                 400

Leu Ala Ile Glu Pro Ala Gln Thr Glu Pro Ala Ala Leu Glu Ala Ala
                405                 410                 415

Pro Ser Thr Ser Ala His His His His His His
            420                 425

<210> SEQ ID NO 4
<211> LENGTH: 1284
<212> TYPE: DNA
<213> ORGANISM: Plasmodium vivax

<400> SEQUENCE: 4

```
atgaagaccg agacggtgac ctccaggagc aacccacacc aagccatcga gtacgccaac    60
cagggcccat ccagggacaa ggtggaggag tggaagcgca acgcctggac cgactggatg   120
gtccaactcg acgacgactg gaaggacttc aacgcccaga tcgaggaaga gaagaaggcc   180
tggattgagg agaaggaagg cgactgggtc atcctcctga agcacctcca aaacaagtgg   240
ctgcacttca acccaaacct cgacgccgag taccagaccg acatgctggc caagtccgag   300
acgtgggaca gaggcagtg gaagatgtgg atcagcaccg agggcaagca gctcctggag   360
atggacctca agaagtggtt caccaacaac gagatgatct actgcaagtg gaccatggac   420
gagtggaaca gtggaagaa cgagaagatc aaggagtggg tgacctccga gtggaaggag   480
agcgaggacc aatactggtc caagtacgac gacgccacca tccaaaccct gaccgtcgcc   540
gagcgcaacc agtggttcaa gtggaaggag aggatctacc gcgagggcat cgagtggaag   600
aactggatcg ccatcaagga gagcaagttc gtgaacgcca actggaactc ctggtctgag   660
tggaagaaca gaaaaggct ggagttcaac gactggatcg aggccttcgt cgagaagtgg   720
atccgccaaa agcagtggct gatctggacc gacgagagga agaacttcgc caaccgccaa   780
aaggctgctc caggcggcgt ggctgccgcc ccaggcgtct tcgccccacg cccagccttc   840
ggcgccccat ccggcttcgc cccaaggcca ggcttcgctg ctccaagcca gccaccacgc   900
tactccttcg ctgccgccag cggctacgtg gctccatccg ctaccagcga ggctgctcca   960
gccacctccg aggcccagc cagcgccgag gctaccaccg ctctctccag cgagacgacc  1020
accccagtca acccagagga gacggctgct agcccggagg ctgctacccc agtgaacccg  1080
gaggagacgg ctgcctccag cgagacgacg acggtcaacc cagaggccac cccggtgaac  1140
ccagaggctc cagtggctga gccagagaag aaggaagagg agccagctgc tgagccactg  1200
ctcgctatcg agccagctca aaccgagcca gctgctctgg aggctgctcc atccaccagc  1260
gcccaccacc accaccacca ctga                                        1284
```

<210> SEQ ID NO 5
<211> LENGTH: 387
<212> TYPE: PRT
<213> ORGANISM: Plasmodium vivax

<400> SEQUENCE: 5

```
Met Gln Leu Glu Leu Glu Pro Ala Pro Asp Tyr Glu Ser Thr Ser Pro
1               5                   10                  15

Thr Val Pro Val Arg Leu Leu Leu His Asp Asp Tyr Ala Pro Asn Ala
            20                  25                  30

Glu Asp Met Phe Gly Pro Glu Ala Ser Gln Val Met Thr Asn Leu Tyr
        35                  40                  45

Glu Thr Ile Asp Glu Asp Gly Thr Thr Thr Asp Gly Tyr Gln Asn Gly
    50                  55                  60

Ser Asp Asp Gln Ser Asn Gln Ser Asp Ser Asn Asp Asp Ala Val
65                  70                  75                  80

Met Leu Asn Tyr Leu Ser Asn Glu Thr Asp Ser Phe Asp Glu Leu Ile
                85                  90                  95

Asp Glu Ile Asp Asn His Lys Lys Lys Lys Ile Tyr Ser Pro Leu
            100                 105                 110

Arg Lys Pro Val Leu Lys Arg Ser Asp Ser Ser Asp Ser Leu Ser Asp
        115                 120                 125

Tyr Glu Leu Asp Glu Val Leu Arg Gln Thr Glu Asn Glu Pro Glu Glu
    130                 135                 140
```

```
Asp Glu Asp Leu Asp Leu Ser Leu Glu Asp Ser Phe Glu Val Ile Asn
145                 150                 155                 160

Tyr Pro Trp Lys Asp Ile Leu Glu Ser Ser Pro Tyr Ser Thr Asp His
                165                 170                 175

Thr Asn Glu Glu Asp Phe Ser Ser Leu Glu Glu Leu Glu Leu Glu Asp
            180                 185                 190

Pro Val Gln Glu Met Asn Phe Gly Lys Leu Lys Phe Phe Glu Ile Gly
        195                 200                 205

Asp Pro Asp Leu Leu Ile Arg Lys Thr Pro Ile Thr Pro Asn Thr Lys
    210                 215                 220

Thr Lys Ser Gly Leu Glu Lys Asn Gly Asn Asn Thr Glu Ala Ser Asn
225                 230                 235                 240

Ile Asn Gln His Glu Lys Glu Lys Met Asp Lys Arg Lys Arg Arg Thr
                245                 250                 255

His Lys Gln Phe Lys Asn Pro Ile Glu Asn Phe Ser Val Thr Thr Thr
            260                 265                 270

Tyr Asp Asp Phe Leu Lys Gln Asn Gly Leu Arg Asp His Pro Ser Lys
        275                 280                 285

His Gln Lys Asp Ser Ser Glu Pro Phe Val Leu Asp Gln Tyr Asn Tyr
    290                 295                 300

Arg Asn Ala Lys Phe Lys Asn Val Arg Phe Tyr Ile Leu Arg Met Leu
305                 310                 315                 320

Tyr Asp Asn Ile Lys Asp Ile Gly Leu Lys Glu Phe Gln Tyr Leu Lys
                325                 330                 335

Ser His Lys Tyr Glu Val Glu Glu Phe Ile Lys Asn Ile Leu Arg Asn
            340                 345                 350

Asn Leu Ile Cys Leu Thr Phe Ser Gln Glu Asp His Leu Phe Asn Asp
        355                 360                 365

Ala His Leu Leu Ile Glu Lys Ala Ser Ile Lys Ser Glu His His His
    370                 375                 380

His His His
385

<210> SEQ ID NO 6
<211> LENGTH: 1164
<212> TYPE: DNA
<213> ORGANISM: Plasmodium vivax

<400> SEQUENCE: 6
atgcagctgg agctggagcc agccccagac tacgagtcca ccagcccaac cgtgccagtc     60
aggctcctgc tccacgacga ctacgcccca aacgccgagg acatgttcgg cccagaggcc    120
tcccaagtga tgaccaacct ctacgagacg atcgacgagg acggcaccac caccgacggc    180
taccaaaacg gctccgacga cgaccaaagc aaccagtccg acagcaacga cgacgccgtc    240
atgctcaact acctgtccaa cgagacggac agcttcgacg agctcatcga cgagatcgac    300
aaccacaaga agaagaagaa gatctactcc ccactcagga agccagtgct gaagcgcagc    360
gactccagcg actccctgag cgactacgag ctcgacgagg tcctgcgcca gaccgagaac    420
gagccagagg aagacgagga cctggacctc tccctggagg acagcttcga ggtcatcaac    480
tacccatgga aggacatcct ggagtccagc ccatacagca ccgaccacac caacgaggaa    540
gacttctcca gcctggagga gctggagctg gaggacccag tccaagagat gaacttcggc    600
aagctgaagt tcttcgagat cggcgaccca gacctgctca tcaggaagac cccaatcacc    660
```

-continued

```
ccaaacacca agaccaagtc cggcctggag aagaacggca acaacaccga ggccagcaac    720
atcaaccagc acgagaagga gaagatggac aagcgcaaga ggcgcaccca caagcaattc    780
aagaacccaa tcgagaactt ctccgtgacc accacctacg acgacttcct caagcaaaac    840
ggcctgaggg accacccaag caagcaccag aaggactcca gcgagccatt cgtgctcgac    900
caatacaact accgcaacgc caagttcaag aacgtcaggt tctacatcct ccgcatgctg    960
tacgacaaca tcaaggacat cggcctcaag gagttccagt acctgaagtc ccacaagtac   1020
gaggtcgagg agttcatcaa gaacatcctc aggaacaacc tcatctgcct gaccttcagc   1080
caagaggacc acctgttcaa cgacgcccac ctgctcatcg agaaggcctc catcaagagc   1140
gagcaccacc accaccacca ctga                                           1164
```

<210> SEQ ID NO 7
<211> LENGTH: 822
<212> TYPE: PRT
<213> ORGANISM: Plasmodium vivax

<400> SEQUENCE: 7

```
Met Asn Ala Gly Asp Gly Gln Gly Val Tyr Gly Gly Asn Gly Ile Asn
1               5                   10                  15

Asn Pro Leu Val Tyr His Val Gln His Gly Val Asn Ile Pro Asn Ser
            20                  25                  30

Asn Ser Asp Lys Lys Ala Ser Asp His Thr Pro Asp Glu Asp Glu Asp
        35                  40                  45

Thr Tyr Gly Arg Thr Arg Asn Lys Arg Tyr Met His Arg Asn Pro Gly
    50                  55                  60

Glu Lys Tyr Lys Gly Ser Asn Ser Pro His Asp Ser Asn Asp Asp Ser
65                  70                  75                  80

Gly Asp Thr Glu Tyr Glu Leu Asn Glu Gly Asp Val Lys Arg Leu Thr
                85                  90                  95

Pro Lys Asn Lys Lys Gly Ala Thr Thr Glu Glu Val Asp Thr Tyr Pro
            100                 105                 110

Tyr Gly Lys Lys Thr Asn Gly Ser Glu Phe Pro Arg Met Asn Gly Ser
        115                 120                 125

Glu Thr Gly His Tyr Gly Tyr Asn Asn Thr Gly Ser Gly Gly His Asn
    130                 135                 140

Asp Glu Asn Gly Tyr Thr Pro Ile Ile Val Lys Tyr Asp Asn Thr His
145                 150                 155                 160

Ala Lys Asn Arg Ala Asn Glu Ile Glu Glu Asn Leu Asn Lys Gly Glu
                165                 170                 175

Tyr Ser Arg Ile Lys Met Ala Lys Gly Lys Lys Gly Gln Lys Ser Gly
            180                 185                 190

Gly Tyr Glu Ser Asp Gly Glu Asp Ser Asp Val Asp Ser Ser Asn Val
        195                 200                 205

Phe Tyr Val Asp Asn Gly Gln Asp Met Leu Ile Lys Glu Lys Met Ser
    210                 215                 220

Arg Ser Glu Gly Pro Asp Glu Met Ser Glu Glu Gly Leu Asn Val Lys
225                 230                 235                 240

Tyr Lys Ala Gln Arg Gly Pro Val Asn Tyr His Phe Ser Asn Tyr Met
                245                 250                 255

Asn Leu Asp Lys Arg Asn Thr Leu Ser Ser Asn Glu Ile Glu Leu Gln
            260                 265                 270

Lys Met Ile Gly Pro Lys Phe Ser Glu Glu Val Asn Lys Tyr Cys Arg
        275                 280                 285
```

-continued

```
Leu Asn Glu Pro Ser Ser Lys Lys Gly Glu Phe Leu Asn Val Ser Phe
    290                 295                 300
Glu Tyr Ser Arg Ala Leu Glu Glu Leu Arg Ser Glu Met Ile Asn Glu
305                 310                 315                 320
Leu Gln Lys Arg Lys Ala Val Gly Ser Asn Tyr Tyr Asn Asn Ile Leu
                325                 330                 335
Asn Ala Ile Tyr Thr Ser Met Asn Arg Lys Asn Ala Asn Phe Gly Arg
            340                 345                 350
Asp Ala Tyr Glu Asp Lys Ser Phe Ile Ser Glu Ala Asn Ser Phe Arg
        355                 360                 365
Asn Glu Glu Met Gln Pro Leu Ser Ala Lys Tyr Asn Lys Ile Leu Arg
370                 375                 380
Gln Tyr Leu Cys His Val Phe Val Gly Asn Pro Gly Val Asn Gln Leu
385                 390                 395                 400
Glu Arg Leu Tyr Phe His Asn Leu Ala Leu Gly Glu Leu Ile Glu Pro
                405                 410                 415
Ile Arg Arg Lys Tyr Asn Lys Leu Ala Ser Ser Ser Val Gly Leu Asn
            420                 425                 430
Tyr Glu Ile Tyr Ile Ala Ser Ser Ser Asn Ile Tyr Leu Met Gly His
        435                 440                 445
Leu Leu Met Leu Ser Leu Ala Tyr Leu Ser Tyr Asn Ser Tyr Phe Val
450                 455                 460
Gln Gly Leu Lys Pro Phe Tyr Ser Leu Glu Thr Met Leu Met Ala Asn
465                 470                 475                 480
Ser Asp Tyr Ser Phe Phe Met Tyr Asn Glu Val Cys Asn Val Tyr Tyr
                485                 490                 495
His Pro Lys Gly Thr Phe Asn Lys Asp Ile Thr Phe Ile Pro Ile Glu
            500                 505                 510
Ser Arg Pro Gly Arg His Ser Thr Tyr Val Gly Glu Arg Lys Val Thr
        515                 520                 525
Cys Asp Leu Leu Glu Leu Ile Leu Asn Ala Tyr Thr Leu Ile Asn Val
530                 535                 540
His Glu Ile Gln Lys Val Phe Asn Thr Ser Ala Tyr Gly Tyr Glu
545                 550                 555                 560
Asn Ser Ile Ser Phe Gly His Asn Ala Val Arg Ile Phe Ser Gln Val
                565                 570                 575
Cys Pro Arg Asp Asp Ala Lys Asn Thr Phe Gly Cys Asp Phe Glu Lys
            580                 585                 590
Ser Thr Leu Tyr Asn Ser Lys Val Leu Lys Met Asp Glu Gly Asp Lys
        595                 600                 605
Glu Asn Gln Arg Ser Leu Lys Arg Ala Phe Asp Met Leu Arg Thr Phe
610                 615                 620
Ala Glu Ile Glu Ser Thr Ser His Leu Gly Asp Pro Ser Pro Asn Tyr
625                 630                 635                 640
Ile Ser Leu Ile Phe Glu Gln Asn Leu Tyr Thr Asp Phe Tyr Lys Tyr
                645                 650                 655
Leu Phe Trp Tyr Asp Asn Arg Glu Leu Ile Asn Val Gln Ile Arg Asn
            660                 665                 670
Ala Gly Arg Arg Lys Lys Gly Lys Lys Val Lys Phe Val Tyr Asp Glu
        675                 680                 685
Phe Val Lys Arg Gly Lys Gln Leu Lys Asp Lys Leu Ile Lys Ile Asp
690                 695                 700
```

```
Ala Lys Tyr Asn Ala Arg Ser Lys Ala Leu Leu Val Phe Tyr Ala Leu
705                 710                 715                 720

Val Asp Lys Tyr Ala Asn Ile Phe Arg Lys Ser Glu Asn Val Arg Lys
            725                 730                 735

Phe Phe Leu Asn Asp Val Ser Ser Ile Arg His His Leu Tyr Leu Asn
            740                 745                 750

Ser Val Leu Thr Lys Ser Pro Lys Ser Asn Leu Asp Ser Met Lys Lys
            755                 760                 765

Thr Leu Glu Glu Leu Gln Ser Leu Thr Asn Ala Pro Leu Lys Phe Ile
            770                 775                 780

Val Arg Gly Asn Asn Leu Lys Phe Leu Asn Asn Val Ala Lys Phe Glu
785                 790                 795                 800

Asn Leu Phe Tyr Val Asn Leu Phe Ile Met Ser Ser Leu Ser Arg Lys
            805                 810                 815

His His His His His His
            820

<210> SEQ ID NO 8
<211> LENGTH: 2469
<212> TYPE: DNA
<213> ORGANISM: Plasmodium vivax

<400> SEQUENCE: 8
atgaacgctg cgacggcca aggcgtgtac ggcggaaacg gcatcaacaa cccactcgtg      60
taccacgtcc agcacggcgt caacatccca aactccaaca gcgacaagaa ggccagcgac     120
cacaccccag acgaggacga ggacacctac ggcaggaccc gcaacaagag gtacatgcac     180
cgcaacccag gcgagaagta caagggctcc aacagcccac acgactccaa cgacgacagc     240
ggcgacaccg agtacgagct gaacgagggc gacgtgaaga ggctcacccc aaagaacaag     300
aagggcgcca ccaccgagga agtggacacc tacccatacg gcaagaagac caacggcagc     360
gagttcccac gcatgaacgg ctccgagacg gccactacg gctacaacaa caccggcagc     420
ggcggccaca cgacgagaa cggctacacc ccaatcatcg tgaagtacga caacacccac     480
gccaagaaca gggccaacga gatcgaggag aacctcaaca agggcgagta ctcccgcatc     540
aagatggcca agggcaagaa gggccaaaag tccggcggct acgagagcga cggcgaggac     600
tccgacgtcg actccagcaa cgtgttctac gtcgacaacg gccaggacat gctgatcaag     660
gagaagatgt ccaggagcga gggcccagac gagatgagcg aggaaggcct caacgtgaag     720
tacaaggccc aaaggggccc agtcaactac cacttctcca actacatgaa cctggacaag     780
cgcaacaccc tctccagcaa cgagatcgag ctccagaaga tgatcggccc aaagttcagc     840
gaggaagtga acaagtactg caggctgaac gagccatcca gcaagaaggg cgagttcctc     900
aacgtctcct tcgagtacag cagggccctg gaggagctga ggtccgagat gatcaacgag     960
ctgcaaaagc gcaaggccgt gggcagcaac tactacaaca acatcctcaa cgccatctac    1020
acctccatga caggaagaa cgccaacttc ggccgcgacg cctacgagga caagtccttc    1080
atcagcgagg ccaacagctt caggaacgag gagatgcaac cactctccgc caagtacaac    1140
aagatcctgc gccagtacct ctgccacgtg ttcgtcggca acccaggcgt gaaccaactg    1200
gagcgcctgt acttccacaa cctcgccctg ggcgagctga tcgagccaat caggcgcaag    1260
tacaacaagc tggcctccag ctccgtcggc ctcaactacg agatctacat cgccagctcc    1320
agcaacatct acctcatggg ccacctcctg atgctcagcc tggcctacct gtcctacaac    1380
agctacttcg tgcagggcct caagccattc tactccctcg aaaccatgct catggccaac    1440
```

```
tccgactaca gcttcttcat gtacaacgag gtgtgcaacg tctactacca cccaaagggc    1500
accttcaaca aggacatcac cttcatccca atcgagagca ggccaggcag gcactccacc    1560
tacgtgggcg agaggaaggt cacctgcgac ctcctggagc tcatcctgaa cgcctacacc    1620
ctgatcaacg tgcacgagat ccaaaaggtc ttcaacacca gcgaggccta cggctacgag    1680
aactccatca gcttcggcca acgccgtg aggatcttct cccaggtctg cccacgcgac    1740
gacgccaaga acaccttcgg ctgcgacttc gagaagagca ccctgtacaa ctccaaggtg    1800
ctcaagatgg acgagggcga caaggagaac cagaggtccc tgaagcgcgc cttcgacatg    1860
ctccgcacct tcgccgagat cgagtccacc agccacctcg gcgacccaag cccaaactac    1920
atctccctga tcttcgagca aaacctctac accgacttct acaagtacct gttctggtac    1980
gacaacaggg agctcatcaa cgtgcagatc cgcaacgccg gcaggcgcaa gaagggcaag    2040
aaggtgaagt tcgtctacga cgagttcgtc aagaggggca agcaactgaa ggacaagctc    2100
atcaagatcg acgccaagta caacgcccgc agcaaggccc tcctggtgtt ctacgccctg    2160
gtcgacaagt acgccaacat cttcaggaag tccgagaacg tgcgcaagtt cttcctcaac    2220
gacgtctcca gcatcaggca ccacctctac ctgaacagcg tgctgaccaa gtccccaaag    2280
agcaacctcg acagcatgaa gaagaccctg gaggagctgc agtccctcac caacgcccca    2340
ctgaagttca tcgtcagggg caacaacctg aagttcctca caacgtggc caagttcgag    2400 aacctgttct acgtgaacct cttcatcatg tccagcctct cccgcaagca ccaccaccac    2460
caccactga                                                            2469
```

<210> SEQ ID NO 9
<211> LENGTH: 337
<212> TYPE: PRT
<213> ORGANISM: Plasmodium vivax

<400> SEQUENCE: 9

```
Met Asn Val Asn Lys Lys Ser Ser Gly Glu Glu Asn Asn Thr Lys Gln
1               5                   10                  15

Ala Leu Gly Leu Arg Val Ser Arg Thr Leu Ala Lys Asp Gly Ala Asn
            20                  25                  30

Glu Asn Ala Glu Glu Gly Leu Ser Glu Glu Glu Glu Ala Val Glu
        35                  40                  45

Glu Gly Glu Glu Glu Ala Val Glu Gly Glu Glu Glu Val Val Glu
    50                  55                  60

Glu Glu Gly Glu Glu Val Val Glu Gly Glu Glu Glu Val Val Glu
65                  70                  75                  80

Gly Glu Glu Glu Val Val Glu Asp Glu Glu Val Val Glu Gly Glu Glu
                85                  90                  95

Tyr Ala Glu Gly Glu Glu Pro Val Glu Gly Glu Glu Tyr Ala Glu Gly
            100                 105                 110

Glu Glu Pro Val Glu Gly Glu Glu Pro Val Val Glu Glu Tyr Ala
        115                 120                 125

Glu Gly Glu Glu Pro Val Glu Gly Glu Glu Tyr Ala Glu Gly Glu Glu
    130                 135                 140

Pro Val Glu Gly Glu Glu Val Val Gly Glu Glu Val Val Glu Gly
145                 150                 155                 160

Glu Glu Val Ala Glu Gly Glu Glu Val Ala Glu Gly Glu Glu Val Ala
                165                 170                 175

Glu Gly Glu Glu Ala Val Glu Gly Glu Glu Val Ala Glu Gly Glu Glu
```

```
            180                 185                 190
Val Ala Glu Gly Glu Val Ala Glu Gly Glu Ala Ala Glu Glu
        195                 200                 205
Gly Ala Ala Glu Glu Gly Ala Thr Glu Glu Gly Ala Thr Glu Glu Gly
        210                 215                 220
Ala Thr Lys Glu Glu Ala Thr Glu Lys Ala Ala Glu Gly Glu Glu Thr
225                 230                 235                 240
Ala Glu Ser Glu Lys Pro Ala Glu Glu Gln Pro Thr Thr Phe Val Glu
                245                 250                 255
Thr Val Glu Lys Lys Val Glu Pro Val Ser Lys Pro Pro Phe Lys Pro
                260                 265                 270
Leu Phe Pro Val Asp Glu Lys Tyr Leu Glu Thr Leu Glu Asp Ile Ala
                275                 280                 285
Gln Ser Phe Leu Lys Glu Phe Gln Glu Ala Glu Gly Lys Arg Lys Gln
        290                 295                 300
Lys Lys Val Lys Lys Arg Ala Lys Lys Ile Thr Lys Lys Leu Ala Lys
305                 310                 315                 320
Glu Tyr Ala Lys Lys Phe Lys Ser Lys Lys Lys His His His His His
                325                 330                 335
His
```

```
<210> SEQ ID NO 10
<211> LENGTH: 1014
<212> TYPE: DNA
<213> ORGANISM: Plasmodium vivax

<400> SEQUENCE: 10
atgaacgtca acaagaagtc cagcggcgag gagaacaaca ccaagcaagc tctgggcctg      60
agggtgtccc gcaccctcgc taaggacggc gccaacgaga cgccgaggaa aggcctcagc     120
gaggaagagg aagaggccgt cgaggaaggc gaggaagagg ccgtggagga aggcgaggaa     180
gaggtggtcg aggaagaggg cgaggaagtg gtcgagggcg aggaagagga agtggtggag     240
ggggaggaag aggtggtgga ggatgaggaa gtggtggagg gcgaggagta cgctgagggc     300
gaggagccgg tggaggggga ggagtacgcc gaggggagg agccagtgga gggcgaggag     360
ccagtggagg tggaggagta cgcggagggg gaggagccgg tggaaggtga ggagtacgcc     420
gagggcgagg agcctgtcga gggggaggaa gtggtggaag gcgaggaagt ggtggaaggt     480
gaggaagtgg ctgagggcga ggaagtggcc gaggggagg aagtggccga gggcgaggaa     540
gccgtggagg gcgaggaagt ggcggagggg gaggaagtgg cggaaggcga ggaagtggcc     600
gaaggcgagg aagccgctga ggaaggcgct gccgaggaag gcgccacgga ggaaggcgct     660
accgaggaag gcgccaccaa ggaagaggcc accgagaagg ctgctgaggg cgaggagacg     720
gctgagtccg agaagccagc tgaggagcaa ccaaccacct tcgtggagac ggtcgagaag     780
aaggtggagc cagtcagcaa gccaccattc aagccactct ccccagtcga cgagaagtac     840
ctcgaaaccc tggaggacat cgcccaatcc ttcctgaagg agttccaaga ggccgagggc     900
aagaggaagc agaagaaggt gaagaagcgc gccaagaaga tcaccaagaa gctcgccaag     960
gagtacgcca agaagttcaa gtccaagaag aagcaccacc accaccacca ctga          1014

<210> SEQ ID NO 11
<211> LENGTH: 288
<212> TYPE: PRT
<213> ORGANISM: Plasmodium vivax
```

<400> SEQUENCE: 11

Met Pro Lys Pro Asp Gln Lys Asn Leu Lys Gly Gly Val Lys Asn Ala
1               5                   10                  15

Pro Leu Gln Gln Arg Lys Gly Ser Val Pro Ile Asn Pro Pro Lys Pro
            20                  25                  30

Val Asn Asp Lys Leu Lys Asp Gly Ser Asn Lys Thr Glu Thr Lys Asn
        35                  40                  45

Ala Lys Asn Thr Leu Ser Lys Pro Pro Met Gln Val Thr Asp Lys Ser
50                  55                  60

Lys Asp Glu Ala Lys Lys Thr Pro Leu Gln Ser Thr Pro Lys Leu Thr
65                  70                  75                  80

Pro Lys Thr Lys Glu Val Pro Lys Glu Ser Asn Met Glu Met Trp Leu
                85                  90                  95

Lys Asp Thr Lys Asp Glu Tyr Glu Asn Leu Lys Cys Gln Tyr Arg Thr
            100                 105                 110

Cys Leu Tyr Asp Trp Phe Arg Lys Ile Asn Asp Glu Tyr Asn Glu Leu
        115                 120                 125

Leu Asn Lys Leu Glu Glu Lys Trp Ala Lys Phe Pro Asn Asp Pro Lys
    130                 135                 140

Asn Lys Asp Val Phe Asp Asn Leu Lys Thr Ser Ser Leu Lys Asn Asp
145                 150                 155                 160

Glu Lys Lys Ala Gln Trp Met Arg Lys Asn Leu Lys Asp Leu Met Arg
                165                 170                 175

Glu Gln Val Asp Glu Trp Leu Glu Gly Lys Lys Ile Tyr Glu Gly Gly
            180                 185                 190

Met Ser Pro Thr Tyr Trp Asp Ala Trp Glu Lys Lys Ile Ala Lys Gly
        195                 200                 205

Leu Met Gly Ala Ala Trp Tyr Lys Met Asn Ser Ser Gly Arg Thr Lys
    210                 215                 220

Glu Trp Asp Lys Leu Arg Asn Glu Leu Glu Thr Arg Tyr Asn Lys Lys
225                 230                 235                 240

Ile Lys Ser Leu Trp Gly Gly Phe His Arg Asp Val Tyr Phe Arg Phe
                245                 250                 255

Lys Glu Trp Ile Glu Glu Val Phe Asn Lys Trp Ile Glu Asn Lys Gln
            260                 265                 270

Ile Asp Thr Trp Met Asn Ser Gly Lys Lys His His His His His His
        275                 280                 285

<210> SEQ ID NO 12
<211> LENGTH: 867
<212> TYPE: DNA
<213> ORGANISM: Plasmodium vivax

<400> SEQUENCE: 12
atgccaaagc cagaccaaaa gaacctcaag ggcggcgtga agaacgcccc actgcaacag    60
aggaagggct ccgtgccaat caacccacca aagccagtca cgacaagct caaggacggc    120 agcaacaaga ccgagacgaa gaacgccaag acaccctgt ccaagccacc aatgcaagtg    180
accgacaaga gcaaggacga ggccaagaag acccactcc agtccacccc aaagctgacc    240
ccaaagacca aggaagtgcc aaaggagagc aacatggaga tgtggctcaa ggacaccaag    300
gacgagtacg agaacctcaa gtgccagtac aggacctgcc tgtacgactg gttccgcaag    360
atcaacgacg agtacaacga gctcctgaac aagctggagg agaagtgggc caagttccca    420
aacgacccaa agaacaagga cgtgttcgac aacctcaaga cctccagcct gaagaacgac    480

```
gagaagaagg cccagtggat gaggaagaac ctcaaggacc tgatgaggga gcaggtgg

```
Arg Ala Pro Ser Pro Pro Pro Pro Ala Lys Pro Glu Ala Ala Pro
305                 310                 315                 320

Pro Ala Lys Glu Val Ala Pro Ala Val Thr Thr Pro Glu Ala Pro Lys
            325                 330                 335

Glu Glu Ala Pro Lys Ala Asp Ala Ala Pro Ala Ala Pro Gln Pro Ala
        340                 345                 350

Ala Glu Ser Lys Val Ala Lys Glu Pro Thr Asp Gln Ser Ala Glu Asn
        355                 360                 365

Gln Ser Asp Ser Leu Tyr Lys Glu Thr Asn Ile Lys Glu Gly Thr Glu
    370                 375                 380

Glu Ala Gly Thr Gly Gln Glu Gln Lys Gln Pro Glu Leu Gln Asn
385                 390                 395                 400

Leu Leu Glu Gln Gln Met Asn Ile Phe Tyr Ile Leu Val Gln Phe Phe
                405                 410                 415

Lys Ser Lys Ile Lys Ala Leu Ile Lys Phe Leu Leu Ile Leu Val Ser
            420                 425                 430

His His His His His His
        435

<210> SEQ ID NO 14
<211> LENGTH: 1317
<212> TYPE: DNA
<213> ORGANISM: Plasmodium vivax

<400> SEQUENCE: 14
atgcaatact ccatcgtgaa gaacgagatc accaagaggc gcaagccaaa gatcaggaac      60
gagtccccac cagacggcaa cagcccaggc ggcggcaaga caacgctgc tggcaacaac     120 ggcggcggcg acaacaacgc caagaacaag gctgctaaca aggctgctaa caacgccgcc     180
aacaaggccg ccaacaacgc tgctaacaac gccgcgaaca acgccgccaa caacgccgcc     240
aacaacgcag ctaacaacgc cgctaacaac gcggccaaca acgccgcgaa caacgcggcg     300
aacaacgctg ccaacaacgc caacgagcaa acggcaaca agaagaagaa gggcaagcca     360
aagaaggaag aggccgacct cccagtgcaa gcccagaacg agaacgacag gaacaagatc     420
gaggacatcg ctgacgaggc tgagctgttc gctgaggaag ccaagatgct cgccgacctg     480
gcctccaagc gcagcaagga agtggagcag atcctctcca gcatcccaga gaacaagttc     540
ggctccgagc caaaggaaga cgccatcttc gctgctaagg acgccgtgag ggctagcgag     600
gacgccatga ggctgctca aaaggccagg gccgctgaga cggtcacccca ggccaacgag     660 gagaaggaca aggctaagac cgctaaggag ctggctgaga ggtccgctca aatcgtgaag     720
aagaacgccg tcgaggccct gaaggagttc ggcaagatcg ccgaggccgc cgagatggag     780
gccatcaaga tcccaatccc agagaacctg aagccaaaga gaaggtgaa gcaaccaagg     840 gccgccgccc aaaaggtgga gccaacccaa gctaccgctc acaaggtggt gccaccacca     900
gctgagccac cacgcgcccc atccccacca ccaccaccag ctaagccaga ggctgcccca     960
ccagctaagg aagtggctcc agctgtcacc accccagagg ctccaaagga gaggccccca    1020
aaggctgacg ctgctccagc tgccccacag ccagccgccg agtccaaggt cgccaaggag    1080
ccaaccgacc agagcgccga gaaccaatcc gacagcctct acaaggagac gaacatcaag    1140
gaaggcaccg aggaagccgg caccggccaa gagcagaagc aagagccaga gctccaaaac    1200
ctcctggagc aacagatgaa catcttctac atcctggtgc agttcttcaa gtccaagatc    1260
aaggccctca tcaagttcct cctgatcctg gtcagccatc accaccacca ccactga      1317
```

<210> SEQ ID NO 15
<211> LENGTH: 355
<212> TYPE: PRT
<213> ORGANISM: Plasmodium vivax

<400> SEQUENCE: 15

```
Met Asp Glu Asn Thr Gly Trp Pro Ile Asp Tyr Glu Phe Asn Ser Lys
1               5                   10                  15

Thr Leu Pro Ser Ile Glu Val Lys Leu Ser Pro Pro Glu Asn Pro Leu
            20                  25                  30

Pro Gln Val Ala Ala Glu Ile Lys Leu Leu Glu Ser Ala Arg Leu Lys
        35                  40                  45

Leu Glu Glu Gly Met Met Gln Lys Leu Glu Asp Glu Tyr Asn Lys Ser
50                  55                  60

Leu Ser Ser Ala Lys Ile Lys Ile Gln Asp Thr Val Glu Lys Ser Leu
65                  70                  75                  80

Ser Ile Phe Asn Asp Pro Asn Met Leu Gly Ser Val Ile Ser Asn Ser
                85                  90                  95

Val Lys Met Leu Arg Ser Glu Asn Val Lys Lys Arg Thr Glu Asn Val
            100                 105                 110

Gln Ala Lys His Asn Leu Lys Lys Met Gln Thr Val Asn Gln Ala Lys
        115                 120                 125

Ser Gly Pro Leu Pro Pro Glu Leu Arg Lys His Thr Ser Phe Leu
130                 135                 140

Glu Gln Asn Tyr Val Asn Arg Val Leu Pro Ser Val Lys Ile Ser Leu
145                 150                 155                 160

Ser Glu Leu Thr Glu Pro Ser Val Glu Ile Lys Glu Lys Ile Glu Glu
                165                 170                 175

Met Glu Gln Tyr Arg Thr Asp Glu Glu Val Ala Met Phe Glu Met Ala
            180                 185                 190

Ile Ser Glu Phe Ser Ile Leu Thr Asp Ile Thr Ile Leu Glu Leu Glu
        195                 200                 205

Lys Gln Ile Gln Leu Gln Leu Asn Pro Phe Leu Val Asp Lys Lys Val
210                 215                 220

Val His Arg Ala Leu Thr Lys Glu Leu Lys Glu Leu Glu Gln Arg Glu
225                 230                 235                 240

Glu Lys Gln Lys Ile Lys Glu Asn Phe Gln Arg Gln Ser Ser Phe Ile
                245                 250                 255

Glu Ala Gly Glu Asp Glu Asp Thr Gly Asn Ile Leu Asn Val Lys Ile
            260                 265                 270

Ser Gln Thr Asp Tyr Gly Tyr Pro Thr Val Asp Glu Leu Val Met Gln
        275                 280                 285

Met Gln Lys Arg Arg Asp Ile Ser Glu Lys Leu Glu Arg Gln Lys Ile
290                 295                 300

Leu Asp Leu Gln Met Lys Leu Leu Lys Ala Gln Ser Glu Met Ile Lys
305                 310                 315                 320

Asp Ala Leu His Phe Ala Leu Ser Lys Val Ile Ala Gln Tyr Ser Pro
                325                 330                 335

Leu Val Glu Thr Met Lys Leu Glu Ser Met Arg Met Leu His His
            340                 345                 350

His His His
        355
```

<210> SEQ ID NO 16
<211> LENGTH: 1068
<212> TYPE: DNA
<213> ORGANISM: Plasmodium vivax

<400> SEQUENCE: 16

```
atggacgaga caccggctg gccaatcgac tacgagttca actccaagac cctgccaagc    60
atcgaggtga agctctcccc accagagaac ccactgccac aagtcgccgc cgagatcaag   120
ctcctggaga gcgcccgcct caagctcgaa gagggcatga tgcagaagct ggaggacgag   180
tacaacaagt ccctgtccag cgccaagatc aagatccaag acaccgtgga agtccctc    240
agcatcttca cgacccaaa catgctgggc tccgtgatct ccaacagcgt caagatgctc   300
aggagcgaga acgtgaagaa gcgcaccgag aacgtccagg ccaagcacaa cctcaagaag   360
atgcagaccg tcaaccaagc caagagcggc ccactcccac accagagct gcgcaagcac   420
acctccttcc tggagcaaaa ctacgtgaac agggtcctgc catccgtgaa gatctccctc   480
agcgagctga ccgagccaag cgtcgagatc aaggagaaga tcgaggagat ggagcagtac   540
aggaccgacg aggaagtggc catgttcgag atggccatct ccgagttcag catcctcacc   600
gacatcacca tcctggagct ggagaagcaa atccagctcc aactgaaccc attcctcgtc   660
gacaagaagg tggtccacag ggccctgacc aaggagctca aggagctgga gcagcgcgag   720
gagaagcaaa agatcaagga gaacttccag aggcaatcca gcttcatcga ggctggcgag   780
gacgaggaca ccggcaacat cctcaacgtg aagatctccc cagaccgacta cggctaccca   840
accgtggacg agctcgtcat gcagatgcaa aagaggcgcg acatctccga aagctggag   900
cgccagaaga tcctcgacct gcagatgaag ctcctgaagg cccagagcga gatgatcaag   960
gacgccctcc acttcgccct gtccaaggtc atcgcccaat acagcccact cgtcgagacg  1020
atgaagctgg agagcatgag gatgctccac caccaccacc accactga                1068
```

<210> SEQ ID NO 17
<211> LENGTH: 624
<212> TYPE: PRT
<213> ORGANISM: Plasmodium vivax

<400> SEQUENCE: 17

```
Met Ser Ser Asp Gly Lys Ser Ser Ala Ser Lys Ser Gly Ser Lys
1               5                   10                  15

Ser Gly Ser Lys Tyr Gly Gly Ser Ser Tyr Ser Asp Tyr Ser Ala Tyr
                20                  25                  30

Asp Ser Gly Ser Ala Ser Ser Val Gly Ser Arg Glu Phe Glu Asn Glu
            35                  40                  45

Met Tyr Glu Phe Ala Leu Gln His Pro Met Glu Lys Leu Thr Lys Glu
        50                  55                  60

Met Asp Ile Leu Lys Asn Asp Tyr Thr Lys Val Lys Glu Glu Glu Gly
65                  70                  75                  80

Lys Ile Leu Asp Glu Glu His Lys Glu Ile Glu Lys Arg Lys Glu
                85                  90                  95

Glu Arg Leu Lys Met Leu Ala Glu Gly Asp Val Glu Lys Asn Lys Gly
            100                 105                 110

Asp Glu Glu Ile Asn Phe Ile Lys His Asp Tyr Thr Asp Thr Arg Ile
        115                 120                 125

Arg Gly Gly Phe Thr Glu Phe Leu Ser Asn Leu Asn Pro Phe Lys Lys
    130                 135                 140

Glu Ile Lys Pro Met Lys Lys Glu Ile Ser Leu Ile Thr Tyr Ile Pro
```

```
            145                 150                 155                 160
Asp Lys Ile Val Asn Lys Glu Lys Ile Met Arg Asp Leu Gly Ile Ser
                    165                 170                 175

His Lys Tyr Glu Pro Tyr Gln Gln Ser Ile Leu Tyr Thr Cys Pro Asn
                    180                 185                 190

Ser Val Phe Phe Asp Ser Met Glu Asn Leu Arg Lys Glu Leu Asp
                195                 200                 205

Lys Asn His Glu Lys Glu Ala Ile Thr Asn Lys Ile Leu Asp His Asn
        210                 215                 220

Lys Glu Cys Leu Lys Asn Phe Gly Leu Phe Asp Phe Glu Leu Pro Asp
225                 230                 235                 240

Asn Lys Thr Lys Leu Gly Asn Val Ile Gly Ser Ile Gly Glu Tyr His
                    245                 250                 255

Val Arg Leu Tyr Glu Ile Glu Asn Asp Leu Leu Lys Tyr Gln Pro Ser
                    260                 265                 270

Leu Asp Tyr Met Thr Leu Ala Asp Asp Tyr Lys Leu Val Lys Asn Asp
                275                 280                 285

Val Asn Thr Leu Glu Asn Val Asn Phe Cys Leu Leu Asn Pro Lys Thr
        290                 295                 300

Leu Glu Asp Phe Leu Lys Lys Glu Ile Met Glu Leu Met Gly Glu
305                 310                 315                 320

Asp Pro Ile Ala Tyr Glu Glu Lys Phe Thr Lys Tyr Met Glu Glu Ser
                    325                 330                 335

Ile Asn Cys His Leu Glu Ser Leu Ile Tyr Glu Asp Leu Asp Ser Ser
                340                 345                 350

Gln Asp Thr Lys Ile Val Leu Lys Asn Val Lys Ser Lys Leu Tyr Leu
            355                 360                 365

Leu Gln Asn Gly Leu Thr Tyr Lys Ser Lys Lys Leu Ile Asn Lys Leu
        370                 375                 380

Phe Asn Glu Ile Gln Lys Asn Pro Glu Pro Ile Phe Glu Lys Leu Thr
385                 390                 395                 400

Trp Ile Tyr Glu Asn Met Tyr His Leu Lys Arg Asp Tyr Thr Phe Leu
                    405                 410                 415

Ala Phe Lys Thr Val Cys Asp Lys Tyr Val Ser His Asn Ser Ile Tyr
                420                 425                 430

Thr Ser Leu Gln Gly Met Thr Ser Tyr Ile Ile Glu Tyr Thr Arg Leu
            435                 440                 445

Tyr Gly Ala Cys Phe Lys Asn Ile Thr Ile Tyr Asn Ala Val Ile Ser
        450                 455                 460

Gly Ile His Glu Gln Met Lys Asn Leu Met Lys Leu Met Pro Arg Ser
465                 470                 475                 480

Gly Leu Leu Ser Asp Val His Phe Glu Ala Leu Leu His Lys Glu Asn
                    485                 490                 495

Lys Lys Ile Thr Arg Thr Asp Tyr Val Leu Asn Asp Tyr Asp Pro Ser
                500                 505                 510

Val Lys Ala Tyr Ala Leu Thr Gln Val Glu Arg Leu Pro Met Val Ser
            515                 520                 525

Val Ile Asn Ser Phe Phe Glu Ala Lys Lys Ala Leu Ser Lys Met
        530                 535                 540

Leu Ala Gln Met Lys Leu Asp Leu Phe Thr Leu Thr Asn Glu Asp Leu
545                 550                 555                 560

Lys Ile Pro Asn Asp Lys Gly Ala Asn Ser Lys Leu Thr Ala Lys Leu
                    565                 570                 575
```

```
Ile Ser Ile Tyr Lys Ala Glu Ile Lys Lys Tyr Phe Lys Glu Met Arg
            580                 585                 590

Asp Asp Tyr Val Phe Leu Ile Lys Ala Arg Tyr Lys Gly His Tyr Lys
        595                 600                 605

Lys Asn Tyr Leu Leu Tyr Lys Arg Leu Glu His His His His His His
    610                 615                 620

<210> SEQ ID NO 18
<211> LENGTH: 1875
<212> TYPE: DNA
<213> ORGANISM: Plasmodium vivax

<400> SEQUENCE: 18
atgagcagcg acggcaagtc cagcgcttcc gctaagtccg gcagcaagtc cggcagcaag      60
tacggcggct ccagctactc cgactacagc gcctacgact ccggcagcgc ctccagcgtg     120
ggcagccgcg agttcgagaa cgagatgtac gagttcgccc tgcaacaccc gatggagaag     180
ctcaccaagg agatggacat cctgaagaac gactacacca aggtgaagga agaggaaggc     240
aagatcctcg acgaggagca aggagatc gaggagaaga ggaaggaaga gcgcctcaag      300
atgctggccg agggcgacgt ggagaagaac aagggcgacg aggagatcaa cttcatcaag     360
cacgactaca ccgacaccag gatccgcggc ggcttcaccg agttcctctc caacctgaac     420
ccattcaaga aggagatcaa gccgatgaag aaggagatct ccctcatcac ctacatccca     480
gacaagatcg tcaacaagga agatcatg cgcgacctgg gcatctccca agtacgag        540 ccataccaac agagcatcct ctacacctgc caaactccg tgttcttctt cgacagcatg     600
gagaacctca ggaaggagct ggacaagaac cacgagaagg aagccatcac caacaagatc     660
ctcgaccaca caaggagtg cctcaagaac ttcggcctgt cgacttcga gctcccagac      720 aacaagacca agctgggcaa cgtcatcggc tccatcggcg agtaccacgt gaggctctac     780
gagatcgaga cgaccctcct gaagtaccaa ccaagcctgg actacatgac cctcgccgac     840
gactacaagc tggtgaagaa cgacgtcaac accctggaga cgtgaacttt ctgcctcctg    900
aacccaaaga ccctggagga cttcctcaag aagaaggaga tcatggagct gatgggcgag     960
gacccaatcg cctacgagga agttcacc aagtacatgg aggagtccat caactgccac     1020
ctggagagcc tgatctacga ggacctcgac tccagccaag acaccaagat cgtgctcaag    1080
aacgtcaagt ccaagctgta cctcctgcag aacggcctca cctacaagag caagaagctc    1140
atcaacaagc tgttcaacga gatccagaag aaccccagagc caatcttcga gaagctcacc    1200
tggatctacg agaacatgta ccacctgaag cgcgactaca ccttcctcgc cttcaagacc    1260
gtgtgcgaca gtatgtgtc ccacaacagc atctacacct ccctgcaagg catgaccagc    1320
tacatcatcg agtacaccag gctctacggc gcctgcttca gaacatcac catctacaac    1380 gccgtcatct ccggcatcca cgagcagatg aagaacctca tgaagctgat gccaaggtcc    1440
ggcctcctga cgacgtgca cttcgaggcc ctcctgcaca aggagaacaa gaagatcacc    1500
cgcaccgact acgtgctcaa cgactacgac ccatccgtca aggcctacgc cctgacccaa    1560
gtggagaggc tcccaatggt gtccgtcatc aacagcttct cgaggccaa gaagaaggcc    1620 ctcagcaaga tgctggccca gatgaagctc gacctgttca ccctgaccaa cgaggacctc    1680
aagatcccaa cgacaaggg cgccaactcc aagctcaccg ccaagctgat cagcatctac    1740
aaggccgaga tcaagaagta cttcaaggag atgagggacg actacgtctt cctgatcaag    1800
gcccgctaca aggggcacta caagaagaac tacctcctgt acaagcgcct ggagcaccac    1860
```
caccaccacc actga 1875

<210> SEQ ID NO 19
<211> LENGTH: 239
<212> TYPE: PRT
<213> ORGANISM: Plasmodium vivax

<400> SEQUENCE: 19

Met Asn Thr Arg Ala Ser Lys Phe Ala Asn Ser Lys Arg Lys Arg Asn
1               5                   10                  15

Gly Asn Ala Met Arg Glu Asn Lys Leu Asn Asn Asp Asp Val Asp His
            20                  25                  30

Tyr Ser Phe Leu Ser Leu Arg Thr Ala Asn Glu Glu Lys Ala Ala Thr
        35                  40                  45

Glu Asn Asp Ser Asn Asn Ala Lys Lys Glu Gly Glu Glu Asn Thr Asn
    50                  55                  60

Gly Asn Glu Lys Lys Asn Glu Glu Asn Gly Ser Gly Asn Glu Lys Arg
65                  70                  75                  80

Asn Glu Glu Asn Asn Ala Asn Glu Lys Lys Asn Glu Gln Thr Asn Asp
                85                  90                  95

Gln Ser Asn Gly Gln Ser Asn Ser Gln Thr Asn Ile Pro Lys Lys Asn
            100                 105                 110

Glu Ala Val Pro Pro Glu Lys Lys Ile Asn Lys Glu Asn Leu Leu Glu
        115                 120                 125

Tyr Gly Thr His Asp Lys Asp Gly His Phe Ile Pro Ser Tyr Lys Thr
    130                 135                 140

Leu Thr Asp Glu Ile Leu Ser Thr Asn Asn Ser Leu Glu Arg Ala Ser
145                 150                 155                 160

Ser Phe Leu Lys Ile Ala Cys Ser His Ile Met Lys Ile Val Glu Phe
                165                 170                 175

Ile Pro Glu Ser Lys Leu Ser Ser Gln Tyr Ile Lys Val Glu Ser Lys
            180                 185                 190

Asn Val Tyr Ile Lys Asp Ile Thr Ser Glu Cys Gln Asn Ile Phe Phe
        195                 200                 205

Ser Leu Glu Lys Leu Thr Met Thr Met Ile Val Leu Asn Ser Lys Met
    210                 215                 220

Asn Lys Leu Val Tyr Val Gln Asp Lys His His His His His His
225                 230                 235

<210> SEQ ID NO 20
<211> LENGTH: 720
<212> TYPE: DNA
<213> ORGANISM: Plasmodium vivax

<400> SEQUENCE: 20
atgaacacca gggcctccaa gttcgccaac agcaagagga agcgcaacgg caacgccatg 60
cgcgagaaca agctcaacaa cgacgacgtg gaccactact ccttcctcag cctgaggacc 120
gctaacgagg agaaggctgc taccgagaac gactccaaca acgccaagaa ggaaggcgag 180
gagaacacca acggcaacga gaagaagaac gaggagaacg gcagcggcaa cgagaagcgc 240
aacgaggaga acaacgctaa cgagaagaag aacgagcaaa ccaacgacca gtccaacggc 300
caatccaaca gccagaccaa catcccaaag aagaacgagg ccgtcccacc agagaagaag 360
atcaacaagg agaacctcct ggagtacggc acccacgaca aggacggcca cttcatccca 420
agctacaaga ccctcaccga cgagatcctg tccaccaaca acagcctgga gagggcctcc 480

```
agcttcctga agatcgcctg ctcccacatc atgaagatcg tggagttcat cccagagtcc    540
aagctgtcca gccaatacat caaggtggag agcaagaacg tctacatcaa ggacatcacc    600
tccgagtgcc agaacatctt cttcagcctg gagaagctga ccatgaccat gatcgtcctc    660
aacagcaaga tgaacaagct ggtctacgtg caagacaagc accaccacca ccaccactga    720
```

<210> SEQ ID NO 21
<211> LENGTH: 287
<212> TYPE: PRT
<213> ORGANISM: Plasmodium vivax

<400> SEQUENCE: 21

Met Pro Lys Pro Ala Gln Asn Leu Lys Gly Gly Val Lys Lys Pro Ser
1               5                   10                  15

Leu Gln Gln Thr Lys Ser Pro Leu Pro Ser Lys Pro Pro Lys Pro Val
            20                  25                  30

Asn Asp Lys Leu Lys Asp Asp Ser Asn Lys Thr Glu Thr Lys Asp Ala
        35                  40                  45

Lys Asn Gly Leu Asn Lys Pro Pro Lys Asn Ile Asn Asp Lys Val Lys
    50                  55                  60

Asp Gly Glu Asn Lys Thr Pro Ser Gln Asp Leu Asn Glu Pro Ser Phe
65                  70                  75                  80

Lys Leu Pro Met Arg Gln Lys Ala Ser Ser Trp Asp Ala Trp Leu Lys
                85                  90                  95

Gly Thr Lys Lys Asp Tyr Glu Asn Leu Lys Cys Phe Ala Lys Gly Asn
            100                 105                 110

Leu Tyr Asp Trp Leu Cys Ser Val Arg Asp Ser Phe Glu Leu Tyr Leu
        115                 120                 125

Gln Ser Leu Glu Ser Lys Trp Thr Ser Cys Ser Asp Asn Thr Thr Thr
    130                 135                 140

Val Phe Leu Cys Glu Cys Leu Ala Glu Ser Ser Gly Trp Gly Asp Pro
145                 150                 155                 160

Gln Trp Glu Ser Trp Val Lys Lys Glu Leu Lys Glu Gln Leu Lys Thr
                165                 170                 175

Glu Ala Gln Ala Trp Ile Ser Thr Lys Lys Lys Asp Phe Asp Gly Leu
            180                 185                 190

Thr Ser Lys Tyr Phe Ser Leu Trp Lys Asp His Arg Arg Lys Glu Leu
        195                 200                 205

Glu Glu Glu Ala Trp Lys Thr Lys Ala Ser Ser Gly Gly Leu Ser Glu
    210                 215                 220

Trp Glu Glu Leu Thr Asp Lys Met Asn Thr Arg Tyr Thr Asn Asn Leu
225                 230                 235                 240

Asp Asn Met Trp Ser Asn Tyr Ser Gly Asp Leu Leu Phe Arg Phe Asp
                245                 250                 255

Glu Trp Ser Pro Glu Val Leu Glu Lys Trp Ile Glu Ser Lys Gln Trp
            260                 265                 270

Asn Gln Trp Val Lys Lys Val Arg Lys His His His His His His
        275                 280                 285

<210> SEQ ID NO 22
<211> LENGTH: 864
<212> TYPE: DNA
<213> ORGANISM: Plasmodium vivax

<400> SEQUENCE: 22

```
atgccaaagc cagcccaaaa cctcaagggc ggcgtgaaga agccatccct ccaacagacc    60
aagtccccac tgccaagcaa gccaccaaag ccagtcaacg acaagctcaa ggacgacagc   120
aacaagaccg agacgaagga cgccaagaac ggcctgaaca agccaccaaa gaacatcaac   180
gacaaggtga aggacggcga gaacaagacc ccatcccaag acctcaacga gccaagcttc   240
aagctgccaa tgaggcaaaa ggcctccagc tgggacgctt ggctcaaggg caccaagaag   300
gactacgaga acctgaagtg cttcgccaag ggcaacctct acgactggct gtgctccgtc   360
cgcgacagct tcgagctcta cctgcaatcc ctggagagca gtggacctc ctgcagcgac   420 aacaccacca ccgtgttcct ctgcgagtgc ctcgctgagt ccagcggctg ggcgaccca   480 cagtgggagt cctgggtcaa gaaggagctc aaggagcaac tgaagaccga ggcccaggcc   540
tggatcagca ccaagaagaa ggacttcgac ggcctcacct ccaagtactt cagcctgtgg   600
aaggaccaca ggcgcaagga gctggaggaa gaggcctgga gaccaaggc ctccagcggc   660 ggcctctccg agtgggagga gctgaccgac aagatgaaca ccaggtacac caacaacctc   720
gacaacatgt ggtccaacta cagcggcgac ctcctgttcc gcttcgacga gtggtcccca   780
gaggtgctgg agaagtggat cgagagcaag cagtggaacc agtgggtgaa gaaggtcagg   840
aagcaccacc accaccacca ctga                                          864

<210> SEQ ID NO 23
<211> LENGTH: 309
<212> TYPE: PRT
<213> ORGANISM: Plasmodium vivax

<400> SEQUENCE: 23

Met Val Thr Glu Gly Gly Asp Asn Leu Asp Asp Asp Leu Gly Gly Asp
1               5                   10                  15

Leu Glu Gly Leu Leu Gly Asp Asp Ala Glu Gly Gly Ala Ala Gly Gly
            20                  25                  30

Glu Gly Ala Ala Ala Ala Ser Ala Glu Gly Leu Ser Gly Glu Val
        35                  40                  45

Glu Asn Glu Leu Leu Tyr Val Lys Glu Asp Asp Asp Ala Pro Ala
    50                  55                  60

Ala Thr Pro Asp Glu Lys Pro Ser Thr Ser Gly Glu Glu Thr Pro Ala
65                  70                  75                  80

Ala Phe Val Asp Leu Val Asn Glu Thr Val Pro Pro Ala Lys Ala
                85                  90                  95

Pro Leu Pro Leu Gln Thr Lys Ala Pro Gln Gly Pro Lys Ile Lys Asp
            100                 105                 110

Trp Asn Gln Trp Met Lys Gln Ala Lys Lys Asp Phe Ser Gly Tyr Lys
        115                 120                 125

Gly Thr Met His Thr Gln Arg His Glu Trp Thr Lys Glu Lys Glu Asp
    130                 135                 140

Glu Leu Gln Lys Phe Cys Lys Tyr Leu Glu Lys Arg Trp Met Asn Tyr
145                 150                 155                 160

Thr Gly Asn Ile Asp Arg Glu Cys Arg Ser Asp Phe Leu Lys Ser Thr
                165                 170                 175

Gln Asn Trp Asn Glu Ser Gln Trp Asn Lys Trp Val Lys Ser Glu Gly
            180                 185                 190

Lys His His Met Asn Lys Gln Phe Gln Lys Trp Leu Asp Tyr Asn Lys
        195                 200                 205

Tyr Lys Leu Gln Asp Trp Thr Asn Thr Glu Trp Asn Lys Trp Lys Thr
    210                 215                 220
```

```
Thr Val Lys Glu Gln Leu Asp Asp Glu Glu Trp Lys Lys Glu Ala
225                 230                 235                 240

Ala Gly Lys Thr Lys Glu Trp Ile Lys Cys Thr Asp Lys Met Glu Lys
            245                 250                 255

Lys Cys Leu Lys Lys Thr Lys His Cys Lys Asn Trp Glu Lys Lys
        260                 265                 270

Ala Asn Ser Ser Phe Lys Lys Trp Glu Gly Asp Phe Thr Lys Lys Trp
        275                 280                 285

Thr Ser Asn Lys Gln Trp Asn Ser Trp Cys Lys Glu Leu Glu Lys His
    290                 295                 300

His His His His His
305

<210> SEQ ID NO 24
<211> LENGTH: 930
<212> TYPE: DNA
<213> ORGANISM: Plasmodium vivax

<400> SEQUENCE: 24
atggtgaccg agggcggcga caacctcgac gacgacctcg gcggcgacct ggagggcctc      60
ctgggcgacg acgctgaggg cggcgccgcc ggcggcgagg gcgctgccgc cgccgcctcc     120
gccgagggcc tgagcggcga ggtggagaac gagctcctct acgtgaagga agacgacgac     180
gacgctccag ctgctacccc agacgagaag ccatccacca gcggcgagga gacgccagct     240
gctttcgtgg acctcgtcaa cgagacggtg ccaccaccag ctaaggcccc actcccactg     300
caaaccaagg ccccacaggg cccaaagatc aaggactgga ccagtggat gaagcaggcc      360 aagaaggact ctccggcta caagggcacc atgcacaccc aaaggcacga gtggaccaag      420
gagaaggaag acgagctgca gaagttctgc aagtacctgg agaagcgctg gatgaactac     480
accggcaaca tcgacaggga gtgccgctcc gacttcctga gagcacccca aaactggaac     540
gagtcccagt ggaacaagtg ggtgaagagc gagggcaagc accacatgaa caagcaattc     600
cagaagtggc tggactacaa caagtacaag ctccaagact ggaccaacac cgagtggaac     660
aagtggaaga ccaccgtcaa ggagcagctg acgacgagg agtggaagaa gaggaagcc      720 gccggcaaga ccaaggagtg gatcaagtgc accgacaaga tggagaagaa gtgcctcaag     780
aagaccaaga agcactgcaa gaactgggag aagaaggcca actccagctt caagaagtgg     840
gagggcgact tcaccaagaa gtggacctcc aacaagcagt ggaacagctg gtgcaaggag     900
ctggagaagc accaccacca ccaccactga                                      930

<210> SEQ ID NO 25
<211> LENGTH: 933
<212> TYPE: PRT
<213> ORGANISM: Plasmodium vivax

<400> SEQUENCE: 25

Met Ala Val Glu Val Val Gln Glu Ala Ala Asp Glu Val Leu Glu Glu
1               5                   10                  15

Glu Lys Ile Glu Glu Pro Leu Glu Ile Val Glu Glu Pro Val Gln
            20                  25                  30

Val Ala Ala Glu Glu Pro Val Glu Val Leu Glu Glu Val Val Gln
        35                  40                  45

Glu Ala Ala Asp Glu Val Met Glu Glu Glu Lys Ile Glu Glu Pro Leu
    50                  55                  60
```

-continued

Glu Ile Val Ala Glu Glu Pro Leu Glu Ile Val Ala Glu Glu Pro Val
65                  70                  75                  80

Gln Val Ala Ala Glu Glu Val Leu Val Glu Lys Glu Glu Val Asn Glu
                85                  90                  95

Asn Ile Leu Asn Ile Val Glu Glu Ile Lys Glu Ser Ile Val Asp Lys
            100                 105                 110

Leu Glu Ala Asn Glu Glu Ala Ser Glu Glu Gly Asn Glu Asp Leu Leu
        115                 120                 125

Glu Ser Ala Glu Glu Ala Glu Glu Val Ala Glu Glu Ala Val Asp
    130                 135                 140

Thr Thr Thr Glu Ala Asp Val Val Glu Thr Val Glu Glu Glu Ala Ala
145                 150                 155                 160

Asn Ala Thr Thr Glu Val Ser Ala Glu Ser Leu Glu Val Ser Thr
                165                 170                 175

Glu Ala Pro Glu Glu Thr Thr Glu Ser Glu Ser His Glu Thr Phe Glu
                180                 185                 190

Glu Asp Ile Leu Lys Asn Leu Glu Glu Asn Lys Glu Ala Asn Glu Asn
            195                 200                 205

Ala Leu Glu Asp Ile Lys Glu Met Lys Glu Glu Phe Leu Asp Tyr Val
        210                 215                 220

Glu Gln Arg Val Glu Asp Asn Glu Asn Val Leu Val Asp Leu Leu Gln
225                 230                 235                 240

His Leu Glu Arg Asn Ala His Val Asn Glu Ser Val Leu Glu Asp Leu
                245                 250                 255

Glu Glu Ile Lys Glu Asp Leu Leu Ala Asn Ile Gln Met Ala Glu Glu
                260                 265                 270

Thr Arg Lys Glu Val Thr Asp Ala Ser Ala Glu Ser Ala Glu Glu Val
        275                 280                 285

Glu Glu Pro Val Glu Val Ser Ala Glu Val Ala Ala Glu Glu Pro Val
    290                 295                 300

Glu Val Ala Ala Glu Glu Pro Val Glu Val Thr Ala Glu Glu Pro Val
305                 310                 315                 320

Glu Val Thr Ala Glu Glu Pro Val Glu Ile Pro Thr Glu Glu Asn Ile
                325                 330                 335

Phe Asp Val Ile Glu Glu Ile Lys Glu Lys Val Leu Glu Asn Leu Glu
            340                 345                 350

Glu Thr Thr Ala Glu Ser Val Ala Glu Ser Val Gly Glu Gly Ala Asp
        355                 360                 365

Glu Asn Ala Leu Asp Val Leu Lys Glu Met Gln Glu Ser Leu Leu Glu
    370                 375                 380

Asn Phe Gly Gln Lys Ile Glu Ala Asn Glu Asn Ile Leu Ala Ser Val
385                 390                 395                 400

Leu Glu Asn Ile Gln Glu Lys Val Glu Leu Asn Lys Ser Val Leu Val
                405                 410                 415

Asp Val Leu Ala Glu Leu Lys Glu Glu Ala Val Ser Gln Arg Glu Thr
                420                 425                 430

Ala Gln Glu Val Ala Ala Glu Leu Val Glu Glu Ala Ala Glu Val Pro
        435                 440                 445

Ala Val Glu Pro Val Glu Glu Val Val Glu Pro Ala Val Glu Val
    450                 455                 460

Val Glu Glu Pro Val Glu Glu Val Val Glu Pro Val Val Asp Val
465                 470                 475                 480

Ile Glu Glu Pro Ala Val Glu Val Val Glu Val Pro Val Glu Glu Thr

```
                485                 490                 495
Val Glu Glu Pro Val Glu Val Thr Ala Glu Pro Val Glu Val Thr
                500                 505                 510
Ala Glu Glu Pro Val Glu Glu Thr Val Glu Pro Val Val Glu Val
                515                 520                 525
Val Glu Glu Pro Val Glu Glu Pro Val Val Glu Ala Ile Glu Glu Pro
                530                 535                 540
Val Val Glu Pro Val Val Glu Pro Ala Val Glu Val Ile Glu Asp Ala
545                 550                 555                 560
Thr Glu Glu Pro Val Glu Glu Ala Ala Glu Glu Pro Asp Val Glu Val
                565                 570                 575
Ala Glu Gly Ser Ala Ile Glu Ser Val Glu Glu Ala Phe Glu Gln Ile
                580                 585                 590
Ile Glu Asp Ala Ala Gln Val Ile Ala Glu Glu Ser Val Glu Glu Thr
                595                 600                 605
Ala Glu Gln Ile Leu Glu Gln Ala Thr Gln Ala Val Thr Glu Glu Ala
                610                 615                 620
Ala Asp Ala Ala Asp Val Ala Asp Ala Glu Glu Ala Val Gly Thr Ala
625                 630                 635                 640
Gln Val Val Thr Glu Glu Ser Val Ala Glu Ala Ile Glu Asp Thr Val
                645                 650                 655
Glu Glu Ile Ser Ala Glu Pro Ile Gln Ala Thr Ile Glu Gly Ile Val
                660                 665                 670
Gly Glu Val Val Glu Ser Val Glu Glu Asn Ile Glu Ala Val Glu Glu
                675                 680                 685
Ala Ile Lys Asp Ile Val Glu Gly Ala Val Glu Gly Ala Pro Glu Leu
                690                 695                 700
Ser Leu Glu Glu Met Ile Glu Asp Val Met Val Gly Thr Val Ala Glu
705                 710                 715                 720
Glu Asp Ser Ala Lys Glu Ala Ala Glu Glu Thr Val Glu Glu Val Val
                725                 730                 735
Gln Glu Asp Ala Ala Glu Glu Ala Ala Lys Glu Ala Ala Glu Glu
                740                 745                 750
Thr Val Glu Glu Ala Glu Arg Glu Ala Thr Gln Glu Ala Val Glu Glu
                755                 760                 765
Thr Val Glu Asp Val Val Glu Glu Val Ser Ala Glu Ala Val Glu Glu
                770                 775                 780
Ile Val Leu Glu Thr Pro Glu Gly Thr Ser Asp Glu Ser Val Glu Thr
785                 790                 795                 800
Val Val Glu His Ala Val Glu Asp Ser Leu Gly Glu Thr Ile Ala Thr
                805                 810                 815
Ile Val Asp Asp Val Ala Glu Glu Thr Thr Glu Lys Ser Glu Glu Ser
                820                 825                 830
Val Val Asp Asn Leu Gly Val Lys Val Glu Glu Val Leu Asp Val Asp
                835                 840                 845
Val Glu Glu Val Ala Gln Glu Ala Ala Asp Asp Val Ile Met Arg Val
                850                 855                 860
Ser Glu Asn Glu Ser Glu Gly Glu Ser Gly Ala Glu Ser Gly Glu Glu
865                 870                 875                 880
Val Glu Glu Leu Glu Ser Ala Leu Phe Glu Val Glu Lys Asp Ile Lys
                885                 890                 895
Lys Lys Val Leu Asp Met Phe Ser Gly Asn Val Glu Phe Asp Glu Lys
                900                 905                 910
```

Glu Ser Glu Lys Leu Ala Leu Asp Leu Gln Lys Asn Leu Leu Ser His
        915                 920                 925
His His His His His
    930

<210> SEQ ID NO 26
<211> LENGTH: 2802
<212> TYPE: DNA
<213> ORGANISM: Plasmodium vivax

<400> SEQUENCE: 26

| | | | | |
|---|---|---|---|---|
| atggctgtgg | aggtggtcca | agaggccgct | gacgaggtgc | tcgaagagga | gaagatcgag | 60 |
| gagccactgg | agatcgtgga | ggaagagcca | gtgcaagtcg | ccgccgagga | gccagtcgag | 120 |
| gaagtgctcg | aagaggtggt | gcaagaggcc | gccgacgagg | tcatggagga | agagaagatc | 180 |
| gaggagcctc | tggagatcgt | cgctgaagaa | cctctggaga | tcgtggctga | ggagcctgtg | 240 |
| caggtggctg | ccgaggaagt | gctggtcgag | aaggaagagt | gaacgagaa | catcctcaac | 300 |
| atcgtggagg | agatcaagga | gagcatcgtc | gacaagctgg | aggccaacga | ggaagccagc | 360 |
| gaggaaggca | acgaggacct | cctggagtcc | gctgaggaag | ccgctgagga | agtggctgag | 420 |
| gaagccgtgg | acaccaccac | cgaggctgac | gtggtggaga | cggtggagga | agaggccgct | 480 |
| aacgctacca | ccgaggtgtc | cgctgaggag | agcctggagt | gtccaccga | ggctccagag | 540 |
| gagacgaccg | agtccgagag | ccacgagacg | ttcgaggaag | acatcctgaa | gaacctggag | 600 |
| gagaacaagg | aagccaacga | gaacgccctg | gaggacatca | aggagatgaa | ggaagagttc | 660 |
| ctcgactacg | tggagcaaag | ggtcgaggac | aacgagaacg | tgctggtcga | cctcctgcag | 720 |
| cacctggagc | gcaacgccca | cgtgaacgag | agcgtcctgg | aggacctgga | ggagatcaag | 780 |
| gaagacctcc | tggccaacat | ccaaatggcc | gaggagacga | ggaaggaagt | gaccgacgct | 840 |
| tccgctgaga | gcgctgagga | agtggaggag | cccgtcgagg | tgtccgctga | ggtggctgct | 900 |
| gaggagcctg | tcgaggtggc | cgccgaggag | ccagtggagg | tcaccgctga | ggagcctgtt | 960 |
| gaggtgacgg | ctgaggagcc | agtggagatc | ccaaccgagg | agaacatctt | cgacgtgatc | 1020 |
| gaggagatca | aggagaaggt | cctggagaac | ctggaggaga | cgaccgctga | gagcgtggct | 1080 |
| gagtccgtgg | gcgagggcgc | tgacgagaac | gccctggacg | tgctcaagga | gatgcaagag | 1140 |
| agcctcctgg | agaacttcgg | ccagaagatc | gaggccaacg | agaacatcct | ggccagcgtg | 1200 |
| ctggagaaca | tccaggagaa | ggtcgagctg | aacaagtccg | tgctcgtcga | cgtgctggcc | 1260 |
| gagctcaagg | aagaggccgt | gtcccaaagg | gagacggctc | aagaggtggc | tgctgagctg | 1320 |
| gtggaggaag | ccgctgaggt | cccagctgtg | gagccagtcg | aggaagaggt | ggtggagcca | 1380 |
| gctgtggagg | tggtgagga | gcctgtggag | gaagaggtgt | cgagccagt | ggtcgacgtg | 1440 |
| atcgaggagc | ctgccgtgga | ggtcgtggag | gtcccagtgg | aggagacggt | cgaggagcct | 1500 |
| gtggaggtta | ccgcggagga | gcctgtggag | gtcacggccg | aggagcctgt | cgaggagacg | 1560 |
| gtggaggagc | cagtggtcga | ggtggtcgag | gagccagttg | aggagcctgt | ggtcgaggcc | 1620 |
| atcgaggagc | ccgtcgtcga | gccagtggtc | gagccagccg | tcgaggtcat | cgaggacgct | 1680 |
| acggaggagc | ccgtggagga | agccgccgag | gagccggacg | tggaggtggc | tgagggcagc | 1740 |
| gctatcgagt | ccgtggagga | agccttcgag | caaatcatcg | aggacgccgc | ccaagtgatc | 1800 |
| gctgaggaga | gcgtggagga | gacggctgag | caaatcctgg | agcaagccac | ccaggccgtg | 1860 |
| accgaggaag | ccgctgacgc | tgctgacgtg | gctgacgctg | aggaagccgt | gggcaccgct | 1920 |

```
caagtcgtca ccgaggagag cgtggctgag gctatcgagg acaccgtcga ggagatctcc    1980
gccgagccaa tccaggccac catcgagggc atcgtgggcg aggtcgtcga gtccgtcgag    2040
gagaacatcg aggccgtgga ggaagccatc aaggacatcg tggagggcgc tgtggagggc    2100
gctccagagc tcagcctgga ggagatgatc gaggacgtca tggtgggcac cgtggctgag    2160
gaagactccg ctaaggaagc cgctgaggag acggtggagg aagtggtgca agaggacgct    2220
gctgaggaag aggccgccaa ggaagccgcc gaagagacgg tggaggaagc cgagagggag    2280
gctacccaag aggccgtcga ggagacggtt gaggacgtgg tcgaggaagt gtccgctgag    2340
gctgtggagg agatcgtcct cgaaaccccg gagggcacct ccgacgagag cgtggagacg    2400
gtggtggagc acgctgtgga ggactccctg ggcgagacga tcgccaccat cgtggacgac    2460
gtcgccgagg agacgaccga gaagtccgag gagagcgtgg tcgacaacct gggcgtcaag    2520
gtggaggaag tgctcgacgt cgacgtggag gaagtggccc aagaggccgc cgacgacgtg    2580
atcatgcgcg tcagcgagaa cgagtccgag ggcgagagcg gcgctgagtc cggcgaggaa    2640
gtggaggagc tggagagcgc cctcttcgag gtggagaagg acatcaagaa gaaggtcctc    2700
gacatgttca gcggcaacgt ggagttcgac gagaaggagt ccgagaagct cgccctggac    2760
ctccagaaga acctcctgtc ccaccaccac caccaccact ga                       2802
```

<210> SEQ ID NO 27
<211> LENGTH: 242
<212> TYPE: PRT
<213> ORGANISM: Plasmodium vivax

<400> SEQUENCE: 27

```
Met Thr Tyr Met Leu Met Lys Asp Asp Ser His Asp Asp Lys Asp
1               5                   10                  15

Asp Glu Asn Glu Glu Lys Lys Lys Lys Glu Gly Lys Thr Asn Lys Asp
            20                  25                  30

Thr Asn Lys Ile Ile Lys Gly Glu Ser Met Thr Arg Glu Asp Leu Leu
        35                  40                  45

Gln Leu Leu Asn Glu Met Leu Lys Leu Gln Thr Asp Met Lys Asn Ile
    50                  55                  60

Val Lys Asp Leu Ile Val Val Ala Lys Lys Asn Ser Tyr Asp Phe Met
65                  70                  75                  80

Ser Val Tyr Asn Val Ala Lys Thr Tyr Asn Thr Val Asp Pro Leu Gly
                85                  90                  95

Lys Tyr Gln Ile Glu Met Pro Glu Phe Asp Lys Val Val Glu Asn Tyr
            100                 105                 110

His Phe Asp Pro Glu Val Lys Glu Thr Val Ser Lys Leu Met Ser Ser
        115                 120                 125

Gln Glu Asn Tyr Tyr Ala Asn Met Ser Glu Thr Ala Thr Leu Asn Val
    130                 135                 140

Asp Lys Ile Ile Glu Ile His His Phe Leu Asn Glu Leu Tyr Lys
145                 150                 155                 160

Ile Asp Pro Glu Phe Lys Lys Ile Pro Asn Lys His Glu Leu Asp Pro
                165                 170                 175

Lys Leu Ile Ala Leu Val Ile Gln Ser Ile Val Ser Ala Lys Val Glu
            180                 185                 190

Glu Glu Phe Asn Leu Thr Ser Glu Asp Val Glu Ala Ser Ile Ala Asn
        195                 200                 205

Gln Gln Tyr Ala Leu Thr Ser Asn Met Glu Phe Ala Arg Val Asn Ile
    210                 215                 220
```

Gln Met Gln Thr Ile Met Asn Lys Phe Met Gly Asp His His His
225                 230                 235                 240

His His

<210> SEQ ID NO 28
<211> LENGTH: 729
<212> TYPE: DNA
<213> ORGANISM: Plasmodium vivax

<400> SEQUENCE: 28
atgacctaca tgctcatgaa ggacgacgac tcccacgacg acaaggacga cgagaacgag     60
gagaagaaga agaaggaagg caagaccaac aaggacacca acaagatcat caagggcgag    120
agcatgacca gggaggacct cctgcaactc ctgaacgaga tgctcaagct gcagaccgac    180
atgaagaaca tcgtcaagga cctcatcgtg gtcgccaaga agaactccta cgacttcatg    240
agcgtgtaca acgtcgccaa gacctacaac accgtggacc cactgggcaa gtaccaaatc    300
gagatgccag agttcgacaa ggtggtcgag aactaccact cgacccaga ggtgaaggag    360 acggtgtcca agctcatgtc cagccaggag aactactacg ccaacatgag cgagacggcc    420
accctgaacg tcgacaagat catcgagatc caccacttca tgctcaacga gctgtacaag    480
atcgacccag agttcaagaa gatcccaaac aagcacgagc tggacccaaa gctcatcgcc    540
ctcgtgatcc aatccatcgt gagcgccaag gtcgaggaag agttcaacct cacctccgag    600
gacgtcgagg ccagcatcgc caaccaacag tacgccctga cctccaacat ggagttcgcc    660
cgcgtgaaca tccaaatgca gaccatcatg aacaagttca tgggcgacca ccaccaccac    720
caccactga                                                           729

<210> SEQ ID NO 29
<211> LENGTH: 245
<212> TYPE: PRT
<213> ORGANISM: Plasmodium vivax

<400> SEQUENCE: 29

Met Ala Gly Gly Val Ser Glu Glu Ala Ile Lys Lys Leu Lys Glu Ile
1               5                   10                  15

Lys Lys Leu Glu Leu Asp Ile Leu Lys Asp Phe Met Lys Gln Asp Ala
                20                  25                  30

Gly His Ala Asp Leu Tyr Lys Lys Tyr His Cys Ile Ala Ser Asp Tyr
            35                  40                  45

Ile Ser Gly Asn Pro Lys Gly Ser Ala Glu Gly Pro Asn Leu Ala
        50                  55                  60

Lys Lys Gly Glu Lys Ser Lys Lys Gly Glu Lys His Gln Asn Gly Glu
65                  70                  75                  80

Lys Pro Gln Asn Gly Glu Lys Pro Lys Lys Ser Phe Ile Glu Lys Ile
                85                  90                  95

Ala Ser Phe Val Ser Ile Phe Ser Tyr Asn Asn Val Ser Lys Ile Tyr
            100                 105                 110

Ser Glu His Val Gln Arg Ile Phe Pro Lys Ala Arg Asp His Ala Gly
        115                 120                 125

Asp Gly Ser Ala Gly Asp Ala Ile Tyr Pro Asp Lys Ile Glu Thr
    130                 135                 140

Gly Lys Lys Gln Asn Gln Ser Ser Tyr Val Gln Leu Ser Ala Leu Asn
145                 150                 155                 160

Leu Met Lys Arg Asn Met Phe Leu Gly Gly Lys Asp Lys Ser Ser Glu

```
                    165                 170                 175
His Phe Glu Val Gly Asn Leu Gly Ser Phe Tyr Met Ile Phe Gly Ala
            180                 185                 190

Arg Asn Thr Asp Tyr Pro Trp Ala Cys Ser Cys Asp Pro Leu Gln Leu
            195                 200                 205

Ile Asp Tyr Lys Glu Lys Arg Asn Tyr Val Leu Cys Ser Asn Gln
            210                 215                 220

Val Asp Met Ser Ile Gln Asn Ala Asp Leu Phe Cys Asn Pro Lys His
225                 230                 235                 240

His His His His His
            245

<210> SEQ ID NO 30
<211> LENGTH: 738
<212> TYPE: DNA
<213> ORGANISM: Plasmodium vivax

<400> SEQUENCE: 30
atggccggcg gcgtcagcga ggaagccatc aagaagctca aggagatcaa gaagctggag      60
ctggacatcc tgaaggactt catgaagcaa gacgccggcc acgccgacct ctacaagaag     120
taccactgca tcgccagcga ctacatctcc ggcaacccaa agggctccag cgctgagggc     180
ccaaacctgg ccaagaaggg cgagaagagc aagaagggcg agaagcacca aaacggcgag     240
aagccacaga acggcgagaa gccaaagaag tccttcatcg agaagatcgc ctccttcgtg     300
agcatcttct cctacaacaa cgtcagcaag atctactccg agcacgtgca aaggatcttc     360
ccaaaggccc gcgaccacgc tggcgacggc agcgccggcg acgccatcta cccagacgac     420
aagatcgaga cgggcaagaa gcaaaaccag tccagctacg tccagctctc cgccctcaac     480
ctgatgaagc gcaacatgtt cctgggcggc aaggacaagt ccagcgagca cttcgaagtg     540
ggcaacctcg gcagcttcta catgatcttc ggcgccagga acaccgacta cccatgggcc     600
tgctcctgcg acccactcca gctgatcgac tacaaggaga agaagcgcaa ctacgtgctc     660
tgcagcaacc aagtcgacat gtccatccag aacgccgacc tgttctgcaa cccaaagcac     720
caccaccacc accactga                                                    738

<210> SEQ ID NO 31
<211> LENGTH: 363
<212> TYPE: PRT
<213> ORGANISM: Plasmodium vivax

<400> SEQUENCE: 31

Met Val Ser Cys Thr Ser Leu Cys Leu Tyr Ile Ile Tyr Ser Leu Phe
1               5                   10                  15

Leu Leu Asn Asn Val Ser Leu Ser Ile Gln Val Lys Thr Asn Glu Ile
            20                  25                  30

Lys Asn Gly Gln Asn Gly Ser Val Gln Leu Lys Glu Lys Gly Gly Gly
        35                  40                  45

Val Asn Leu Ala Pro Lys Val Gly Thr Asn Ile Thr Gln Lys Arg Asp
    50                  55                  60

Thr Lys Met Ala Lys Lys Thr Val Thr Lys Val Ala Lys Lys Val
65                  70                  75                  80

Thr Lys Val Ala Glu Lys Thr Gly Thr Lys Val Ala Asp Lys Thr Gly
                85                  90                  95

Thr Lys Val Ala Asp Lys Thr Gly Thr Lys Val Ala Asp Lys Thr Gly
            100                 105                 110
```

-continued

```
Thr Lys Val Ala Glu Lys Thr Gly Thr Lys Val Ala Asp Lys Thr Gly
        115                 120                 125
Thr Lys Val Ala Glu Lys Thr Gly Thr Asn Ile Ser Gln Lys Glu Asp
    130                 135                 140
Glu Lys Gly Pro Pro Lys Glu Asp Thr Gln Gly Thr Gln Lys Ala Asp
145                 150                 155                 160
Ala Lys Ala Ile Gln Gln Ala Asp Ala Gln Val Ser Glu Lys Trp Lys
                165                 170                 175
Lys Lys Glu Trp Lys Glu Trp Ile Lys Lys Ala Glu Ser Asp Leu Asp
            180                 185                 190
Ile Phe Asn Ala Leu Met Asp Asn Glu Lys Glu Lys Lys Trp Tyr Ser
        195                 200                 205
Glu Lys Glu Lys Glu Trp Asn Lys Trp Ile Lys Gly Val Glu Lys Lys
    210                 215                 220
Trp Met His Tyr Asn Lys Asn Ile Tyr Val Glu Tyr Arg Ser Leu Val
225                 230                 235                 240
Phe Trp Val Gly Leu Lys Trp Val Glu Ser Gln Trp Glu Lys Trp Ile
                245                 250                 255

Leu Ser Asp Gly Leu Glu Phe Leu Val Met Asp Trp Lys Lys Trp Ile
            260                 265                 270

Lys Glu Asn Lys Ser Asn Phe Asp Glu Trp Leu Lys Ser Glu Trp Asp
        275                 280                 285

Thr Trp Thr Asn Ser Gln Met Glu Glu Trp Lys Ser Ser Asn Trp Lys
    290                 295                 300

Leu Asn Glu Asp Lys Arg Trp Glu Met Trp Glu Asn Asp Lys Lys Trp
305                 310                 315                 320

Ile Lys Trp Leu Tyr Leu Lys Asp Trp Ile Asn Cys Ser Lys Trp Lys
                325                 330                 335

Lys Arg Ile Gln Lys Glu Ser Lys Glu Trp Leu Arg Trp Thr Lys Leu
            340                 345                 350

Lys Glu Glu Met Tyr His His His His His His
        355                 360

<210> SEQ ID NO 32
<211> LENGTH: 1092
<212> TYPE: DNA
<213> ORGANISM: Plasmodium vivax

<400> SEQUENCE: 32
atggtgtcct gcaccagcct ctgcctgtac atcatctaca gcctcttcct cctgaacaac      60
gtgtccctga gcatccaagt caagaccaac gagatcaaga acggccaaaa cggctccgtc     120
cagctcaagg agaagggcgg cggcgtgaac ctggctccaa aggtcggcac caacatcacc     180
cagaagaggg acaccaagat ggccaagaag accgtgacca aggtcgccaa gaagaaggtc     240
acgaaggtcg ccgagaagac cggcaccaag gtggccgaca agaccggcac caaggtcgct     300
gataagacgg ggacgaaggt cgctgataag accgggacga aggtggctga gaagacgggg     360
acgaaggttg ctgataagac ggggaccaag gtggctgaga agaccggcac caacatcagc     420
caaaaggaag acgagaaggg cccaccaaag gaagacaccc aaggcaccca gaaggccgac     480
gccaaggcca tccaacaggc cgacgcccag gtgagcgaga agtggaagaa gaaggagtgg     540
aaggagtgga tcaagaaggc cgagtccgac ctcgacatct tcaacgccct gatggacaac     600
gagaaggaga agaagtggta cagcgagaag gagaaggagt ggaacaagtg gatcaagggc     660
```

-continued

```
gtggagaaga agtggatgca ctacaacaag aacatctacg tcgagtacag gtccctcgtg    720
ttctgggtcg gcctgaagtg ggtggagtcc caatgggaga agtggatcct cagcgacggc    780
ctggagttcc tggtcatgga ctggaagaag tggatcaagg agaacaagtc caacttcgac    840
gagtggctca agagcgagtg ggacacctgg accaactccc agatggagga gtggaagtcc    900
agcaactgga agctgaacga ggacaagcgc tgggagatgt gggagaacga caagaagtgg    960
atcaagtggc tctacctgaa ggactggatc aactgcagca gtggaagaa gaggatccaa   1020 aaggagtcca aggagtggct ccgctggacc aagctgaagg aagagatgta ccaccaccac   1080
caccaccact ga                                                        1092

<210> SEQ ID NO 33
<211> LENGTH: 415
<212> TYPE: PRT
<213> ORGANISM: Plasmodium vivax

<400> SEQUENCE: 33

Met Gly Glu Asp Ala Glu Val Glu Asn Ala Lys Tyr Arg Ile Pro Ala
1               5                   10                  15

Gly Arg Cys Pro Val Phe Gly Lys Gly Ile Val Ile Glu Asn Ser Asp
            20                  25                  30

Val Ser Phe Leu Arg Pro Val Ala Thr Gly Asp Gln Lys Leu Lys Asp
        35                  40                  45

Gly Gly Phe Ala Phe Pro Asn Ala Asn Asp His Ile Ser Pro Met Thr
    50                  55                  60

Leu Ala Asn Leu Lys Glu Arg Tyr Lys Asp Asn Val Glu Met Met Lys
65                  70                  75                  80

Leu Asn Asp Ile Ala Leu Cys Arg Thr His Ala Ala Ser Phe Val Met
                85                  90                  95

Ala Gly Asp Gln Asn Ser Ser Tyr Arg His Pro Ala Val Tyr Asp Glu
            100                 105                 110

Lys Glu Lys Thr Cys His Met Leu Tyr Leu Ser Ala Gln Glu Asn Met
        115                 120                 125

Gly Pro Arg Tyr Cys Ser Pro Asp Ala Gln Asn Arg Asp Ala Val Phe
    130                 135                 140

Cys Phe Lys Pro Asp Lys Asn Glu Ser Phe Glu Asn Leu Val Tyr Leu
145                 150                 155                 160

Ser Lys Asn Val Arg Asn Asp Trp Asp Lys Lys Cys Pro Arg Lys Asn
                165                 170                 175

Leu Gly Asn Ala Lys Phe Gly Leu Trp Val Asp Gly Asn Cys Glu Glu
            180                 185                 190

Ile Pro Tyr Val Lys Glu Val Glu Ala Glu Asp Leu Arg Glu Cys Asn
        195                 200                 205

Arg Ile Val Phe Gly Ala Ser Ala Ser Asp Gln Pro Thr Gln Tyr Glu
    210                 215                 220

Glu Glu Met Thr Asp Tyr Gln Lys Ile Gln Gln Gly Phe Arg Gln Asn
225                 230                 235                 240

Asn Arg Glu Met Ile Lys Ser Ala Phe Leu Pro Val Gly Ala Phe Asn
                245                 250                 255

Ser Asp Asn Phe Lys Ser Lys Gly Arg Gly Phe Asn Trp Ala Asn Phe
            260                 265                 270

Asp Ser Val Lys Lys Cys Tyr Ile Phe Asn Thr Lys Pro Thr Cys
        275                 280                 285

Leu Ile Asn Asp Lys Asn Phe Ile Ala Thr Thr Ala Leu Ser His Pro
```

```
                290             295             300
Gln Glu Val Asp Leu Glu Phe Pro Cys Ser Ile Tyr Lys Asp Glu Ile
305                 310                 315                 320

Glu Arg Glu Ile Lys Lys Gln Ser Arg Asn Met Asn Leu Tyr Ser Val
                325                 330                 335

Asp Gly Glu Arg Ile Val Leu Pro Arg Ile Phe Ile Ser Asn Asp Lys
            340                 345                 350

Glu Ser Ile Lys Cys Pro Cys Glu Pro Glu Arg Ile Ser Asn Ser Thr
        355                 360                 365

Cys Asn Phe Tyr Val Cys Asn Cys Val Glu Lys Arg Ala Glu Ile Lys
    370                 375                 380

Glu Asn Asn Gln Val Val Ile Lys Glu Glu Phe Arg Asp Tyr Tyr Glu
385                 390                 395                 400

Asn Gly Glu Glu Lys Ser Asn Lys Gln His His His His His
                405                 410                 415

<210> SEQ ID NO 34
<211> LENGTH: 1248
<212> TYPE: DNA
<213> ORGANISM: Plasmodium vivax

<400> SEQUENCE: 34
atgggcgagg acgccgaggt ggagaacgcc aagtacagga tcccagctgg caggtgccca        60
gtgttcggca agggcatcgt catcgagaac tccgacgtga gcttcctccg cccagtggct       120
accggcgacc aaaagctgaa ggacggcgga ttcgccttcc caaacgccaa cgaccacatc       180
tccccaatga ccctcgccaa cctgaaggag aggtacaagg acaacgtgga gatgatgaag       240
ctcaacgaca tcgctctgtg caggacccac gctgctagct tcgtgatggc tggcgaccag       300
aactccagct acaggcaccc agccgtctac gacgagaagg agaagacctg ccacatgctc       360
tacctgtccg cccaagagaa catgggccca aggtactgct ccccagacgc tcagaacagg       420
gacgctgtct tctgcttcaa gccagacaag aacgagtcct tcgagaacct cgtgtacctg       480
agcaagaacg tcaggaacga ctgggacaag aagtgcccac gcaagaacct cggcaacgcc       540
aagttcggcc tgtgggtgga cggcaactgc gaggagatcc catacgtgaa ggaagtggag       600
gccgaggacc tcagggagtg caacaggatc gtcttcggcg cttccgctag cgaccaacca       660
acccagtacg aggaagagat gaccgactac caaaagatcc aacagggctt caggcagaac       720
aaccgcgaga tgatcaagtc cgccttcctc ccagtgggcg ccttcaactc gacaacttc        780 aagagcaagg ccgcggctt caactgggcc aacttcgaca gcgtgaagaa gaagtgctac       840
atcttcaaca ccaagccaac ctgcctgatc aacgacaaga acttcatcgc caccaccgcc       900
ctctcccacc acaagaggt cgacctggag ttcccatgca gcatctacaa ggacgagatc       960
gagagggaga tcaagaagca gtcccgcaac atgaacctct acagcgtgga cggcgagagg      1020
atcgtcctgc cacgcatctt catctccaac gacaaggaga gcatcaagtg cccatgcgag      1080
ccagagagga tctccaacag cacctgcaac ttctacgtgt gcaactgcgt cgagaagagg      1140
gccgagatca aggagaacaa ccaagtggtc atcaaggaag agttcaggga ctactacgag      1200
aacggcgagg agaagtccaa caagcagcac caccaccacc accactga                  1248

<210> SEQ ID NO 35
<211> LENGTH: 892
<212> TYPE: PRT
<213> ORGANISM: Plasmodium vivax
```

<400> SEQUENCE: 35

```
Met Asn Gly Asn Arg Asn Leu Asn Ile Lys Pro Thr Cys His Lys Ser
1               5                   10                  15

Gly Lys Asn Asp Lys Ala Asn Gly Ser Asp Asn Ile Ala Asn Lys Gly
            20                  25                  30

Gly Ala Gln His Ala Ala Asn Gly Ala Thr Gly Thr Pro Ser Gly Ser
        35                  40                  45

Ser Asn Gly Lys Lys Gly Ala Thr Thr Thr Ser Ala Ser Ala Gly Gln
    50                  55                  60

Ala Gly Ala Ser Gly Gly Met Ala Ala Pro Gly Met Asn Pro Asn Phe
65                  70                  75                  80

Glu Gln Met Met Lys Pro Leu Asn Asp Met Phe Lys Gly Asn Gly Glu
                85                  90                  95

Gly Leu Asn Ile Glu Asn Ile Met Asn Ser Asp Met Phe Gln Asn Phe
            100                 105                 110

Phe Asn Ser Leu Met Gly Gly Asn Pro His Asp Gly Ala Gly Gly Gly
        115                 120                 125

Gln Glu Ile Leu Phe Lys Asp Met Leu Asn Ala Met Asn Ala Gln Gly
    130                 135                 140

Gly Gly Ala Pro Gly Ala Ala Thr Ser Gly Gly Ala Asn Lys Asp
145                 150                 155                 160

Pro Asn Ile Ser Val Ser Pro Glu Gln Leu Asn Lys Ile Asn Gln Leu
                165                 170                 175

Lys Asp Lys Leu Glu Asn Val Leu Lys Asn Val Gly Val Asp Val Glu
            180                 185                 190

Gln Leu Lys Glu Asn Met Gln Asn Glu Asn Ile Met Gln Asn Lys Asp
        195                 200                 205

Ala Leu Arg Asp Leu Leu Ala Asn Leu Pro Met Asn Pro Gly Met Met
    210                 215                 220

Gln Asn Met Met Ala Gly Lys Asp Gly Asn Met Phe Asn Met Asp Pro
225                 230                 235                 240

Asn Gln Met Met Asn Met Phe Asn Gln Leu Ser Gln Gly Lys Met Asn
                245                 250                 255

Met Lys Asp Phe Gly Met Gly Asp Phe Met Pro Pro Val His Ala
            260                 265                 270

Asn Asp Gln Asp Ala Glu Asp Ser Arg Gly Lys Ala Phe Val Thr
        275                 280                 285

Asn Ser Ser Asn Asn Asp Ile Asn Phe Ala His Lys Leu Asn Ala Phe
    290                 295                 300

Glu Tyr Ser Asn Gly Pro Ser Glu Gly Met Phe Gln Leu Tyr Gly Met
305                 310                 315                 320

Asn Asn Asp Asp Gly Val Ile Asp Gly Met Ser Asp Ser Val Gly
                325                 330                 335

Lys Asn Ser Ala Leu Asp Val Ser Gly Gly Ser Ile Asn Arg Asn Leu
            340                 345                 350

Ser Asp Gly Asp Ser Ala Lys Glu Asp Ser Asp Glu Ser Asn Ala Asn
        355                 360                 365

Ala Thr Ser Asn Ser Asn Ala Thr Val Pro Asn Lys Gly Gly His Glu
    370                 375                 380

Gly Gly Ser Ala Asn Glu Val Tyr Ser Asn Glu Glu Leu Ile Thr
385                 390                 395                 400

Ser Ser Gly Ser Lys Gly Asp Ala Asn Lys Leu Ala Gly Thr Gly Gly
                405                 410                 415
```

-continued

```
Tyr Lys Asn Asn Asn Ala Phe Leu Asp Leu Asn Asn Leu Lys Lys Asp
                420                 425                 430

Ala Ser Ala Ala Lys Tyr Gly Lys Asp Asn Ser Gly Asp Lys Ser Asn
        435                 440                 445

Gly Gly Asn Ser Asn Gly Gly Asn Asn Lys Val Met Asn Lys Arg Ile
450                 455                 460

Gly Gly Lys Lys Lys Lys Thr Phe Lys Lys Lys Asn Pro Gly Gln
465                 470                 475                 480

Ile Pro Phe Lys Met Glu Thr Leu Gln Lys Leu Val Lys Glu Tyr Thr
                485                 490                 495

Asn Thr Ser Asn Gln Lys Ile Met Glu Lys Ile Ile Lys Lys Tyr Val
            500                 505                 510

Ser Met Ser Asn Gln Ser Ala Arg Gly Asn Ser Glu Glu Glu Asp Asp
        515                 520                 525

Glu Glu Glu Ala Glu Asp Glu Lys Ser Ala Lys Asp Lys Asn Ser Glu
    530                 535                 540

Lys Glu Ala Glu Leu Asn Met Asn Glu Phe Ser Val Lys Asp Ile Lys
545                 550                 555                 560

Lys Leu Ile Ser Glu Gly Ile Leu Thr Tyr Glu Asp Leu Thr Glu Glu
                565                 570                 575

Glu Leu Lys Lys Leu Ala Lys Pro Asp Asp Met Phe Tyr Glu Leu Ser
            580                 585                 590

Pro Tyr Ala Asn Glu Glu Lys Asp Leu Ser Leu Asn Glu Thr Ser Gly
        595                 600                 605

Val Ser Asn Glu Gln Leu Asn Ala Phe Leu Arg Lys Asn Gly Ser Tyr
    610                 615                 620

His Met Ser Tyr Asp Ser Lys Ala Ile Asp Tyr Leu Lys Gln Lys Lys
625                 630                 635                 640

Ala Glu Lys Lys Glu Glu Glu Gln Glu Asp Asp Asn Phe Tyr Asp Ala
                645                 650                 655

Tyr Lys Gln Ile Lys Asn Ser Tyr Glu Gly Ile Pro Ser Asn Tyr Tyr
            660                 665                 670

His Asp Ala Pro Gln Leu Ile Gly Glu Asn Tyr Val Phe Thr Ser Val
        675                 680                 685

Tyr Asp Lys Lys Lys Glu Leu Ile Asp Phe Leu Lys Arg Ser Asn Gly
    690                 695                 700

Ala Thr Asp Ser Ser Asn Ser Ser Ala Gly Lys Asp Lys Gly Asn Ser
705                 710                 715                 720

Ala Glu Ser Gly Thr Tyr Lys Ser Lys Tyr Tyr Asp Lys Tyr Met Lys
                725                 730                 735

Lys Leu Ser Glu Tyr Arg Arg Arg Glu Ala Phe Lys Ile Leu Lys Lys
            740                 745                 750

Arg Arg Ala Gln Glu Lys Lys Met Gln Lys Lys Gln Glu Met Gln Asn
        755                 760                 765

Asn Ser Ser Asn Glu Val Asp Tyr Ser Glu Tyr Phe Lys Lys Asn Gly
    770                 775                 780

Phe Ile Asn Ser Ser Asn Gly Thr Val Lys Thr Phe Ser Lys Asp Gln
785                 790                 795                 800

Leu Asp Asn Met Val Lys Gln Phe Asn Ser Asp Gly Asp Asp Ile Pro
                805                 810                 815

Ser Ser Ser Gly Ala Gly Ala Asp Leu Gly Asp Asn Tyr Ser Gly Val
            820                 825                 830
```

```
Ser Gly Gly Gly Gln Phe Ser Pro Ser Gly Gly Ser Gly Asn Asn Pro
            835                 840                 845

Ser Gly Tyr Val Thr Phe Asp Gly Gln Asn Ile Val Gly Pro Asn Glu
    850                 855                 860

Asn Glu Glu Glu Glu Pro Thr Glu Asp Val Leu Asn Glu Asp Asp Asp
865                 870                 875                 880

Asn Ala Asp Asp Asp Asp His His His His His
                885                 890

<210> SEQ ID NO 36
<211> LENGTH: 2679
<212> TYPE: DNA
<213> ORGANISM: Plasmodium vivax

<400> SEQUENCE: 36
```

| | | | | | |
|---|---|---|---|---|---|
| atgaacggca | acaggaacct | gaacatcaag | ccaacctgcc | acaagagcgg | caagaacgac | 60 |
| aaggccaacg | gctccgacaa | catcgctaac | aagggcggcg | cccaacacgc | tgctaacggc | 120 |
| gccaccggca | ccccaagcgg | ctccagcaac | ggcaagaagg | gcgctacgac | caccagcgct | 180 |
| tccgctggcc | aagctggcgc | ttccggcggc | atggccgccc | aggcatgaa | cccaaacttc | 240 |
| gagcagatga | tgaagccact | gaacgacatg | ttcaagggca | cggcgaggg | cctcaacatc | 300 |
| gagaacatca | tgaacagcga | catgttccag | aacttcttca | actccctgat | gggcggcaac | 360 |
| ccacacgacg | cgctggcgg | cggccaagag | atcctgttca | aggacatgct | caacgccatg | 420 |
| aacgcccaag | gcggcggcgc | cccaggcgct | gccgccacct | ccggcggcgc | caacaaggac | 480 |
| ccaaacatca | gcgtctcccc | agagcagctg | aacaagatca | accaactcaa | ggacaagctg | 540 |
| gagaacgtgc | tcaagaacgt | gggcgtcgac | gtggagcagc | tcaaggagaa | catgcaaaac | 600 |
| gagaacatca | tgcagaacaa | ggacgctctg | agggacctcc | tggctaacct | cccgatgaac | 660 |
| ccaggcatga | tgcaaaacat | gatggccggc | aaggacggca | acatgttcaa | catggaccca | 720 |
| aaccagatga | tgaacatgtt | caaccaactc | agccagggca | agatgaacat | gaaggacttc | 780 |
| ggcatgggcg | acttcatgcc | accaccagtc | cacgccaacg | accaagacgc | tgaggacgac | 840 |
| tcccgcggca | aggctttcgt | gaccaactcc | agcaacaacg | catcaacttc | gcccacaag | 900 |
| ctgaacgcct | tcgagtacag | caacggccca | tccgagggca | tgttccagct | ctacggcatg | 960 |
| aacaacgacg | acgcgtcat | cgacgacggc | atgagcgact | ccgtcggcaa | gaacagcgct | 1020 |
| ctggacgtga | gcggcggctc | catcaacagg | aacctcagcg | acggcgactc | cgccaaggaa | 1080 |
| gacagcgacg | agtccaacgc | caacgccacc | agcaactcca | acgccaccgt | cccaaacaag | 1140 |
| ggcggccacg | agggcggcag | cgctaacgag | gtgtactcca | acgaggaaga | gctgatcacc | 1200 |
| tccagcggct | ccaagggcga | cgctaacaag | ctggctggca | ccggcggcta | caagaacaac | 1260 |
| aacgccttcc | tcgacctgaa | caacctgaag | aaggacgcca | gcgccgccaa | gtacggcaag | 1320 |
| gacaacagcg | cgacaagtc | caacggcggc | aactccaacg | gcggcaacaa | caaggtcatg | 1380 |
| aacagcgca | tcggcggcaa | gaagaagaag | accttcaaga | gaagaagaa | cccaggccaa | 1440 |
| atcccattca | agatggagac | gctccagaag | ctggtcaagg | agtacaccaa | caccagcaac | 1500 |
| caaaagatca | tggagaagat | catcaagaag | tatgtgtcca | tgtccaacca | gagcgccagg | 1560 |
| ggcaactccg | aggaagagga | cgacgaggaa | gaggccgagg | acgagaagag | cgccaaggac | 1620 |
| aagaactccg | agaaggaagc | cgagctgaac | atgaacgagt | tcagcgtcaa | ggacatcaag | 1680 |
| aagctcatct | ccgagggcat | cctgacctac | gaggacctca | ccgaggaaga | gctcaagaag | 1740 |
| ctggccaagc | cagacgacat | gttctacgag | ctcagcccat | acgccaacga | ggagaaggac | 1800 |

-continued

```
ctctccctga acgagacgag cggcgtgtcc aacgagcaac tgaacgcctt cctccgcaag   1860
aacggctcct accacatgag ctacgactcc aaggccatcg actacctgaa gcaaaagaag   1920
gccgagaaga aggaagagga gcaagaggac gacaacttct acgacgccta caagcaaatc   1980
aagaacagct acgagggcat cccatccaac tactaccacg acgccccaca gctcatcggc   2040
gagaactacg tcttcaccag cgtgtacgac aagaagaagg agctgatcga cttcctcaag   2100
aggtccaacg cgctaccga ctccagcaac tccagcgctg caaggacaa gggcaacagc    2160 gctgagtccg gcacctacaa gagcaagtac tacgacaagt acatgaagaa gctgtccgag   2220
tacaggcgca gggaggcctt caagatcctc aagaagcgca gggcccagga gaagaagatg   2280
caaaagaagc aggagatgca aaacaactcc agcaacgagg tggactactc cgagtacttc   2340
aagaagaacg gcttcatcaa ctccagcaac ggcaccgtca agaccttcag caaggaccaa   2400
ctggacaaca tggtgaagca gttcaactcc gacggcgacg acatcccatc cagctccggc   2460
gctggcgctg acctcggcga caactacagc ggcgtgtccg gcgcggcca attcagccca   2520 tccggcggca gcggcaacaa cccatccggc tacgtcacct cgacggcca gaacatcgtg   2580 ggcccaaacg agaacgagga agaggagcca accgaggacg tgctcaacga ggacgacgac   2640
aacgccgacg acgacgacca ccaccaccac caccactga                           2679
```

```
<210> SEQ ID NO 37
<211> LENGTH: 350
<212> TYPE: PRT
<213> ORGANISM: Plasmodium vivax

<400> SEQUENCE: 37
```

Met Pro Leu Glu Val Ser Leu Trp Gly Gln Gly Asn Ala His Leu Gly
1               5                   10                  15

Thr Gln Thr Ser Arg Leu Leu Arg Glu Ser Gly Arg Asn Gly Gln Ala
            20                  25                  30

Asn Arg Val Asn Gln Ala Asp Gln Ala Asp Gln Val Ala Ser Pro Pro
        35                  40                  45

Ile Ser Gly Lys Glu Arg Arg Arg Gly Ile Gly Met Thr Ser Asn Leu
    50                  55                  60

Gln Leu Leu Ser Gly Glu Asp Glu Lys Asp Ser Thr Ser Glu Glu Ala
65                  70                  75                  80

Pro Asn Leu Glu Gly Lys Asp Asn Ala Asp Ala Gly Lys Asp Gly Glu
                85                  90                  95

Lys Glu Pro Ser Glu Lys Gln Ser Gly Asp Val Asp Pro Thr Val Thr
            100                 105                 110

Asp Ala Glu Arg Ala Lys Asp Glu Asn Ala Ser Val Ser Glu Glu Glu
        115                 120                 125

Gln Met Lys Thr Leu Asp Ser Gly Glu Asp His Thr Asp Asp Gly Asn
    130                 135                 140

Ala Asp Gly Gly Gln Gly Gly Asp Gly Asn Asp Glu Asn Gln Lys
145                 150                 155                 160

Gly Asp Gly Lys Glu Lys Glu Gly Gly Glu Glu Lys Lys Glu Asp Gly
                165                 170                 175

Lys Asp Asp His Glu Lys Gly Glu Lys Gly Ser Glu Gly Glu Ser Gly
            180                 185                 190

Glu Lys Asp Glu Ala Ala Pro Lys Gly Asp Ala Glu Lys Asp Lys
        195                 200                 205

Lys Leu Glu Ser Lys Thr Ala Asp Ala Lys Val Ser Glu His Lys Ala

Asp Ala Asn Pro Gly Gly Asn Lys Asp Ser Pro Glu Gly Glu Ser
225                 230                 235                 240

Pro Lys Glu Gly Asn Pro Asp Pro Ser Gln Lys Asn Pro Glu Ala
            245                 250                 255

Ala Gly Asp Asp Ser Arg Leu His Leu Asp Asn Leu Asp Asp Lys
        260                 265                 270

Val Pro His Tyr Ser Ala Leu Arg Asn Asn Arg Val Glu Lys Gly Val
    275                 280                 285

Thr Asp Thr Met Val Leu Asn Asp Ile Ile Gly Glu Asn Ala Lys Ser
290                 295                 300

Cys Ser Val Asp Asn Gly Gly Cys Ala Asp Asp Gln Ile Cys Ile Arg
305                 310                 315                 320

Ile Asp Asn Ile Gly Ile Lys Cys Ile Cys Lys Glu Gly His Leu Phe
                325                 330                 335

Gly Asp Lys Cys Ile Leu Thr Lys His His His His His
            340                 345                 350

<210> SEQ ID NO 38
<211> LENGTH: 1053
<212> TYPE: DNA
<213> ORGANISM: Plasmodium vivax

<400> SEQUENCE: 38

```
atgccgctgg aggtgtccct gtggggccag ggcaacgctc acctcggcac ccaaacctcc      60
cgcctgctca gggagtccgg caggaacggc caggccaaca gggtgaacca ggctgaccag     120
gctgaccaag tggcttcccc accaatctcc ggcaaggaga ggcgcagggg catcggcatg     180
acctccaacc tccaactcct gagcggcgag acgagaagga actccaccag cgaggaagcc     240
ccaaacctgg agggcaagga caacgctgac gctggcaagg atggcgagaa ggagccatcc     300
gagaagcaga gcggcgacgt ggacccaacc gtcaccgacg ctgagagggc taaggacgag     360
aacgcttccg tcagcgagga agagcagatg aagaccctgg acagcggcga ggaccacacc     420
gacgacggca acgctgacgg cggacaaggc ggcggcgacg caacgacga gaaccaaaag     480
ggcgacggca aggagaagga aggcggcgag gagaagaagg aagacggcaa ggacgaccac     540
gagaagggcg agaagggctc cgagggcgag agcggcgaga aggacgaggc tgctccaaag     600
ggcgacgctg ccgagaagga caagaagctg gagtccaaga ccgccgacgc caaggtgagc     660
gagcacaagg ctgacgacgc taacccaggc ggcaacaagg actccccaga gggcgagagc     720
ccaaaggaag gcaacccaga cgacccatcc cagaagaacc cggaggctgc tggcgacgac     780
gacagccgcc tccacctgga caacctcgac gacaaggtcc cacactactc cgccctgcgc     840
aacaacaggg tggagaaggg cgtcaccgac accatggtgc tgaacgacat catcggcgag     900
aacgccaagt cctgcagcgt ggacaacggc ggctgcgctg acgaccaaat ctgcatcagg     960
atcgacaaca tcggcatcaa gtgcatctgc aaggaaggcc acctcttcgg cgacaagtgc    1020
atcctgacca agcaccacca ccaccaccac tga                                 1053
```

<210> SEQ ID NO 39
<211> LENGTH: 296
<212> TYPE: PRT
<213> ORGANISM: Plasmodium vivax

<400> SEQUENCE: 39

Met Asp Val Leu Gln Leu Val Ile Pro Ser Glu Glu Asp Ile Gln Leu

```
              1               5                  10                 15
            Asp Lys Pro Lys Lys Asp Glu Leu Gly Ser Gly Ile Leu Ser Ile Leu
                            20                 25                 30

Asp Val His Tyr Gln Asp Val Pro Lys Glu Phe Met Glu Glu Glu
                        35                 40                  45

Glu Thr Ala Val Tyr Pro Leu Lys Pro Glu Asp Phe Ala Lys Glu Asp
                    50                 55                 60

Ser Gln Ser Thr Glu Trp Leu Thr Phe Ile Gln Gly Leu Glu Gly Asp
             65                 70                 75                 80

Trp Glu Arg Leu Glu Val Ser Leu Asn Lys Ala Arg Glu Arg Trp Met
                            85                 90                 95

Glu Gln Arg Asn Lys Glu Trp Ala Gly Trp Leu Arg Leu Ile Glu Asn
                        100                105                 110

Lys Trp Ser Glu Tyr Ser Gln Ile Ser Thr Lys Gly Lys Asp Pro Ala
                        115                120                 125

Gly Leu Arg Lys Arg Glu Trp Ser Asp Glu Lys Trp Lys Lys Trp Phe
                    130                135                 140

Lys Ala Glu Val Lys Ser Gln Ile Asp Ser His Leu Lys Lys Trp Met
            145                150                 155                160

Asn Asp Thr His Ser Asn Leu Phe Lys Ile Leu Val Lys Asp Met Ser
                            165                170                 175

Gln Phe Glu Asn Lys Lys Thr Lys Glu Trp Leu Met Asn His Trp Lys
                        180                185                 190

Lys Asn Glu Arg Gly Tyr Gly Ser Gly Ser Phe Glu Val Met Thr Thr
                        195                200                 205

Ser Lys Leu Leu Asn Val Ala Lys Ser Arg Glu Trp Tyr Arg Ala Asn
                    210                215                 220

Pro Asn Ile Asn Arg Glu Arg Glu Leu Met Lys Trp Phe Leu Leu
            225                230                 235                240

Lys Glu Asn Glu Tyr Leu Gly Gln Glu Trp Lys Lys Trp Thr His Trp
                            245                250                 255

Lys Lys Val Lys Phe Phe Val Phe Asn Ser Met Cys Thr Thr Phe Ser
                        260                265                 270

Gly Lys Arg Leu Thr Lys Glu Glu Trp Asn Gln Phe Val Asn Glu Ile
                        275                280                 285

Lys Val His His His His His His
                        290                295

<210> SEQ ID NO 40
<211> LENGTH: 891
<212> TYPE: DNA
<213> ORGANISM: Plasmodium vivax

<400> SEQUENCE: 40
atggacgtgc tccaactggt catcccaagc gaggaagaca tccagctcga caagccaaag      60
aaggacgagc tgggcagcgg catcctctcc atcctggacg tgcactacca agacgtccca     120
aaggagttca tggaggaaga ggaagagacg gccgtgtacc cactcaagcc agaggacttc     180
gccaaggaag actcccaaag caccgagtgg ctcaccttca tccaaggcct ggagggcgac     240
tgggagaggc tggaggtgtc cctgaacaag gccagggagc gctggatgga gcaaggaac     300 aaggagtggg ctggctggct caggctgatc gagaacaagt ggtccgagta cagccagatc     360
tccaccaagg gcaaggaccc ggctggcctc aggaagcgcg agtggtccga cgaaaagtgg     420
aagaagtggt tcaaggccga ggtgaagagc caaatcgact cccacctgaa gagtggatg     480
```

```
aacgacaccc acagcaacct cttcaagatc ctggtcaagg acatgtccca gttcgagaac    540
aagaagacca aggagtggct catgaaccac tggaagaaga acgagagggg ctacggctcc    600
gagagcttcg aggtcatgac caccagcaag ctcctgaacg tcgccaagtc cagggagtgg    660
taccgcgcca acccaaacat caaccgcgag aggcgcgagc tcatgaagtg gttcctcctg    720
aaggagaacg agtacctggg ccaagagtgg aagaagtgga cccactggaa gaaggtgaag    780
ttcttcgtct tcaacagcat gtgcaccacc ttctccggca agcgcctgac caaggaagag    840
tggaaccagt tcgtgaacga gatcaaggtc caccaccacc accaccactg a              891
```

<210> SEQ ID NO 41
<211> LENGTH: 291
<212> TYPE: PRT
<213> ORGANISM: Plasmodium vivax

<400> SEQUENCE: 41

```
Met Glu Ala Met Pro Lys Phe Pro Gln Asn Asn Leu Lys Gly Gly Leu
1               5                   10                  15

Lys Asp Ser Pro Leu Lys Gln Pro Lys Ser Pro Leu Ile Asn Gly Pro
            20                  25                  30

Pro Lys Pro Val Asn Asp Lys Leu Asp Asp Ser Asn Lys Thr Glu
        35                  40                  45

Thr Lys Asp Ala Lys Asn Gly Leu Asn Lys Pro Lys Asn Ile Asn
50                  55                  60

Asp Lys Val Lys Asp Gly Glu Asn Lys Thr Pro Ser Gln Asp Leu Asn
65                  70                  75                  80

Glu Pro Ser Phe Lys Leu Pro Met Arg Gln Lys Ser Ser Trp Tyr
            85                  90                  95

Thr Trp Leu Lys Gly Thr Lys Lys Asp Tyr Glu Thr Leu Lys Cys Phe
        100                 105                 110

Ala Lys Gly Asn Leu Tyr Asp Trp Leu Cys Asn Val Arg Glu Ser Phe
        115                 120                 125

Asp Leu Tyr Leu Gln Ser Leu Glu Lys Lys Trp Thr Thr Cys Ser Asp
    130                 135                 140

Ser Ala Thr Thr Leu Phe Leu Cys Glu Cys Phe Ala Glu Ser Ser Gly
145                 150                 155                 160

Trp Asn Asp Ser Gln Trp Gly Asn Trp Met Asn Asn Gln Leu Lys Glu
                165                 170                 175

Gln Leu Lys Thr Glu Ala Glu Ala Trp Ile Ser Thr Lys Lys Lys Asp
            180                 185                 190

Phe Asp Gly Leu Thr Ser Lys Tyr Phe Ser Leu Trp Lys Asp His Arg
        195                 200                 205

Arg Lys Glu Leu Asp Ala Asp Glu Trp Lys Asn Lys Val Ser Ser Gly
    210                 215                 220

Gly Leu Ser Glu Trp Glu Glu Leu Thr Asn Lys Met Asn Thr Arg Tyr
225                 230                 235                 240

Arg Asn Asn Leu Asp Asn Met Trp Ser His Phe Ser Arg Asp Leu Phe
                245                 250                 255

Phe Asn Phe Asp Glu Trp Ala Pro Gln Val Leu Glu Lys Trp Ile Glu
            260                 265                 270

Asn Lys Gln Trp Asn Arg Trp Val Lys Lys Val Arg Lys His His His
        275                 280                 285

His His His
    290
```

<210> SEQ ID NO 42
<211> LENGTH: 876
<212> TYPE: DNA
<213> ORGANISM: Plasmodium vivax

<400> SEQUENCE: 42

```
atggaggcca tgccaaagtt cccacaaaac aacctcaagg gcggcctgaa ggactcccca     60
ctcaagcagc caaagagccc actgatcaac ggcccaccaa agccagtgaa cgacaagctc    120
aaggacgact ccaacaagac cgagacgaag gacgccaaga acggcctgaa caagccacca    180
aagaacatca acgacaaggt caaggacggc gagaacaaga ccccatccca agacctcaac    240
gagccaagct tcaagctgcc aatgaggcag aaggagtcca gctggtacac ctggctcaag    300
ggcaccaaga aggactacga gacgctgaag tgcttcgcca agggcaacct ctacgactgg    360
ctgtgcaacg tgcgcgagtc cttcgacctc tacctgcaaa gcctggagaa gaagtggacc    420
acctgctccg acagcgctac caccctcttc ctgtgcgagt gcttcgccga gtccagcggc    480
tggaacgact cccagtgggg caactggatg aacaaccaac tcaaggagca gctgaagacc    540
gaggccgagg cctggatcag caccaagaag aaggacttcg acggcctcac ctccaagtac    600
ttcagcctgt ggaaggacca caggcgcaag gagctcgacg ccgacgagtg gaagaacaag    660
gtgtccagcg gcggcctcag cgagtgggag gagctgacca acaagatgaa caccaggtac    720
cgcaacaacc tcgacaacat gtggtcccac ttcagcaggg acctgttctt caacttcgac    780
gagtgggccc cacaagtcct ggagaagtgg atcgagaaca agcagtggaa ccgctgggtg    840
aagaaggtcc gcaagcacca ccaccaccac cactga                              876
```

<210> SEQ ID NO 43
<211> LENGTH: 866
<212> TYPE: PRT
<213> ORGANISM: Plasmodium vivax

<400> SEQUENCE: 43

```
Met Gln Lys Ala Pro Asn Asn Gly Lys Asn Asn Tyr Gly Leu Asn Asp
1               5                   10                  15

Asp Glu Leu Gly Ala Ile Leu Phe Gly Leu Asn Tyr Asp Ser Ile Ala
            20                  25                  30

Lys Asn Lys Asp Asn Leu Glu Lys Arg Lys Asn Val Glu Asn Glu Ser
        35                  40                  45

Ile Phe Leu Arg Asn Phe Ala Asn Glu Asp Thr Ser Lys Asn Thr Gln
    50                  55                  60

Ser Glu Lys Ala Gln Lys Glu Ile Lys Ile Glu Thr Glu Thr Glu Ser
65                  70                  75                  80

Val Asn Ser Asn Glu Lys Glu Val Ala Thr Ser Gln Lys Ser Asp Thr
                85                  90                  95

Ser Asn Lys Asn Ser Ser Val Glu Asn Glu Lys Ile Glu Leu Lys Asn
            100                 105                 110

Asp Glu Leu Leu Gly Lys Asn Phe Glu Lys Asp Lys Val Asn Lys Lys
        115                 120                 125

Gly Asp Asn Thr Asn Thr Thr Asn Asn His Asp Leu Thr Asn Ser Ser
    130                 135                 140

Glu Lys Gln Gly Val Asp Ile Arg Gly Ser Lys Asn Met Asn Asn Tyr
145                 150                 155                 160

Leu Gln Lys Thr Gly Asp Thr Asn Ile Glu Lys Ser Glu Ser Leu Gln
                165                 170                 175
```

-continued

```
Lys Asp Val Asn Ile Lys Asn His Asn Glu Glu Ala Asn Asp Ala Lys
            180                 185                 190

Arg Leu Asp Ser Ala Gln Thr Asn Asn Glu Lys Ser Lys Ile Ser Lys
            195                 200                 205

Asp Thr Ile Asp Lys Asp Val Gln Ser Asn Glu Leu Thr Asn Leu Ala
            210                 215                 220

Ser Asn Arg Ser Asn Lys Lys Ser Gln Gly Leu Ala Lys Lys Glu Asn
225                 230                 235                 240

Glu Leu Lys Ser Ala Asn Leu Glu Glu Asn His Asn Ala Lys Lys Asp
                245                 250                 255

Leu Leu Lys Lys Asp Gln Lys Arg Glu Asp Gly Lys Lys Ile Thr His
            260                 265                 270

Pro Glu Asn Ser Asn Ser Asp Gln Tyr Gly Val Gln Val Ser Leu Asn
            275                 280                 285

Asp Glu Glu Lys Asn Thr Asn Thr Lys Ser Val Ser His Ser Glu Asp
            290                 295                 300

His Ser Ala Ser Tyr Ser Gly Glu Lys Phe Gly Thr His Val Ser Asn
305                 310                 315                 320

Ser Gln Lys Asp Met Leu Lys Asn Ile Arg Pro Val Gln Phe Asp Glu
                325                 330                 335

Ser Ala Tyr Gly Lys Leu Asn Gly Gly Ser Pro Glu Asn Asp Glu Asn
            340                 345                 350

Glu Ile Leu Asn Lys Ile Asn Lys Asn Asn Glu Asn Asn Phe Ser Glu
            355                 360                 365

Lys Val Ala Leu Arg Lys Gly Thr Lys Asp Arg Asn Glu Tyr Glu Tyr
            370                 375                 380

Phe Lys Leu Lys Ser Asn Asp Phe Lys Val Leu Gly Ile Ile Asn Lys
385                 390                 395                 400

Tyr Ser Ser Arg Gly Gly Phe Ser Ile Ser Val Asp Cys Gly Gly Tyr
                405                 410                 415

Asp Asp Phe Asp Glu Val Pro Gly Val Ser Asn Leu Leu Gln His Ala
            420                 425                 430

Ile Phe Tyr Lys Ser Glu Lys Arg Asn Thr Thr Leu Leu Ser Glu Leu
            435                 440                 445

Gly Lys Tyr Ser Ser Glu Tyr Asn Ser Cys Thr Ser Glu Ser Ser Thr
            450                 455                 460

Ser Tyr Tyr Ala Thr Ala His Ser Glu Asp Ile Tyr His Leu Leu Asn
465                 470                 475                 480

Leu Phe Ala Glu Asn Leu Phe Tyr Pro Val Phe Ser Glu Glu His Ile
                485                 490                 495

Gln Asn Glu Val Lys Glu Ile Asn Asn Lys Tyr Ile Ser Ile Glu Asn
            500                 505                 510

Asn Leu Glu Ser Cys Leu Lys Ile Ala Ser Gln Tyr Ile Thr Asn Phe
            515                 520                 525

Lys Tyr Ser Lys Phe Phe Val Asn Gly Asn Tyr Thr Thr Leu Cys Glu
            530                 535                 540

Asn Val Leu Lys Asn Arg Leu Ser Ile Lys Asn Ile Leu Thr Glu Phe
545                 550                 555                 560

His Lys Lys Cys Tyr Gln Pro Arg Asn Met Ser Leu Thr Ile Leu Leu
                565                 570                 575

Gly Asn Lys Val Asn Thr Ala Asp His Tyr Asn Met Lys Asp Val Glu
            580                 585                 590
```

Asn Met Val Val His Ile Phe Gly Lys Ile Lys Asn Glu Ser Tyr Pro
         595                 600                 605

Ile Asp Gly Asp Val Ile Gly Lys Arg Ile Asn Arg Met Glu Ser Glu
    610                 615                 620

Arg Val Asn Leu Tyr Gly Lys Lys Asp Ser Tyr Asn Asp Ala Asn Phe
625                 630                 635                 640

Ile His Ile Glu Gly Arg Asn Glu Lys Glu Ala Ala Phe Leu Gln Ser
                645                 650                 655

Met Asn Glu Leu His Tyr Ala Leu Asp Leu Asn Gln Lys Ser Arg Tyr
            660                 665                 670

Val Glu Ile Ile Lys Lys Glu Glu Trp Gly Asp Gln Leu Tyr Leu Tyr
        675                 680                 685

Trp Ser Ser Lys Thr Asn Ala Glu Leu Cys Lys Lys Ile Glu Glu Phe
    690                 695                 700

Gly Ser Met Thr Phe Leu Arg Glu Ile Phe Ser Asp Phe Arg Arg Asn
705                 710                 715                 720

Gly Leu Tyr Tyr Lys Ile Ser Val Glu Asn Lys Tyr Val Tyr Asp Leu
                725                 730                 735

Glu Val Thr Ser Ile Cys Asn Lys Tyr Tyr Leu Asn Phe Gly Ile Leu
            740                 745                 750

Val Lys Leu Thr Gln Arg Gly Arg Thr Asn Leu Ala His Leu Ile His
        755                 760                 765

Ile Cys Asn Val Phe Val Asn Glu Ile Gly Lys Leu Phe Asp Arg Asp
    770                 775                 780

Ser Leu Asp Lys Gly Ile Ser Lys Tyr Ile Leu Asp Tyr Tyr Arg Glu
785                 790                 795                 800

Lys Ala Leu Val Thr Asp Leu Lys Phe Asn Ser Asp Asn Val Asn Val
                805                 810                 815

Ser Leu Asp Asp Leu Val Ile Tyr Ser Lys Arg Leu Leu Val His Ala
            820                 825                 830

Asp Asp Pro Ser Ser Leu Leu Thr Ile His Ser Leu Ile Glu Asp Lys
        835                 840                 845

His Lys Asn Asp Phe Arg Asn His Ile Lys Ile Thr His His His His
    850                 855                 860

His His
865

<210> SEQ ID NO 44
<211> LENGTH: 2601
<212> TYPE: DNA
<213> ORGANISM: Plasmodium vivax

<400> SEQUENCE: 44
atgcaaaagg ccccaaacaa cggcaagaac aactacggcc tcaacgacga cgagctgggc     60
gccatcctct tcggcctgaa ctacgacagc atcgccaaga caaggacaa cctggagaag    120 aggaagaacg tcgagaacga gtccatcttc ctgcgcaact cgccaacga ggacaccagc    180 aagaacaccc aatccgagaa ggcccagaag gagatcaaga tcgagacgga gacggagtcc    240
gtcaacagca cgagaagga gtggccacc tcccagaaga gcgacacctc caacaagaac    300
tccagcgtcg agaacgagaa gatcgagctg aagaacgacg agctcctggg caagaacttc    360
gagaaggaca aggtgaacaa gaagggcgac aacaccaaca ccaccaacaa ccacgacctc    420
accaactcca gcgagaagca aggcgtcgac atcaggggca gcaagaacat gaacaactac    480
ctccaaaaga ccggcgacac caacatcgag aagtccgaga gcctgcagaa ggacgtgaac    540

```
atcaagaacc acaacgagga agccaacgac gccaagaggc tggacagcgc ccagaccaac      600
aacgagaaga gcaagatctc caaggacacc atcgacaagc acgtgcaatc caacgagctc      660
accaacctgg ccagcaaccg ctccaacaag aagagccagg cctcgccaa gaaggagaac       720 gagctcaagt ccgccaacct ggaggagaac acaacgcca agaaggacct cctgaagaag       780
gaccaaaaga gggaggacgg caagaagatc acccacccag agaactccaa cagcgaccaa      840
tacggcgtgc aagtgtccct gaacgacgag gagaagaaca ccaacaccaa gtccgtcagc      900
cactccgagg accacagcgc ttcctacagc ggcgagaagt cggcaccca cgtctccaac       960 agccaaaagg acatgctcaa gaacatccgc ccagtgcagt tcgacgagag cgcttacggc      1020
aagctcaacg gcggctcccc agagaacgac gagaacgaga tcctgaacaa gatcaacaag      1080
aacaacgaga caacttcag cgagaaggtg gccctcagga agggcaccaa ggaccgcaac       1140
gagtacgagt acttcaagct caagtccaac gacttcaagg tcctgggcat catcaacaag      1200
tactccagca ggggcggctt ctccatcagc gtggactgcg gcggatacga cgacttcgac      1260
gaggtgccag gcgtctccaa cctcctgcaa cacgccatct tctacaagag cgagaagcgc      1320
aacaccaccc tcctgtccga gctcggcaag tactccagcg agtacaacag ctgcacctcc      1380
gagtccagca ccagctacta cgccaccgcc cactccgagg acatctacca cctcctgaac      1440
ctcttcgccg agaacctgtt ctacccagtc ttcagcgagg agcacatcca aaacgaggtg      1500
aaggagatca caacaagta catctccatc gagaacaacc tggagagctg cctgaagatc      1560
gcctcccagt acatcaccaa cttcaagtac agcaagttct tcgtcaacgg caactacacc      1620
accctctgcg agaacgtgct caagaacagg ctgagcatca agaacatcct gaccgagttc      1680
cacaagaagt gctaccagcc acgcaacatg tccctcacca tcctcctggg caacaaggtc      1740
aacaccgccg accactacaa catgaaggac gtggagaaca tggtggtcca catcttcggc      1800
aagatcaaga cgagtccta cccaatcgac ggcgacgtca tcggcaagag gatcaaccgc      1860
atggagagcg agagggtcaa cctctacggc aagaaggact cctacaacga cgccaacttc      1920
atccacatcg agggccgcaa cgagaaggaa ccgccttcc tccaaagcat gaacgagctg       1980
cactacgccc tcgacctgaa ccagaagtcc cgctacgtgg agatcatcaa gaaggaagag      2040
tggggcgacc aactctacct gtactggtcc agcaagacca cgccgagct ctgcaagaag       2100 atcgaggagt tcggcagcat gaccttcctc cgcgagatct tctccgactt caggcgcaac      2160
ggcctgtact acaagatcag cgtggagaac aagtatgtgt acgacctgga ggtgacctcc      2220
atctgcaaca gtactacct gaacttcggc atcctcgtca gctgacccca aggggccgc        2280 accaacctcg ctcacctgat ccacatctgc aacgtgttcg tcaacgagat cggcaagctc      2340
ttcgacaggg acagcctgga caagggcatc tccaagtaca tcctcgacta ctaccgcgag      2400
aaggccctcg tgaccgacct gaagttcaac agcgacaacg tgaacgtctc cctcgatgac      2460
ctggtcatct acagcaagag gctcctggtg cacgccgacg acccatccag cctcctgacc      2520
atccactccc tcatcgagga caagcataag aacgacttcc gcaaccacat caagatcacc      2580
caccaccacc accaccactg a                                                2601
```

<210> SEQ ID NO 45
<211> LENGTH: 276
<212> TYPE: PRT
<213> ORGANISM: Plasmodium vivax

<400> SEQUENCE: 45

```
Met Lys Glu Ala Val Lys Lys Gly Ser Lys Ala Met Lys Gln Pro
1               5                   10                  15

Met His Lys Pro Asn Leu Leu Glu Glu Glu Asp Phe Glu Glu Lys Glu
            20                  25                  30

Ser Phe Ser Asp Asp Glu Met Asn Gly Phe Met Glu Glu Ser Met Asp
        35                  40                  45

Ala Ser Lys Leu Asp Ala Lys Lys Ala Lys Thr Thr Leu Arg Ser Ser
    50                  55                  60

Glu Lys Lys Lys Thr Pro Thr Ser Gly Met Ser Gly Met Ser Gly Ser
65                  70                  75                  80

Gly Ala Thr Ser Ala Ala Thr Glu Ala Ala Thr Asn Met Asn Ala Thr
                85                  90                  95

Ala Met Asn Ala Ala Ala Lys Gly Asn Ser Glu Ala Ser Lys Lys Gln
            100                 105                 110

Thr Asp Leu Ser Asn Glu Asp Leu Phe Asn Asp Glu Leu Thr Glu Glu
        115                 120                 125

Val Ile Ala Asp Ser Tyr Glu Glu Gly Gly Asn Val Gly Ser Glu Glu
    130                 135                 140

Ala Glu Ser Leu Thr Asn Ala Phe Asp Asp Lys Leu Leu Asp Gln Gly
145                 150                 155                 160

Val Asn Glu Asn Thr Leu Leu Asn Asp Asn Met Ile Tyr Asn Val Asn
                165                 170                 175

Met Val Pro His Lys Lys Arg Glu Leu Tyr Ile Ser Pro His Lys His
            180                 185                 190

Thr Ser Ala Ala Ser Ser Lys Asn Gly Lys His His Ala Ala Asp Ala
        195                 200                 205

Asp Ala Leu Asp Lys Lys Leu Arg Ala His Glu Leu Leu Glu Leu Glu
    210                 215                 220

Asn Gly Glu Gly Ser Asn Ser Val Ile Val Glu Thr Glu Glu Val Asp
225                 230                 235                 240

Val Asp Leu Asn Gly Gly Lys Ser Ser Gly Ser Val Ser Phe Leu Ser
                245                 250                 255

Ser Val Val Phe Leu Leu Ile Gly Leu Leu Cys Phe Thr Asn His His
            260                 265                 270

His His His His
        275

<210> SEQ ID NO 46
<211> LENGTH: 831
<212> TYPE: DNA
<213> ORGANISM: Plasmodium vivax

<400> SEQUENCE: 46
atgaaggaag ccgtgaagaa gggctccaag aaggccatga agcaaccaat gcacaagcca     60
aacctcctgg aggaagagga cttcgaggag aaggagtcct tcagcgacga cgagatgaac    120
ggcttcatgg aggagtccat ggacgccagc aagctggacg ccaagaaggc caagaccacc    180
ctcaggtcca gcgagaagaa gaagacccca acctccggca tgagcggcat gtccggcagc    240
ggcgctacca gcgctgctac cgaggccgcc accaacatga acgctaccgc catgaacgct    300
gccgccaagg gcaactccga ggctagcaag aagcaaaccg acctctccaa cgaggacctg    360
ttcaacgacg agctcaccga ggaagtgatc gccgacagct acgaggaagg cggcaacgtg    420
ggctccgagg aagccgagag cctgaccaac gccttcgacg acaagctcct ggaccagggc    480
gtgaacgaga cacccctcct gaacgacaac atgatctaca cgtgaacat ggtcccacac     540
```

-continued

```
aagaagaggg agctctacat ctccccacac aagcacacca gcgccgcctc cagcaagaac     600
ggcaagcacc acgctgctga cgctgacgct ctggacaaga agctcagggc tcacgagctc     660
ctggagctgg agaacggcga gggctccaac agcgtgatcg tcgagacgga ggaagtggac     720
gtggacctga acgcggcaa gtcctccggc tccgtcagct tcctctccag cgtggtcttc      780
ctcctgatcg gcctcctgtg cttcaccaac caccaccacc accaccactg a              831
```

<210> SEQ ID NO 47
<211> LENGTH: 649
<212> TYPE: PRT
<213> ORGANISM: Plasmodium vivax

<400> SEQUENCE: 47

| | | | | | | | | | | | | | | |
|---|---|---|---|---|---|---|---|---|---|---|---|---|---|---|
| Met | Asp | Asp | Asn | Gly | Arg | Arg | Leu | Pro | Arg | Lys | Ala | Ala | Pro | Val |
| 1 | | | | 5 | | | | | 10 | | | | | 15 |
| Asp | Lys | Ala | Lys | Gln | Asp | Val | Met | Lys | Asp | Ile | Val | Asn | Tyr | Leu | Ser |
| | | | 20 | | | | | 25 | | | | | 30 | | |
| Lys | Asn | Met | Leu | Ala | Phe | Val | Arg | Gln | Lys | Arg | Asn | Val | Ser | Gly | Lys |
| | | | 35 | | | | | 40 | | | | | 45 | | |
| Glu | Gly | Glu | Ala | Pro | Thr | Gly | Pro | Ser | Gly | Ala | Gln | Gly | Gly | Asp | Ser |
| | 50 | | | | | 55 | | | | | 60 | | | | |
| Ser | Gln | Tyr | Ala | Ser | Lys | Phe | Thr | Phe | Thr | Asp | His | Ser | Val | Asp | Phe |
| 65 | | | | | 70 | | | | | 75 | | | | | 80 |
| Ser | Lys | Tyr | Asn | Lys | Leu | Asp | Lys | Glu | Lys | Phe | Ala | Ala | Lys | Asp | Asp |
| | | | | 85 | | | | | 90 | | | | | 95 | |
| Leu | Lys | Ser | Arg | Leu | Lys | Asn | Glu | Val | Val | Ala | Ser | Met | Leu | Asp | Thr |
| | | | 100 | | | | | 105 | | | | | 110 | | |
| Glu | Gly | Asp | Ile | Leu | Thr | Glu | Glu | Phe | Gly | Tyr | Leu | Leu | Arg | Asn | Tyr |
| | | 115 | | | | | 120 | | | | | 125 | | | |
| Phe | Asp | Lys | Val | Lys | Leu | Glu | Glu | Lys | Lys | Ser | Gln | Glu | Ala | Glu | Ser |
| 130 | | | | | 135 | | | | | 140 | | | | | |
| Ala | Lys | Pro | Ala | Glu | Gln | Glu | Glu | Ala | Glu | Ala | Pro | Glu | Gln |
| 145 | | | | 150 | | | | | 155 | | | | | 160 |
| Lys | Glu | Glu | Ala | Thr | Ala | Glu | Lys | Ala | Thr | Glu | Glu | Thr | Thr | Glu | Ala |
| | | | | 165 | | | | | 170 | | | | | 175 | |
| Ala | Thr | Glu | Glu | Thr | Thr | Glu | Ala | Ala | Thr | Glu | Glu | Thr | Thr | Glu | Ala |
| | | | 180 | | | | | 185 | | | | | 190 | | |
| Ala | Thr | Glu | Glu | Thr | Thr | Glu | Ala | Ala | Thr | Glu | Glu | Thr | Thr | Glu | Ala |
| | | | 195 | | | | | 200 | | | | | 205 | | |
| Ala | Thr | Glu | Glu | Thr | Thr | Glu | Ala | Ala | Thr | Glu | Glu | Thr | Thr | Glu | Ala |
| | | 210 | | | | | 215 | | | | | 220 | | | |
| Ala | Thr | Glu | Glu | Thr | Thr | Glu | Ala | Ala | Thr | Glu | Glu | Ala | Thr | Glu | Gly |
| 225 | | | | | 230 | | | | | 235 | | | | | 240 |
| Ala | Thr | Glu | Glu | Gly | Ala | Glu | Glu | Thr | Thr | Glu | Glu | Ala | Thr | Glu | Glu |
| | | | | 245 | | | | | 250 | | | | | 255 | |
| Gly | Ala | Glu | Glu | Ala | Thr | Glu | Glu | Gly | Ala | Glu | Ala | Thr | Glu | Glu |
| | | | 260 | | | | | 265 | | | | | 270 | | |
| Gly | Ala | Glu | Glu | Thr | Thr | Glu | Glu | Ala | Thr | Glu | Glu | Gly | Ala | Glu | Glu |
| | | | 275 | | | | | 280 | | | | | 285 | | |
| Thr | Thr | Glu | Glu | Thr | Thr | Glu | Glu | Gly | Ala | Glu | Glu | Ala | Thr | Glu |
| | | 290 | | | | | 295 | | | | | 300 | | | |
| Glu | Gly | Ala | Glu | Glu | Thr | Thr | Glu | Glu | Gly | Ala | Glu | Glu | Ala | Ala | Glu |
| 305 | | | | | 310 | | | | | 315 | | | | | 320 |

| | | | | | | | | | | | |
|---|---|---|---|---|---|---|---|---|---|---|---|
|Glu|Gly|Ala|Glu|Glu|Gly|Ala|Glu|Ala|Ala|Thr|Glu|Glu|Ala|Thr|Glu|
| | | |325| | | |330| | | |335| | | | |

Glu Ala Thr Glu Glu Ala Thr Glu Glu Ala Thr Glu Glu Ala Thr Glu
              340                 345                 350

Glu Ala Thr Glu Glu Ala Thr Ala Glu Val Ala Glu Ala Ala Thr Pro
              355                 360                 365

Glu Lys Val Thr Glu Ala Thr Glu Glu Ala Thr Glu Glu Gly Asp
              370                 375                 380

Asn Glu Pro Ala Glu Gln Ala Ala Glu Lys Glu Asp Val Lys Gly
385                 390                 395                 400

Gly Leu Met Asp Asn Glu Thr Tyr Tyr Asn Thr Leu Gln Glu Leu Tyr
                405                 410                 415

Glu Glu Ile Glu Asn Asp Asp Lys Lys Glu Lys Glu Lys Ile Gln Lys
              420                 425                 430

Ala Lys Glu Gln Glu Glu Leu Glu Lys Lys Leu Phe Lys Glu Ser Lys
              435                 440                 445

Lys Gly Lys Lys Lys Glu Lys Lys Arg Arg Lys Lys Leu Cys Lys Met
              450                 455                 460

Ala Lys Ile Val Glu Lys Tyr Ala Glu Glu Ile Pro Lys Asp Ser Glu
465                 470                 475                 480

Arg Ser Leu Arg Tyr Asp Lys Glu Glu His Ile Asp Asp Pro Asp Glu
                485                 490                 495

Met Asp Asp Leu Leu Phe Gly Glu Phe Lys Thr Leu Glu Lys Tyr Gly
              500                 505                 510

Thr His Lys Thr Ser Thr Phe Tyr Tyr Glu Met Thr Cys Phe Asp Glu
              515                 520                 525

Arg Leu Arg Asp Phe Glu Ile Asn Thr Lys Leu Lys Glu Met Glu Glu
530                 535                 540

Val Pro Glu Lys Trp Glu Leu Leu Ser Leu Tyr Trp Gln Ser Tyr Arg
545                 550                 555                 560

Asn Glu Arg His Lys Tyr Leu Ala Val Lys Lys Tyr Leu Leu Glu Lys
                565                 570                 575

Phe Leu Glu Leu Lys Thr Asn Gln Ser Thr Glu Ala Leu Pro Lys Tyr
              580                 585                 590

Asn Lys Lys Trp Lys Gln Cys Glu Glu Ile Val Asp Asn Asn Phe Thr
              595                 600                 605

Lys Gln His Glu His Val Asn Asp Val Phe Tyr Thr Phe Val Ala Lys
              610                 615                 620

Glu Asn Leu Ser Arg Asp Glu Phe Lys Glu Ile Leu Asn Asp Val Arg
625                 630                 635                 640

Ala Ser Trp His His His His His His
                645

<210> SEQ ID NO 48
<211> LENGTH: 1950
<212> TYPE: DNA
<213> ORGANISM: Plasmodium vivax

<400> SEQUENCE: 48

| | |
|---|---|
|atggacgaca acggcaggcg cctcccaagg aaggctgccc caccagtgga caaggccaag|60|
|caggacgtga tgaaggacat cgtcaactac ctctccaaga acatgctggc cttcgtgagg|120|
|caaaagcgca acgtctccgg caaggaaggc gaggctccaa ccggcccaag cggcgctcaa|180|
|ggcggcgact ccagccagta cgccagcaag ttcaccttca ccgaccactc cgtggacttc|240|

```
agcaagtaca acaagctcga caaggagaag ttcgccgcca aggacgacct caagtccagg    300
ctgaagaacg aggtggtcgc cagcatgctc gacaccgagg gcgacatcct gaccgaggag    360
ttcggctacc tcctgcgcaa ctacttcgac aaggtcaagc tggaggagaa gaagtcccaa    420
gaggccgaga gcgctaagcc agctgagcaa gaggaagagg ccgaggaagc cccagagcaa    480
aaggaagagg ccaccgctga gaaggctacc gaggagacga ccgaggctgc cacggaggag    540
acgacggagg ccgccacgga ggagacgacc gaggccgcca ccgaggagac gacggaggct    600
gccactgaag agacgaccga ggctgcgacg gaagagacga ccgaggccgc gacggaagag    660
acgactgagg ctgccactga ggagacgacg gaagctgcta ccgaggaagc caccgagggc    720
gctaccgagg aaggcgctga ggagacgacg gaggaagcca cggaggaagg cgctgaggaa    780
gccaccgagg aaggcgccga ggaagccacg gaggaaggcg cagaggagac gacagaggaa    840
gccacggagg aaggcgccga agagacgacc gaagagacga ccgaggaagg cgcggaggaa    900
gaggccactg aggaaggcgc cgaggagacg actgaggaag gcgcagagga agccgctgag    960
gaaggcgctg aggaaggcgc tgaggccgcc acggaggaag ccaccgagga agccacggag   1020
gaagccacgg aggaagccac agaggaagcc actgaggaag ccacagagga agccacagct   1080
gaggtggctg aggctgctac cccagagaag gtcacagagg aagccacaga ggaagccacc   1140
gaggaaggcg acaacgagcc agctgagcag gctgctgaga aggaagagga cgtgaagggc   1200
ggcctcatgg acaacgagac gtactacaac accctccaag agctgtacga ggagatcgag   1260
aacgacgaca agaaggagaa ggagaagatc caaaaggcca aggagcaaga ggagctggag   1320
aagaagctgt tcaaggagtc caagaagggc aagaagaagg agaagaagag gcgcaagaag   1380
ctctgcaaga tggccaagat cgtcgagaag tacgccgagg agatcccaaa ggactccgag   1440
aggagcctgc gctacgacaa ggaagagcac atcgacgacc cagacgagat ggacgacctc   1500
ctgttcggcg agttcaagac cctggagaag tacggcaccc acaagacctc caccttctac   1560
tacgagatga cctgcttcga cgagaggctc cgcgacttcg agatcaacac caagctgaag   1620
gagatggagg aagtgccaga gaagtgggag ctcctgtccc tctactggca gagctacagg   1680
aacgagcgcc acaagtacct ggccgtcaag aagtacctcc tggagaagtt cctggagctg   1740
aagaccaacc aaagcaccga ggccctgcca aagtacaaca agaagtggaa gcagtgcgag   1800
gagatcgtcg acaacaactt caccaagcaa cacgagcacg tgaacgacgt cttctacacc   1860
ttcgtggcca aggagaacct ctccagggac gagttcaagg agatcctgaa cgacgtccgc   1920
gccagctggc accaccacca ccaccactga                                    1950
```

<210> SEQ ID NO 49
<211> LENGTH: 332
<212> TYPE: PRT
<213> ORGANISM: Plasmodium vivax

<400> SEQUENCE: 49

```
Met Arg Cys Cys Thr Lys Asp Ala Val Asn Val Glu Ser Pro Lys Lys
1               5                   10                  15

Val Val Val Gly Glu Thr Glu Glu Asp Thr Arg Glu Glu Glu Asn Pro
            20                  25                  30

Tyr Glu Asp Leu Pro Thr Val Thr Val Thr Leu Ser Asp Gly Ser Val
        35                  40                  45

Tyr Thr Gly Thr Thr Lys Asp Asn Arg Val His Gly Arg Gly Val Leu
    50                  55                  60

Lys Tyr Val Asn Gly Asp Gln Tyr Glu Gly Glu Phe Val Asp Gly Lys
```

```
                65                  70                  75                  80
Lys Glu Gly Lys Gly Lys Trp Thr Asp Lys Glu Asn Asn Thr Tyr Glu
                    85                  90                  95

Gly Asp Trp Val Lys Asp Lys Arg His Gly His Gly Val Tyr Lys Thr
               100                 105                 110

Ala Glu Gly Phe Ile Phe Glu Gly Phe Ala Asn Asn Lys Arg Glu
           115                 120                 125

Gly Lys Gly Thr Ile Ile Thr Pro Glu Lys Thr Lys Tyr Val Cys Ser
    130                 135                 140

Phe Gln Asp Asp Glu Glu Val Gly Glu Val Glu Phe Phe Phe Ala Asn
145                 150                 155                 160

Gly Asp His Ala Leu Gly Tyr Ile Lys Asp Gly Tyr Leu Cys Gln Asn
                165                 170                 175

Gly Arg Tyr Glu Phe Lys Asn Gly Asp Ile Tyr Val Gly Asn Phe Glu
            180                 185                 190

Lys Gly Leu Phe His Gly Glu Gly Tyr Tyr Lys Trp Asn Asn Asp Ala
        195                 200                 205

Asn Tyr Thr Ile Tyr Glu Gly Asn Tyr Ser Glu Gly Lys Lys His Gly
    210                 215                 220

Lys Gly Gln Leu Ile Asn Lys Asp Gly Arg Ile Leu Cys Gly Met Phe
225                 230                 235                 240

Arg Asp Asn Asn Met Asp Gly Glu Phe Leu Glu Ile Ser Pro Gln Gly
                245                 250                 255

Asn Gln Thr Lys Val Leu Tyr Asp Lys Gly Phe Phe Val Lys Val Leu
            260                 265                 270

Asp Lys Ile Glu Glu Asn Leu Asp Val Gln Glu Phe Leu Lys Asp Ser
        275                 280                 285

Ile Ile His Thr Thr Ile Phe Ser Asp Pro Thr Thr Tyr Lys Lys Leu
    290                 295                 300

Tyr Glu Ile Thr Glu Lys Lys Pro Gln Phe Arg Leu Asn Leu Lys
305                 310                 315                 320

Arg Thr Gln Pro Thr Ser His His His His His
                325                 330

<210> SEQ ID NO 50
<211> LENGTH: 999
<212> TYPE: DNA
<213> ORGANISM: Plasmodium vivax

<400> SEQUENCE: 50
atgaggtgct gcaccaagga cgccgtcaac gtggagtccc caaagaaggt ggtcgtgggc    60
gagacggagg aagacaccag ggaggaagag aacccatacg aggacctccc aaccgtcacc   120
gtgaccctgt ccgacggcag cgtctacacc ggcaccacca aggacaacag ggtgcacggc   180
cgcggcgtcc tcaagtatgt gaacggcgac caatacgagg cgagttcgt cgacggcaag   240 aaggaaggca agggcaagtg gaccgacaag gagaacaaca cctacgaggg cgactgggtc   300
aaggacaaga ggcacggcca cggcgtgtac aagaccgctg agggcttcat cttcgagggc   360
gagttcgcca acaacaagcg cgagggcaag ggcaccatca tcaccccaga gaagaccaag   420
tatgtgtgca gcttccaaga cgacgaggaa gtgggcgagg tggagttctt cttcgccaac   480
ggcgaccacg ccctcggcta catcaaggac ggctacctgt gccagaacgg ccgctacgag   540
ttcaagaacg gcgacatcta cgtgggcaac ttcgagaagg gcctgttcca cggcgagggc   600
tactacaagt ggaacaacga cgccaactac accatctacg agggcaacta ctccgagggc   660
```

```
aagaagcacg gcaagggcca actcatcaac aaggacggca ggatcctgtg cggcatgttc      720
cgcgacaaca acatggacgg cgagttcctg gagatcagcc acaaggcaa ccagaccaag       780 gtcctctacg acaagggctt cttcgtcaag gtgctggaca agatcgagga gaacctcgac      840
gtgcaggagt tcctgaagga ctccatcatc cacaccacca tcttcagcga cccaaccacc      900
tacaagaagc tgtacgagat caccgagaag aagaagccac aattcaggct caacctgaag      960
cgcacccagc caacctccca ccaccaccac caccactga                             999
```

<210> SEQ ID NO 51
<211> LENGTH: 309
<212> TYPE: PRT
<213> ORGANISM: Plasmodium vivax

<400> SEQUENCE: 51

```
Met Asn Lys Leu Gly Thr Ser Leu Val Glu Asp Ala Thr Ala Asn Gly
1               5                   10                  15

Glu Phe Gly Leu Arg Val Gln Arg Leu Leu Gly Gly Ser Arg Ser Ser
            20                  25                  30

Arg Asp Ser Ile Phe Ala Asp Ser Phe Tyr Asp Asp Asp Asp Asp
        35                  40                  45

Asp Asp Asn Asn Asp Lys Leu Phe Asp Tyr Asp Ser Asp His Lys Ser
    50                  55                  60

Arg Arg Glu Val Lys Asp Arg His His Arg His Arg Ser His Ser
65                  70                  75                  80

His Arg His Lys Arg Arg His Ser His Lys His Arg Thr Ser Ser Arg
                85                  90                  95

Ser Arg Arg Glu Lys Glu Glu Ser Ser Thr Thr Asn Asp Asp Asp Asp
            100                 105                 110

Glu Val Leu Ser Leu Ser Arg Phe Asp Val Asp Asp Asp Lys Asp Asp
        115                 120                 125

Arg Ser His Ser Arg Tyr Ser Val Asp Tyr Asp Glu Asn Asp Asp
    130                 135                 140

Glu Pro Ser Ser Ser Arg Pro Ala Ser Thr Asp Tyr Asp Asp Ile Ile
145                 150                 155                 160

Asp Leu Thr Asn Ala Arg Arg Ser Gly Ser Lys Tyr Arg Ile Ser Ser
                165                 170                 175

Met Asp Ile Glu Leu Tyr Pro Glu His Glu Asp Glu Tyr Leu Phe Glu
            180                 185                 190

Gly Lys Arg Arg Ser Gly Gly Val Leu Lys Lys Ala Asp Asn Tyr Cys
        195                 200                 205

Glu Asn Lys Ile Phe Asp Ala Leu Ser Ala Leu Asp Lys Tyr Lys Glu
    210                 215                 220

Tyr Tyr Gly Glu Glu Arg Arg Val Met Lys Gln Ala Ala Tyr Arg Lys
225                 230                 235                 240

Ala Thr Lys Val Phe Ala Ile Pro Gly Ala Ala Leu Ser Pro Leu
                245                 250                 255

Ile Ile Thr Leu Phe Leu Thr Thr Ser Asn Val Val Ala Leu Pro Leu
            260                 265                 270

Ala Ala Ser Ala Val Ile Leu Gly Gly Ile Leu Tyr Lys Lys Ser Lys
        275                 280                 285

Asp Lys Ser Asp Tyr Gly Arg Pro His Leu Lys Ser Ile Thr Tyr His
    290                 295                 300

His His His His
```

<210> SEQ ID NO 52
<211> LENGTH: 930
<212> TYPE: DNA
<213> ORGANISM: Plasmodium vivax

<400> SEQUENCE: 52

| | | | | | |
|---|---|---|---|---|---|
| atgaacaagc | tgggcaccag | cctcgtggag | gacgctaccg | ctaacggcga | gttcggcctc | 60 |
| cgcgtccaaa | ggctgctggg | cggctccagg | tccagccgcg | acagcatctt | cgccgactcc | 120 |
| ttctacgatg | atgacgacga | cgacgacgac | aacaacgaca | agctgttcga | ctacgacagc | 180 |
| gaccacaagt | ccaggcgcga | ggtgaaggac | aggcaccaca | ggcacaggca | cagccactcc | 240 |
| caccgccaca | gaggcgcca | cagccacaag | cacaggacct | ccagccgctc | caggcgcgag | 300 |
| aaggaagagt | ccagcaccac | caacgacgac | gacgacgagg | tgctcagcct | gtccaggttc | 360 |
| gacgtcgacg | acgacaagga | cgacaggagc | cactcccgct | acagcgtgga | ctacgacgac | 420 |
| gagaacgacg | acgagccatc | cagctccagg | ccagcctcca | ccgactacga | cgacatcatc | 480 |
| gacctcacca | acgctaggcg | cagcggctcc | aagtaccgca | tcagctccat | ggacatcgag | 540 |
| ctctacccag | agcacgagga | cgagtacctg | ttcgagggca | gaggcgcag | cggcggcgtc | 600 |
| ctgaagaagg | ctgacaacta | ctgcgagaac | aagatcttcg | acgccctctc | cgccctggac | 660 |
| aagtacaagg | agtactacgg | cgaggagagg | gcgtgatga | agcaggccgc | ctacaggaag | 720 |
| gccaccaagg | tcttcgctat | cccaggcgct | gccgccctca | gcccactgat | catcaccctc | 780 |
| ttcctgacca | ccagcaacgt | ggtggctctc | ccactggctg | cttccgccgt | catcctcggc | 840 |
| ggcatcctgt | acaagaagag | caaggacaag | tccgactacg | ccgcccaca | cctcaagtcc | 900 |
| atcacctacc | accaccacca | ccaccactga | | | | 930 |

<210> SEQ ID NO 53
<211> LENGTH: 332
<212> TYPE: PRT
<213> ORGANISM: Plasmodium vivax

<400> SEQUENCE: 53

Met Glu Ala Ala Arg Gly Val Ser Gly Leu Val Pro Ser Ser Asn Ser
1               5                   10                  15

Leu Gln Glu Ile Thr Leu Arg Tyr Lys Asp Lys Leu Leu Asn Met Asp
            20                  25                  30

Lys Glu Gln Met Ile Leu Thr Leu Gly Val Thr Met Ile Ala Ile Thr
        35                  40                  45

Ser Ala Val Ala Phe Gly Val Leu Ala Thr His Gly Asp Ile Asn Asp
    50                  55                  60

Phe Leu Gly Val Glu Ser Asp Glu Glu Ser Lys Lys Lys Glu Ile
65                  70                  75                  80

Val Glu Lys Ser Glu Glu Trp Lys Arg Lys Glu Trp Ser Asn Trp Leu
                85                  90                  95

Lys Lys Leu Glu Gln Asp Trp Lys Val Phe Asn Glu Lys Leu Gln Asn
            100                 105                 110

Glu Lys Lys Thr Phe Leu Glu Glu Lys Glu Glu Asp Trp Asn Thr Trp
        115                 120                 125

Ile Lys Ser Val Glu Lys Lys Trp Thr His Phe Asn Pro Asn Met Asp
    130                 135                 140

Lys Glu Phe His Thr Asn Met Met Arg Arg Ser Ile Asn Trp Thr Glu
145                 150                 155                 160

```
Ser Gln Trp Arg Glu Trp Ile Gln Thr Glu Gly Arg Leu Tyr Leu Asp
                165                 170                 175

Ile Glu Trp Lys Lys Trp Phe Phe Glu Asn Gln Ser Arg Leu Asp Glu
            180                 185                 190

Leu Ile Val Lys Lys Trp Ile Gln Trp Lys Lys Asp Lys Ile Ile Asn
        195                 200                 205

Trp Leu Met Ser Asp Trp Lys Arg Ala Glu Gln Glu His Trp Glu Glu
    210                 215                 220

Phe Glu Glu Lys Ser Trp Ser Ser Lys Phe Phe Gln Ile Phe Glu Lys
225                 230                 235                 240

Arg Asn Tyr Glu Asp Phe Lys Asp Arg Val Ser Asp Glu Trp Glu Asp
                245                 250                 255

Trp Phe Glu Trp Val Lys Arg Lys Asp Asn Ile Phe Ile Thr Asn Val
            260                 265                 270

Leu Asp Gln Trp Ile Lys Trp Lys Glu Glu Lys Asn Leu Leu Tyr Asn
        275                 280                 285

Asn Trp Ala Asp Ala Phe Val Thr Asn Trp Ile Asn Lys Lys Gln Trp
    290                 295                 300

Val Val Trp Val Asn Glu Arg Arg Asn Leu Ala Ala Lys Ala Lys Ala
305                 310                 315                 320

Ala Leu Asn Lys Lys Lys His His His His His His
                325                 330
```

<210> SEQ ID NO 54
<211> LENGTH: 999
<212> TYPE: DNA
<213> ORGANISM: Plasmodium vivax

<400> SEQUENCE: 54

```
atggaggctg ccaggggcgt gtccggcctc gtcccatcca gcaacagcct ccaagagatc      60
accctgcgct acaaggacaa gctcctgaac atggacaagg agcagatgat cctcaccctg     120
ggcgtcacca tgatcgctat cacctccgct gtggctttcg gcgtcctggc tacccacggc     180
gacatcaacg acttcctggg cgtcgagtcc gacgaggaga gcgagaagaa gaaggagatc     240
gtggagaagt ccgaggagtg gaagaggaag gagtggagca actggctcaa gaagctggag     300
caagactgga aggtcttcaa cgagaagctc cagaacgaga agaagacctt cctggaggag     360
aaggaagagg actggaacac ctggatcaag tccgtggaga agaagtggac ccacttcaac     420
ccaaacatgg acaaggagtt ccacaccaac atgatgaggc gctccatcaa ctggaccgag     480
agccaatggc gcgagtggat ccagaccgag ggcaggctct acctggacat cgagtggaag     540
aagtggttct tcgagaacca aagcaggctc gacgagctga tcgtgaagaa gtggatccag     600
tggaagaagg acaagatcat caactggctc atgtccgact ggaagcgcgc cgagcaagag     660
cactgggagg agttcgagga gaagagctgg tccagcaagt tcttccagat cttcgagaag     720
cgcaactacg aggacttcaa ggaccgcgtg agcgacgagt gggaggactg gttcgagtgg     780
gtcaagcgca aggacaacat cttcatcacc aacgtgctgg accagtggat caagtggaag     840
gaagagaaga acctcctgta caacaactgg gccgacgcct tcgtcaccaa ctggatcaac     900
aagaagcagt gggtggtctg ggtgaacgag aggcgcaacc tcgctgctaa ggctaaggct     960
gccctgaaca agaagaagca ccaccaccac caccactga                            999
```

<210> SEQ ID NO 55
<211> LENGTH: 405

<212> TYPE: PRT
<213> ORGANISM: Plasmodium vivax

<400> SEQUENCE: 55

```
Met Thr Lys Gly Pro Ser Gly Pro Pro Asn Lys Lys Leu Asn Ala
1               5                   10                  15

Asn Ala Leu His Phe Leu Arg Gly Lys Leu Glu Leu Leu Asn Lys Ile
            20                  25                  30

Ser Glu Glu Gln Val Val Ser Pro Asp Phe Lys Lys Asn Val Glu Leu
        35                  40                  45

Leu Lys Lys Lys Ile Glu Glu Leu Gln Gly Lys Ala Glu Lys Asp Lys
    50                  55                  60

Ser Lys Thr Asp Gly Glu Asp Thr Thr Pro Lys Gln Gln Glu Asp
65                  70                  75                  80

Gln Asn Val Ser Gln Asn Gly Leu Glu Glu Ala Pro Ser Asp Ser
                85                  90                  95

Asn Glu Gly Glu Ala Gln Glu Glu Asn Thr Gln Val Lys Asn Val Ile
            100                 105                 110

Phe Thr Glu Lys Glu Glu Ala Val Asp Glu Glu Ala Glu Lys Glu Asp
        115                 120                 125

Thr Ala Val Ile Ser Glu Lys Ala Asn Phe Pro Asn Glu Glu Ser Gln
130                 135                 140

Gly Asn Asp Glu Thr Gln Thr Gln Glu Ser Ile Glu Gly Glu Ala Ser
145                 150                 155                 160

Pro Gly Val Val Val Asp Glu Thr Asp Ser Pro Glu Gly Glu Pro
                165                 170                 175

Leu Ser Gly Leu Glu Thr Glu Gly Asn Ser Ser Ala Glu Ser Ala Pro
            180                 185                 190

Asn Glu Pro Asp Val Asn Thr Thr His Thr Ala Val Asp Thr His Met
        195                 200                 205

Pro Ala Asp Ala Asn Ile Gly Val Asp Thr Asn Met Pro Phe Asp Thr
    210                 215                 220

Pro Pro His Pro Ser Gly Glu Asn Pro Gly Ala Pro Gln Glu Thr His
225                 230                 235                 240

Leu Pro Ser Ile Asp Glu Asn Ala Asn Arg Arg Ala Ser Arg Met Lys
                245                 250                 255

His Met Ser Ser Phe Leu Asn Gly Leu Leu Thr Asn Gln Ser Asn Asn
            260                 265                 270

Lys Lys Glu Ile Phe Phe His Pro Tyr Tyr Gly Pro Tyr Phe Asn His
        275                 280                 285

Gly Gly Tyr Tyr Asn Tyr Asp Pro Tyr Asn Tyr Ala Pro Ala Tyr
    290                 295                 300

Asn Pro Phe Val Ser Gln Ala Arg Asp Tyr Glu Val Ile Lys Lys Leu
305                 310                 315                 320

Leu Asp Ala Cys Phe Asn Lys Gly Glu Gly Ala Asp Pro Asn Val Pro
                325                 330                 335

Cys Ile Ile Asp Ile Phe Lys Lys Val Leu Asp Asp Glu Arg Phe Arg
            340                 345                 350

Asn Glu Leu Lys Thr Phe Met Tyr Asp Leu Tyr Glu Phe Leu Lys Lys
        355                 360                 365

Asn Asp Val Leu Ser Asp Asp Glu Lys Lys Asn Glu Leu Met Arg Phe
    370                 375                 380

Phe Phe Asp Asn Ala Phe Gln Leu Val Asn Pro Met Pro Tyr Tyr His
385                 390                 395                 400
```

His His His His His
            405

<210> SEQ ID NO 56
<211> LENGTH: 1218
<212> TYPE: DNA
<213> ORGANISM: Plasmodium vivax

<400> SEQUENCE: 56

| | | | |
|---|---|---|---|
| atgaccaagg gcccatccgg cccaccacca aacaagaagc tcaacgccaa cgccctccac | 60 |
| ttcctgaggg gcaagctgga gctcctgaac aagatctccg aggagcaagt ggtcagccca | 120 |
| gacttcaaga agaacgtcga gctcctcaag aagaagatcg aggagctcca gggcaaggcc | 180 |
| gagaaggaca gtccaagac cgacggcgag acaccaccc caaggagca acaagaggac | 240 |
| caaaacgtga gccagaacgg cctggaggag caagctccgt ccgacagcaa cgagggcgag | 300 |
| gctcaagagg agaacaccca ggtcaagaac gtgatcttca ccgagaagga agaggccgtc | 360 |
| gacgaggaag ccgagaagga agacaccgcc gtgatctccg agaaggccaa cttcccaaac | 420 |
| gaggagagcc agggcaacga cgagacgcaa acccaagagt ccatcgaggg cgaggctagc | 480 |
| ccgggcgtgg tggtggacga gacggacgac tccccggagg gcgagccact cagcggcctc | 540 |
| gaaaccgagg gcaactccag cgctgagtcc gctccaaacg agccagacgt caacaccacc | 600 |
| cacaccgctg tggacaccca catgccagct gacgccaaca tcggcgtcga caccaacatg | 660 |
| ccattcgaca ccccaccaca cccaagcggc gagaacccgg gcgccccaca agagacgcac | 720 |
| ctcccatcca tcgacgagaa cgccaacagg cgcgccagca ggatgaagca catgtccagc | 780 |
| ttcctgaacg gcctcctgac caaccagtcc aacaacaaga aggagatctt cttccaccca | 840 |
| tactacggcc catacttcaa ccacggcgga tactacaact acgacccata ctacaactac | 900 |
| gccccagcct acaacccatt cgtcagccaa gcccgcgact acgaggtcat caagaagctc | 960 |
| ctggacgcct gcttcaacaa gggcgagggc gctgacccaa cgtcccatg catcatcgac | 1020 |
| atcttcaaga aggtgctcga cgacgagagg ttccgcaacg agctgaagac cttcatgtac | 1080 |
| gacctctacg agttcctgaa gaagaacgac gtcctcagcg acgacgagaa gaagaacgag | 1140 |
| ctgatgaggt tcttcttcga caacgccttc cagctcgtga acccaatgtt ctactaccac | 1200 |
| caccaccacc accactga | 1218 |

<210> SEQ ID NO 57
<211> LENGTH: 875
<212> TYPE: PRT
<213> ORGANISM: Plasmodium vivax

<400> SEQUENCE: 57

Met Phe Ser Gly Gly Val Gly Asp Asp Glu Glu Glu Glu Glu Glu Glu
1               5                   10                  15

Glu Gly Glu Gly Glu Gly Glu Ser Glu Arg Asp Asp Ser Glu Arg Asp Tyr
            20                  25                  30

Ala Gly Arg Asp Asp Ala Gly Arg Asp Ala Glu Arg Asn Asp Ala
            35                  40                  45

Glu Arg Asp Asp Ala Glu Arg Asn Asp Ala Glu Arg Asp Asp Ala Glu
            50                  55                  60

Arg Asp His Ala Glu Arg Asp His Ala Asp Lys Ala Glu Ser Asp Arg
65                  70                  75                  80

Glu Ser Ser Leu Glu Ala Asn Glu Asn Arg Leu Val Lys Leu Ser Glu
            85                  90                  95

```
Gly Gly Glu Ser Glu Pro Ala Leu Leu Glu Val Glu Asp Ile Lys
            100                 105                 110

Gln Thr Val Leu Gly Met Phe Ser Leu Lys Gly Glu Phe Asp Glu Ala
        115                 120                 125

Glu Ser Glu Lys Leu Ala Leu Asp Leu Gln Lys Asn Leu Leu Ser Met
130                 135                 140

Leu Ser Gly Asn Met Glu Asp Asn Asp Glu Tyr Glu Asp Ile Asp
145                 150                 155                 160

Glu Glu Tyr Glu Glu Val Glu Asp Tyr Glu Glu Lys Leu Gly
                165                 170                 175

Lys Pro Val Glu Val Val Glu Asp Ala Thr Glu Glu Ala Val Asp
            180                 185                 190

Glu Val Val Gly Val Val Gln Glu Pro Glu Glu Gly Ala Glu Glu
        195                 200                 205

Ser Asp Lys Asp Thr Gly Glu Val Ser Glu Glu Val Ala Lys Glu
    210                 215                 220

Ala Ala Asp Glu Val Met Glu Glu Lys Lys Glu Glu Ala Gly Glu
225                 230                 235                 240

Pro Ser Val Val Glu Glu Pro Ser Val Val Lys Glu Pro Ser
            245                 250                 255

Val Val Val Lys Glu Pro Ser Val Val Glu Glu Pro Ser Val Val
            260                 265                 270

Val Glu Glu Pro Ser Val Val Glu Glu Pro Ser Val Val Glu
        275                 280                 285

Glu Pro Ala Phe Thr Val Glu Glu Pro Ala Phe Thr Val Glu Glu Pro
    290                 295                 300

Ala Ile Thr Val Glu Glu Pro Ala Ile Thr Val Glu Glu Pro Val Phe
305                 310                 315                 320

Thr Val Glu Glu Pro Val Phe Thr Val Glu Glu Pro Ala Phe Thr Val
            325                 330                 335

Glu Glu Pro Ala Phe Thr Val Glu Glu Pro Ala Phe Thr Val Glu Glu
            340                 345                 350

Pro Ala Thr Thr Val Glu Glu Leu Val Glu Glu Val Leu Lys Val Ala
            355                 360                 365

Glu Glu Glu Val Ala Thr Glu Ala Val Glu Lys Asp Gly Glu Glu Ala
370                 375                 380

Glu Glu Gln Val Thr Glu Glu Ser Val Glu Glu Asp Glu Glu Glu Ser
385                 390                 395                 400

Gly Glu Glu Glu Gly Glu Glu Ser Glu Glu Glu Thr Glu Glu Ser
                405                 410                 415

Ala Glu Glu Glu Val Ala Lys Glu Ser Val Glu Glu Glu Val Ala Lys
            420                 425                 430

Glu Ala Glu Glu Ser Glu Glu Ser Gly Glu Glu Ser Ala Glu Glu Glu
        435                 440                 445

Lys Glu Lys Ala Glu Glu Pro Val Ala Pro Val Asp Glu Val Leu Lys
    450                 455                 460

Glu Gly Met Gln Lys Ile Glu Glu Ser Val Lys Glu Ala Leu Gly Val
465                 470                 475                 480

Val Gln Glu Ala Val Asp Lys Val Ala Glu Glu Glu Gln Thr Glu Gln
                485                 490                 495

Ala Gln Gly Pro Ala Glu Ala Gly Pro Val Gly Val Val Lys Glu Pro
            500                 505                 510
```

| | | | | | | | | | | | |
|---|---|---|---|---|---|---|---|---|---|---|---|
|Glu|Glu|Glu|Glu|Ser|Glu|Glu|Gly|Glu|Gly|Glu|Gly|
| |515| | |520| | | |525| | | |
|Glu|Glu|Gly|Glu|Glu|Glu|Glu|Glu|Ser|Glu|Glu|Ser|
|530| | | |535| | | |540| | | |
|Glu|Glu|Gly|Glu|Ser|Glu|Ala|Gly|Glu|Ser|Glu|Ala|Gly|Lys|Ser|Asp|
|545| | | |550| | | |555| | | |560|
|Ala|Ala|Glu|Ser|Glu|Val|Ala|Glu|Ser|Glu|Ala|Gly|Glu|Pro|Ala|Glu|
| | | | |565| | | |570| | | |575|
|Asp|Gln|Ala|Gly|Met|Asp|Ala|Lys|Met|Lys|Asp|Glu|Leu|Leu|Gly|Met|
| | | |580| | | | |585| | | |590|
|Leu|Ser|Glu|Lys|Met|Lys|Ala|Glu|Gly|Lys|Asp|Leu|Asp|Lys|Leu|Pro|
| |595| | | | |600| | | | |605|
|Pro|Glu|Val|Lys|Lys|Asn|Leu|Leu|Asp|Met|Leu|Ala|Gly|Asn|Met|Glu|
| |610| | | | |615| | | | |620|
|Met|Asp|Asp|Glu|Glu|Glu|Gly|Glu|Glu|Gly|Glu|Asp|Leu|Gly|
|625| | | | |630| | | | |635| | | |640|
|Asn|Glu|Glu|Leu|Asp|Leu|Gln|Lys|Asn|Leu|Glu|Met|Leu|Ser|Gly|
| | | | |645| | | |650| | | |655|
|Lys|Gly|Gly|Phe|Asn|Pro|Asn|Met|Leu|Gly|Asn|Leu|Lys|Glu|Leu|Glu|
| | | |660| | | | |665| | | |670|
|Ala|Leu|Gln|Lys|Ser|Val|Pro|Gly|Leu|Met|Gly|Lys|Ala|Gln|Gly|Ile|
| | |675| | | | |680| | | | |685|
|Ser|Pro|Ala|Glu|Ile|Glu|Ser|Leu|Lys|Ser|Met|Phe|Ser|Gly|Ala|Phe|
| |690| | | | |695| | | | |700|
|Asp|Ser|Arg|Gly|Phe|Lys|Gly|Met|Pro|Gln|Met|Lys|Leu|Pro|Ala|Glu|
|705| | | | |710| | | | |715| | | | |720|
|Leu|Gln|Ser|Ile|Met|Met|Pro|Lys|Lys|Glu|Lys|Gly|Lys|Pro|Gln|
| | | | |725| | | |730| | | |735|
|Gly|Ala|Gln|Ala|Lys|Ala|Lys|Val|Pro|Ala|Lys|Ala|Gly|Gln|Val|Gln|
| | | |740| | | | |745| | | | |750|
|Lys|Pro|Lys|Ala|Gln|Asp|Ile|Met|Pro|Ser|Arg|Arg|Ile|Arg|Asp|Leu|
| | |755| | | | |760| | | | |765|
|Phe|Val|Leu|Pro|Lys|Glu|Ile|Phe|Gly|Ser|Leu|Lys|Asn|Phe|Lys|Glu|
| |770| | | | |775| | | | |780|
|Ser|Ala|Leu|Lys|Phe|Ala|Asn|His|Ile|Gly|Leu|Asn|Leu|Glu|Thr|Ile|
|785| | | | |790| | | | |795| | | | |800|
|Lys|Lys|His|Leu|Thr|Thr|Val|Lys|Asn|Phe|Leu|Leu|Arg|Val|Asp|Ala|
| | | | |805| | | |810| | | |815|
|Val|Val|Asp|Lys|Glu|Ile|Gly|Asn|Ile|Ile|Glu|Ala|Gly|Lys|Ser|Pro|
| | | |820| | | | |825| | | | |830|
|Gln|Asn|Val|Val|Gln|Ala|Asn|Glu|Gly|Phe|Leu|Asp|Lys|Met|Lys|Arg|
| | | |835| | | | |840| | | | |845|
|Leu|Val|Asn|Lys|Tyr|Lys|Ile|Phe|Ser|Ile|Pro|Phe|Phe|Ala|Gly|Met|
| |850| | | | |855| | | | |860|
|Gly|Ser|Phe|Gly|Phe|His|His|His|His|His|
|865| | | |870| | | |875| |

<210> SEQ ID NO 58
<211> LENGTH: 2628
<212> TYPE: DNA
<213> ORGANISM: Plasmodium vivax

<400> SEQUENCE: 58
atgttcagcg gcggcgtggg cgacgacgag gaagaggaag aggaagagga aggcgaggaa    60

-continued

```
ggcgagagcg agagggacga ctccgagagg gactacgctg gcagggacga tgccggcagg      120
gacgacgccg agaggaacga cgccgagcgc gatgatgctg agcgcaacga cgccgagcgc      180
gacgacgccg agagggacca cgccgagcgc gaccacgccg acaaggccga gtccgacagg      240
gagtccagcc tggaggccaa cgagaacagg ctggtgaagc tcagcgaggg cggcgagtcc      300
gagccagctc tcctggaggt ggaggaagac atcaagcaaa ccgtcctggg catgttcagc      360
ctcaagggcg agttcgacga ggccgagtcc gagaagctcg ccctggacct ccagaagaac      420
ctcctgtcca tgctcagcgg caacatggag acaacgacg acgagtacga ggacatcgac      480
gaggagtacg aggaagtgga ggaagactac gaggaagaga agctcggcaa gccagtggag      540
gtggtcgtgg aggacgccac cgaggaagcc gtggacgagg tggtgggcgt cgtgcaagag      600
ccagaggaag agggcgctga ggagagcgac aaggacaccg gcgaggtgtc cgaggaagag      660
gtggccaagg aagccgccga cgaggtcatg gaggaagaga agaaggaaga ggccggcgag      720
ccatccgtgg tggtggagga gccaagcgtg gtcgtgaagg agccatccgt cgtggtcaag      780
gagccttccg tggtcgtgga ggagcctagc gtcgtcgtcg aggagccttc cgtcgtggtg      840
gaggagccca gcgtggtcgt cgaggagcca gccttcaccg tggaggagcc tgccttcacc      900
gtcgaggagc cagccatcac cgtggaggag cccgctatca cggtggagga gccagtgttc      960
accgtggaag aacccgtgtt caccgtggaa gagcccgcct tcaccgttga ggagcccgcc     1020
ttcaccgtag aagagcctgc cttcaccgtt gaagaaccag ctaccaccgt ggaggagctg     1080
gtggaggaag tgctcaaggt ggctgaggaa gaggtggcta ccgaggctgt ggagaaggac     1140
ggcgaggaag ccgaggagca agtcaccgag gagagcgtcg aggaagacga ggaagagtcc     1200
ggcgaggaag agggcgagga gagcgaggaa gaggagaccg aggagtccgc tgaggaagag     1260
gtggcgaagg agagcgtgga ggaagaggtg gctaaggaag ccgaggagtc cgaggagagc     1320
ggggaggaga gcgctgagga agagaaggag aaggccgagg agccagtggc tccagtggac     1380
gaggtcctga aggaaggcat gcagaagatc gaggagagct gaaggaagc cctgggcgtg     1440 gtccaagagg ccgtggacaa ggtcgccgag gaagagcaga ccgagcaggc tcagggccca     1500
gctgaggctg gccagtcgg cgtggtcaag gagcctgagg aagaggaaga gtctgaggaa     1560
gagggcgagg aaggcgagga aggcgaggaa ggcgaggaag aggaagagga agagagtgag     1620
gaagaggagt ctgaggaagg cgagtccgag gctggggaga gcgaggctgg caagagcgac     1680
gccgccgagt ccgaggtggc cgagagcgag gccggcgagc cggctgagga ccaagctggc     1740
atggacgcca agatgaagga cgagctcctg gcatgctga gcgagaagat gaaggccgag     1800
ggcaaggacc tggacaagct cccaccagag gtcaagaaga acctcctgga catgctcgcc     1860
ggcaacatgg agatgacga tgaggaagag gaaggcgagg aagagggcga agacctgggc     1920
aacgaggagc tcgacctcca gaagaacctc ctggagatgc tctccggcaa gggcggcttc     1980
aacccaaaca tgctgggcaa cctcaaggag ctggaggccc tccaaaagag cgtgccaggc     2040
ctgatgggca aggctcaggg catctcccca gctgagatcg agtccctcaa gagcatgttc     2100
tccggcgcct tcgacagcag gggcttcaag ggcatgccac agatgaagct gccagccgag     2160
ctccagtcca tcatgatgcc aaagaaggaa gagaagggca gccacaaagg cgctcaagct     2220
aaggctaagg tgccagctaa ggctggccaa gtccagaagc caaaggccca ggacatcatg     2280
ccaagcaggg catccgcga cctgttcgtg ctcccaaagg agatcttcgg cagcctgaag     2340
aacttcaagg agtccgccct caagttcgcc aaccacatcg gcctgaacct ggagaccatc     2400
aagaagcacc tcaccaccgt gaagaacttc ctcctgaggg tcgacgccgt ggtcgacaag     2460
```

```
gagatcggca acatcatcga ggccggcaag tccccacaaa acgtggtcca ggccaacgag    2520
ggcttcctgg acaagatgaa gcgcctcgtg aacaagtaca agatcttcag catcccattc    2580
ttcgccggca tgggctcctt cggcttccac catcaccacc atcactga                 2628
```

<210> SEQ ID NO 59
<211> LENGTH: 437
<212> TYPE: PRT
<213> ORGANISM: Plasmodium vivax

<400> SEQUENCE: 59

```
Met Gln Leu Gly Ile Gln Lys Lys Lys Asn Leu Glu Gln Asp Ala
1               5                   10                  15

Met His Ala Leu Met Lys Lys Leu Glu Ser Leu Tyr Lys Leu Ser Ala
            20                  25                  30

Thr Asp Asn Gly Glu Ile Phe Asn Lys Glu Ile Asp Ala Leu Lys Lys
        35                  40                  45

Gln Ile Asp Gln Leu His Gln His Gly Gly Asn Glu Gly Glu Ser
    50                  55                  60

Leu Gly His Leu Leu Glu Ser Glu Ala Ala Asp Asp Ser Gly Lys Lys
65                  70                  75                  80

Thr Ile Phe Gly Val Asp Glu Asp Leu Asp Asn Tyr Asp Ala Asp
                85                  90                  95

Phe Ile Gly Gln Ser Lys Gly Lys Ile Lys Gly Gln Ala Asp Thr Thr
            100                 105                 110

Ala Val Ala Lys Pro Pro Thr Gly Ser Gly Ala Gly Ala His Gly Ser
        115                 120                 125

His Ser Pro Pro Lys Pro Ser Val Leu Val Val Pro Gly Lys Ser Gly
    130                 135                 140

Lys Glu Asp Ser Val Ala Thr Leu Glu Asn Gly Tyr Glu Ser Ile His
145                 150                 155                 160

Gly Glu Asp Glu Pro Arg Glu Asp Ser Thr Ser His Asp Ser Pro Pro
                165                 170                 175

Ala Leu Pro Val Gly Arg Ser Glu Gly Asp Ser Ser Ala Ser Gly Gly
            180                 185                 190

Gly Thr Glu Gly Gln Gln Pro Asp Pro Ala Ser Ala Arg Gly Ser Gln
        195                 200                 205

Ala Ser Gly Gly Arg Gly Gly Asp Gln Thr Asn Thr Thr Gln Pro
    210                 215                 220

Ala Gly Gly Gln Gln Ser Ser Ala Ala Arg Ser Leu Gln Ala Pro
225                 230                 235                 240

His Ala Gly Asp Ser Gln Leu Pro Asn Ala Gly Gly Asp Pro Gln Ser
                245                 250                 255

Pro Ala Ala Gly His Gln Gln Pro Pro Thr Ser Pro Pro Ala Asn
            260                 265                 270

Asn Glu Gly Thr Thr Val Thr Gln Glu Ser Ala Leu Ala Ala Thr Pro
        275                 280                 285

Pro Lys Gly Thr Ala Asp Ser Asn Asp Ala Lys Ile Lys Tyr Leu Asp
    290                 295                 300

Lys Leu Tyr Asp Glu Val Leu Thr Thr Ser Asp Asn Thr Ser Gly Ile
305                 310                 315                 320

His Val Pro Asp Tyr His Ser Lys Tyr Asn Thr Ile Arg Gln Lys Tyr
                325                 330                 335

Glu Tyr Ser Met Asn Pro Val Glu Tyr Glu Ile Val Lys Asn Leu Phe
```

```
              340           345           350
Asn Val Gly Phe Lys Asn Asp Gly Ala Ala Ser Ser Asp Ala Thr Pro
        355                   360                   365

Leu Val Asp Val Phe Lys Lys Ala Leu Ala Asp Glu Lys Phe Gln Ala
        370                   375                   380

Glu Phe Asp Asn Phe Val His Gly Leu Tyr Gly Phe Ala Lys Arg His
385                   390                   395                   400

Ser Tyr Leu Ser Glu Ala Arg Met Lys Asp Asn Lys Leu Tyr Ser Asp
                405                   410                   415

Leu Leu Lys Asn Ala Ile Ser Leu Met Ser Thr Leu Gln Val Ser His
                420                   425                   430

His His His His His
        435

<210> SEQ ID NO 60
<211> LENGTH: 1314
<212> TYPE: DNA
<213> ORGANISM: Plasmodium vivax

<400> SEQUENCE: 60
atgcagctcg gcatccaaaa gaagaagaag aacctggagc aggacgccat gcacgccctc      60
atgaagaagc tggagagcct gtacaagctc tccgccaccg acaacggcga gatcttcaac     120
aaggagatcg acgccctgaa gagcaaatc gaccagctcc accaacacgg cggcggaaac     180
gagggcgaga gcctgggcca cctcctggag agcgaggctg ctgacgactc cggcaagaag     240
accatcttcg gcgtggacga ggacgacctg gacaactacg acgccgactt catcggccag     300
tccaagggca agatcaaggg ccaggctgac accaccgctg tggctaagcc accaaccggc     360
agcggcgctg cgctcacgg cagccactcc ccaccaaagc catccgtgct cgtggtccca     420
ggcaagagcg gcaaggaaga ctccgtcgcc accctggaga acggctacga gagcatccac     480
ggcgaggacg agccaaggga ggacagcacc tcccacgact ccccaccagc tctcccagtg     540
ggccgcagcg agggcgactc cagcgcttcc ggcggcggca ccgagggcca acagccagac     600
ccagctagcg ccaggggcag ccaggcttcc ggcggcaggg gcggcggcga ccaaaccaac     660
accacccaac cagctggcgg ccaacagtcc agctccgctg ctaggagcct gcaggcccca     720
cacgctggcg acagccagct cccaaacgcc ggcggcgacc acaatcccc agctgccgcc     780 ggccaccaac agccaccaac ctccccacca gccaacaacg agggcaccac cgtgacccaa     840
gagtccgctc tggctgctac cccaccaaag gcaccgccg actccaacga cgccaagatc     900
aagtacctgg acaagctcta cgacgaggtg ctgaccacca gcgacaacac ctccggcatc     960
cacgtcccag actaccacag caagtacaac accatccgcc aaaagtacga gtactccatg    1020
aacccagtgg agtacgagat cgtcaagaac ctcttcaacg tgggcttcaa gaacgacggc    1080
gctgccagct ccgacgctac cccactggtg gacgtcttca agaaggccct cgccgacgag    1140
aagttccagg ccgagttcga caacttcgtc cacggcctgt acggcttcgc caagaggcac    1200
agctacctct ccgaggcccg catgaaggac aacaagctgt acagcgacct cctgaagaac    1260
gccatcagcc tgatgtccac cctccaagtg tcccaccacc accaccacca ctga          1314

<210> SEQ ID NO 61
<211> LENGTH: 675
<212> TYPE: PRT
<213> ORGANISM: Plasmodium vivax

<400> SEQUENCE: 61
```

```
Met Ala Ala Tyr Asn Thr Val Leu Gln Ile Tyr Lys Tyr Ser Asp Asp
1               5                   10                  15

Ile Val Arg Lys Gln Glu Lys Cys Glu Gln Leu Val Lys Asp Gly Lys
            20                  25                  30

Asp Ile Cys Leu Lys Phe Lys Ser Ile Asn Glu Ile Lys Val Met Ile
            35                  40                  45

Gln Asn Ser Lys Gly Lys Glu Ser Thr Leu Ser Ala Lys Val Ser His
            50                  55                  60

Ser Phe Asn Lys Leu Ser Glu Leu Asn Lys Ile Lys Cys Asn Asp Glu
65                  70                  75                  80

Ser Tyr Asp Ala Ile Leu Glu Thr Pro Ser Arg Glu Glu Leu Asn Lys
                85                  90                  95

Leu Arg Ser Thr Phe Lys Gln Glu Lys Asp Thr Ile Ala Asn Gln Ala
            100                 105                 110

Lys Leu Ser Gly Tyr Lys Thr Asp Phe Glu Thr His Ile Gly Lys Leu
            115                 120                 125

Asn Asp Leu Ala Lys Ile Val Asp Asn Leu Lys Ala Ser Glu Thr Leu
            130                 135                 140

Pro Lys Asn Ile Glu Glu Lys Lys Thr Ser Ile Asn Leu Ile Ser Thr
145                 150                 155                 160

Lys Leu Glu Thr Ile Glu Lys Glu Ile Glu Ser Ile Asn Ser Ser Phe
                165                 170                 175

Asp Gln Leu Leu Glu Lys Gly Lys Lys Cys Glu Met Thr Lys Tyr Lys
            180                 185                 190

Leu Val Arg Asp Ser Leu Ser Thr Lys Ile Asn Asp His Ser Ala Ile
            195                 200                 205

Ile Lys Asp Asn Gln Lys Lys Ala Thr Glu Tyr Leu Thr Tyr Ile Gln
            210                 215                 220

Asn Asn His Ile Ser Ile Phe Lys Asp Ile Asp Met Leu Asn Glu Asn
225                 230                 235                 240

Leu Gly Glu Lys Ser Val Ser Arg Tyr Ala Ile Ala Lys Ile Glu Glu
                245                 250                 255

Ala Asn Asp Leu Ser Ala Gln Leu Thr Ala Ala Val Ser Glu Tyr Glu
            260                 265                 270

Ala Ile Ala Asn Ser Ile Arg Lys Glu Phe Thr Asn Ile Ser Asp His
            275                 280                 285

Thr Glu Met Asp Thr Leu Glu Asn Gly Ala Lys Met Leu Lys Glu His
            290                 295                 300

Tyr Asp Asn Leu Ile Asn Lys Lys Asn Ile Ile Thr Glu Leu His Asn
305                 310                 315                 320

Lys Ile Asn Leu Ile Lys Leu Leu Glu Ile Arg Ala Thr Ser Asp Lys
                325                 330                 335

Tyr Val Asp Ile Ala Glu Leu Leu Gly Glu Val Val Lys Asp Gln Lys
            340                 345                 350

Lys Lys Leu Gln Glu Ala Lys Asn Lys Leu Asp Thr Leu Lys Asp His
            355                 360                 365

Ile Ala Val Lys Glu Lys Glu Leu Ile Asn His Asp Ser Ser Phe Thr
            370                 375                 380

Leu Val Ser Ile Lys Ala Phe Asp Glu Ile Tyr Asp Asp Ile Lys Tyr
385                 390                 395                 400

Asn Val Gly Gln Leu His Thr Leu Glu Val Thr Asn Phe Asp Glu Leu
                405                 410                 415
```

```
Lys Lys Gly Lys Thr Tyr Glu Glu Asn Val Thr His Leu Leu Asn Arg
                420                 425                 430

Arg Glu Thr Leu Gln Asn Asp Leu His Asn Tyr Glu Glu Lys Asp Lys
            435                 440                 445

Leu Lys Asn Thr Asn Ile Glu Met Ser Asn Glu Glu Asn Asn Gln Ile
        450                 455                 460

Arg Gln Thr Ser Glu Val Ile Lys Lys Leu Glu Ser Glu Phe Gln Asn
465                 470                 475                 480

Leu Leu Lys Ile Ile Gln Gln Ser Asn Thr Leu Cys Ser Asn Asp Asn
                485                 490                 495

Ile Lys Gln Phe Ile Ser Asp Ile Leu Lys Lys Val Glu Thr Ile Arg
            500                 505                 510

Glu Arg Phe Val Lys Asn Phe Pro Glu Arg Glu Lys Tyr His Gln Ile
        515                 520                 525

Glu Ile Asn Tyr Asn Glu Ile Lys Gly Ile Val Lys Glu Val Asp Thr
530                 535                 540

Asn Pro Glu Ile Ser Ile Phe Thr Glu Lys Ile Asn Thr Tyr Ile Arg
545                 550                 555                 560

Gln Lys Ile Arg Ser Ala His His Leu Glu Asp Ala Gln Lys Ile Lys
                565                 570                 575

Asp Ile Ile Glu Asp Val Thr Ser Asn Tyr Arg Lys Ile Lys Ser Lys
            580                 585                 590

Leu Ser Gln Val Asn Asn Ala Leu Asp Arg Ile Lys Ile Lys Lys Ser
        595                 600                 605

Glu Met Asp Thr Leu Phe Glu Ser Leu Ser Lys Glu Asn Ala Asn Asn
610                 615                 620

Tyr Asn Ser Ala Lys Tyr Phe Leu Val Asp Ser Asp Lys Ile Ile Lys
625                 630                 635                 640

His Leu Glu Asp Gln Val Ser Lys Met Ser Ser Leu Ile Ser Tyr Ala
                645                 650                 655

Glu Arg Glu Ile Lys Glu Leu Glu Glu Lys Val Tyr Ser His His His
            660                 665                 670

His His His
        675

<210> SEQ ID NO 62
<211> LENGTH: 2028
<212> TYPE: DNA
<213> ORGANISM: Plasmodium vivax

<400> SEQUENCE: 62
atggccgcct acaacaccgt gctccaaatc tacaagtact ccgacgacat cgtgaggaag     60
caagagaagt gcgagcagct ggtcaaggac ggcaaggaca tctgcctcaa gttcaagtcc    120
atcaacgaga tcaaggtcat gatccagaac agcaagggca aggagtccac cctcagcgcc    180
aaggtgtccc acagcttcaa caagctcagc gagctgaaca agatcaagtg caacgacgag    240
agctacgacg ccatcctcga aaccccatcc agggaggagc tcaacaagct gcgcagcacc    300
ttcaagcaag agaaggacac catcgccaac caggccaagc tctccggcta caagaccgac    360
ttcgagacgc acatcggcaa gctcaacgac ctggccaaga tcgtggacaa cctcaaggcc    420
agcgagacgc tgccaaagaa catcgaggag aagaagacct ccatcaacct catcagcacc    480
aagctcgaaa ccatcgagaa ggagatcgag tccatcaact ccagcttcga ccaactcctg    540
gagaagggca agaagtgcga gatgaccaag tacaagctcg tcagggactc cctgagcacc    600
```

| | |
|---|---|
| aagatcaacg accactccgc catcatcaag gacaaccaaa agaaggccac cgagtacctc | 660 |
| acctacatcc agaacaacca catcagcatc ttcaaggaca tcgacatgct caacgagaac | 720 |
| ctgggcgaga agtccgtgag caggtacgcc atcgccaaga tcgaggaagc caacgacctc | 780 |
| tccgctcaac tcaccgctgc cgtcagcgag tacgaggcta tcgccaactc catccgcaag | 840 |
| gagttcacca acatctccga ccacaccgag atggacaccc tggagaacga ggccaagatg | 900 |
| ctgaaggagc actacgacaa cctcatcaac aagaagaaca tcatcaccga gctccacaac | 960 |
| aagatcaacc tgatcaagct cctggagatc cgcgccacca gcgacaagta tgtggacatc | 1020 |
| gccgagctcc tgggcgaggt ggtcaaggac caaaagaaga agctgcaaga ggccaagaac | 1080 |
| aagctcgaca ccctgaagga ccacatcgcc gtgaaggaga aggagctgat caaccacgac | 1140 |
| tccagcttca ccctcgtcag catcaaggcc ttcgacgaga tctacgacga catcaagtac | 1200 |
| aacgtgggcc aactccacac cctggaggtc accaacttcg acgagctcaa gaagggcaag | 1260 |
| acctacgagg agaacgtgac ccacctcctg aacaggcgcg agacgctcca gaacgacctg | 1320 |
| cacaactacg aggagaagga caagctcaag aacaccaaca tcgagatgtc caacgaggag | 1380 |
| aacaaccaaa tcaggcagac cagcgaggtc atcaagaagc tggagtccga gttccaaaac | 1440 |
| ctcctgaaga tcatccaaca gtccaacacc ctctgcagca acgataacat caagcagttc | 1500 |
| atcagcgaca tcctgaagaa ggtggagacg atcagggagc gcttcgtcaa gaacttccca | 1560 |
| gagcgcgaga agtaccacca aatcgagatc aactacaacg agatcaaggg catcgtgaag | 1620 |
| gaagtggaca ccaacccaga gatctccatc ttcaccgaga agatcaacac ctacatcagg | 1680 |
| caaaagatca ggagcgctca ccacctggag gacgctcaga agatcaagga catcatcgag | 1740 |
| gacgtgacct ccaactacag gaagatcaag tccaagctga gccaagtcaa caacgccctc | 1800 |
| gaccgcatca agatcaagaa gagcgagatg gacaccctct tcgagtccct gagcaaggag | 1860 |
| aacgccaaca actacaacag cgccaagtac ttcctggtgg actccgacaa gatcatcaag | 1920 |
| cacctggagg accaagtgtc caagatgtcc agcctgatca gctacgccga gcgcgagatc | 1980 |
| aaggagctgg aggagaaggt ctactcccac caccaccacc accactga | 2028 |

<210> SEQ ID NO 63
<211> LENGTH: 1003
<212> TYPE: PRT
<213> ORGANISM: Plasmodium vivax

<400> SEQUENCE: 63

Met Asn Val Ala Thr Arg Gly Glu Ile Val Asn Leu Lys Asn Pro Asn
1               5                   10                  15

Leu Arg Asn Gly Trp Ser Met Lys Asn Leu Ser Ala Gln Asn Glu Glu
            20                  25                  30

Asn Ile Val His Ser Asp Gly Ser Asp Asp Val Thr Asp Lys Glu Glu
        35                  40                  45

Asp Gly Glu Val Leu Glu Gly Gln Lys Gly Ser Pro Lys Lys Ser Ala
    50                  55                  60

Glu Gln Lys Val His Ala Gln Glu Glu Val Asn Lys Glu Ser Leu Lys
65                  70                  75                  80

Ser Lys Ala Gln Asn Ala Lys Ala Glu Ala Glu Lys Ala Ala Lys Ala
                85                  90                  95

Ala Glu Ser Ala Lys Glu Asn Thr Leu Asp Ala Leu Glu Lys Val Asn
            100                 105                 110

Val Pro Thr Glu Leu Asn Asn Glu Lys Asn Phe Ala Glu Ser Ala Ala
        115                 120                 125

```
Thr Glu Ala Lys Lys Gln Lys Ile Ser Thr Ala Glu Glu
    130                 135                 140
Val Lys Glu Ile Glu Val Asp Gly Gln Leu Glu Lys Leu Lys Asn Glu
145                 150                 155                 160
Glu Glu Lys Thr Ala Lys Lys Ala Arg Lys Gln Glu Ile Lys Thr Glu
                165                 170                 175
Ile Ala Glu Gln Ala Ala Lys Ala Gln Ala Ala Lys Thr Glu Ala Glu
                180                 185                 190
Thr Ala Gln Lys Asp Ala Thr Thr Ala Lys Asp Glu Ala Ile Lys Glu
            195                 200                 205
Thr Gly Lys Pro Lys Ser Gln Asn Thr Thr Lys Ala Val Thr Met Ala
    210                 215                 220
Thr Glu Glu Glu Lys Lys Thr Lys Asp Glu Ala Gln Thr Ala Ser Glu
225                 230                 235                 240
Lys Ala Gly Lys Thr Ala Glu Glu Ala Gln Lys Glu Val Gly Lys Glu
                245                 250                 255
Thr Ala Asp Asp Lys Glu Val Ser Gln Leu Glu Glu Ile Lys
                260                 265                 270
Glu Leu Glu Arg Ile Leu Lys Ile Val Lys Asp Leu Ala Ser Glu Ala
            275                 280                 285
Ser Ser Ala Ser Asp Asn Ala Lys Lys Ala Lys Leu Lys Thr Gln Ile
    290                 295                 300
Ala Ala Glu Val Val Lys Ala Glu Lys Ala Arg Ile Glu Ala Glu Glu
305                 310                 315                 320
Ala Glu Lys Glu Ala Gly Glu Ala Lys Thr Lys Thr Glu Ala Thr Glu
                325                 330                 335
Lys Glu Val Leu Lys Ile Ser Asp Glu Ser Lys Ala Ala Lys Val Lys
            340                 345                 350
Lys Ala Val Glu Lys Ala Lys Glu Ala Glu Lys Gln Ala Lys Ser Glu
    355                 360                 365
Ala Glu Lys Ala Lys Gly Met Ala Asp Asp Ala Gly Gly Lys Gly Thr
370                 375                 380
Thr Asn Leu Glu Asp Val Leu Thr Lys Leu Ser Glu Val Leu Thr Ser
385                 390                 395                 400
Val Lys Ser Leu Ala Ser Asn Ala Glu Val Ala Ser Lys Asn Ala Lys
                405                 410                 415
Lys Glu Met Thr Lys Ala Gln Ile Ala Ala Glu Val Ala Lys Ala Glu
            420                 425                 430
Lys Ala Lys Ile Glu Ala Glu Asn Ala Lys Leu Leu Ala Asp Thr Ala
    435                 440                 445
Ser Lys Ala Ala Glu Asn Ile Ala Lys Ser Ser Lys Ala Ala Lys Ile
450                 455                 460
Ala Asn Asn Val Ser Thr Ile Ala Ala Glu Lys Ser Lys Val Ala Thr
465                 470                 475                 480
Glu Ala Ala Asp Glu Ala Ala Lys Ala Leu Asp Glu Thr Glu Asn Pro
                485                 490                 495
Glu Ser Lys Ile Ala Glu Val Thr Glu Lys Ala Thr Lys Ala Val Asn
            500                 505                 510
Ala Ala Glu Glu Ala Lys Lys Glu Lys Ala Lys Ala Glu Val Ala Val
    515                 520                 525
Glu Val Ala His Ala Glu Val Ala Lys Glu Lys Ala Gln Glu Ala Lys
    530                 535                 540
```

```
Glu Ala Ala Lys Gln Val Ala Asp Lys Ser Lys Leu Glu Lys Ala Ile
545                 550                 555                 560

Gln Ala Ala Asp Lys Ala Ser Glu Lys Ala Asn Glu Ala Ser Lys Leu
            565                 570                 575

Ala Glu Glu Ala Leu Ser Asn Leu Glu Ser Leu Glu Lys Glu Thr Gly
        580                 585                 590

Glu Ile Val Glu Lys Val Asn Ala Ile Glu Gln Lys Val Gln Thr Ala
    595                 600                 605

Lys Asn Ala Ala Ile Glu Ala His Lys Glu Lys Thr Lys Ala Glu Ile
610                 615                 620

Ala Val Glu Val Ala Lys Ala Glu Glu Ala Lys Lys Glu Ala Asp Asn
625                 630                 635                 640

Ala Lys Val Ala Ala Glu Lys Ala Lys Glu Thr Ala Glu Lys Ile Ala
            645                 650                 655

Lys Thr Ser Lys Ser Thr Glu Lys Ile Thr Glu Glu Val Arg Lys Ala
        660                 665                 670

Thr Glu Phe Ala Lys Thr Ala Gly Asp Glu Thr Thr Leu Ala Ala Thr
    675                 680                 685

Lys Ala Glu Ser Glu Ile Pro Ser Glu Glu Lys Asn Gln Lys Glu Leu
690                 695                 700

Leu Asp Ser Ile Lys Gln Lys Ala Glu Ser Ala Phe Gln Ala Ser Gln
705                 710                 715                 720

Glu Ala Ile Lys Ala Lys Thr Glu Ala Glu Asn Phe Leu Glu Ile Ala
            725                 730                 735

Lys Glu Val Pro Lys Ala Glu Ala Ala Lys Glu Ala Gln Lys Ala
        740                 745                 750

Ala Thr Ala Ala Glu Glu Ala Lys Thr Glu Val Leu Lys Ile Ala Glu
    755                 760                 765

Glu Val Asn Lys Ser Asp Ala Ser Glu Ser Glu Lys Lys Ile Glu
770                 775                 780

Thr Ala Ala Asn Glu Thr Ala Gly Glu Ala Glu Lys Ala Ala Thr Phe
785                 790                 795                 800

Ala Lys Glu Ala Ala Asp Ala Ala Lys Asp Thr Asn Lys Ala Val Thr
            805                 810                 815

Leu Ala Val Ala Lys Glu Lys Val Glu Lys Ala Leu Lys Ala Ala Lys
        820                 825                 830

Glu Ala Lys Lys Ala Asn Glu Lys Ala Ser Tyr Ala Leu Ile Arg Thr
    835                 840                 845

Lys Lys Gln Tyr Ala Leu Glu Pro Leu Glu Ile Thr Ser Glu Ala Gly
850                 855                 860

Tyr Asn Ile Thr Glu Lys Glu Glu Val Lys Glu Glu Ile Glu Glu
865                 870                 875                 880

Gln Asp Asp Lys Ala Ser Glu Glu Glu Glu Asp Thr Gln Gln Ile
            885                 890                 895

Asp Gln Thr Gln Ile Asp Glu Val Asp Ile Ser Val Asp Asn Glu Glu
        900                 905                 910

Glu Glu Glu Gly Ala Ala Glu Glu Gln Ile Glu Gly Glu Lys Asp Thr
    915                 920                 925

Pro Thr Lys Glu Ala Lys Glu Glu Gln Thr Ser Gly Glu Lys Ile Leu
        930                 935                 940

Asp Asp Lys Glu Ala His Lys Thr Leu Ala Glu Lys Phe Lys Asp Ser
945                 950                 955                 960

Asn Thr Ala Lys Thr Gly Gly Val Glu Phe Leu Glu Thr Leu Ile Ser
```

965                 970                 975
Asp Val Gly Glu Asp Thr Leu Lys Asn Leu Gln Gln Asp Leu His Gln
            980                 985                 990
Tyr Phe Lys Gly Lys His His His  His His His
            995             1000

<210> SEQ ID NO 64
<211> LENGTH: 3012
<212> TYPE: DNA
<213> ORGANISM: Plasmodium vivax

<400> SEQUENCE: 64

| | | | |
|---|---|---|---|
| atgaacgtcg ccaccagggg cgagatcgtg aacctgaaga acccaaacct ccgcaacggc | | | 60 |
| tggagcatga agaacctgtc cgcccaaaac gaggagaaca tcgtccactc cgacggcagc | | | 120 |
| gacgacgtga ccgacaagga gaggacggc gaggtgctgg agggccagaa gggcagccca | | | 180 |
| aagaagtccg ccgagcaaaa ggtccacgcc aagaggaag tgaacaagga gtccctcaag | | | 240 |
| agcaaggccc aaaacgccaa ggctgaggct gagaaggctg ctaaggctgc cgagtccgcc | | | 300 |
| aaggagaaca ccctcgacgc cctggagaag gtgaacgtcc caaccgagct caacaacgag | | | 360 |
| aagaacttcg ctgagagcgc tgctaccgag gccaagaagc aggagaagat ctccaccgag | | | 420 |
| gccgccgagg aagtgaagga gatcgaggtg gacggccaac tggagaagct gaagaacgag | | | 480 |
| gaagagaaga ccgccaagaa ggccaggaag caggagatca gaccgagat cgctgagcaa | | | 540 |
| gctgctaagg ctcaggctgc taagaccgag gccgagacgg cccaaaagga cgccaccacc | | | 600 |
| gccaaggacg aggccatcaa ggagacgggc aagccaaaga ccagaacac caccaaggcc | | | 660 |
| gtcaccatgg ccaccgagga agagaagaag accaaggacg aggctcaaac cgcttccgag | | | 720 |
| aaggctggca agaccgctga ggaagcccag aaggaagtgg gcaaggagac ggccgacgac | | | 780 |
| gacaaggaag tgtcccaact cgaagaggag atcaaggagc tggagaggat cctcaagatc | | | 840 |
| gtgaaggacc tggctagcga ggcctccagc gcttccgaca cgccaagaa ggccaagctc | | | 900 |
| aagacccaaa tcgctgctga ggtggtcaag gctgagaagg ctaggatcga ggctgaggaa | | | 960 |
| gccgagaagg aagccggcga ggctaagacc aagaccgagg ctaccgagaa ggaagtgctg | | | 1020 |
| aagatctccg acgagagcaa ggccgccaag gtcaagaagg ccgtggagaa ggccaaggaa | | | 1080 |
| gccgagaagc aagccaagtc cgaggctgag aaggctaagg gcatggctga cgacgccggc | | | 1140 |
| ggcaagggca ccaccaacct ggaggacgtg ctcaccaagc tgagcgaggt cctgacctcc | | | 1200 |
| gtgaagtccc tggcttccaa cgctgaggtg gcttccaaga cgccaagaa ggagatgacc | | | 1260 |
| aaggctcaga tcgctgctga ggtggctaag gctgagaagg ccaagatcga ggccgagaac | | | 1320 |
| gccaagctgc tggctgacac cgctagcaag gctgccgaga catcgccaa gtccagcaag | | | 1380 |
| gccgccaaga tcgccaacaa cgtcagcacc atcgccgccg agaagtccaa ggtggctacc | | | 1440 |
| gaggctgctg acgaggctgc caaggccctc gacgagacgg agaacccaga gtccaagatc | | | 1500 |
| gccgaggtga ccgagaaggc taccaaggct gtgaacgctg ctgaggaagc caagaaggag | | | 1560 |
| aaggccaagg ctgaggtggc tgtggaggtg gctcacgctg aggtggctaa ggagaaggcc | | | 1620 |
| caagaggcca ggaagccgc caagcaggtg ccgacaaga gcaagctgga aaggccatc | | | 1680 |
| caagccgccg acaaggccag cgagaaggcc aacgaggcct ccaagctcgc cgaggaagcc | | | 1740 |
| ctcagcaacc tggagtccct ggagaaggag acgggcgaga tcgtcgagaa ggtgaacgcc | | | 1800 |
| atcgagcaaa aggtgcagac cgccaagaac gccgccatcg aggcccacaa ggagaagacc | | | 1860 |
| aaggctgaga tcgctgtgga ggtcgccaag gccgaggaag ccaagaagga agccgacaac | | | 1920 |

```
gccaaggtgg ctgctgagaa ggctaaggag acggccgaga agatcgccaa gacctccaag   1980
agcaccgaga agatcaccga ggaagtgagg aaggctaccg agttcgctaa gaccgctggc   2040
gacgagacga ccctggctgc taccaaggct gagagcgaga tcccatccga ggagaagaac   2100
caaaaggagc tcctggacag catcaagcag aaggccgaga gcgccttcca gcctcccaa    2160 gaggccatca aggccaagac cgaggccgag aacttcctgg agatcgccaa ggaagtgcca   2220
aaggccgagg ccgccaagga agaggcccaa aaggctgcta cggccgctga ggaagccaag   2280
accgaggtcc tcaagatcgc cgaggaagtg aacaagtccg acgcctccga gagcgagaag   2340
aagaagatcg agacggctgc taacgagacg gctggcgagg ccgagaaggc cgctaccttc   2400
gctaaggaag ccgctgacgc tgctaaggac accaacaagg ccgtcaccct ggccgtggcc   2460
aaggagaagg tcgagaaggc cctcaaggcc gccaaggaag ccaagaaggc caacgagaag   2520
gccagctacg ccctgatccg caccaagaag cagtacgccc tggagccact ggagatcacc   2580
tccgaggccg gctacaacat caccgagaag gaagagcaag tgaaggaaga gatcgaggag   2640
caggacgaca aggccagcga ggaagaggaa gaggacaccc aacagatcga ccaaacccag   2700
atcgacgagg tcgacatctc cgtggacaac gaggaagagg aagagggcgc tgctgaggag   2760
caaatcgagg gcgagaagga cacccccaacc aaggaagcca aggaagagca gacctccggc   2820
gagaagatcc tggacgacaa ggaagcccac aagaccctcg ccgagaagtt caaggacagc   2880
aacaccgcta agaccggcgg cgtcgagttc ctcgaaaccc tcatctccga cgtgggcgag   2940 gacacccctga agaacctcca acaggacctc caccagtact tcaagggcaa gcaccaccac   3000
caccaccact ga                                                      3012
```

<210> SEQ ID NO 65
<211> LENGTH: 656
<212> TYPE: PRT
<213> ORGANISM: Plasmodium vivax

<400> SEQUENCE: 65

```
Met Asn Asn Tyr Gly Lys Leu Lys His Gly Lys Trp Asp Asp Gly Ser
1               5                   10                  15

Tyr Ser Glu Arg Thr Arg Trp Arg Met Leu Ser Gly Asp Asp His Asp
            20                  25                  30

Asp Leu Leu Pro Ser Cys Asp Ser Pro Gly Gly Arg Asn Asp Glu His
        35                  40                  45

Gln Val Asn Lys Glu Val Ser Arg Thr Ala Pro Ser Glu Lys Val Lys
    50                  55                  60

Val Val Asp Lys Glu Thr Gly Glu Ser Met Leu Val Asp Val Gly Glu
65                  70                  75                  80

Ser Gly Gly Lys Ser Ser Pro Gly Val Ala Glu Glu Ser Gly Pro Ser
                85                  90                  95

Leu Arg Gly Arg Asp Val Arg Asp Val Arg Val Asp Gln Glu Thr Arg
            100                 105                 110

Glu Thr Leu Gln Gly Gly Ala Thr Asn Arg Arg Asp Leu Thr Gln His
        115                 120                 125

Gly Glu Glu Glu Thr Gly Asp Asp Ser Lys Arg Ala Lys Gln Asp Asp
    130                 135                 140

Glu Ala Gly Val Arg Ser Met Leu Asn Asp Thr Val Thr Ala Ile Lys
145                 150                 155                 160

Asp Asn Gly Ser Asn Leu Leu Arg Ser Val Ile Gly Gln Ile Asn Phe
                165                 170                 175
```

-continued

```
Val Gln Gly Ser Ala Glu Leu Leu Lys Val Ala Asn Glu Glu Arg
            180                 185                 190

Gln Pro Ser Gly Gly Ser Val Leu Ser Lys Glu Gly Glu Glu Ala Thr
            195                 200                 205

Pro Gly Asp Phe Leu Gly Gly Asn Asn Pro Asn Gly Gly Glu Lys Gly
            210                 215                 220

Glu Leu Pro Asn Gly Thr Lys Asn Asp Val Met Ile Lys Gly Tyr Ala
225                 230                 235                 240

Asn Val Leu Leu Asn Glu Gly Lys His Val Leu Val Gly Asn Val Arg
                245                 250                 255

Asn Phe Leu Ser Arg Val Phe Asn Leu Ile Val Arg Glu Lys Ile Met
            260                 265                 270

Thr Arg Met Cys His Arg Gly Gly Glu Ala Ser Ile Glu Arg Ser Gly
            275                 280                 285

Glu Pro Val Gly Glu Arg Ser Gly Glu Pro Thr Gly Glu Arg Ser Gly
            290                 295                 300

Asp Pro Thr Gly Glu Arg Ser Gly Asp Pro Thr Gly Glu Arg Ser Gly
305                 310                 315                 320

Glu Pro Thr Gly Glu Arg Ser Gly Glu Pro Thr Gly Glu Arg Ser Gly
            325                 330                 335

Glu Pro Thr Ala Glu Arg Ser Gly Glu Pro Thr Ala Glu Arg Ser Asp
            340                 345                 350

Glu Pro Thr Ala Glu Arg Ser Asp Glu Pro Thr Ala Asp Pro Lys Gly
            355                 360                 365

Asp Pro Thr Asn Cys Arg Leu Pro Lys Arg Ser Ala Thr Lys Phe Tyr
            370                 375                 380

Gln Ser Glu Asp Leu Tyr Asn Tyr Tyr Ser Ser Leu Glu Glu Met Leu
385                 390                 395                 400

Lys Gly Arg Gly Ile Arg Trp Lys Thr Asp Arg Val Ser Arg Tyr Phe
                405                 410                 415

Thr Phe Ser Pro Ser Lys Lys Ile Lys Asp Asn Phe Glu Glu Val Met
            420                 425                 430

Asn Asn Lys Val Phe Ile Glu Ser Val Arg Ser Ile Leu Phe Asp Ser
            435                 440                 445

His Lys Lys Asn Lys Lys Ala Val Phe Ser Ser Phe Ala Val Val Val
450                 455                 460

Glu Thr Leu Phe Ser Leu Ile Lys Glu Glu Lys Val Ile Ala Asp Met
465                 470                 475                 480

Tyr Ser Tyr Val Lys Leu Phe Phe Gln Asp Leu Asp Ile Leu Asn Leu
                485                 490                 495

Lys Val Leu His Phe Leu Ser Ser Ser Thr Glu Asn Thr Gln Phe
            500                 505                 510

Val Gly Pro Pro Asp Leu Ser Leu Thr Asn Phe Glu Tyr Ile Leu Ala
            515                 520                 525

Lys Ile Tyr Ser Arg Ser Val Leu Ala Asn Ile Leu Ser Pro Lys Met
            530                 535                 540

Asn His Ser Asp Ser Lys Lys Leu Ser Lys Leu Leu Thr Arg Arg Glu
545                 550                 555                 560

Asn Asn Leu Lys Phe Ser Phe Leu Glu Gly Val Lys Met Val His Ser
            565                 570                 575

Ala Ile Pro Ser Glu Gly Val Ser Ala Val Val Leu Gly Asn Ala Gly
            580                 585                 590
```

```
Gly Gln Val Asn Val Pro Ile Pro Gly Ala Asp Asp Thr Leu Cys Lys
            595                 600                 605

Phe Ile Pro Ile Arg Lys Lys Leu Leu Tyr Glu Arg Leu Ser Val Thr
610                 615                 620

Arg Lys Val Ala Glu Val Ile Leu Asp Tyr Leu Phe Arg Leu Leu
625                 630                 635                 640

Leu Arg Lys Val His Glu Tyr Val Leu Glu His His His His His
                645                 650                 655

<210> SEQ ID NO 66
<211> LENGTH: 1971
<212> TYPE: DNA
<213> ORGANISM: Plasmodium vivax

<400> SEQUENCE: 66
atgaacaact acggcaagct caagcacggc aagtgggacg acggctccta cagcgagagg        60
accaggtgga ggatgctgtc cggcgacgac cacgacgacc tcctcccatc ctgcgacagc       120
ccaggcggca ggaacgacga gcaccaagtc aacaaggaag tgtccaggac cgccccaagc       180
gagaaggtga aggtggtcga caaggagacc ggcgagtcca tgctggtgga cgtgggcgag       240
agcggcggca agtcctcccc aggcgtggct gaggagtccg cccaagcct gcgcggcagg        300 gacgtgcgcg acgtcagggt ggaccaagag acccgcgaga ccctgcaggg cggcgccacc       360
aacaggcgcg acctcaccca cacggcgag gaagagaccg cgacgacag caagcgcgct        420 aagcaggacg acgaggctgg cgtcaggtcc atgctcaacg acaccgtgac cgccatcaag       480
gacaacggct ccaacctcct gcgcagcgtc atcggccaaa tcaacttcgt gcaaggcagc       540
gctgagctcc tgaaggtcgc caacgaggaa gagcgccagc catccggcgg cagcgtgctg       600
tccaaggaag gcgaggaagc cacccagggc gacttcctcg gcggcaacaa cccgaacggc       660
ggcgagaagg gcgagctgcc aaacggcacc aagaacgacg tcatgatcaa gggctacgcc       720
aacgtgctcc tgaacgaggg caagcacgtc ctcgtgggca acgtccgcaa cttcctgtcc       780
agggtgttca acctcatcgt cagggagaag atcatgacca ggatgtgcca caggggcggc       840
gaggctagca tcgagaggtc cggcgagcca gtggggagc gctccggcga gccaaccggc       900
gagaggagcg gcgacccaac cggcgagagg tctggcgacc ctacggggga gaggagcggg       960
gagcctaccg gcgagcgcag cggggagcct acgggcgaga ggtccgggga gcctaccgct      1020
gagagaagcg gcgagccaac cgctgagagg agcgatgagc ctaccgctga gaggtccgac      1080
gagccaaccg ctgacccaaa gggcgaccca accaactgcc gcctcccaaa gaggtccgcc      1140
accaagttct accaaagcga ggacctgtac aactactact ccagcctgga ggagatgctc      1200
aagggcaggg gcatcaggtg gaagaccgac cgcgtcagca ggtacttcac cttctccca       1260 agcaagaaga tcaaggacaa cttcgaggaa gtgatgaaca caaggtctt catcgagagc       1320 gtgcgctcca tcctcttcga ctcccacaag aagaacaaga aggccgtgtt ctccagcttc      1380
gccgtggtcg tggagaccct gttcagcctc atcaaggaag agaaggtcat cgccgacatg      1440
tactcctacg tgaagctgtt cttccaagac ctcgacatcc tgaacctcaa ggtcctgcac      1500
ttcctctcca gctccagcac cgagaacacc cagttcgtgg gcccaccaga cctgagcctc      1560
accaacttcg agtacatcct cgccaagatc tactcccgca gcgtcctggc caacatcctc      1620
agcccaaaga tgaaccactc cgacagcaag aagctgtcca agctcctgac caggcgcgag      1680
aacaacctga agttctccct cctggagggc gtcaagatgg tgcacagcgc tatcccatcc      1740
gagggcgtga gcgctgtggt gctgggcaac gctggcggcc aggtcaacgt gccaatccca      1800
```

```
ggcgccgacg acaccctctg caagttcatc ccaatcagga agaagctcct gtacgagcgc    1860
ctgtccgtca ccaggaaggt ggccgaggaa gtgatcctgg actacctctt ccgcctcctg    1920
ctcaggaagg tgcacgagta tgtgctggag caccatcacc accatcactg a             1971
```

<210> SEQ ID NO 67
<211> LENGTH: 447
<212> TYPE: PRT
<213> ORGANISM: Plasmodium vivax

<400> SEQUENCE: 67

```
Met Gly Asn Val Ser Pro Pro Asn Phe Asn Asp Asn Arg Val Asn Gly
1               5                   10                  15

Asn Asn Gly Asn Lys Gly Asn Gly Asn Asp Asn Asp Val Pro Ser Phe
            20                  25                  30

Ile Gly Gly Asn Asn Asn Val Asn Gly Asn Asn Asp Asp Asn Ile
        35                  40                  45

Phe Asn Lys Asn Gly Lys Asp Val Thr Arg Asn Asp Gly Asp Ala Lys
    50                  55                  60

Asp Gly Glu Asn Arg Asn Asn Lys Lys Asn Glu Asn Gly Ser Gly Ser
65                  70                  75                  80

Asn Glu Asn Asn Ser Ile Ala Asn Ala Asp Asn Gly Ser Gly Lys Ser
                85                  90                  95

Asp Ala Asn Ala Asn Gln Ile Asp Glu Asp Gly Asn Lys Met Asp Glu
            100                 105                 110

Ala Ser Leu Lys Lys Ile Leu Lys Ile Val Asp Glu Met Glu Asn Ile
        115                 120                 125

Gln Gly Leu Leu Asp Gly Asp Tyr Ser Ile Leu Asp Lys Tyr Ser Val
    130                 135                 140

Lys Leu Val Asp Glu Asp Gly Glu Thr Asn Lys Arg Lys Ile Ile
145                 150                 155                 160

Gly Glu Tyr Asp Leu Lys Met Leu Lys Asn Ile Leu Leu Phe Arg Glu
                165                 170                 175

Lys Ile Ser Arg Val Cys Glu Asn Lys Tyr Asn Lys Asn Leu Pro Val
            180                 185                 190

Leu Leu Lys Lys Cys Ser Asn Val Asp Asp Pro Lys Leu Ser Lys Ser
        195                 200                 205

Arg Glu Lys Ile Lys Lys Gly Leu Ala Lys Asn Asn Met Ser Ile Glu
    210                 215                 220

Asp Phe Val Val Gly Leu Leu Glu Asp Leu Phe Glu Lys Ile Asn Glu
225                 230                 235                 240

His Phe Ile Lys Asp Asp Ser Phe Asp Leu Ser Asp Tyr Leu Ala Asp
                245                 250                 255

Phe Glu Leu Ile Asn Tyr Ile Ile Met His Glu Thr Ser Glu Leu Ile
            260                 265                 270

Asp Glu Leu Leu Asn Ile Ile Glu Ser Met Asn Phe Arg Leu Glu Ser
        275                 280                 285

Gly Ser Leu Glu Lys Met Val Lys Ser Ala Glu Ser Gly Met Asn Leu
    290                 295                 300

Asn Cys Lys Met Lys Glu Asp Ile Ile His Leu Leu Lys Lys Ser Ser
305                 310                 315                 320

Ala Lys Phe Phe Lys Ile Glu Ile Asp Arg Lys Thr Lys Met Ile Tyr
                325                 330                 335

Pro Val Gln Ala Thr His Lys Gly Ala Asn Met Lys Gln Leu Ala Leu
```

```
                340                 345                 350
Ser Phe Leu Gln Lys Asn Asn Val Cys Glu His Lys Lys Cys Pro Leu
            355                 360                 365

Asn Ser Asn Cys Tyr Val Ile Asn Gly Glu Glu Val Cys Arg Cys Leu
        370                 375                 380

Pro Gly Phe Ser Asp Val Lys Ile Asp Asn Val Met Asn Cys Val Arg
385                 390                 395                 400

Asp Asp Thr Leu Asp Cys Ser Asn Asn Gly Gly Cys Asp Val Asn
                405                 410                 415

Ala Thr Cys Thr Leu Ile Asp Lys Lys Ile Val Cys Glu Cys Lys Asp
            420                 425                 430

Asn Phe Glu Gly Asp Gly Ile Tyr Cys His His His His His His
            435                 440                 445
```

<210> SEQ ID NO 68
<211> LENGTH: 1344
<212> TYPE: DNA
<213> ORGANISM: Plasmodium vivax

<400> SEQUENCE: 68

```
atgggcaacg tgtccccacc aaacttcaac gacaacaggg tcaacggcaa caacggcaac      60
aagggcaacg gcaacgacaa cgacgtgcca agcttcatcg gcggcaacaa caacaacgtc     120
aacggcaaca acgacgacaa catcttcaac aagaacggca aggacgtgac ccgcaacgac     180
ggcgacgcta aggacggcga gaaccgcaac aacaagaaga cgagaacgg ctccggcagc      240
aacgagaaca actccatcgc caacgctgac aacggctccg gcaagagcga cgccaacgcc     300
aaccaaatcg acgaggacgg caacaagatg gacgaggcca gcctcaagaa gatcctgaag     360
atcgtggacg agatggagaa catccagggc ctcctggacg cgactactc catcctcgac      420
aagtacagcg tgaagctggt cgacgaggac gacggcgaga cgaacaagag gaagatcatc     480
ggcgagtacg acctcaagat gctgaagaac atcctcctgt tcagggagaa gatctcccgc     540
gtctgcgaga caagtacaa caagaacctc ccagtgctcc tgaagaagtg cagcaacgtc      600
gacgacccaa agctctccaa gagccgcgag aagatcaaga agggcctggc taagaacaac     660
atgtccatcg aggacttcgt ggtcggcctc ctggaggacc tgttcgagaa gatcaacgag     720
cacttcatca aggacgactc cttcgacctc agcgactacc tggccgactt cgagctcatc     780
aactacatca tcatgcacga gacgtccgag ctgatcgacg agctcctgaa catcatcgag     840
agcatgaact tcaggctgga gtccggcagc ctggagaaga tggtgaagtc cgccgagagc     900
ggcatgaacc tcaactgcaa gatgaaggaa gacatcatcc acctcctgaa gaagtccagc     960
gccaagttct tcaagatcga gatcgaccgc aagaccaaga tgatctaccc agtgcaagcc    1020
acccacaagg gcgccaacat gaagcaactc gccctgtcct tcctccagaa gaacaacgtc    1080
tgcgagcaca gaagtgccc actgaacagc aactgctacg tgatcaacgg cgaggaagtg     1140
tgcaggtgcc tcccaggctt ctccgacgtc aagatcgaca cgtgatgaa ctgcgtccgc      1200
gacgacaccc tcgactgcag caacaacaac ggcggctgcg acgtgaacgc tacctgcacc    1260
ctgatcgaca agaagatcgt ctgcgagtgc aaggacaact tcgagggcga cggcatctac    1320
tgccaccacc accaccacca ctga                                           1344
```

<210> SEQ ID NO 69
<211> LENGTH: 226
<212> TYPE: PRT
<213> ORGANISM: Plasmodium vivax

<400> SEQUENCE: 69

```
Met Glu Thr Leu Leu Asp Ser Glu Thr Leu Lys Asn Tyr Glu Lys Glu
1               5                   10                  15

Thr Asn Glu Tyr Ile Arg Lys Lys Val Glu Lys Leu Phe Asp Val
            20                  25                  30

Ile Leu Lys Asn Val Leu Val Asn Lys Pro Glu Asn Val Tyr Leu Tyr
        35                  40                  45

Ile Tyr Lys Asn Ile Tyr Ser Phe Leu Leu Asn Lys Ile Phe Val Ile
    50                  55                  60

Gly Pro Pro Leu Leu Lys Ile Thr Pro Thr Leu Cys Ser Ala Ile Ala
65                  70                  75                  80

Ser Cys Phe Ser Tyr Tyr His Leu Ser Ala Ser His Met Ile Glu Ser
                85                  90                  95

Tyr Thr Thr Gly Glu Val Asp Asp Ala Ala Glu Ser Thr Ser Lys
            100                 105                 110

Lys Leu Val Ser Asp Asp Leu Ile Cys Ser Ile Val Lys Ser Asn Ile
        115                 120                 125

Asn Gln Leu Asn Ala Lys Gln Lys Arg Gly Tyr Val Val Glu Gly Phe
    130                 135                 140

Pro Gly Thr Asn Leu Gln Ala Asp Ser Cys Leu Arg His Leu Pro Ser
145                 150                 155                 160

Tyr Val Phe Val Leu Tyr Ala Asp Glu Glu Tyr Ile Tyr Asp Lys Tyr
                165                 170                 175

Glu Gln Glu Asn Asn Val Lys Ile Arg Ser Asp Met Asn Ser Gln Thr
            180                 185                 190

Phe Asp Glu Asn Thr Gln Leu Phe Glu Val Ala Glu Phe Asn Thr Asn
        195                 200                 205

Pro Leu Lys Asp Glu Val Lys Val Tyr Leu Arg Asn His His His
210                 215                 220

His His
225
```

<210> SEQ ID NO 70
<211> LENGTH: 681
<212> TYPE: DNA
<213> ORGANISM: Plasmodium vivax

<400> SEQUENCE: 70

```
atggagacgc tcctggactc cgagacgctc aagaactacg agaaggagac gaacgagtac    60
atcaggaaga agaaggtgga gaagctcttc gacgtcatcc tcaagaacgt gctggtcaac   120
aagccagaga acgtgtacct gtacatctac aagaacatct acagcttcct cctgaacaag   180
atcttcgtca tcggcccacc actcctgaag atcaccccaa ccctctgctc cgccatcgcc   240
tcctgcttca gctactacca cctgtccgcc agccacatga tcgagagcta caccaccggc   300
gaggtggacg acgctgctga gtccagcacc tccaagaagc tcgtgagcga cgacctgatc   360
tgctccatcg tcaagagcaa catcaaccaa ctcaacgcca agcagaagag gggctacgtg   420
gtcgagggct tcccaggcac caacctccag gctgactcct gcctcaggca cctgccaagc   480
tacgtgttcg tcctgtacgc cgacgaggag tacatctacg acaagtacga gcaggagaac   540
aacgtgaaga tcaggtccga catgaacagc caaaccttcg acgagaacac ccagctgttc   600
gaggtcgccg agttcaacac caacccactc aaggacgagg tgaaggtcta cctgcgcaac   660
caccaccacc accaccactg a                                              681
```

```
<210> SEQ ID NO 71
<211> LENGTH: 395
<212> TYPE: PRT
<213> ORGANISM: Plasmodium vivax

<400> SEQUENCE: 71

Met Lys Pro Gly Val Glu Lys Lys Lys Lys Leu Glu Glu Asp Val Ile
1               5                   10                  15

Gly Ile Leu Arg Arg Lys Leu Glu Ser Leu Gln Lys Arg Ser Leu Thr
            20                  25                  30

Asn Ser Asp Gly Lys Leu Lys Lys Glu Ile Glu Leu Val Lys Lys Gln
        35                  40                  45

Ile Gln Glu Leu Gln Lys Tyr Glu Lys Gly Glu Ala Gly Lys Lys Val
    50                  55                  60

Asp Ala Thr Leu Gly Glu Glu Pro Gly Val Glu Ser Ala Glu Glu Gln
65                  70                  75                  80

Pro Leu Ser Val Glu Glu Ala Gly Asp Thr Gln Asp Glu Asp Arg Leu
                85                  90                  95

Asp Glu Leu Glu Gly Val Glu Asp Phe Glu Glu Glu Asn Leu Glu Gln
            100                 105                 110

Ser Glu Gln Val Glu Glu Ala Glu Val Val Glu Glu Ala Glu Glu Glu
        115                 120                 125

Ala Gly Asp Ala Glu Glu Glu Gln Pro Ala Glu Ala Glu Glu Asp Gly
    130                 135                 140

Ser Leu Leu Glu Glu Ala Pro Asn Ser Val Glu Arg Lys Ala Glu Gly
145                 150                 155                 160

Ala Ile Ala Glu Phe Glu Glu Ala Asp Val Glu Glu Gly Ala Glu Ala
                165                 170                 175

Asp Glu Gly Val Glu Thr Asp Glu Gly Ala Asp Ala Asp Glu Ala Ser
            180                 185                 190

Leu Gly Ser Phe Asp Leu Glu Gly Glu Leu Ile Glu Glu Asp Leu Gln
        195                 200                 205

Glu Ser Phe Asp Leu Glu Gly Glu Gln Glu Glu Glu Asp Leu Gln Glu
    210                 215                 220

Gly Phe Lys Ser Glu Glu Glu Ala Asn Gln Gly Gly Gln Leu Pro Arg
225                 230                 235                 240

Glu Ile Pro Pro His Gly Glu Glu Ala Val Glu Pro Pro Leu Arg Gly
                245                 250                 255

Asn Lys Pro Ser Met Glu Tyr Val Gly Asn Leu His Ser Asp Val Gly
            260                 265                 270

Pro Thr Glu Gly Ser Ala Asn Gln Ile Ser Pro Pro Ser Val Asp Glu
        275                 280                 285

Lys Gly Lys Glu Asp Gly Asp Lys Tyr Lys Ser Ala Ser Gln Asp Gly
    290                 295                 300

Gly Asn Ser Val Gly Ile Asn Asn Phe Gly Gly Cys Phe Gln Gly Gly
305                 310                 315                 320

Asn Ser Asn Gly Ile Cys Pro Leu Asp Ile Phe Lys Lys Val Leu Glu
                325                 330                 335

Asp Glu Asn Phe Leu Gln Glu Phe Asp Ser Phe Ile His Asn Leu Tyr
            340                 345                 350

Gly Ser Ser Lys Asn Asn Thr Pro Trp Gly Gly Asp Lys Met Gly Asn
        355                 360                 365

Glu Asn Leu Tyr Met Asp Leu Phe Thr Asn Ala Leu Ser Phe Leu Asn
```

|  |  |  | 370 |  |  |  | 375 |  |  |  | 380 |  |  |
|--|--|--|--|--|--|--|--|--|--|--|--|--|--|

Thr Ile Glu Val Ile His His His His His
385             390             395

<210> SEQ ID NO 72
<211> LENGTH: 1188
<212> TYPE: DNA
<213> ORGANISM: Plasmodium vivax

<400> SEQUENCE: 72

| atgaagccag | gcgtggagaa | gaagaagaag | ctcgaagagg | acgtcatcgg | catcctgcgc | 60 |
|---|---|---|---|---|---|---|
| aggaagctgg | agtccctgca | aaagaggtcc | ctcaccaaca | gcgacggcaa | gctcaagaag | 120 |
| gagatcgagc | tggtcaagaa | gcaaatccag | gagctgcaga | agtacgagaa | gggcgaggct | 180 |
| ggcaagaagg | tggacgctac | cctgggcgag | gagccgggcg | tggagtccgc | tgaggagcaa | 240 |
| ccactgagcg | tggaggaagc | cggcgacacc | caggacgagg | acaggctcga | cgagctggag | 300 |
| ggcgtcgaga | cttcgagga | agagaacctg | gagcaaagcg | agcaggtgga | ggaagccgag | 360 |
| gtggtggagg | aagccgagga | gaggccggc | gacgctgagg | aagagcaacc | ggctgaggct | 420 |
| gaggaagacg | gctcccctcct | cgaagaggcc | ccaaacagcg | tggagaggaa | ggctgagggc | 480 |
| gctatcgctg | agttcgagga | agccgacgtc | gaggaaggcg | ccgaggccga | cgagggcgtg | 540 |
| gagacggacg | agggcgctga | cgctgacgag | gcttccctgg | gcagcttcga | cctggagggc | 600 |
| gagctgatcg | aggaagacct | ccaggagtct | ttcgacctgg | aggggagca | agaggaagag | 660 |
| gacctccaag | agggcttcaa | gagcgaggaa | gaggccaacc | aaggcggcca | gctgccaagg | 720 |
| gagatcccac | cacacggcga | ggaagccgtg | gagccaccac | tccgcggcaa | caagccatcc | 780 |
| atggagtatg | tgggcaacct | gcacagcgac | gtgggcccaa | ccgagggcag | cgccaaccaa | 840 |
| atctccccac | caagcgtcga | cgagaagggc | aaggaagacg | gcgacaagta | caagtccgcc | 900 |
| agccaagacg | gcggaaactc | cgtgggcatc | aacaacttcg | gcggatgctt | ccagggcggc | 960 |
| aacagcaacg | gcatctgccc | actcgacatc | ttcaagaagg | tcctggagga | cgagaacttc | 1020 |
| ctgcaggagt | tcgactcctt | catccacaac | ctgtacggct | ccagcaagaa | caacacccca | 1080 |
| tgggggcggcg | acaagatggg | caacgagaac | ctctacatgg | acctgttcac | caacgccctc | 1140 |
| agcttcctga | acaccatcga | ggtcatccac | caccaccacc | accactga |  | 1188 |

<210> SEQ ID NO 73
<211> LENGTH: 372
<212> TYPE: PRT
<213> ORGANISM: Plasmodium vivax

<400> SEQUENCE: 73

Met Glu Leu Ser His Ser Leu Ser Val Lys Asn Ala Pro Asp Ala Ser
1               5                   10                  15

Ala Leu Asn Ile Glu Val Glu Lys Asp Lys Lys Ile Cys Lys Asn
            20                  25                  30

Ala Phe Gln Tyr Ile Asn Val Ala Glu Leu Leu Ser Pro Arg Glu Glu
        35                  40                  45

Glu Thr Tyr Val Gln Lys Cys Glu Glu Val Leu Asp Thr Ile Lys Asn
    50                  55                  60

Asp Ser Pro Asp Glu Ser Ala Glu Ala Glu Ile Asn Glu Phe Ile Leu
65                  70                  75                  80

Ser Leu Leu His Ala Arg Ser Lys Tyr Thr Ile Ile Asn Asp Ser Asp
                85                  90                  95

```
Glu Glu Val Leu Ser Lys Leu Leu Arg Ser Ile Asn Gly Ser Ile Ser
            100                 105                 110
Glu Glu Ala Ala Leu Lys Arg Ala Lys Gln Leu Ile Thr Phe Asn Arg
        115                 120                 125
Phe Ile Lys Asp Lys Ala Lys Val Lys Asn Val Gln Glu Met Leu Val
    130                 135                 140
Ile Ser Ser Lys Ala Asp Asp Phe Met Asn Glu Pro Lys Gln Lys Met
145                 150                 155                 160
Leu Gln Lys Ile Ile Asp Ser Phe Glu Leu Tyr Asn Asp Tyr Leu Val
                165                 170                 175
Ile Leu Gly Ser Asn Ile Asn Ile Ala Lys Arg Tyr Ser Ser Glu Thr
            180                 185                 190
Phe Leu Ser Ile Lys Asn Glu Lys Phe Cys Ser Asp His Ile His Leu
        195                 200                 205
Cys Gln Lys Phe Tyr Glu Gln Ser Ile Ile Tyr Tyr Arg Leu Lys Val
    210                 215                 220
Ile Phe Asp Asn Leu Val Thr Tyr Val Asp Gln Asn Ser Lys His Phe
225                 230                 235                 240
Lys Lys Glu Lys Leu Leu Glu Leu Leu Asn Met Asp Tyr Arg Val Asn
                245                 250                 255
Arg Glu Ser Lys Val His Glu Asn Tyr Val Leu Glu Asp Glu Thr Val
            260                 265                 270
Ile Pro Thr Met Arg Ile Thr Asp Ile Tyr Asp Gln Asp Arg Leu Ile
        275                 280                 285
Val Glu Val Val Gln Asp Gly Asn Ser Lys Leu Met His Gly Arg Asp
    290                 295                 300
Ile Glu Lys Arg Glu Ile Ser Glu Arg Tyr Ile Val Thr Val Lys Asn
305                 310                 315                 320
Leu Arg Lys Asp Leu Asn Asp Glu Gly Leu Tyr Ala Asp Leu Met Lys
                325                 330                 335
Thr Val Lys Asn Tyr Val Leu Ser Ile Thr Gln Ile Asp Asn Asp Ile
            340                 345                 350
Ser Asn Leu Val Arg Glu Leu Asp His Glu Asp Val Glu Lys His His
        355                 360                 365
His His His His
    370

<210> SEQ ID NO 74
<211> LENGTH: 1119
<212> TYPE: DNA
<213> ORGANISM: Plasmodium vivax

<400> SEQUENCE: 74
atggagctct cccacagcct gtccgtgaag aacgctccag acgctagcgc tctcaacatc      60
gaggtcgaga aggacaagaa gaagatctgc aagaacgcct tccaatacat caacgtcgcc     120
gagctcctgt ccccaaggga ggaagagact tacgtgcaga agtgcgagga agtgctggac     180
accatcaaga acgacagccc agacgagtcc gctgaggctg agatcaacga gttcatcctc     240
agcctcctgc acgcccgctc caagtacacc atcatcaacg acagcgacga ggaagtgctg     300
agcaagctcc tgaggtccat caacggcagc atctccgagg aagccgctct caagagggct     360
aagcaactga tcaccttcaa caggttcatc aaggacaagg ccaaggtgaa gaacgtccag     420
gagatgctcg tcatctccag caaggccgac gacttcatga acgagccaaa gcaaaagatg     480
ctccagaaga tcatcgacag cttcgagctg tacaacgact acctcgtgat cctgggctcc     540
```

-continued

```
aacatcaaca tcgccaagcg ctactccagc gagacgttcc tcagcatcaa gaacgagaag    600
ttctgctccg accacatcca cctgtgccaa aagttctacg agcagagcat catctactac    660
aggctcaagg tcatcttcga caacctggtg acctacgtcg accaaaactc caagcacttc    720
aagaaggaga agctcctgga gctcctgaac atggactaca gggtgaaccg cgagtccaag    780
gtgcacgaga actacgtcct ggaggacgag actgtgatcc caaccatgcg catcaccgac    840
atctacgacc aagacaggct catcgtggag gtggtccagg acggcaacag caagctgatg    900
cacggcaggg acatcgagaa gcgcgagatc tccgagaggt acatcgtgac cgtcaagaac    960
ctccgcaagg acctgaacga cgagggcctc tacgccgacc tgatgaagac cgtgaagaac    1020
tacgtcctca gcatcaccca gatcgacaac gacatctcca acctcgtgag ggagctggac    1080
cacgaggacg tcgagaagca ccaccaccac caccactga                           1119
```

<210> SEQ ID NO 75
<211> LENGTH: 450
<212> TYPE: PRT
<213> ORGANISM: Plasmodium vivax

<400> SEQUENCE: 75

```
Met Glu Lys Leu Asp Ile Pro Pro His Glu Met Tyr Glu Asp Met Gln
1               5                   10                  15

Gln Ala Phe Arg Glu Gln Asp Lys Tyr Asp Phe Leu Ala Ile Ser Asp
            20                  25                  30

Gly Ser Val Ile Asn Ser Tyr Met Lys Lys Asn Val Val Asp Trp Asn
        35                  40                  45

Asn Arg Tyr Ser Tyr Asn Gln Leu Lys Asn Lys Asp Ser Leu Ile Met
    50                  55                  60

Phe Leu Val Asp Ile Phe Arg Ser Leu Phe Leu Ser Asn Cys Ile Asp
65                  70                  75                  80

Lys Asn Ile Asp Asn Val Leu Ser Ser Ile Glu Glu Met Phe Thr Asp
                85                  90                  95

His Tyr Tyr Asn Pro Met His Ser Arg Leu Lys Tyr Leu Ile Asp Asp
            100                 105                 110

Val Gly Ile Phe Phe Thr Lys Leu Pro Ile Thr Lys Ala Phe His Thr
        115                 120                 125

Tyr Asn Lys Lys Tyr Arg Ile Thr Lys Arg Leu Tyr Ala Pro Pro Thr
    130                 135                 140

Phe Asn Glu Val Arg His Ile Leu Asn Leu Ala Gln Ile Leu Ser Leu
145                 150                 155                 160

Glu Asp Gly Leu Asp Leu Leu Thr Phe Asp Ala Asp Glu Thr Leu Tyr
                165                 170                 175

Pro Asp Gly Tyr Asp Phe His Asp Glu Val Leu Ala Ser Tyr Ile Ser
            180                 185                 190

Ser Leu Leu Lys Lys Met Asn Ile Ala Ile Val Thr Ala Ala Ser Tyr
        195                 200                 205

Ser Asn Asp Ala Glu Lys Tyr Gln Lys Arg Leu Glu Asn Leu Leu Arg
    210                 215                 220

Tyr Phe Ser Lys His Asn Ile Glu Asp Gly Ser Tyr Glu Asn Phe Tyr
225                 230                 235                 240

Val Met Gly Gly Glu Ser Asn Tyr Leu Phe Lys Cys Asn Glu Asp Ala
                245                 250                 255

Asn Leu Tyr Ser Val Pro Glu Glu Glu Trp Tyr His Tyr Lys Lys Tyr
            260                 265                 270
```

```
Val Asn Lys Glu Thr Val Glu Gln Ile Leu Asp Ile Ser Gln Lys Cys
        275                 280                 285

Leu Gln Gln Val Ile Thr Asp Phe Lys Leu Cys Ala Gln Ile Gln Arg
    290                 295                 300
Lys Glu Lys Ser Ile Gly Leu Val Pro Asn Lys Ile Pro Ser Ala Asn
305                 310                 315                 320
Asn Gln Lys Glu Gln Lys Asn Tyr Met Ile Lys Tyr Glu Val Leu Glu
                325                 330                 335
Glu Ala Val Ile Arg Val Lys Lys Glu Ile Val Lys Asn Lys Ile Thr
            340                 345                 350

Ala Pro Tyr Cys Ala Phe Asn Gly Gly Gln Asp Leu Trp Val Asp Ile
        355                 360                 365

Gly Asn Lys Ala Glu Gly Leu Ile Ile Leu Gln Lys Leu Leu Lys Ile
    370                 375                 380
Glu Lys Lys Lys Cys Cys His Ile Gly Asp Gln Phe Leu His Ser Gly
385                 390                 395                 400
Asn Asp Phe Pro Thr Arg Phe Cys Ser Leu Thr Leu Trp Ile Ser Asn
                405                 410                 415
Pro Gln Glu Thr Lys Ala Cys Leu Lys Ser Ile Met Asn Leu Asn Met
            420                 425                 430

Lys Ser Phe Ile Pro Glu Val Leu Tyr Glu Asn Glu His His His His
        435                 440                 445

His His
    450
```

<210> SEQ ID NO 76
<211> LENGTH: 1353
<212> TYPE: DNA
<213> ORGANISM: Plasmodium vivax

<400> SEQUENCE: 76

```
atggagaagc tcgacatccc accacacgag atgtacgagg acatgcaaca ggccttcagg      60
gagcaagaca agtacgactt cctggccatc tccgacggca gcgtgatcaa ctcctacatg     120
aagaagaacg tggtcgactg gaacaacagg tactcctaca accagctcaa gaacaaggac     180
agcctcatca tgttcctggt ggacatcttc cgctccctct tcctgagcaa ctgcatcgac     240
aagaacatcg acaacgtcct gtccagcatc gaggagatgt tcaccgacca ctactacaac     300
ccaatgcaca gcaggctcaa gtacctgatc gacgacgtgg gcatcttctt caccaagctc     360
ccaatcacca aggccttcca cacctacaac aagaagtaca ggatcaccaa gcgcctgtac     420
gccccaccaa ccttcaacga ggtccgccac atcctcaacc tggcccaaat cctctccctg     480
gaggacggcc tcgacctcct gaccttcgac gccgacgaga cgctgtaccc agacggctac     540
gacttccacg acgaggtgct cgccagctac atctccagcc tcctgaagaa gatgaacatc     600
gccatcgtca ccgccgcctc ctacagcaac gacgccgaga agtaccagaa gaggctggag     660
aacctcctgc gctacttctc caagcacaac atcgaggacg gcagctacga gaacttctac     720
gtgatgggcg gcgagtccaa ctacctcttc aagtgcaacg aggacgccaa cctgtacagc     780
gtcccagagg aagagtggta ccactacaag aagtatgtga acaaggagac ggtcgagcaa     840
atcctcgaca tctcccagaa gtgcctgcaa caagtgatca ccgacttcaa gctctgcgcc     900
caaatccaga ggaaggagaa gtccatcggc ctggtcccaa acaagatccc aagcgccaac     960
aaccaaaagg agcagaagaa ctacatgatc aagtacgagg tgctcgaaga ggccgtgatc    1020
```

```
cgcgtcaaga aggagatcgt caagaacaag atcaccgctc catactgcgc cttcaacggc      1080
ggccaagacc tgtgggtgga catcggcaac aaggccgagg gcctcatcat cctgcaaaag      1140
ctcctgaaga tcgagaagaa gaagtgctgc cacatcggcg accagttcct ccacagcggc      1200
aacgacttcc caacccgctt ctgctccctc accctgtgga tcagcaaccc acaggagacg      1260
aaggcctgcc tcaagtccat catgaacctg aacatgaaga gcttcatccc agaggtcctc      1320
tacgagaacg agcaccacca ccaccaccac tga                                   1353
```

```
<210> SEQ ID NO 77
<211> LENGTH: 527
<212> TYPE: PRT
<213> ORGANISM: Plasmodium vivax

<400> SEQUENCE: 77

Met Glu Ile Ile Ala Glu Lys Pro Lys Val Lys Phe Asn Phe Ala Ser
1               5                   10                  15

Glu Glu Tyr Lys Asn Cys Asp Ser Ser Asp Tyr Ser Glu Cys Ala Glu
            20                  25                  30

Asp Tyr Gly Arg Pro Asn Gly Lys Asp Tyr Phe Tyr Ala Asn Arg Ile
        35                  40                  45

Leu Ser Leu Asp Arg Asn Ser Glu Gln Arg Arg Lys Glu Ser Pro Ser
    50                  55                  60

Lys Arg Pro Gly Leu Cys Val Asp Glu Ile Cys Thr Cys Gly Phe His
65                  70                  75                  80

Arg Cys Pro Lys Ile Val Lys Ser Leu Pro Phe Asp Gly Glu Ser Asn
                85                  90                  95

Tyr Arg Ser Glu Phe Gly Pro Lys Pro Leu Pro Glu Leu Pro Pro Arg
            100                 105                 110

Gln Glu Ala Lys Leu Thr Arg Ser Leu Pro Phe Glu Gly Glu Ser Asn
        115                 120                 125

Tyr Arg Ser Glu Phe Gly Pro Lys Pro Leu Pro Glu Leu Pro Pro Arg
    130                 135                 140

Val Glu Gln Lys Pro Pro Lys Ser Leu Pro Phe Asp Gly Glu Ser Asn
145                 150                 155                 160

Tyr Arg Ser Glu Phe Gly Pro Lys Pro Leu Pro Glu Leu Pro Pro Arg
                165                 170                 175

Val Glu Gln Lys Pro Pro Lys Ser Leu Pro Phe Asp Gly Glu Ser Asn
            180                 185                 190

Tyr Arg Ser Glu Phe Gly Pro Lys Pro Leu Pro Glu Leu Pro Pro Arg
        195                 200                 205

Val Glu Gln Lys Pro Pro Lys Ser Leu Pro Phe Glu Gly Glu Ser Asn
    210                 215                 220

Tyr Arg Ser Glu Phe Gly Pro Lys Pro Leu Pro Glu Leu Pro Pro Arg
225                 230                 235                 240

Val Glu Gln Lys Pro Pro Lys Ser Leu Pro Phe Glu Gly Glu Ser Asn
                245                 250                 255

Tyr Arg Ser Glu Phe Gly Pro Lys Ala Leu Pro Glu Leu Pro Pro Arg
            260                 265                 270

Val Glu Gln Lys Pro Pro Lys Ser Leu Pro Phe Glu Gly Glu Ser Asn
        275                 280                 285

Tyr Arg Ser Glu Phe Gly Pro Lys Pro Leu Ala Leu Pro Pro Arg
    290                 295                 300

Val Glu Thr Lys Leu Val Lys Ser Leu Pro Phe Glu Gly Glu Ser Asn
305                 310                 315                 320
```

```
Tyr Arg Ser Glu Phe Gly Pro Lys Pro Leu Pro Glu Leu Pro Pro Arg
            325                 330                 335

Val Glu Gln Lys Pro Pro Lys Ser Leu Pro Phe Glu Gly Glu Ser Asn
        340                 345                 350

Tyr Arg Ser Glu Phe Gly Pro Lys Pro Leu Pro Ala Leu Pro Pro Arg
            355                 360                 365

Val Val Thr Lys Leu Val Lys Ser Leu Pro Phe Glu Gly Glu Ser Asn
        370                 375                 380

Tyr Arg Ser Glu Phe Gly Pro Lys Pro Leu Pro Glu Ile Pro Pro Arg
385                 390                 395                 400

Val Glu Gln Lys Pro Pro Lys Ser Leu Pro Phe Glu Gly Glu Ser Asn
            405                 410                 415

Tyr Arg Ser Glu Phe Gly Pro Lys Pro Leu Pro Glu Leu Pro Pro Arg
            420                 425                 430

Val Glu Gln Lys Pro Pro Lys Ser Leu Pro Phe Glu Gly Glu Ser Asn
        435                 440                 445

Tyr Arg Ser Glu Phe Gly Pro Lys Gln Leu Pro Glu Leu Pro Pro Arg
        450                 455                 460

Gln Glu Ala Lys Leu Thr Arg Ser Leu Pro Phe Glu Gly Glu Ser Ser
465                 470                 475                 480

Tyr Arg Ser Glu Tyr Val Arg Lys Ala Ile Pro Ile Cys Pro Val Asn
            485                 490                 495

Leu Leu Pro Lys Tyr Pro Ala Pro Thr Tyr Pro Ser Glu His Val Phe
            500                 505                 510

Trp Asp Ser Ala Cys Lys Arg Trp Tyr His His His His His
            515                 520                 525

<210> SEQ ID NO 78
<211> LENGTH: 1584
<212> TYPE: DNA
<213> ORGANISM: Plasmodium vivax

<400> SEQUENCE: 78
atggagatca tcgccgagaa gccaaaggtc aagttcaact tcgcctccga ggagtacaag      60
aactgcgact ccagcgacta ctccgagtgc gctgaggact acggcaggcc aaacggcaag     120
gactacttct acgccaacag gatcctctcc ctggaccgca cagcgagca gaggcgcaag      180 gagtccccaa gcaagaggcc aggcctctgc gtggacgaga tctgcacctg cggcttccac     240
cgctgcccaa agatcgtcaa gtccctgcca ttcgacggcg agtccaacta ccgcagcgag     300
ttcggcccaa agccactccc agagctgcca ccaaggcaag aggccaagct cacccgcagc     360
ctgccattcg agggcgagtc caactacagg tccgagttcg gcctaagcc tctgcctgag      420 ctgccaccac gcgtggagca aaagccacca aagtccctcc ctttcgatgg ggagagcaac     480
tacaggagtg aattcgggcc taagccgctg cccgagctgc caccacgcgt cgagcagaag     540
ccaccaaaga gcctcccttt cgatggcgag agcaactaca ggagcgaatt ggggcctaag     600
ccgctgccgg aactgccacc acgcgtggaa caaaagccac caaagagcct gcctttcgag     660
ggggagtcca actacaggag tgagtttggg cctaagccgt tgcctgaact gccaccacgc     720
gtcgaacaga accaccaaa aagcctccct ttcgagggcg agagcaacta ccgctccgag     780
ttcggcccaa aggctctgcc ggagctgcca ccacgcgtgg aacagaaacc accaaagagc     840
ctccccttcg aggggagag caattatcgc tctgagttcg gccaaagcc gctgccggct     900 ctgccaccac gcgtggagac gaagctcgtc aagagcctcc cgttcgaggg ggagagcaac     960
```

```
tatcgctccg aatttgggcc taaaccactg cctgaactgc caccacgcgt ggaacagaag    1020
ccaccaaaaa gcctcccctt tgaaggggag agcaattacc gctccgagtt cgggcccaag    1080
ccgctgccgg ccctgccacc acgcgtggtc accaagctcg tgaagtccct cccctttgaa    1140
ggcgagagca actacagatc tgagttcggg cctaagccac tcccagagat cccaccacgc    1200
gtcgagcaaa aaccaccaaa atctctcccc tttgagggtg agagcaatta tcgctcagag    1260
ttcgggccca agcctctgcc ggagctgcca ccacgcgtcg aacagaagcc accaaagagc    1320 ttacctttg aaggggagag caactaccgc agtgaattcg cccaaagca gctgccagaa      1380 ctgccaccaa ggcaagaggc caaactcacc cgctccctgc ctttcgaggg cgagtccagc    1440
tacaggagcg agtatgtgag gaaggccatc ccaatctgcc cagtcaacct cctgccaaag    1500
tacccagccc caacctaccc atccgagcac gtgttctggg acagcgcctg caagcgctgg    1560
taccaccacc accaccacca ctga                                           1584
```

<210> SEQ ID NO 79
<211> LENGTH: 266
<212> TYPE: PRT
<213> ORGANISM: Plasmodium vivax

<400> SEQUENCE: 79

```
Met Ala Ala Ala Asn Arg Pro Asn Ala Asn Gly Phe Val Ser Pro Thr
1               5                   10                  15

Leu Ile Gly Phe Gly Glu Leu Ser Ile Gln Glu Ser Glu Glu Phe Lys
            20                  25                  30

Arg Met Ala Trp Asn Asn Trp Met Leu Arg Leu Glu Ser Asp Trp Lys
        35                  40                  45

His Phe Asn Asp Ser Val Glu Glu Ala Lys Thr Lys Trp Leu His Glu
    50                  55                  60

Arg Asp Ser Ala Trp Ser Asp Trp Leu Arg Ser Leu Gln Ser Lys Trp
65                  70                  75                  80

Ser His Tyr Ser Glu Lys Met Leu Lys Glu His Lys Ser Asn Val Met
                85                  90                  95

Glu Lys Ser Ala Asn Trp Asn Asp Thr Gln Trp Gly Asn Trp Ile Lys
            100                 105                 110

Thr Glu Gly Arg Lys Ile Leu Glu Ala Gln Trp Glu Lys Trp Ile Lys
        115                 120                 125

Lys Gly Asp Asp Gln Leu Gln Lys Leu Ile Leu Asp Lys Trp Val Gln
130                 135                 140

Trp Lys Asn Asp Lys Ile Arg Ser Trp Leu Ser Ser Glu Trp Lys Thr
145                 150                 155                 160

Glu Glu Asp Tyr Tyr Trp Ala Asn Val Glu Arg Ala Thr Thr Ala Lys
                165                 170                 175

Trp Leu Gln Glu Ala Glu Lys Met His Trp Leu Lys Trp Lys Glu Arg
            180                 185                 190

Ile Asn Arg Glu Ser Glu Gln Trp Val Asn Trp Val Gln Met Lys Glu
        195                 200                 205

Ser Val Tyr Ile Asn Val Glu Trp Lys Lys Trp Pro Lys Trp Lys Asn
    210                 215                 220

Asp Lys Lys Ile Leu Phe Asn Lys Trp Ser Thr Asn Leu Val Tyr Lys
225                 230                 235                 240

Trp Thr Leu Lys Lys Gln Trp Asn Val Trp Ile Lys Glu Ala Asn Thr
                245                 250                 255
```

Ala Pro Gln Val His His His His His His
        260                 265

<210> SEQ ID NO 80
<211> LENGTH: 801
<212> TYPE: DNA
<213> ORGANISM: Plasmodium vivax

<400> SEQUENCE: 80

```
atggctgccg ccaacaggcc aaacgccaac ggcttcgtct ccccaaccct catcggcttc      60
ggcgagctgt ccatccaaga gagcgaggag ttcaagagga tggcctggaa caactggatg     120
ctccgcctgg agtccgactg gaagcacttc aacgacagcg tggaggaagc caagaccaag     180
tggctgcacg agagggactc cgcttggagc gactggctcc gctccctgca gagcaagtgg     240
tcccactaca gcgagaagat gctgaaggag cacaagtcca acgtcatgga gaagagcgcc     300
aactggaacg acacccaatg ggcaactgg atcaagaccg agggccgcaa gatcctggag      360
gcccagtggg agaagtggat caagaagggc gacgaccaac tgcagaagct catcctggac     420
aagtgggtcc agtggaagaa cgacaagatc aggtcctggc tctccagcga gtggaagacc     480
gaggaagact actactgggc taacgtggag agggctacca ccgctaagtg gctccaagag     540
gccgagaaga tgcactggct gaagtggaag gagaggatca accgcgagtc cgagcaatgg     600
gtgaactggg tccagatgaa ggagagcgtg tacatcaacg tcgagtggaa gagtggcca     660 aagtggaaga acgataagaa gatcctgttc aacaagtgga gcaccaacct cgtgtacaag     720 tggacccctga agaagcagtg gaacgtctgg atcaaggaag ccaacaccgc cccacaggtg    780
caccaccacc accaccactg a                                               801
```

<210> SEQ ID NO 81
<211> LENGTH: 475
<212> TYPE: PRT
<213> ORGANISM: Plasmodium vivax

<400> SEQUENCE: 81

Met Glu Lys Val Val Asp Glu Val Lys Tyr Ser Glu Glu Val Cys Asn
1               5                   10                  15

Glu Ser Val Asp Leu Tyr Leu Leu Val Asp Gly Ser Gly Ser Ile Gly
                20                  25                  30

Tyr Pro Asn Trp Ile Thr Lys Val Ile Pro Met Leu Asn Gly Leu Ile
            35                  40                  45

Asn Ser Leu Ser Leu Ser Arg Asp Thr Ile Asn Leu Tyr Met Asn Leu
        50                  55                  60

Phe Gly Asn Tyr Thr Thr Glu Leu Ile Arg Leu Gly Ser Gly Gln Ser
65                  70                  75                  80

Ile Asp Lys Arg Gln Ala Leu Ser Lys Val Thr Glu Leu Arg Lys Thr
                85                  90                  95

Tyr Thr Pro Tyr Gly Thr Thr Asn Met Thr Ala Ala Leu Asp Glu Val
            100                 105                 110

Gln Lys His Leu Asn Asp Arg Val Asn Arg Glu Lys Ala Ile Gln Leu
        115                 120                 125

Val Ile Leu Met Thr Asp Gly Val Pro Asn Ser Lys Tyr Arg Ala Leu
    130                 135                 140

Glu Val Ala Asn Lys Leu Lys Gln Arg Asn Val Ser Leu Ala Val Ile
145                 150                 155                 160

Gly Val Gly Gln Gly Ile Asn His Gln Phe Asn Arg Leu Ile Ala Gly
                165                 170                 175

```
Cys Arg Pro Arg Glu Pro Asn Cys Lys Phe Tyr Ser Tyr Ala Asp Trp
                180                 185                 190

Asn Glu Ala Val Ala Leu Ile Lys Pro Phe Ile Ala Lys Val Cys Thr
            195                 200                 205

Glu Val Glu Arg Val Ala Asn Cys Gly Pro Trp Asp Pro Trp Thr Ala
    210                 215                 220

Cys Ser Val Thr Cys Gly Arg Gly Thr His Ser Arg Ser Arg Pro Ser
225                 230                 235                 240

Leu His Glu Lys Cys Thr Thr His Met Val Ser Glu Cys Glu Glu Gly
                245                 250                 255

Glu Cys Pro Val Glu Pro Glu Pro Leu Pro Val Pro Ala Pro Leu Pro
                260                 265                 270

Thr Val Pro Glu Asp Val Asn Pro Arg Asp Thr Asp Glu Asn Glu
            275                 280                 285

Asn Pro Asn Phe Asn Lys Gly Leu Asp Val Pro Asp Glu Asp Asp
    290                 295                 300

Glu Val Pro Pro Ala Asn Glu Gly Ala Asp Gly Asn Pro Val Glu Glu
305                 310                 315                 320

Asn Val Phe Pro Pro Ala Asp Asp Ser Val Pro Asp Glu Ser Asn Val
                325                 330                 335

Leu Pro Leu Pro Pro Ala Val Pro Gly Gly Ser Ser Glu Glu Phe Pro
                340                 345                 350

Ala Asp Val Gln Asn Asn Pro Asp Ser Pro Glu Glu Leu Pro Met Glu
            355                 360                 365

Gln Glu Val Pro Gln Asp Asn Asn Val Asn Glu Pro Glu Arg Ser Asp
    370                 375                 380

Ser Asn Gly Tyr Gly Val Asn Glu Lys Val Ile Pro Asn Pro Leu Asp
385                 390                 395                 400

Asn Glu Arg Asp Met Ala Asn Lys Asn Lys Thr Val His Pro Gly Arg
                405                 410                 415

Lys Asp Ser Ala Arg Asp Arg Tyr Ala Arg Pro His Gly Ser Thr His
            420                 425                 430

Val Asn Asn Arg Ala Asn Glu Asn Ser Asp Ile Pro Asn Asn Pro
    435                 440                 445

Val Pro Ser Asp Tyr Glu Gln Pro Glu Asp Lys Ala Lys Lys Ser Ser
450                 455                 460

Asn Asn Gly Tyr Lys His His His His His His
465                 470                 475

<210> SEQ ID NO 82
<211> LENGTH: 1428
<212> TYPE: DNA
<213> ORGANISM: Plasmodium vivax

<400> SEQUENCE: 82
atggagaagg tggtcgacga ggtgaagtac agcgaggaag tgtgcaacga gtccgtcgac    60
ctctacctcc tggtggacgg ctccggcagc atcggctacc aaactggat caccaaggtc   120 atcccaatgc tcaacggcct gatcaactcc ctcagcctgt cccgcgacac catcaacctc   180
tacatgaacc tgttcggcaa ctacaccacc gagctcatca ggctgggcag cggccaatcc   240
atcgacaagc gccaggccct cagcaaggtg accgagctga ggaagaccta caccccatac   300
ggcaccacca acatgaccgc cgccctcgac gaggtgcaaa agcacctgaa cgacagggtc   360
aaccgcgaga aggccatcca gctcgtgatc ctgatgaccg acggcgtccc aaacagcaag   420
```

```
taccgcgccc tggaggtggc caacaagctg aagcaaagga acgtctccct ggccgtgatc    480
ggcgtgggcc aaggcatcaa ccaccagttc aacaggctga tcgctggctg caggccacgc    540
gagccaaact gcaagttcta cagctacgct gactggaacg aggctgtggc tctcatcaag    600
ccattcatcg ccaaggtctg caccgaggtg gagagggtgg ctaactgcgg ccatgggac     660 ccgtggaccg cttgctccgt gacctgcggc aggggcaccc acagcaggtc ccgcccaagc    720
ctgcacgaga gtgcaccac ccacatggtg tccgagtgcg aggaaggcga gtgcccagtg     780
gagccagagc cactgccggt cccagccca ctgccaaccg tgccagagga cgtcaaccca     840
agggacaccg acgacgagaa cgagaaccca aacttcaaca agggcctcga cgtgccagac    900
gaggacgacg acgaggtccc accagctaac gagggcgctg acggcaaccc agtggaggag    960
aacgtcttcc caccagccga cgacagcgtg ccagacgagt ccaacgtgct gccactgcca    1020
ccagctgtgc caggcggctc cagcgaggag ttcccagctg acgtccaaaa caacccagac    1080
tccccagagg agctcccgat ggagcaagag gtgccacagg acaacaacgt caacgagcca    1140
gagcgcagcg actccaacgg ctacggcgtg aacgagaagg tcatcccaaa cccactggac    1200
aacgagaggg acatggccaa caagaacaag accgtgcacc cgggcaggaa ggacagcgcc    1260
agggaccgct acgccaggcc acacggctcc acccacgtga caacaacag ggccaacgag     1320 aacagcgaca tcccaaacaa cccagtccca tccgactacg agcagccaga ggacaaggcc    1380
aagaagtcca gcaacaacgg ctacaagcac caccaccacc accactga                1428
```

<210> SEQ ID NO 83
<211> LENGTH: 362
<212> TYPE: PRT
<213> ORGANISM: Plasmodium vivax

<400> SEQUENCE: 83

```
Met Asp Asp Lys Lys Asp Lys Glu Asn Glu His Lys Glu Asp Ala Asp
1               5                   10                  15

Lys Lys Asn Asn Asp Glu Leu Lys Thr Leu Lys Gly Lys Leu Gln Lys
            20                  25                  30

Ile Arg Val Gln Ile Lys Asp Asp Lys Leu Pro Gln Lys Ile Ser Glu
        35                  40                  45

Glu Gln Ile Ser Val Leu Lys Lys Lys Leu Glu Asp Phe Lys Asn Leu
    50                  55                  60

Lys Ser Glu His Glu Ala Lys Leu Ala Ser Glu Lys Gly Asp Thr Ser
65                  70                  75                  80

Ala Gly Gly Glu Gly Glu Leu Gly Leu Ser Asp Lys Glu Phe Val Gly
                85                  90                  95

Gln Asn Val Lys Ala Asn Gly Asp Ala Ala Gly Val Ser Gly Glu Gln
            100                 105                 110

Gly Ala Ser Gly Gly Ser Gly Gln Gly Glu Ala Gly Pro Ser Ser Pro
        115                 120                 125

Ala Asp Glu Gln Asp Asp Asp Asn Glu Ala Val Gln Trp Gly Pro Ala
    130                 135                 140

Thr Glu Glu Val Val Ala Glu Ala Met Ser Asp Glu Gly Pro Gln Glu
145                 150                 155                 160

Gln Gly Ala Glu Gly Gly Pro Ser Asn Pro Thr Asp Asp Gln Ala Glu
                165                 170                 175

Glu Ala Thr Pro Gly Pro Ser Lys Pro Ala Ser Gly Ala Ser Gly Ser
            180                 185                 190
```

Gln Gly Ala Ser Asp Ser Ser Asn Asp Ser Ala Glu Pro Thr Ser Ala
            195                 200                 205

Ala Ala Ala Ala Ala Pro Ala Gly Pro Thr Ala Ala Ala Ser Pro
    210                 215                 220

Gln Val Lys His Val Asp Thr Leu Cys Asp Glu Leu Leu Ala Gly Glu
225                 230                 235                 240

Asn Lys Lys Asn Val Leu Asp Glu Gly Glu Asp His Ser Gln Tyr Asn
                245                 250                 255

Ile Phe Arg Lys Gln Tyr Asp Lys Met Val Leu Asn Lys Thr Glu Tyr
            260                 265                 270

Asn Ile Ser Leu Lys Leu Leu Asp Thr Met Leu Thr Asn Gly Gln Val
        275                 280                 285

Glu Arg Glu Lys Lys Asn Thr Leu Ile Lys Thr Phe Lys Lys Ala Leu
    290                 295                 300

Tyr Asp Lys Gln Tyr Ser Glu Lys Leu Arg Asn Leu Ile Ser Gly Val
305                 310                 315                 320

Tyr Ala Phe Ala Lys Arg Asn Asn Phe Ile Asp Gly Asp Lys Val Lys
                325                 330                 335

Glu Gly Asp Tyr Ser Lys Leu Phe Glu Tyr Ile Gly Cys Met Met Asn
            340                 345                 350

Thr Leu Glu Leu His His His His His His
        355                 360

<210> SEQ ID NO 84
<211> LENGTH: 1089
<212> TYPE: DNA
<213> ORGANISM: Plasmodium vivax

<400> SEQUENCE: 84
atggacgaca agaaggacaa ggagaacgag cacaaggaag acgccgataa gaagaacaac      60
gacgagctca agaccctgaa gggcaagctc caaaagatca gggtgcagat caaggacgac     120
aagctgccac aaaagatctc cgaggagcag atcagcgtcc tcaagaagaa gctggaggac     180
ttcaagaacc tcaagtccga gcacgaggcc aagctggcct ccgagaaggg cgacaccctcc    240 gccggcggcg agggcgagct gggcctgtcc gacaaggagt tcgtgggcca aaacgtcaag     300
gccaacggcg acgccgccgg cgtgagcggc gagcaaggcg cctccggcgg cagcggccag     360
ggcgaggctg gcccatccag cccagccgac gagcaagacg acgacaacga ggctgtccag     420
tggggcccag ctaccgagga agtggtggct gaggctatgt ccgacgaggg cccacaagag     480
cagggcgctg agggcggccc aagcaaccca accgacgacc aagctgagga agccaccccca    540 ggcccatcca agccagcttc cggcgcttcc ggcagccagg gcgcttccga ctccagcaac     600
gactccgccg agccaaccag cgctgccgcc gccgccgccc cagctggccc aaccgctgcc     660
gccgccagcc cacaggtgaa gcacgtggac accctctgcg acgagctcct ggctggcgag     720
aacaagaaga acgtgctgga cgagggcgag gaccactccc aatacaacat cttcaggaag     780
cagtacgaca agatggtcct caacaagacc gagtacaaca tcagcctcaa gctcctggac     840
accatgctga ccaacggcca agtggagcgc gagaagaaga acaccctcat caagaccttc     900
aagaaggccc tgtacgacaa gcagtactcc gagaagctca ggaacctgat cagcggcgtg     960
tacgccttcg ccaagcgcaa caacttcatc gacggcgaca aggtgaagga aggcgactac    1020
agcaagctct tcgagtacat cggctgcatg atgaacaccc tggagctgca ccaccaccac    1080
caccactga                                                            1089

<210> SEQ ID NO 85
<211> LENGTH: 723
<212> TYPE: PRT
<213> ORGANISM: Plasmodium vivax

<400> SEQUENCE: 85

```
Met Lys Arg His Ala Thr Arg Gly Ala Leu His Ser Leu Lys Ser Ile
1               5                   10                  15

Glu His Glu Val Gln Arg Lys Lys Asn Lys Lys Lys Ile Ile Leu
            20                  25                  30

Tyr Ser Ile Gly Ser Ile Leu Ala Leu Ala Ala Val Ile Ala Thr Gly
            35                  40                  45

Val Gly Ile Gly Met Tyr Ile Lys Lys Lys Lys Asn Ser Leu Glu
50                  55                  60

Lys Leu Gln Gln Ile Glu Pro Gln Lys Leu Ser Lys Thr Asp Glu
65                  70                  75                  80

Ser Asp Pro Leu Leu Gly Lys Ser Glu Ala Ala Lys Val Glu Val Lys
                85                  90                  95

Gly Asp Ser Glu Glu Val Pro Gln Glu Val Ser Ser Pro Ser Glu Ala
            100                 105                 110

Leu Asp Val Glu Pro Val Ser Glu Ala Leu Asn Met Glu Pro Ala
            115                 120                 125

Val Gly Glu Ser Ala Asn Phe Glu Asp Ser Ala Lys Gly Glu Val Asp
130                 135                 140

Ile Glu Pro Val Ser Glu Val Glu Ser Ile Glu Pro Val Ser Glu Val
145                 150                 155                 160

Glu Ser Ile Glu Pro Val Ser Glu Val Glu Ser Ile Glu Pro Ser Val
            165                 170                 175

Asp Glu Val Met Asp Ala Ala Glu Pro Ile Ser Thr Glu Pro Val Asn
            180                 185                 190

Val Glu Pro Ala Gly Asn Glu Thr Glu Asn Ile Val Pro Thr Ser Phe
            195                 200                 205

Glu Gln Val Asn Ile Glu Pro Ala Val Ser Glu Ala Phe Ser Gln Glu
            210                 215                 220

Arg Ser Gly Glu Glu Thr Ala Asp Phe Glu Asp Ser Val Lys Glu Asp
225                 230                 235                 240

Val Ile Pro Glu Ser Pro Val Glu Ser Val Thr Ile Glu Ala Glu
                245                 250                 255

Asn Ile Gln Pro Met Asn Val Glu Gln Met Asn Val Asp Pro Thr Val
            260                 265                 270

Ser Asp Ala Glu Ser Ile Glu Pro Thr Pro Val Glu Ala Val Asp Ile
            275                 280                 285

Glu Pro Val Asn Val Glu Pro Val Asn Val Glu Pro Ala Val Ser Glu
            290                 295                 300

Thr Met Ser Gln Glu Pro Ser Leu Asp Glu Val Glu Asn Val Glu Ser
305                 310                 315                 320

Ala Val Asn Glu Met Met Ser Gln Glu Pro Ser Ala Glu Glu Thr Ala
                325                 330                 335

Asn Phe Ala His Ser Ile Lys Glu Asp Val Ser Pro Glu Ser Thr Ser
            340                 345                 350

Val Glu Ser Leu Asp Val Glu Ser Ser Val Ser Glu Pro Met Ser Thr
            355                 360                 365

Asp Pro Ser Pro Val Glu Ser Val Ser Met Glu Ser Val Asp Ser Glu
            370                 375                 380
```

Thr Val Asn Val Glu Ser Ile Asp Ser Glu Thr Val Asn Val Glu Pro
385                 390                 395                 400

Ser Asp Glu Thr Ser Lys Val Glu Ala Asp Val Gln Gln Phe Thr Asp
            405                 410                 415

Glu Glu Leu Ser Thr Ile Gly Asn Val Ala Asp Lys Ala Ser Asp Gly
        420                 425                 430

Pro Ala Pro Glu Ala Ser Asp Phe Pro Asp Ser Ile Phe Glu Glu Asn
    435                 440                 445

Leu Asp Asn Ala Asn Pro Pro Leu Lys Leu Glu Asp Ala Leu Val Asp
450                 455                 460

Pro Pro Ala Ser Asp Glu Ala Gln Pro Glu Pro Ser His Pro Asn Glu
465                 470                 475                 480

Ala Val Gly Ala Ala Lys Ser Ala Glu Ser Ala Glu Ala Asp Gln Ile
                485                 490                 495

Ser His Ser Gly Ser Gly Asp Ala Ser Pro Ser Ala Pro Ser Ser Ser
            500                 505                 510

Asp Asp Thr Ser Gly Ser Lys Asn Ser Gly Thr Ser Gly Lys Asp Arg
        515                 520                 525

Leu Phe Lys Thr Tyr Asp Ser Asp Val Glu Pro Ile Val Pro Glu
530                 535                 540

Lys Tyr Pro Thr Val Gly Val Lys Glu Ala Pro Lys Met Gly Phe Ala
545                 550                 555                 560

Glu Met Ala Phe Lys Asn Ile Phe Asp Thr Phe Ser Lys Val Ala Asp
                565                 570                 575

Ala Ser Lys Val Leu Thr Pro Glu Lys Gln Ser Ala Pro Glu Lys Gln
            580                 585                 590

Ser Ala Pro Glu Lys Gln Ser Ala Pro Glu Lys Gln Ser Ala Pro Glu
        595                 600                 605

Lys His Ser Thr Pro Pro Lys Gln Ser Thr Pro Lys Glu Ser Thr
610                 615                 620

Ser Pro Lys Gln Pro Ala Pro Pro Lys Pro Ser Thr Ser Pro Lys Gln
625                 630                 635                 640

Ser Ala Pro Ala Lys Gln Ser Ala Pro Lys Gln Ser Ala Pro Ala
                645                 650                 655

Lys Gln Ser Ala Pro Ala Lys Asn Ala Ala Pro Pro Gln Ser Ala Ser
            660                 665                 670

Ser Ser Arg Phe Phe Ser Ser Ser Asn Gly Asn Lys Gly Phe Gly
        675                 680                 685

Leu Arg Leu Phe Ser Asp Ala Ser Ser Ser Asn Asn Lys Lys Gly Arg
690                 695                 700

Ala Gly Asn Pro Ile Ile Arg Phe Lys Arg Arg Ala Asn His His
705                 710                 715                 720

His His His

<210> SEQ ID NO 86
<211> LENGTH: 2172
<212> TYPE: DNA
<213> ORGANISM: Plasmodium vivax

<400> SEQUENCE: 86
atgaagaggc acgctacccg cggcgccctc cactccctga gagcatcga gcacgaggtg      60 caaaggaaga agaacaagaa gaagaagatc atcctctact ccatcggcag catcctggct     120
ctggctgccg tgatcgctac cggcgtcggc atcggcatgt acatcaagaa gaagaagaag     180

```
aacagcctgg agaagctgca acagatcgag ccacaaaagc tggagtccaa gaccgacgag    240
agcgacccac tcctgggcaa gagcgaggct gctaaggtgg aggtcaaggg cgactccgag    300
gaagtgccac aagaggtgtc ctccccgagc gaggctctgg acgtggagcc accagtctcc    360
gaggccctga acatggagcc agccgtgggc gagtccgcca acttcgagga cagcgccaag    420
ggcgaggtcg acatcgagcc agtgtccgag gtcgagtcta ttgaaccagt gtccgaggtg    480
gagtctattg agccagtgtc cgaagtcgag agcatcgagc catccgtgga cgaggtcatg    540
gacgctgctg agccaatcag caccgagcca gtgaacgtcg agccagccgg caacgagacg    600
gagaacatcg tgccaacctc cttcgagcaa gtgaacatcg agccagccgt cagcgaggcc    660
ttctcccaag agaggagcgg cgaggagacg gctgacttcg aggactccgt gaaggaagac    720
gtcatcccag agtccccacc agtggagagc gtcaccatcg aggccgagaa catccaaccg    780
atgaacgtgg agcagatgaa cgtggaccca accgtctccg acgccgagag catcgagcca    840
accccagtgg aggccgtgga tatcgagcct gtcaacgtgg agcctgtcaa cgttgagcca    900
gccgtgtccg agacgatgag ccaagagcca tccctcgacg aggtggagaa cgtcgagagc    960
gccgtcaacg agatgatgtc ccaggagcca tccgctgagg agacggccaa cttcgcccac   1020
tccatcaagg aagacgtgag cccagagagc acctccgtcg agtccctgga cgtggagtcc   1080
agcgtcagcg agccaatgtc caccgaccca agcccagtgg agagcgtctc catggagtcc   1140
gtggacagcg agacggtgaa cgtcgagtcc atcgattccg agcggtcaa cgtggagcca   1200 tccgacgaga cgagcaaggt ggaggccgac gtccaacagt tcaccgacga ggagctcagc   1260
accatcggca acgtggctga caaggcttcc gacggcccag ctccagaggc ctccgacttc   1320
ccagacagca tcttcgagga gaacctcgac aacgccaacc caccactcaa gctggaggac   1380
gctctggtgg acccaccagc tagcgacgag gctcaaccag agccatccca cccaaacgag   1440
gctgtgggcg ctgctaagtc cgctgagagc gctgaggctg accaaatcag ccactccggc   1500
agcggcgacg cttccccaag cgctccatcc agctccgacg cacctccgg cagcaagaac   1560 tccggcacca gcggcaagga caggctcttc aagacctacg actccgacgt ggagccacca   1620
atcgtcccag agaagtaccc aaccgtgggc gtgaaggaag ccaaagat gggcttcgcc    1680 gagatggcct tcaagaacat cttcgacacc ttctccaagg tggctgacgc tagcaaggtc   1740
ctgaccccag agaagcaatc cgccccgag aagcagagcg ctcctgagaa gcagagcgct   1800
cccgagaagc agagcgcccc agagaagcac tccaccccac caaagcaatc caccagccca   1860
aaggagtcca ccagcccaaa gcagccagcc ccaccaaagc catccaccag ccctaagcag   1920
tccgctccag ctaagcagtc cgccccacca aagcagagcg ctccagctaa gcaatccgct   1980
ccagctaaga cgctgcccc accacagagc gccagctcca gcaggttctt ctccagctcc   2040
agcaacggca caagggctt cggcctcagg ctgttctccg acgcctccag ctccaacaac   2100
aagaagggca gggccggcaa cccaatcatc cgcttcaaga ggcgcgccaa ccaccaccac   2160
caccaccact ga                                                       2172
```

<210> SEQ ID NO 87
<211> LENGTH: 373
<212> TYPE: PRT
<213> ORGANISM: Plasmodium vivax

<400> SEQUENCE: 87

Met Asn Asn Pro Ala Glu Val Val Ala Ala His Leu Arg Arg Thr Gly
1               5                   10                  15

```
Asn Ser Asn Glu Ile Arg Gln Ala Ser His Val Glu Ser Val Gly Gly
         20                  25                  30

Ser Ala Asn Ser Ser Leu Asp Asp Asp Gly Gly Tyr Asp Ser
         35                  40                  45

Ala Ala Pro Pro Gly Glu Leu His Thr Thr Gly Asp Ala Pro Pro Gly
 50                  55                  60

Glu Phe Arg Thr Thr Gly Val Val Pro Pro Gly Arg Gln Lys Gly Gly
 65                  70                  75                  80

Lys Lys Arg Met Phe Lys Ile Lys Lys Lys Ser Leu Thr Pro Leu
                 85                  90                  95

His Ile Asp Asp Gly Gly Phe Thr Gln Gly Gly Glu Ala Lys Gly Pro
            100                 105                 110

Asp Val Ala Leu Glu Ser Phe Ala Ile Thr Arg Lys Arg Arg Arg Pro
            115                 120                 125

Pro Leu Leu Gly Arg Gly Val Val Glu Ser Ser Asn Ile Glu Leu Thr
130                 135                 140

Ser Lys Leu Gly Gly Lys Leu Gly Ser Lys Leu Gly Gly Lys Leu Asn
145                 150                 155                 160

Pro Thr Leu Ser Leu Val Ala Ser Arg Ala Val Asp Gly Leu Leu Gly
                165                 170                 175

Gly Val His Lys His Met Gln Gly Pro Phe Ser Leu Asp Leu Asp Gly
            180                 185                 190

Thr Asn Asn Ser Pro Leu Ala Thr Pro Ile Val Thr Pro Asn Leu Tyr
            195                 200                 205

Ser Asn Ile Ser Thr Pro Phe Asn Met His Asn Gly Ile Pro Pro Ser
            210                 215                 220

Ala Pro Ala Pro Met Ala Leu Pro Pro Gln Gly Val Gln Val Pro Leu
225                 230                 235                 240

Pro Asn Ala Gln Pro Gln Pro Pro Ser Val Ala Thr Thr Ala Thr
                245                 250                 255

Ala Ala Pro Ala Ala Thr Ser Pro Met Ala Ser Pro Thr Thr Pro Thr
            260                 265                 270

Pro Ala Ala Ser Thr Gly Val Pro Pro Pro Gly Ile Gln Leu Ala
            275                 280                 285

Thr Asn Ala Met Thr Tyr Pro Gln Met Asn Met Gln Asn Val Met Thr
290                 295                 300

Ala Asn Gln Met Ala Gln Asn Pro Ala Phe Asn Ile His Pro Thr Ala
305                 310                 315                 320

Thr Asn Leu Arg Asp Asp Pro Gly Asn Val Asn Tyr Asn Glu Val Val
                325                 330                 335

Thr Ile Thr Ile Gly Ile Val Ile Cys Leu Phe Leu Phe Cys Phe Val
            340                 345                 350

Phe Gly Cys Ile Val Lys Met Cys Lys Pro Ala Lys Arg Arg Arg His
            355                 360                 365

His His His His
    370

<210> SEQ ID NO 88
<211> LENGTH: 1122
<212> TYPE: DNA
<213> ORGANISM: Plasmodium vivax

<400> SEQUENCE: 88
atgaacaacc cagctgaggt ggtggctgct cacctgaggc gcaccggcaa ctccaacgag    60
```

```
atcaggcagg ctagccacgt ggagagcgtc ggcggctccg ctaactccag cctcgacgac    120
gacgacggcg gcggatacga cagcgctgcc ccaccaggcg agctccacac caccggcgac    180
gccccaccag gcgagttccg caccaccggc gtggtcccac caggcaggca aaagggcggc    240
aagaagcgca tgttcaagat caagaagaag aagtccctca ccccactgca catcgacgac    300
ggcggcttca cccagggcgg cgaggctaag ggcccagacg tggctctgga gtccttcgcc    360
atcaccagga agaggcgcag gccaccactc ctgggccgcg gcgtggtcga gtccagcaac    420
atcgagctca ccagcaagct gggcggcaag ctcggctcca agctgggcgg caagctcaac    480
ccgaccctca gcctggtggc ctccagggcc gtggacggcc tcctgggcgg cgtgcacaag    540
cacatgcaag gcccattcag cctcgacctg gacggcacca acaactcccc actggccacc    600
ccaatcgtca ccccaaacct ctactccaac atcagcaccc cattcaacat gcacaacggc    660
atcccaccaa gcgctccagc tccaatggct ctgccaccac aaggcgtgca ggtcccactc    720
ccaaacgccc aaccacaacc accaccatcc gtggctacca ccgctaccgc tgctccagct    780
gctaccagcc caatggcttc ccaaccacc  ccaaccccag ctgctagcac cggcgtgcca    840
ccaccaccag gcatccagct ggccaccaac gccatgacct acccacagat gaacatgcag    900
aacgtcatga ccgccaacca aatggcccag aacccagcct tcaacatcca cccgaccgct    960
accaacctca gggacgaccc aggcaacgtg aactacaacg aggtggtcac catcaccatc   1020
ggcatcgtca tctgcctctt cctgttctgc ttcgtgttcg gctgcatcgt caagatgtgc   1080
aagccggcta agcgcaggcg ccatcaccac caccaccact ga                      1122
```

<210> SEQ ID NO 89
<211> LENGTH: 361
<212> TYPE: PRT
<213> ORGANISM: Plasmodium vivax

<400> SEQUENCE: 89

```
Met Ser Lys Thr Gly Asn Asn Asn Arg Asn Ala Lys Asn Ala Lys Gly
1               5                   10                  15

Gly Gly Gly Gly Gly Lys Arg Gly Asn Asn Glu Ala Asn Lys Asn Asp
            20                  25                  30

Gly Met Ser Gly Lys Gly Ser Gln Lys Gly Lys Lys Lys Asp Pro Gly
        35                  40                  45

Gly Gly Gly Thr Pro Lys Gly Gln Gly Lys Gly Pro Glu Gln Gly Lys
    50                  55                  60

Gln Lys Asn Lys Lys Gly Glu Asp Ser His Phe Asp Glu Tyr Ile Lys
65                  70                  75                  80

Asp Met Lys Asn Ser Gln Asp Glu Asp Asn Phe Met Asp Glu Leu Asn
                85                  90                  95

Arg Phe Glu Lys Asn Phe His Asp Glu Asp Phe Glu Ser Asp Glu Asn
            100                 105                 110

Leu Phe Asn Tyr Gly Lys Gly Gly Thr His Ser Gly Glu Phe Asn Lys
        115                 120                 125

Ile Gly Glu Leu Asn Ser Gly Asn Tyr Asn Glu Met Lys Pro Asp Ala
    130                 135                 140

Asn Asp Tyr Gln Tyr Phe Asp Asn Glu Asp Ile Leu Glu Gly Asp Glu
145                 150                 155                 160

Asp Leu Thr Asn Ile Trp Asn Lys Asn Met Gln Asn Phe Glu Pro Ser
                165                 170                 175

Thr Leu Leu Thr Phe Glu Ile Gln Gly Asn Ser Glu Glu Tyr Leu Phe
```

```
                    180                 185                 190
Glu Glu Val Thr Ser Leu Asn Thr Tyr Phe Arg Gly Val Phe Tyr Ser
            195                 200                 205
Asn Asn Glu Ser Asp Asp Asn Lys Ile Leu Phe Phe Ile Thr Asp Pro
            210                 215                 220
Asp Gly Glu Val Ile Tyr Lys Lys Glu Ala Ser Glu Gly Ile Phe Tyr
225                 230                 235                 240
Phe Tyr Thr Gln Lys Ile Gly Val Tyr Thr Ile Thr Leu Lys Asn Ser
                245                 250                 255
Lys Trp Met Gly Lys Lys Leu Thr Thr Val Ala Leu Gly Leu Gly Glu
            260                 265                 270
Ser Pro Ser Leu Lys Ser Glu His Ile Lys Asp Phe Thr Asn Tyr Ile
            275                 280                 285
Asp Lys Ile Val Ala Glu Thr Lys Arg Leu Lys Asn Glu Leu Lys Tyr
            290                 295                 300
Leu Ser Ser Lys His Met Thr His Ile Glu Lys Met Lys Lys Ile Thr
305                 310                 315                 320
Asn Lys Ala Phe Leu Tyr Cys Phe Ile Lys Leu Phe Val Leu Val Phe
                325                 330                 335
Leu Ser Leu Phe Thr Ile Tyr Tyr Ile Lys Asn Leu Val Ser Asn Lys
            340                 345                 350
Arg Val Leu His His His His His His
            355                 360

<210> SEQ ID NO 90
<211> LENGTH: 1086
<212> TYPE: DNA
<213> ORGANISM: Plasmodium vivax

<400> SEQUENCE: 90
atgtccaaga ccggcaacaa caacaggaac gccaagaacg ctaagggcgg cggcggcggc    60
ggcaagaggg gcaacaacga ggccaacaag aacgacggca tgtccggcaa gggcagccaa   120
aagggcaaga agaaggaccc aggcggcggc ggcacccccga agggccaggg caagggccca   180
gagcaaggca agcagaagaa caagaagggc gaggactccc acttcgacga gtacatcaag   240
gacatgaaga cagccaagac gcaggacaac ttcatggacg agctcaacag gttcgagaag   300
aacttccacg acgaggactt cgagtccgac gagaacctgt tcaactacgg caagggcggc   360
acccactccg gcgagttcaa caagatcggc gagctcaaca gcggcaacta caacgagatg   420
aagccagacg ccaacgacta ccagtacttc gacaacgagg acatcctgga gggcgacgag   480
gacctgacca catctggaa caagaacatg caaaacttcg agccaagcac cctcctgacc   540
ttcgagatcc agggcaactc cgaggagtac ctcttcgagg aagtgaccag cctgaacacc   600
tacttccgcg gcgtcttcta ctccaacaac gagagcgacg acaacaagat cctgttcttc   660
atcaccgacc cagacggcga ggtcatctac aagaaggaag cctccgaggg catcttctac   720
ttctacaccc caaaagatcgg cgtgtacacc atcacctca gaacagcaa gtggatgggc   780
aagaagctga ccaccgtggc tctgggcctg ggcgagtccc caagcctcaa gagcgagcac   840
atcaaggact tcaccaacta catcgacaag atcgtcgccg agacgaagag gctgaagaac   900
gagctcaagt acctgtccag caagcacatg acccacatcg agaagatgaa gaagatcacc   960
aacaaggcct tcctctactg cttcatcaag ctcttcgtgc tggtcttcct ctccctgttc  1020
accatctact acatcaagaa cctcgtgagc aacaagcgcg tcctgcacca ccaccaccac  1080
``` cactga                                                                              1086

<210> SEQ ID NO 91
<211> LENGTH: 501
<212> TYPE: PRT
<213> ORGANISM: Plasmodium vivax

<400> SEQUENCE: 91

Met Asn Asn His Gln Ala Val Lys Gln Gln Met Asn Pro Lys Gly Ser
1               5                   10                  15

Lys Glu Gln Asn Arg Met Val Ala Pro Asn Ser Asn Met Pro Gly Gly
            20                  25                  30

Met Arg Asp Leu Ala Tyr His Arg Asn Asn Gly Asn Asn Glu Met Gly
        35                  40                  45

Lys Met Asn Met Asn Ala Asn Gly Gln Gln His Asn Ala Gly Ser Ser
    50                  55                  60

Asn Thr Tyr Asn Ser Asn Ser Ile Asn Asn Asn Tyr Ser Leu Gly
65                  70                  75                  80

Leu Tyr Ile Asp Asn Pro Gln Asn Ala Phe Val Phe Asp Glu Asn Asp
                85                  90                  95

Leu Lys Thr Leu Phe Ser His Tyr Lys Gly Ala Lys Asn Ile Arg Ile
            100                 105                 110

Leu Asn Asp Lys Ala Ala Ala Gln Ile Thr Phe Asn Asp Lys Asn Met
        115                 120                 125

Ile Gln Gln Val Arg Lys Asp Ile Asn Gly Leu Thr Ile Thr Asp Ile
130                 135                 140

Gly Thr Ile Arg Cys Ile Ile Leu Asn Glu Gly Lys Ile Val Glu Gln
145                 150                 155                 160

Phe Leu Pro Phe Ser Ala Asn Asp Pro Ala Ser Ala Gln Gln Lys Gly
                165                 170                 175

Gly Ser Asn Gln Ser Gly Asp Ser Thr Val Asp Met Leu Lys Lys Leu
            180                 185                 190

Ala Asn Leu Leu Gln Pro Glu Arg Ala Met Asp Ser Ser Met Ala Pro
        195                 200                 205

Lys Met Gly Asp Asn Gly Gly Leu Ser Ala Thr Gly Ser Val Asn Met
210                 215                 220

Gly Ala Ser Ile Ala Thr Asn Val Gly Met Gly Gly Asn Met Pro Thr
225                 230                 235                 240

Asn Ala Asn Met Gly Gly Val Ile Thr Thr Asn Ala Asn Val Ser Ala
                245                 250                 255

Asn Val Ser Ala Asn Val Ser Ala Asn Pro Met Pro Gly Lys Asn Gln
            260                 265                 270

Val Lys Asn Lys Met Gly Asn His Ala Ile Tyr Asn Asn Gly Gly Ser
        275                 280                 285

His Phe Asn Gln Ala His Met Asn Lys Gly Glu Pro Gly Glu Asn Asn
290                 295                 300

Pro Tyr Ala Thr Lys Arg Leu Ser Arg Ile Glu Leu Ile Asp Ile Phe
305                 310                 315                 320

Gly Phe Pro Val Glu Phe Asp Val Met Lys Lys Ile Leu Gly Lys Asn
                325                 330                 335

Asn Ser Asn Ile Ser Tyr Ile Lys Glu Gln Thr Asn Asn Ser Val Ser
            340                 345                 350

Ile Glu Ile Lys Gly Lys Pro Phe Asn Glu Ala Pro Ile Val Glu Arg
        355                 360                 365

```
Met His Val Ser Val Ser Ser Asp Asp Leu Ile Gly Tyr Lys Lys Ala
            370             375             380
Thr Glu Leu Ile Val Lys Leu Leu Asn Ser Ile Phe Glu Glu Phe Tyr
385             390             395             400
Asp Phe Cys Tyr Glu Lys Asn Tyr Pro Val Pro Glu Asn Leu Ser Phe
                405             410             415
Lys Arg His Glu Tyr Met Tyr Asn Pro Asp Gly Ser Thr Lys Tyr Val
            420             425             430
Gly Phe Lys Asp Lys Trp His Val Met Lys Asp Ser Tyr Arg Thr Asp
            435             440             445
Tyr Ser Phe Arg Lys Asn Lys Gly Leu Gln Lys Asn Asp Lys Asp Lys
450             455             460
Arg Met His Gly Gly Ala Phe Gly Gly His Pro Asn Leu Ser Ile Gly
465             470             475             480
Tyr Ala Asn Gln Asn Ala Pro Gln Gly Asp Phe Lys Glu Met Asn His
                485             490             495
His His His His His
            500

<210> SEQ ID NO 92
<211> LENGTH: 1506
<212> TYPE: DNA
<213> ORGANISM: Plasmodium vivax

<400> SEQUENCE: 92
atgaacaacc accaagccgt caagcaacag atgaacccaa agggctccaa ggagcagaac    60
aggatggtgg ccccaaacag caacatgcca ggcggcatga gggacctcgc ttaccacagg   120
aacaacggca caacgagat gggcaagatg aacatgaacg ccaacggcca acagcacaac    180
gccggctcca gcaacaccta caactccaac tccatcaaca caacaactac tccctcggc    240 ctgtacatcg acaacccaca aaacgccttc gtcttcgacg agaacgacct caagaccctg   300
ttcagccact acaagggcgc caagaacatc aggatcctca cgacaaggc tgccgcccag   360 atcaccttca cgacaagaa catgatccaa caggtcagga aggacatcaa cggcctgacc   420
atcaccgaca tcggcaccat ccgctgcatc atcctcaacg agggcaagat cgtggagcaa   480
ttcctgccat tctccgccaa cgaccccggct agcgctcaac agaagggcgg ctccaaccaa   540
agcggcgact ccaccgtgga catgctcaag aagctcgcta acctcctgca gccagagagg   600
gccatggact ccagcatggc cccaaagatg ggcgacaacg gcggcctctc cgctaccggc   660
tccgtcaaca tgggcgcctc catcgccacc aacgtgggca tgggcggcaa catgccaacc   720
aacgccaaca tgggcggcgt catcaccacc aacgccaacg tgagcgccaa cgtctccgct   780
aacgtgagcg ctaacccaat gccaggcaag aaccaagtga agaacaagat gggcaaccac   840
gccatctaca caacggcgg ctcccacttc aaccaggccc acatgaacaa gggcgagcca   900
ggcgagaaca acccatacgc caccaagagg ctcagccgca tcgagctgat cgacatcttc   960
ggcttcccag tcgagttcga cgtgatgaag aagatcctcg gcaagaacaa cagcaacatc  1020
tcctacatca aggagcaaac caacaactcc gtcagcatcg agatcaaggg caagccattc  1080
aacgaggccc caatcgtgga gcgcatgcac gtgtccgtct ccagcgacga cctcatcggc  1140
tacaagaagg ccaccgagct gatcgtcaag ctcctgaaca gcatcttcga ggagttctac  1200
gacttctgct acgagaagaa ctacccagtg ccagagaacc tgtccttcaa gaggcacgag  1260
tacatgtaca cccagacgg cagcaccaag tatgtgggct tcaaggacaa gtggcacgtg  1320
```

```
atgaaggact cctacaggac cgactacagc ttccgcaaga acaagggcct ccagaagaac    1380
gacaaggaca agaggatgca cggcggcgct ttcggcggac acccaaacct gagcatcggc    1440
tacgccaacc aaaacgcccc acagggcgac ttcaaggaga tgaaccacca ccaccaccac    1500
cactga                                                                1506
```

<210> SEQ ID NO 93
<211> LENGTH: 185
<212> TYPE: PRT
<213> ORGANISM: Plasmodium vivax

<400> SEQUENCE: 93

```
Met Arg Glu Ala Lys Gly Ser Val Arg Asp Gly Lys Gln Tyr Val Lys
1               5                   10                  15

Thr Lys Ser Pro Thr Tyr Thr Pro Gln Lys Lys Thr Lys Val Ile Phe
            20                  25                  30

Tyr Met Pro Gly Gln Glu Gln Glu Glu Glu Asp Asp Asn Asp Pro
        35                  40                  45

Asn Gly Ser Lys Lys Asn Gly Lys Ser Asp Thr Gly Ala Asn Lys Gly
    50                  55                  60

Thr His Met Gly Ser Lys Thr Asp Ala Gly Asn Ser Pro Ser Gly Leu
65                  70                  75                  80

Asn Lys Gly Ser Gly Val Gly Ser Gly Ser Arg Pro Ala Ser Asn Asn
                85                  90                  95

Tyr Lys Gly Asn Ala Gly Gly Ile Asn Ile Asp Met Ser Pro His
            100                 105                 110

Gly Asp Asn Ser Asn Lys Gly Gln Gln Gly Asn Ala Gly Leu Asn Lys
        115                 120                 125

Asn Gln Glu Asp Thr Leu Arg Asp Glu Tyr Lys Ile Arg Lys Gln
    130                 135                 140

Glu Glu Glu Glu Glu Glu Arg Ile Asn Asn Gln Arg Arg Ala Asp Met
145                 150                 155                 160

Lys Arg Ala Gln Arg Gly Lys Asn Lys Phe Gly Asp Asp Lys Gly Val
                165                 170                 175

Gln Asp Ser His His His His His
            180                 185
```

<210> SEQ ID NO 94
<211> LENGTH: 558
<212> TYPE: DNA
<213> ORGANISM: Plasmodium vivax

<400> SEQUENCE: 94

```
atgcgcgagg ctaagggctc cgtgcgcgac ggcaagcaat acgtcaagac caagagccca      60
acctacaccc cacagaagaa gaccaaggtc atcttctaca tgccaggcca agagcaagag     120
gaagaggaag acgacaacga cccaaacggc tccaagaaga acggcaagag cgacaccggc     180
gccaacaagg gcacccacat gggctccaag accgacgctg gcaactcccc gagcggcctc     240
aacaagggct ccggcgtggg ctccggcagc aggccagcca gcaacaacta caagggcaac     300
gccggcggcg gcatcaacat cgacatgtcc ccacacggcg acaacagcaa caagggccaa     360
cagggcaacg ccggcctcaa caagaaccaa gaggacaccc tgagggacga gtacgagaag     420
atccgcaaac aagaggaaga ggaagaggag cgcatcaaca accaaaggcg cgctgacatg     480
aagagggctc agaggggcaa gaacaagttc ggcgacgaca agggcgtgca agacagccac     540
caccaccacc accactga                                                    558
```

<210> SEQ ID NO 95
<211> LENGTH: 259
<212> TYPE: PRT
<213> ORGANISM: Plasmodium vivax

<400> SEQUENCE: 95

```
Met Ser Ser Gln Ser Ala Val Asp Tyr Ile Glu Gln Glu Pro Leu Asp
1               5                   10                  15

Ile Leu Asn Leu Glu Glu Gly Asp Leu Glu Val Thr Glu Gln Trp Lys
            20                  25                  30

Asp Asn Glu Trp His Asn Trp Lys Leu Lys Leu Glu Glu Asp Trp Asp
        35                  40                  45

Ser Phe Ser Thr Ser Leu Ile Arg Asp Lys Lys Asp Phe Met Lys Ile
    50                  55                  60

Lys Thr Asp Glu Leu Asn Gly Trp Leu Asn Leu Glu Glu Asn Lys Trp
65                  70                  75                  80

Asn Asn Phe Ser Gly Tyr Leu Ser Asp Gly Tyr Lys Asn Tyr Leu Leu
                85                  90                  95

Lys Lys Ser Glu Lys Trp Asn Asp Ala Asp Trp Glu Asn Trp Ala Asn
            100                 105                 110

Thr Glu Met Val Ala His Leu Asp Lys Asp Tyr His Leu Trp Ser Leu
        115                 120                 125

Asn Thr Glu Arg Ser Val Asn Ala Leu Val Arg Gly Glu Trp Asn Gln
    130                 135                 140

Trp Gln His Asp Lys Met Ser Ser Trp Leu Ser Ser Asp Trp Lys Lys
145                 150                 155                 160

Val Gly Ala Met Tyr Trp Asp Leu Gln Glu Ser Arg Asn Trp Ala Ser
                165                 170                 175

Tyr Ser His Thr Asp Asp Met Lys Glu His Trp Ile Lys Trp Asn Asp
            180                 185                 190

Arg Asn Ala Arg Glu Asn Ile Glu Trp Ser Lys Trp Val Gln Asn Lys
        195                 200                 205

Glu Tyr Phe Ile Met Tyr Ala Arg His Ser Asp Ile Glu Gln Trp Lys
    210                 215                 220

Tyr Asp Asn Tyr Ala Leu Tyr Ser Thr Trp Arg Asn Asp Phe Ile Asn
225                 230                 235                 240

Arg Trp Val Ser Glu Lys Lys Trp Asn Ser Ile Leu Asn His His His
                245                 250                 255

His His His
```

<210> SEQ ID NO 96
<211> LENGTH: 780
<212> TYPE: DNA
<213> ORGANISM: Plasmodium vivax

<400> SEQUENCE: 96

```
atgtccagcc aaagcgccgt ggactacatc gagcaggagc cactcgacat cctcaacctc      60
gaagagggcg acctggaggt caccgagcag tggaaggaca acgagtggca caactggaag     120
ctcaagctcg aagaggactg ggactccttc agcacctccc tcatcaggga caagaaggac     180
ttcatgaaga tcaagaccga cgagctgaac ggctggctca acctggagga gaacaagtgg     240
aacaacttca gcggctacct ctccgacggc tacaagaact acctcctgaa gaagtccgag     300
aagtggaacg acgccgactg ggagaactgg gccaacaccg agatggtggc ccacctcgac     360
```

```
aaggactacc acctctggag cctgaacacc gagaggtccg tgaacgctct ggtccgcggc    420
gagtggaacc aatggcagca cgacaagatg tccagctggc tctccagcga ctggaagaag    480
gtcggcgcca tgtactggga cctgcaggag agcaggaact gggccagcta ctcccacacc    540
gacgacatga aggagcactg gatcaagtgg aacgacagga acgcccgcga gaacatcgag    600
tggtccaagt gggtgcaaaa caaggagtac ttcatcatgt acgcccgcca cagcgacatc    660
gagcagtgga agtacgacaa ctacgccctc tactccacct ggaggaacga cttcatcaac    720
cgctgggtca gcgagaagaa gtggaactcc atcctgaacc accaccacca ccaccactga    780
```

<210> SEQ ID NO 97
<211> LENGTH: 257
<212> TYPE: PRT
<213> ORGANISM: Plasmodium vivax

<400> SEQUENCE: 97

```
Met Lys Ser Ser Asn Glu Ile Glu Arg Leu Thr His Val Lys Leu Lys
1               5                   10                  15

Asp Thr Ser Glu Trp Thr Glu Asn Val Glu Trp Val Lys Asp Glu
            20                  25                  30

Trp His Glu Trp Met Asp Glu Val Gln Met Asp Trp Lys Glu Phe Asn
        35                  40                  45

Ser Ser Leu Glu Ser Gly Lys Asn Lys Trp Phe Gly Lys Lys Glu Lys
    50                  55                  60

Glu Met Met Glu Leu Ile Lys Ser Ile Glu Asp Lys Trp Leu Asp Phe
65                  70                  75                  80

Asn Glu Asn Met His Glu Val Leu Asn Tyr Ala Ile Leu Lys Ile Ser
                85                  90                  95

Leu Met Trp Ser Phe Ser Glu Trp Gln Lys Trp Ile Asn Lys Asp Gly
            100                 105                 110

Lys Arg Ile Ile Glu Asn Gln Trp Glu Arg Trp Thr Ile Ser Asn Lys
        115                 120                 125

Asn Leu Tyr Tyr Lys Ile Ile Met Lys Glu Trp Phe Lys Trp Lys Asn
    130                 135                 140

Lys Lys Ile Lys Gln Trp Leu Lys Arg Asn Trp Leu His His Glu Gly
145                 150                 155                 160

Arg Ile Leu Glu Asn Trp Glu Arg Leu Pro Tyr Thr Lys Ile Leu Ala
                165                 170                 175

Met Ser Glu Lys Lys Pro Trp Phe Asn Ser Asn Ala Gln Val Ile Asn
            180                 185                 190

Glu Arg Asp Tyr Phe Leu Ile Trp Ile Lys Lys Glu Asp Phe Leu
        195                 200                 205

Val Asn Glu Glu Arg Asp Lys Trp Glu Asn Trp Glu Tyr Tyr Lys Asn
    210                 215                 220

Asp Phe Phe Gln Thr Trp Met Asp Ser Phe Leu Ser His Trp Leu Asn
225                 230                 235                 240

Ile Lys Lys Arg Asp Ile Leu His Ser Gln Ser His His His His
                245                 250                 255

His
```

<210> SEQ ID NO 98
<211> LENGTH: 774
<212> TYPE: DNA
<213> ORGANISM: Plasmodium vivax

<400> SEQUENCE: 98

```
atgaagtcca gcaacgagat cgagaggctc acccacgtga agctgaagga caccctccgag    60 tggaccgaga acgtggagga gtgggtcaag gacgagtggc acgagtggat ggacgaggtc    120
cagatggact ggaaggagtt caactccagc ctggagtccg agaagaacaa gtggttcggc    180
aagaaggaga aggagatgat ggagctgatc aagagcatcg aggacaagtg gctcgacttc    240
aacgagaaca tgcacgaggt gctcaactac gccatcctca gatctccct gatgtggtcc    300 ttcagcgagt ggcaaaagtg gatcaacaag gacggcaaga ggatcatcga gaaccagtgg    360
gagcgctgga ccatcagcaa caagaacctg tactacaaga tcatcatgaa ggagtggttc    420
aagtggaaga caagaagat caagcaatgg ctcaaggaga actggctgca ccacgagggc    480
aggatcctgg agaactggga gcgcctgcca taccaccaaga tcctcgccat gtccgagaag    540
aagccatggt tcaacagcaa cgcccaagtg atcaacgaga gggactactt cctgatctgg    600
atcaagaaga aggaagactt cctcgtcaac gaggagcgcg acaagtggga gaactgggag    660
tactacaaga acgacttctt ccaaacctgg atggactcct tcctcagcca ctggctgaac    720
atcaagaagc gcgacatcct ccactcccag agccaccacc accaccacca ctga          774

<210> SEQ ID NO 99
<211> LENGTH: 118
<212> TYPE: PRT
<213> ORGANISM: Plasmodium vivax

<400> SEQUENCE: 99

Met Arg Leu Lys His Asp His Asn Leu Leu Pro Asn Tyr Ala Asn Leu
1               5                   10                  15

Met Arg Asp Asp Gln Asn Gly Gln Asn Ser Glu Asn Arg Gly Asp Asn
            20                  25                  30

Ile Asn Asn His Asn Lys Asn His Asn Asp Gln Asn Asn His Asn Gly
        35                  40                  45

Asn Asn Asp Asn Ser Ile Asn Ser Glu Tyr Leu Lys Thr Ser His Leu
    50                  55                  60

Gln Asn Ser Ser Ala Met Val His Leu Asn Asp His Lys Ile Thr Thr
65                  70                  75                  80

Lys Pro Ala Arg Tyr Ser Tyr Ile Gln Arg Ser Lys Ile Tyr Ala Phe
                85                  90                  95

Asn Pro Asn Asn Lys Lys Ile Glu Asn Ile Asn Asn Glu Leu His Ser
            100                 105                 110

His His His His His His
        115

<210> SEQ ID NO 100
<211> LENGTH: 357
<212> TYPE: DNA
<213> ORGANISM: Plasmodium vivax

<400> SEQUENCE: 100
atgaggctca agcacgacca caacctcctg ccaaactacg ccaacctgat gagggacgac    60
caaaacggcc agaactccga gaaccgcggc gacaacatca caaccacaa caagaaccac    120 aacgaccaaa caaccacaa cggcaacaac gacaactcca tcaacagcga gtacctcaag    180
accagccacc tgcagaactc cagcgccatg gtgcacctca acgaccacaa gatcaccacc    240
aagccagcca ggtactccta catccaacgc agcaagatct acgccttcaa cccaaacaac    300
aagaagatcg agaacatcaa caacgagctg cactcccacc accaccacca ccactga      357
```

```
<210> SEQ ID NO 101
<211> LENGTH: 651
<212> TYPE: PRT
<213> ORGANISM: Plasmodium vivax

<400> SEQUENCE: 101

Met Ser Met Glu Gln Gly Thr Pro Ile Val Phe Pro His Lys Glu Gly
1               5                   10                  15

Thr Ile Leu Thr Lys Gly Thr Asn Asn Leu Ala Val Ala His Lys Glu
            20                  25                  30

Glu Val His Arg Ser Glu Glu Thr Thr Leu Lys Gly Leu Lys Glu
        35                  40                  45

Glu Leu Pro His Glu His Thr Leu Ala Ile Gln Lys Tyr Asp Pro Ser
    50                  55                  60

Phe Gly Arg Gly Gly Ser Pro Gly Ser Gly Ser Thr Glu His Thr Asn
65                  70                  75                  80

Gly Ser Phe Ser Asn Ser Tyr Glu Thr Ile Leu Tyr Asn Lys Ser Asn
                85                  90                  95

Asp Val Val Lys Asn Leu Lys Glu Ile Lys Lys Gly Ala Pro Phe Gly
            100                 105                 110

Gly Val Ile Ser Asp Ala Val Ser Cys Pro Ala Ser Ser Ser Ser Asn
        115                 120                 125

Thr Gly Gly Asn Lys Asn Leu Cys Phe Ser Asn Met Met Lys Leu Ser
    130                 135                 140

Lys Lys Ile Leu Gly Phe Pro Leu Leu Thr Asp Phe Glu Arg Gly Met
145                 150                 155                 160

Ser Thr Asn Gln Pro Cys Leu Pro Leu Ser Asp His Leu Lys Arg Leu
                165                 170                 175

Ser Val Cys Thr Val Cys Tyr Ser Lys His Asn Asp Leu Ala Lys Ala
            180                 185                 190

Ile Ile Cys Arg Val Thr Lys Met His Phe Glu Ala Asn Tyr Asn Asp
        195                 200                 205

Gly Leu Gly Asp Glu Asp Met Phe Lys Thr Ser Ser Glu Cys Ile Gln
    210                 215                 220

Ser Val Ile Arg Glu Leu Ala Asn Thr Ile Lys Glu Tyr Arg Lys Arg
225                 230                 235                 240

Glu Leu Ser Gly Ala Tyr Val Gln Glu Leu Ala Arg Ser Gly Ser Ser
                245                 250                 255

Ser Tyr Arg Ser Cys Ser Ser Ser Tyr Ser Ser Arg Gly Gly Ser
            260                 265                 270

Cys Ala Gly Ser Arg Gly Asp Gly Leu Ala Gly Ser His Gly Glu Ile
    275                 280                 285

His Ala Val Ile Ala Gly Pro Leu Thr Asp Asp His Asn Asp Ile
    290                 295                 300

Gly Ala Glu Ala His Ser Pro Ser Ser Ser Leu Lys Leu Pro Pro Gln
305                 310                 315                 320

Lys Pro Phe Tyr Gly Met Met Ser Asp Pro Cys Ser Asp Arg Arg
                325                 330                 335

Pro Gly Asp Thr Asn Asn Pro Phe Glu Asn Thr Pro Pro Leu Leu
            340                 345                 350

Trp Asp Asn Lys Val Asn Tyr Thr Asp Tyr Thr Cys Lys Arg Gly
        355                 360                 365

Glu Val Asn Ser Thr Leu Gly Lys Arg Pro His Glu Glu Asp Asn Lys
    370                 375                 380
```

```
Gly Ser Ser Gln Lys Lys Ser Lys Leu Arg Thr Lys Pro Ser Asn Asp
385                 390                 395                 400

Thr Ile Gly Gly Glu Asn Gly Asp Ser Leu Lys Gly Gly Thr Asp Glu
            405                 410                 415

Gly Lys Thr His Glu Gly Gly Asn Val Gly Ser Cys Thr Ala Gln
            420                 425                 430

Gly Gly Ala Asp Gln Leu Pro Arg Ser Asp Leu Cys Arg Asp Pro Arg
            435                 440                 445

Gly Asp Pro Cys Val Asp Pro Leu Pro Glu Gln His Ala His Arg Ser
450                 455                 460

Lys Asp Glu Asn Gln Lys Gly Asp Lys Asn Asp Ile His Phe Ala Gly
465                 470                 475                 480

Glu Lys Leu Asp Glu Ile Glu Ala Pro Gly Asp Gln Lys Gly Asn Tyr
            485                 490                 495

Val Thr Leu Glu Asn Ile Ser Lys Ala Ser Asn Phe Ile Pro Leu Leu
            500                 505                 510

Gly Val Glu Leu Gly Ser Thr Lys Ile Gln Arg Glu Phe Thr Asn Gly
            515                 520                 525

Thr Tyr Val Gly Thr Val Thr Glu Gln Ile Lys Asp Glu His Gly Asn
530                 535                 540

Pro Phe Phe Val Val Thr Tyr Glu Asp Gly Asp Ala Glu Trp Met Thr
545                 550                 555                 560

Pro Cys Phe Leu Phe Gln Glu Leu Leu Lys Gln Ser Thr Asn Ser Val
            565                 570                 575

Asp Tyr Pro Leu Ala Thr Thr Phe Lys Glu Val Phe Asn Pro Glu Phe
            580                 585                 590

Lys Lys Asp Leu Lys Leu Ser Asn Cys Ser Leu Glu Leu Lys Ile Glu
            595                 600                 605

Arg Arg Lys Arg Lys Ser Asn Cys Glu Ser Ala Ser Asn Asn Asn Ser
610                 615                 620

Val Ser Lys Arg Gln Lys His Ala Gln Glu Glu Asn Ser Ser Arg Lys
625                 630                 635                 640

Lys Lys Gln Arg Phe His His His His His His
            645                 650

<210> SEQ ID NO 102
<211> LENGTH: 1956
<212> TYPE: DNA
<213> ORGANISM: Plasmodium vivax

<400> SEQUENCE: 102
atgtccatgg agcaaggcac cccaatcgtg ttcccacaca aggaaggcac catcctcacc      60
aagggcacca caacctggcc cgtggcccac aaggaagagg tgcacaggag cgaggaagag     120
acgaccctca agggcctgaa ggaagagctc ccacacgagc acaccctggc catccagaag     180
tacgacccaa gcttcggccg cggcggctcc ccaggcagcg gcagcaccga gcacaccaac     240
ggctccttca gcaactccta cgagacgatc ctctacaaca gtccaacga cgtggtcaag     300 aacctgaagg agatcaagaa gggcgctcca ttcggcggcg tgatctccga cgccgtctcc     360
tgcccggcct ccagctccag caacaccggc ggcaacaaga acctctgctt cagcaacatg     420
atgaagctct ccaagaagat cctgggcttc ccactcctga ccgacttcga gggggcatg     480 agcaccaacc aacatgcct cccactgagc gaccacctca gcgcctgtc cgtgtgcacc     540 gtctgctaca gcaagcacaa cgacctggcc aaggccatca tctgcagggt gaccaagatg     600
```

```
cacttcgagg ccaactacaa cgacggcctc ggcgacgagg acatgttcaa gacctccagc    660
gagtgcatcc aatccgtgat ccgcgagctg ccaacacca tcaaggagta caggaagcgc    720
gagctgtccg gcgcctacgt ccaagagctc gctaggtccg gctccagctc ctacaggagc    780
tgcagctcca gctcctacag ctccaggggc ggcagctgcg ctggctcccg cggcgacggc    840
ctcgccggct ccacggcga gatccacgcc gtcatcgctg cccaccact gaccgacgac     900 cacaacgaca tcggcgctga ggctcacagc ccaagctcca gcctcaagct gccaccacaa    960
aagccattct acggcatgat gtccgaccca ccatgctccg acaggcgccc aggcgacacc   1020
aacaacccat cgagaacaa caccccacca ctcctgtggg acaacaaggt gaactacacc    1080
gacgactaca cctgcaagag gggcgaggtc aactccaccc tcggcaagcg cccacacgag   1140
gaagacaaca agggctccag ccagaagaag tccaagctca ggaccaagcc aagcaacgac   1200
accatcggcg gcgagaacgg cgacagcctg aagggcggca ccgacgaggg caagacccac   1260
gagggcggcg caacgtggg ctcctgcacc gccaaggcg cgccgacca gctcccaagg    1320 tccgacctgt gcagggaccc cgcggcgac ccatgcgtcg acccactccc agagcaacac   1380
gcccaccgct ccaaggacga gaaccagaag ggcgacaaga cgacatcca cttcgccggc   1440 gagaagctcg acgagatcga ggcccaggc gaccaaaagg gcaactacgt gaccctggag   1500
aacatcagca aggcctccaa cttcatcccg ctcctgggcg tggagctggg cagcaccaag   1560
atccaacgcg agttcaccaa cggcacctac gtgggcaccg tcaccgagca gatcaaggac   1620
gagcacggca acccattctt cgtggtcacc tacgaggacg cgacgctga gtggatgacc    1680 ccatgcttcc tcttccaaga gctcctgaag cagagcacca actccgtgga ctacccactg   1740
gccaccacct tcaaggaagt gttcaaccca gagttcaaga aggacctcaa gctgagcaac   1800
tgctccctgg agctgaagat cgagaggcgc aagaggaagt ccaactgcga gagcgcctcc   1860
aacaacaaca gcgtgtccaa gcgccaaaag cacgcccaag aggagaactc ctccaggaag   1920
aagaagcagc gcttccacca ccaccaccac cactga                            1956
```

<210> SEQ ID NO 103
<211> LENGTH: 793
<212> TYPE: PRT
<213> ORGANISM: Plasmodium vivax

<400> SEQUENCE: 103

```
Met Thr Phe Asn Asp Gly Ser Asp Glu Ile Ser Thr Ala Gln Lys Tyr
1               5                   10                  15

Lys Thr Asp Val Glu Gly Ile Ile Asp Lys Leu Asn Val Ile Asp Glu
            20                  25                  30

Thr Ile Asn Gly Ile Asn Ser Thr Leu Asp Glu Leu Leu Glu Leu Gly
        35                  40                  45

Asn Asn Cys Gln Leu His Arg Thr Phe Leu Ile Ser Ser Ser Leu Asn
    50                  55                  60

Asn Lys Ile Ala Lys Phe Leu Val Glu Ile Arg Glu Gln Lys Glu Asn
65                  70                  75                  80

Thr Lys Lys Cys Phe Gln Tyr Val Lys Arg Asn His Gln His Leu Ala
                85                  90                  95

Asn Phe Val Ser Glu Leu His Lys Thr Gln Gly Gly Ile Phe Glu Asn
            100                 105                 110

Val Asn Leu Val Asp Asn Thr Pro Asp Ala Asp Lys Tyr Tyr His Glu
        115                 120                 125
```

```
Phe Met Glu Ile Glu Gln Glu Ala Thr Lys Ile Val Lys Asp Ile Lys
    130                 135                 140

Lys Glu Ile Tyr His Leu Asn Asp Val Asp Glu Pro Val Leu Glu
145                 150                 155                 160

Lys Arg Ile Lys Asp Val Ile Asn Thr Tyr Asn Lys Leu Lys Thr Lys
                165                 170                 175

Lys Val Gln Met Asp Gln Ser Tyr Lys Asn Met Tyr Ile Thr Lys Leu
                180                 185                 190

Arg Glu Val Glu Gly Ser His Asp Leu Phe Asn Gln Val Ala Gln Leu
                195                 200                 205

Ile Arg Gly Glu Thr Asp Lys Lys Gly Lys Ala Leu Ser Glu Arg Glu
    210                 215                 220

Asn Asn Leu His Ser Ile Tyr Asn Phe Val Lys Leu His Glu Thr Glu
225                 230                 235                 240

Leu His Asn Leu Tyr Ala Lys Tyr Thr Pro Glu Tyr Met Glu Lys Ile
                245                 250                 255

Asn Lys Ile Phe Asp Asp Ile Asn Ala Arg Met Ile Ala Val Asp Leu
                260                 265                 270

Asn Asp Asp His Ser Ser Glu Tyr Ser Asp Val Lys Arg His Glu His
                275                 280                 285

Glu Ala Met Leu Leu Met Asp Ala Thr Asn Asn Leu Ser Lys Glu Val
    290                 295                 300

Glu Met Met Gln Asn Glu Ser Gly Gly Lys Asn Asp Gly Ile Asn Gly
305                 310                 315                 320

Gly Lys Ser Gln Leu Val Glu Asp Tyr Thr Asn Thr Met Ser Glu Phe
                325                 330                 335

Thr Glu Gln Ala Lys Thr Val Ala Lys Lys Ile His Asp Ser Lys Gly
                340                 345                 350

Asp Tyr Ala Asn Met Phe Asp His Ile Arg Glu Asn Glu Ala Met Leu
                355                 360                 365

Glu Arg Ile Asp Leu Lys Lys Lys Asp Ile Lys Glu Ile Leu Ala His
    370                 375                 380

Leu Asn Arg Met Lys Glu Tyr Leu Leu Lys Lys Leu Ser Glu Glu
385                 390                 395                 400

Lys Leu His His Met Arg Glu Lys Leu Glu Glu Val Asn Thr Ser Thr
                405                 410                 415

Asp Glu Ile Val Lys Lys Phe Arg Thr Tyr Asp Gln Met Val Asp Ile
                420                 425                 430

Ser Gln Asn Ile Asp Ile Lys Asn Val Gln Ser Lys Arg Tyr Asp Ser
                435                 440                 445

Val Asp Glu Ile Asp Lys Glu Met Ser Tyr Ile Lys Thr His Asn Lys
    450                 455                 460

Asp Leu Ile Asp Ser Lys Phe Ile Val Glu Arg Ala Leu Glu Asn Asp
465                 470                 475                 480

Lys Arg Lys Lys Ser Glu Met Ala Gln Ile Phe Ser Thr Ile Ser Arg
                485                 490                 495

Asp Asn Ser Ser Met Tyr Glu Tyr Ala Lys Ser Phe Phe Asp Ser Val
                500                 505                 510

Leu Lys Glu Ile Glu Lys Leu Thr Gln Met Ile Arg Asn Met Asp Lys
                515                 520                 525

Leu Ile Asn Glu Asn Glu Ala Val Met Glu Lys Leu Lys Asp Gln Arg
    530                 535                 540

Arg Glu Leu Gln Asn Val Glu Asn Ala Ser Thr Asp Leu Gly Lys Leu
```

```
                545                 550                 555                 560
Glu Glu Val Asp Lys Met Ala Gln Thr Lys Ser Glu Thr Glu Leu Ser
                    565                 570                 575
Glu Arg Asn Asp Ser Arg Asn Ala Lys Asp Gly Ala Thr Tyr Ser Thr
                580                 585                 590
Leu Met Asp Asp Lys Glu Thr Asp Ser Val Asn Gly Glu Thr Lys
            595                 600                 605
Gln Glu Asn Val Val Lys Lys Gly Leu Pro Pro Gln Thr Asp Ile
610                 615                 620
Tyr Thr Ser Val Val Leu Lys Asn Asp Arg Asn Asp Gln Lys Ser Glu
625                 630                 635                 640
Lys Ile Gly Glu Lys Lys Ser Asn Lys Pro Val Gly Thr Glu Glu Asn
                    645                 650                 655
Ile Gln His Ser Ser Tyr Leu Asn Asp Asn Ser Asn Asn Asp Ile
                660                 665                 670
Asp Val Gly Thr Leu Tyr Thr Leu Gly Gly Tyr Asn Ala Pro Asn Asp
            675                 680                 685
Asn Tyr Asn Thr Asn Glu Ser Gly Asp Asp Ile Asn Glu Glu Ala Lys
            690                 695                 700
Lys Lys Arg Asn Ala Val Leu Phe Val Tyr Val Gly Gly Leu Phe Ser
705                 710                 715                 720
Ala Leu Phe Ile Cys Ile Gly Ala Val Phe Tyr Leu Leu His Arg Lys
                    725                 730                 735
Ile Gly Ile Glu Gly Val Gly Lys Ser Asp His Glu Lys Lys Pro Thr
            740                 745                 750
Ile Glu Asp Thr Lys Ile Glu Val Phe Glu Glu Thr Asn Gly Ser Lys
            755                 760                 765
Arg Asn Val Lys Asp Glu Val Ile Asp Val Pro Phe Val Asp Met Glu
        770                 775                 780
Asp Asn Leu His His His His His His
785                 790

<210> SEQ ID NO 104
<211> LENGTH: 2382
<212> TYPE: DNA
<213> ORGANISM: Plasmodium vivax

<400> SEQUENCE: 104
atgaccttca acgacggcag cgacgagatc tccaccgccc aaaagtacaa gaccgacgtg      60
gagggcatca tcgacaagct gaacgtcatc gacgagacga tcaacggcat caacagcacc     120
ctggacgagc tcctggagct cggcaacaac tgccaactcc acaggacctt cctgatctcc     180
agctccctca caacaagat cgccaagttc ctcgtggaga tcaggagca aaggagaac        240 accaagaagt gcttccaata cgtgaagcgc aaccaccagc acctggccaa cttcgtctcc     300
gagctccaca gacccaagg cggcatcttc gagaacgtca acctggtgga acaccccca      360 gacgccgaca gtactacca cgagttcatg gagatcgagc aagaggccac caagatcgtc      420
aaggacatca gaaggagat ctaccacctg aacgacgacg tggacgagcc agtcctggag      480
aagaggatca aggacgtgat caacacctac aacaagctga gaccaagaa ggtccagatg      540 gaccagtcct acaagaacat gtacatcacc aagctgaggg aggtggaggg cagccacgac     600
ctgttcaacc aagtcgccca gctcatcagg ggcgagacgg acaagaaggg caaggccctg     660
tccgagcgcg agaacaacct ccacagcatc tacaacttcg tgaagctgca cgagacggag     720
```

| | |
|---|---|
| ctccacaacc tgtacgccaa gtacacccca gagtacatgg agaagatcaa caagatcttc | 780 |
| gacgacatca acgccaggat gatcgccgtg gacctcaacg acgaccacag ctccgagtac | 840 |
| agcgacgtca agcgccacga gcacgaggcc atgctcctga tggacgccac caacaacctg | 900 |
| tccaaggaag tggagatgat gcagaacgag agcggcggca agaacgacgg catcaacggc | 960 |
| ggcaagtccc aactcgtgga ggactacacc aacaccatga gcgagttcac cgagcaggcc | 1020 |
| aagaccgtcg ccaagaagat ccacgactcc aagggcgact acgccaacat gttcgaccac | 1080 |
| atcagggaga acgaggccat gctggagcgc atcgacctca agaagaagga catcaaggag | 1140 |
| atcctcgccc acctgaacag gatgaaggag tacctcctga gaagctgtc cgaggaagag | 1200 |
| aagctccacc acatgcgcga agctcgaa gaggtgaaca cgagcaccga cgagatcgtc | 1260 |
| aagaagttcc gcacctacga ccaaatggtg gacatctccc agaacatcga catcaagaac | 1320 |
| gtgcaaagca agcgctacga ctccgtcgac gagatcgaca aggagatgtc ctacatcaag | 1380 |
| acccacaaca aggacctgat cgacagcaag ttcatcgtcg agagggccct ggagaacgac | 1440 |
| aagcgcaaga agagcgagat ggcccaaatc ttcagcacca tctccaggga caacagctcc | 1500 |
| atgtacgagt acgccaagag cttcttcgac tccgtgctga aggagatcga gaagctcacc | 1560 |
| cagatgatcc gcaacatgga caagctcatc aacgagaacg aggccgtcat ggagaagctg | 1620 |
| aaggaccaaa ggcgcgagct ccagaacgtg gagaacgcct ccaccgacct cggcaagctc | 1680 |
| gaagaggtgg acaagatggc ccagaccaag agcgagacg agctgtccga ggagaacgac | 1740 |
| agccgcaacg ctaaggacgg cgctacctac tccaccctca tggacgacaa ggagacggac | 1800 |
| agcgtgaacg cgcaggagac gaagcaagag aacgtggtcg tgaagaaggg cctgccacca | 1860 |
| cagaccgaca tctacaccag cgtcgtgctc aagaacgaca ggaacgacca aaagtccgag | 1920 |
| aagatcggcg agaagaagag caacaagcca gtgggcaccg aggagaacat ccagcacagc | 1980 |
| tcctacctca acaacgacaa ctccaacaac gacatcgacg tgggcaccct ctacaccctg | 2040 |
| ggcggctaca acgcccccaaa cgacaactac aacaccaacg agagcggcga cgacatcaac | 2100 |
| gaggaagcca agaagaagag gaacgccgtg ctcttcgtct acgtgggcgg cctcttctcc | 2160 |
| gccctgttca tctgcatcgg cgccgtgttc tacctcctgc accgcaagat cggcatcgag | 2220 |
| ggcgtcggca agagcgacca cgagaagaag ccaaccatcg aggacaccaa gatcgaggtg | 2280 |
| ttcgaggaga cgaacggctc caagcgcaac gtcaaggacg aggtcatcga cgtgccattc | 2340 |
| gtcgacatgg aggacaacct ccaccaccac caccaccact ga | 2382 |

<210> SEQ ID NO 105
<211> LENGTH: 396
<212> TYPE: PRT
<213> ORGANISM: Plasmodium vivax

<400> SEQUENCE: 105

Met Gly Glu His Lys Thr Asp Ser Lys Thr Asp Asn Gly Lys Gly Ala
1               5                   10                  15

Asn Asn Leu Val Met Leu Asp Tyr Glu Thr Ser Ser Asn Gly Gln Pro
            20                  25                  30

Ala Gly Thr Leu Asp Asn Val Leu Glu Phe Val Thr Gly His Glu Gly
        35                  40                  45

Asn Ser Arg Lys Asn Ser Ser Asn Gly Gly Asn Pro Tyr Asp Ile Asp
    50                  55                  60

His Lys Lys Thr Ile Ser Ser Ala Ile Ile Asn His Ala Phe Leu Gln
65                  70                  75                  80

```
Asn Thr Val Met Lys Asn Cys Asn Tyr Lys Arg Lys Arg Arg Glu Arg
                 85                  90                  95

Asp Trp Asp Cys Asn Thr Lys Lys Asp Val Cys Ile Pro Asp Arg Arg
            100                 105                 110

Tyr Gln Leu Cys Met Lys Glu Leu Thr Asn Leu Val Asn Asn Thr Asp
        115                 120                 125

Thr Asn Phe His Arg Asp Ile Thr Phe Arg Lys Leu Tyr Leu Lys Arg
    130                 135                 140

Lys Leu Ile Tyr Asp Ala Val Glu Gly Leu Leu Leu Lys Leu
145                 150                 155                 160

Asn Asn Tyr Arg Tyr Asn Lys Asp Phe Cys Lys Asp Ile Arg Trp Ser
                165                 170                 175

Leu Gly Asp Phe Gly Asp Ile Ile Met Gly Thr Asp Met Glu Gly Ile
            180                 185                 190

Gly Tyr Ser Lys Val Val Glu Asn Asn Leu Arg Ser Ile Phe Gly Thr
        195                 200                 205

Asp Glu Lys Ala Gln Gln Arg Arg Lys Gln Trp Trp Asn Glu Ser Lys
    210                 215                 220

Ala Gln Ile Trp Thr Ala Met Met Tyr Ser Val Lys Lys Arg Leu Lys
225                 230                 235                 240

Gly Asn Phe Ile Trp Ile Cys Lys Leu Asn Val Ala Val Asn Ile Glu
                245                 250                 255

Pro Gln Ile Tyr Arg Trp Ile Arg Glu Trp Gly Arg Asp Tyr Val Ser
            260                 265                 270

Glu Leu Pro Thr Glu Val Gln Lys Leu Lys Lys Cys Asp Gly Lys
        275                 280                 285

Ile Asn Tyr Thr Asp Lys Lys Val Cys Lys Val Pro Pro Cys Gln Asn
    290                 295                 300

Ala Cys Lys Ser Tyr Asp Gln Trp Ile Thr Arg Lys Lys Asn Gln Trp
305                 310                 315                 320

Asp Val Leu Ser Asn Lys Phe Ile Ser Val Lys Asn Ala Glu Lys Val
                325                 330                 335

Gln Thr Ala Gly Ile Val Thr Pro Tyr Asp Ile Leu Lys Gln Glu Leu
            340                 345                 350

Asp Glu Phe Asn Glu Val Ala Phe Glu Asn Glu Ile Asn Lys Arg Asp
        355                 360                 365

Gly Ala Tyr Ile Glu Leu Cys Val Cys Ser Val Glu Glu Ala Lys Lys
    370                 375                 380

Asn Thr Gln Glu Val Val His His His His His
385                 390                 395

<210> SEQ ID NO 106
<211> LENGTH: 1191
<212> TYPE: DNA
<213> ORGANISM: Plasmodium vivax

<400> SEQUENCE: 106
atgggcgagc acaagaccga ctccaagacc gacaacggca agggcgccaa caacctggtc        60
atgctcgact acgagacgtc ctccaacggc cagccagctg gcaccctgga caacgtgctg       120
gagttcgtca ccggccacga gggcaacagc aggaagaact ccagcaacgg cggcaaccca       180
tacgacatcg accacaagaa gaccatctcc agcgccatca tcaaccacgc cttcctgcag       240
aacaccgtga tgaagaactg caactacaag aggaagaggc gcgagcgcga ctgggactgc       300
aacaccaaga aggacgtctg catcccagac aggcgctacc aactctgcat gaaggagctg       360
```

```
accaacctcg tgaacaacac cgacaccaac ttccacaggg acatcacctt ccgcaagctg    420
tacctcaaga ggaagctgat ctacgacgct gctgtggagg cgacctcct gctcaagctc    480 aacaactaca ggtacaacaa ggacttctgc aaggacatcc gctggtccct gggcgacttc    540
ggcgacatca tcatgggcac cgacatggag ggcatcggct actccaaggt ggtcgagaac    600
aacctccgca gcatcttcgg caccgacgag aaggcccaac agaggcgcaa gcaatggtgg    660
aacgagtcca aggcccagat ctggaccgcc atgatgtaca gcgtgaagaa gaggctgaag    720
ggcaacttca tctggatctg caagctcaac gtggccgtca catcgagcc acagatctac    780 aggtggatca gggagtgggg cagggactac gtctccgagc tgccaaccga ggtgcaaaag    840
ctcaaggaga agtgcgacgg caagatcaac tacaccgaca agaaggtgtg caaggtccca    900
ccatgccaaa acgcctgcaa gagctacgac cagtggatca ccaggaagaa gaaccaatgg    960
gacgtcctgt ccaacaagtt catcagcgtg aagaacgccg agaaggtcca gaccgccggc   1020
atcgtgaccc catacgacat cctgaagcaa gagctcgacg agttcaacga ggtggccttc   1080
gagaacgaga tcaacaagcg cgacggcgcc tacatcgagc tctgcgtgtg cagcgtcgag   1140
gaagccaaga gaacacccca agaggtggtc caccaccacc accaccactg a            1191
```

<210> SEQ ID NO 107
<211> LENGTH: 835
<212> TYPE: PRT
<213> ORGANISM: Plasmodium vivax

<400> SEQUENCE: 107

```
Met Val Ile Gly Gly Ser Pro Asn Asn Glu Ala Pro Asn Ser Ser Arg
1               5                   10                  15

His His Leu Arg Asn Gly Phe Pro Gly Lys Asn Asp Ser Leu Pro His
            20                  25                  30

Glu Glu Pro Asn Asn Leu Glu Gly Lys Asn Glu Ser Ser Asp Gln Cys
        35                  40                  45

Asp Thr Ile Asn Leu Gly Gln Val Thr Glu Lys Glu Lys Lys Thr Ile
    50                  55                  60

Glu Gln Ala Ser Val Gln Ala Gln Asp Ala Thr Lys Pro Glu Ala Asn
65                  70                  75                  80

Asn Ala Glu Gln Ile Gln Ala Glu Leu Gln Lys Val Lys Thr Ala Lys
                85                  90                  95

Asp Glu Ser Ala Thr Ala Ala Lys Asp Ala Glu Thr Ala Lys Lys Asn
            100                 105                 110

Ala Val Asp Ala Gly Lys Gly Leu Asp Ala Ala Lys Gly Ala Ile Lys
        115                 120                 125

Lys Ala Glu Glu Ala Ala Ala Glu Ala Lys Lys Gln Ala Gly Ile Ala
    130                 135                 140

Glu Lys Ala Glu Lys Asp Ala Glu Ala Ala Gly Lys Lys Asp Lys Leu
145                 150                 155                 160

Glu Asp Val Asn Ser Gln Val Gln Ile Ala Val Glu Ala Ser Thr Lys
                165                 170                 175

Ala Lys Asp Lys Lys Thr Glu Ala Glu Ile Ala Val Glu Ile Val Lys
            180                 185                 190

Ala Val Val Ala Lys Glu Glu Ala Gln Lys Ala Ser Asp Glu Ala Gln
        195                 200                 205

Lys Ala Cys Glu Lys Ala Gln Lys Ala His Ala Lys Ala Gln Lys Ala
    210                 215                 220
```

-continued

Ser Asp Thr Thr Lys Thr Val Glu Thr Phe Lys Thr Asn Ala Glu Ala
225                 230                 235                 240

Ala Ala Lys Asn Ala Lys Glu Lys Ala Gly Asn Ala Asn Lys Ala Ala
            245                 250                 255

Thr Glu Ala Glu Ser Ala Asn Glu Leu Ser Val Ala Lys Gln Lys Ala
        260                 265                 270

Lys Asp Ala Glu Glu Ala Ala Lys Glu Ala Lys Glu Gln Val Lys
    275                 280                 285

Ala Glu Ile Ala Ala Glu Val Ala Lys Ala Lys Val Ala Lys Glu Glu
    290                 295                 300

Ala Asp Ala Ala Gln Lys Lys Ala Glu Ala Ala Lys Lys Ile Val Asp
305                 310                 315                 320

Lys Ile Ala Gln Asp Thr Lys Val Pro Glu Ala Gln Arg Glu Ala Lys
            325                 330                 335

Leu Ala Thr Gln Thr Ala Ser Lys Ala Thr Glu Ala Ala Thr Glu Ala
            340                 345                 350

Gly Lys Lys Ala Gln Glu Ala Glu Glu Ser Ser Lys Glu Ala Glu Glu
        355                 360                 365

Lys Ala Glu Thr Ser Asp Ala Val Lys Gly Lys Ala Asp Ala Ala Glu
    370                 375                 380

Lys Ala Ala Gly Glu Ala Lys Lys Ala Ser Ile Glu Thr Glu Ile Ala
385                 390                 395                 400

Ile Glu Val Ala Lys Ala Glu Val Leu Asn Ala Glu Val Lys Lys Thr
            405                 410                 415

Ala Gln Glu Ala Glu Lys Asp Ala Thr Glu Ala Lys Glu Gln Ala Glu
            420                 425                 430

Lys Ala Lys Ala Ala Glu Glu Ala Lys Thr His Gly Glu Lys Ala
    435                 440                 445

Glu Lys Val Gly Glu Ser Thr Lys Ala His Ser Asp Glu Ala Gln Gln
    450                 455                 460

Glu Asn Lys Asn Ala Lys Asp Ala Ser Glu Glu Ala Glu Asn Arg Ala
465                 470                 475                 480

Val Asp Ala Leu Glu Glu Ala Tyr Ala Val Glu Ala His Leu Ala Arg
            485                 490                 495

Thr Lys Asn Ala Ala Glu Ser Ala Lys Ser Ala Thr Asp Met Ser Glu
            500                 505                 510

Leu Glu Lys Ala Lys Glu Glu Ala Ile Asp Ala Ala Asn Ile Ala His
        515                 520                 525

Gln Lys Trp Leu Lys Ala Thr Gln Ala Ala Thr Ile Ala Lys Glu Lys
    530                 535                 540

Lys Glu Ala Ala Lys Val Ala Ala Glu Lys Ala Gln Thr Ala Ala Asn
545                 550                 555                 560

Val Val Lys Asp Lys Ala Ala Lys Ala Glu Ala Lys Lys Ala Glu Thr
            565                 570                 575

Glu Ala Val Lys Ala Ala Val Glu Ala Arg Ala Ala Glu Glu Ala
        580                 585                 590

Lys Gln Glu Ala Ala Lys Val Gly Ala Ser Lys Glu Pro Gln Glu Thr
    595                 600                 605

Lys Asn Lys Ala Asn Val Glu Ala Ala Thr Gly Asn Glu Ala Lys
    610                 615                 620

Lys Ala Glu Asp Ala Ala Glu Glu Ala Lys Glu Ala Ala Lys Lys Ala
625                 630                 635                 640

Asn Glu Ala Thr Asp Ala Asn Val Ala Arg Ser Glu Ala Asp Lys Ala

```
                  645                 650                 655
Ile Ala Ala Ala Lys Ala Lys Ala Arg Glu Lys Ala Tyr
            660                 665                 670

Gly Leu Leu Lys Thr Lys Asn Gln Tyr Val Leu Glu Pro Leu Asp Ile
            675                 680                 685

Ser Pro Glu Ser Ala Asp Asn Ile Thr Ser Lys Glu Glu Gln Val Lys
            690                 695                 700

Glu Glu Met Glu Asp Gln Gly Asp Glu Asp Ser Asn Glu Ala Glu Val
705                 710                 715                 720

Glu Glu Ala Leu Pro Asn Gly Ser Gly Ala Gln Glu Glu Asp Val Asn
            725                 730                 735

Leu Glu Met Asp Asp Glu Glu Val Glu Glu Val Glu Glu Asn Val
            740                 745                 750

Ala Thr Asn Gln Gln Thr Gly Gly Lys Arg Glu Lys Arg Asn Thr Asn
            755                 760                 765

Asp Thr Val Asp Asp Thr Asn Ala Asp Lys Gln Phe Gly Asp Glu Phe
            770                 775                 780

Asp Thr Tyr Asn Asp Ile Lys Lys Val Thr Glu Ala Leu Val Lys Ser
785                 790                 795                 800

Met Thr Ser Leu Val Ser Asp Asp Pro Ser Val Gly Asp Thr Ile Asn
                    805                 810                 815

Glu Phe Leu Ser Asp Met Asn His Leu Phe Leu Ser Trp His His His
            820                 825                 830

His His His
        835

<210> SEQ ID NO 108
<211> LENGTH: 2508
<212> TYPE: DNA
<213> ORGANISM: Plasmodium vivax

<400> SEQUENCE: 108
atggtcatcg gcggctcccc aaacaacgag gccccaaact ccagcaggca ccacctccgc      60
aacggcttcc caggcaagaa cgactccctc ccacacgagg agccaaacaa cctggagggc     120
aagaacgagt ccagcgacca atgcgacacc atcaacctgg gccaggtgac cgagaaggag     180
aagaagacca tcgagcaagc tagcgtccaa gctcaggacg ctaccaagcc agaggccaac     240
aacgccgagc aaatccaggc cgagctccaa aaggtgaaga ccgctaagga cgagtccgct     300
accgctgcta aggacgctga cacgccaag aagaacgctg tggacgctgg caagggcctg     360
gacgccgcca agggcgccat caagaaggct gaggaagccg ccgccgaggc caagaagcag     420
gctggcatcg ccgagaaggc tgagaaggac gctgaggctg ctggcaagaa ggacaagctg     480
gaggacgtga acagccaagt ccagatcgcc gtggaggcct ccaccaaggc caaggacaag     540
aagaccgagg ccgagatcgc cgtggagatc gtcaaggccg tggtcgccaa ggaagaggcc     600
caaaaggcta gcgacgaggc tcagaaggct tgcgagaagg cccaaaaggc tcacgctaag     660
gctcagaagg cttccgacac caccaagacc gtggagacgt tcaagaccaa cgccgaggct     720
gccgccaaga acgccaagga gaaggctgga acgctaaca aggctgctac cgaggctgag     780
agcgctaacg agctctccgt ggccaagcag aaggccaagg acgccgagga agccgccaag     840
gaagccaaga aggagcaagt caaggctgag atcgctgctg aggtggctaa ggctaaggtg     900
gctaaggaag aggccgacgc tgctcagaag aaggctgagg ccgccaagaa gatcgtggac     960
aagatcgccc aagacaccaa ggtgccggag gctcagaggg aggctaagct ggctacccag    1020
```

```
accgctagca aggctaccga ggccgccacc gaggctggca agaaggctca agaggccgag    1080
gagtccagca aggaagccga ggagaaggct gagacgagcg acgctgtgaa gggcaaggct    1140
gacgctgctg agaaggctgc tggcgaggcc aagaaggctt ccatcgagac ggagatcgcc    1200
atcgaggtcg ccaaggccga ggtgctcaac gccgaggtca agaagaccgc tcaagaggcc    1260
gagaaggacg ctaccgaggc caaggagcaa gccgagaagg ccaaggctgc cgccgaggaa    1320
gccaagaccc acggcgagaa ggctgagaag gtgggcgaga gcaccaaggc ccactccgac    1380
gaggcccaac aggagaacaa gaacgccaag gacgccagcg aggaagccga acagggct     1440 gtggacgctc tcgaagaggc ctacgctgtg gaggctcacc tggctaggac caagaacgct    1500
gctgagtccg ctaagagcgc taccgacatg tccgagctgg agaaggccaa ggaagaggcc    1560
atcgacgccg ccaacatcgc ccaccaaaag tggctcaagg ctacccaggc tgctaccatc    1620
gctaaggaga agaaggaagc cgccaaggtg gctgctgaga aggctcagac cgctgccaac    1680
gtggtcaagg acaaggctgc taaggctgag gccaagaagg ctgagacgga ggccgtcaag    1740
gctgctgtgg aggccagggc cgccgccgag gaagccaaac aagaggccgc taaggtcggc    1800
gctagcaagg agccacaaga gacgaagaac aaggctaacg tggaggctga ggctaccggc    1860
aacgaggcca agaaggccga ggacgctgct gaggaagcca aggaagccgc caagaaggct    1920
aacgaggcta ccgacgctaa cgtggctagg tccgaggctg acaaggctat cgccgccgcc    1980
aagaaggcca agaaggcccg cgagaaggct gcttacggcc tcctgaagac caagaaccaa    2040
tacgtgctgg agccactgga catctcccca gagagcgccg acaacatcac ctccaaggaa    2100
gagcaggtga aggaagagat ggaggaccaa ggcgacgagg acagcaacga ggccgaggtg    2160
gaggaagccc tgccaaacgg ctccggcgct caagaggaag acgtcaacct ggagatggac    2220
gacgaggaag aggtggagga agtggaggag aacgtggcca ccaaccaaca gaccggcggc    2280
aagagggaga agcgcaacac caacgacacc gtcgacgaca ccaacgccga caagcaattc    2340
ggcgacgagt tcgacaccta caacgacatc aagaaggtga ccgaggccct cgtcaagtcc    2400
atgaccagcc tggtgtccga cgacccatcc gtgggcgaca ccatcaacga gttcctcagc    2460
gacatgaacc acctcttcct gtcctggcac caccaccacc accactga                 2508
```

<210> SEQ ID NO 109
<211> LENGTH: 117
<212> TYPE: PRT
<213> ORGANISM: Plasmodium vivax

<400> SEQUENCE: 109

```
Met Glu Asn Asn Lys Ile Lys Gly Gly Lys Val Pro Pro Pro Ser Val
1               5                   10                  15

Pro Thr Gly Asn Asn Ser Asp Asn Val Pro Lys Lys Asp Gly Gly
            20                  25                  30

Glu Asn Asn Pro Pro Asp Ala Glu Asn Ala Leu Gln Glu Leu Lys
        35                  40                  45

Asn Phe Thr Lys Asn Leu Glu Lys Lys Thr Thr Asn Arg Asn Ile
    50                  55                  60

Ile Ile Ser Thr Thr Val Ile Asn Met Val Leu Leu Val Leu Leu Ser
65                  70                  75                  80

Gly Leu Ile Gly Tyr Asn Thr Lys Lys Gly Phe Lys Lys Gly Gln Met
                85                  90                  95

Gly Ser Val Lys Glu Val Thr Pro Glu Ala Gln Lys Gly Lys Leu His
            100                 105                 110
```

```
His His His His His
        115

<210> SEQ ID NO 110
<211> LENGTH: 354
<212> TYPE: DNA
<213> ORGANISM: Plasmodium vivax

<400> SEQUENCE: 110
atggagaaca acaagatcaa gggcggcaag gtgccaccac catccgtccc aaccggcaac     60
aactccgaca acaacgtgcc aaagaaggac ggcggcgaga acaacccacc accagacgcc    120
gagaacgccc tccaagagct gaagaacttc accaagaacc tggagaagaa gaccaccacc    180
aacaggaaca tcatcatctc caccaccgtc atcaacatgg tgctcctggt cctcctgagc    240
ggcctgatcg gctacaacac caagaagggc ttcaagaagg gccaaatggg ctccgtgaag    300
gaagtgaccc cagaggccca gaagggcaag ctccaccacc accaccacca ctga          354

<210> SEQ ID NO 111
<211> LENGTH: 614
<212> TYPE: PRT
<213> ORGANISM: Plasmodium vivax

<400> SEQUENCE: 111

Glu Asn Pro Val Arg His Ser Val Asp Ile Lys Ser Glu Asp Phe Val
1               5                   10                  15

Val Leu Ile Ser Leu Gln Asn Leu Gln Thr Phe Ile Met Ile Gly Tyr
            20                  25                  30

Thr Ala Val Asn Lys Asp His Leu Asn Phe Asp Phe Ser Tyr Leu Trp
        35                  40                  45

Ala Leu Cys Ile Gly Thr Gly Leu Phe Ile Tyr Ser Leu Ile Ser Phe
    50                  55                  60

Val Leu Ile Arg Ser Leu Ala Leu Ser Lys Ile Asp Ile Gly Lys Tyr
65                  70                  75                  80

Val Leu Glu Leu Leu Phe Ser Leu Ser Ile Ile Ala Thr Cys Ser Leu
                85                  90                  95

Ser Ile Ile Ile Asp Ser Phe Lys Ile Ala Asn Met Gln Leu Leu Phe
            100                 105                 110

Phe Ser Phe Ala Leu Thr Gly Tyr Ala Tyr Tyr Asn Leu Met Ser Leu
        115                 120                 125

Phe Phe Phe Cys Thr Leu Val Gly Met Thr Ile Gln Tyr Asn Leu Ser
    130                 135                 140

Phe Thr Gly Phe Arg Ala His Ser Thr Ser Phe Phe Phe Leu Asp Met
145                 150                 155                 160

Leu Ser Tyr Leu Val Gln Met Ile Gly Gly Asn Ile Leu Tyr Phe Arg
                165                 170                 175

Met Tyr Glu Leu Cys Thr Leu Ile Val Ile Ser Lys Arg Asn Pro Cys
            180                 185                 190

Lys Tyr Val Val Ala Ser Lys Glu Val Lys Gln Val Glu Lys Gln Ile
        195                 200                 205

Phe Ser Ser Leu Phe Asn Ser Tyr Met Cys Ile Lys Ser Lys Thr Tyr
    210                 215                 220

Ser Asp Leu Thr Cys Thr Asn Asp Leu Leu Asn Lys Asp Ser Gln Ser
225                 230                 235                 240

Val Val Gly Arg Asp Thr Asn Pro Lys Trp Asn Ser Pro Ile Gly Thr
                245                 250                 255
```

-continued

```
Ser Tyr Gln Asp Lys Val Asn His Thr Lys Lys Leu Leu Arg Arg
        260                 265                 270

Gly Lys Arg Asp Lys Arg Tyr Pro Lys Gly Gly Gly Ala Arg Leu
    275                 280                 285

Thr Cys Ala Lys His Ser Ala Tyr His Asn Ser Arg Ser Leu Ala Asn
290                 295                 300

Cys Ala Ser Lys Asn Thr Pro Ile Cys Thr Thr Asn Phe Arg Ile Ser
305                 310                 315                 320

Asn Thr Leu Ser Leu Lys Asn His Phe Asn Pro Asn Leu Thr Leu Glu
                325                 330                 335

Ala Ser Pro Pro Val Cys Lys Lys Cys Val Ser Glu Lys Asn Ser His
            340                 345                 350

Lys Asp Asn Glu Tyr Lys Asn Gly Glu Glu Arg Lys Lys Ala Lys Arg
        355                 360                 365

Gly Ile Lys Ser Gly Thr Ala Asn Lys Ser Asn Gln Leu Gly Asn His
    370                 375                 380

Gly Gly Asp Ala Thr Gln Val Ala Asn Pro Thr Tyr Arg Thr Thr Ser
385                 390                 395                 400

His Gly Gly Asp Ala Thr Gln Val Ala Tyr Pro Thr Tyr Arg Thr Thr
                405                 410                 415

Ser His Gly Gly Asp Ala Thr Gln Val Asp Ser Pro Thr His Pro Thr
            420                 425                 430

Thr Ser His Gly Gly Asn Asn Ser Ser Gly His Pro Gln Asp Asp
        435                 440                 445

Glu Val Leu Ile Pro Ile Arg Gly Thr Asn Ala Thr Asn Asp Ala Ala
    450                 455                 460

Ala Thr Tyr Asn Ser Asn Ala Ser Trp Ile Lys Thr Ala Ala Val Ile
465                 470                 475                 480

Asp Val Ser Val Glu Gly Lys Gln Lys Gly Gly His Gln Thr Phe
                485                 490                 495

Ala Gly Asn Pro Val Asn Ser Ser Ala Asn Phe Pro Ser Asp Lys Lys
            500                 505                 510

Pro Ser Tyr Asn Ser His Arg Asn Gly Gly Thr Pro Pro Asn Glu
        515                 520                 525

Gln Leu Arg Tyr Tyr Ala Cys Pro Cys Tyr Gln Thr His Ser Ser Gly
    530                 535                 540

Ser Ser Leu Ser Glu Val Pro Ser Gly Gln Thr Thr Lys Arg Lys Asn
545                 550                 555                 560

Ser Ala His Asn Ser Val Glu Gly Gly Asn Pro Lys Met Asp Asn Gln
                565                 570                 575

Gln Ser Arg Arg Val Ser Asn Lys Arg Val Asp Gly Ala Thr Gly Glu
            580                 585                 590

Glu His Asp His Pro Ser Asp Pro Ala Asp Asn Pro Asn Gly Asn
        595                 600                 605

Ser Asn Thr Tyr His Cys
    610

<210> SEQ ID NO 112
<211> LENGTH: 365
<212> TYPE: PRT
<213> ORGANISM: Plasmodium vivax

<400> SEQUENCE: 112

Glu Leu Ser His Ser Leu Ser Val Lys Asn Ala Pro Asp Ala Ser Ala
```

```
            1               5                   10                  15
          Leu Asn Ile Glu Val Glu Lys Asp Lys Lys Ile Cys Lys Asn Ala
                         20                  25                  30

Phe Gln Tyr Ile Asn Val Ala Glu Leu Leu Ser Pro Arg Glu Glu
                         35                  40                  45

Thr Tyr Val Gln Lys Cys Glu Glu Val Leu Asp Thr Ile Lys Asn Asp
                         50                  55                  60

Ser Pro Asp Glu Ser Ala Glu Ala Glu Ile Asn Glu Phe Ile Leu Ser
          65                  70                  75                  80

Leu Leu His Ala Arg Ser Lys Tyr Thr Ile Ile Asn Asp Ser Asp Glu
                         85                  90                  95

Glu Val Leu Ser Lys Leu Leu Arg Ser Ile Asn Gly Ser Ile Ser Glu
                         100                 105                 110

Glu Ala Ala Leu Lys Arg Ala Lys Gln Leu Ile Thr Phe Asn Arg Phe
                         115                 120                 125

Ile Lys Asp Lys Ala Lys Val Lys Asn Val Gln Glu Met Leu Val Ile
                         130                 135                 140

Ser Ser Lys Ala Asp Asp Phe Met Asn Glu Pro Lys Gln Lys Met Leu
          145                 150                 155                 160

Gln Lys Ile Ile Asp Ser Phe Glu Leu Tyr Asn Asp Tyr Leu Val Ile
                         165                 170                 175

Leu Gly Ser Asn Ile Asn Ile Ala Lys Arg Tyr Ser Glu Thr Phe
                         180                 185                 190

Leu Ser Ile Lys Asn Glu Lys Phe Cys Ser Asp His Ile His Leu Cys
                         195                 200                 205

Gln Lys Phe Tyr Glu Gln Ser Ile Ile Tyr Tyr Arg Leu Lys Val Ile
                         210                 215                 220

Phe Asp Asn Leu Val Thr Tyr Val Asp Gln Asn Ser Lys His Phe Lys
          225                 230                 235                 240

Lys Glu Lys Leu Leu Glu Leu Leu Asn Met Asp Tyr Arg Val Asn Arg
                         245                 250                 255

Glu Ser Lys Val His Glu Asn Tyr Val Leu Glu Asp Glu Thr Val Ile
                         260                 265                 270

Pro Thr Met Arg Ile Thr Asp Ile Tyr Asp Gln Asp Arg Leu Ile Val
                         275                 280                 285

Glu Val Val Gln Asp Gly Asn Ser Lys Leu Met His Gly Arg Asp Ile
                         290                 295                 300

Glu Lys Arg Glu Ile Ser Glu Arg Tyr Ile Val Thr Val Lys Asn Leu
          305                 310                 315                 320

Arg Lys Asp Leu Asn Asp Glu Gly Leu Tyr Ala Asp Leu Met Lys Thr
                         325                 330                 335

Val Lys Asn Tyr Val Leu Ser Ile Thr Gln Ile Asp Asn Asp Ile Ser
                         340                 345                 350

Asn Leu Val Arg Glu Leu Asp His Glu Asp Val Glu Lys
                         355                 360                 365

<210> SEQ ID NO 113
<211> LENGTH: 162
<212> TYPE: PRT
<213> ORGANISM: Plasmodium vivax

<400> SEQUENCE: 113

Leu Pro Trp Thr Lys Lys Arg Lys Ala Val Asn Gln Met Gly Ile Ile
1               5                   10                  15
```

```
Lys Asp Met Ser Gln Glu Leu Arg Thr Lys Ala Glu Gln Leu Pro Thr
            20                  25                  30

Pro Glu Asp Ile Ser Ala Lys Ile His Arg Val Asp Lys Glu Val Ile
        35                  40                  45

Asp Lys Leu Asn Lys Asp Ile Ile Glu Glu Glu Asn Leu Asp Lys His
    50                  55                  60

Lys Pro His Val Cys Gln Glu Pro Ala Tyr Glu Arg Asp Tyr Ser Tyr
65                  70                  75                  80

Leu Cys Pro Glu Asp Trp Val Lys Asn Ser Asn Asp Gln Cys Trp Gly
                85                  90                  95

Ile Asp Tyr Asp Gly His Cys Glu Ala Leu Lys Tyr Phe Gln Asp Tyr
            100                 105                 110

Ser Val Glu Glu Lys Lys Glu Phe Glu Met Asn Cys Cys Val Leu Trp
        115                 120                 125

Pro Lys Leu Lys Asn Glu Gly Met Lys Gly Ala His Lys Lys Asp Leu
    130                 135                 140

Leu Arg Gly Ser Ile Ser Ser Asn Asn Gly Leu Ile Ile Lys Pro Lys
145                 150                 155                 160

Tyr Leu

<210> SEQ ID NO 114
<211> LENGTH: 315
<212> TYPE: PRT
<213> ORGANISM: Plasmodium vivax

<400> SEQUENCE: 114

Glu Leu Lys Lys Asn Asn Ala Ala Leu Thr Ser Gln Arg Ser Ser Ser
1               5                   10                  15

Arg Thr Thr Ser Thr Arg Ser Tyr Lys Asn Ala Pro Lys Asn Ser Thr
            20                  25                  30

Ser Phe Leu Ser Arg Leu Ser Ile Leu Ile Phe Ala Leu Ser Cys Ala
        35                  40                  45

Ile Phe Val Asn Thr Ala Ser Gly Ala Ala Ala Asn Arg Pro Asn Ala
    50                  55                  60

Asn Gly Phe Val Ser Pro Thr Leu Ile Gly Phe Gly Glu Leu Ser Ile
65                  70                  75                  80

Gln Glu Ser Glu Glu Phe Lys Arg Met Ala Trp Asn Asn Trp Met Leu
                85                  90                  95

Arg Leu Glu Ser Asp Trp Lys His Phe Asn Asp Ser Val Glu Glu Ala
            100                 105                 110

Lys Thr Lys Trp Leu His Glu Arg Asp Ser Ala Trp Ser Asp Trp Leu
        115                 120                 125

Arg Ser Leu Gln Ser Lys Trp Ser His Tyr Ser Glu Lys Met Leu Lys
    130                 135                 140

Glu His Lys Ser Asn Val Met Glu Lys Ser Ala Asn Trp Asn Asp Thr
145                 150                 155                 160

Gln Trp Gly Asn Trp Ile Lys Thr Glu Gly Arg Lys Ile Leu Glu Ala
                165                 170                 175

Gln Trp Glu Lys Trp Ile Lys Lys Gly Asp Asp Gln Leu Gln Lys Leu
            180                 185                 190

Ile Leu Asp Lys Trp Val Gln Trp Lys Asn Asp Lys Ile Arg Ser Trp
        195                 200                 205

Leu Ser Ser Glu Trp Lys Thr Glu Glu Asp Tyr Tyr Trp Ala Asn Val
    210                 215                 220
```

-continued

```
Glu Arg Ala Thr Thr Ala Lys Trp Leu Gln Glu Ala Glu Lys Met His
225                 230                 235                 240

Trp Leu Lys Trp Lys Glu Arg Ile Asn Arg Glu Ser Glu Gln Trp Val
            245                 250                 255

Asn Trp Val Gln Met Lys Glu Ser Val Tyr Ile Asn Val Glu Trp Lys
        260                 265                 270

Lys Trp Pro Lys Trp Lys Asn Asp Lys Lys Ile Leu Phe Asn Lys Trp
    275                 280                 285

Ser Thr Asn Leu Val Tyr Lys Trp Thr Leu Lys Lys Gln Trp Asn Val
290                 295                 300

Trp Ile Lys Glu Ala Asn Thr Ala Pro Gln Val
305                 310                 315

<210> SEQ ID NO 115
<211> LENGTH: 529
<212> TYPE: PRT
<213> ORGANISM: Plasmodium vivax

<400> SEQUENCE: 115

Lys Gly Val Thr Leu Ser Cys Val Phe Ser His Ala Ser Glu Glu Arg
1               5                   10                  15

Glu Gly Gly Thr Gly Thr Phe Ala Leu Ser Asn Glu Pro Ile Tyr Tyr
            20                  25                  30

Ala Pro Ser Gly Gly Leu Ala Pro Cys Ala Leu Ile Ser Arg Gly Leu
        35                  40                  45

Ser Gly Asp Glu Glu Gly Ser Gly Glu Asp Gly Gly Glu Asp Gly Asp
    50                  55                  60

Gly Asp Gly Gly Glu Asp Ser Ala Glu Asp Asn Ala Glu Asp Gly Asp
65                  70                  75                  80

Asp Asp Gly Gly Glu Asp Gly Gly Leu Pro Gly Gly Arg Phe Pro Tyr
                85                  90                  95

Glu Glu Gly Lys Lys Ser Ser Leu Val Ser Asp Ala Pro Ser Asp Leu
            100                 105                 110

Leu Asp Gly Asp Ala Asp Glu His Ala Ala Glu Asp Gly Gly Ala Lys
        115                 120                 125

Arg Lys Met Ser Lys Lys Glu Glu Glu Ala Glu Asp Asn Lys Ile Asp
    130                 135                 140

Lys Leu Val Asn Ala Glu Met Lys Lys Leu Glu Ala Gly Glu Glu Ala
145                 150                 155                 160

Asn Lys Asp Pro Asp Ala Glu Pro Glu Lys Glu Asp Gln Gly Ser Gly
                165                 170                 175

Gln Gly Gln Arg Ala Lys Leu Arg Cys Ser Asn Lys Leu Asn Tyr Ile
            180                 185                 190

Gln Val Thr Ala Asn Gly Gln Arg Glu Gly Asp Leu Phe Gly Glu Asn
        195                 200                 205

Asp Gly Glu Ser Ala Pro Ala Phe Val Glu Ile Pro His Glu Val Glu
    210                 215                 220

Glu Glu Ser Gly Gly Val Pro Thr Lys His Asp Glu Ala Gly Glu Ala
225                 230                 235                 240

Ala Ala Ala Glu Glu Pro His Asn Arg Val Asp Arg Ala Glu Lys Glu
                245                 250                 255

Asn Asn Ala Lys Asp Leu Lys Phe Val Glu Gly Glu Arg Glu Arg Gln
            260                 265                 270

Arg Ser Ser Pro Pro Ser Asn Gly Tyr Ser Gln Asn Ser Phe Val Glu
        275                 280                 285
```

```
Leu Lys Gly Val Pro Asp Lys Leu Pro Pro Asn Phe Thr Asn Ser Leu
            290                 295                 300
Gly Ser Ser Pro Thr His Ser Asn Leu Glu Lys Pro Val Tyr Lys His
305                 310                 315                 320
Leu Pro Trp Ser Ile Leu Ala Ser Asp Ser Gly Ser Asn Thr Gly Ser
                325                 330                 335
Trp Ala Asp Val Asn Ser Ser Thr Tyr Asn Val Ser Pro Phe Ser Phe
                340                 345                 350
Thr Ser Ile Arg Ser Gly Asn Ser Leu His Leu Leu Pro Met Asn Phe
                355                 360                 365
Gln Ile Gln Asn Ser Ile Val Lys Val Thr Asp Glu Glu Tyr Asp Lys
            370                 375                 380
Leu Lys Leu Lys Asn Ser Val Lys Val Tyr Asp Lys Asn Ala Leu Val
385                 390                 395                 400
Asp Tyr Lys Tyr Glu Ile Phe Glu Val Lys Glu Gly Glu Tyr Asn
                405                 410                 415
Asp Gly Asn Asp Pro Tyr Glu Glu Arg Asn Gly Glu Gly Asp Ala
                420                 425                 430
Gly Gly Glu Gly Gly Ser Asp Gly Glu Gly Asp Ala Asp Ser Lys Ser
            435                 440                 445
Tyr Gln Asn Asn Lys Ser Asp Gly Arg Gly Phe Phe Asp Gly Thr Leu
            450                 455                 460
Val Thr Tyr Thr Ile Ile Ile Leu Ala Gly Val Ile Ile Leu Leu Leu
465                 470                 475                 480
Ser Phe Val Ile Tyr Tyr Asp Ile Ile Asn Lys Val Lys Arg Arg
                485                 490                 495
Met Ser Ala Lys Arg Lys Asn Asn Lys Ser Met Ala Ile Ala Asn Asp
            500                 505                 510
Thr Ser Ala Gly Met Tyr Met Gly Asp Thr Tyr Met Glu Asn Pro His
            515                 520                 525
Val

<210> SEQ ID NO 116
<211> LENGTH: 334
<212> TYPE: PRT
<213> ORGANISM: Plasmodium vivax

<400> SEQUENCE: 116

Ser Gln Gly Cys Ser Gly Tyr Arg Leu Pro Pro Lys Arg Trp Phe
1               5                   10                  15
Thr Phe Thr Ser Arg Pro Tyr Cys Lys Thr Ala Ala Tyr Tyr Glu Leu
                20                  25                  30
Lys His Met Pro Tyr Tyr Val Asp Ala Val Ser Ala Ser Glu Asn Val
                35                  40                  45
Lys His Glu Lys Trp Asn Asn Trp Leu Lys Glu Met Lys Ile Ser Leu
            50                  55                  60
Thr Glu Lys Leu Glu Lys Glu Ser Gln Glu Tyr Met Glu Lys Leu Glu
65                  70                  75                  80
Gln Gln Trp Asp Glu Phe Met Lys Asn Ser Asp Lys Trp Arg His
                85                  90                  95
Tyr Asn Pro Gln Met Glu Glu Tyr Gln Cys Ser Val Tyr Pro Leu
                100                 105                 110
Gly Leu Lys Trp Asp Asp Glu Lys Trp Thr Ala Trp Phe Tyr Glu Lys
            115                 120                 125
```

```
Gly Leu Trp Cys Leu Lys Lys Ser Phe Lys Thr Trp Leu Thr Asp Ser
            130                 135                 140

Lys Lys Gly Tyr Asn Thr Tyr Met Lys Asn Leu Leu Gln Glu Phe Gly
145                 150                 155                 160

Lys Gln Phe Tyr Glu Asp Trp Cys Arg Arg Pro Glu Lys Arg Arg Glu
                165                 170                 175

Asp Lys Ile Cys Lys Arg Trp Gly Gln Lys Gly Leu Arg Asn Asp Asn
            180                 185                 190

Tyr Tyr Ser Leu Lys Trp Met Gln Trp Arg Asn Trp Lys Asn Arg Asn
            195                 200                 205

His Asp Gln Lys His Val Trp Val Thr Leu Met Lys Asp Ala Leu Lys
            210                 215                 220

Glu Tyr Thr Gly Pro Glu Phe Lys Leu Trp Thr Glu Phe Arg Lys Glu
225                 230                 235                 240

Lys Ile Asp Phe Tyr Lys Gln Trp Met Gln Ala Phe Ala Glu Gln Trp
                245                 250                 255

Thr Gln Asp Lys Gln Trp Asn Thr Trp Thr Glu Arg Asn Glu Tyr
                260                 265                 270

Met Lys Lys Lys Glu Glu Ala Lys Lys Ala Ala Ser Lys
            275                 280                 285

Lys Lys Ala Ala Ser Lys Gly Gly Ala Ala Lys Lys Ala Pro Ala
            290                 295                 300

Lys Lys Ala Pro Thr Lys Lys Ala Ala Pro Gly Thr Lys Ala Pro Ala
305                 310                 315                 320

Lys Lys Ala Ala Pro Lys Lys Val Ala Ala Pro Asn Ala Ala
                325                 330
```

<210> SEQ ID NO 117
<211> LENGTH: 269
<212> TYPE: PRT
<213> ORGANISM: Plasmodium vivax

<400> SEQUENCE: 117

```
Lys Glu Ala Val Lys Lys Gly Ser Lys Lys Ala Met Lys Gln Pro Met
1               5                   10                  15

His Lys Pro Asn Leu Leu Glu Glu Asp Phe Glu Glu Lys Glu Ser
                20                  25                  30

Phe Ser Asp Asp Glu Met Asn Gly Phe Met Glu Ser Met Asp Ala
                35                  40                  45

Ser Lys Leu Asp Ala Lys Lys Ala Lys Thr Thr Leu Arg Ser Ser Glu
50                  55                  60

Lys Lys Lys Thr Pro Thr Ser Gly Met Ser Gly Met Ser Gly Ser Gly
65                  70                  75                  80

Ala Thr Ser Ala Ala Thr Glu Ala Ala Thr Asn Met Asn Ala Thr Ala
                85                  90                  95

Met Asn Ala Ala Ala Lys Gly Asn Ser Glu Ala Ser Lys Lys Gln Thr
                100                 105                 110

Asp Leu Ser Asn Glu Asp Leu Phe Asn Asp Glu Leu Thr Glu Glu Val
                115                 120                 125

Ile Ala Asp Ser Tyr Glu Glu Gly Gly Asn Val Gly Ser Glu Glu Ala
            130                 135                 140

Glu Ser Leu Thr Asn Ala Phe Asp Asp Lys Leu Leu Asp Gln Gly Val
145                 150                 155                 160

Asn Glu Asn Thr Leu Leu Asn Asp Asn Met Ile Tyr Asn Val Asn Met
```

```
                        165                 170                 175
Val Pro His Lys Lys Arg Glu Leu Tyr Ile Ser Pro His Lys His Thr
                180                 185                 190

Ser Ala Ala Ser Ser Lys Asn Gly Lys His Ala Ala Asp Ala Asp
            195                 200                 205

Ala Leu Asp Lys Lys Leu Arg Ala His Glu Leu Glu Leu Glu Asn
        210                 215                 220

Gly Glu Gly Ser Asn Ser Val Ile Val Glu Thr Glu Val Asp Val
225                 230                 235                 240

Asp Leu Asn Gly Gly Lys Ser Ser Gly Ser Val Ser Phe Leu Ser Ser
                245                 250                 255

Val Val Phe Leu Leu Ile Gly Leu Leu Cys Phe Thr Asn
            260                 265
```

<210> SEQ ID NO 118
<211> LENGTH: 771
<212> TYPE: PRT
<213> ORGANISM: Plasmodium vivax

<400> SEQUENCE: 118

```
Asn Leu Ser Asn Asp Cys Lys Lys Gly Ala Asn Asn Ser Phe Lys Leu
1               5                   10                  15

Ile Val His Thr Ser Asp Asp Ile Leu Thr Leu Lys Trp Lys Val Thr
                20                  25                  30

Gly Glu Gly Ala Ala Pro Gly Asn Lys Ala Asp Val Lys Lys Tyr Lys
            35                  40                  45

Leu Pro Thr Leu Glu Arg Pro Phe Thr Ser Val Gln Val His Ser Ala
    50                  55                  60

Asn Ala Lys Ser Lys Ile Ile Glu Ser Lys Phe Tyr Asp Ile Gly Ser
65                  70                  75                  80

Gly Met Pro Ala Gln Cys Ser Ala Ile Ala Thr Asn Cys Phe Leu Ser
                85                  90                  95

Gly Ser Leu Glu Ile Glu His Cys Tyr His Cys Thr Leu Leu Glu Lys
            100                 105                 110

Lys Leu Ala Gln Asp Ser Glu Cys Phe Lys Tyr Val Ser Ser Glu Ala
        115                 120                 125

Lys Glu Leu Ile Glu Lys Asp Thr Pro Ile Lys Ala Gln Glu Glu Asp
    130                 135                 140

Ala Asn Ser Ala Asp His Lys Leu Ile Glu Ser Ile Asp Val Ile Leu
145                 150                 155                 160

Lys Ala Val Tyr Lys Ser Asp Lys Asp Glu Lys Lys Glu Leu Ile
                165                 170                 175

Thr Pro Glu Glu Val Asp Glu Asn Leu Lys Lys Glu Leu Ala Asn Tyr
            180                 185                 190

Cys Thr Leu Leu Lys Glu Val Asp Thr Ser Gly Thr Leu Asn Asn His
        195                 200                 205

Gln Met Ala Asn Glu Glu Thr Phe Arg Asn Leu Thr Arg Leu Leu
    210                 215                 220

Arg Met His Ser Glu Glu Asn Val Val Thr Leu Gln Asp Lys Leu Arg
225                 230                 235                 240

Asn Ala Ala Ile Cys Ile Lys His Ile Asp Lys Trp Ile Leu Asn Lys
                245                 250                 255

Arg Gly Leu Thr Leu Pro Glu Glu Gly Tyr Pro Ser Glu Gly Tyr Pro
            260                 265                 270
```

-continued

```
Pro Glu Glu Tyr Pro Pro Glu Glu Leu Leu Lys Glu Ile Glu Lys Glu
            275                 280                 285

Lys Ser Ala Leu Asn Asp Glu Ala Phe Ala Lys Asp Thr Asn Gly Val
        290                 295                 300

Ile His Leu Asp Lys Pro Pro Asn Glu Met Lys Phe Lys Ser Pro Tyr
305                 310                 315                 320

Phe Lys Lys Ser Lys Tyr Cys Asn Asn Glu Tyr Cys Asp Arg Trp Lys
                325                 330                 335

Asp Lys Thr Ser Cys Met Ser Asn Ile Glu Val Glu Glu Gln Gly Asp
            340                 345                 350

Cys Gly Leu Cys Trp Ile Phe Ala Ser Lys Leu His Leu Glu Thr Ile
        355                 360                 365

Arg Cys Met Arg Gly Tyr Gly His Phe Arg Ser Ser Ala Leu Phe Val
    370                 375                 380

Ala Asn Cys Ser Lys Arg Lys Pro Glu Asp Arg Cys Asn Val Gly Ser
385                 390                 395                 400

Asn Pro Thr Glu Phe Leu Gln Ile Val Lys Asp Thr Gly Phe Leu Pro
                405                 410                 415

Leu Glu Ser Asp Leu Pro Tyr Ser Tyr Ser Asp Ala Gly Asn Ser Cys
            420                 425                 430

Pro Asn Lys Arg Asn Lys Trp Thr Asn Leu Trp Gly Asp Thr Lys Leu
        435                 440                 445

Leu Tyr His Lys Arg Pro Asn Gln Phe Ala Gln Thr Leu Gly Tyr Val
    450                 455                 460

Ser Tyr Glu Ser Ser Arg Phe Glu His Ser Ile Asp Leu Phe Ile Asp
465                 470                 475                 480

Ile Leu Lys Arg Glu Ile Gln Asn Lys Gly Ser Val Ile Ile Tyr Ile
                485                 490                 495

Lys Thr Asn Asn Val Ile Asp Tyr Asp Phe Asn Gly Arg Val Val His
            500                 505                 510

Ser Leu Cys Gly His Lys Asp Ala Asp His Ala Ala Asn Leu Ile Gly
        515                 520                 525

Tyr Gly Asn Tyr Ile Ser Ala Gly Gly Glu Lys Arg Ser Tyr Trp Ile
    530                 535                 540

Val Arg Asn Ser Trp Gly Tyr Tyr Trp Gly Asp Glu Gly Asn Phe Lys
545                 550                 555                 560

Val Asp Met Tyr Gly Pro Glu Gly Cys Lys Arg Asn Phe Ile His Thr
                565                 570                 575

Ala Val Val Phe Lys Ile Asp Leu Gly Ile Val Glu Val Pro Lys Lys
            580                 585                 590

Asp Glu Gly Ser Ile Tyr Ser Tyr Phe Val Gln Tyr Val Pro Asn Phe
        595                 600                 605

Leu His Ser Leu Phe Tyr Val Ser Tyr Gly Lys Gly Ala Asp Lys Gly
    610                 615                 620

Ala Ala Val Val Thr Gly Gln Ala Gly Gly Ala Val Thr Gly Gln
625                 630                 635                 640

Thr Glu Thr Pro Thr Pro Glu Ala Ala Lys Asn Gly Asp Gln Pro Gly
                645                 650                 655

Ala Gln Gly Ser Glu Ala Glu Val Ala Glu Gly Gly Gln Ala Gly Asn
            660                 665                 670

Glu Ala Pro Gly Gly Leu Gln Glu Ser Ala Val Ser Ser Gln Thr Ser
        675                 680                 685

Glu Val Thr Pro Gln Ser Ser Ile Thr Ala Pro Gln Ile Gly Ala Val
```

```
                    690                 695                 700

Ala Pro Gln Ile Gly Ala Ala Pro Gln Ile Asp Val Ala Ala Pro
705                 710                 715                 720

Gln Ile Asp Val Val Ala Pro Gln Thr Arg Ser Val Asp Ala Pro Gln
                    725                 730                 735

Thr Ser Ser Val Ala Ala His Pro Pro Asn Val Thr Pro Gln Asn Val
                    740                 745                 750

Thr Leu Gly Glu Gly Gln His Ala Gly Gly Val Gly Ser Leu Ile Pro
                755                 760                 765

Ala Asp Asn
    770

<210> SEQ ID NO 119
<211> LENGTH: 219
<212> TYPE: PRT
<213> ORGANISM: Plasmodium vivax

<400> SEQUENCE: 119

Glu Thr Leu Leu Asp Ser Glu Thr Leu Lys Asn Tyr Glu Lys Glu Thr
1               5                   10                  15

Asn Glu Tyr Ile Arg Lys Lys Val Glu Lys Leu Phe Asp Val Ile
                20                  25                  30

Leu Lys Asn Val Leu Val Asn Lys Pro Glu Asn Val Tyr Leu Tyr Ile
            35                  40                  45

Tyr Lys Asn Ile Tyr Ser Phe Leu Leu Asn Lys Ile Phe Val Ile Gly
        50                  55                  60

Pro Pro Leu Leu Lys Ile Thr Pro Thr Leu Cys Ser Ala Ile Ala Ser
65                  70                  75                  80

Cys Phe Ser Tyr Tyr His Leu Ser Ala Ser His Met Ile Glu Ser Tyr
                85                  90                  95

Thr Thr Gly Glu Val Asp Asp Ala Ala Glu Ser Ser Thr Ser Lys Lys
                100                 105                 110

Leu Val Ser Asp Asp Leu Ile Cys Ser Ile Val Lys Ser Asn Ile Asn
            115                 120                 125

Gln Leu Asn Ala Lys Gln Lys Arg Gly Tyr Val Val Glu Gly Phe Pro
        130                 135                 140

Gly Thr Asn Leu Gln Ala Asp Ser Cys Leu Arg His Leu Pro Ser Tyr
145                 150                 155                 160

Val Phe Val Leu Tyr Ala Asp Glu Glu Tyr Ile Tyr Asp Lys Tyr Glu
                165                 170                 175

Gln Glu Asn Asn Val Lys Ile Arg Ser Asp Met Asn Ser Gln Thr Phe
            180                 185                 190

Asp Glu Asn Thr Gln Leu Phe Glu Val Ala Glu Phe Asn Thr Asn Pro
        195                 200                 205

Leu Lys Asp Glu Val Lys Val Tyr Leu Arg Asn
    210                 215

<210> SEQ ID NO 120
<211> LENGTH: 113
<212> TYPE: PRT
<213> ORGANISM: Plasmodium vivax

<400> SEQUENCE: 120

Tyr Pro Lys Lys Asn Phe Asp Lys Pro Asp Pro Thr Ser Pro Tyr Gln
1               5                   10                  15

Gly Gln Tyr Gly Glu Ser Glu Glu Gln Arg Gln Gly Tyr Gly Ile Pro
```

```
                20                  25                  30
Pro Asn Pro Thr Met Ile Asn Leu Thr Gly Asn Gln Asp Gln Arg Pro
            35                  40                  45

Asn Val Leu Gln Gln Phe Gly Ile Asn Asn Lys Asn Val Met Gln Phe
 50                  55                  60

Leu Ile Asn Met Phe Val Tyr Val Ala Ala Ile Leu Val Ser Leu Lys
 65                  70                  75                  80

Ile Trp Asp Tyr Met Ser Tyr Ser Lys Cys Asp Tyr Tyr Lys Asp Leu
                85                  90                  95

Leu Leu Arg Ile Val Arg Tyr Gln Ser His Met Asn Asp Gly Lys Met
            100                 105                 110

Ala

<210> SEQ ID NO 121
<211> LENGTH: 666
<212> TYPE: PRT
<213> ORGANISM: Plasmodium vivax

<400> SEQUENCE: 121

Ser Arg Ile Asp Lys Gln Pro Ile Gln Ser Ser Tyr Leu Phe Gln Asp
  1               5                  10                  15

Asn Ala Val Pro Pro Val Arg Phe Ser Ala Val Asp Ala Asp Leu Phe
                 20                  25                  30

Ser Ile Gly Val Val His Thr Glu Glu Gln Ile Phe Met Asp Asp Ala
             35                  40                  45

Asn Trp Val Ile Ser Ser Val Pro Ser Lys Tyr Leu Asn Leu His Leu
 50                  55                  60

Leu Lys Thr Gly Ser Arg Pro His Phe Ser His Phe Ser Val Ser Met
 65                  70                  75                  80

Asn Thr Gly Cys Asn Leu Phe Ile Ala Ser Pro Val Gly Glu Thr Phe
                85                  90                  95

Pro Leu Ser Pro Ser Lys Asp Gly Ala Thr Trp Lys Ala Phe Glu Thr
            100                 105                 110

Asp Asp Ser Val Glu Val Ile His Arg Glu Thr Lys Glu Lys Arg Ile
        115                 120                 125

Tyr Lys Leu Lys Phe Ile Pro Leu Lys Ser Gly Ala Leu Leu Lys Val
130                 135                 140

Asp Val Leu Lys Gly Ile Pro Phe Trp Val Ile Ser Gln Gly Arg Lys
145                 150                 155                 160

Ile Leu Pro Thr Ile Cys Ser Gly Asp Glu Glu Val Leu Ser Asn Pro
                165                 170                 175

Gln Asn Glu Val Phe Lys Glu Cys Thr Ser Ser Ser Leu Ser Pro
            180                 185                 190

Glu Phe Asp Cys Leu Ala Gly Leu Ser Thr Tyr His Arg Asp Lys Lys
        195                 200                 205

Asn His Thr Trp Lys Thr Ser Gly Ser Ile Gly Gln Phe Ile Lys
    210                 215                 220

Ile Phe Phe Asn Lys Pro Val Gln Ile Thr Lys Phe Arg Phe Lys Pro
225                 230                 235                 240

Arg Asp Asp Leu Leu Ser Trp Pro Ser Glu Val Ala Leu Gln Phe Asp
                245                 250                 255

Thr Asp Glu Glu Val Ile Ile Pro Ile Leu His Thr His Asn Met Gly
            260                 265                 270

Gln Asn Thr Thr Arg Leu Glu His Pro Ile Ile Thr Thr Ser Val Lys
```

```
            275                 280                 285
Val Glu Val Arg Asp Met Tyr Glu Arg Ala Ser Glu Asn Thr Gly Gly
290                 295                 300

Ser Phe Glu Val Ile Gly Ser Thr Cys Gln Met Met Glu Asp Asp Tyr
305                 310                 315                 320

Met Thr His His Ala Val Ile Asp Ile Thr Glu Cys Asp Arg Arg Leu
                325                 330                 335

Glu Ser Leu Pro Asp Val Met Pro Leu Thr Lys Gly Ser Lys Phe Leu
            340                 345                 350

Ala Ile Cys Pro Arg Pro Cys Leu Ser Ser Asn Gly Gly Val Ile
                355                 360                 365

Tyr Gly Ser Asp Val Tyr Ser Thr Asp Ser Ala Val Cys Gly Ala Ala
            370                 375                 380

Val His Ala Gly Val Cys Ser Arg Glu Gly Gly Ser Cys His Phe
385                 390                 395                 400

Leu Val Val Val Arg Gly Gly Arg Ala Asn Phe Val Gly Ala Leu Gln
                405                 410                 415

Asn Asn Val Leu Ser Leu Ser Arg Gly Gly Gly Ser Gly Ser Gly
            420                 425                 430

Ser Ser Thr Ser Ser Asp Gly Asp Gly Asp Ser Asp Ser Ser Thr Ser
                435                 440                 445

Arg Ala Asn Phe Ser Phe Ser Leu Ser Ser Ala Ser Gly Phe Gly Gly
450                 455                 460

Gly Pro Arg Gly Ala His Ala Glu Ala Ala Pro Ser Ser Tyr Ser Ile
465                 470                 475                 480

Val Phe Lys Pro Arg Asp His Leu Ala Pro Thr Asn Gly Phe Leu Val
                485                 490                 495

Asp Ser Gly Arg Glu Phe Thr Ser Tyr Gly Ser Val Ala Tyr Gly Trp
            500                 505                 510

Lys Arg Glu Val Ser Pro Ser Ser Phe Ser Ser Pro Ser Pro Ser
                515                 520                 525

Tyr Thr Ser Pro Pro Leu Glu Glu Pro Thr Leu Leu Arg Gly Asp Ser
            530                 535                 540

Ser Ser Phe Asn Gly Ile Tyr Ser Gly Gly Ile Glu Phe Pro Pro Ala
545                 550                 555                 560

Ser Ala Ser Gln Asn Cys Ile Ser Gln Leu Asp Cys Gln Thr Asn Phe
                565                 570                 575

Trp Lys Phe Gln Met Gln Glu Asn Gly Thr Tyr Phe Val Gln Val Leu
            580                 585                 590

Val Gly Asn Lys Thr Ser Pro Glu Lys Gln Lys Ala Phe Val Glu Leu
            595                 600                 605

Asn Gly Val Pro Ile Ile Lys Gly Val Asp Leu Gly Pro Asp Glu Val
            610                 615                 620

Phe Val Ala Thr Asp Arg Val Gln Val Thr Asn Arg Ala Leu Val Leu
625                 630                 635                 640

Thr Ser Thr Cys Leu Gly Gly Glu Ser Ala Cys Ser Arg Ala Arg Val
                645                 650                 655

Ser Ile Met Ala Val Gln Ile Val Lys Thr
            660                 665

<210> SEQ ID NO 122
<211> LENGTH: 582
<212> TYPE: PRT
<213> ORGANISM: Plasmodium vivax
```

<400> SEQUENCE: 122

```
Asn Gly Met Asn Lys Asp Lys Asp Ala Glu Ile Thr Pro Pro Phe
1               5                   10                  15

Ile Val Leu Pro Gly Lys Lys Ile His Met Leu Gln Ser Glu Tyr
                20                  25                  30

Glu Tyr Asp Val Leu Arg Asp Met Tyr Arg Thr Asp Glu Ala Asn Gly
            35                  40                  45

Gly Ser Gly Glu Lys Glu Ser His Pro Ser Gly Asp Gly Ala Ile Arg
    50                  55                  60

Arg Asn Glu Phe Phe Lys Leu Phe His His Arg Glu Gly His Tyr Lys
65                  70                  75                  80

Phe Val Ile Lys Asn Val Pro Thr Lys Leu Ser Asp Leu Leu Gln Lys
                85                  90                  95

Gly Gly Asn Glu Gln Glu Thr Asp Leu Phe Pro Leu Leu Tyr Arg Ser
                100                 105                 110

Leu Gln Phe Ala Cys Ser Ala Asp Gly Thr Trp Pro Tyr Ala Arg Arg
            115                 120                 125

Glu Val Ala Phe Phe Lys Asn Gly Ser Val His Cys Glu Ala Glu Phe
            130                 135                 140

Gln Asn Glu Leu Ser Val Arg Arg Thr Pro Arg Ser Gly Lys Lys Ser
145                 150                 155                 160

Phe Gly Arg Phe Pro Arg Gly Thr Leu Ile Lys Ser Ser Asp Leu Arg
                165                 170                 175

Ser Lys Ile Val Glu Gly Asn Ser Tyr Asp Lys Arg Ala Ala Pro Leu
                180                 185                 190

Lys Ser Glu Lys Lys Lys Lys Ala Leu Phe Leu His Pro Glu Ser Val
            195                 200                 205

Leu Tyr Lys Met Glu Glu Ile Phe Phe Tyr Glu Asn Pro Ser Val Lys
            210                 215                 220

Ser Glu Ile Val Gly Phe Val Leu Phe His Asp Val Cys Thr Val Thr
225                 230                 235                 240

Ser Leu Gly His Gly Ala His Pro Val Asn Ser Pro Phe Leu Gly Ser
                245                 250                 255

Asp Leu Leu Glu Met Ile Phe Gly Tyr Cys Ile Leu His Gly Phe Lys
                260                 265                 270

Lys Ile Arg Val Lys Ser Glu Ser Leu Asn Tyr Glu Thr Gly Ile Arg
                275                 280                 285

Thr Ser Phe Ile Glu Ile Leu Leu Asn Gly Lys Thr Ala Leu Glu His
            290                 295                 300

Leu Gly Leu Arg Leu Thr Asn Val Ala Lys Phe Ser Lys Glu Leu Tyr
305                 310                 315                 320

Tyr Val Ile Thr Gly Tyr Thr Trp Lys Ser Asp Leu Val Leu Ser Pro
                325                 330                 335

Ile Val Arg Phe Glu His Asp Leu Tyr Val His His Asp Ile Glu Glu
                340                 345                 350

Arg Phe Phe Leu Tyr Val Asn Lys Met Tyr Arg Asn Met Leu His Asp
            355                 360                 365

Leu Ser Phe Ser Cys Asp Glu Asn Tyr Tyr Pro Tyr Lys Asn Cys Tyr
            370                 375                 380

Asp Ile Tyr Pro Ser Val Arg Arg Ser Gln Asn Asn Leu Cys Leu Phe
385                 390                 395                 400

Glu Leu Asn Pro Ile Tyr Glu Glu Leu Lys Glu Leu Phe Pro Asp Ser
```

```
            405                 410                 415
Cys Asn Ile Gly Gln Arg Val Arg Lys Cys Tyr Glu Ile Lys Lys
            420                 425                 430

Asn Val Val Cys Thr His Asn Gly Glu Gly Gly Glu Asp Gly Cys Lys
            435                 440                 445

Tyr Tyr Gln Phe Ile Val Asn Thr Phe Ile Lys Pro Arg Arg Lys Thr
            450                 455                 460

Ser Phe Phe Ile Tyr His Asn Met Tyr Val Gln Glu Tyr Leu Ser Lys
465                 470                 475                 480

Lys Ser Tyr Pro Tyr Tyr Leu Leu Leu Ser Glu Val Ile Lys Asn Glu
            485                 490                 495

Glu Asn Asn Phe Leu Glu Lys Gly Asn Tyr Asp Leu Val Ala Asp Ala
            500                 505                 510

Gln Thr His Leu Phe Leu Asn Tyr Val Leu Gln Asn Ser Thr Phe Phe
            515                 520                 525

Ile Phe Trp Asn Phe Ser Thr Glu Phe Trp Lys Arg Phe Arg Tyr Ile
            530                 535                 540

Gln Ala Gly Pro Thr Gly Ala Thr Ser Thr Pro Gln Lys Gly Gln Ala
545                 550                 555                 560

Val Phe Cys Pro Met Ala Tyr Ala Tyr Glu Phe Val Glu His Leu Asp
            565                 570                 575

Thr Phe Tyr Val Arg Gly
            580

<210> SEQ ID NO 123
<211> LENGTH: 392
<212> TYPE: PRT
<213> ORGANISM: Plasmodium vivax

<400> SEQUENCE: 123

Ser Val Glu Glu Ala Lys Lys Asn Thr Gln Glu Val Val Thr Asn Val
1               5                   10                  15

Asp Asn Ala Ala Lys Ser Gln Ala Thr Asn Ser Asn Pro Ile Ser Gln
            20                  25                  30

Pro Val Asp Ser Ser Lys Ala Glu Lys Val Pro Gly Asp Ser Thr His
        35                  40                  45

Gly Asn Val Asn Ser Gly Gln Asp Ser Ser Thr Thr Gly Lys Ala Val
    50                  55                  60

Thr Gly Asp Gly Gln Asn Gly Asn Gln Thr Pro Ala Glu Ser Asp Val
65                  70                  75                  80

Gln Arg Ser Asp Ile Ala Glu Ser Val Ser Ala Lys Asn Val Asp Pro
            85                  90                  95

Gln Lys Ser Val Ser Lys Arg Ser Asp Asp Thr Ala Ser Val Thr Gly
            100                 105                 110

Ile Ala Glu Ala Gly Lys Glu Asn Leu Gly Ala Ser Asn Ser Arg Pro
        115                 120                 125

Ser Glu Ser Thr Val Glu Ala Asn Ser Pro Gly Asp Asp Thr Val Asn
    130                 135                 140

Ser Ala Ser Ile Pro Val Val Ser Gly Glu Asn Pro Leu Val Thr Pro
145                 150                 155                 160

Tyr Asn Gly Leu Arg His Ser Lys Asp Asn Ser Asp Ser Asp Gly Pro
            165                 170                 175

Ala Glu Ser Met Ala Asn Pro Asp Ser Asn Ser Lys Gly Glu Thr Gly
            180                 185                 190
```

Lys Gly Gln Asp Asn Asp Met Ala Lys Ala Thr Lys Asp Ser Ser Asn
            195                 200                 205

Ser Ser Asp Gly Thr Ser Ala Thr Gly Asp Thr Thr Asp Ala Val
210                 215                 220

Asp Arg Glu Ile Asn Lys Gly Val Pro Glu Asp Arg Asp Lys Thr Val
225                 230                 235                 240

Gly Ser Lys Asp Gly Gly Glu Asp Asn Ser Ala Asn Lys Asp Ala
            245                 250                 255

Ala Thr Val Val Gly Glu Asp Arg Ile Arg Glu Asn Ser Ala Gly Gly
            260                 265                 270

Ser Thr Asn Asp Arg Ser Lys Asn Asp Thr Glu Lys Asn Gly Ala Ser
            275                 280                 285

Thr Pro Asp Ser Lys Gln Ser Glu Asp Ala Thr Ala Leu Ser Lys Thr
            290                 295                 300

Glu Ser Leu Glu Ser Thr Glu Ser Gly Asp Arg Thr Thr Asn Asp Thr
305                 310                 315                 320

Thr Asn Ser Leu Glu Asn Lys Asn Gly Gly Lys Glu Lys Asp Leu Gln
                325                 330                 335

Lys His Asp Phe Lys Ser Asn Asp Thr Pro Asn Glu Glu Pro Asn Ser
            340                 345                 350

Asp Gln Thr Thr Asp Ala Glu Gly His Asp Arg Asp Ser Ile Lys Asn
            355                 360                 365

Asp Lys Ala Glu Arg Arg Lys His Met Asn Lys Asp Thr Phe Thr Lys
            370                 375                 380

Asn Thr Asn Ser His His Leu Asn
385                 390

<210> SEQ ID NO 124
<211> LENGTH: 530
<212> TYPE: PRT
<213> ORGANISM: Plasmodium vivax

<400> SEQUENCE: 124

Ile Arg Asn Gly Asn Asn Pro Gln Ala Leu Val Pro Glu Lys Gly Ala
1               5                   10                  15

Asp Pro Ser Gly Gly Gln Asn Asn Arg Ser Gly Glu Asn Gln Asp Thr
                20                  25                  30

Cys Glu Ile Gln Lys Met Ala Glu Glu Met Met Glu Lys Met Met Lys
            35                  40                  45

Glu Lys Asp Val Phe Ser Ser Ile Met Glu Pro Leu Gln Ser Lys Leu
        50                  55                  60

Thr Asp Asp His Leu Cys Ser Lys Met Lys Tyr Thr Asn Ile Cys Leu
65                  70                  75                  80

His Glu Lys Asp Lys Thr Pro Leu Thr Phe Pro Cys Thr Ser Pro Gln
                85                  90                  95

Tyr Glu Gln Leu Ile His Arg Phe Thr Tyr Lys Lys Leu Cys Asn Ser
            100                 105                 110

Lys Val Ala Phe Ser Asn Val Leu Leu Lys Ser Phe Ile Asp Lys Lys
        115                 120                 125

Asn Glu Glu Asn Thr Phe Asn Thr Ile Ile Gln Asn Tyr Lys Val Leu
    130                 135                 140

Ser Thr Cys Ile Asp Asp Leu Lys Asp Ile Tyr Asn Ala Ser Ile
145                 150                 155                 160

Glu Leu Phe Ser Asp Ile Arg Thr Ser Val Thr Glu Ile Thr Glu Lys
                165                 170                 175

```
Leu Trp Ser Lys Asn Met Ile Glu Val Leu Lys Thr Arg Glu Gln Thr
            180                 185                 190

Ile Ala Gly Ile Leu Cys Glu Leu Arg Asn Gly Asn Ser Pro Leu
        195                 200                 205

Val Ser Asn Ser Phe Ser Tyr Glu Asn Phe Gly Ile Leu Lys Val Asn
210                 215                 220

Tyr Glu Gly Leu Leu Asn Gln Ala Tyr Ala Ala Phe Ser Asp Tyr Tyr
225                 230                 235                 240

Ser Tyr Phe Pro Ala Phe Ala Ile Ser Met Leu Glu Lys Gly Gly Leu
                245                 250                 255

Val Asp Arg Leu Val Ala Ile His Glu Ser Leu Thr Asn Tyr Arg Thr
            260                 265                 270

Arg Asn Ile Leu Lys Lys Ile Asn Glu Lys Ser Lys Asn Glu Val Leu
        275                 280                 285

Asn Asn Glu Glu Ile Met His Ser Leu Ser Ser Tyr Lys His His Ala
    290                 295                 300

Gly Gly Thr Arg Gly Ala Phe Leu Gln Ser Arg Asp Val Arg Glu Val
305                 310                 315                 320

Thr Gln Gly Asp Val Ser Val Asp Glu Lys Gly Asp Arg Ala Thr Thr
                325                 330                 335

Ala Gly Gly Asn Gln Ser Ala Ser Val Ala Ala Ala Pro Lys Asp
            340                 345                 350

Ala Gly Pro Thr Val Ala Ala Pro Asn Thr Ala Thr Leu Lys Thr
        355                 360                 365

Ala Ala Ser Pro Asn Ala Ala Thr Asn Thr Ala Ala Pro Pro Asn
    370                 375                 380

Met Gly Ala Thr Ser Pro Leu Ser Asn Pro Leu Tyr Gly Thr Ser Ser
385                 390                 395                 400

Leu Gln Pro Lys Asp Val Ala Val Leu Val Arg Asp Leu Leu Lys Asn
                405                 410                 415

Thr Asn Ile Ile Lys Phe Glu Asn Asn Glu Pro Thr Ser Gln Met Asp
            420                 425                 430

Asp Glu Glu Ile Lys Lys Leu Ile Glu Ser Ser Phe Phe Asp Leu Ser
        435                 440                 445

Asp Asn Thr Met Leu Met Arg Leu Leu Ile Lys Pro Gln Ala Ala Ile
    450                 455                 460

Leu Leu Ile Ile Glu Ser Phe Ile Met Met Thr Pro Ser Pro Thr Arg
465                 470                 475                 480

Asp Ala Lys Thr Tyr Cys Lys Lys Ala Leu Val Asn Gly Gln Leu Ile
                485                 490                 495

Glu Thr Ser Asp Leu Asn Ala Ala Thr Glu Glu Asp Asp Leu Ile Asn
            500                 505                 510

Glu Phe Ser Ser Arg Tyr Asn Leu Phe Tyr Glu Arg Leu Lys Leu Glu
        515                 520                 525

Glu Leu
    530

<210> SEQ ID NO 125
<211> LENGTH: 524
<212> TYPE: PRT
<213> ORGANISM: Plasmodium vivax

<400> SEQUENCE: 125

Lys Glu Tyr Cys Asp Gln Leu Ser Phe Cys Asp Val Gly Leu Thr His
```

-continued

```
1               5                   10                  15
His Phe Asp Thr Tyr Cys Lys Asn Asp Gln Tyr Leu Phe Val His Tyr
                20                  25                  30

Thr Cys Glu Asp Leu Cys Lys Thr Cys Gly Pro Asn Ser Ser Cys Tyr
                35                  40                  45

Gly Asn Lys Tyr Lys His Lys Cys Leu Cys Asn Ser Pro Phe Glu Ser
            50                  55                  60

Lys Lys Asn His Ser Ile Cys Glu Ala Arg Gly Ser Cys Asp Ala Gln
65                  70                  75                  80

Val Cys Gly Lys Asn Gln Ile Cys Lys Met Val Asp Ala Lys Ala Thr
                85                  90                  95

Cys Thr Cys Ala Asp Lys Tyr Gln Asn Val Asn Gly Val Cys Leu Pro
                100                 105                 110

Glu Asp Lys Cys Asp Leu Leu Cys Pro Ser Asn Lys Ser Cys Leu Leu
                115                 120                 125

Glu Asn Gly Lys Lys Ile Cys Lys Cys Ile Asn Gly Leu Thr Leu Gln
                130                 135                 140

Asn Gly Glu Cys Val Cys Ser Asp Ser Ser Gln Ile Glu Glu Gly His
145                 150                 155                 160

Leu Cys Val Pro Lys Asn Lys Cys Lys Arg Lys Glu Tyr Gln Gln Leu
                165                 170                 175

Cys Thr Asn Glu Lys Glu His Cys Val Tyr Asp Glu Gln Thr Asp Ile
                180                 185                 190

Val Arg Cys Asp Cys Val Asp His Phe Lys Arg Asn Glu Arg Gly Ile
                195                 200                 205

Cys Ile Pro Val Asp Tyr Cys Lys Asn Val Thr Cys Lys Glu Asn Glu
                210                 215                 220

Ile Cys Lys Val Val Asn Asn Thr Pro Thr Cys Glu Cys Lys Glu Asn
225                 230                 235                 240

Leu Lys Arg Asn Ser Asn Asn Glu Cys Val Phe Asn Asn Met Cys Leu
                245                 250                 255

Val Asn Lys Gly Asn Cys Pro Ile Asp Ser Glu Cys Ile Tyr His Glu
                260                 265                 270

Lys Lys Arg His Gln Cys Leu Cys His Lys Lys Gly Leu Val Ala Ile
                275                 280                 285

Asn Gly Lys Cys Val Met Gln Asp Met Cys Arg Ser Asp Gln Asn Lys
                290                 295                 300

Cys Ser Glu Asn Ser Ile Cys Val Asn Gln Val Asn Lys Glu Pro Leu
305                 310                 315                 320

Cys Ile Cys Leu Phe Asn Tyr Val Lys Ser Arg Ser Gly Asp Ser Pro
                325                 330                 335

Glu Gly Gly Gln Thr Cys Val Val Asp Asn Pro Cys Leu Ala His Asn
                340                 345                 350

Gly Gly Cys Ser Pro Asn Glu Val Cys Thr Phe Lys Asn Gly Lys Val
                355                 360                 365

Ser Cys Ala Cys Gly Glu Asn Tyr Arg Pro Arg Gly Lys Asp Ser Pro
                370                 375                 380

Thr Gly Gln Ala Val Lys Arg Gly Glu Ala Thr Lys Arg Gly Asp Ala
385                 390                 395                 400

Gly Gln Pro Gly Gln Ala His Ser Ala Asn Glu Asn Ala Cys Leu Pro
                405                 410                 415

Lys Thr Ser Glu Ala Asp Gln Thr Phe Thr Phe Gln Tyr Asn Asp Asp
                420                 425                 430
```

```
Ala Ala Ile Ile Leu Gly Ser Cys Gly Ile Ile Gln Phe Val Gln Lys
            435                 440                 445

Ser Asp Gln Val Ile Trp Lys Ile Asn Ser Asn Asn His Phe Tyr Ile
450                 455                 460

Phe Asn Tyr Asp Tyr Pro Ser Glu Gly Gln Leu Ser Ala Gln Val Val
465                 470                 475                 480

Asn Lys Gln Glu Ser Ser Ile Leu Tyr Leu Lys Lys Thr His Ala Gly
            485                 490                 495

Lys Val Phe Tyr Ala Asp Phe Glu Leu Gly His Gln Gly Cys Ser Tyr
            500                 505                 510

Gly Asn Met Phe Leu Tyr Ala His Arg Glu Glu Ala
            515                 520

<210> SEQ ID NO 126
<211> LENGTH: 340
<212> TYPE: PRT
<213> ORGANISM: Plasmodium vivax

<400> SEQUENCE: 126

Ser Lys Asn Ile Ile Ile Leu Asn Asp Glu Ile Thr Thr Ile Lys Ser
1               5                   10                  15

Pro Ile His Cys Ile Thr Asp Ile Tyr Phe Leu Phe Arg Asn Glu Leu
                20                  25                  30

Tyr Lys Thr Cys Ile Gln His Val Ile Lys Gly Arg Thr Glu Ile His
            35                  40                  45

Val Leu Val Gln Lys Lys Ile Asn Ser Ala Trp Glu Thr Gln Thr Thr
50                  55                  60

Leu Phe Lys Asp His Met Trp Phe Glu Leu Pro Ser Val Phe Asn Phe
65                  70                  75                  80

Ile His Asn Asp Glu Ile Ile Val Ile Cys Arg Tyr Lys Gln Arg
                85                  90                  95

Ser Lys Arg Glu Gly Thr Ile Cys Lys Arg Trp Asn Ser Val Thr Gly
            100                 105                 110

Thr Ile Tyr Gln Lys Glu Asp Val Gln Ile Asp Lys Glu Ala Phe Ala
            115                 120                 125

Asn Lys Asn Leu Glu Ser Tyr Gln Ser Val Pro Leu Thr Val Lys Asn
130                 135                 140

Lys Lys Phe Leu Leu Ile Cys Gly Ile Leu Ser Tyr Glu Tyr Lys Thr
145                 150                 155                 160

Ala Asn Lys Asp Asn Phe Ile Ser Cys Val Ala Ser Glu Asp Lys Gly
                165                 170                 175

Arg Thr Trp Gly Thr Lys Ile Leu Ile Asn Tyr Glu Glu Leu Gln Lys
            180                 185                 190

Gly Val Pro Tyr Phe Tyr Leu Arg Pro Ile Ile Phe Gly Asp Glu Phe
            195                 200                 205

Gly Phe Tyr Phe Tyr Ser Arg Ile Ser Thr Asn Thr Ala Arg Gly
            210                 215                 220

Gly Asn Tyr Met Thr Cys Thr Leu Asp Val Thr Asn Glu Gly Lys Lys
225                 230                 235                 240

Glu Tyr Lys Phe Lys Cys Lys His Val Ser Leu Ile Lys Pro Asp Lys
                245                 250                 255

Ser Leu Gln Asn Val Ala Lys Leu Asn Gly Tyr Tyr Ile Thr Ser Tyr
            260                 265                 270

Val Lys Lys Asp Asn Phe Asn Glu Cys Tyr Leu Tyr Tyr Thr Glu Gln
```

|     |     |     |     | 275 |     |     |     | 280 |     |     |     | 285 |     |     |
| --- | --- | --- | --- | --- | --- | --- | --- | --- | --- | --- | --- | --- | --- | --- |
| Asn | Ala | Ile | Val | Val | Lys | Pro | Lys | Val | Gln | Asn | Asp | Asp | Leu | Asn | Gly |
|     |     |     | 290 |     |     |     |     | 295 |     |     |     |     | 300 |     |     |

| Cys | Tyr | Gly | Gly | Ser | Phe | Val | Lys | Leu | Asp | Glu | Ser | Lys | Ala | Leu | Phe |
| --- | --- | --- | --- | --- | --- | --- | --- | --- | --- | --- | --- | --- | --- | --- | --- |
| 305 |     |     |     |     | 310 |     |     |     |     | 315 |     |     |     |     | 320 |

| Ile | Tyr | Ser | Thr | Gly | Tyr | Gly | Val | Gln | Asn | Ile | His | Thr | Leu | Tyr | Tyr |
| --- | --- | --- | --- | --- | --- | --- | --- | --- | --- | --- | --- | --- | --- | --- | --- |
|     |     |     |     | 325 |     |     |     |     | 330 |     |     |     |     | 335 |     |

Thr Arg Tyr Asp
          340

<210> SEQ ID NO 127
<211> LENGTH: 1842
<212> TYPE: DNA
<213> ORGANISM: Plasmodium vivax

<400> SEQUENCE: 127

```
gagaaccccg tgaggcactc ggtggacata aagtcggaag acttcgtcgt cctgatttcg      60
ctccaaaacc tgcagacctt catcatgata gggtacacac ccgtgaacaa agaccacctg     120
aatttcgact tctcctactt atgggccctc tgcatcggga cgggcctctt catatactcc     180
ctcatcagct ttgtactcat aagatcccta gcactgtcaa aaatagacat aggcaaatac     240
gtcctggagc tgctattcag tttgagtata atcgccacat gttcactctc cataataatt     300
gactctttca aaatagccaa catgcagttg cttttttttt cgttcgcttt aacgggctat     360
gcctactaca atttgatgag cctcttcttt ttctgcacac tggtaggaat gaccattcag     420
tacaattta gttcactgg gttcagagcg cattcgactt cttcttctt tttagatatg     480
ctatcttacc tagtgcaaat gataggaggg aacatcctct actttcgcat gtacgagctg     540
tgtacccta tcgtcatttc gaagaggaac ccctgcaagt atgttgtcgc atcgaaggaa     600
gtgaaacaag tggagaagca aattttctct tctttattta attcttacat gtgcatcaag     660
tccaaaactt attcagattt aacctgcact aatgatctgt taaataaga cagtcaatct     720
gttgtcggta gggatacgaa ccctaagtgg aactcccca ttggtacttc ctaccaggat     780
aaggtcaatc atacgaagaa gttactcctt cggaggggaa acgggacaa acgctacccc     840
aaaggggag ggggagctcg actaacatgt gcaaaacata gtgcctacca taatagccga     900
agtcttgcca actgtgccag taagaatacc cccatttgca caactaactt taggatatct     960
aacacccttt cacttaaaaa tcatttcaac cctaacctaa ccttagaagc gtctccccc    1020
gtttgtaaaa aatgcgtttc ggaaaagaat agccataagg ataatgagta caaaaacggg    1080
gaagagagaa aaaaagcaaa acgtggtatc aagtcgggca ctgcaaacaa gtctaaccag    1140
ttgggcaacc acgggggga cgctacgcag gtggctaatc ctacctacag aactacttcc    1200
cacgggggg acgcaaccca ggtggcttat cctacctaca gaactacttc ccacgggggg    1260
gacgcaacgc aggtggatag tcctacccac ccaactacct cccatggggg gaacaactcg    1320
tcgagcgggc accccaaga cgacgaagtg ctcatcccca ttagggggaac caacgccact    1380
aacgatgcag ccgccaccta caactcgaac gctagttgga tcaaaaccgc tgcggttatt    1440
gacgtgtctg tggaggggaa gcagaaaaag ggggacatc aaacgttcgc gggcaatccc    1500
gtaaattcat ccgctaattt cccatcggac aagaaacctt cctacaactc gcaccgcaac    1560
ggaggtactc ccccccaaa tgaacaactc aggtactacg cctgcccctg ctaccagacc    1620
cactccagcg gatcgtccct cagtgaggtg ccctcgggac aaacgacgaa gcggaaaat    1680
agtgcgcaca actcggttga agggggaaac cccaaaatgg ataatcagca aagtcgccgc    1740
```

```
gtgagtaaca agcgggtaga tggcgcaacg ggtgaggaac atgaccaccc aagtgacccc 1800
cccgcagata acccaaatgg aaactccaac acctaccact gc 1842

<210> SEQ ID NO 128
<211> LENGTH: 1095
<212> TYPE: DNA
<213> ORGANISM: Plasmodium vivax
<400> SEQUENCE: 128
gagctgagcc acagcttgtc cgtgaagaac gcgccggacg cgagcgcgct gaacatcgag 60
gtggagaagg acaaaaagaa gatctgcaaa aacgcattcc aatacataaa cgtagctgag 120
ctgttgtccc caagggagga agaaacctac gtgcagaaat gtgaagaggt cctagacaca 180
ataaagaatg acagtccaga tgaatcggca gaagcagaga taaacgaatt tatactgagc 240
ttactgcacg ctcgttctaa gtataccata ataaatgact cagatgagga ggtactgagc 300
aagctcctga ggagtatcaa cggatcgata agtgaagagg cagcgttgaa gagagccaaa 360
cagctaatca cattcaatcg gtttataaaa gacaaagcga aggtaaaaaa tgtgcaagag 420
atgctagtaa taagtagcaa agcagatgac ttcatgaatg agccgaagca aaaaatgctc 480
caaaaaatta tagattcgtt tgaactgtat aatgattacc tagtcatttt agggtcaaat 540
attaacatcg ccaagaggta ctcctcagaa acgtttcttt ctattaaaaa tgaaaagttc 600
tgctcagacc acatccactt atgccagaag ttctacgagc agtctatcat ttactacaga 660
ttgaaggtta tttttgataa cctggtgact tatgtagatc aaaattccaa gcattttaaa 720
aaggaaaagt tgctggagct tctaaatatg gattataggg tcaatcgaga gtcgaaggtg 780
catgaaaatt acgtgctgga ggatgagacg gtcatcccca cgatgcgcat tacagacatt 840
tacgatcaag ataggctaat tgttgaggtc gttcaggatg gaaatagcaa gctgatgcac 900
ggcagggata ttgagaagag ggaaatcagc gagaggtaca tcgtcaccgt gaagaacctg 960
cgcaaggacc tcaacgacga ggggctctac gccgacttga tgaagaccgt caagaactac 1020
gtgctctcca tcacgcagat cgacaacgac atttccaacc tcgtgcgcga gctcgaccac 1080
gaggatgtgg agaag 1095

<210> SEQ ID NO 129
<211> LENGTH: 486
<212> TYPE: DNA
<213> ORGANISM: Plasmodium vivax
<400> SEQUENCE: 129
ctaccatgga cgaagaaaag aaaggcggtg aaccaaatgg gcatcataaa agatatgtcg 60
caggagctta ggactaaggc cgaacagctt ccaacccccg aggatatatc agccaaaatt 120
cacagagtag ataaagaggt catcgataag ttaaacaaag acatcataga ggaagaaaat 180
ttagacaagc acaaaccgca cgtctgccag gagccagcat acgagaggga ctattcgtac 240
ctatgtcccg aagactgggt gaagaactcc aacgatcagt gctggggcat agactacgat 300
ggtcactgtg aagcgctaaa atatttccaa gattattctg tagaggagaa aaaagaattt 360
gaaatgaact gctgcgtctt gtggcctaag ctaaaaaatg aaggcatgaa aggagcgcac 420
aagaaggacc tcctaagggg atcgataagt tcaaacaatg ggttaataat aaagccgaaa 480
tatttg 486

<210> SEQ ID NO 130

```
<211> LENGTH: 945
<212> TYPE: DNA
<213> ORGANISM: Plasmodium vivax

<400> SEQUENCE: 130
gaattgaaga agaacaatgc cgcgttgacc tcacaaaggt catcttctag aaccacatcc     60
acaaggagct acaaaaatgc cccaaaaaat tccacttcat tcctttctcg tttatctatt    120
ctgatatttg ccttatcatg tgctattttt gtaaatactg catcaggggc ggcagctaat    180
agaccaaacg cgaatggctt tgtgtcacct actttaatag gatttggcga attaagcatc    240
caagaatcag aagaattcaa aagaatggct tggaataatt ggatgttgcg attggagtcc    300
gactggaaac attttaacga ttctgttgaa gaagccaaaa ccaaatggct tcatgaaaga    360
gactcagctt ggtctgattg gcttcgttcc ttgcaaagta aatggtctca ctatagtgaa    420
aaaatgctta agaacacaa aagtaatgtt atggaaaaat cagccaactg gaatgacacg     480
caatggggaa attggataaa aactgaagga gaaaaattc tagaagcgca atgggaaaaa    540
tggattaaaa aaggtgatga ccaattacaa aagttaattt tagataaatg ggttcaatgg    600
aaaaatgata agatccgatc ctggttatcc agtgaatgga aaccgaaga agattactac      660
tgggcaaatg tagagcgcgc tacaacagca aaatggttgc aagaagcaga gaaaatgcat    720
tggcttaaat ggaaagaaag aattaacaga gagtctgaac aatgggtgaa ctgggtccaa    780
atgaaagaaa gcgtttacat caatgtagaa tggaaaaaat ggcccaaatg gaaaaatgat    840
aaaaaaattc tatttaacaa atggtcaact aaccttgtct acaaatggac actgaaaaag    900
cagtggaacg tttggattaa ggaagcaaat actgcacccc aagtt                    945

<210> SEQ ID NO 131
<211> LENGTH: 1587
<212> TYPE: DNA
<213> ORGANISM: Plasmodium vivax

<400> SEQUENCE: 131
aagggtgtca ccttgagttg cgttttttcc catgcgagtg aggaacgtga gggtggcaca     60
gggacatttg ctttgagcaa tgagccgatt tattacgccc ctagtggggg gctggcgccg    120
tgcgcgctca tcagcagagg gttaagcggg gatgaggagg gtagcggcga ggacggcggt    180
gaagatggcg acggagatgg tggtgaagac agcgctgagg acaacgctga ggatggagac    240
gatgatggtg gcgaagatgg cggcttgccc gggggacgct tcccatacga agaaggaaaa    300
aagagtagcc ttgtgagcga cgcacccagc gacctcctgg atggagatgc ggatgaacat    360
gccgccgaag atgggggagc gaagcgaaag atgagtaaga aggaggaaga ggcggaggat    420
aacaaaattg acaagttggt aaatgcggaa atgaaaaagc tcgaggcagg ggaagaggcg    480
aacaaggatc ccgacgcaga accagaaaaa gaggaccagg gaagtggcca aggacaaagg    540
gcgaagctga ggtgctcaaa caagctaaat tacatacagg tgacggcgaa tggccaaagg    600
gagggcgacc tctttggcga gaacgacggg gagagcgccc cagctttcgt ggagataccc    660
cacgaggttg aggaggaaag cggcggtgtg cccacaaagc atgacgaagc gggggaagca    720
gctgcggcgg aggaaccaca taaccgcgtc gaccgagcgg aaaaagaaaa caacgcgaag    780
gacttaaaat ttgtggaggg ggagcgagaa agacaaagga gcagccccc ctcgaatgga      840
tattcccaaa acagctttgt cgaactgaaa ggtgtgcccg ataaattgcc ccctaatttt    900
accaactcgc ttggtagctc cccaacgcac agtaatttgg agaaaccagt ttataagcac    960
ttaccctggt ctatcctggc atccgactct ggttcgaaca ccgggtcctg ggcagacgtc   1020
```

```
aacagtagta cctacaatgt gagtccattc agtttcacct caatacgtag tggtaactct   1080
ctgcatctac tgccgatgaa tttccaaatc caaaactcca tcgtgaaagt aactgatgag   1140
gagtatgaca aattgaagct taaaaacagc gtcaaagtgt atgacaaaaa tgccctggta   1200
gattataagt atgaaatttt tgaggtgaag gaaggggagg aatataatga tgggaatgac   1260
ccttatgagg aaaggaatgg ggaagaaggg gatgcaggtg gagagggggg ttccgatggg   1320
gagggagatg cagattctaa atcatatcaa aataacaaat cggatggacg tgggttcttc   1380
gatgggacct tagtaaccta caccattatc attttagctg gtgttataat tctgctgcta   1440
agttttgtca tttattacta cgatataata aataaggtga agaggcgaat gagtgccaag   1500
cggaagaaca acaaatctat ggccatcgcg aatgatacat ccgcggggat gtacatgggc   1560
gacacctaca tggagaatcc ccacgtt                                       1587
```

<210> SEQ ID NO 132
<211> LENGTH: 1002
<212> TYPE: DNA
<213> ORGANISM: Plasmodium vivax

<400> SEQUENCE: 132

```
tcacaaggat gttcaggata ccgtttacca ccaccaaaaa gatggtttac cttcacttct     60
cgaccatact gtaaaacagc tgcatattat gaacttaaac atatgccata ttatgtagat    120
gcagttagtg catcagaaaa cgtaaaacat gagaaatgga ataactggtt aaaagaaatg    180
aaaatatcat taactgaaaa attagaaaaa gaatcacaag aatatatgga aaaattggaa    240
cagcaatggg atgaatttat gaaaaattca gaagataaat ggaggcatta taatccccaa    300
atggaagaag aatatcaatg tagtgtttat ccacttggat taaaatggga tgatgaaaag    360
tggactgcat ggttttatga aaaaggatta tggtgtttga agaaaagctt taaaacatgg    420
ctcactgatt ctaaaaaagg ttacaacacc tacatgaaaa atcttttaca ggaatttggt    480
aaacaatttt atgaagattg gtgtcgtaga cctgaaaaac gtcgtgaaga taaaatttgc    540
aagagatggg gacaaaaagg attacgtaat gacaattact attcgttaaa gtggatgcag    600
tggagaaatt ggaaaaacag aaaccacgat caaaaacatg tgtgggtaac tcttatgaag    660
gatgcgctaa aggaatatac ggggcccgaa ttcaaattat ggactgagtt tagaaaagaa    720
aagatagact tttacaagca atggatgcaa gctttcgccg aacagtggac acaagacaaa    780
caatggaata cgtggactga agaaagaaat gaatatatga aaaagaaaaa agaagaagaa    840
gcaaaaaaaa aagcagcatc aaaaaaaaaa gcagcatcaa aaaaaggagg agcagcaaaa    900
aaggcaccag caaaaaaggc accaacaaaa aaagccgcac caggaacaaa ggcaccagca    960
aaaaaagcag cacctaaaaa agttgcagca ccaaatgcag ca                      1002
```

<210> SEQ ID NO 133
<211> LENGTH: 807
<212> TYPE: DNA
<213> ORGANISM: Plasmodium vivax

<400> SEQUENCE: 133

```
aaggaggcag tgaagaaggg gtccaagaag gcaatgaagc agcccatgca caagccgaac     60
cttcttgaag aggaagactt tgaggagaaa gaatcctttt cggatgacga gatgaatggg    120
ttcatggagg agagcatgga tgcttctaag ttggatgcga agaaggccaa gacgaccctc    180
aggagctcgg agaagaagaa gactccaacg agcggaatga gtggaatgag tggaagcggc    240
```

| | |
|---|---|
| gccaccagcg cagccaccga ggcagccacg aacatgaacg ccaccgccat gaacgccgct | 300 |
| gctaagggca acagcgaggc gagcaaaaag caaaccgact tgtccaacga agacctgttc | 360 |
| aacgacgagc tcacagaaga ggtcattgca gattcgtacg aagagggagg aaacgtggga | 420 |
| agcgaggaag ccgaaagcct cacaaatgca tttgacgaca agctactaga ccaaggagtg | 480 |
| aatgaaaata ctctgctgaa cgacaacatg atttacaacg tcaatatggt tccacataag | 540 |
| aagcgagaat tatacatctc cccacacaag catacctctg cagcaagcag taaaaatggc | 600 |
| aaacatcatg cggcggacgc ggacgctttg dacaaaaaac tgagggctca cgagctgctc | 660 |
| gagctggaaa acgagaagg cagcaactca gtcattgtcg aaacggaaga agtggatgtt | 720 |
| gacctaaacg gaggaaagtc aagcggctcc gtgtccttcc tcagctccgt agtcttcttg | 780 |
| ctcatcggat tgttatgttt caccaat | 807 |

<210> SEQ ID NO 134
<211> LENGTH: 2313
<212> TYPE: DNA
<213> ORGANISM: Plasmodium vivax

<400> SEQUENCE: 134

| | |
|---|---|
| aacctgagca acgattgcaa aaaggagcc aacaacagct ttaagttaat cgtgcacacc | 60 |
| agcgatgata tttgacact caagtggaag gtcactgggg aagggcagc tccaggcaac | 120 |
| aaagcagatg taaagaagta caaactccct accctagaga ggcctttcac ttccgtgcaa | 180 |
| gtgcattcag ccaacgccaa gtcgaagata tcgaaagca aattttacga cattggcagc | 240 |
| ggcatgccag cccagtgcag cgcgatcgcc acgaactgct tcctcagcgg cagcctcgaa | 300 |
| atcgagcact gctaccactg caccctgttg gagaagaagc tggcccaaga cagcgagtgc | 360 |
| ttcaagtacg tctcgagtga agcgaaggag ttgatcgaga agacacgcc gattaaagct | 420 |
| caagaagaag acgccaactc tgcagaccac aaactgatcg agtccataga cgtgatacta | 480 |
| aaggcagtgt acaaatcaga taagatgag gaaaagaagg agctcatcac cccggaggaa | 540 |
| gtggacgaaa atttgaagaa agagctagcc aattattgta ccctactgaa ggaggtagac | 600 |
| acaagtggca ctcttaacaa ccaccagatg gcaaacgaag aggaaacgtt cagaaatttg | 660 |
| actcgactgt tgcgaatgca tagcgaagaa aacgtggtga cccttcagga caaactgaga | 720 |
| aacgcagcca tatgcatcaa gcacatcgac aagtggattc ttaacaagag ggggttgacc | 780 |
| ctaccggaag aagggtaccc atcggaaggg tacccccag aagagtaccc cccggaggaa | 840 |
| ctcctcaaag aaatcgagaa ggaaaaaagc gctctgaatg atgaagcgtt cgctaaagat | 900 |
| accaacggag tcatccacct ggataagcct cccaacgaaa tgaaatttaa atccccctat | 960 |
| tttaaaaaga gcaaatactg taacaatgag tactgtgata ggtggaaaga taaaacgagt | 1020 |
| tgcatgtcaa atatagaagt ggaagagcaa ggggattgcg ggctctgttg gattttcgcc | 1080 |
| tctaagttac acttagaaac gatcaggtgc atgagagggt atggccactt ccgcagctcc | 1140 |
| gctctgtttg tggccaactg ctcgaagagg aagccagaag atagatgcaa cgtgggttct | 1200 |
| aaccctacag agtttcttca aattgttaag gacacgggat ttttacctct agagtccgat | 1260 |
| ctcccctaca gctatagcga cgcggggaac tcctgcccca ataaaagaaa caagtggacc | 1320 |
| aacctgtggg gggataccaa actgctgtat cataagagac ccaatcagtt tgcacaaaca | 1380 |
| ctcgggtacg tttcctacga aagcagtcgc tttgagcaca gcatcgacct cttcatagac | 1440 |
| atcctcaaaa gggaaattca aaacaaaggc tccgttatca tttacataaa aaccaacaat | 1500 |
| gtcatcgatt atgactttaa tggaagagtc gtccacagcc tatgtggcca taaggatgca | 1560 |

```
gatcatgccg ctaacctgat cggttatggt aactacatca gtgctggtgg ggagaagagg    1620
tcctattgga ttgtgcgaaa cagctggggg tactactggg gagatgaagg caactttaag    1680
gttgacatgt acggcccgga gggatgcaaa cggaacttca tccacacggc tgttgtgttt    1740
aagatagacc tgggcatcgt cgaagtcccg aagaaggacg aggggtccat ttatagctac    1800
ttcgttcagt acgtccccaa cttttttgcac agccttttct acgtgagtta cggtaagggt    1860
gctgataagg gagcggcggt ggtgacaggg caggcgggag gagcggtagt cacaggacag    1920
actgaaacgc ccactccgga ggccgctaaa atgggatc agccaggagc acagggtagc     1980
gaggcagaag tcgcggaggg tggccaggca ggaaatgaag ccccgggagg gttgcaagag    2040
agtgctgttt cgtcgcaaac gagtgaggtt acgccgcaat ctagtataac tgctccgcaa    2100
atcggtgcag ttgccccaca aatcggtgca gctgccccac aaatcgatgt agccgcccca    2160
caaatcgatg tagtcgcccc acaaacgagg tccgttgacg ccccccaaac gagctcggtt    2220 gccgccacc ccccaaacgt gacgccgcag aacgtgacgc ttggggaggg ccagcacgcg     2280
gggggtgtag gctccctcat ccccgcggac aac                                  2313

<210> SEQ ID NO 135
<211> LENGTH: 657
<212> TYPE: DNA
<213> ORGANISM: Plasmodium vivax

<400> SEQUENCE: 135
gaaaccctgc tagacagcga aacgttaaag aactacgaaa aggaaacgaa cgaatacatt      60
cgcaaaaaaa aagtggagaa actgttcgat gttattttaa aaaatgttct ggtaaacaaa    120
ccggaaaatg tataccgta catatacaag aacatttatt ccttccttt gaacaaaatt      180 tttgtgatcg gccctccttt gctgaaaatt actcccacct tatgttctgc gattgccagc    240
tgctttagct actaccacct cagcgcctcg cacatgatcg agtcttacac tactggtgaa    300
gtagatgacg ctgcagagag ttccacaagc aaaaagttag tcagtgacga cttaatctgc    360
tccatcgtta aaagcaacat aaaccagctg aacgcgaagc aaaagcgggg gtatgtagtc    420
gaagggttcc ccggcaccaa tcttcaggca gacagttgcc tacggcatt gccatcttac     480 gttttttgtcc tgtacgccga cgaagagtac atttatgaca agtacgaaca agagaacaac    540
gtaaaaattc gttcagacat gaacagccaa acttttgatg aaaacacaca gttgttcgaa    600
gtggccgagt tcaacacgaa tccgctgaag gatgaggtaa aggtctactt aaggaac       657

<210> SEQ ID NO 136
<211> LENGTH: 339
<212> TYPE: DNA
<213> ORGANISM: Plasmodium vivax

<400> SEQUENCE: 136
tatccaaaaa agaacttcga caaacccgac ccaacttccc cataccaagg acaatatgga      60
gagtctgagg aacaaagaca aggttatgga atccccccca acccaaccat gattaacctt    120
actggtaacc aagaccaacg accaaatgta ttgcaacaat ttggaataaa caacaaaaat    180
gtaatgcagt ttttaataaa catgtttgtg tacgttgctg ctatattagt tagtttaaaa    240 atatggggact acatgtctta cagcaaatgt gattattaca agatttatt attaagaatt    300 gtaagatacc aatcacacat gaatgatggt aagatggcc                            339

<210> SEQ ID NO 137
```

<211> LENGTH: 1998
<212> TYPE: DNA
<213> ORGANISM: Plasmodium vivax

<400> SEQUENCE: 137

```
agccgcatcg acaagcagcc catccagagc agctacctct tccaggataa cgcagtcccg      60
cctgttcgat tctccgcagt agatgcagac ctgttttcca ttggagtagt tcacacagag     120
gagcaaatat ttatggacga cgccaactgg gtgattagca gcgtgcccag taagtacctg     180
aacttgcatc tactcaaaac gggttctaga ccccattttt cgcacttctc cgtatctatg     240
aacacgggtt gcaacctatt catcgcttca ccggtggggg aaaccttccc cttgagtccc     300
tccaaagatg gagcgacgtg gaaagcattt gaaacggacg acagtgtaga ggtgattcac     360
agagagacga aggaaaagag aatctataag ctcaagttca ttcctctgaa gagtggggct     420
ctcctaaagg ttgacgtttt gaagggaatt ccctttgggt tatctcaca agggaggaaa     480
atcctaccaa cgatttgttc tggagatgag gaggtgctat caaacccaca gaatgaggtc     540
ttcaaagagt gcacatcgtc gagtagtctc tctcccgaat tgattgtct agccgggctg     600
agcacctacc ataggataa gaagaaccac acgtggaaaa cgtctagcgg atctataggt     660
cagtttataa agatcttctt caataagccc gtacaaatta ccaagtttag gtttaagccc     720
agagacgacc tgctgtcttg gccctccgaa gtagctctcc aattcgatac cgatgaggag     780
gtgatcatac caattctgca tacgcacaat atggggcaga acacgactag gctagaacac     840
ccaatcatca ccacctctgt taaggtagaa gtgagagaca tgtacgaacg ggcaagtgaa     900
aatacaggag gttcttttcga ggtaattgga agcacatgcc agatgatgga agacgactac     960
atgacgcacc atgctgttat agacatcacc gagtgtgatc gtaggttgga gtccctccca    1020
gatgttatgc ccttaacgaa ggggagcaaa tttctggcca tttgtcccg cccctgcttg    1080
agcagctcca atgggggagt catttacggg tcagatgttt attccacaga ttctgccgta    1140
tgtgggggcgg ccgtacacgc ggggggtgtgc agccgtgagg gggagggcag ctgccacttc    1200
ctcgttgtgg tgcgcggcgg gcgggccaac ttcgtggggg ctctccagaa caacgtcctg    1260
tctctcagtc ggggtggtgg cggtagcggt agcggtagct ccaccagtag cgatggcgat    1320
ggcgatagcg atagctccac cagtagggcc aacttctcat tttccctctc cagtgcgtca    1380
gggtcggggg gggtccgcg cggggcccac gcagaagccg cgccaagcag ctactccatt    1440
gtgttcaagc cgagggacca tttggctcca acgaacggct ttctagtaga ctcagggaga    1500
gagttcacca gctacggaag cgttgcctac ggatggaaga gggaggttc tccttcgtcc    1560
tcttttttcct ctccttctcc tagctacact tccccccgt tggaagaacc gacgctgctt    1620
agggggggact cctcctcatt caatgggatt tactccgggg ggatagaatt ccccccgcc    1680
tcggctagcc aaaattgcat ttcccaactg gattgccaga ccaacttctg gaagtttcag    1740
atgcaagaaa atggcaccta ctttgtgcag gtgctagtgg ggataaaaac ttcccctgag    1800
aagcagaagg ccttcgtcga gctgaatggc gttcccatca taaaggggt ggaccttggc    1860
ccagacgagg tcttcgtcgc cactgaccgc gtgcaggtga cgaaccgggc cctcgtcctc    1920
acgtccactt gcctgggcgg cgagagtgcc tgctcgcggg cgcgcgtcag catcatggcg    1980
gtccagattg tgaagacg                                                  1998
```

<210> SEQ ID NO 138
<211> LENGTH: 1746
<212> TYPE: DNA
<213> ORGANISM: Plasmodium vivax

<400> SEQUENCE: 138

```
aacggtatga ataaagacaa agacgcagag attactcccc ctccgttcat cgtcttgccg    60
ggtggaaaaa aaatccacat gctgcaaagc gaatacgagt atgacgttct gcgggatatg   120
taccgaacgg atgaggcgaa tgggggaagt ggtgagaagg agagtcaccc ctctggggat   180
ggtgcaatca gaagaaacga attttttaaa cttttcacc acagggaggg tcattataag    240
tttgttatca aaaatgttcc caccaaattg agcgaccttt tgcagaaagg tggcaacgaa   300
caggagacag acctatttcc tcttttatac aggagtctgc aattcgcatg cagcgcagac   360
gggacgtggc catatgccag aagagaggtg gcctttttta aaaacgggag cgtccactgc   420
gaagcggaat tcaaaacga gttatcagtg aggagaaccc cccgaagtgg aagaaatca    480
tttgacgtt ttccaagggg gacactaata aaaagtagcg acctgaggag caaaattgtg    540
gaggggaatt cttatgataa aagggccgca cccctgaaga gtgaaaaaaa aagaaggct    600
ctctttttac acccagaaag tgtgctatac aaaatggaag aaatattttt ttatgaaaat   660
ccaagtgtca aaagtgaaat tgtcgggttt gttcttttc atgatgtgtg cacagtaacg    720
tccttaggac atggagcaca tcccgttaac tccccctttt tgggaagcga cctgctggag   780
atgatatttg gctactgcat tttacacggg tttaaaaaaa tcagagtgaa aagcgaatcc   840
ttaaattacg aaactgggat aaggacctca ttcattgaga ttttactcaa cggaaaaaca   900
gcacttgaac atttagggtt aagacttaca aacgtagcga agttttctaa agaactgtat   960
tatgtaatca ctgggtatac gtggaaaagt gatttggtgc tatcacccat agtaaggttt  1020
gaacatgatt tatacgtgca tcacgacata gaggagcgat ttttccttta cgtgaataaa  1080
atgtatagga atatgctcca cgatttgtcc ttctcttgtg atgaaaatta ttatcttat   1140
aaaaattgtt atgacatcta cccctccgtg agaaggagtc aaaataatct ttgtctcttc  1200
gaactgaatc ccatatatga agaattgaag gagctctttc cagactcttg taatattggc  1260
caacgcgtta gaaaatgcta tgaggagata aaaaaaaacg ttgtctgcac acataacggt  1320
gaaggaggag aagacggatg taagtactac caatttattg taaatacatt cataaagccg  1380
aggaggaaaa cgtccttttt tatttatcac aatatgtatg tacaggaata tctttcaaag  1440
aaatcctacc cctattactt gctactcagt gaggttataa aaaatgaaga aaataacttt  1500
ctcgaaaaag gcaactacga cttagtggcc gatgcacaga cgcacctctt cttaaattac  1560
gttttgcaaa attctacctt ttttatctttt tggaatttct ctaccgaatt ttggaaaagg  1620
tttcggtaca tccaggctgg cccaaccggg gccacttcca caccgcagaa ggggcaagct  1680
gtgttttgcc ccatggccta tgcgtacgaa tttgtggagc acctcgacac gttttatgtg  1740
aggggg                                                              1746
```

<210> SEQ ID NO 139
<211> LENGTH: 1176
<212> TYPE: DNA
<213> ORGANISM: Plasmodium vivax

<400> SEQUENCE: 139

```
tccgttgaag aggctaaaaa aaatactcag gaagttgtga caaatgtgga caatgctgct    60
aaatctcagg ccaccaattc aaatccgata agtcagcctg tagatagtag taaagcggag   120
aaggttccag gagattctac gcatggaaat gttaacagtg gccaagatag ttctaccaca   180
ggtaaagctg ttacggggga tggtcaaaat ggaaatcaga cacctgcaga aagcgatgta   240
```

| | |
|---|---|
| cagcgaagtg atattgccga aagtgtaagt gctaaaaatg ttgatccgca gaaatctgta | 300 |
| agtaaaagaa gtgacgacac tgcaagcgtt acaggtattg ccgaagctgg aaaggaaaac | 360 |
| ttaggcgcat caaatagtcg accttctgag tccaccgttg aagcaaatag cccaggtgat | 420 |
| gatactgtga acagtgcatc tatacctgta gtgagtggtg aaaacccatt ggtaaccccc | 480 |
| tataatggtt tgaggcattc gaaagacaat agtgatagcg atggacctgc ggaatcaatg | 540 |
| gcgaatcctg attcaaatag taaaggtgag acgggaaagg ggcaagataa tgatatggcg | 600 |
| aaggctacta agatagtag taatagttca gatggtacca gctctgctac gggtgatact | 660 |
| actgatgcag ttgatanggga aattaataaa ggtgttcctg aggatanggga taaaactgta | 720 |
| ggaagtaaag atggaggggg ggaagataac tctgcaaata aggatgcagc gactgtagtt | 780 |
| ggtgaggata gaattcgtga aacagcgct ggtggtagca ctaatgatag atcaaaaaat | 840 |
| gacacggaaa agaacggggc ctctaccct gacagtaaac aaagtgagga tgcaactgcg | 900 |
| ctaagtaaaa ccgaaagttt agaatcaaca gaaagtggag atagaactac taatgataca | 960 |
| actaacagtt tagaaaataa aaatggagga aaagaaaagg atttacaaaa gcatgatttt | 1020 |
| aaaagtaatg atacgccgaa tgaagaacca aattctgatc aaactacaga tgcagaagga | 1080 |
| catgacaggg atagcatcaa aaatgataaa gcagaaagga gaaagcatat gaataaagat | 1140 |
| acttttacga aaaatacaaa tagtcaccat ttaaat | 1176 |

<210> SEQ ID NO 140
<211> LENGTH: 1590
<212> TYPE: DNA
<213> ORGANISM: Plasmodium vivax

<400> SEQUENCE: 140

| | |
|---|---|
| atacggaatg gaaacaaccc gcaggcatta gttcctgaaa agggcgctga cccgagtggg | 60 |
| ggccagaaca accgctccgg agaaaaccaa gacacgtgcg aaattcaaaa gatggccgaa | 120 |
| gaaatgatgg aaaaaatgat gaaggaaaaa gacgtgttta gctccatcat ggaacctctc | 180 |
| cagagcaaat taactgacga tcatctgtgt tcaaaaatga aatatacgaa catttgtctt | 240 |
| cacgaaaagg acaaaactcc cttgaccttc ccctgcacaa gtccgcagta cgaacagcta | 300 |
| attcatcgct tcacttataa aaagttgtgc aactccaagg tggccttttag caacgtcttg | 360 |
| ctcaaatcct tcatcgataa aaaaaatgaa gaaaacacat taacacgat catacagaat | 420 |
| tacaaagttc tgtccacttg cattgacgat gatttgaagg acatttataa tgcatccata | 480 |
| gagttattct ccgacataag aacctccgtc acagaaatta ccgaaaagtt gtggtccaaa | 540 |
| aatatgatcg aagttttaaa gacaagagag caaaccattg caggcatttt atgtgagtta | 600 |
| agaaatggaa ataattctcc cctagtatcg aacagttttt cctatgaaaa ttttggaatt | 660 |
| ctcaaggtta attatgaggg attactaaac caggcgtatg cggccttttc agactactat | 720 |
| tcatactttc ccgcttttgc cattagcatg ttagaaaagg gagggttggt cgaccgcttg | 780 |
| gtcgccatcc atgagagctt gaccaactac aggacgagaa atattctcaa gaagatcaat | 840 |
| gagaagtcca aaaatgaggt cctcaataat gaagaaatta tgcacagctt gagcagttac | 900 |
| aagcaccatg ccggggggcac gcgtggcgcc ttcctgcagt ccagagatgt gcgcgaagtt | 960 |
| acgcaaggag atgtgagcgt tgatgagaag ggcgaccggg ccaccaccgc gggggggcaac | 1020 |
| caaagcgcaa gcgtggctgc ggcggcccccg aaggatgcgg gcccaaccgt ggctgctcct | 1080 |
| aacactgctg ctacgctcaa aacgctgct tcccccaacg cggctgctac taacactgct | 1140 |
| gctcccccca acatgggtgc cacctccccg ctgagcaacc ccctgtacgg caccagctcc | 1200 |

```
ctgcagccaa aggacgtcgc ggtgctggtc agagatctgc tcaagaacac gaacatcatc   1260
aagttcgaga ataacgaacc gactagccaa atggacgatg aagaaattaa gaagctcatt   1320
gagagctcct ttttcgactt gagcgacaac accatgttaa tgcggttgct cataaagccg   1380
caggcggcca tcttactaat cattgagtcc ttcattatga tgacgccctc ccccacgagg   1440
gacgccaaga cctattgcaa gaaagcccta gttaatggcc agctaatcga aacctcagat   1500
ttaaacgcgg cgacggagga agacgacctc ataaacgagt tttccagcag gtacaattta   1560
ttctacgaga ggctcaagct ggaggagttg                                    1590
```

<210> SEQ ID NO 141
<211> LENGTH: 1572
<212> TYPE: DNA
<213> ORGANISM: Plasmodium vivax

<400> SEQUENCE: 141

```
aaggagtact gcgaccagct tagcttttgc gatgtgggat tgacacacca ctttgatacg     60
tattgtaaga atgaccagta cctgttcgtt cactacactt gtgaggacct ctgcaaaacg    120
tgtggcccta ttcgtcctg ctacggaaac aagtacaaac ataagtgcct gtgcaatagc    180
cccttcgaga gtaaaaagaa ccattccatt tgcgaagcac gaggtagctg cgatgcacag    240
gtatgcggca agaatcaaat ttgcaaaatg gtagacgcta agcaacatg cacatgtgca    300 gataaatacc aaaatgtgaa tggggtgtgt ctaccggaag ataagtgcga ccttctgtgc    360
ccctcaaaca aatcgtgcct gctggaaaat gggaaaaaaa tatgcaagtg cattaatggg    420
ttgactctac agaacggcga gtgcgtctgc tcggatagca gccaaattga agaaggacac    480
ctctgtgtgc ccaagaataa atgtaaacgg aaggagtacc aacagctctg caccaatgag    540
aaggaacact gtgtgtatga tgagcagacg gacattgtgc ggtgcgactg cgtggaccac    600
ttcaagcgga acgaacgggg aatttgcatc ccagtcgact actgcaaaaa tgtcacctgc    660
aaggaaaatg agatttgcaa agttgttaat aatacaccca catgtgagtg taaagaaaat    720
ttaaaaagaa atagtaacaa tgaatgtgta ttcaataaca tgtgtcttgt taataaaggg    780
aactgcccca ttgattcgga gtgcatttat cacgagaaaa aaaggcatca gtgtttgtgc    840
cataagaagg gcctcgtcgc cattaatggc aagtgcgtca tgcaggacat gtgcaggagc    900
gatcagaaca aatgctccga aaattccatt tgtgtaaatc aagtgaataa agaaccgctg    960
tgcatatgtt tgtttaatta tgtgaagagt cggtcgggcg actcgcccga gggtggacag   1020
acgtgcgtgg tggacaatcc ctgcctcgcg cacaacgggg gctgctcgcc aaacgaggtt   1080
tgcacgttca aaaatggaaa ggtaagttgc gcctgcgggg agaactaccg ccccaggggg   1140
aaggacagcc caacgggaca gcggtcaaa cggggggaag cgaccaaacg gggtgacgcg   1200
ggtcagcccg ggcaggcgca ctcagcaaat gagaacgcgt gcctgcccaa gacgtccgag   1260
gcggaccaaa ccttcacctt ccagtacaac gacgacgcgg ccatcattct cgggtcctgc   1320
ggaattatac agtttgtgca aaagagcgat caggtcattt ggaaaattaa cagcaacaat   1380
cacttttaca tttttaatta tgactatcca tctgagggtc agctgtcggc acaagtcgtg   1440
aacaagcagg agagcagcat tttgtactta agaaaaccc acgcggggaa agtcttttac   1500
gccgactttg agttgggtca tcagggatgc tcctacggaa acatgtttct ctacgcccac   1560
cgggaggagg ct                                                       1572
```

<210> SEQ ID NO 142

-continued

```
<211> LENGTH: 1020
<212> TYPE: DNA
<213> ORGANISM: Plasmodium vivax

<400> SEQUENCE: 142
agcaaaaaca ttattattct gaacgatgaa attaccacca ttaaaagccc gattcattgc      60
attaccgata tttattttct gtttcgcaac gaactgtata aaacctgcat tcagcatgtg     120
attaaaggcc gcaccgaaat tcatgtgctg gtgcagaaaa aaattaacag cgcgtgggaa     180
acccagacca ccctgtttaa agatcatatg tggtttgaac tgccgagcgt gtttaacttt     240
attcataacg atgaaattat tattgtgatt tgccgctata aacagcgcag caaacgcgaa     300
ggcaccattt gcaaacgctg gaacagcgtg accggcacca tttatcagaa agaagatgtg     360
cagattgata aagaagcgtt tgcgaacaaa aacctggaaa gctatcagag cgtgccgctg     420
accgtgaaaa acaaaaaatt tctgctgatt tgcggcattc tgagctatga atataaaacc     480
gcgaacaaag ataactttat tagctgcgtg gcgagcgaag ataaaggccg cacctggggc     540
accaaaattc tgattaacta tgaagaactg cagaaaggcg tgccgtattt ttatctgcgc     600
ccgattattt ttggcgatga atttggcttt tatttttata gccgcattag caccaacaac     660
accgcgcgcg gcggcaacta tatgacctgc accctggatg tgaccaacga aggcaaaaaa     720
gaatataaat ttaaatgcaa acatgtgagc ctgattaaac cggataaaag cctgcagaac     780
gtggcgaaac tgaacggcta ttatattacc agctatgtga aaaaagataa ctttaacgaa     840
tgctatctgt attataccga acagaacgcg attgtggtga aaccgaaagt gcagaacgat     900
gatctgaacg gctgctatgg cggcagcttt gtgaaactgg atgaaagcaa agcgctgttt     960
atttatagca ccggctatgg cgtgcagaac attcataccc tgtattatac ccgctatgat    1020
```